United States Patent
Beigelman et al.

(10) Patent No.: US 11,787,833 B2
(45) Date of Patent: Oct. 17, 2023

(54) MODIFIED CYCLIC DINUCLEOSIDE COMPOUNDS AS STING MODULATORS

(71) Applicant: ALIGOS THERAPEUTICS, INC., South San Francisco, CA (US)

(72) Inventors: Leonid Beigelman, San Mateo, CA (US); Santhosh Kumar Thatikonda, Fremont, CA (US); Antitsa Dimitrova Stoycheva, Half Moon Bay, CA (US)

(73) Assignee: Aligos Therapeutics, Inc., South San Francisco, CA (US)

( * ) Notice: Subject to any disclaimer, the term of this patent is extended or adjusted under 35 U.S.C. 154(b) by 327 days.

(21) Appl. No.: 16/868,013

(22) Filed: May 6, 2020

(65) Prior Publication Data

US 2020/0369711 A1  Nov. 26, 2020

Related U.S. Application Data

(60) Provisional application No. 62/981,475, filed on Feb. 25, 2020, provisional application No. 62/845,703, filed on May 9, 2019.

(51) Int. Cl.
C07H 21/02 (2006.01)
A61P 35/04 (2006.01)
A61K 9/00 (2006.01)

(52) U.S. Cl.
CPC .............. C07H 21/02 (2013.01); A61P 35/04 (2018.01); A61K 9/0019 (2013.01)

(58) Field of Classification Search
None
See application file for complete search history.

(56) References Cited

U.S. PATENT DOCUMENTS

| | | | |
|---|---|---|---|
| 5,547,941 | A | 8/1996 | Battistini et al. |
| 6,153,742 | A | 11/2000 | Pedroso et al. |
| 8,859,237 | B2 | 10/2014 | Liang et al. |
| 2002/0111496 | A1 | 8/2002 | Horenstein et al. |
| 2005/0203051 | A1 | 9/2005 | Karaolis et al. |
| 2005/0215513 | A1 | 9/2005 | Boojamra et al. |
| 2006/0167241 | A1 | 7/2006 | Hayakawa |
| 2012/0009147 | A1 | 1/2012 | Cho et al. |
| 2012/0041057 | A1 | 2/2012 | Jones et al. |
| 2012/0077814 | A1 | 3/2012 | Atkinson et al. |
| 2013/0315868 | A1 | 11/2013 | Mayes et al. |
| 2014/0155345 | A1 | 6/2014 | Jones et al. |
| 2014/0178338 | A1 | 6/2014 | Mayes et al. |
| 2014/0341976 | A1 | 11/2014 | Dubensky et al. |
| 2015/0174268 | A1 | 6/2015 | Li |
| 2016/0254456 | A1 | 9/2016 | Heil et al. |
| 2017/0239283 | A1 | 8/2017 | Gough et al. |
| 2018/0273578 | A1 | 9/2018 | Oost et al. |
| 2020/0040028 | A1 | 2/2020 | Genieser et al. |

FOREIGN PATENT DOCUMENTS

| | | |
|---|---|---|
| AU | 2004233898 | 11/2004 |
| AU | 2005221717 | 9/2005 |
| CN | 102199183 | 9/2011 |
| CN | 105367617 | 3/2016 |
| CN | 106539814 | 3/2017 |
| CN | 106552265 | 4/2017 |
| CN | 107286190 | 10/2017 |
| CN | 108276463 | 7/2018 |
| CN | 108913737 | 11/2018 |
| CN | 110724174 | 1/2020 |
| EP | 1782826 | 5/2007 |
| ES | 2109177 | 1/1998 |
| GB | 2257704 | 1/1993 |
| WO | WO 2004/096235 | 11/2004 |
| WO | WO 2005/005450 | 1/2005 |
| WO | WO 2005/030186 | 4/2005 |
| WO | WO 2006/045041 | 4/2006 |
| WO | WO 2006/091905 | 8/2006 |
| WO | WO 2009/132123 | 10/2009 |
| WO | WO 2009/132135 | 10/2009 |
| WO | WO 2009/133560 | 11/2009 |
| WO | WO 2010/002877 | 1/2010 |
| WO | WO 2010/101526 | 9/2010 |
| WO | WO 2011/003025 | 1/2011 |
| WO | WO 2011/035231 | 3/2011 |
| WO | WO 2012/012465 | 1/2012 |
| WO | WO 2012/012776 | 2/2012 |
| WO | WO 2013/185052 | 12/2013 |

(Continued)

OTHER PUBLICATIONS

Chawla et al. Phys. Chem. Chem. Phys, 18, pp. 18045-18053. (Year: 2016).*
Second Written Opinion dated Apr. 7, 2021 for PCT Application No. PCT/US2020/031696, filed May 6, 2020.
International Preliminary Report on Patentability dated Aug. 25, 2021 for PCT Application No. PCT/US2020/031696, filed May 6, 2020.
"IUPAC-IUB Commission on Biochemical Nomenclature Abbreviated Nomenclature of Synthetic Polypeptides (Polymerized Amino Acids)* Revised Recommendations (1971)" *Biochemistry*. (1972) 11(5) :942-944.
Lioux et al., "Design, Synthesis, and Biological Evaluation of Novel Cyclic Adenosine-Inosine Monophosphate (cAIMP) Analogs That Activate Stimulator or Interferon Genes (Sting" J. Med. Chem. (2016) 59(22):10253-10267.

(Continued)

*Primary Examiner* — Katherine Peebles
(74) *Attorney, Agent, or Firm* — Knobbe Martens Olson & Bear LLP

(57) ABSTRACT

Provided herein are compounds of Formula (I), Formula (II) and/or Formula (III), or pharmaceutically acceptable salts of any of the foregoing, pharmaceutical compositions that include a compound described herein (including pharmaceutically acceptable salts of a compound described herein) and methods of synthesizing the same. Also provided herein are methods of treating diseases and/or conditions with a compound of Formula (I), Formula (II) and/or Formula (III), or a pharmaceutically acceptable salt of any of the foregoing.

18 Claims, 4 Drawing Sheets

(56) References Cited

FOREIGN PATENT DOCUMENTS

| | | |
|---|---|---|
| WO | WO 2014/012479 | 1/2014 |
| WO | WO 2014/111269 | 7/2014 |
| WO | WO 2014/179335 | 11/2014 |
| WO | WO 2014/179760 | 11/2014 |
| WO | WO 2014/189805 | 11/2014 |
| WO | WO 2014/189806 | 11/2014 |
| WO | WO 2015/074145 | 5/2015 |
| WO | WO 2015/077354 | 5/2015 |
| WO | WO 2015/130584 | 9/2015 |
| WO | WO 2015/142910 | 9/2015 |
| WO | WO 2015/185565 | 12/2015 |
| WO | WO 2016/041877 | 3/2016 |
| WO | WO 2014/093936 | 6/2016 |
| WO | WO 2016/096174 | 6/2016 |
| WO | WO 2016/096577 | 6/2016 |
| WO | WO 2016120305 | 8/2016 |
| WO | WO 2016/145102 | 9/2016 |
| WO | WO 2017/027645 | 2/2017 |
| WO | WO 2017/027646 | 2/2017 |
| WO | WO 2017/075477 | 5/2017 |
| WO | WO 2017/093933 | 6/2017 |
| WO | WO 2017/096963 | 6/2017 |
| WO | WO 2017/100305 | 6/2017 |
| WO | WO 2017/106740 | 6/2017 |
| WO | WO 2017/123657 | 7/2017 |
| WO | WO 2017/161349 | 9/2017 |
| WO | WO 2017/165489 | 9/2017 |
| WO | WO 2017/185180 | 11/2017 |
| WO | WO 2017/186711 | 11/2017 |
| WO | WO 2018/009466 | 1/2018 |
| WO | WO 2018/009648 | 1/2018 |
| WO | WO 2018/009652 | 1/2018 |
| WO | WO 2018/031818 | 2/2018 |
| WO | WO 2018/045058 | 3/2018 |
| WO | WO 2018/053508 | 3/2018 |
| WO | WO 2018/060323 | 4/2018 |
| WO | WO 2018/065360 | 4/2018 |
| WO | WO 2018/068132 | 4/2018 |
| WO | WO 2018/098203 | 5/2018 |
| WO | WO 2018/100558 | 6/2018 |
| WO | WO 2018/118664 | 6/2018 |
| WO | WO 2018/118665 | 6/2018 |
| WO | WO 2018/119117 | 6/2018 |
| WO | WO 2018/119274 | 6/2018 |
| WO | WO 2018/129270 | 7/2018 |
| WO | WO 2018/138684 | 8/2018 |
| WO | WO 2018/138685 | 8/2018 |
| WO | WO 2018/140831 | 8/2018 |
| WO | WO 2018/152450 | 8/2018 |
| WO | WO 2018/152453 | 8/2018 |
| WO | WO 2018/156625 | 8/2018 |
| WO | WO 2018/198084 | 11/2018 |
| WO | WO 2018/200812 | 11/2018 |
| WO | WO 2018/208667 | 11/2018 |
| WO | WO 2018/226529 | 12/2018 |
| WO | WO 2018/232217 | 12/2018 |
| WO | WO 2019/046498 | 3/2019 |
| WO | WO 2019/125974 | 6/2019 |

OTHER PUBLICATIONS

Shirasishi et al., "Synthesis and evaluation of c-di-4'-thioAMP as an artificial ligand for c-di-AMP riboswitech" Bioorg. Med. Chem. (2017) 25(14):3883-3889.
Amiot et al., "New approach for the synthesis of c-di-GMP and its Analogues" Synthesis (2006) (24):4230-4236.
Battistini et al., "Stereoselective synthesis of cyclic dinucleotide Phosphorothioates" Tetrahedron (1993) 49(5):1115-1132.
CAS Reg. No. 1053697-49-6, Entered Sep. 28, 2008.
Ching et al., "Synthesis of cyclic di-nucleotidic acids as potential inhibitors targeting diguanylate cyclase" Bioorganic & Medicinal Chemistry (2010) 18(18):6657-6665.
Cook et al., "Formation of a cyclic dianhydrodiadenylic acid by the alkaline degradation of adenosine-5'-triphosphoric acid" Journal of the American Chemical Society (1957) 79:3607-3608.
Fei et al., "Catalytic carbene transfer allows the direct customization of cyclic purine dinucleotides" Chemical Communications (2014), 50(62):8499-8502.
Fu et al., "STING agonist formulated cancer vaccines can cure established tumors resistant to PD-1 blockade" Science Translational Medicine (2015) 7(283):1-11.
Gaffney et al., "One-Flask Syntheses of c-di-GMP and the [Rp,Rp] and [Rp,Sp] Thiophosphate Analogues" Organic Letters (2010) 12(14):3269-3271.
Gaffney et al., "Synthesis of biotinylated cyclic-di-GMP and cyclic-di-AMP using click conjugation" Nucleosides, Nucleotides & Nucleic Acids (2013) 32(1):1-16.
Guan et al., "Molecular structure of cyclic diguanylic acid at 1Å resolution of two crystal forms: self-association, interactions with metal ion/planar dyes and modeling studies" Journal of Biomolecular Structure & Dynamics (1993) 11(2):253-76.
Hamoir et al., "The cyclic dimer of 5-fluoro-2'-deoxyuridylic acid: a potent anticancer agent" Nucleosides & Nucleotides (1989) 8(2):285-295.
Hamoir et al., "3'-5' Cyclic oligothymidylic acids: conformation and complexation of intercalating agents" Bulletin des Societes Chimiques Belges (1993) 102(5):335-342.
Hyodo et al., "Synthesis of cyclic bis(3'-5')diguanylic acid (c-di-GMP) analogs" Tetrahedron (2006) 62(13):3089-3094.
Hyodo et al., "Organic synthesis, chemical properties, and biological activities of cyclic bis(3'-5)diguanylic acid (c-di-GMP) and its analogs" Yuki Gosei Kagaku Kyokaishi (2006) 64(4):359-370.
Ishihara et al., "Effect of cyclic bis(3'-5')diguanylic acid and its analogs on bacterial biofilm formation" FEMS Microbiology Letters (2009) 301(2):193-200.
Kellenberger et al., "RNA-Based Fluorescent Biosensors for Live Cell Imaging of Second Messengers Cyclic di-GMP and Cyclic AMP-GMP" Journal of the American Chemical Society (2013) 135(13):4906-4909.
Kiburu et al., "A simple solid-phase synthesis of the ubiquitous bacterial signaling molecule, c-di-GMP and analogues" Molecular BioSystems (2008) 4(12):1220.
Kiburu et al., "A simple solid-phase synthesis of the ubiquitous bacterial signaling molecule, c-di-GMP and analogues" Molecular BioSystems (2008) 4(6):518-520.
Knouse et al., "Unlocking P(V): Reagents for chiral phosphorothioate synthesis" Science (2018),361(6408):1234-1238.
Kranzusch et al., "Ancient Origin of cGAS-STING Reveals Mechanism of Universal 2',3' cGAMP Signaling" Molecular Cell (2015) 59(6):891-903.
Markham et al., "Studies on transfer ribonucleic acids and related compounds. XXVII. Linear and cyclic oligonucleotides obtained by polymerization of protected ribonucleoside 3'-phosphates" Chemical & Pharmaceutical Bulletin (1979), 27(12):2988-2996.
Meehan et al., "Nuclease-Resistant c-di-AMP Derivatives That Differentially Recognize RNA and Protein Receptors" Biochemistry (2016) 55(6):837-849.
Namasivayam et al., "The promiscuous ectonucleotidase NPP1: molecular insights into substrate binding and hydrolysis" Biochimica et Biophysica Acta, General Subjects (2017) 1861(3):603-614.
Ohtsuka et al., "Transfer ribonucleic acids and related compounds. VII. Synthesis and properties of cyclic oligoadenylic Acids" Chemical & Pharmaceutical Bulletin (1974) 22(5):1022-1028.
Ramanjulu et al., "Design of amidobenzimidazole STING receptor agonists with systemic activity" Nature (2018) 564(7736):439-443.
Roembke et al., "A cyclic dinucleotide containing 2-aminopurine is a general fluorescent sensor for c-di-GMP and 3',3'-cGAMP" Molecular BioSystems (2014) 10(6):1568-1575.
Ross et al., "The cyclic diguanylic acid regulatory system of cellulose synthesis in Acetobacter xylinum. Chemical synthesis and biological activity of cyclic nucleotide dimer, trimer, and phosphothioate derivatives" Journal of Biological Chemistry (1990) 265(31):18933-18943.

(56) References Cited

OTHER PUBLICATIONS

Sabareesh et al., "Understanding dissociation of cyclic dinucleotide ions by electrospray mass spectrometry" International Journal of Mass Spectrometry (2014) 364:9-15.

Sawai et al., "Synthesis of oligoinosinates with 2',5' internucleotide linkage in aqueous solution using lead(2+) ion" Bulletin of the Chemical Society of Japan (1981) 54(9):2759-2762.

Shanahan et al., "Differential Analogue Binding by Two Classes of c-di-GMP Riboswitches" Journal of the American Chemical Society (2011) 133(39):15578-15592.

Shanahan et al., "Identification of c-di-GMP Derivatives Resistant to an EAL Domain Phosphodiesterase" Biochemistry (2013) 52(2):365-377.

Tezuka et al., "Cyclic Bis(3'-5')diadenylic acid (c-di-AMP) analogs promote the activities of photosynthesis and respiration of Chlamydomonas reinhardtii" American Journal of Plant Sciences (2014) 5(1):24-28.

Veliath et al., "Synthesis and Characterization of C8 Analogs of c-di-GMP" Nucleosides, Nucleotides & Nucleic Acids (2011) 30(11):961-978.

Yi et al., "Single nucleotide polymorphisms of human STING can affect innate immune response to cyclic dinucleotides" PLoS One (2013) 8(10):e77846.

Zhang et al., "Polymorphism of the Signaling Molecule c-di-GMP" Journal of the American Chemical Society (2006) 128(21):7015-7024.

Zhao et al., "Thiophosphate analogs of c-di-GMP: impact on Polymorphism" Nucleosides, Nucleotides & Nucleic Acids (2009) 28(5-7):352-378.

Zhou et al., "Potent suppression of c-di-GMP synthesis via I-site allosteric inhibition of diguanylate cyclases with 2'-F-c-di-GMP" Bioorganic & Medicinal Chemistry (2013) 21(14):4396-4404.

Choi et al., "Stereoselective synthesis and anti-HCV activity of conformationally restricted 2'-C-substituted carbanucleosides" Tetrahedron (2012) 68(4):1253-1261.

Jeong et al., "Asymmetric Synthesis of Cyclopropyl-fused 2'-C-Methylcarbanucleosides as Potential Anti-HCV Agents" Nucleosides, Nucleotides & Nucleic Acids (2007) 26(8-9):1021-1024.

Lee et al., "Stereoselective Synthesis of 2'-C-Methyl-cyclopropyl-Fused Carbanucleosides as Potential Anti-HCV Agents" Organic Letters (2006) 8(22):5081-5083 with Supplementary Information.

\* cited by examiner

CT26 Mouse Colon Carcinoma Model

CT26 Mouse Colon Carcinoma Model

MODIFIED CYCLIC DINUCLEOSIDE COMPOUNDS AS STING MODULATORS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application Nos. 62/845,703, filed May 9, 2019, and 62/981,475, filed Feb. 25, 2020.

BACKGROUND

Field

The present application relates to the fields of chemistry, biochemistry and medicine. Disclosed herein are compounds of Formula (I), Formula (II) and Formula (III), or pharmaceutically acceptable salt of any of the foregoing, pharmaceutical compositions that include a compound described herein (including pharmaceutically acceptable salts of a compound described herein) and methods of synthesizing the same. Also disclosed herein are methods of treating diseases and/or conditions with a compound of Formula (I), Formula (II) and Formula (III), or a pharmaceutically acceptable salt of any of the foregoing.

Description

The innate immune response comprises a series of cellular sensors and signaling pathways that activates the defense mechanisms of the host in response to the host's exposure to microbial pathogens (for example, viruses, bacteria, and fungi). Exposure to intracellular DNA and/or DNA pathogens can trigger the activation of innate immune responses that can stimulate the host's defense mechanisms.

SUMMARY

Some embodiments disclosed herein relate to a compound of Formula (I), or a pharmaceutically acceptable salt thereof. Other embodiments disclosed herein relate to a compound of Formula (II), or a pharmaceutically acceptable salt thereof. Still other embodiments disclosed herein relate to a compound of Formula (III), or a pharmaceutically acceptable salt thereof.

Some embodiments disclosed herein relate to a pharmaceutical composition that can contain an effective amount of a compound of Formula (I), Formula (II) and/or Formula (III), or a pharmaceutically acceptable salt of any of the foregoing.

Some embodiments described herein relate to a method of treating of a disease or condition in a subject in which modulation STING is beneficial that can include administering to the subject an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating of a disease or condition in a subject in which modulation STING is beneficial.

Some embodiments disclosed herein relate to a method of treating an inflammatory condition, an infectious disease, a viral disease and/or a cancer in which the modulation of STING is beneficial in a subject that can include administering to the subject an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating an inflammatory condition, an infectious disease a viral disease and/or a cancer in which the modulation of STING is beneficial.

Some embodiments disclosed herein relate to a method for inducing an immune response in a subject that can include administering to the subject an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inducing an immune response.

Some embodiments disclosed herein relate to a method for inducing a STING-dependent type I interferon production in a cell that can include contacting the cell an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inducing a STING-dependent type I interferon production.

Some embodiments disclosed herein relate to a method for activating a STING receptor in a cell that can include contacting the cell an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of activating a STING receptor.

These are other embodiments are described in greater detail below.

Figure 1:
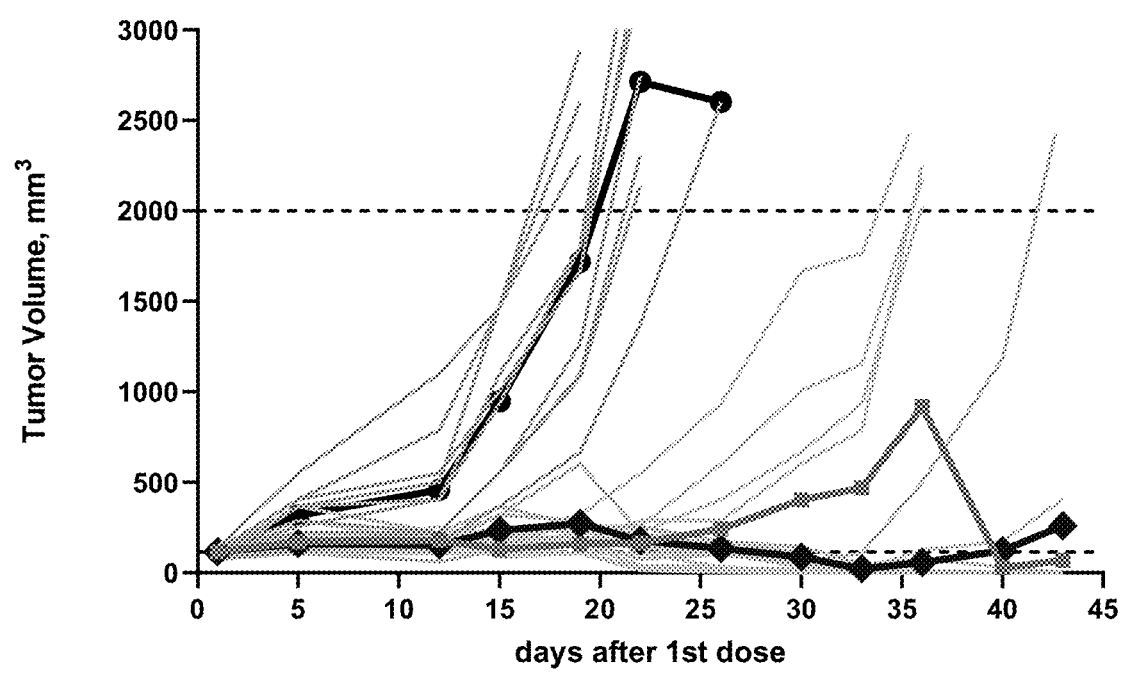
FIG. 1 shows the results of a colon carcinoma study using compound 1-10b at two different dosing levels.

DETAILED DESCRIPTION cGAS (cyclic GMP-AMP synthase), senses foreign, double-stranded DNA in the cytosol and activates STING (stimulator of interferon genes, also known as MITA, MPYS, ERIS or TMEM173) via the production of the CDN (cyclic dinucleotide) 2'3'cGAMP. STING is a transmembrane protein localized to the endoplasmic reticulum that undergoes a conformational change in response to direct binding of cyclic dinucleotides (CDNs). This in turn triggers a signaling cascade involving the phosphorylating of TBK1 (TANK Binding Kinase 1) and IRF3 (Interferon Regulatory Factor 3), leads to the expression of type I interferon genes and production of IFN-β and other cytokines (such as and to production of pro-inflammatory cytokines (IL-1a, IL-1β, IL-2, IL-6, TNF-α, etc.). This pathway can be exploited for cancer immunotherapy, where synthetic STING agonists are injected intratumorally. After engagement of the STING pathway, expression of interferons results in the maturation of dendritic cells, which in turn primes activated CD8 T-cells to attack tumor cells.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from deuterium, alkyl, alkenyl, alkynyl, cycloalkyl, cycloalkenyl, aryl, heteroaryl, heterocyclyl, aryl (alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl) and their benzo-fused analogs.

A "(heterocyclyl)alkyl" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—) and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(═O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "$RC(=O)O-$" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "$-C(=O)OR$" group in which R can be the same as defined with respect to O-carboxy. An ester and C-carboxy may be substituted or unsubstituted.

A "thiocarbonyl" group refers to a "$-C(=S)R$" group in which R can be the same as defined with respect to O-carboxy. A thiocarbonyl may be substituted or unsubstituted.

A "trihalomethanesulfonyl" group refers to an "$X_3CSO_2-$" group wherein each X is a halogen.

A "trihalomethanesulfonamido" group refers to an "$X_3CS(O)_2N(R_A)-$" group wherein each X is a halogen, and $R_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a "$-NH_2$" group.

As used herein, the term "hydroxy" refers to a "$-OH$" group.

A "cyano" group refers to a "$-CN$" group.

The term "azido" as used herein refers to a $-N_3$ group.

An "isocyanato" group refers to a "$-NCO$" group.

A "thiocyanato" group refers to a "$-CNS$" group.

An "isothiocyanato" group refers to an "$-NCS$" group.

A "mercapto" group refers to an "$-SH$" group.

A "carbonyl" group refers to a $C=O$ group.

An "S-sulfonamido" group refers to a "$-SO_2N(R_AR_B)$" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "$RSO_2N(R_A)-$" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "$-OC(=O)N(R_AR_B)$" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "$ROC(=O)N(R_A)-$" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "$-OC(=S)-N(R_AR_B)$" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "$ROC(=S)N(R_A)-$" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "$-C(=O)N(R_AR_B)$" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "$RC(=O)N(R_A)-$" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt (for example, ammonium or triethylammonium salt), an alkali metal salt, such as a lithium, a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

The terms "phosphorothioate" and "phosphothioate" refer to a moiety of the general formula

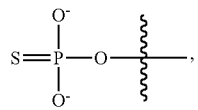

its protonated forms (for example,

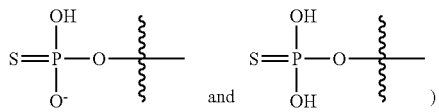 [SMILES: *OP([O-])(O)=S ; *OP(O)(O)=S]

and its tautomers (such as

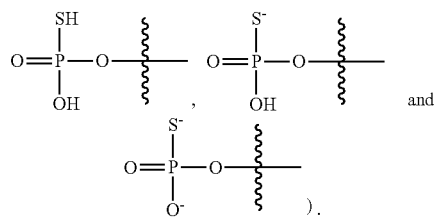

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound selected from Formula (I), Formula (II) and Formula (III), or a pharmaceutically acceptable salt of any of the foregoing:

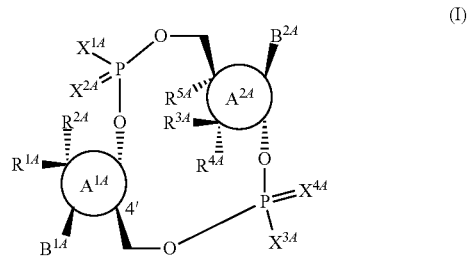

(I)

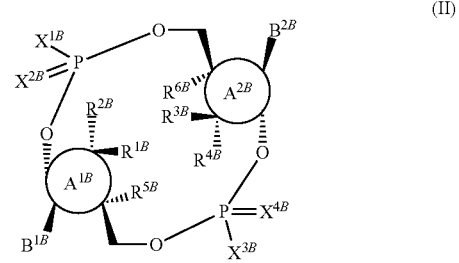

(II)

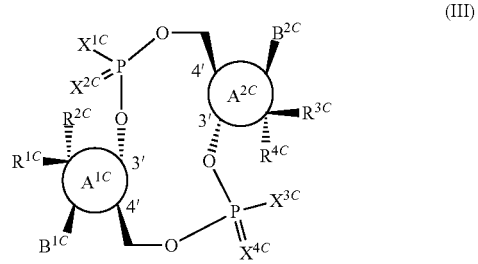

(III)

wherein: Ring $A^{1A}$, Ring $A^{1B}$ and Ring $A^{1C}$ can be independently selected from

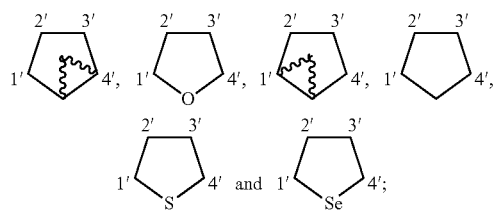

Ring $A^{2A}$, Ring $A^{2B}$ and Ring $A^{2C}$ can be independently selected from

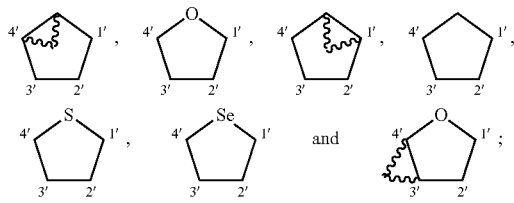

$B^{1A}$ can be an optionally substituted [5,6] bicyclic heteroaryl and an optionally substituted [5,6] bicyclic heterocyclyl, and wherein $B^{1A}$ can be attached to the 1'-position of Ring $A^{1A}$; $B^{2A}$ can be an optionally substituted [5,6] bicyclic heteroaryl and an optionally substituted [5,6] bicyclic heterocyclyl 1, and wherein $B^{2A}$ can be attached to the 1'-position of Ring $A^{2A}$; $B^{1B}$ can be an optionally substituted [5,6] bicyclic heteroaryl and an optionally substituted [5,6] bicyclic heterocyclyl, and wherein $B^{1B}$ can be attached to the 1'-position of Ring $A^{1B}$; $B^{2B}$ can be an optionally substituted [5,6] bicyclic heteroaryl and an optionally substituted [5,6] bicyclic heterocyclyl, and wherein $B^{2B}$ can be attached to the 1'-position of Ring $A^{2B}$; $B^{1C}$ can be an optionally substituted [5,6] bicyclic heteroaryl and an optionally substituted [5,6] bicyclic heterocyclyl, and wherein $B^{1C}$ can be attached to the 1'-position of Ring $A^{1C}$; $B^{2C}$ can be an optionally substituted [5,6] bicyclic heteroaryl and an optionally substituted [5,6] bicyclic heterocyclyl, and wherein $B^{2C}$ can be attached to the 1'-position of Ring $A^{2C}$; $X^{1A}$, $X^{3A}$, $X^{1B}$, $X^{3B}$, $X^{1C}$ and $X^{3C}$ can be independently OH, O—, SH, S—, O(unsubstituted $C_{1-4}$ alkyl), S(unsubstituted $C_{1-4}$ alkyl), O—CH$_2$—O—C(=O)-(unsubstituted $C_{1-4}$ alkyl), S—CH$_2$—O—C(=O)-(unsubstituted $C_{1-4}$ alkyl), O—CH$_2$—O—C(=O)—O-(unsubstituted $C_{1-4}$ alkyl), S—CH$_2$—O—C(=O)—O-(unsubstituted $C_{1-4}$ alkyl),

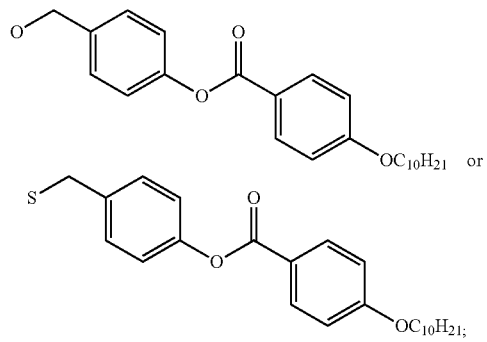

$X^{2A}$, $X^{4A}$, $X^{2B}$, $X^{4B}$, $X^{2C}$ and $X^{4C}$ can be independently O (oxygen) or S (sulfur); $R^{1A}$ can be hydrogen or halogen, and wherein R can be attached to the 2'-position of Ring $A^{1A}$; $R^{2A}$ can be selected from hydrogen, halogen, hydroxy, an unsubstituted $C_{1-4}$ alkoxy and

and wherein $R^{2A}$ can be attached to the 2'-position of Ring $A^{1A}$, and when $R^{2A}$ is

then the * indicates an attachment point to the 4'-position of Ring $A^{1A}$; $R^{3A}$ can be hydrogen or halogen, and wherein $R^{3A}$ can be attached to the 3'-position of Ring $A^{2A}$; $R^{4A}$ can be selected from hydrogen, halogen, hydroxy and an unsubstituted $C_{1-4}$ alkoxy, and wherein $R^{4A}$ can be attached to the 3'-position of Ring $A^{2A}$; $R^{5A}$ can be hydrogen, and wherein $R^{5A}$ is attached to the 4'-position of Ring $A^{2A}$; or $R^{4A}$ and $R^{5A}$ can be taken together to form

wherein each * indicates a point of attachment to ring $A^{2A}$, and wherein $R^{4A}$ is attached to the 3'-position and $R^{5A}$ is attached to the 4'-position; $R^{1B}$ can be independently hydrogen or halogen, wherein $R^{1B}$ can be attached to the 3'-position of Ring $A^{1B}$; $R^{2B}$ can be selected from hydrogen, halogen, hydroxy and an unsubstituted $C_{1-4}$ alkoxy, and wherein $R^{2B}$ can be attached to the 3'-position of Ring $A^{1B}$; $R^{3B}$ can be hydrogen or halogen, and wherein $R^{3B}$ can be attached to the 3'-position of Ring $A^{2B}$; $R^{4B}$ can be selected from hydrogen, halogen, hydroxy and an unsubstituted $C_{1-4}$ alkoxy, and wherein $R^{4B}$ can be attached to the 3'-position of Ring $A^{2B}$; $R^{5B}$ can be hydrogen, and wherein $R^{5B}$ is attached to the 4'-position of Ring $A^{1B}$; $R^{6B}$ can be hydrogen, and wherein $R^{6B}$ is attached to the 4'-position of Ring $A^{1B}$; or $R^{2B}$ and $R^{5B}$ can be taken together to form

wherein each * indicates a point of attachment to ring $A^{1B}$, and wherein $R^{2B}$ is attached to the 3'-position and $R^{5B}$ is attached to the 4'-position; $R^{4B}$ and $R^{6B}$ can be taken together to form

wherein each * indicates a point of attachment to ring $A^{2B}$; $R^{1C}$ can be hydrogen or halogen, wherein $R^{1C}$ can be attached to the 2'-position of Ring $A^{1C}$, and wherein $R^{4B}$ is attached to the 3'-position and $R^{6B}$ is attached to the 4'-position; $R^{2C}$ can be selected from hydrogen, halogen, hydroxy, an unsubstituted $C_{1-4}$ alkoxy and

and wherein $R^{2C}$ can be attached to the 2'-position of Ring $A^{1C}$, and when $R^{2C}$ is

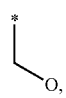

then the * indicates an attachment point to the 4'-position of Ring $A^{1C}$; $R^{3C}$ can be hydrogen or halogen, wherein $R^{3C}$ can be attached to the 2'-position of Ring $A^{2C}$; and $R^{4C}$ can be selected from hydrogen, halogen, hydroxy, an unsubstituted $C_{1-4}$ alkoxy and

and wherein $R^{4C}$ can be attached to the 2'-position of Ring $A^{2C}$, and when $R^{4C}$ is

then the * indicates an attachment point to the 4'-position of Ring $A^{2C}$.

Some embodiments disclosed herein relate to a compound of Formula (I), or a pharmaceutically acceptable salt thereof. As described herein, Ring $A^{1A}$ and Ring $A^{2A}$ can be various 5-membered rings. For example, in some embodiments, Ring $A^{1A}$ can be

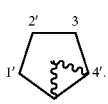

In other embodiments, Ring $A^{1A}$ can be

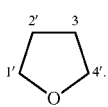

In still other embodiments, Ring $A^{1A}$ can be

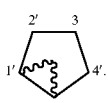

In yet still other embodiments, Ring $A^{1A}$ can be

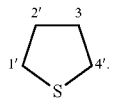

In some embodiments, Ring $A^{A1}$ can be

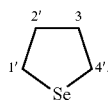

In other embodiments, Ring $A^{1A}$ can be

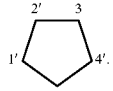

In some embodiments, including those of the previous paragraph, Ring $A^{2A}$ can be

In other embodiments, including those of the previous paragraph, Ring $A^{2A}$ can be

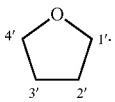

Instill other embodiments, including those of the previous paragraph, Ring $A^{2A}$ can be

In yet still other embodiments, including those of the previous paragraph, Ring $A^{2A}$ can be

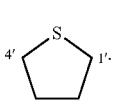

In some embodiments, including those of the previous paragraph, Ring $A^{2A}$ can be

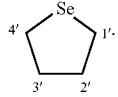

In other embodiments, including those of the previous paragraph, Ring $A^{2A}$ can be

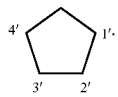

In still other embodiments, including those of the previous paragraph, Ring $A^{2A}$ can be

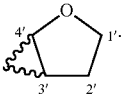

Those skilled in the art understand that Formula (I), or a pharmaceutically acceptable salt thereof, can be 2',3'-cyclic di-nucleotides (2',3'-CDNs). Exemplary structures of a compound of Formula (I), or a pharmaceutically acceptable salt thereof, include the following:

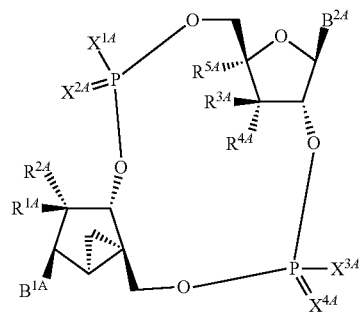

(Ia)

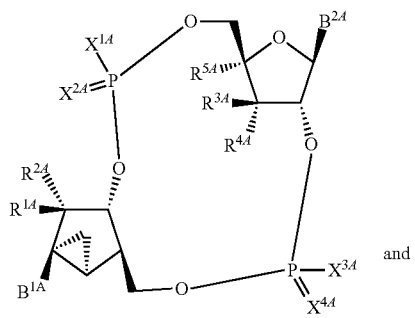

(Ib)

and

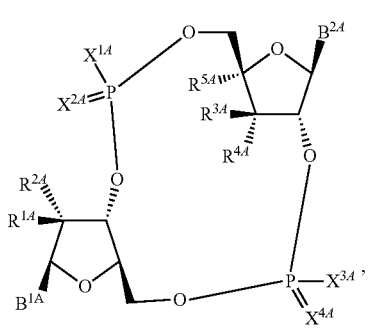

(Ic)

including pharmaceutically acceptable salts of any of the foregoing. In some embodiments of this paragraph, at least of one $B^{1A}$ and $B^{2A}$ is not

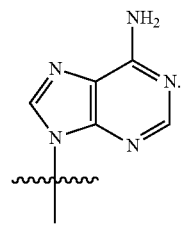

In some embodiments of this paragraph, at least of one $B^{1A}$ and $B^{2A}$ is not

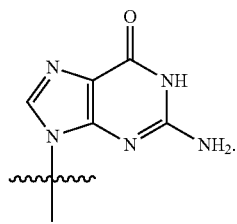 [SMILES: *n1cnc2c(=O)[nH]c(N)nc21]

In some embodiments of this paragraph, one $B^{1A}$ and $B^{2A}$ can be selected from

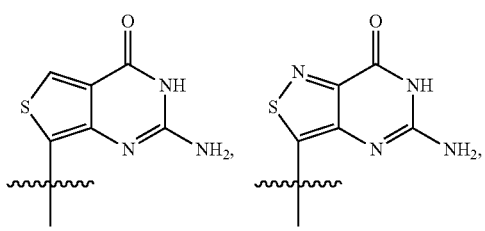

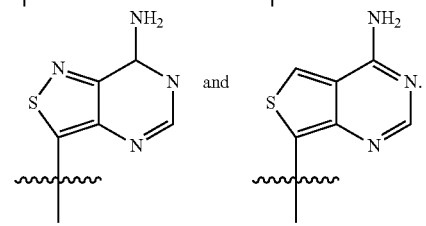

and

In some embodiments of this paragraph, $R^{1A}$, $R^{3A}$ and $R^{5A}$ can be each hydrogen; and $R^{4A}$ can be methoxy. In some embodiments of this paragraph, $R^{2A}$ can be hydrogen, halogen or hydroxy. In some embodiments of this paragraph, $X^{1A}$ and $X^{3A}$ can be each OH; and $X^{2A}$ and $X^{4A}$ can be each O. In some embodiments of this paragraph, $X^{1A}$ and $X^{3A}$ can be each OH; and at least one of $X^{2A}$ and $X^{4A}$ can be S.

In some embodiments, Ring $A^{1A}$ can be

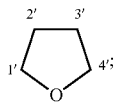

and Ring $A^{2A}$ can be

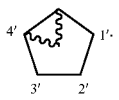

In other embodiments, Ring $A^{1A}$ can be

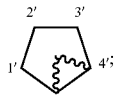

and Ring $A^{2A}$ can be

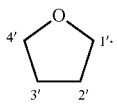

In still other embodiments, Ring $A^{1A}$ can be

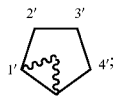

and Ring $A^{2A}$ can be

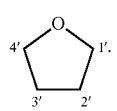

In yet still other embodiments, Ring $A^{1A}$ can be

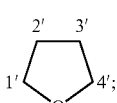

Ring $A^{2A}$ can be

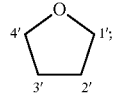

and at least one of $B^{1A}$ and $B^{2A}$ is not selected from adenine and guanine. In some embodiments, Ring $A^{1A}$ can be

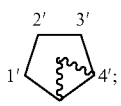

and Ring $A^{2A}$ can be

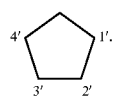

In other embodiments, Ring $A^{1A}$ can be

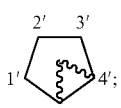

and Ring $A^{2A}$ can be

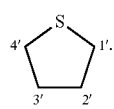

In still other embodiments, Ring $A^{1A}$ can be

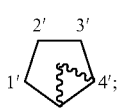

and Ring $A^{2A}$ can be

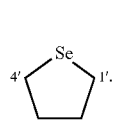

In yet still other embodiments, Ring $A^{1A}$ can be

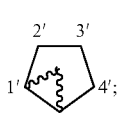

and Ring $A^{2A}$ can be

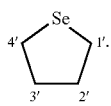

In some embodiments, Ring $A^{1A}$ can be

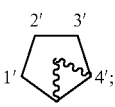

and Ring $A^{2A}$ can be

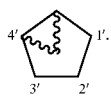

In other embodiments, Ring $A^{1A}$ can be

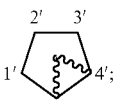

and Ring $A^{2A}$ can be

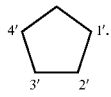

A variety of bicyclic heteroaryls and bicyclic heterocyclyls can be attached to Ring $A^{1A}$ and Ring $A^{2A}$. A bicyclic heteroaryl or a bicyclic heterocyclyl can be attached to the 1'-position of Ring $A^{1A}$ and another bicyclic heteroaryl or bicyclic heterocyclyl can be attached to the 1'-position of Ring $A^{2A}$. The bicyclic heteroaryl can be an optionally substituted 9-membered heteroaryl (for example, an optionally substituted [5,6] bicyclic heteroaryl), and the bicyclic heterocyclyl can be an optionally substituted 9-membered heterocyclyl (such as an optionally substituted [5,6] bicyclic heterocyclyl). The bicyclic heteroaryl can be an optionally substituted, nitrogen-containing bicyclic heteroaryl, and the bicyclic heterocyclyl can be an optionally substituted, nitrogen-containing bicyclic heterocyclyl. When $B^{1A}$ is attached to the 1'-position of Ring $A^{1A}$, $B^{1A}$ can be attached via a carbon or nitrogen atom. In some embodiments, $B^{1A}$ can be an optionally substituted C-linked bicyclic heteroaryl, an optionally substituted C-linked bicyclic heterocyclyl, an optionally substituted N-linked bicyclic heteroaryl or an optionally substituted N-linked bicyclic heterocyclyl. Similarly, $B^{2A}$ can be attached to the 1'-position of Ring $A^{2A}$ vi a carbon or nitrogen atom. In some embodiments, $B^{2A}$ can be an optionally substituted C-linked bicyclic heteroaryl, an optionally substituted C-linked bicyclic heterocyclyl, an optionally substituted N-linked bicyclic heteroaryl or an optionally substituted N-linked bicyclic heterocyclyl.

In some embodiments, $B^{1A}$ and/or $B^{2A}$ can have the general structure

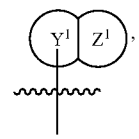

wherein $Y^1$ can be a 5-membered ring; and $Z^1$ can be a 6-membered, nitrogen-containing ring. In some embodiments, Ring $Y^1$ can be selected from an unsubstituted or substituted imidazole, an unsubstituted or substituted furan, an unsubstituted or substituted thiophene, an unsubstituted or substituted isothiazole, an unsubstituted or substituted isoxazole, an unsubstituted or substituted pyrrole, an unsubstituted or substituted pyrazole and an unsubstituted or substituted 1,2,3-triazole. In some embodiments, Ring $Z^1$ can be selected from

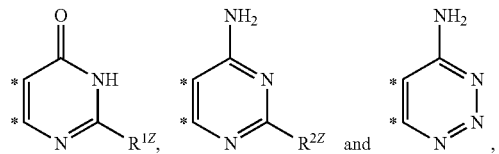

wherein $R^{1Z}$ and $R^{2Z}$ can be independently hydrogen or amino; and each "*" indicates an attachment points to Ring $Y^1$.

In some embodiments, $B^{1A}$ can be an optionally substituted purine base. In some embodiments, $B^{2A}$ can be an optionally substituted purine base. Examples of purine bases include adenine, guanine, hypoxanthine, xanthine, theobromine, caffeine, uric acid and isoguanine. In some embodiments, $B^{1A}$ can be selected from

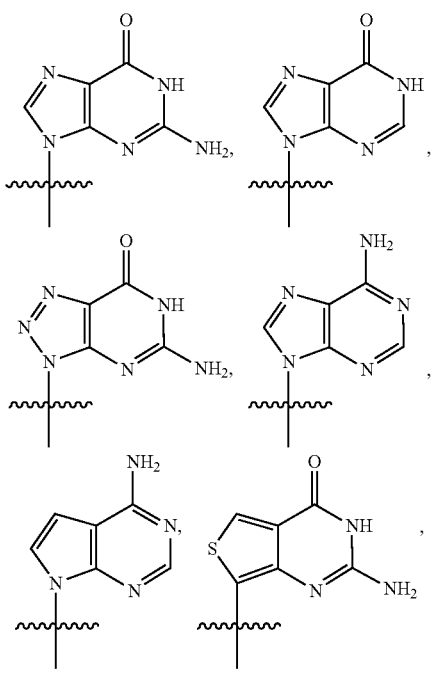

-continued

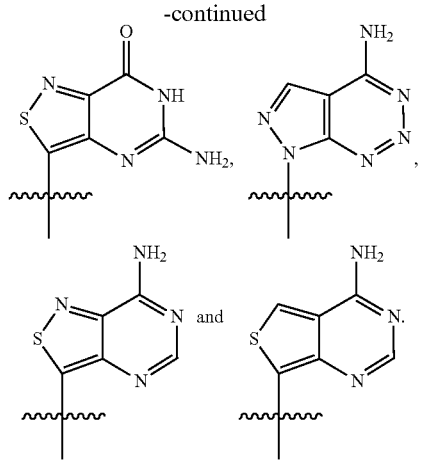

In some embodiments, $B^{2A}$ can be selected from

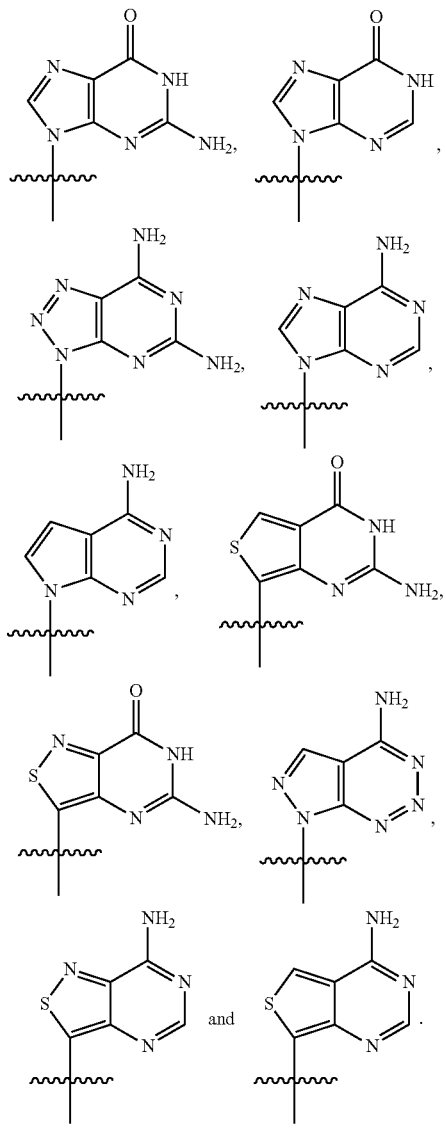

In some embodiments, at least one of $B^{1A}$ and $B^{2A}$ can be

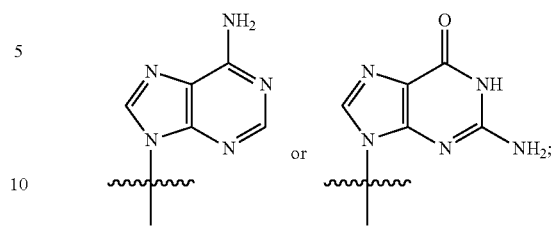

and the other of $B^{1A}$ and $B^{2A}$ can be

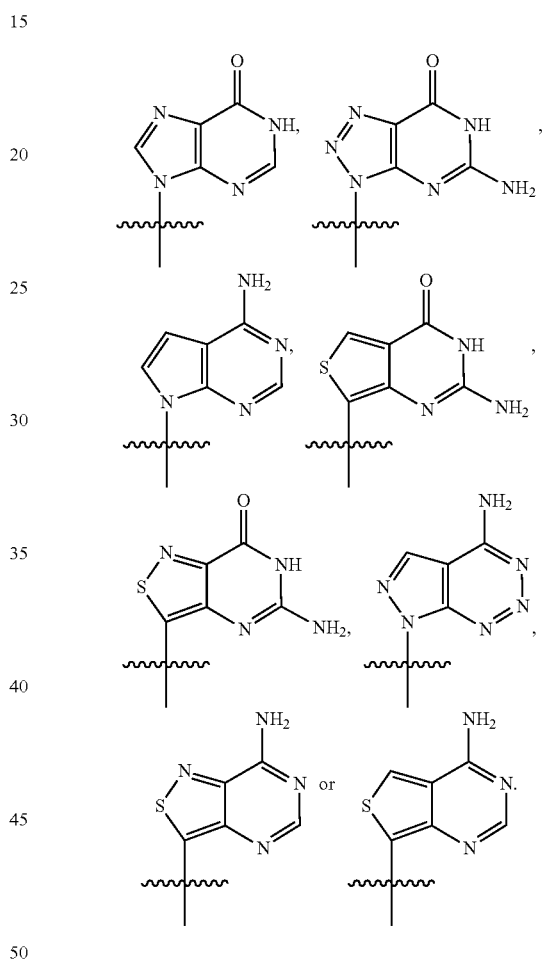

The 2'-position of Ring $A^{1A}$ can include various substituents. In some embodiments, $R^{1A}$ can be hydrogen. In other embodiments, $R^{1A}$ can be halogen, for example, fluoro or chloro. In some embodiments, $R^{2A}$ can be hydrogen. In other embodiments, $R^{2A}$ can be halogen, such as fluoro or chloro. In still other embodiments, $R^{2A}$ can be hydroxy. In yet still other embodiments, $R^{2A}$ can be an unsubstituted $C_{1-4}$ alkoxy. Examples of unsubstituted $C_{1-4}$ alkoxys include methoxy, ethoxy, n-propoxy, isopropoxy, n-butoxy, isobutoxy, secbutoxy and tert-butoxy. In some embodiments, $R^{2A}$ can be

wherein $R^{2A}$ is attached to the 2'-position of Ring $A^{1A}$ and the * indicates an attachment point to the 4'-position of Ring $A^{1A}$. When $R^{2A}$ is

Ring $A^{1A}$ can have the structure

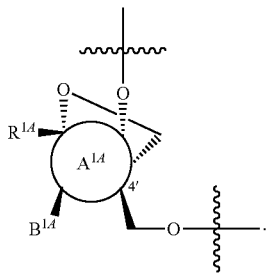

In some embodiments, $R^{1A}$ can be hydrogen; and $R^{2A}$ can be hydroxy. In other embodiments, $R^{1A}$ can be hydrogen; and $R^{2A}$ can be hydrogen. In still other embodiments, $R^{1A}$ can be hydrogen; and $R^{2A}$ can be halogen (for example, F). In yet still other embodiments, $R^{1A}$ can be hydrogen; and $R^{2A}$ can be an unsubstituted $C_{1-4}$ alkoxy. In some embodiments, $R^{1A}$ can be halogen; and $R^{2A}$ can be halogen. In other embodiments, $R^{1A}$ can be halogen (for example, F); and $R^{2A}$ can be hydrogen.

Various substituents can be also present at the 3'-position of Ring $A^{2A}$. In some embodiments, $R^{3A}$ can be hydrogen. In other embodiments, $R^{3A}$ can be halogen, such as fluoro or chloro. In some embodiments, $R^{4A}$ can be hydrogen. In other embodiments, $R^{4A}$ can be halogen. For example, the halogen can be fluoro or chloro. In still other embodiments, $R^{4A}$ can be hydroxy. In yet still other embodiments, $R^{4A}$ can be an unsubstituted $C_{1-4}$ alkoxy, such as methoxy, ethoxy, n-propoxy, isopropoxy, n-butoxy, isobutoxy, secbutoxy and tert-butoxy. In some embodiments, $R^{3A}$ can be hydrogen; and $R^{4A}$ can be hydroxy. In other embodiments, $R^{3A}$ can be hydrogen; and $R^{4A}$ can be an unsubstituted $C_{1-4}$ alkoxy. In still other embodiments, $R^{3A}$ can be halogen (such as F); and $R^{4A}$ can be hydrogen.

The 4'-position of Ring $A^{2A}$ can be hydrogen. In some embodiments, $R^{5A}$ can be hydrogen. The 4'-position of Ring $A^{2A}$ can be connected to the 3'-position of Ring $A^{2A}$ via a $CH_2$ moiety. In some embodiments, $R^{4A}$ and $R^{5A}$ can be taken together to form

wherein each * indicates a point of attachment to ring $A^{2A}$. When $R^{4A}$ and $R^{5A}$ can be taken together to form

of Ring $A^{2A}$ can have the structure

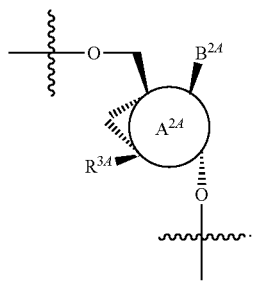

Some embodiments disclosed herein relate to a compound of Formula (II), or a pharmaceutically acceptable salt thereof. Several 5-membered rings are suitable for Ring $A^{1B}$ and Ring $A^{2B}$. In some embodiments, Ring $A^{1B}$ can be

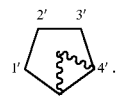

In other embodiments, Ring $A^{1B}$ can be

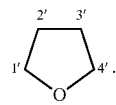

In still other embodiments, Ring $A^{1B}$ can be

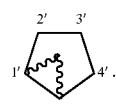

In yet still other embodiments, Ring $A^{1B}$ can be

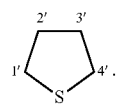

In some embodiments, Ring $A^{1B}$ can be

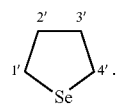

In other embodiments, Ring $A^{1B}$ can be

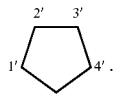

In some embodiments, including those of the previous paragraph, Ring $A^{2B}$ can be

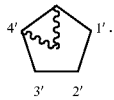

In other embodiments, including those of the previous paragraph, Ring $A^{2B}$ can be

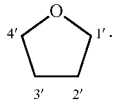

In still other embodiments, including those of the previous paragraph, Ring $A^{2B}$ can be

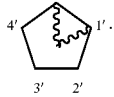

In yet still other embodiments, including those of the previous paragraph, Ring $A^{2B}$ can be

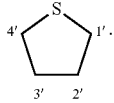

In some embodiments, including those of the previous paragraph, Ring $A^{2B}$ can be

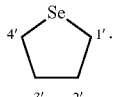

In other embodiments, including those of the previous paragraph, Ring $A^{2B}$ can be

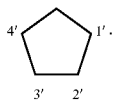

In still other embodiments, including those of the previous paragraph, Ring $A^{2B}$ can be

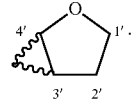

Those skilled in the art understand that Formula (II), or a pharmaceutically acceptable salt thereof, can be 2',2'-cyclic di-nucleotides (2',2'-CDNs). One example of a compound of Formula (II), or a pharmaceutically acceptable salt thereof, is

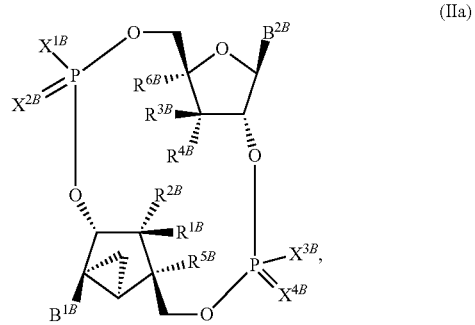

(IIa)

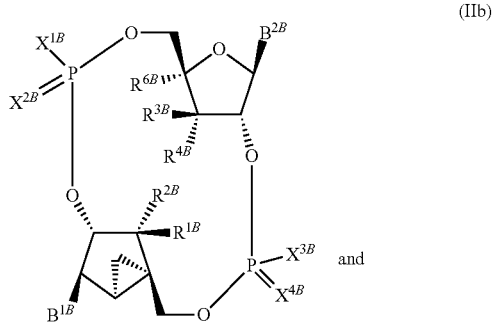

(IIb)

and

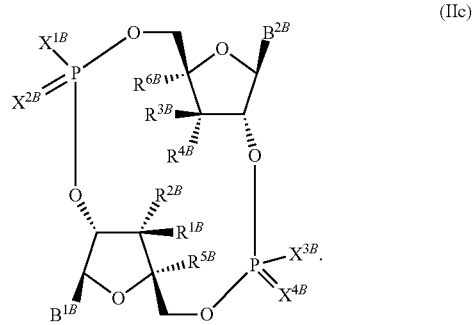

(IIc)

In some embodiments of this paragraph, at least of one $B^{1B}$ and $B^{2B}$ is not

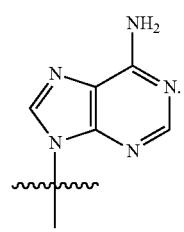

In some embodiments of this paragraph, at least of one $B^{1B}$ and $B^{2B}$ is not

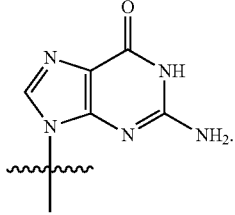 [SMILES: *n1cnc2c(=O)[nH]c(N)nc21]

In some embodiments of this paragraph, one $B^{1B}$ and $B^{2B}$ can be selected from

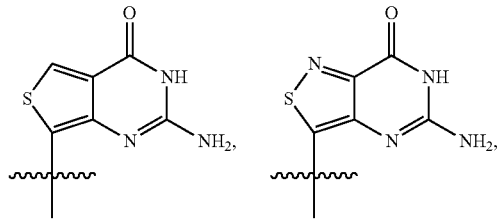

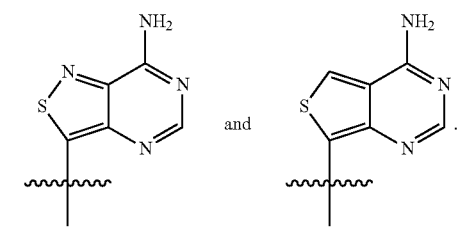

In some embodiments of this paragraph, $R^{1B}$, $R^{3B}$, $R^{6B}$ and $R^{6B}$ can be each hydrogen; and $R^{4B}$ can be hydrogen, halogen, hydroxy or methoxy. In some embodiments of this paragraph, $X^{1B}$ and $X^{3B}$ can be each OH; and $X^{2B}$ and $X^{4B}$ can be each O. In some embodiments of this paragraph, $X^{1B}$ and $X^{3B}$ can be each OH; and at least one of $X^{2B}$ and $X^{4B}$ can be S.

In some embodiments, Ring $A^{1B}$ can be

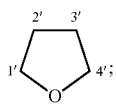

and Ring $A^{2B}$ can be

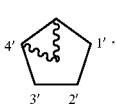

In other embodiments, Ring $A^{1B}$ can be

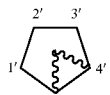

and Ring $A^{2B}$ can be

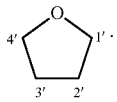

In still other embodiments, Ring $A^{1B}$ can be

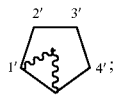

and Ring $A^{2B}$ can be

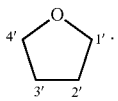

In yet still other embodiments, Ring $A^{1B}$ can be

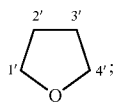

Ring $A^{2B}$ can be

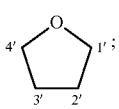

and at least one of $B^{1B}$ and $B^{2B}$ is not selected from adenine and guanine. In some embodiments, Ring $A^{1B}$ can be

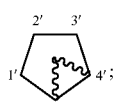

and Ring $A^{2B}$ can be

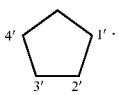

In other embodiments, Ring $A^{1B}$ can be

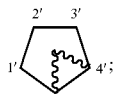

and Ring $A^{2B}$ can be

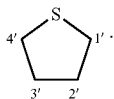

In still other embodiments, Ring $A^{1B}$ can be

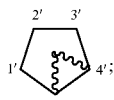

and Ring $A^{2B}$ can be

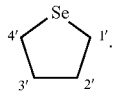

In yet still other embodiments, Ring $A^{1B}$ can be

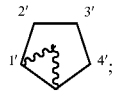

and Ring $A^{2B}$ can be

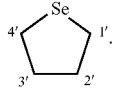

In some embodiments, Ring $A^{1B}$ can be

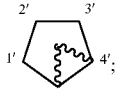

and Ring $A^{2B}$ can be

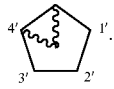

In other embodiments, Ring $A^{1B}$ can be

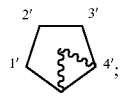

and Ring $A^{2B}$ can be

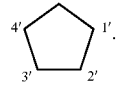

Ring $A^{1B}$ and Ring $A^{2B}$ can have various bicyclic heteroaryls and bicyclic heterocyclyls attached to their respective 1'-position. The bicyclic heteroaryl and the bicyclic heterocyclyl can include 9-atoms in their rings. In some embodiments, Ring $A^{1B}$ and/or Ring $A^{2B}$ can be an optionally substituted 9-membered bicyclic heteroaryl. In other embodiments, Ring $A^{1B}$ and/or Ring $A^{2B}$ can be an optionally substituted 9-membered bicyclic heterocyclyl. The optionally substituted 9-membered bicyclic heteroaryl can be an optionally substituted [5,6] bicyclic heteroaryl, and the optionally substituted 9-membered bicyclic heterocyclyl can be an optionally substituted [5,6] bicyclic heterocyclyl. In some embodiments, Ring $A^{1B}$ and/or Ring $A^{2B}$ can be an optionally substituted, nitrogen-containing bicyclic heteroaryl. In other embodiments, Ring $A^{1B}$ and/or Ring $A^{2B}$ can be an optionally substituted, nitrogen-containing bicyclic heterocyclyl. When $B^{1B}$ is attached to the 1'-position of Ring $A^{1B}$, $B^{1B}$ can be attached via a carbon or nitrogen atom. In some embodiments, $B^{1B}$ can be an optionally substituted C-linked bicyclic heteroaryl or an optionally substituted C-linked bicyclic heterocyclyl. In other embodiments, $B^{1B}$ can be an optionally substituted N-linked bicyclic heteroaryl or an optionally substituted N-linked bicyclic heterocyclyl. When $B^{2B}$ is attached to the 1'-position of Ring $A^{2B}$, $B^{2B}$ can be attached via a carbon or nitrogen atom. In some embodiments, $B^{2B}$ can be an optionally substituted C-linked bicyclic heteroaryl or an optionally substituted C-linked bicyclic heterocyclyl. In other embodiments, $B^{2B}$ can be an optionally substituted N-linked bicyclic heteroaryl or an optionally substituted N-linked bicyclic heterocyclyl.

In some embodiments, $B^{1B}$ and/or $B^{2B}$ can have the general structure

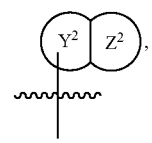

wherein $Y^2$ can be a 5-membered ring; and $Z^2$ can be a 6-membered, nitrogen-containing ring. In some embodiments, Ring $Y^2$ can be selected from an unsubstituted or substituted imidazole, an unsubstituted or substituted furan, an unsubstituted or substituted thiophene, an unsubstituted or substituted isothiazole, an unsubstituted or substituted isoxazole, an unsubstituted or substituted pyrrole, an unsubstituted or substituted pyrazole and an unsubstituted or substituted 1,2,3-triazole. In some embodiments, Ring $Z^2$ can be selected from

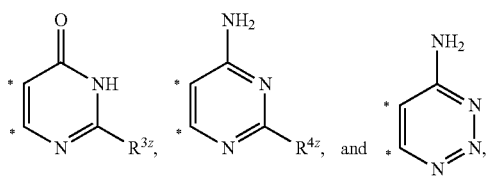

wherein $R^{3z}$ and $R^{4z}$ can be independently hydrogen or amino; and each "*" indicates an attachment points to Ring $Y^2$.

In some embodiments, $B^{1B}$ can be an optionally substituted purine base. In some embodiments, $B^{2B}$ can be an optionally substituted purine base. Exemplary purine bases can include adenine, guanine, hypoxanthine, xanthine, theobromine, caffeine, uric acid and isoguanine. In some embodiments, $B^{1B}$ can be selected from

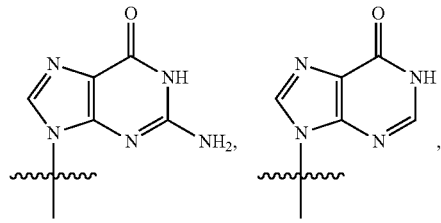

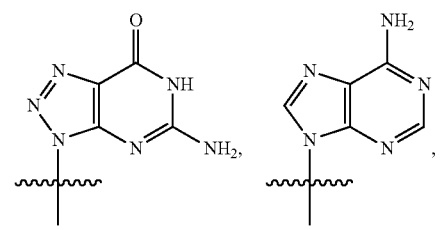

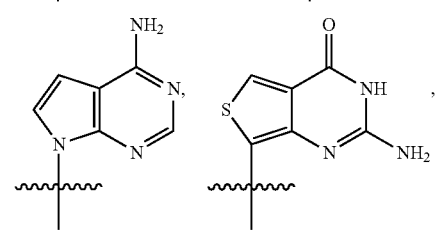

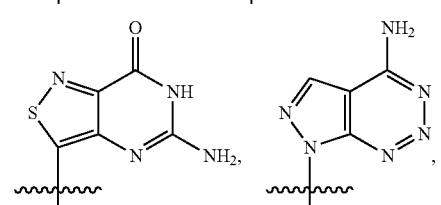

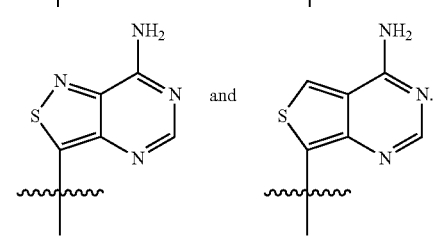

In some embodiments, $B^{2B}$ can be selected from

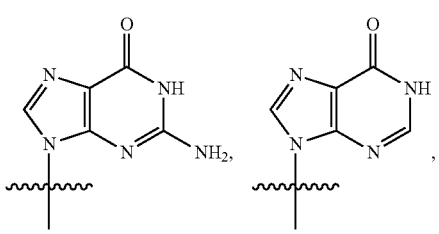

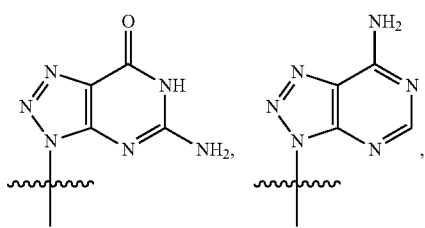

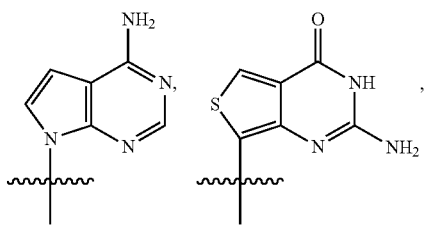

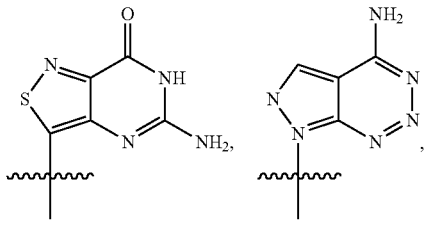

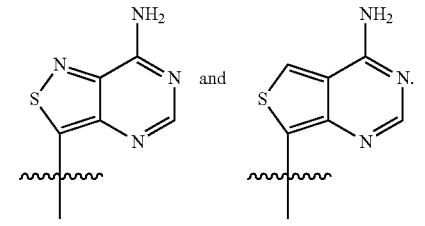

In some embodiments, at least one of $B^{1B}$ and $B^{2B}$ can be

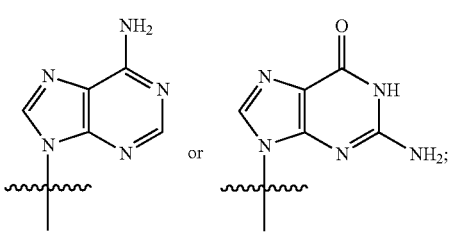 [SMILES: *n1cnc2c(N)ncnc21 ; "or" ; *n1cnc2c(=O)[nH]c(N)nc21]

and the other of $B^{1B}$ and $B^{2B}$ can be

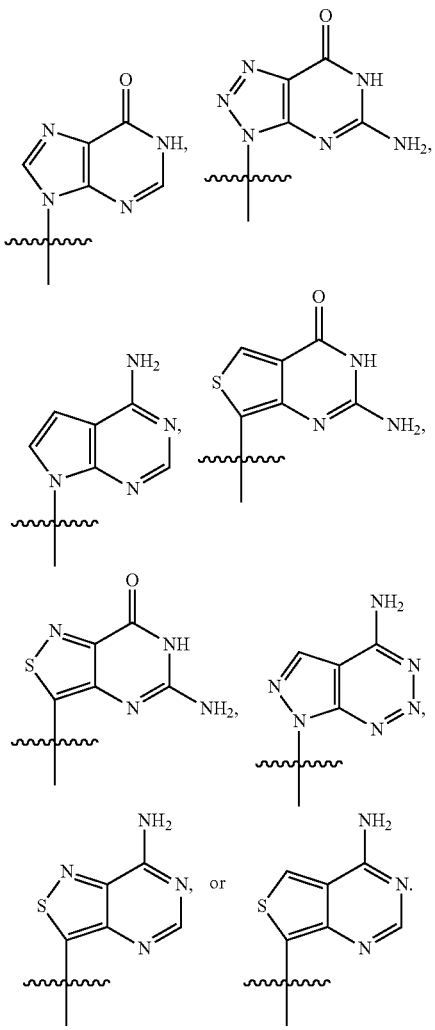

The 3'-position of Ring $A^{1B}$ can have various substituents attached. In some embodiments, $R^{1B}$ can be hydrogen. In some embodiments, $R^{1B}$ can be halogen. For example, $R^{1B}$ can be fluoro. As another example, $R^{1B}$ can be chloro. In some embodiments, $R^{2B}$ can be hydrogen. In other embodiments, $R^{2B}$ can be halogen, such as fluoro or chloro. In still other embodiments, $R^{2B}$ can be hydroxy. In yet still other embodiments, $R^{2B}$ can be an unsubstituted $C_{1-4}$ alkoxy. Exemplary unsubstituted $C_{1-4}$ alkoxys include methoxy, ethoxy, n-propoxy, isopropoxy, n-butoxy, isobutoxy, secbutoxy and tert-butoxy. In some embodiments, $R^{1B}$ can be hydrogen; and $R^{2B}$ can be hydroxy. In other embodiments, $R^{1B}$ can be hydrogen; and $R^{2B}$ can be an unsubstituted $C_{1-4}$ alkoxy, such as those described herein. In still other embodiments, $R^{1B}$ can be halogen (such as F); and $R^{2B}$ can be hydrogen.

The 3'-position of Ring $A^{2B}$ can also have various substituents attached. In some embodiments, $R^{3B}$ can be hydrogen. In other embodiments, $R^{3B}$ can be halogen, for example, chloro or fluoro. In some embodiments, $R^{4B}$ can be hydrogen. In other embodiments, $R^{4B}$ can be halogen, such as fluoro or chloro. In still other embodiments, $R^{4B}$ can be hydroxy. In yet still other embodiments, $R^{4B}$ can be an unsubstituted $C_{1-4}$ alkoxy. Suitable an unsubstituted $C_{1-4}$ alkoxys are described herein and include those provided in the previous paragraph. In some embodiments, $R^{3B}$ can be hydrogen; and $R^{4B}$ can be hydroxy. In other embodiments, $R^{3B}$ can be hydrogen; and $R^{4B}$ can be hydrogen. In still other embodiments, $R^{3B}$ can be hydrogen; and $R^{4B}$ can be halogen (for example, F). In yet still other embodiments, $R^{3B}$ can be hydrogen; and $R^{4B}$ can be an unsubstituted $C_{1-4}$ alkoxy. In some embodiments, $R^{3B}$ can be halogen; and $R^{4B}$ can be halogen. In other embodiments, $R^{3B}$ can be halogen (such as F); and $R^{4B}$ can be hydrogen.

The 4'-position of each of Ring $A^{1B}$ and Ring $A^{2B}$ can be hydrogen. In some embodiments, $R^{5B}$ can be hydrogen. In some embodiments, $R^{6B}$ can be hydrogen. The 3'- and 4'-positions of Ring $A^{1B}$ can be connected via a —CH$_2$— moiety. The 3'- and 4'-positions of Ring $A^{2B}$ also can be connected via a —CH$_2$— moiety. An example structure of Ring $A^{1B}$ and Ring $A^{2B}$ when the 3'- and 4'-positions are connected with a —CH$_2$— moiety are

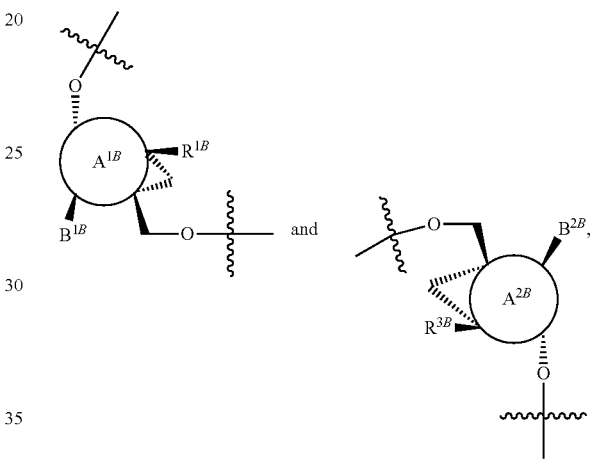

respectively. In some embodiments, $R^{2B}$ and $R^{5B}$ can be taken together to form

wherein each * indicates a point of attachment to ring $A^{1B}$. In some embodiments, $R^{4B}$ and $R^{6B}$ can be taken together to form

wherein each * indicates a point of attachment to ring $A^{2B}$.

Some embodiments disclosed herein relate to a compound of Formula (III), or a pharmaceutically acceptable salt thereof. As shown herein, Ring $A^{1C}$ and Ring $A^{2C}$ can be various 5-membered rings. In some embodiments, Ring $A^{1C}$ can be

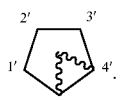

In other embodiments, Ring $A^{1C}$ can be

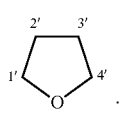

In still other embodiments, Ring $A^{1C}$ can be

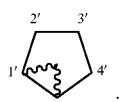

In yet still other embodiments, Ring $A^{1C}$ can be

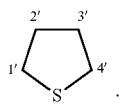

In some embodiments, Ring $A^{1C}$ can be

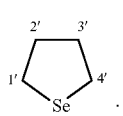

In other embodiments, Ring $A^{1C}$ can be

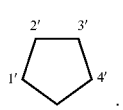

In some embodiments, including those of the previous paragraph, Ring $A^{2C}$ can be

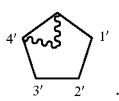

In other embodiments, including those of the previous paragraph, Ring $A^{2C}$ can be

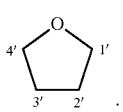

In still other embodiments, including those of the previous paragraph, Ring $A^{2C}$ can be

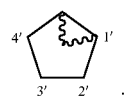

In yet still other embodiments, including those of the previous paragraph, Ring $A^{2C}$ can be

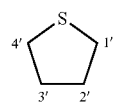

In some embodiments, including those of the previous paragraph, Ring $A^{2C}$ can be

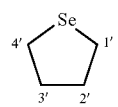

In other embodiments, including those of the previous paragraph, Ring $A^{2C}$ can be

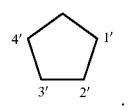

In still other embodiments, including those of the previous paragraph, Ring $A^{2C}$ can be

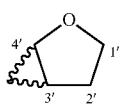

Those skilled in the art understand that Formula (III), or a pharmaceutically acceptable salt thereof, can be 3',3'-cyclic di-nucleotides (3',3'-CDNs). An example of a compound of Formula (III), or a pharmaceutically acceptable salt thereof, is

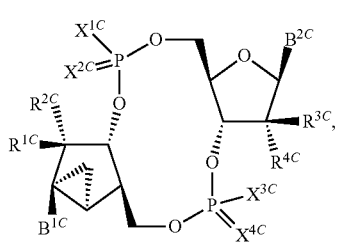

(IIIa)

(IIIb)

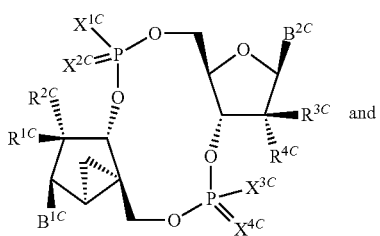

(IIIc)

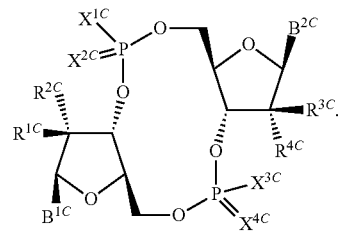

In some embodiments of this paragraph, at least of one $B^{1C}$ and $B^{2C}$ is not

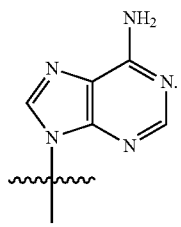 [SMILES: *n1cnc2c(N)ncnc21]

In some embodiments of this paragraph, at least of one $B^{1C}$ and $B^{2C}$ is not

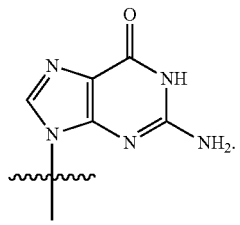 [SMILES: *n1cnc2c(=O)[nH]c(N)nc21]

In some embodiments of this paragraph, one $B^{1C}$ and $B^{2C}$ can be selected from

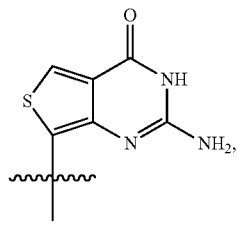 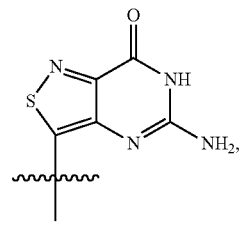

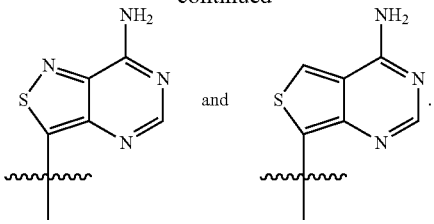 and 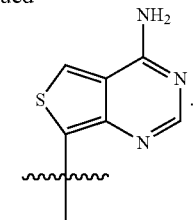.

In some embodiments of this paragraph, $R^{1C}$ and $R^{3C}$ can be each hydrogen; and $R^{4C}$ can be hydrogen, halogen, hydroxy or methoxy. In some embodiments of this paragraph, $X^{1C}$ and $X^{3C}$ can be each OH; and $X^{2C}$ and $X^{4C}$ can be each O. In some embodiments of this paragraph, $X^{1C}$ and $X^{3C}$ can be each OH; and at least one of $X^{2C}$ and $X^{4C}$ can be S.

In some embodiments, Ring $A^{1C}$ can be

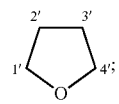

and Ring $A^{2C}$ can be

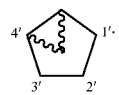

In other embodiments, Ring $A^{1C}$ can be

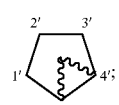

and Ring $A^{2C}$ can be

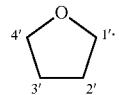

In still other embodiments, $R^{1C}$ can be

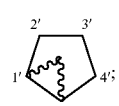

and Ring $A^{2C}$ can be

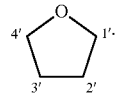

In yet still other embodiments, Ring $A^{1C}$ can be

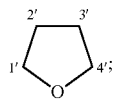

Ring $A^{2C}$ can be

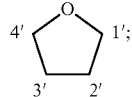

and at least one of $B^{1C}$ and $B^{2C}$ is not selected from adenine and guanine. In some embodiments, Ring $A^{1C}$ can be

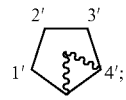

and Ring $A^{2C}$ can be

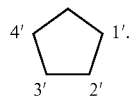

In other embodiments, Ring $A^{1C}$ can be

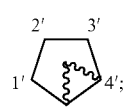

and Ring $A^{2C}$ can be

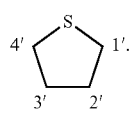

In still other embodiments, Ring $A^{1C}$ can be

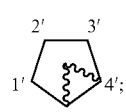

and Ring $A^{2C}$ can be

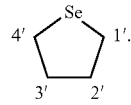

In yet still other embodiments, Ring $A^{1C}$ can be

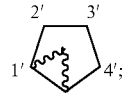

and Ring $A^{2C}$ can be

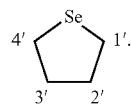

In some embodiments, Ring $A^{1C}$ can be

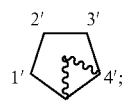

and Ring $A^{2C}$ can be

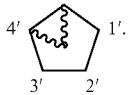

In other embodiments, Ring $A^{1C}$ can be

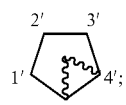

and Ring $A^{2C}$ can be

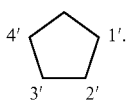

A variety of bicyclic heteroaryls and bicyclic heterocyclyls can be attached to the 1'-position of Ring $A^{1C}$ and Ring $A^{2C}$. In some embodiments, the bicyclic heteroaryl can be an optionally substituted 9-membered bicyclic heteroaryl, for example, an optionally substituted [5,6] bicyclic heteroaryl. In other embodiments, the bicyclic heterocyclyl can be an optionally substituted bicyclic heterocyclyl, such as an optionally substituted [5,6] bicyclic heterocyclyl. The bicyclic heteroaryl can be an optionally substituted, nitrogen-containing bicyclic heteroaryl, and the bicyclic heterocyclyl can be an optionally substituted nitrogen-containing bicyclic heterocyclyl. The bicyclic heteroaryl and the bicyclic heterocyclyl, such as $B^{1C}$ and $B^{2C}$ can be attached to each 5-membered ring via a carbon or nitrogen atom. In some embodiments, $B^{1C}$ can be an optionally substituted C-linked bicyclic heteroaryl or an optionally substituted C-linked bicyclic heterocyclyl. In other embodiments, $B^{1C}$ can be an optionally substituted N-linked bicyclic heteroaryl or an optionally substituted N-linked bicyclic heterocyclyl. In some embodiments, $B^{2C}$ can be an optionally substituted C-linked bicyclic heteroaryl or an optionally substituted C-linked bicyclic heterocyclyl. In other embodiments, $B^{2C}$ can be an optionally substituted N-linked bicyclic heteroaryl or an optionally substituted N-linked bicyclic heterocyclyl.

In some embodiments, $B^{1C}$ and/or $B^{2C}$ can have the general structure

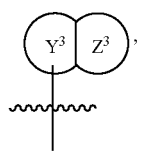

wherein $Y^3$ can be a 5-membered ring; and $Z^3$ can be a 6-membered, nitrogen-containing ring. In some embodiments, Ring $Y^3$ can be selected from an unsubstituted or substituted imidazole, an unsubstituted or substituted furan, an unsubstituted or substituted thiophene, an unsubstituted or substituted isothiazole, an unsubstituted or substituted isoxazole, an unsubstituted or substituted pyrrole, an unsubstituted or substituted pyrazole and an unsubstituted or substituted 1,2,3-triazole. In some embodiments, Ring $Z^3$ can be selected from

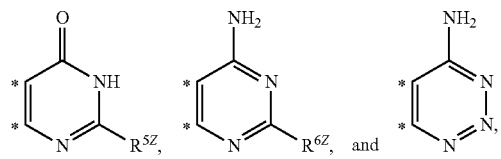

wherein $R^{5Z}$ and $R^{6Z}$ can be independently hydrogen or amino; and each "*" indicates an attachment points to Ring $Y^3$.

In some embodiments, $B^{1C}$ can be an optionally substituted purine base. In some embodiments, $B^{2C}$ can be an optionally substituted purine base. Exemplary purine bases can include adenine, guanine, hypoxanthine, xanthine, theobromine, caffeine, uric acid and isoguanine. In some embodiments, $B^{1C}$ can be selected from

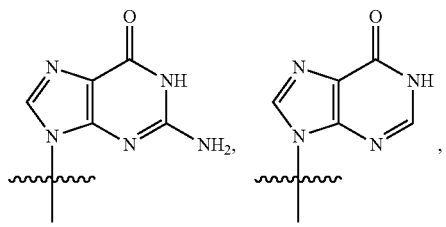

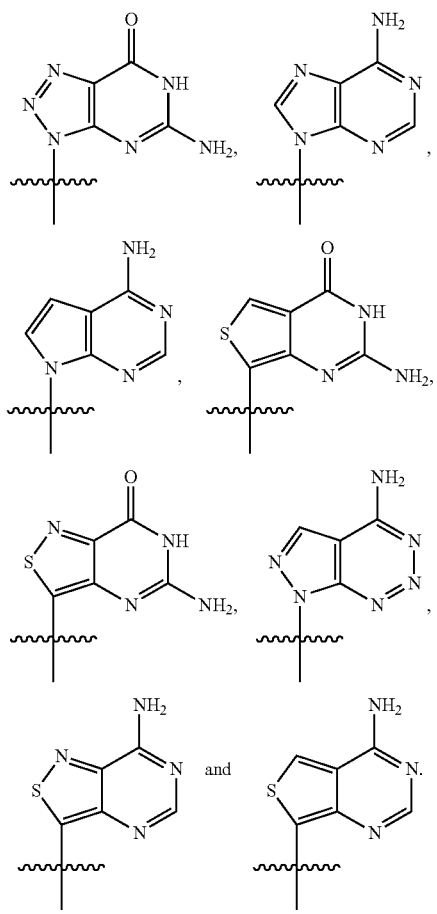

In some embodiments, $B^{2C}$ can be selected from

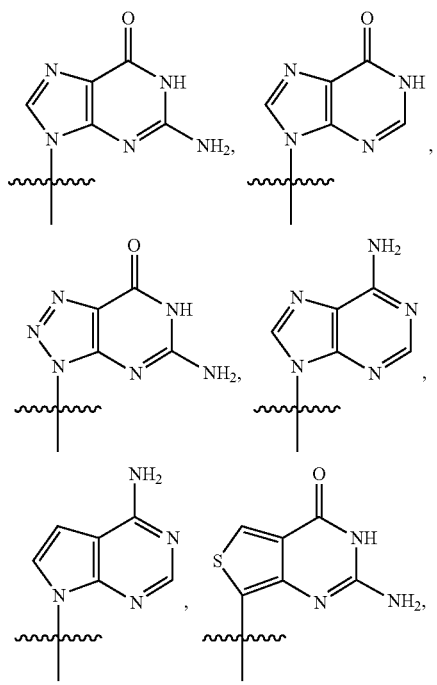

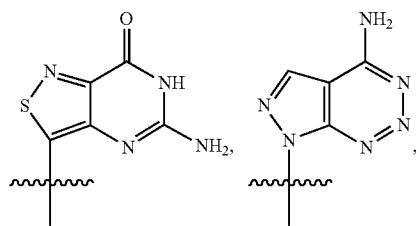

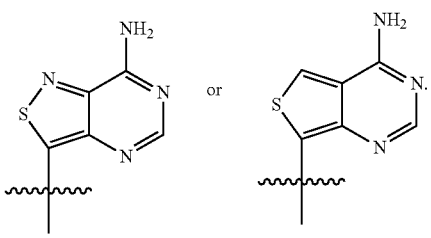

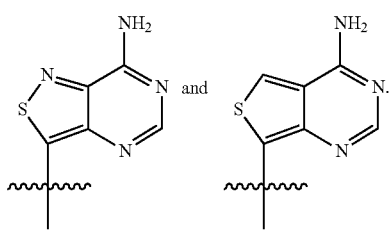

In some embodiments, at least one of $B^{1C}$ and $B^{2C}$ can be

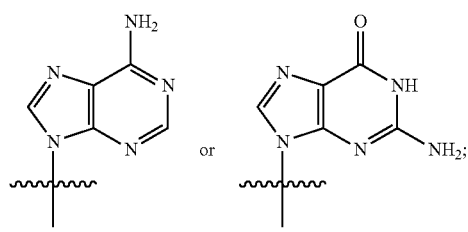 [SMILES: *n1cnc2c(N)ncnc21 ; *n1cnc2c(=O)[nH]c(N)nc21]

and the other of $B^{1C}$ and $B^{2C}$ can be

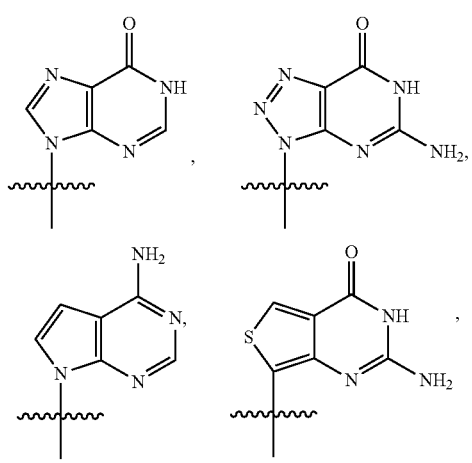

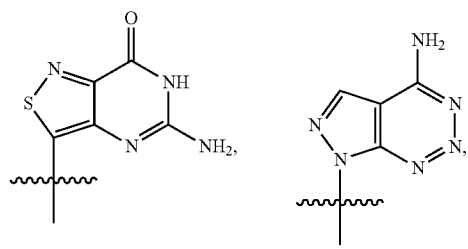

The 2'-positions of Ring $A^{1C}$ and Ring $A^{2C}$ can have a variety of groups attached. In some embodiments, $R^{1C}$ can be hydrogen. In other embodiments, $R^{1C}$ can be halogen, for example, F or Cl. In some embodiments, $R^{2C}$ can be hydrogen. In other embodiments, $R^{2C}$ can be halogen, such as, F or Cl. In still other embodiments, $R^{2C}$ can be hydroxy. In yet still other embodiments, $R^{2C}$ can be an unsubstituted $C_{1-4}$ alkoxy. In some embodiments, $R^{2C}$ can be

wherein $R^{2A}$ is attached to the 2'-position of Ring $A^{1C}$ and the * indicates an attachment point to the 4'-position of Ring $A^{1C}$. When $R^{2C}$ is

Ring $A^{1A}$ can have the structure

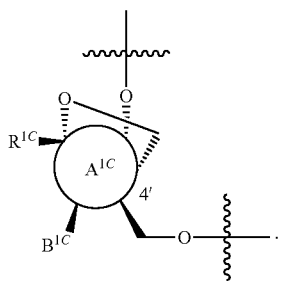

In some embodiments, $R^{1C}$ can be halogen (for example, fluoro); and $R^{2C}$ can be hydrogen.

For Ring $A^{2C}$, in some embodiments, $R^{3C}$ can be hydrogen. In other embodiments, $R^{3C}$ can be halogen. For example, $R^{3C}$ can be fluoro or chloro. In some embodiments, $R^{4C}$ can be hydrogen. In other embodiments, $R^{4C}$ can be halogen, such as fluoro or chloro. In still other embodiments, $R^{4C}$ can be hydroxy. In yet still other embodiments, $R^{4C}$ can be an unsubstituted $C_{1-4}$ alkoxy. Suitable unsubstituted $C_{1-4}$ alkoxys for $R^{2C}$ and/or $R^{4C}$ include the following: methoxy, ethoxy, n-propoxy, isopropoxy, n-butoxy, isobutoxy, secbutoxy and tert-butoxy. In some embodiments, $R^{4C}$ can be

wherein $R^{4C}$ is attached to the 2'-position of Ring $A^{2C}$, then the * indicates an attachment point to the 4'-position of Ring $A^{2C}$. When $R^{4C}$ is

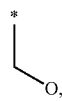

Ring $A^{2C}$ can have the structure

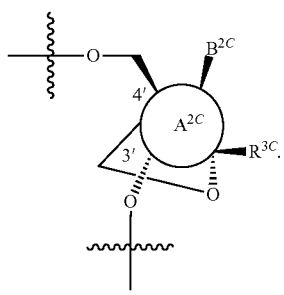

In some embodiments, $R^{1C}$ can be hydrogen; and $R^{2C}$ can be hydroxy. In other embodiments, $R^{1C}$ can be hydrogen; and $R^{2C}$ can be hydrogen. In still other embodiments, $R^{1C}$ can be hydrogen; and $R^{2C}$ can be halogen, such a fluoro. In yet still other embodiments, $R^{1C}$ can be hydrogen; and $R^{2C}$ can be an unsubstituted $C_{1-4}$ alkoxy. In some embodiments, $R^{1C}$ can be halogen; and $R^{2C}$ can be halogen, for example, $R^{1C}$ and $R^{2C}$ can be each F. In some embodiments, $R^{3C}$ can be hydrogen; and $R^{4C}$ can be hydroxy. In other embodiments, $R^{3C}$ can be hydrogen; and $R^{4C}$ can be hydrogen. In still other embodiments, $R^{3C}$ can be hydrogen; and $R^{4C}$ can be halogen (for example, F). In yet still other embodiments, $R^{3C}$ can be hydrogen; and $R^{4C}$ can be an unsubstituted $C_{1-4}$ alkoxy. In some embodiments, $R^{3C}$ can be halogen; and $R^{4C}$ can be halogen. As an example, $R^{3C}$ and $R^{4C}$ can be each fluoro. In other embodiments, $R^{3C}$ can be halogen (for example, fluoro); and $R^{4C}$ can be hydrogen.

Examples of phorphorus-containing groups of Formulae (I), (II) and (III) include phosphate, mono-thiophosphate and dithiophosphate. The phosphorus-containing groups of Formulae (I), (II) and (III) can included prodrug moieties. For example, one or more hydrogens of a phosphate can be replaced with a lower alkyl, pivaloyloxymethyl (POM) or isopropyloxycarbonyloxymethyl (POC) group. Similarly, one or more hydrogens of a mono-thiophosphate and/or dithiophosphate can be replaced with a lower alkyl, pivaloyloxymethyl (POM) or isopropyloxycarbonyloxymethyl (POC) group.

In some embodiments, $X^{1A}$ can be OH or O$^-$; and $X^{2A}$ can be O. In other embodiments, $X^{1A}$ can be SH or S$^-$; and $X^{2A}$ can be O. In still other embodiments, $X^{1A}$ can be SH or S$^-$; and $X^{2A}$ can be S.

In some embodiments, $X^{1A}$ can be O(unsubstituted $C_{1-4}$ alkyl); and $X^{2A}$ can be O. In other embodiments, $X^{1A}$ can be O(unsubstituted $C_{1-4}$ alkyl); and $X^{2A}$ can be S. In still other embodiments, $X^{1A}$ can be S(unsubstituted $C_{1-4}$ alkyl); and $X^{2A}$ can be O. In yet still other embodiments, $X^{1A}$ can be S(unsubstituted $C_{1-4}$ alkyl); and $X^{2A}$ can be S. In some embodiments, $X^{1A}$ can be O—CH$_2$—O—C(=O)-(unsubstituted $C_{1-4}$ alkyl); and $X^{2A}$ can be O. In other embodiments, $X^{1A}$ can be O—CH$_2$—O—C(=O)-(unsubstituted $C_{1-4}$ alkyl); and $X^{2A}$ can be S. In still other embodiments, $X^{1A}$ can be S—CH$_2$—O—C(=O)-(unsubstituted $C_{1-4}$ alkyl); and $X^{2A}$ can be O. In yet still other embodiments, $X^{1A}$ can be S—CH$_2$—O—C(=O)-(unsubstituted $C_{1-4}$ alkyl); and $X^{2A}$ can be S. In some embodiments, $X^{1A}$ can be O—CH$_2$—O—C(=O)—O-(unsubstituted $C_{1-4}$ alkyl); and $X^{2A}$ can be O. In other embodiments, $X^{1A}$ can be O—CH$_2$—O—C(=O)—O-(unsubstituted $C_{1-4}$ alkyl); and $X^{2A}$ can be S. In still other embodiments, $X^{1A}$ can be S—CH$_2$—O—C(=O)—O-(unsubstituted $C_{1-4}$ alkyl); and $X^{2A}$ can be O. In yet still other embodiments, $X^{1A}$ can be S—CH$_2$—O—C(=O)—O-(unsubstituted $C_{1-4}$ alkyl); and $X^{2A}$ can be S. In some embodiments, $X^{1A}$ can be

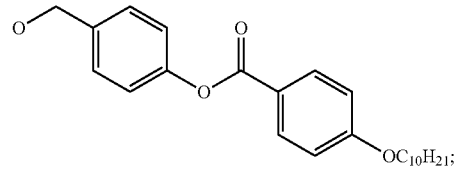

and $X^{2A}$ can be O. In other embodiments, $X^{1A}$ can be

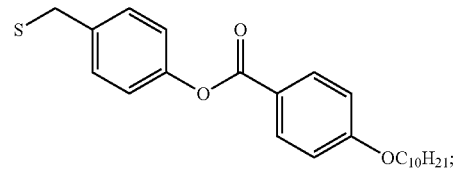

and $X^{2A}$ can be O. In still other embodiments, $X^{1A}$ can be

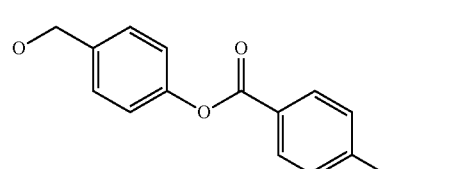

and $X^{2A}$ can be S. In yet still other embodiments, $X^{1A}$ can be

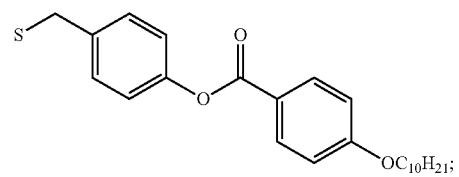

and $X^{2A}$ can be S.

In some embodiments, including those of the previous paragraph, $X^{3A}$ can be OH or O$^-$; and $X^{4A}$ can be O. In other embodiments, $X^{3A}$ can be SH or S$^-$; and $X^{4A}$ can be O. In still other embodiments, $X^{3A}$ can be SH or S$^-$; and $X^{4A}$ can be S.

In some embodiments, $X^{3A}$ can be O(unsubstituted $C_{1-4}$ alkyl); and $X^{4A}$ can be O. In other embodiments, $X^{3A}$ can be O(unsubstituted $C_{1-4}$ alkyl); and $X^{4A}$ can be S. In still other embodiments, $X^{3A}$ can be S(unsubstituted $C_{1-4}$ alkyl); and $X^{4A}$ can be O. In yet still other embodiments, $X^{3A}$ can be S(unsubstituted $C_{1-4}$ alkyl); and $X^{4A}$ can be S. In some embodiments, $X^{3A}$ can be O—$CH_2$—O—C(=O)-(unsubstituted $C_{1-4}$ alkyl); and $X^{4A}$ can be O. In other embodiments, $X^{3A}$ can be O—$CH_2$—O—C(=O)-(unsubstituted $C_{1-4}$ alkyl); and $X^{4A}$ can be S. In still other embodiments, $X^{3A}$ can be S—$CH_2$—O—C(=O)-(unsubstituted $C_{1-4}$ alkyl); and $X^{4A}$ can be O. In yet still other embodiments, $X^{3A}$ can be S—$CH_2$—C(=O)-(unsubstituted $C_{1-4}$ alkyl); and $X^{4A}$ can be S. In some embodiments, $X^{3A}$ can be O—$CH_2$—O—C(=O)—O—(unsubstituted $C_{1-4}$ alkyl); and $X^{4A}$ can be O. In other embodiments, $X^{3A}$ can be O—$CH_2$—O—C(=O)—O-(unsubstituted $C_{1-4}$ alkyl); and $X^{4A}$ can be S. In still other embodiments, $X^{3A}$ can be S—$CH_2$—O—C(=O)—O-(unsubstituted $C_{1-4}$ alkyl); and $X^{4A}$ can be O. In yet still other embodiments, $X^{3A}$ can be S—$CH_2$—O—C(=O)—O-(unsubstituted $C_{1-4}$ alkyl); and $X^{4A}$ can be S. In some embodiments, $X^{3A}$ can be

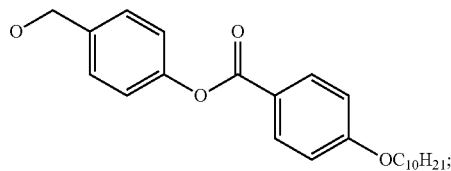

and $X^{4A}$ can be O. In other embodiments, $X^{3A}$ can be

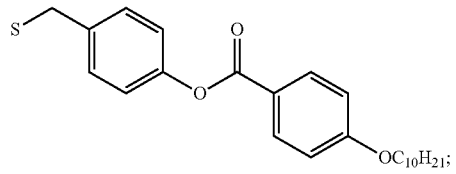

and $X^{4A}$ can be O. In still other embodiments, $X^{3A}$ can be

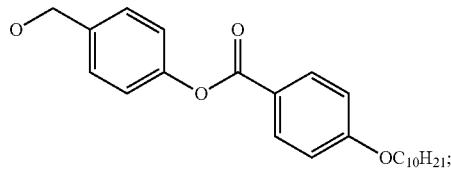

and $X^{4A}$ can be S. In yet still other embodiments, $X^{3A}$ can be

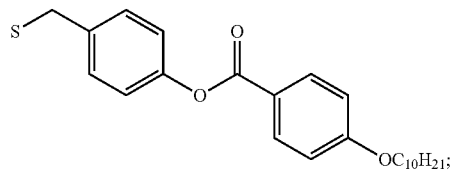

and $X^{4A}$ can be S.

For Formula (II), in some embodiments, $X^{1B}$ can be OH or $O^-$; and $X^{2B}$ can be O. In other embodiments, $X^{1B}$ can be SH or $S^-$; and $X^{2B}$ can be O. In still other embodiments, $X^{1B}$ can be SH or $S^-$; and $X^{2B}$ can be S.

In some embodiments, $X^{1B}$ can be O(unsubstituted $C_{1-4}$ alkyl); and $X^{2B}$ can be O. In other embodiments, $X^{1B}$ can be O(unsubstituted $C_{1-4}$ alkyl); and $X^{2B}$ can be S. In still other embodiments, $X^{1B}$ can be S(unsubstituted $C_{1-4}$ alkyl); and $X^{2B}$ can be O. In yet still other embodiments, $X^{1B}$ can be S(unsubstituted $C_{1-4}$ alkyl); and $X^{2B}$ can be S. In some embodiments, $X^{1B}$ can be O—$CH_2$—O—C(=O)-(unsubstituted $C_{1-4}$ alkyl); and $X^{2B}$ can be O. In other embodiments, $X^{1B}$ can be O—$CH_2$—O—C(=O)-(unsubstituted $C_{1-4}$ alkyl); and $X^{2B}$ can be S. In still other embodiments, $X^{1B}$ can be S—$CH_2$—O—C(=O)-(unsubstituted $C_{1-4}$ alkyl); and $X^{2B}$ can be O. In yet still other embodiments, $X^{1B}$ can be S—$CH_2$—O—C(=O)-(unsubstituted $C_{1-4}$ alkyl); and $X^{2B}$ can be S. In some embodiments, $X^{1B}$ can be O—$CH_2$—O—C(=O)—O-(unsubstituted $C_{1-4}$ alkyl); and $X^{2B}$ can be O. In other embodiments, $X^{1B}$ can be O—$CH_2$—O—C(=O)—O-(unsubstituted $C_{1-4}$ alkyl); and $X^{2B}$ can be S. In still other embodiments, $X^{1B}$ can be S—$CH_2$—C(=O)—O-(unsubstituted $C_{1-4}$ alkyl); and $X^{2B}$ can be O. In yet still other embodiments, $X^{1B}$ can be S—$CH_2$—C(=O)—O-(unsubstituted $C_{1-4}$ alkyl); and $X^{2B}$ can be S. In some embodiments, $X^{1B}$ can be

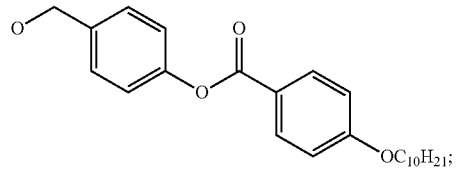

and $X^{2B}$ can be O. In other embodiments, $X^{1B}$ can be

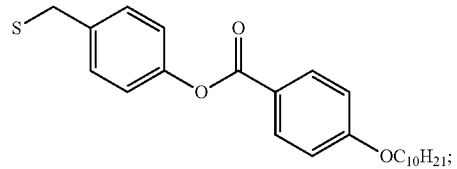

and $X^{2B}$ can be O. In still other embodiments, $X^{1B}$ can be

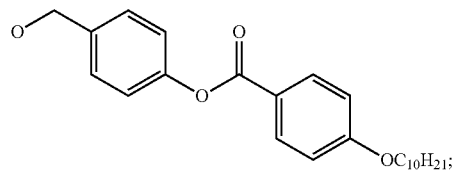

and $X^{2B}$ can be S. In yet still other embodiments, $X^{1B}$ can be

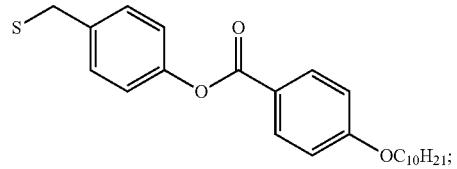

and $X^{2B}$ can be S.

In some embodiments, including those of the previous paragraph, $X^{3B}$ can be OH or O$^-$; and $X^{4B}$ can be O. In other embodiments, $X^{3B}$ can be SH or S$^-$; and $X^{4B}$ can be O. In still other embodiments, $X^{3B}$ can be SH or S$^-$; and $X^{4B}$ can be S.

In some embodiments, $X^{3B}$ can be O(unsubstituted $C_{1-4}$ alkyl); and $X^{4B}$ can be O. In other embodiments, $X^{3B}$ can be O(unsubstituted $C_{1-4}$ alkyl); and $X^{4B}$ can be S. In still other embodiments, $X^{3B}$ can be S(unsubstituted $C_{1-4}$ alkyl); and $X^{4B}$ can be O. In yet still other embodiments, $X^{3B}$ can be S(unsubstituted $C_{1-4}$ alkyl); and $X^{4B}$ can be S. In some embodiments, $X^{3B}$ can be O—CH$_2$—O—C(=O)-(unsubstituted $C_{1-4}$ alkyl); and $X^{4B}$ can be O. In other embodiments, $X^{3B}$ can be O—CH$_2$—O—C(=O)-(unsubstituted $C_{1-4}$ alkyl); and $X^{4B}$ can be S. In still other embodiments, $X^{3B}$ can be S—CH$_2$—O—C(=O)-(unsubstituted $C_{1-4}$ alkyl); and $X^{4B}$ can be O. In yet still other embodiments, $X^{3B}$ can be S—CH$_2$—C(=O)-(unsubstituted $C_{1-4}$ alkyl); and $X^{4B}$ can be S. In some embodiments, $X^{3B}$ can be O—CH$_2$—O—C(=O)—O-(unsubstituted $C_{1-4}$ alkyl); and $X^{4B}$ can be O. In other embodiments, $X^{3B}$ can be O—CH$_2$—O—C(=O)—O-(unsubstituted $C_{1-4}$ alkyl); and $X^{4B}$ can be S. In still other embodiments, $X^{3B}$ can be S—CH$_2$—O—C(=O)—O-(unsubstituted $C_{1-4}$ alkyl); and $X^{4B}$ can be O. In yet still other embodiments, $X^{3B}$ can be S—CH$_2$—O—C(=O)—O-(unsubstituted $C_{1-4}$ alkyl); and $X^{4B}$ can be S. In some embodiments, $X^{3B}$ can be

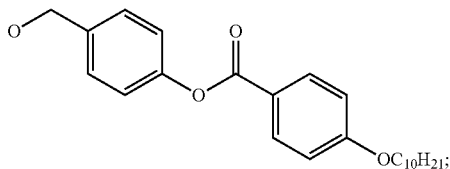

and $X^{4B}$ can be O. In other embodiments, $X^{3B}$ can be

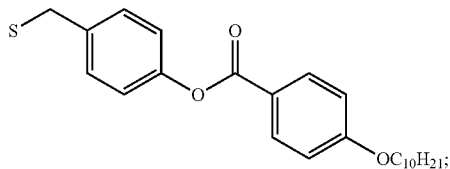

and $X^{4B}$ can be O. In still other embodiments, $X^{3B}$ can be

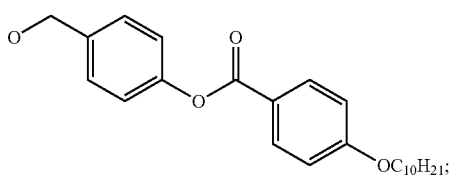

and $X^{4B}$ can be S. In yet still other embodiments, $X^{3B}$ can be

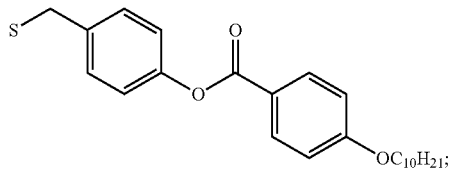

and $X^{4B}$ can be S.

For Formula (III), in some embodiments, $X^{1C}$ can be OH or O$^-$; and $X^{2C}$ can be O. In other embodiments, $X^{1C}$ can be SH or S$^-$; and $X^{2C}$ can be O. In still other embodiments, $X^{1C}$ can be SH or S$^-$; and $X^{2C}$ can be S.

In some embodiments, $X^{1C}$ can be O(unsubstituted $C_{1-4}$ alkyl); and $X^{2C}$ can be O. In other embodiments, $X^{1C}$ can be O(unsubstituted $C_{1-4}$ alkyl); and $X^{2C}$ can be S. In still other embodiments, $X^{1C}$ can be S(unsubstituted $C_{1-4}$ alkyl); and $X^{2C}$ can be O. In yet still other embodiments, $X^{1C}$ can be S(unsubstituted $C_{1-4}$ alkyl); and $X^{2C}$ can be S. In some embodiments, $X^{1C}$ can be O—CH$_2$—O—C(=O)-(unsubstituted $C_{1-4}$ alkyl); and $X^{2C}$ can be O. In other embodiments, $X^{1C}$ can be O—CH$_2$—O—C(=O)-(unsubstituted $C_{1-4}$ alkyl); and $X^{2C}$ can be S. In still other embodiments, $X^{1C}$ can be S—CH$_2$—O—C(=O)-(unsubstituted $C_{1-4}$ alkyl); and $X^{2C}$ can be O. In yet still other embodiments, $X^{1C}$ can be S—CH$_2$—C(=O)-(unsubstituted $C_{1-4}$ alkyl); and $X^{2C}$ can be S. In some embodiments, $X^{1C}$ can be O—CH$_2$—C(=O)—O-(unsubstituted $C_{1-4}$ alkyl); and $X^{2C}$ can be O. In other embodiments, $X^{1C}$ can be O—CH$_2$—O—C(=O)—O-(unsubstituted $C_{1-4}$ alkyl); and $X^{2C}$ can be S. In still other embodiments, $X^{1C}$ can be S—CH$_2$—O—C(=O)—O-(unsubstituted $C_{1-4}$ alkyl); and $X^{2C}$ can be O. In yet still other embodiments, $X^{1C}$ can be S—CH$_2$—O—C(=O)—O-(unsubstituted $C_{1-4}$ alkyl); and $X^{2C}$ can be S. In some embodiments, $X^{1C}$ can be

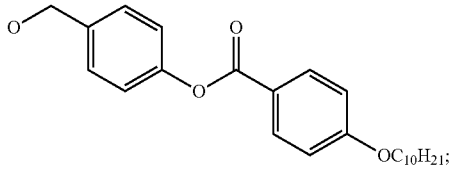

and $X^{2C}$ can be O. In other embodiments, $X^{1C}$ can be

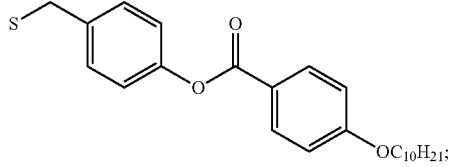

and $X^{2C}$ can be O. In still other embodiments, $X^{1C}$ can be

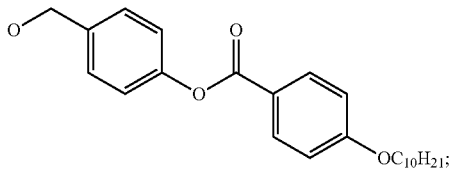

and $X^{2C}$ can be S. In yet still other embodiments, $X^{1C}$ can be

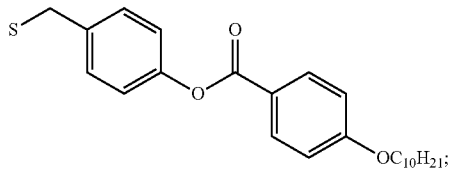

and $X^{2C}$ can be S.

In some embodiments, including those of the previous paragraph, $X^{3C}$ can be OH or O$^-$; and $X^{4C}$ can be O. In other embodiments, $X^{3C}$ can be SH or S$^-$; and $X^{4C}$ can be O. In still other embodiments, $X^{3C}$ can be SH or S$^-$; and $X^{4C}$ can be S.

In some embodiments, $X^{3C}$ can be O(unsubstituted $C_{1-4}$ alkyl); and $X^{4C}$ can be O. In other embodiments, $X^{3C}$ can be O(unsubstituted $C_{1-4}$ alkyl); and $X^{4C}$ can be S. In still other embodiments, $X^{3C}$ can be S(unsubstituted $C_{1-4}$ alkyl); and $X^{4C}$ can be O. In yet still other embodiments, $X^{3C}$ can be S(unsubstituted $C_{1-4}$ alkyl); and $X^{4C}$ can be S. In some embodiments, $X^{3C}$ can be O—CH$_2$—O—C(=O)-(unsubstituted $C_{1-4}$ alkyl); and $X^{4C}$ can be O. In other embodiments, $X^{3C}$ can be O—CH$_2$—O—C(=O)-(unsubstituted $C_{1-4}$ alkyl); and $X^{4C}$ can be S. In still other embodiments, $X^{3C}$ can be S—CH$_2$—O—C(=O)-(unsubstituted $C_{1-4}$ alkyl); and $X^{4C}$ can be O. In yet still other embodiments, $X^{3C}$ can be S—CH$_2$—O—C(=O)-(unsubstituted $C_{1-4}$ alkyl); and $X^{4C}$ can be S. In some embodiments, $X^{3C}$ can be O—CH$_2$—O—C(=O)—O-(unsubstituted $C_{1-4}$ alkyl); and $X^{4C}$ can be O. In other embodiments, $X^{3C}$ can be O—CH$_2$—O—C(=O)—O-(unsubstituted $C_{1-4}$ alkyl); and $X^{4C}$ can be S. In still other embodiments, $X^{3C}$ can be S—CH$_2$—O—C(=O)—O-(unsubstituted $C_{1-4}$ alkyl); and $X^{4C}$ can be O. In yet still other embodiments, $X^{3C}$ can be S—CH$_2$—O—C(=O)—O-(unsubstituted $C_{1-4}$ alkyl); and $X^{4C}$ can be S. In some embodiments, $X^{3C}$ can be

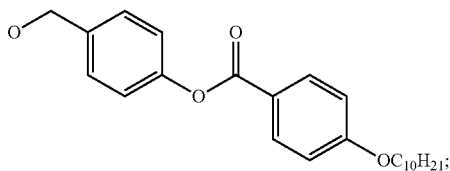

and $X^{4C}$ can be O. In other embodiments, $X^{3C}$ can be

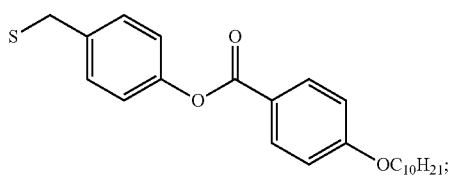

and $X^{4C}$ can be O. In still other embodiments, $X^{3C}$ can be

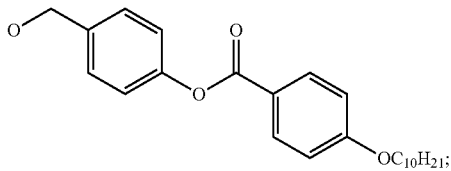

and $X^{4C}$ can be S. In yet still other embodiments, $X^{3C}$ can be

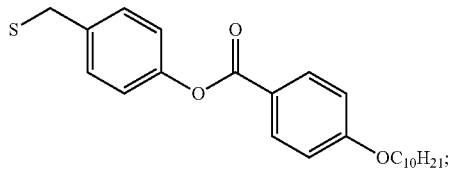

and $X^{4C}$ can be S.

Those skilled in the art understand that each phosphorus can be a chiral center depending on the selection of $X^{1A}$, $X^{3A}$, $X^{1B}$, $X^{3B}$, $X^{1C}$, $X^{3C}$, $X^{2A}$, $X^{4A}$, $X^{2B}$, $X^{4B}$, $X^{2C}$ and $X^{4C}$. As there are two phosphorus-containing moieties on each of Formulae (I), (II) and (III), each of Formulae (I), (II) and (III) can exist as two or four diastereomers. In some embodiments, one phosphorus of Formula (I) can be in the R-confirmation. In some embodiments, one phosphorus of Formula (I) can be in the S-confirmation. In some embodiments, each phosphorus of Formula (I) can be in the S-confirmation. In other embodiments, each phosphorus of Formula (I) can be in the R-confirmation. In still other embodiments, one phosphorus of Formula (I) can be in the S-confirmation and the other phosphorus of Formula (I) can be in the R-confirmation. In some embodiments, one phosphorus of Formula (II) can be in the R-confirmation. In some embodiments, one phosphorus of Formula (II) can be in the S-confirmation. In some embodiments, each phosphorus of Formula (II) can be in the S-confirmation. In other embodiments, each phosphorus of Formula (II) can be in the R-confirmation. In still other embodiments, one phosphorus of Formula (II) can be in the S-confirmation and the other phosphorus of Formula (II) can be in the R-confirmation. In some embodiments, one phosphorus of Formula (III) can be in the R-confirmation. In some embodiments, one phosphorus of Formula (III) can be in the S-confirmation. In some embodiments, each phosphorus of Formula (III) can be in the S-confirmation. In other embodiments, each phosphorus of Formula (III) can be in the R-confirmation. In still other embodiments, one phosphorus of Formula (III) can be in the S-confirmation and the other phosphorus of Formula (III) can be in the R-confirmation.

In some embodiments, a salt of a compound of Formulae (I), (II) and/or (III), can be selected from a sodium, a lithium, a triethylammonium and an ammonium salt. In some embodiments, a salt of a compound of Formulae (I), (II) and/or (III), can be a sodium salt of the salt of a compound of Formulae (I), (II) and/or (III).

Examples of compound of Formulae (I), (II) and (III) include the following:
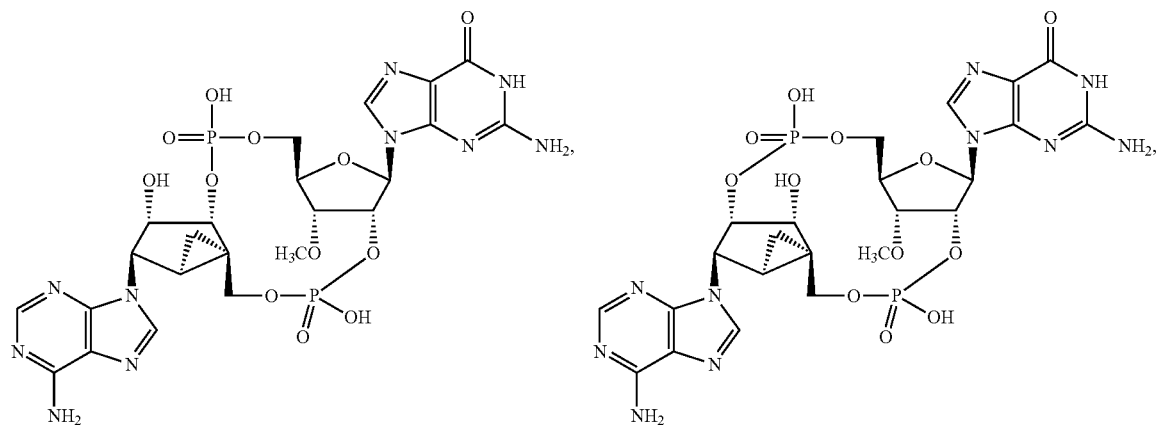
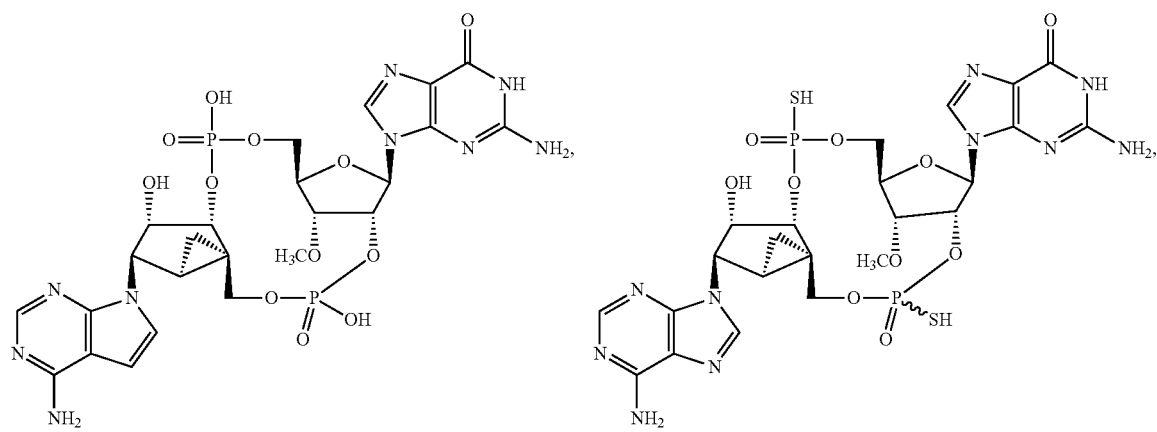
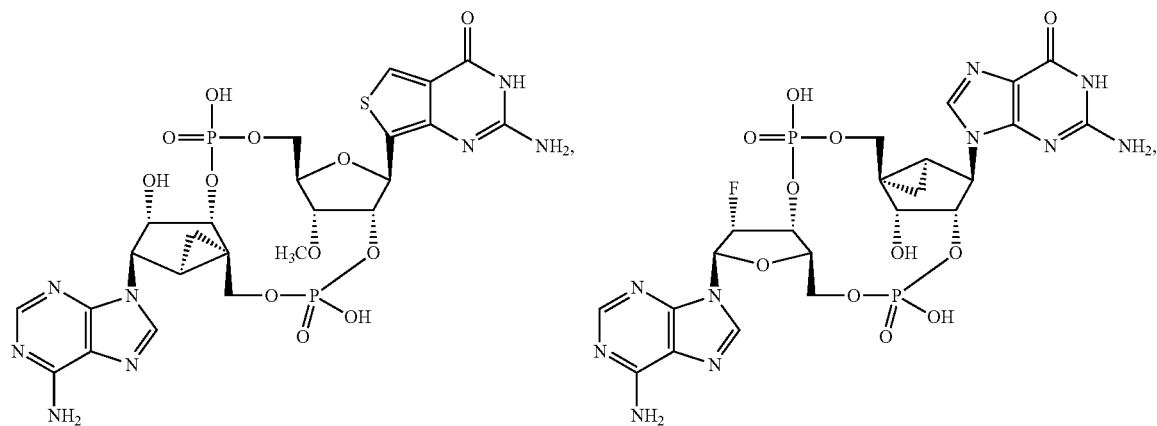

55 56
-continued
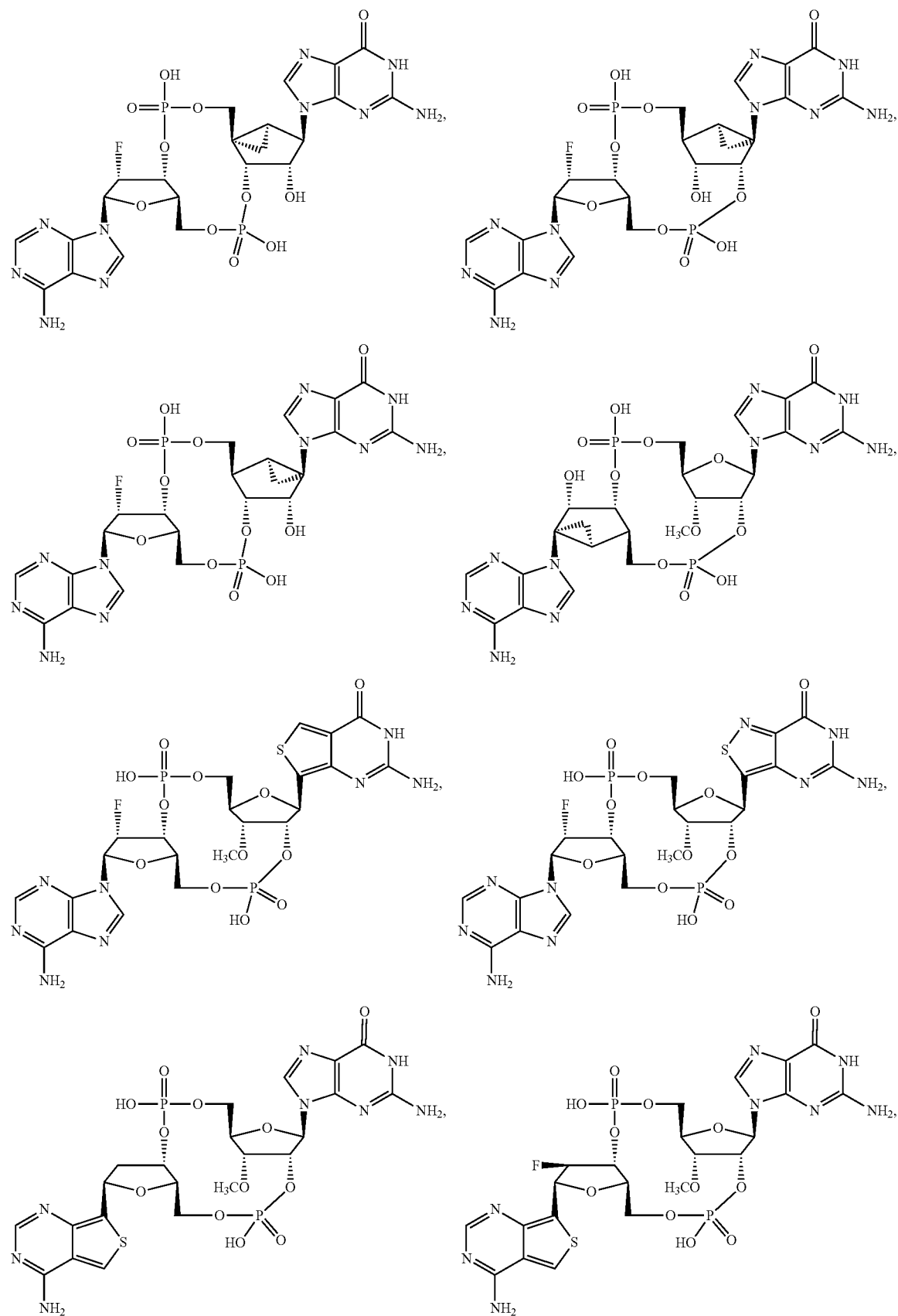

-continued
57
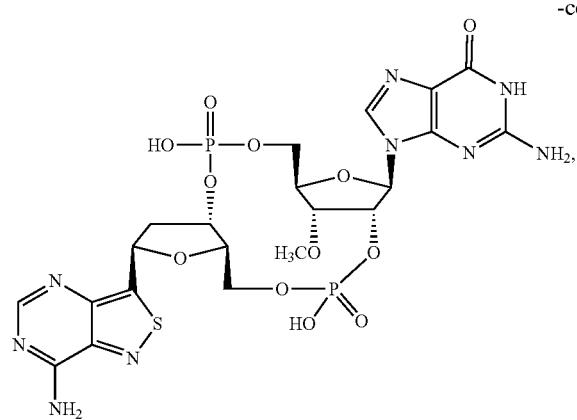
58
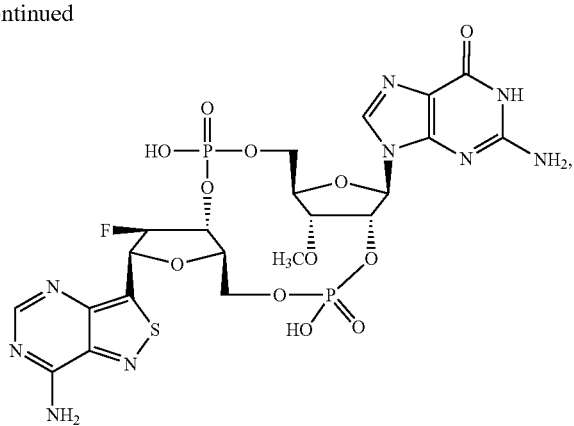
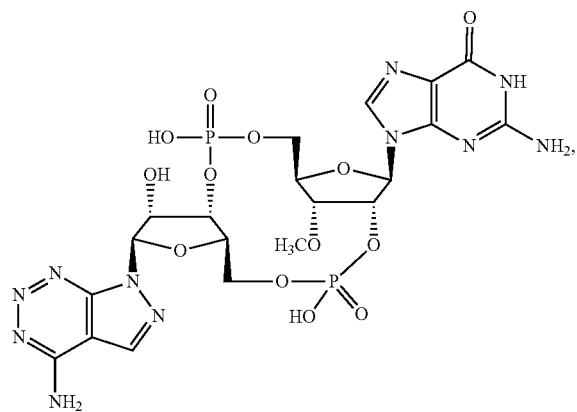
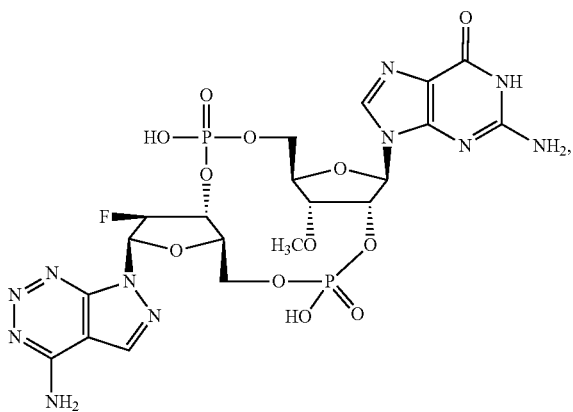
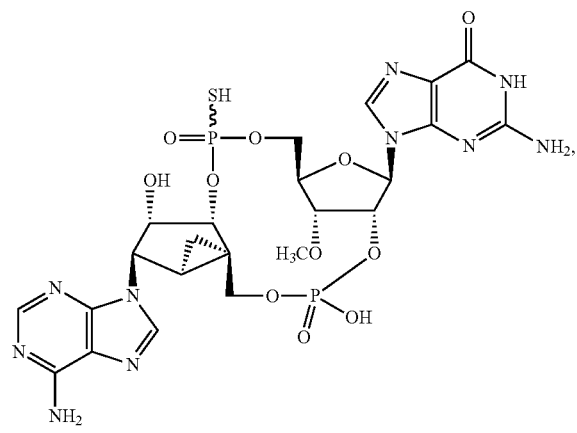
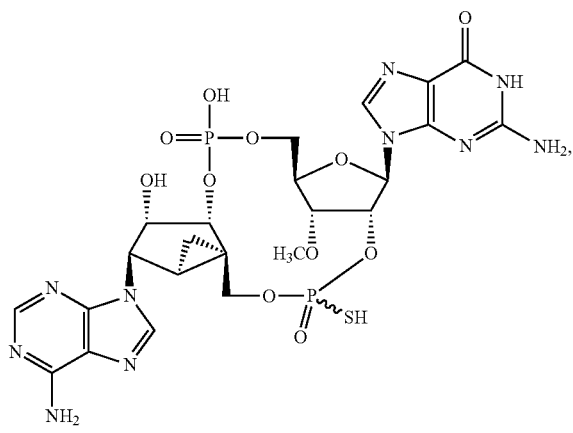
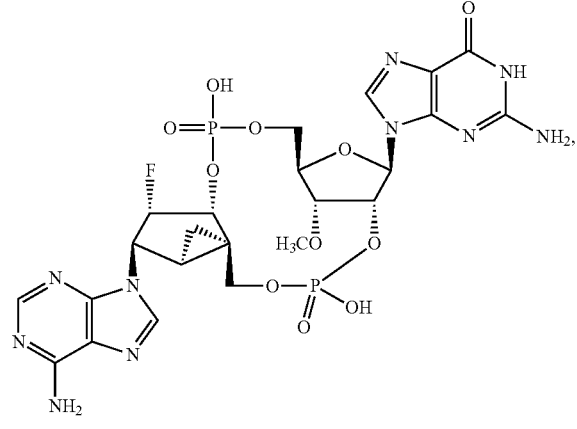
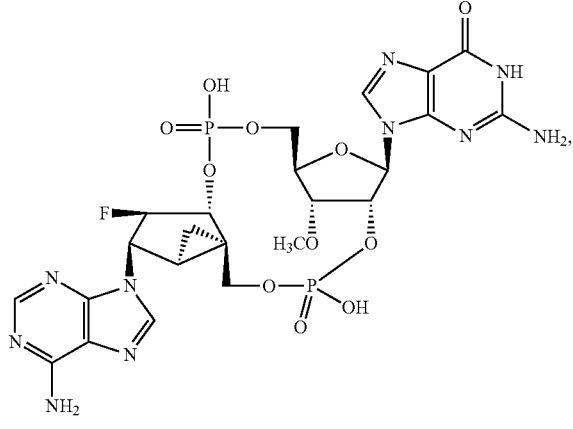

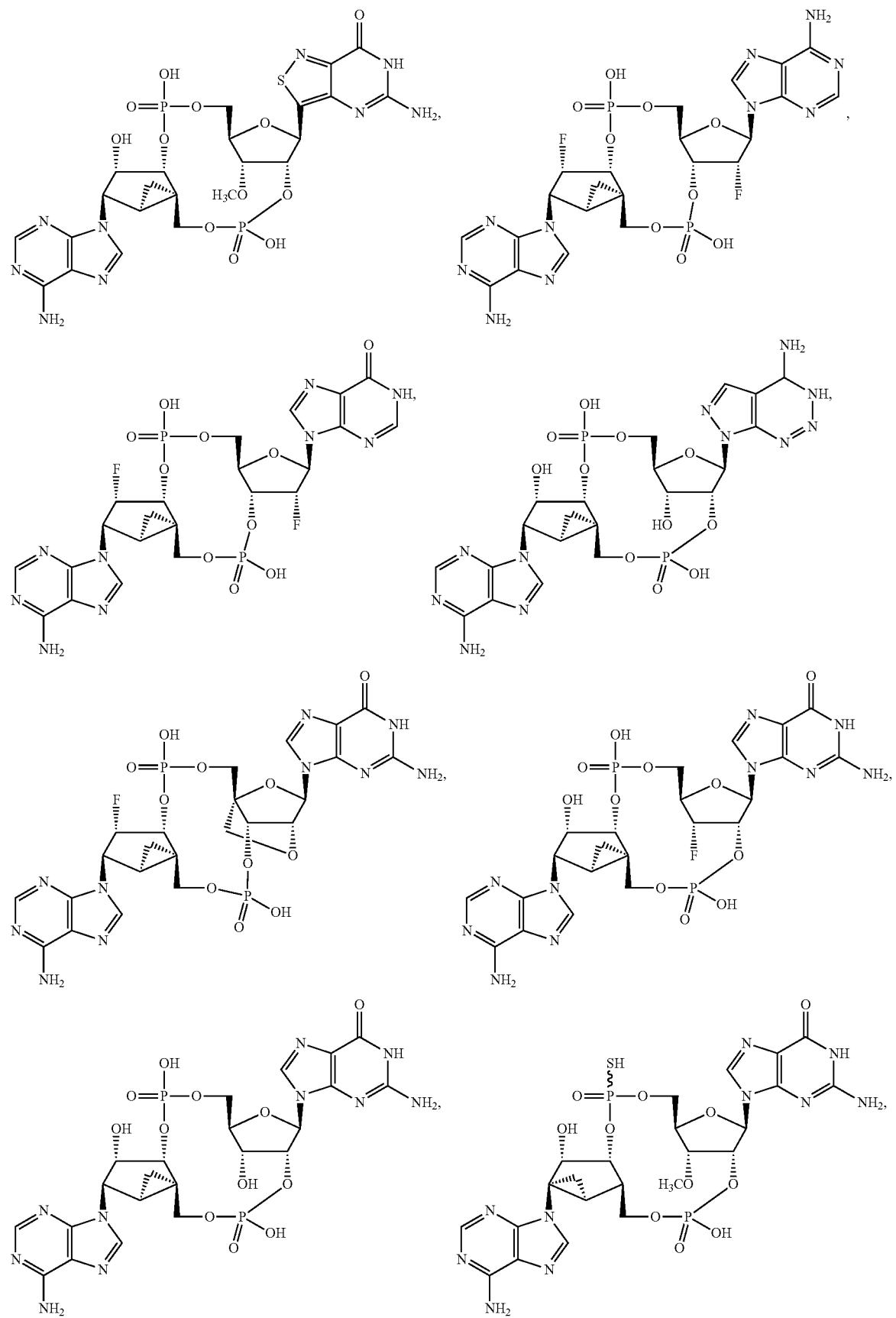

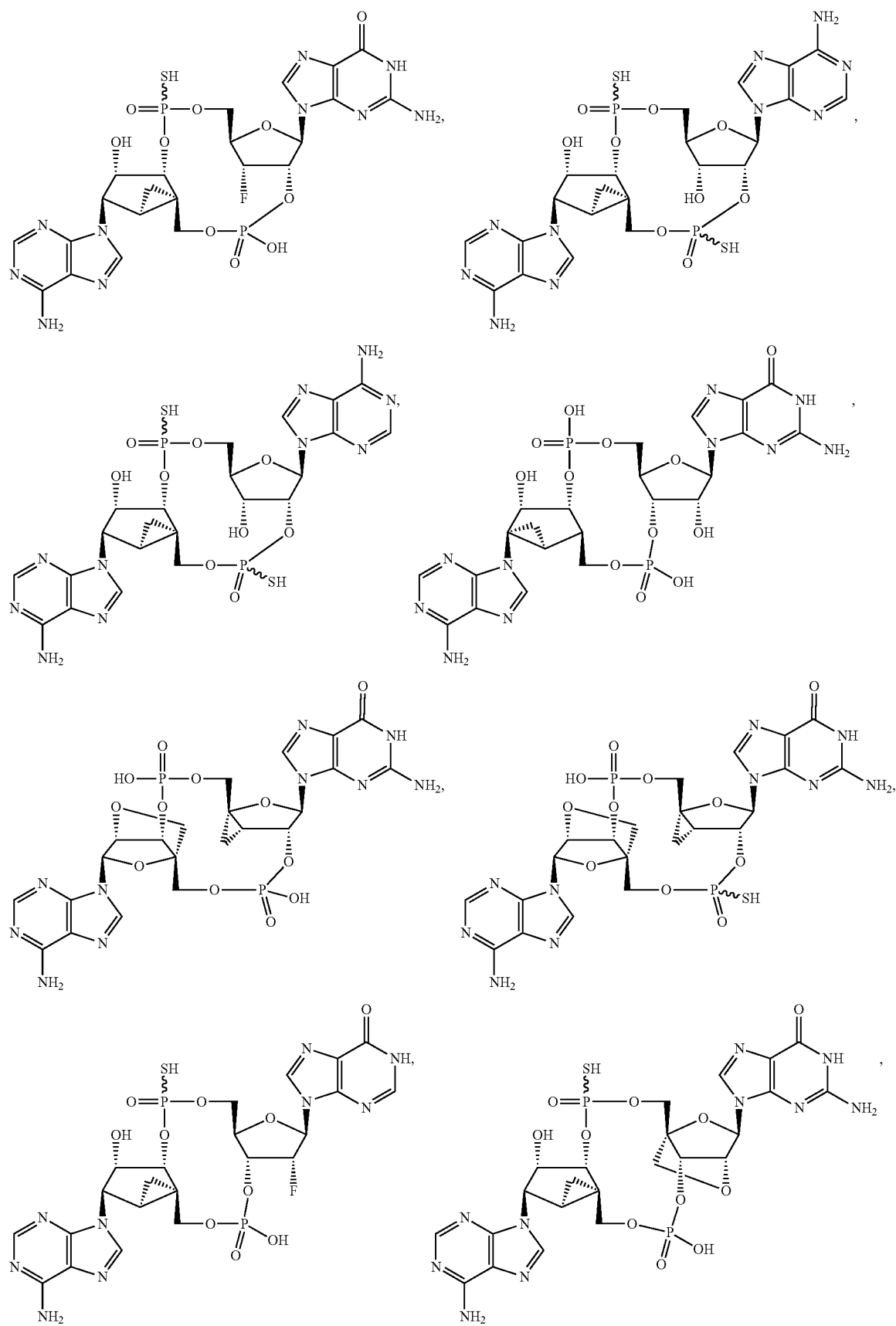

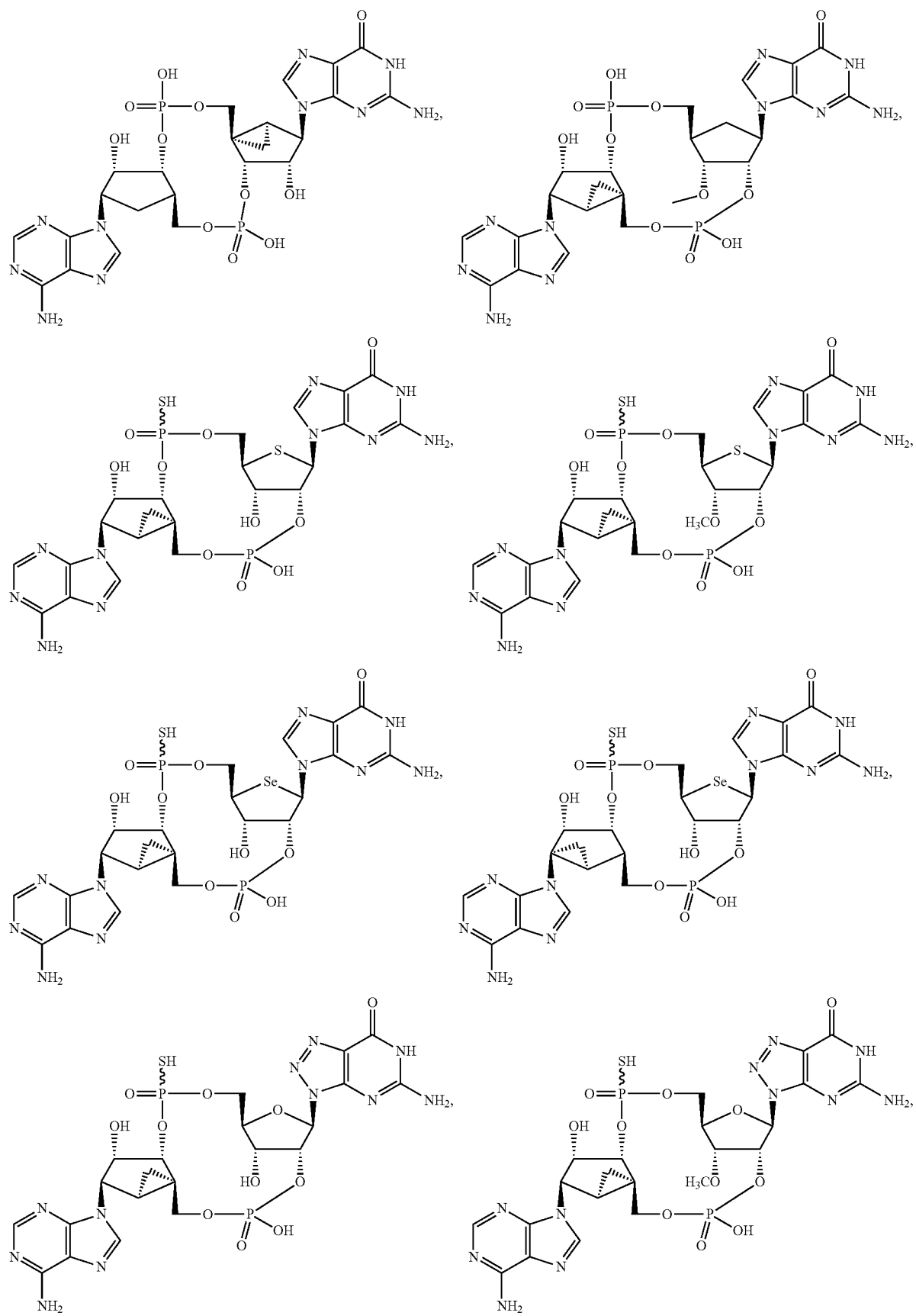

65 66
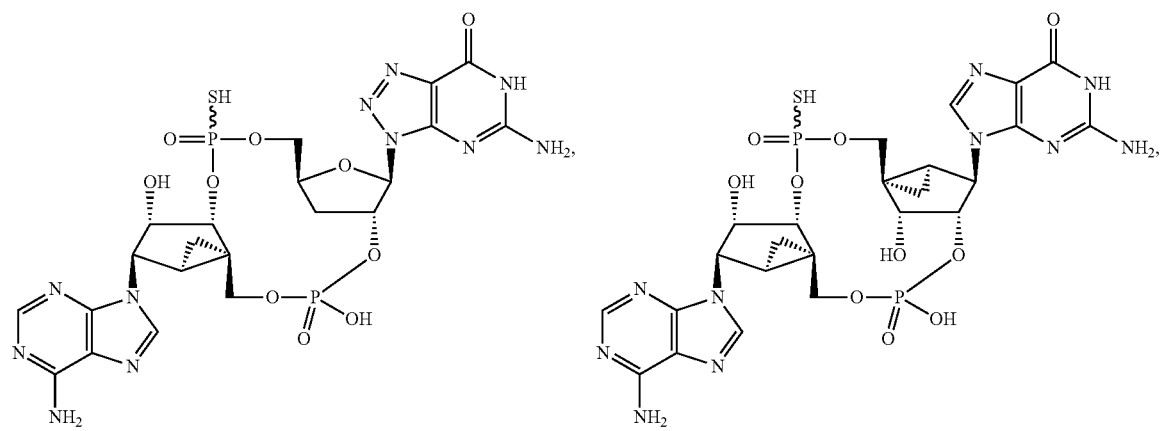
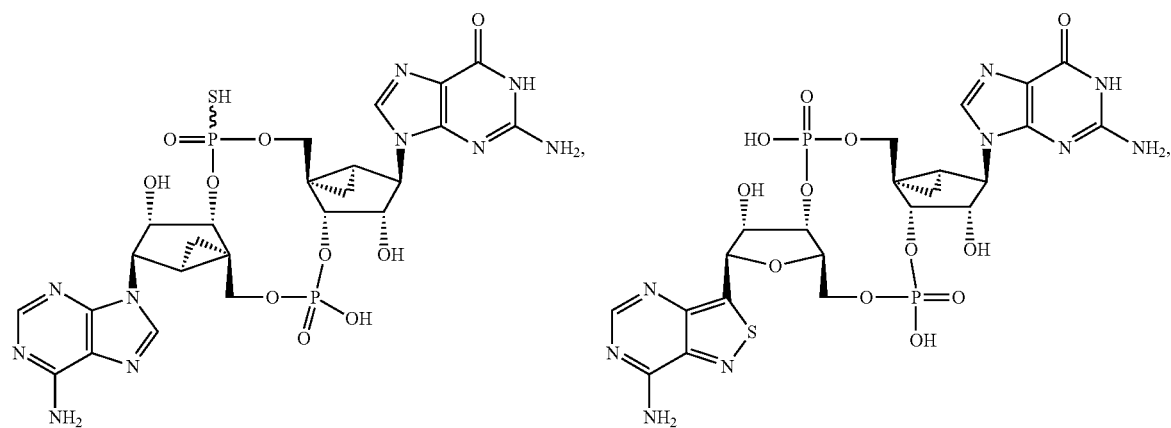
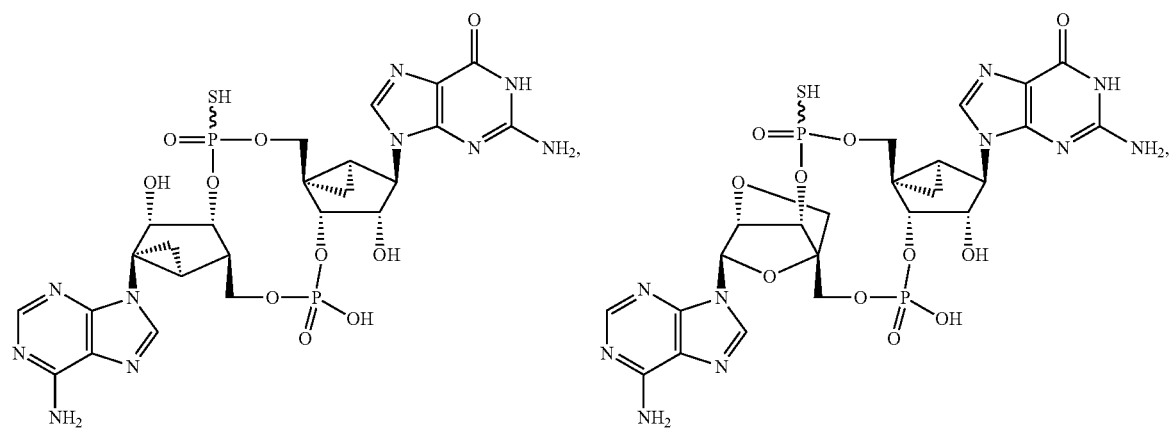
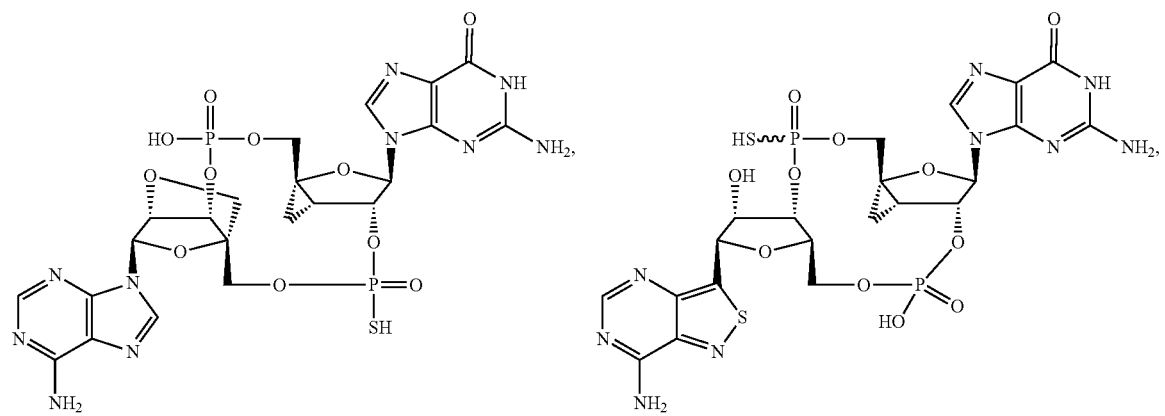

-continued
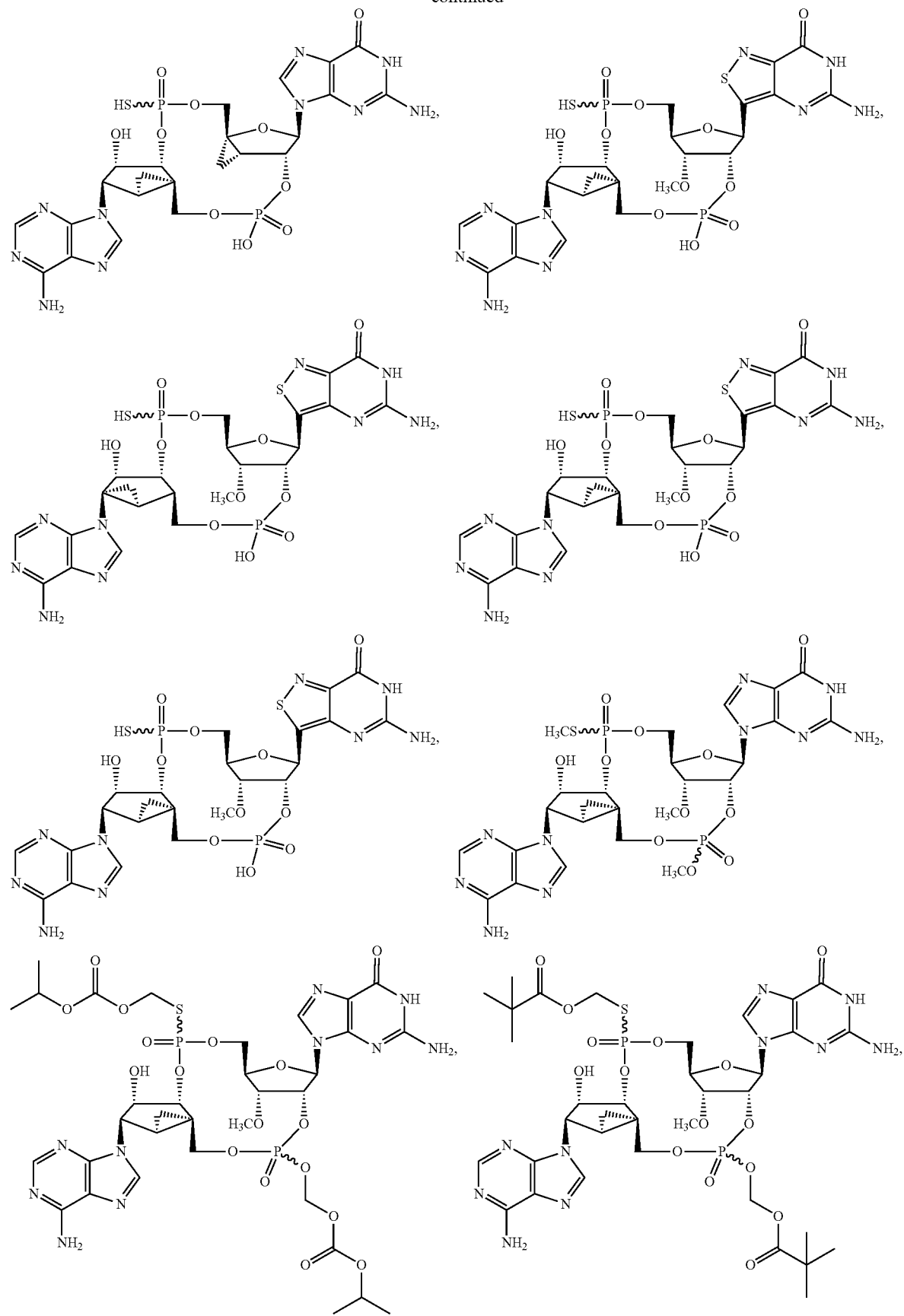

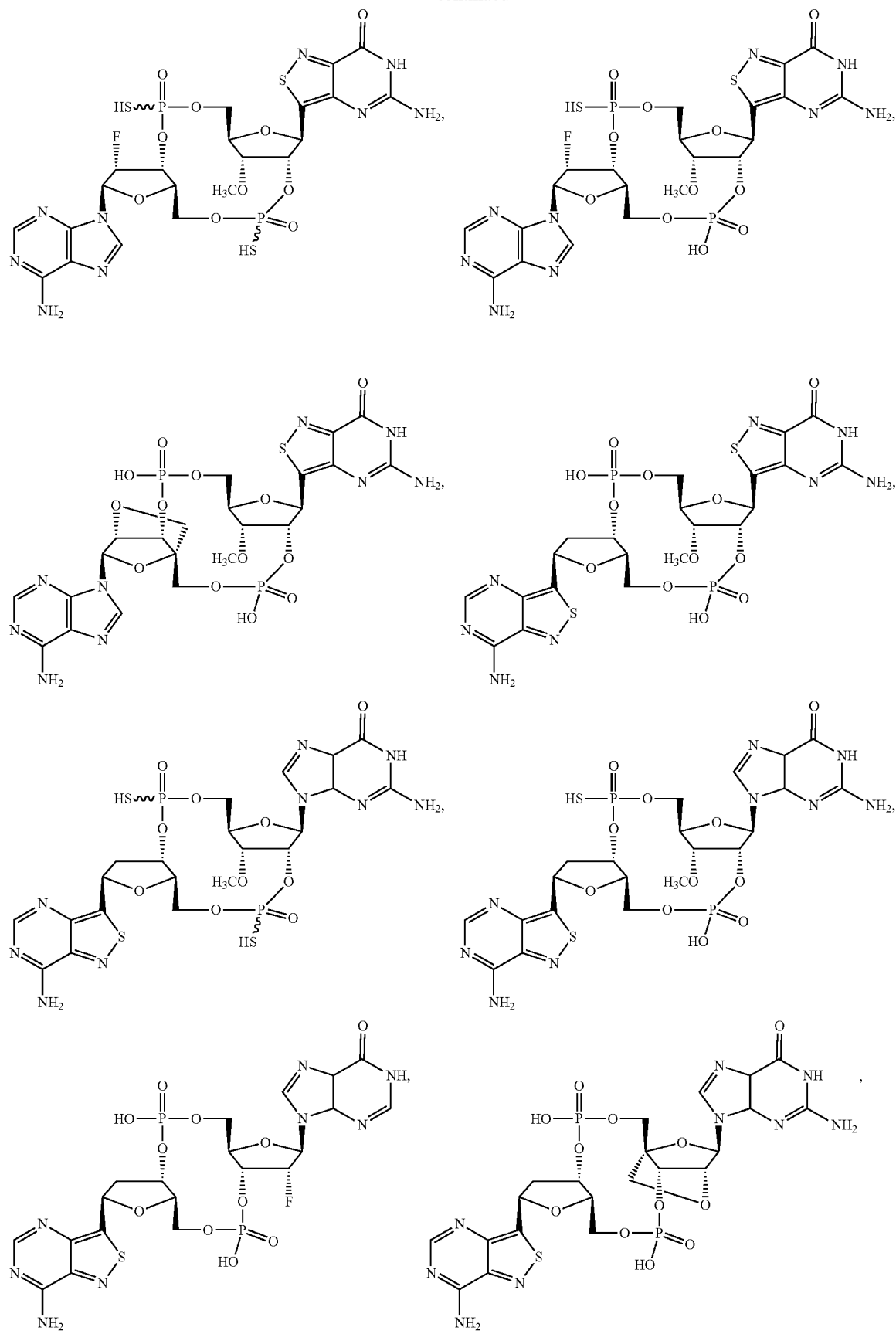

71 72
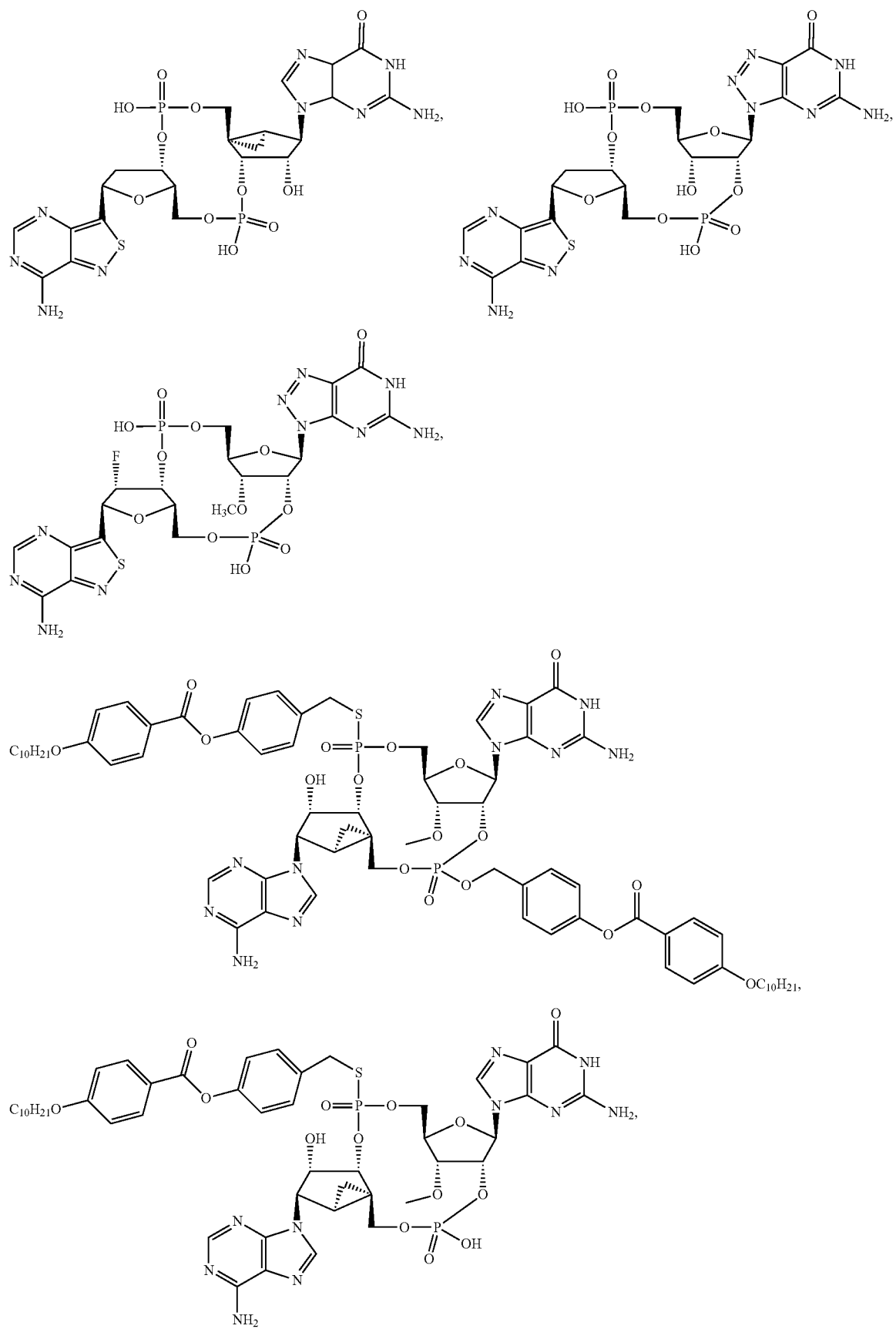
-continued

-continued
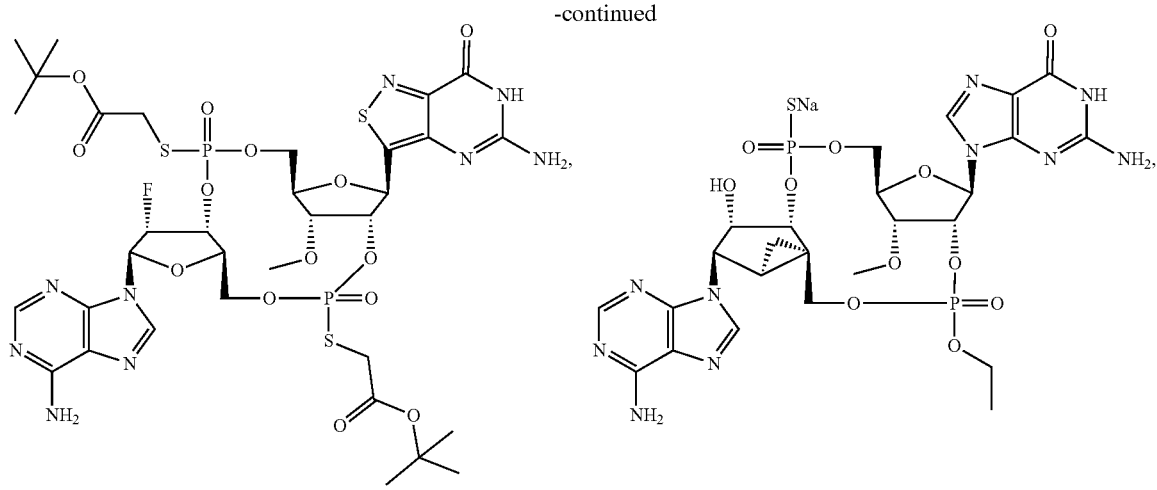
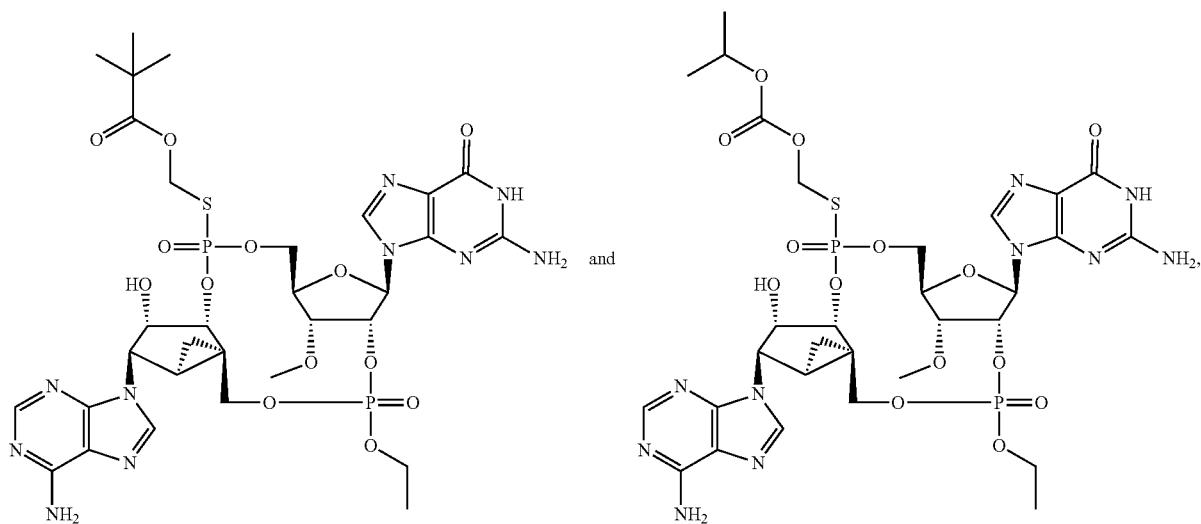
or a pharmaceutically acceptable salt of any of the foregoing.
Those skilled in the art understand that certain compounds described herein can be enantiomers or diastereomers. Examples of some diastereomers are provided below:
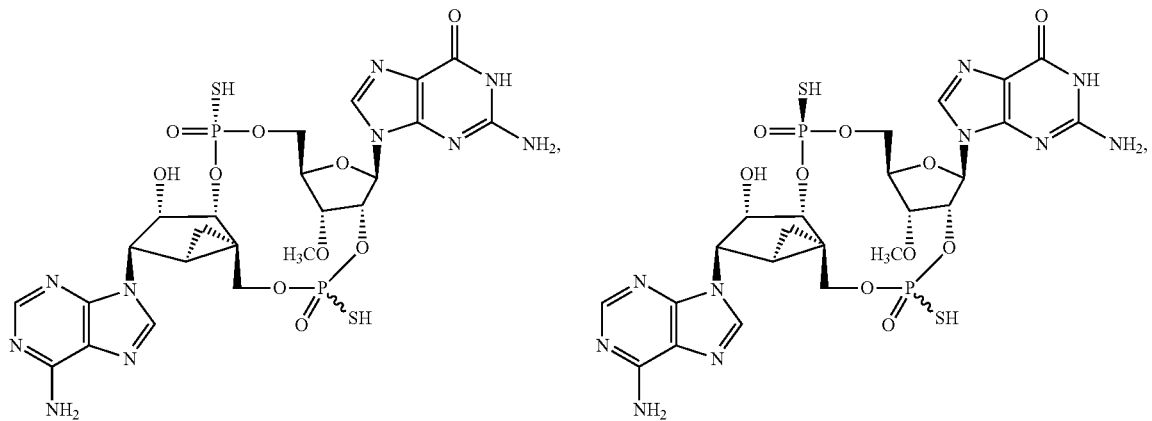

-continued
| 75 | 76 |
|---|---|
| 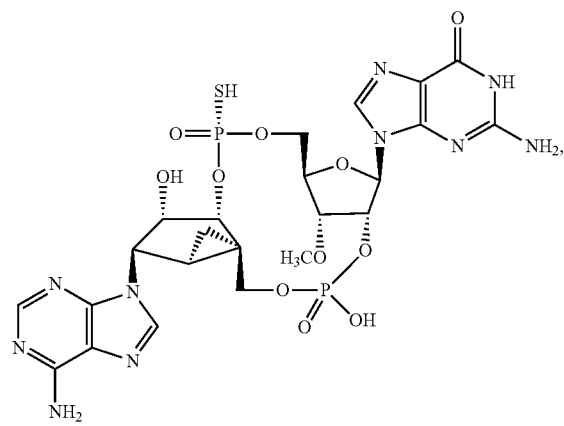 | 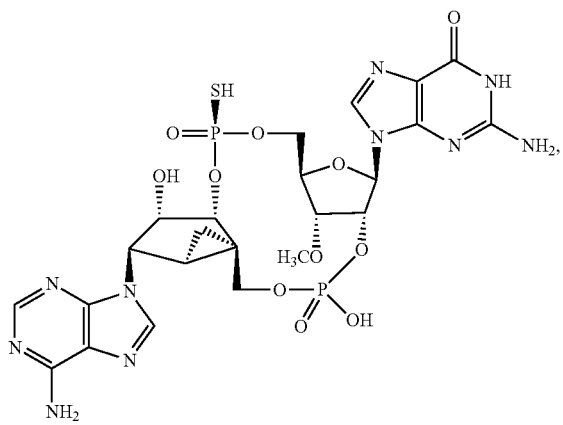 |
| 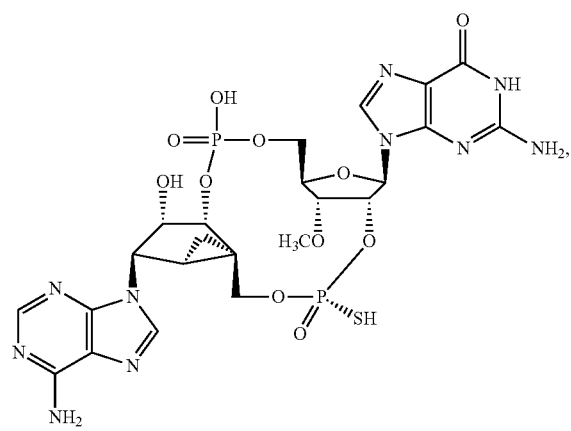 | 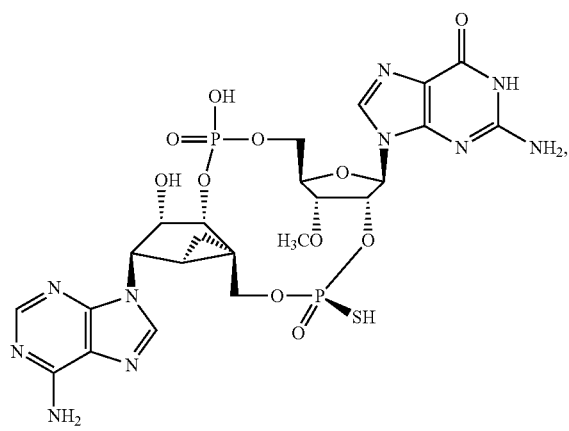 |
| 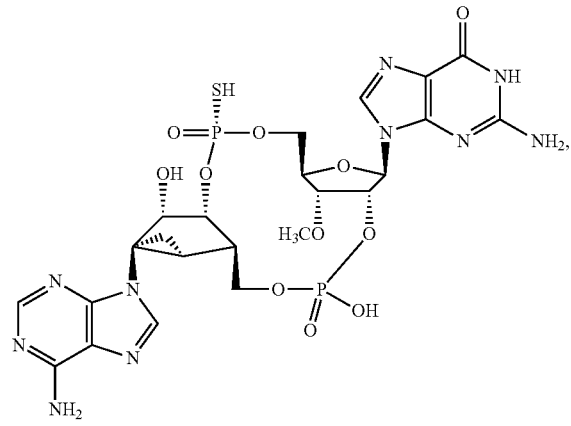 | 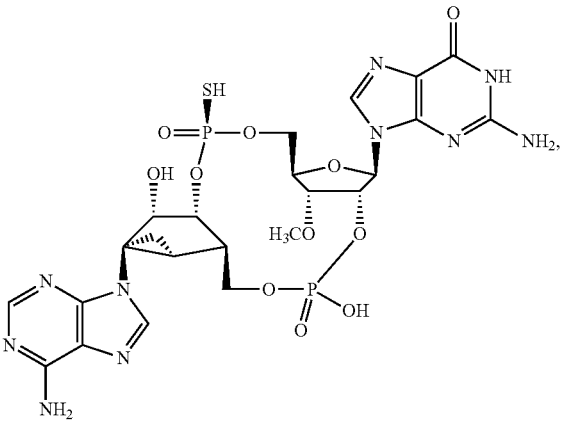 |
| 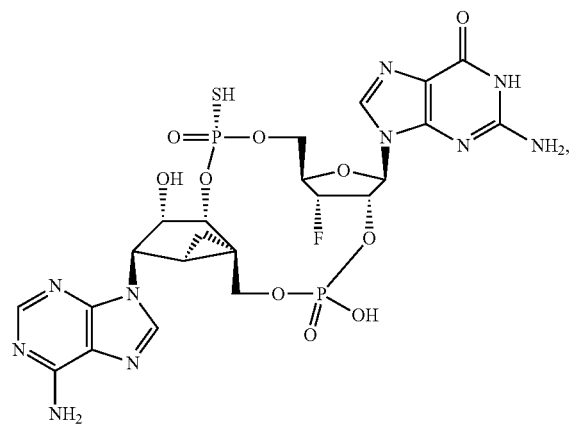 | 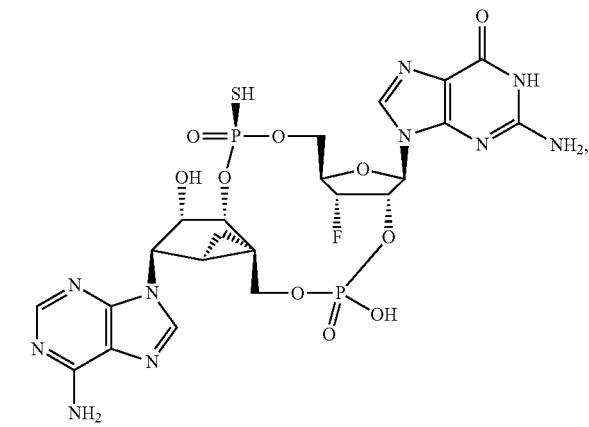 |

| 77 | 78 |
|---|---|
| 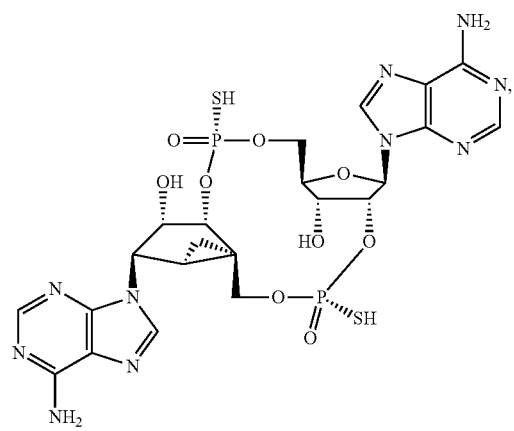 | 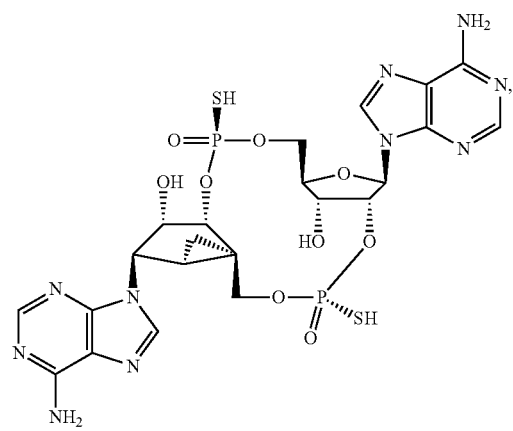 |
| 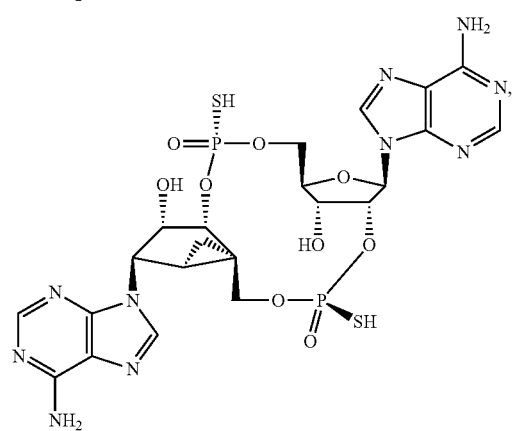 | 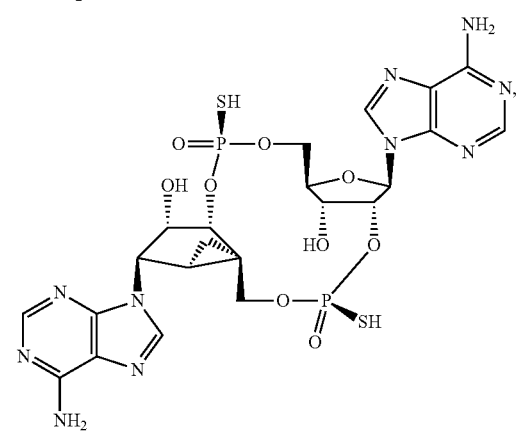 |
| 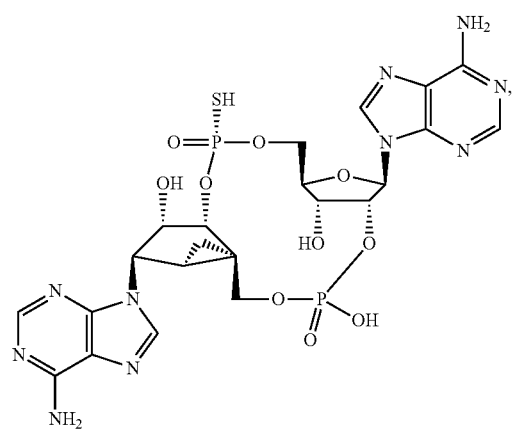 | 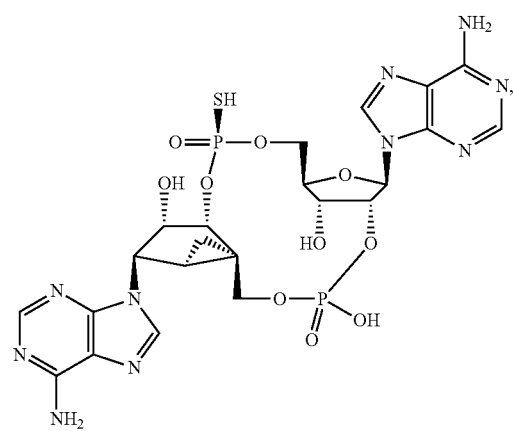 |
| 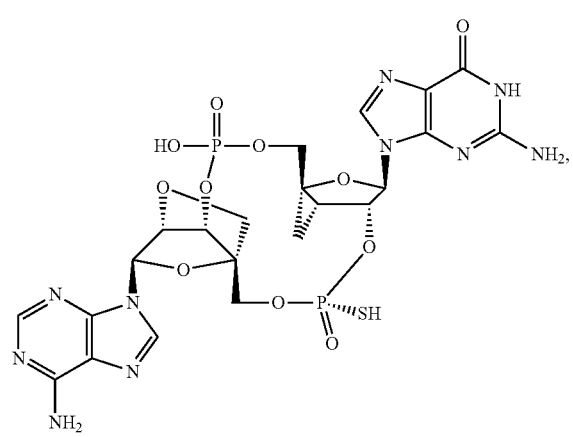 | 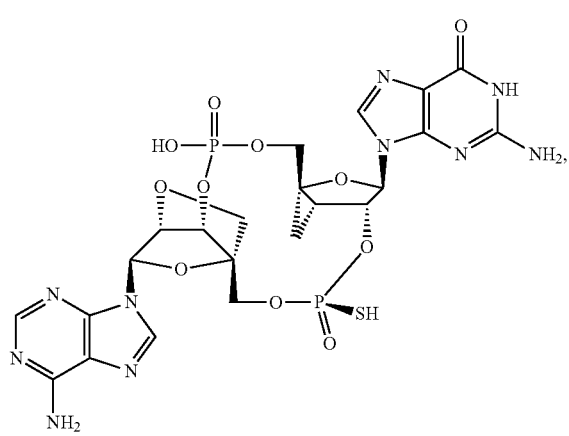 |

-continued
| 79 | 80 |
|---|---|
| 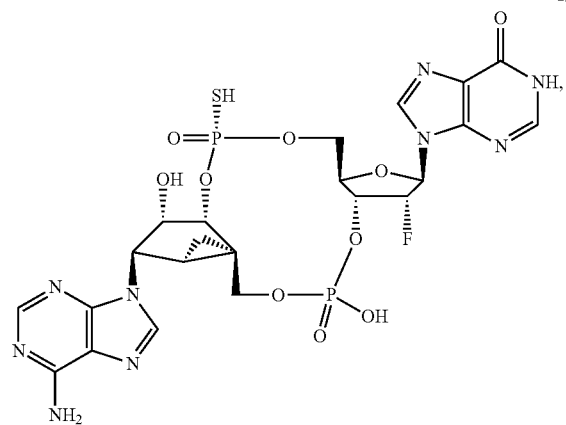 | 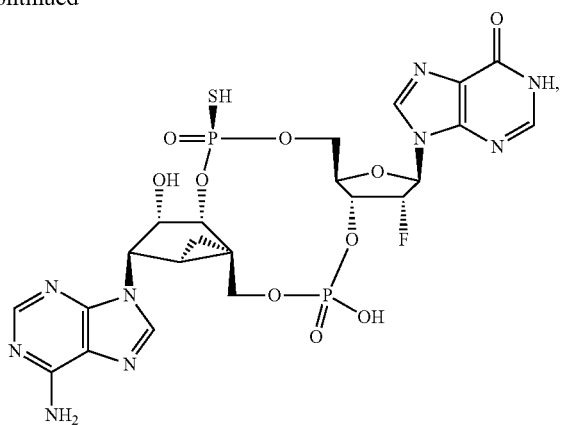 |
| 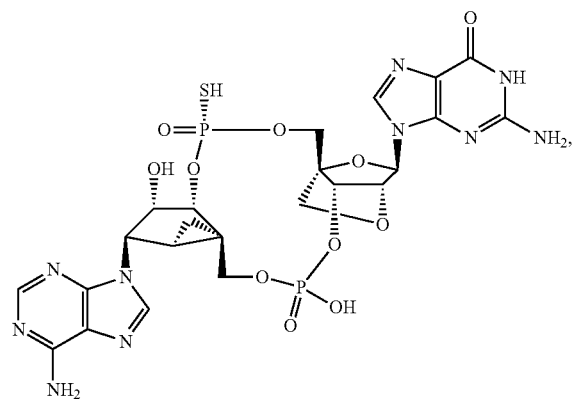 | 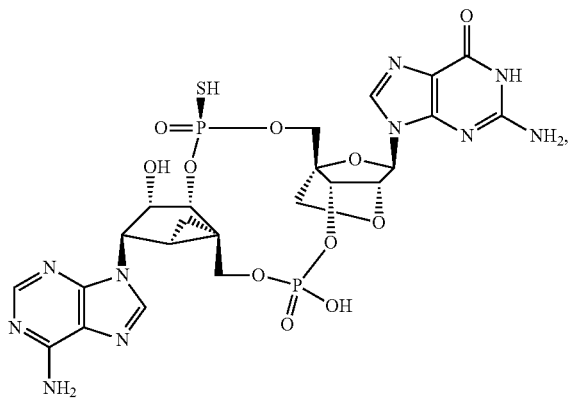 |
| 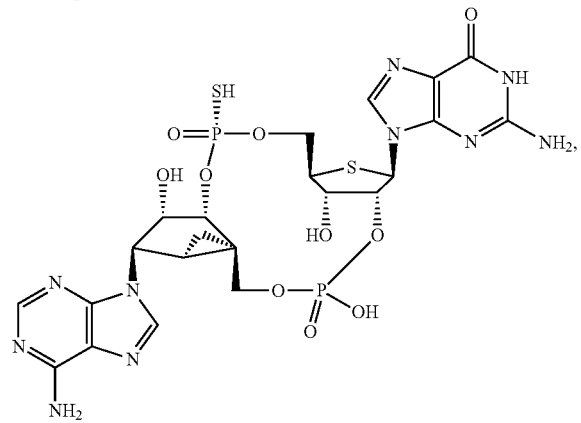 | 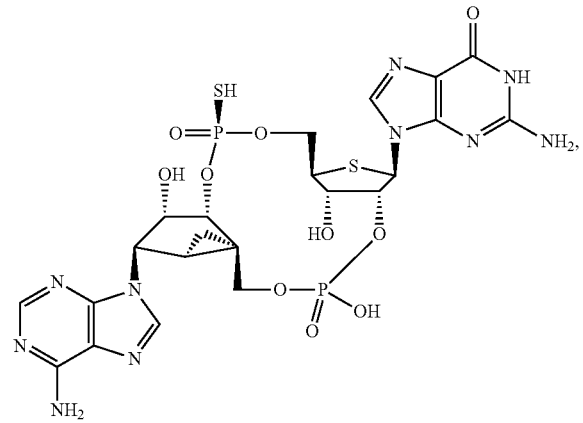 |
| 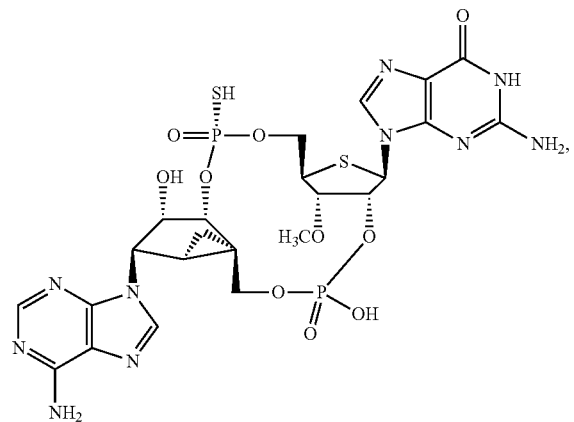 | 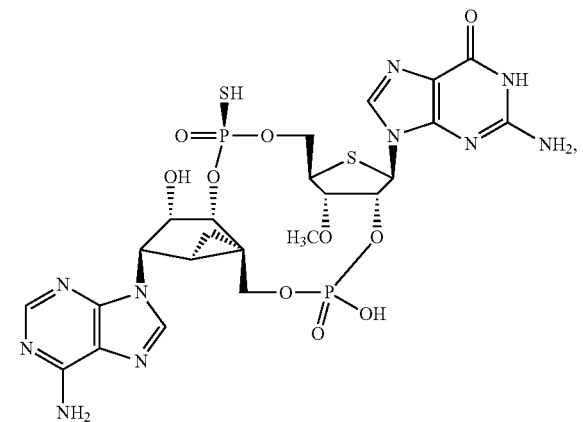 |

81
82
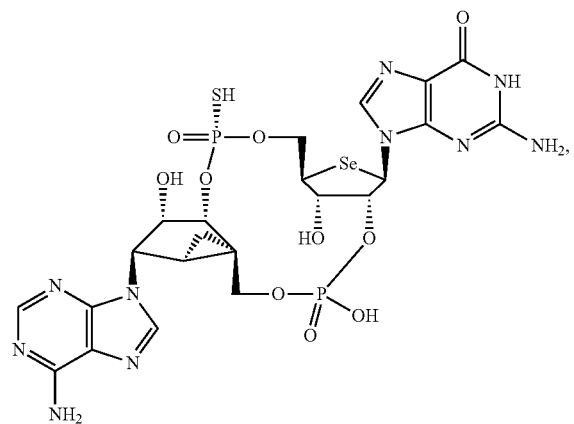
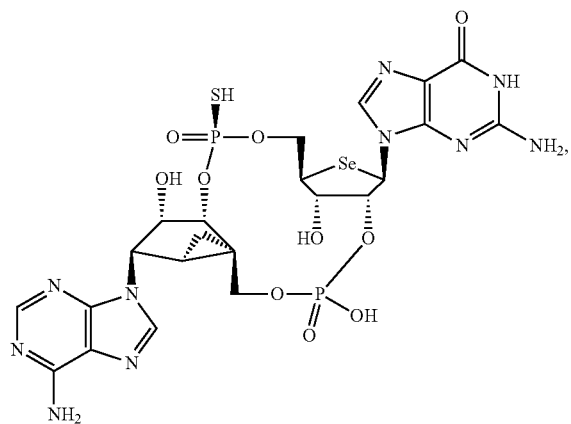
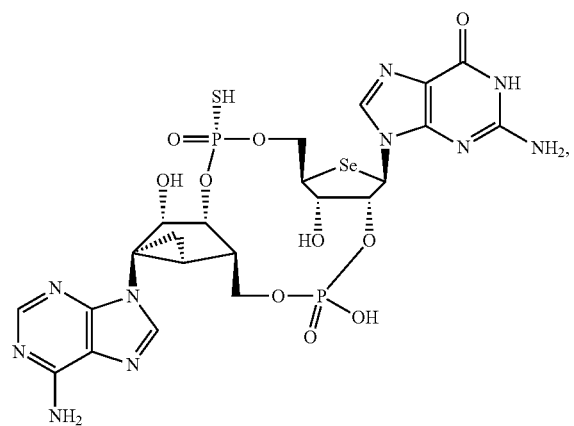
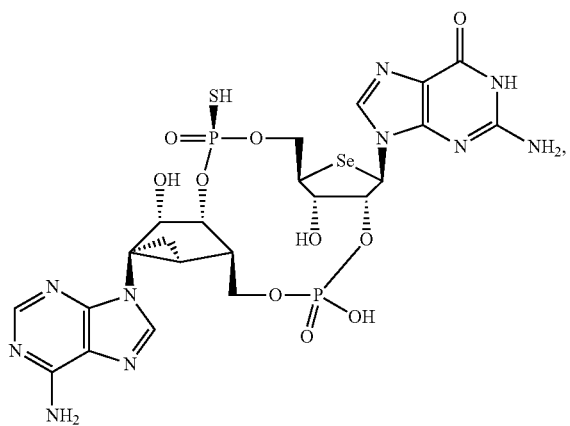
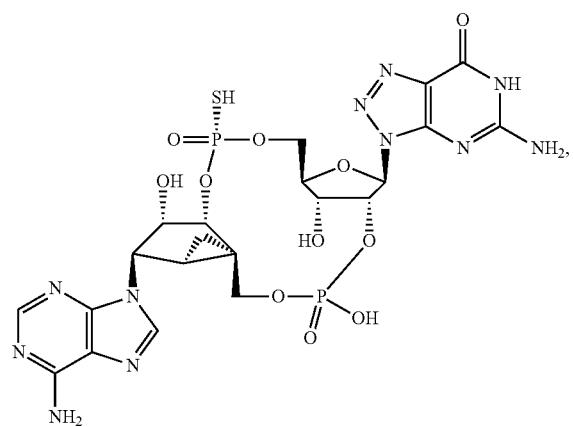
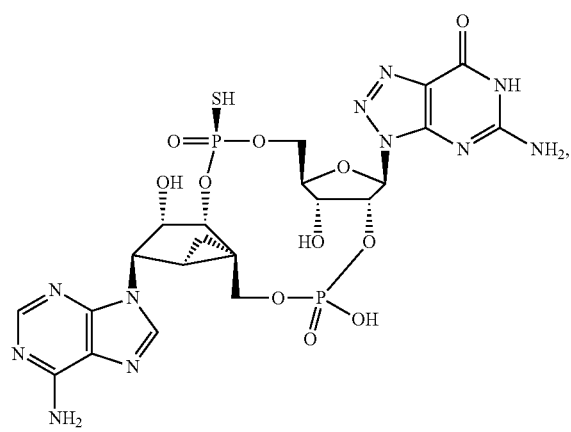
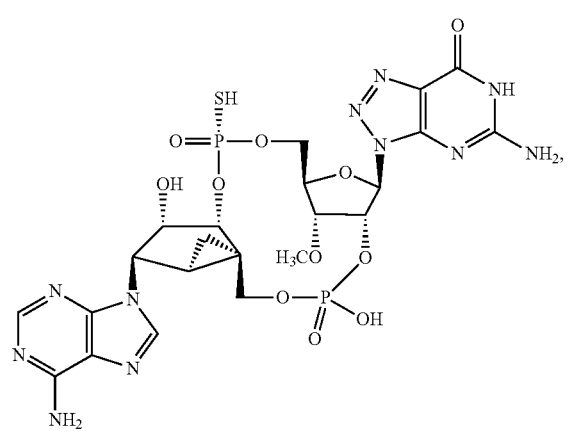
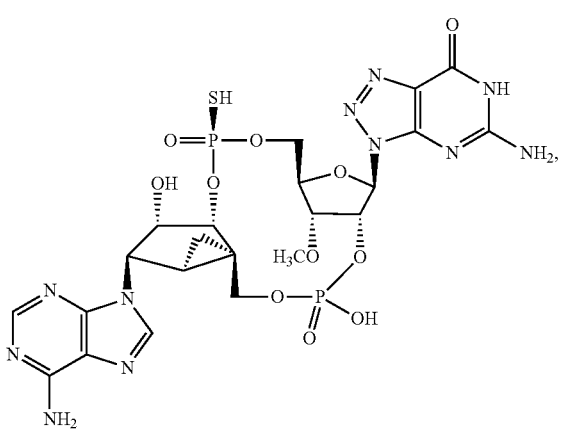

83
84
-continued
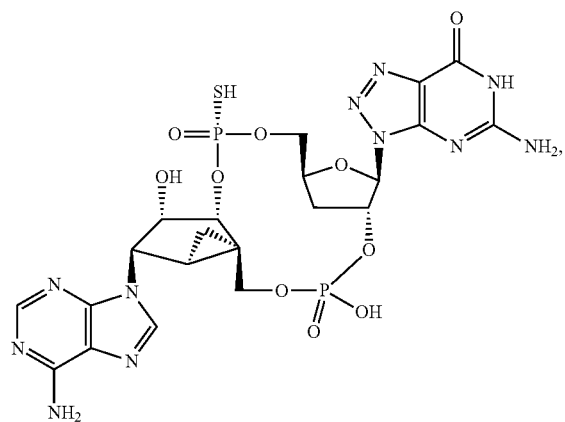
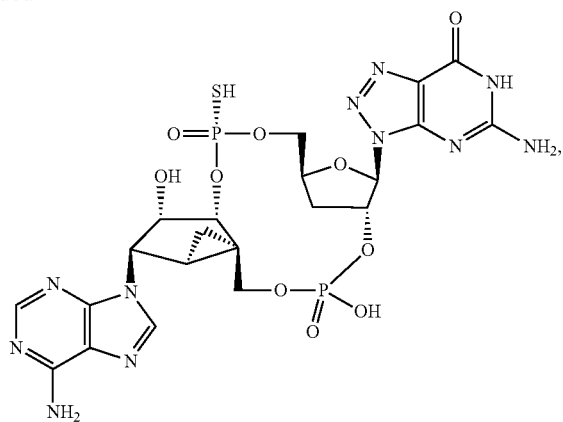
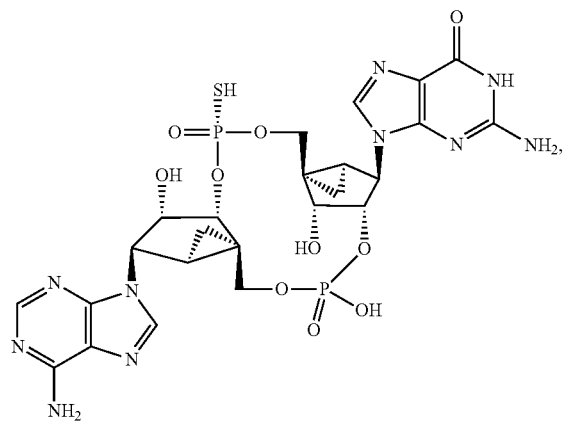
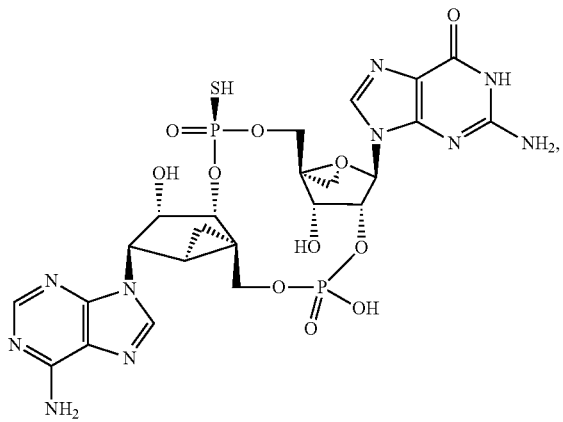
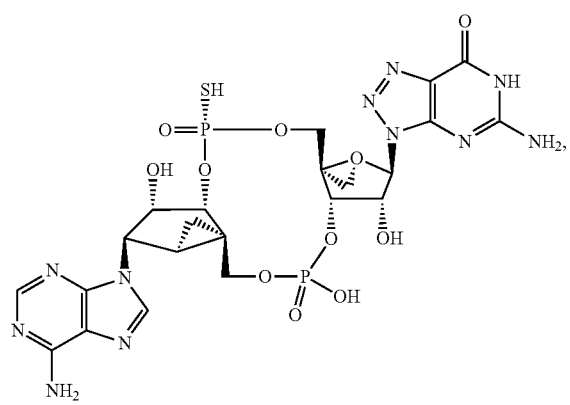
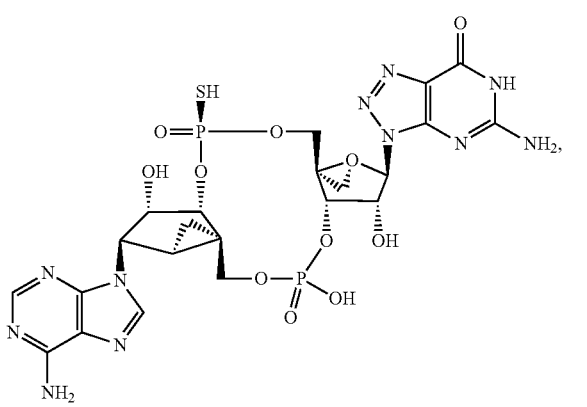
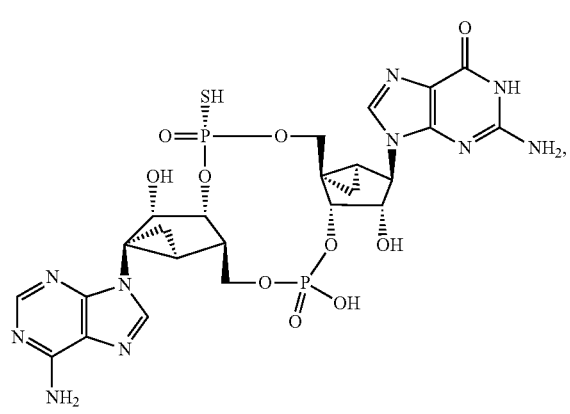
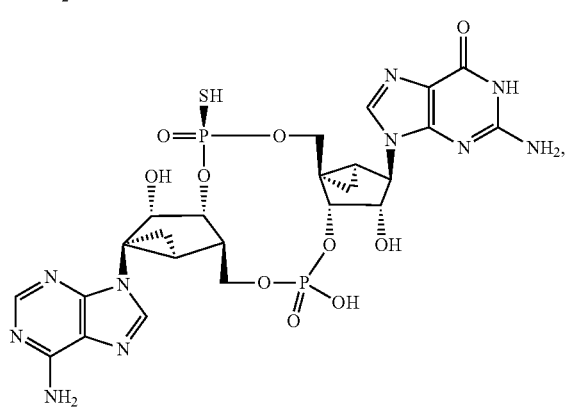

85 86
-continued
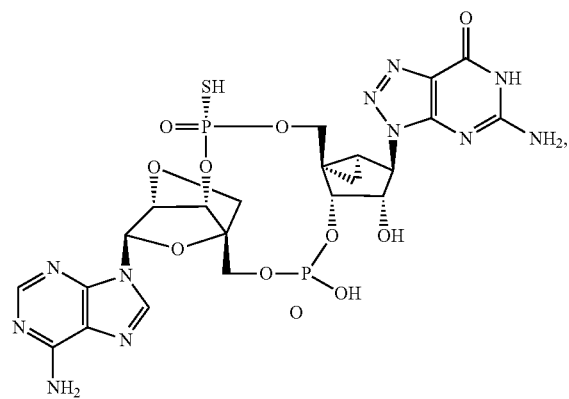 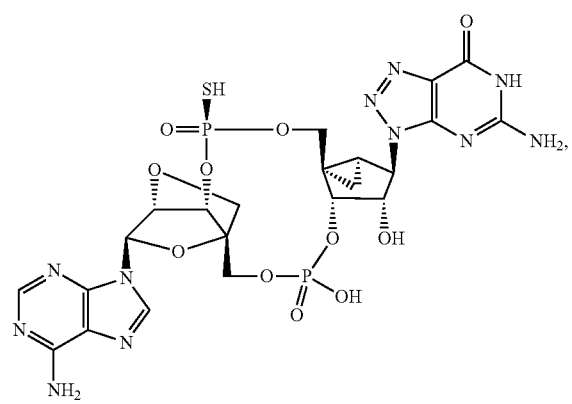
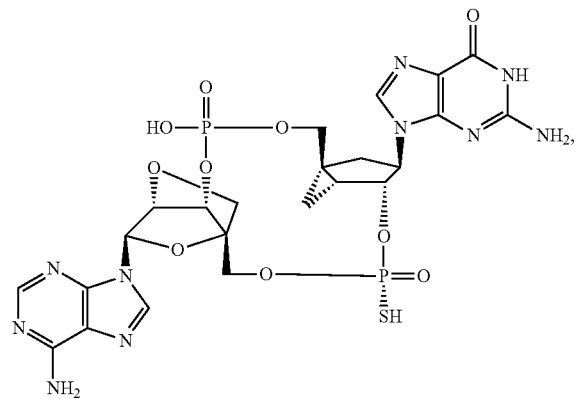 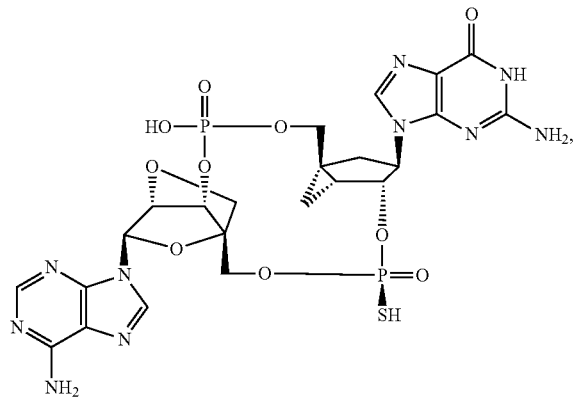
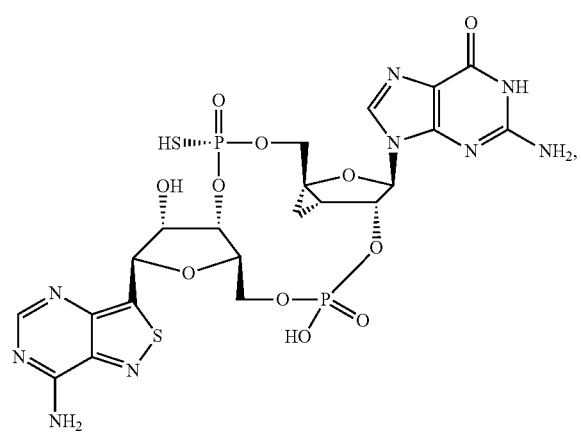 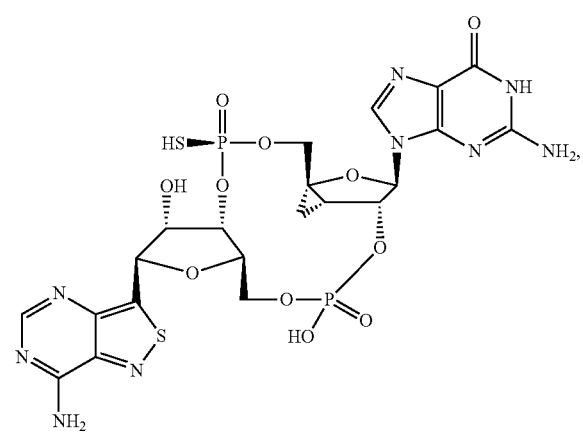
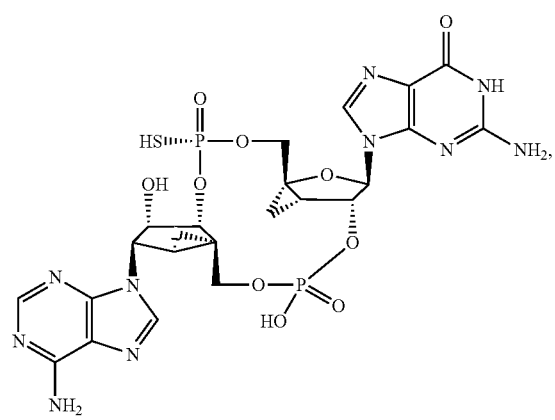 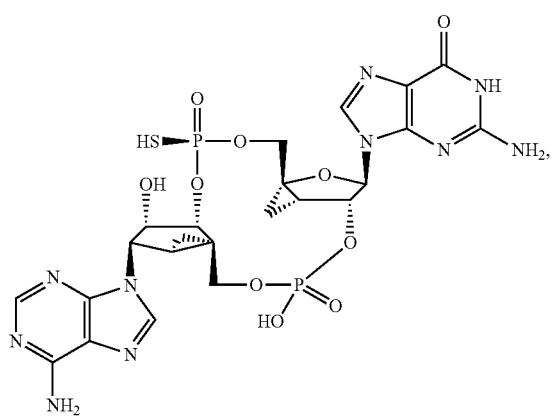

-continued
87
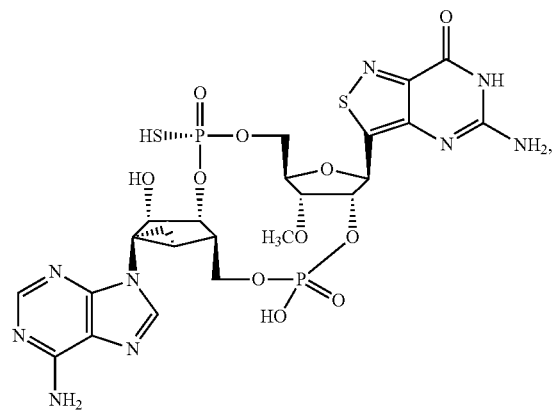
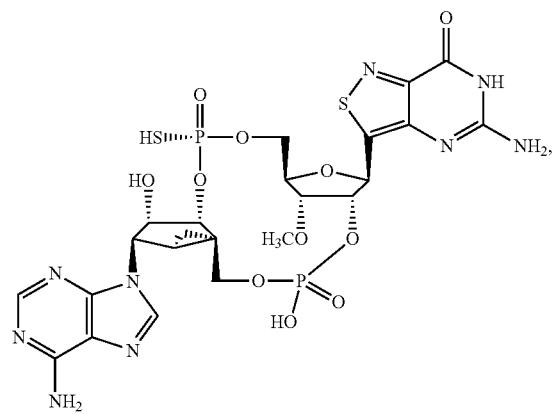
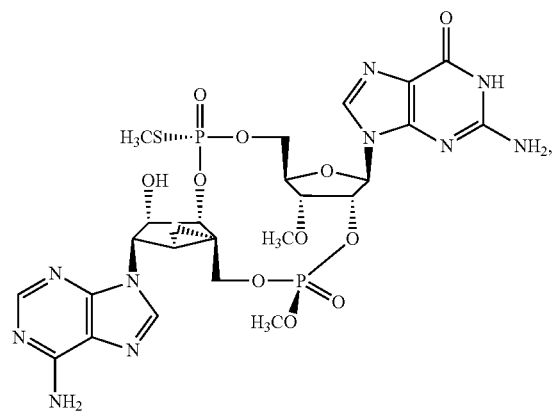
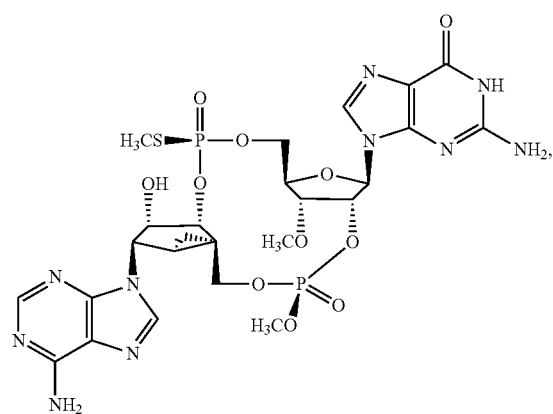
88
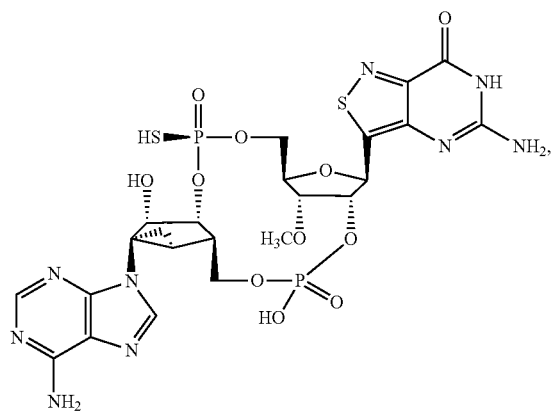
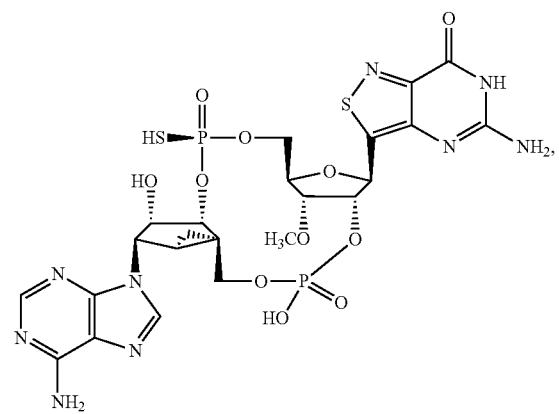
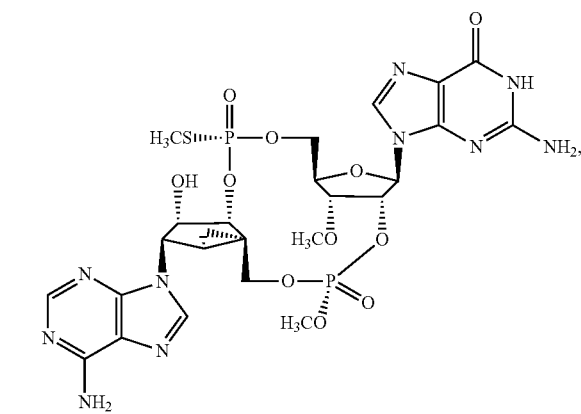
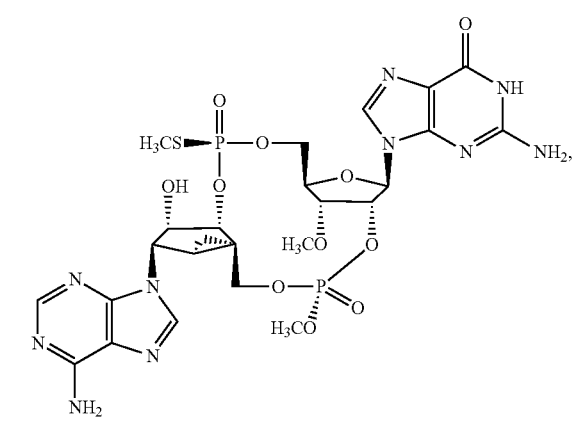

89
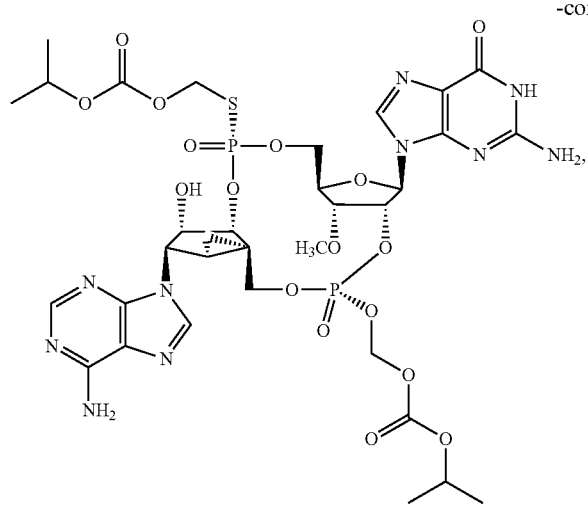
90
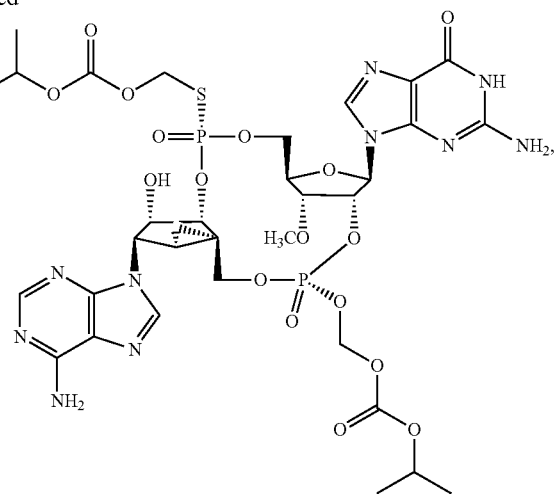
-continued
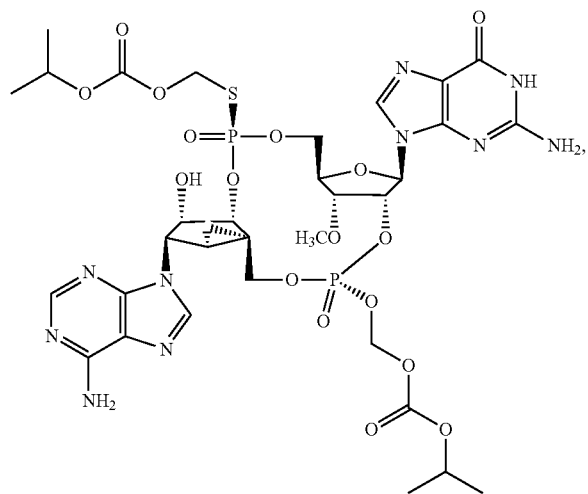
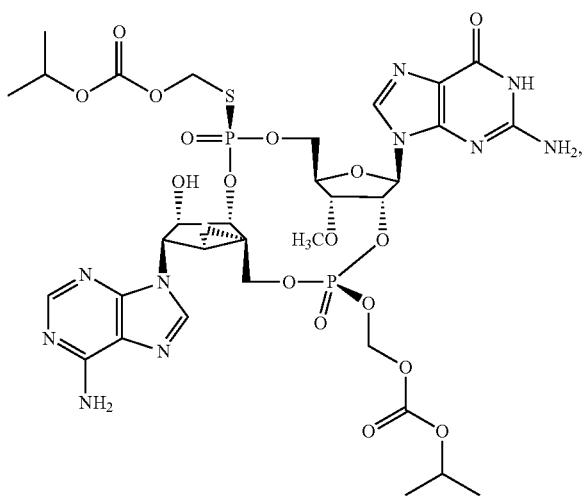
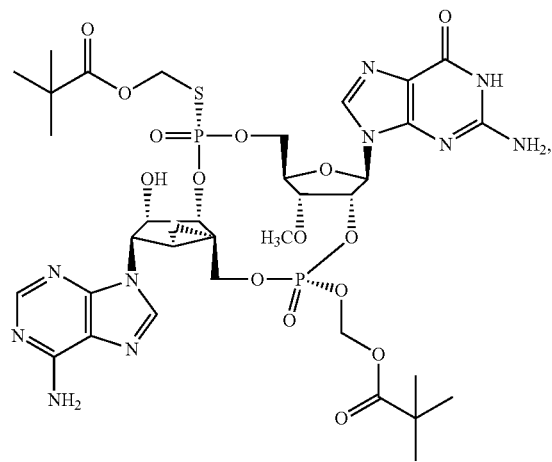
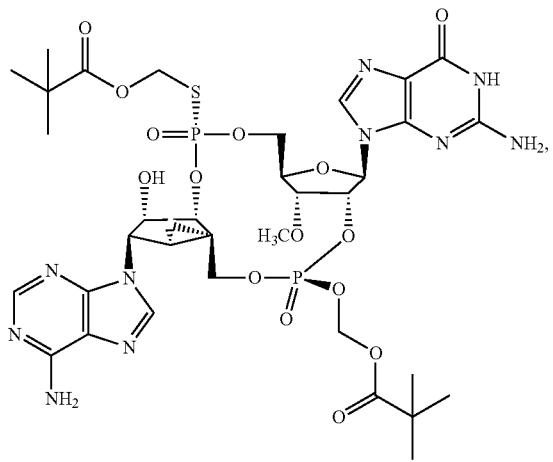

-continued
91
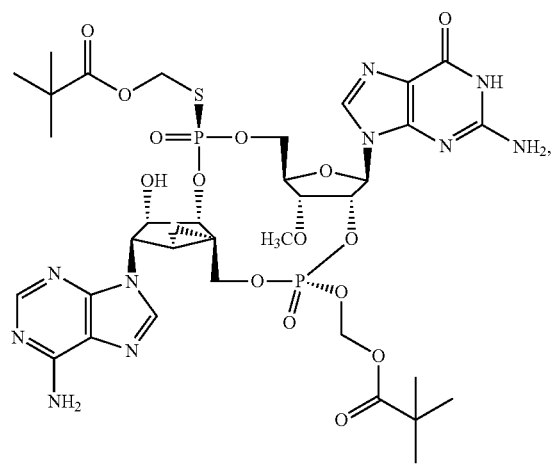
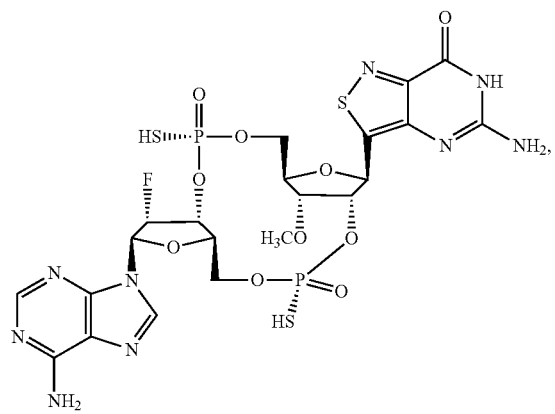
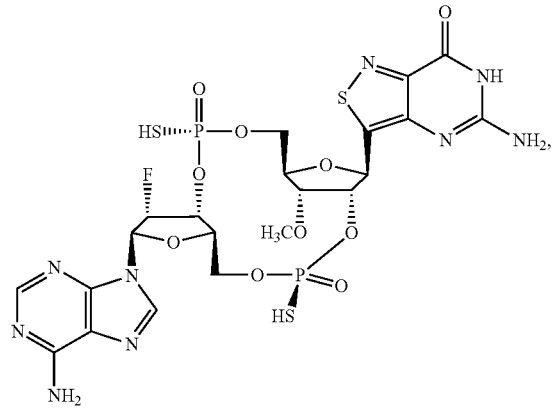
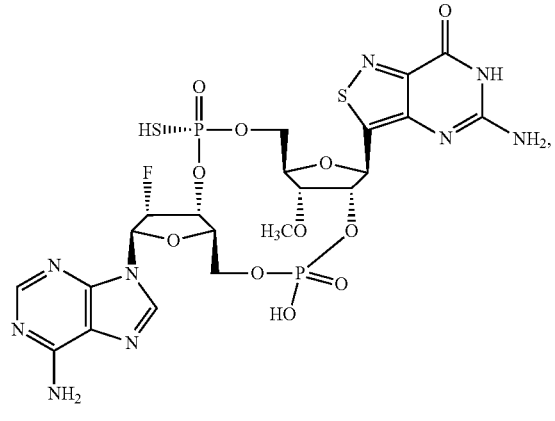
92
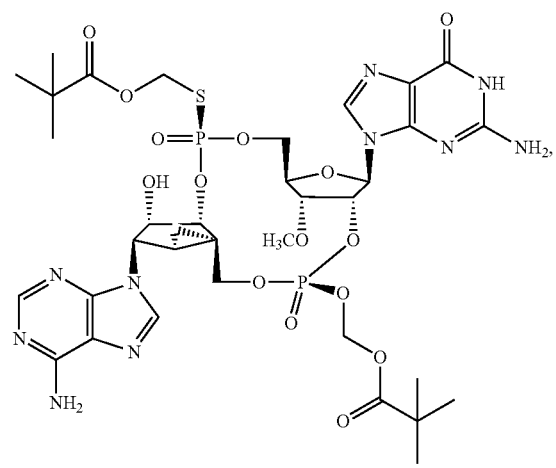
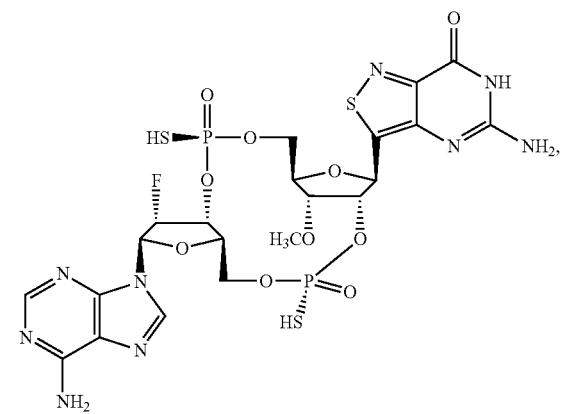
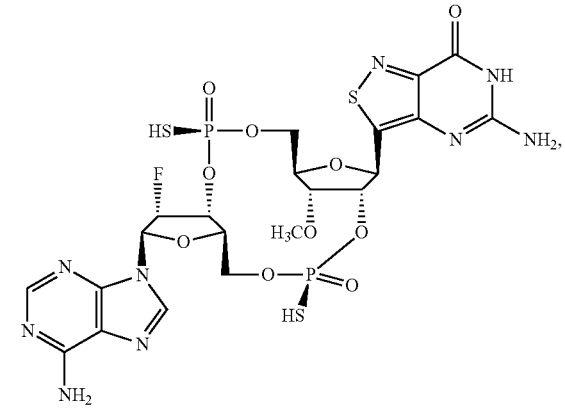
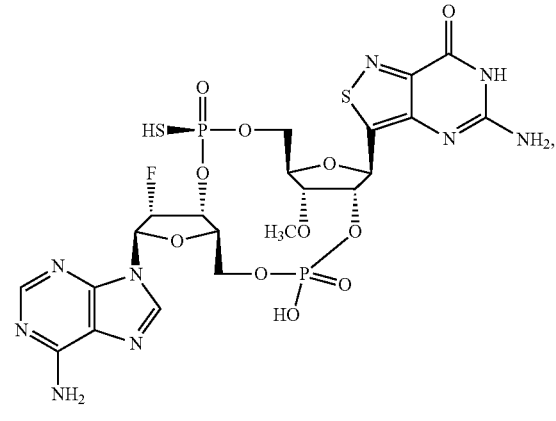

-continued
| 93 | 94 |
|---|---|
| 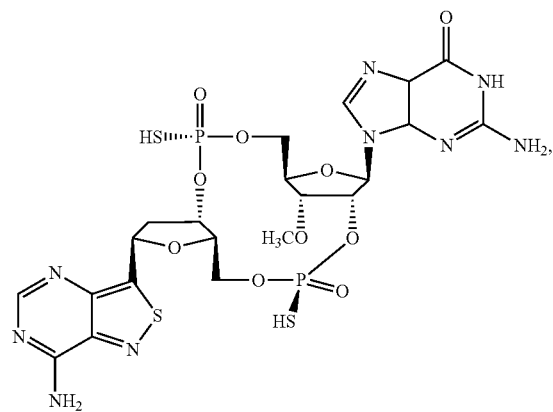 | 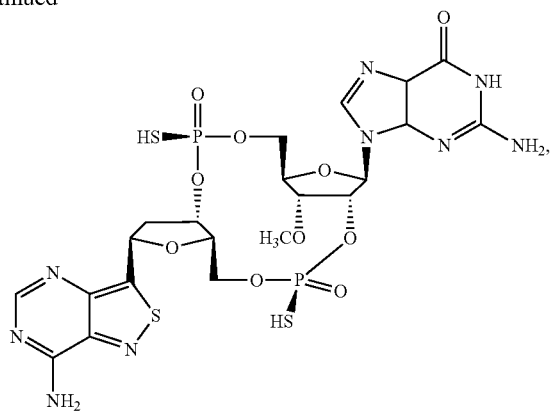 |
| 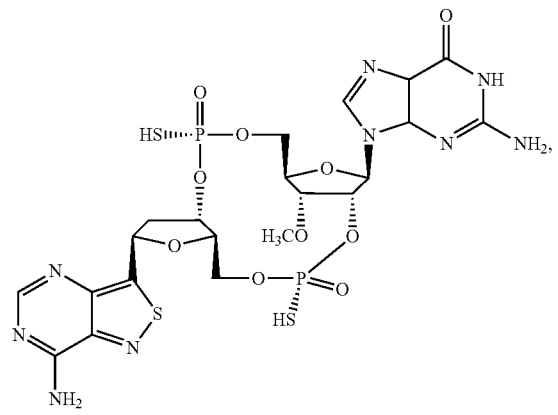 | 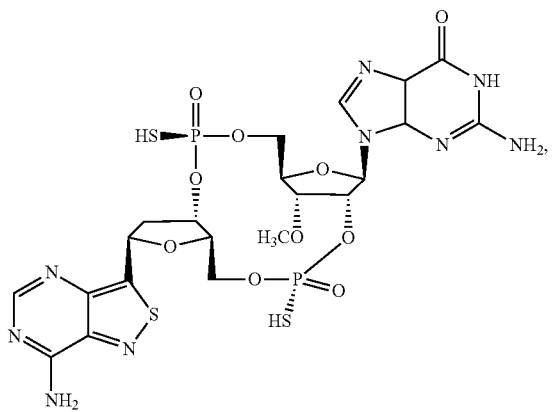 |
| 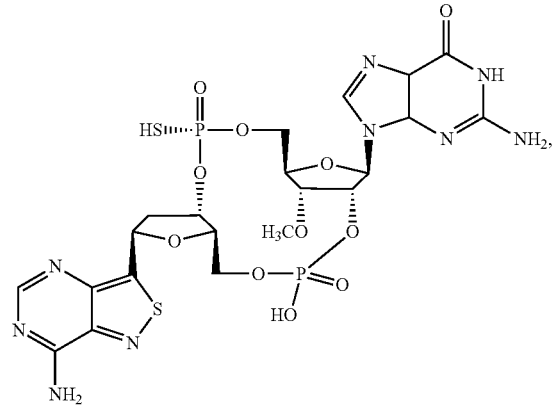 | 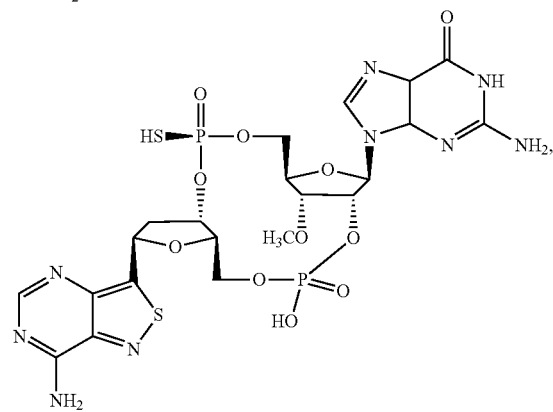 |
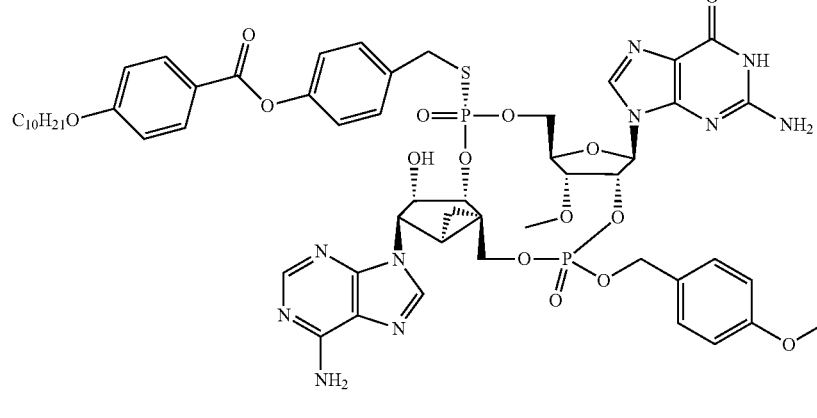

-continued
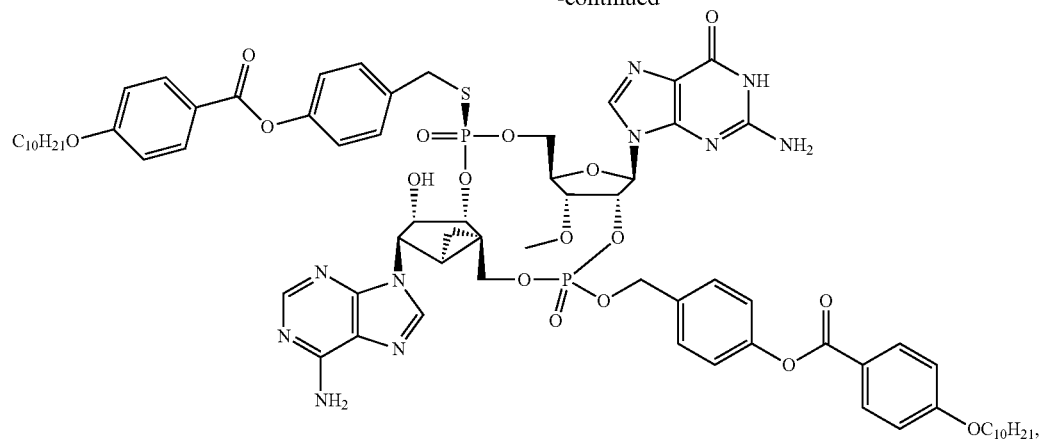
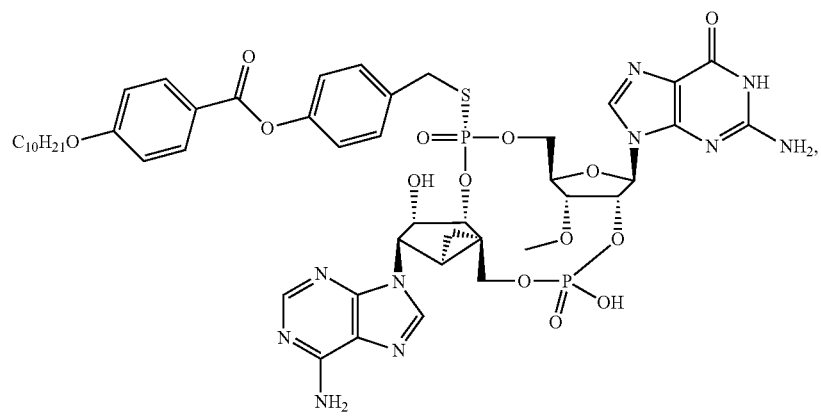
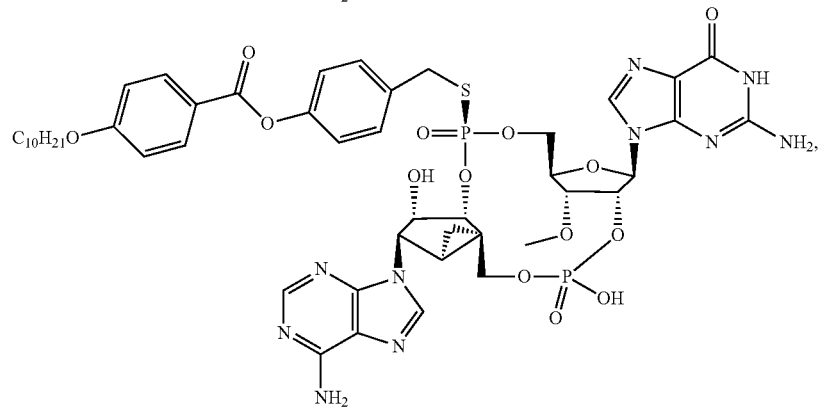
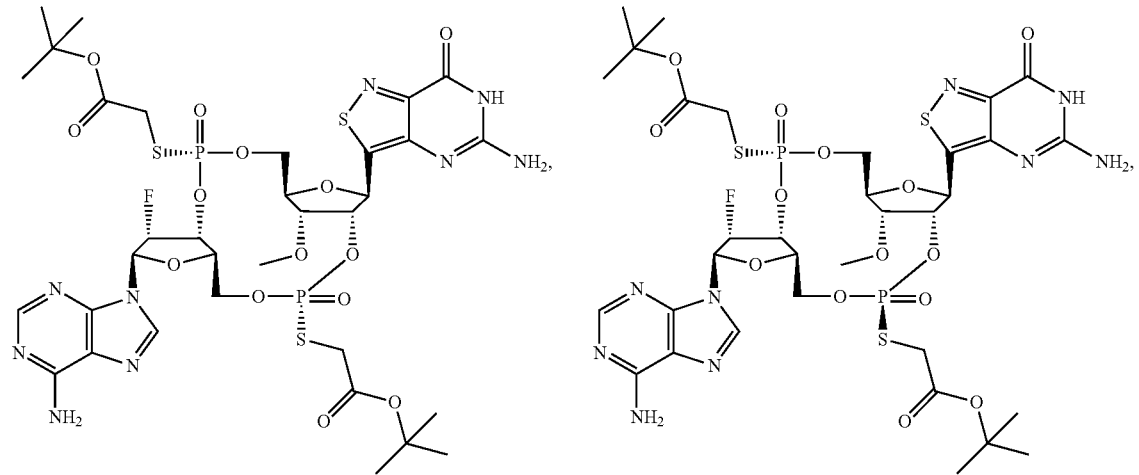

-continued
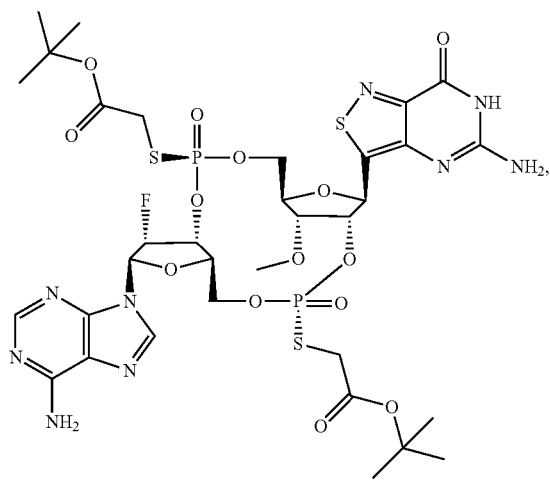
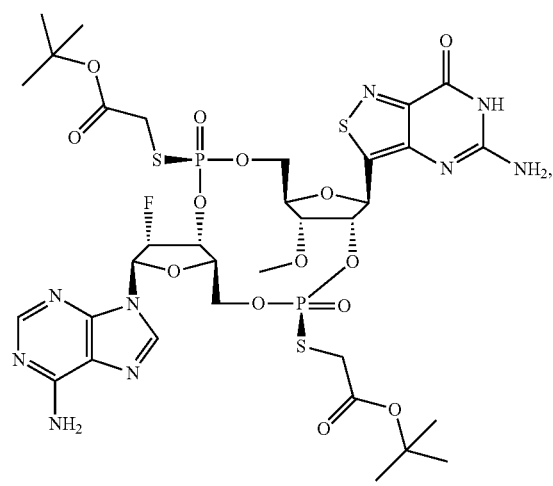
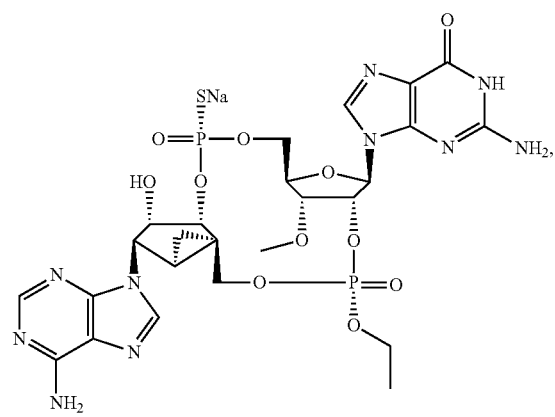
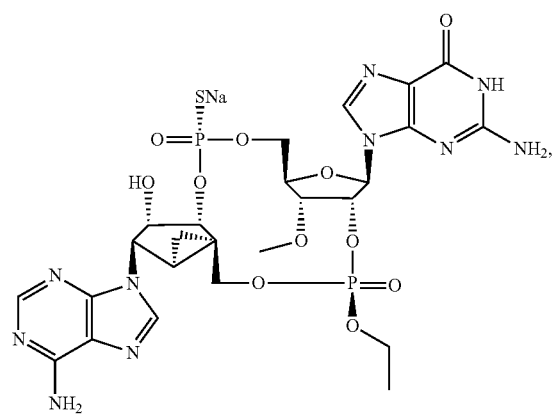
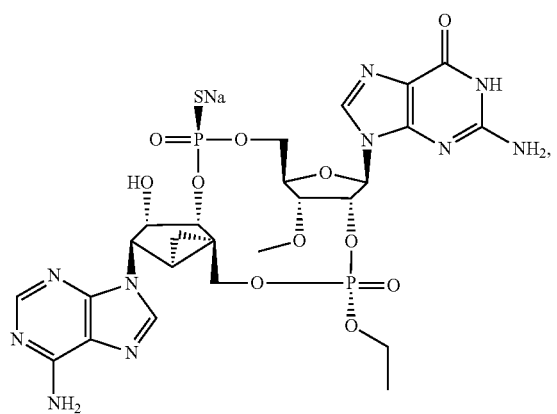

-continued
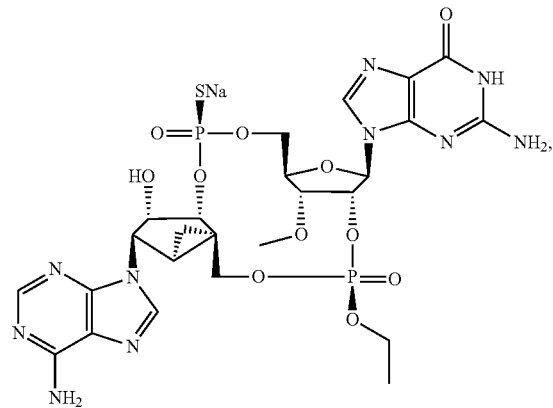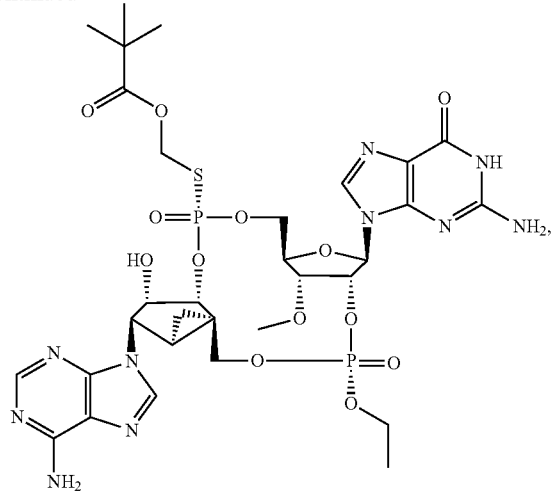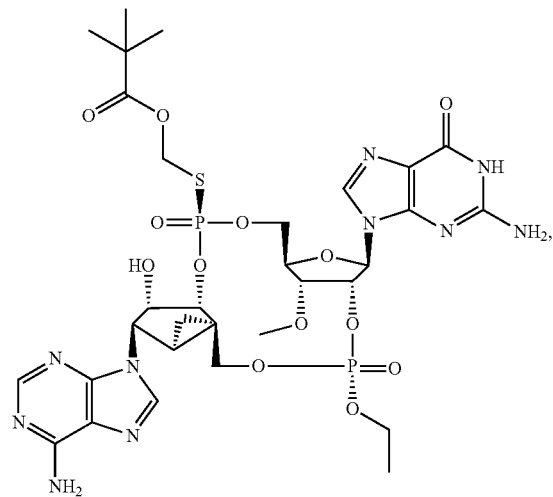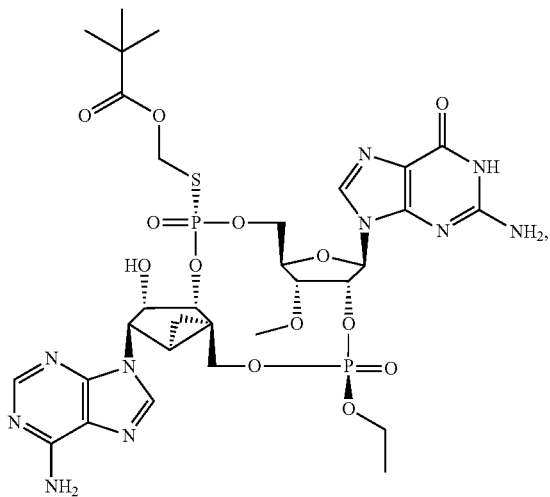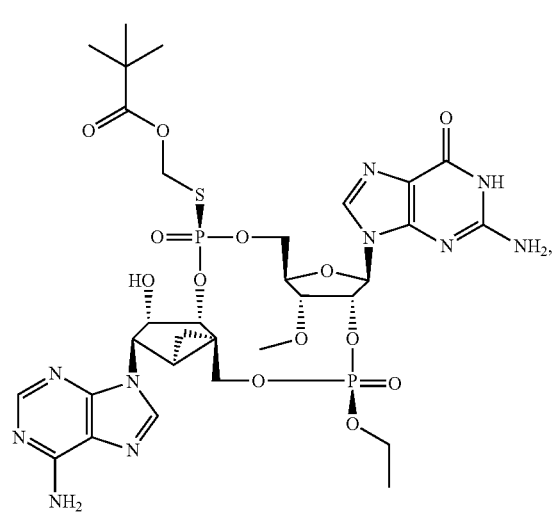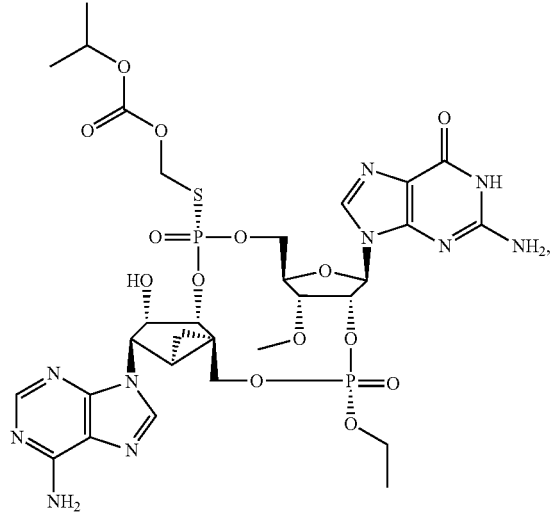

-continued
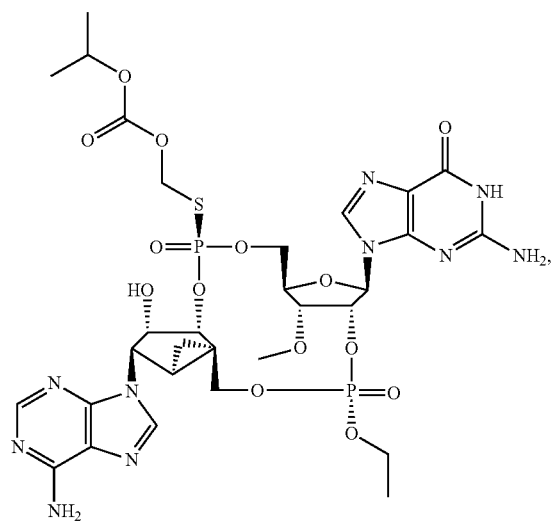
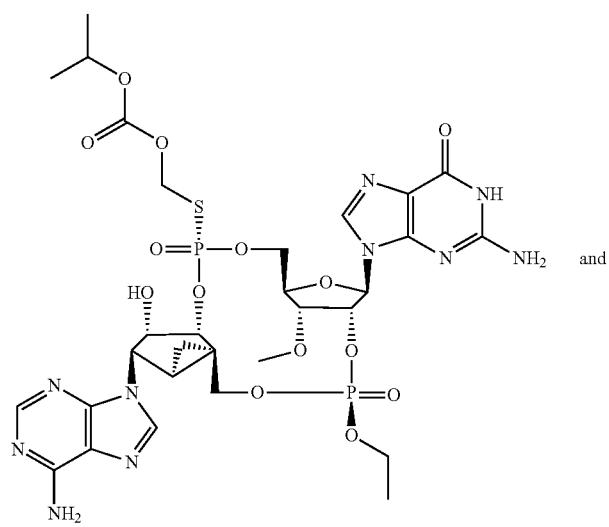
and
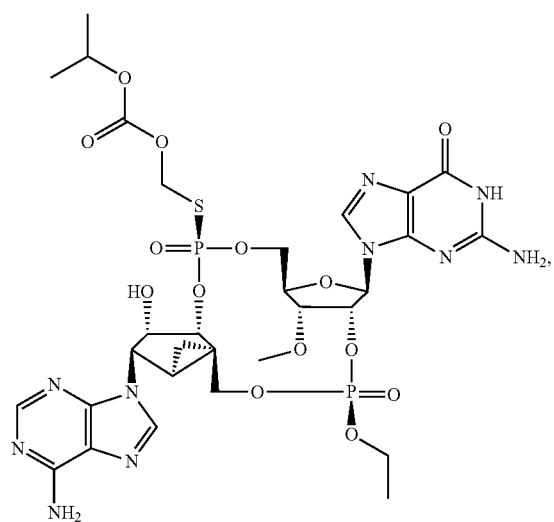

or a pharmaceutically acceptable salt of any of the foregoing.

Those skilled in the art understand that each nucleotide of compounds of Formulae (I), (II) and (III), and pharmaceutically acceptable salts thereof, is depicted as a natural nucleotide. An example showing that each nucleotide is a natural nucleotide is the following:

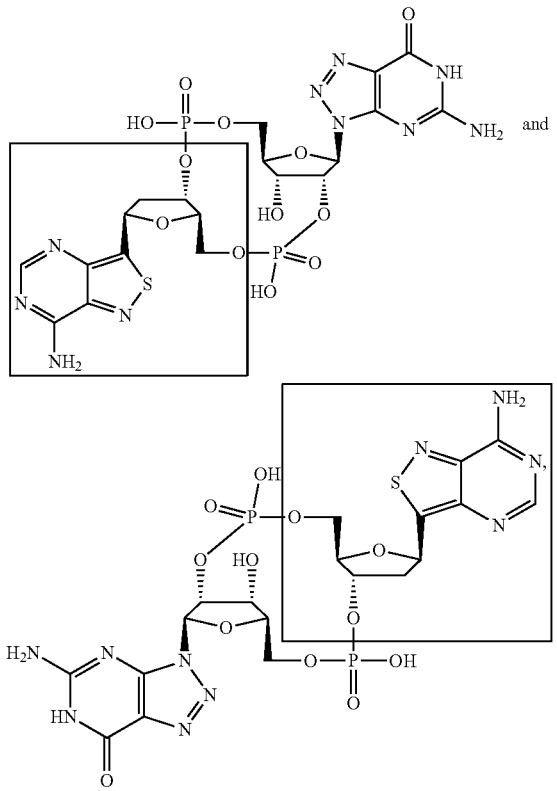

wherein the second structure is the same compound as the first structure, and the second structure is the first structure rotated 180 degrees clockwise. As shown by the first and second structures, when the lower nucleotide of the first structure is rotated 180 degrees clockwise (indicted with square in each structure), this nucleotide is in a natural nucleotide configuration as shown by the second structure.

In some embodiments, a compound of Formula (I), or a pharmaceutically acceptable salt thereof, when Ring $A^{1A}$ is

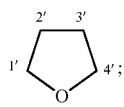

Ring $A^{2A}$ is

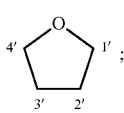

$B^{1A}$ is adenine or guanine; and $B^{2A}$ is adenine or guanine; then at least one of $X^{1A}$ and $X^{3A}$ is SH or S$^-$; or then at least one of $X^{2A}$ and $X^{4A}$ is S (sulfur). In some embodiments, a compound of Formula (II), or a pharmaceutically acceptable salt thereof, when Ring $A^{1B}$ is

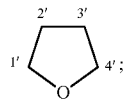

Ring $A^{2B}$ is

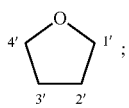

$B^{1B}$ is adenine or guanine; and $B^{2B}$ is adenine or guanine; then at least one of $X^{1B}$ and $X^{3B}$ is SH or S$^-$; or then at least one of $X^{2B}$ and $X^{4B}$ is S (sulfur). In some embodiments, a compound of Formula (III), or a pharmaceutically acceptable salt thereof, when Ring $A^{1C}$ is

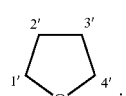

Ring $A^{2C}$ is

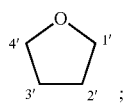

$B^{1C}$ is adenine or guanine; and $B^{2C}$ is adenine or guanine; then at least one of $X^{1C}$ and $X^{3C}$ is SH or S$^-$; or then at least one of $X^{2C}$ and $X^{4C}$ is S (sulfur).

In some embodiments, when Ring $A^{1A}$ is

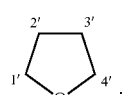

and Ring $A^{2A}$ is

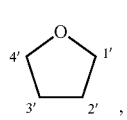

then at least one of $B^{1A}$ and $B^{2A}$ is not adenine or guanine.

In some embodiments, when Ring $A^{1B}$ is

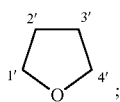;

and Ring $A^{2B}$ is

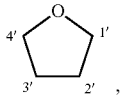, then at least one of $B^{1B}$ and $B^{2B}$ is not adenine or guanine. In some embodiments, when Ring $A^{1C}$ is

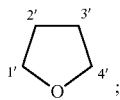;

and Ring $A^{2C}$ is

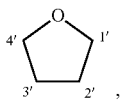, then at least one of $B^{1C}$ and $B^{2C}$ is not adenine or guanine. In some embodiments, when Ring $A^{1A}$ is

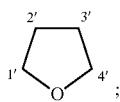;

and Ring $A^{2A}$ is

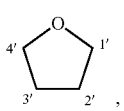, then $B^{1A}$ is not adenine. In some embodiments, when Ring $A^{1A}$ is

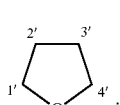;

and Ring $A^{2A}$ is

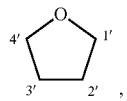, then $B^{1A}$ is not guanine. In some embodiments, when Ring $A^{1B}$ is

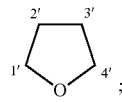;

and Ring $A^{2B}$ is

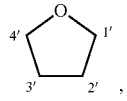, then $B^{1B}$ is not adenine. In some embodiments, when Ring $A^{1B}$ is

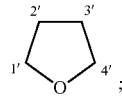;

and Ring $A^{2B}$ is

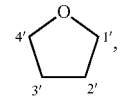, then $B^{1B}$ is not guanine. In some embodiments, when Ring $A^{1C}$ is

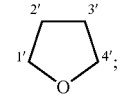;

and Ring $A^{2C}$ is

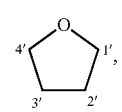, then $B^{1C}$ is not adenine. In some embodiments, when Ring $A^{1C}$ is

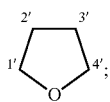

and Ring $A^{2C}$

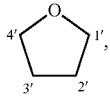

then $B^{1C}$ is not guanine.

In some embodiments, Ring $A^{1A}$ cannot be

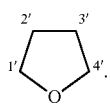

In some embodiments, Ring $A^{2A}$ cannot be

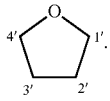

In some embodiments, Ring $A^{1B}$ cannot be

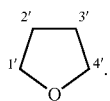

In some embodiments, Ring $A^{2B}$ cannot be

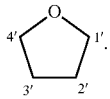

In some embodiments, Ring $A^{1C}$ cannot be

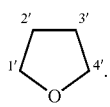

In some embodiments, Ring $A^{2C}$ cannot be

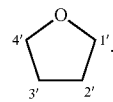

In some embodiments, Ring $A^{1A}$, Ring $A^{1B}$ and/or Ring $A^{1C}$ cannot be

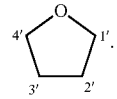

In some embodiments, Ring $A^{2A}$, Ring $A^{2B}$ and/or Ring $A^{2C}$ cannot be

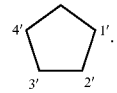

In some embodiments, $B^{1A}$ cannot be adenine or guanine. In some embodiments, $B^{2A}$ cannot be adenine or guanine. In some embodiments, $B^{1B}$ cannot be adenine or guanine. In some embodiments, $B^{2B}$ cannot be adenine or guanine. In some embodiments, $B^{1C}$ cannot be adenine or guanine. In some embodiments, $B^{2C}$ cannot be adenine or guanine. In some embodiments, $R^{2A}$ cannot be hydroxy. In some embodiments, $R^{4A}$ cannot be hydroxy. In some embodiments, $R^{2C}$ cannot be hydroxy.

Synthesis

Compounds of Formulae (I), (II) and (III), along with their pharmaceutically acceptable salts, along with those described herein may be prepared in various ways. General synthetic routes for preparing compounds of Formulae (I), (II) and (III), along with their pharmaceutically acceptable salts, are shown and described herein along with some examples of starting materials used to synthesize compounds described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme 1

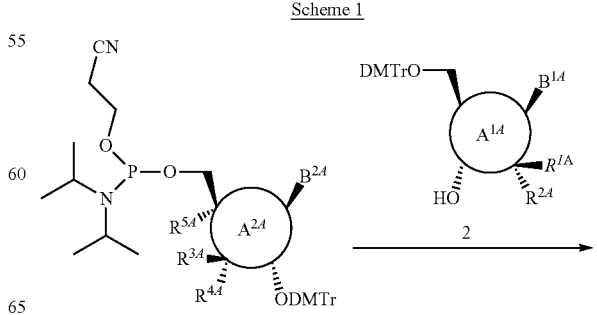

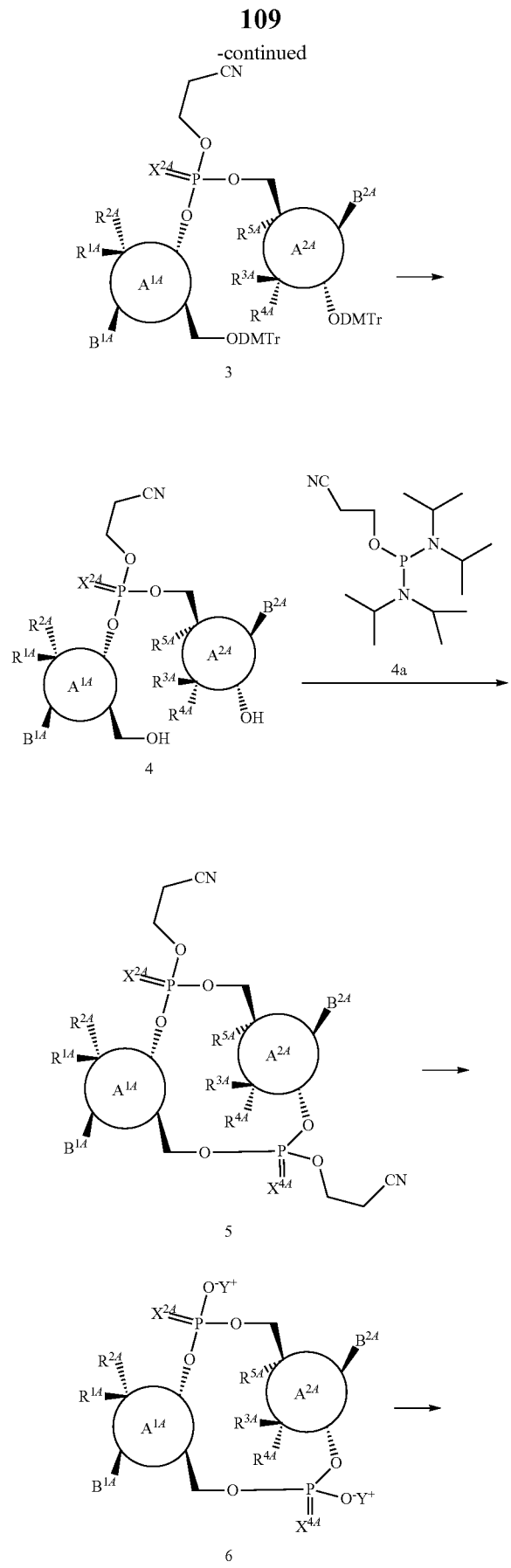

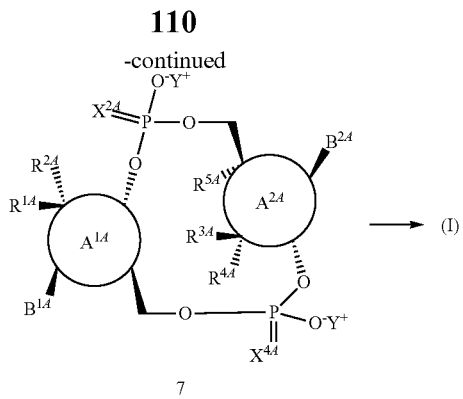

In Scheme 1, Ring $A^{1A}$, Ring $A^{2A}$, $B^{1A}$, $B^{2A}$, $X^{2A}$, $X^{4A}$, $R^{1A}$ and $R^{3A}$ can be as described herein, $R^{2A}$ and $R^{4A}$ can be as described herein or an protected oxygen as described herein (for example, OTBS), and Y can be a suitable salt counter ion A suitable substituted phosphoramidite, 1, can be coupled with an appropriate nucleoside, 2, using an activator (such as, 5-ethylthio-1H-tetrazole, tetrazole and/or dicyanoimidazole) in a suitable solvent or a mixture of solvents (for example, MeCN, $CH_2Cl_2$, THF, dioxane and the like), at a temperature ranging from about −10° C. to about 60° C., to yield the corresponding phosphite compound. This phosphite compound can be reacted with an oxidant (such as iodine, hydrogen peroxide, tert-butylperoxide, (S)-(+)-(10-camphorsulfonyl)oxaziridine, Beaucage reagent, dichloro-diphenyl-trichloroethane (DDTT), 3-amino-1,2,4-dithiazole-5-thione and/or PADS) in a suitable solvent or a mixture of solvents, such as $CHCl_3$, $CH_2Cl_2$, THF, MeCN, dioxane and the like, at a temperature ranging from about −10° C. to about 80° C., to generate a compound Formula 3.

The DMTr groups of a compound of Formula 3 can be removed using a suitable acid (such as, dichloroaceticacid, acetic acid and/or trifluoroacetic acid) in a suitable solvent or a mixture of solvents (for example, MeCN, $CH_2Cl_2$, THF and/or dioxane) to provide a compound of Formula 4.

A compound of Formula 4 can be cyclized using a reagent of Formula 4a along with an activator, such as 5-ethylthio-1H-tetrazole, tetrazole and/or dicyanoimidazole, in a suitable solvent or a mixture of solvents (for example, MeCN, $CH_2Cl_2$, dichloroethane, THF, dioxane and the like) at a temperature ranging from about −10° C. to about 60° C., to provide the corresponding phosphite compound. The phosphite compound can then be reacted with an oxidant (such as iodine, hydrogen peroxide, tert-butylperoxide, (1S)-(+)-(10-camphorsulfonyl)oxaziridine, Beaucage reagent, DDTT, 3-amino-1,2,4-dithiazole-5-thione and/or PADS) in a suitable solvent or a mixture of solvents (such as $CHCl_3$, $CH_2Cl_2$, THF, MeCN, dioxane and the like), at a temperature ranging from about −10° C. to about 80° C., to generate cyclized compound of Formula 5.

The nucleobase and phosphate protecting groups of a compound of Formula 5 can be removed using conditions known to those skilled in the art. Exemplary conditions include basic conditions, such as $MeNH_2$, $tBuNH_2$, ammonium hydroxide and the like, in a suitable solvent or a mixture of solvents at a suitable temperature to provide a compound of Formula 6. Examples of suitable solvent(s) include EtOH, $H_2O$, iPrOH and the like, and a suitable temperature can be in the range of about −10° C. to about 120° C.

Any silyl protecting groups of a compound of Formula 6 can be removed using TBAF, Ammonium fluoride, HF·TEA and like, in a suitable solvent or a mixture of solvents (such as pyridine, THF, dioxane, MeOH and like) at a temperature ranging from about −10° C. to about 120° C. to yield a compound of Formula 7.

An ammonium or triethyl ammonium counter ion of a compound of Formula 7 can be exchanged with a sodium or lithium using an Amberlyst and/or a Dowex resin to provide a compound of Formula (I), or a pharmaceutically acceptable salt thereof.

Scheme 2

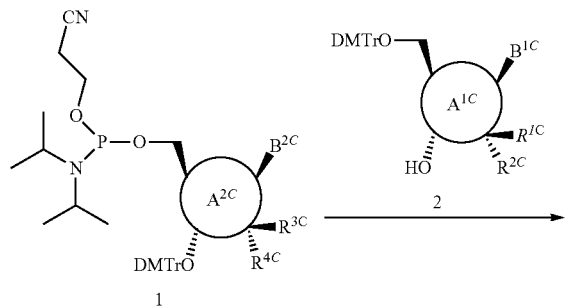

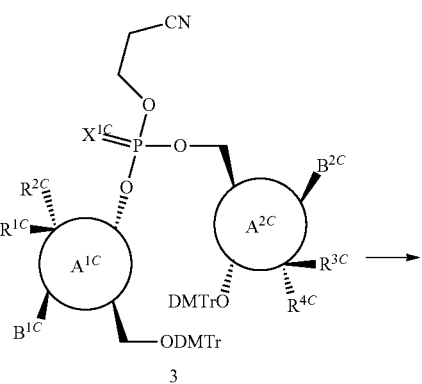

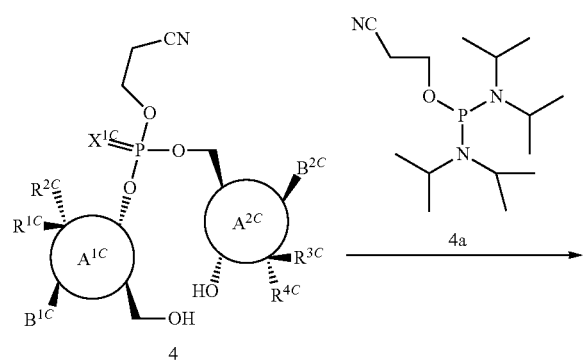

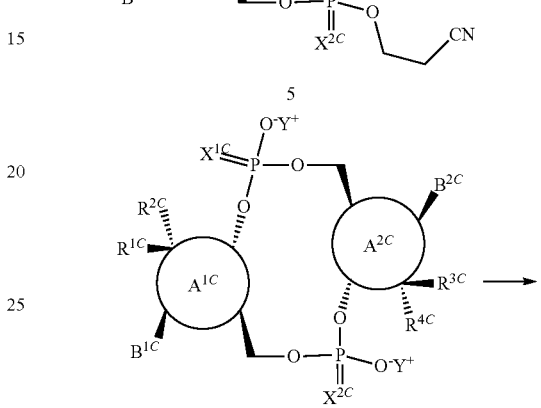

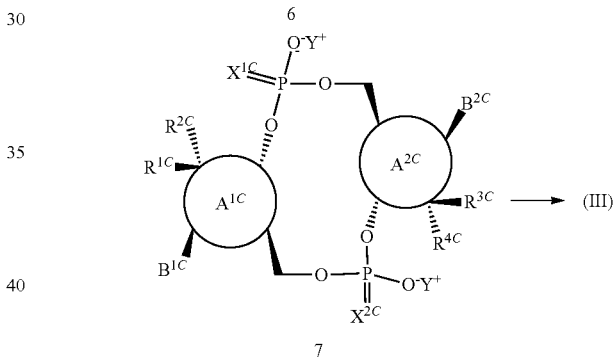

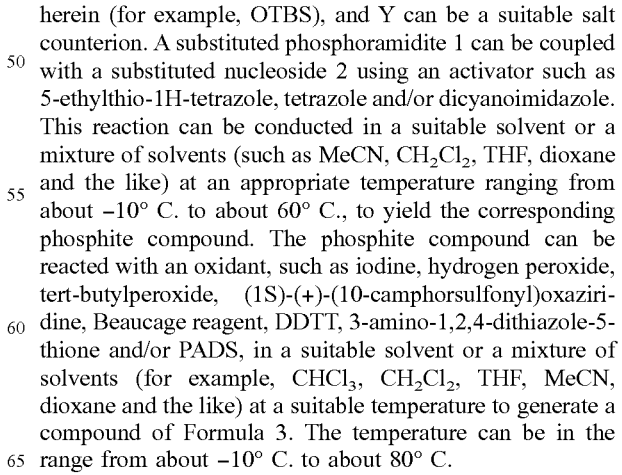

In Scheme 2, Ring $A^{1C}$, Ring $A^{2C}$, $B^{1C}$, $B^{2C}$, $X^{2C}$, $X^{4C}$, $R^{1C}$ and $R^{3C}$ can be as described herein, $R^{2C}$ and $R^{4C}$ can be as described herein or an protected oxygen as described herein (for example, OTBS), and Y can be a suitable salt counterion. A substituted phosphoramidite 1 can be coupled with a substituted nucleoside 2 using an activator such as 5-ethylthio-1H-tetrazole, tetrazole and/or dicyanoimidazole. This reaction can be conducted in a suitable solvent or a mixture of solvents (such as MeCN, CH$_2$Cl$_2$, THF, dioxane and the like) at an appropriate temperature ranging from about −10° C. to about 60° C., to yield the corresponding phosphite compound. The phosphite compound can be reacted with an oxidant, such as iodine, hydrogen peroxide, tert-butylperoxide, (1S)-(+)-(10-camphorsulfonyl)oxaziridine, Beaucage reagent, DDTT, 3-amino-1,2,4-dithiazole-5-thione and/or PADS, in a suitable solvent or a mixture of solvents (for example, CHCl$_3$, CH$_2$Cl$_2$, THF, MeCN, dioxane and the like) at a suitable temperature to generate a compound of Formula 3. The temperature can be in the range from about −10° C. to about 80° C.

The DMTr groups of a compound of Formula 3 can be removed using a suitable acid (such as dichloroaceticacid, acetic acid and/or trifluoroacetic acid) in a suitable solvent or a mixture of solvent to provide a diol compound of Formula 4. Examples of suitable solvents include MeCN, $CH_2Cl_2$, THF and/or dioxane.

A compound of Formula 4 can be cyclized using a compound of Formula 4a and a suitable activator (such as 5-ethylthio-1H-tetrazole, tetrazole and/or dicyanoimidazole) in a suitable solvent or a mixture of solvents (for example, MeCN, $CH_2Cl_2$, dichloroethane, THF, dioxane and the like) at an appropriate temperature ranging from about −10° C. to about 60° C., to yield the corresponding phosphite compound. This phosphite compound can be reacted with an oxidant in a suitably selected solvent or mixture of solvents (such as $CHCl_3$, $CH_2Cl_2$, THF, MeCN, dioxane and the like) at a suitable temperature to generate a compound of Formula 5. Exemplary oxidants include, but are not limited to, iodine, hydrogen peroxide, tert-butylperoxide, (1S)-(+)-(10-camphorsulfonyl)oxaziridine, Beaucage reagent, DDTT, 3-amino-1,2,4-dithiazole-5-thione and/or PADS, and a suitable temperature is in a range from about −10° C. to about 80° C., The protecting groups present on a compound of Formula 5 can be removed using appropriate conditions in a suitable solvent or a mixture of solvents (for example, EtOH, $H_2O$, iPrOH and the like) at a suitable temperature in the range from about −10° C. to about 120° C. to yield a compound of formula 6. Appropriate condition for removing any protecting groups present on a compound of Formula 5 include basic conditions, such as $MeNH_2$, $tBuNH_2$, ammonium hydroxide and the like.

Any silyl protecting group present on a compound of Formula 6 can be removed using acidic conditions, such as TBAF, Ammonium fluoride, HF·TEA and like, in a suitable solvent or a mixture of solvents at an appropriate temperature to yield a compound of Formula 7. Examples of suitable solvents include pyridine, THF, dioxane, MeOH and like. The temperature can be in the range of from about −10° C. to about 120° C.

An ammonium or triethyl ammonium counterion of a compound of Formula 7 can be exchanged to a sodium or lithium using an appropriate resin, such as Amberlyst or Dowex resin, to provide a compound of Formula (III), or a pharmaceutically acceptable salt thereof.

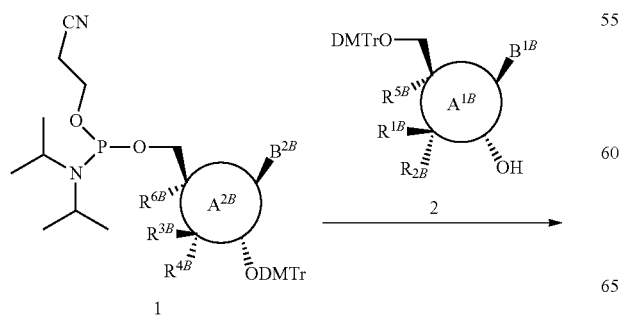

Scheme 3

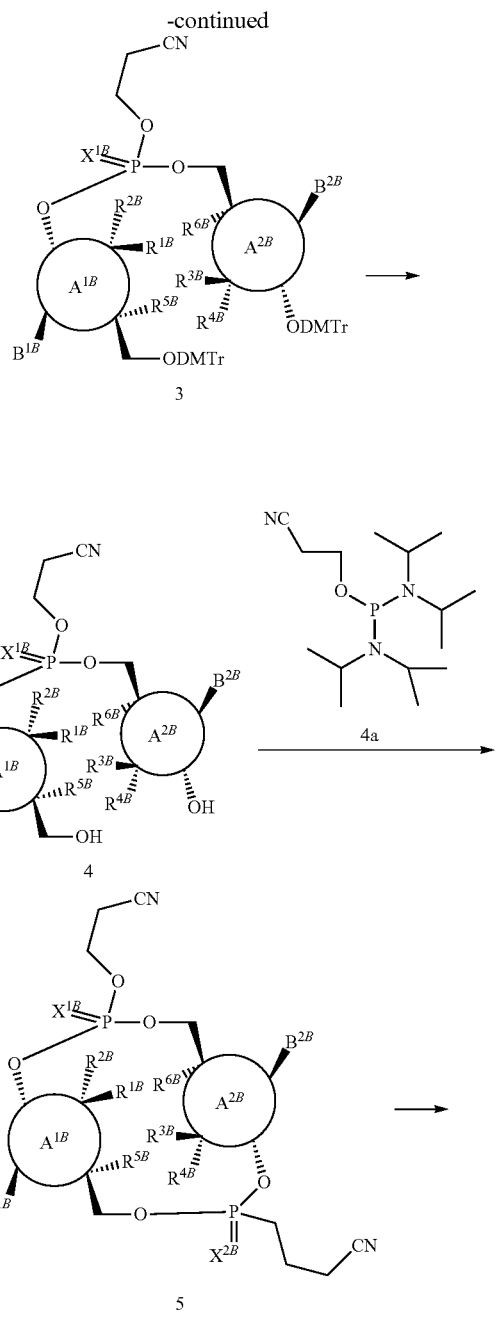

-continued

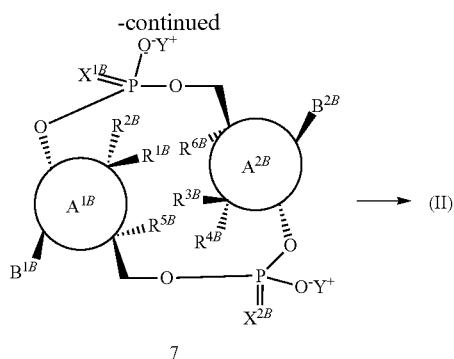

(II)

7

In Scheme 3, Ring $A^{1B}$, Ring $A^{2B}$, $B^{1B}$, $B^{2B}$, $X^{2B}$, $X^{4B}$, $R^{1B}$ and $R^{3B}$ can be as described herein, $R^{2B}$ and $R^{4B}$ can be as described herein or an protected oxygen as described herein (for example, OTBS), and Y can be a suitable salt counterion. A suitable substituted phosphoramidite 1 can be coupled with an appropriate substituted nucleoside 2 using an activator in a suitable solvent or a mixture of solvents at an appropriate temperature (for example, a temperature in the range of from about −10° C. to about 60° C.) to yield the corresponding phosphite compound. Suitable activators are described herein, and include 5-ethylthio-1H-tetrazole, tetrazole and/or dicyanoimidazole. Examples of suitable solvents include MeCN, $CH_2Cl_2$, THF, dioxane and the like. The corresponding phosphite compound can be reacted with an oxidant (such as, iodine, hydrogen peroxide, tert-butylperoxide, (1S)-(+)-(10-camphorsulfonyl)oxaziridine, Beaucage reagent, DDTT, 3-amino-1,2,4-dithiazole-5-thione and/or PADS) in a suitable solvent or a mixture of solvents (for example, $CHCl_3$, $CH_2Cl_2$, THF, MeCN, dioxane and the like) at a suitable temperature ranging from about −10° C. to about 80° C., to generate a compound of Formula 3.

The protecting groups present on a compound of Formula 3 can be removed using suitable acidic conditions (such as, dichloroaceticacid, acetic acid and/or trifluoroacetic acid) in a suitable solvent or a mixture of solvents to provide a compound of Formula 4. Exemplary solvents include MeCN, $CH_2Cl_2$, THF and/or dioxane.

A compound of Formula 4 can be cyclized using a compound of Formula 4a and an appropriate activator in a suitable selected solvent or a mixture of solvents (for example, MeCN, $CH_2Cl_2$, dichloroethane, THF, dioxane and the like) at an appropriate temperature to yield the corresponding phosphite compound. Examples of an appropriate temperature is in the range from about −10° C. to about 60° C. Suitable activators are described herein and include 5-ethylthio-1H-tetrazole, tetrazole and dicyanoimidazole. The corresponding phosphite compound can be reacted with an oxidant (such as iodine, hydrogen peroxide, tert-butylperoxide, (S)-(+)-(10-camphorsulfonyl)oxaziridine, Beaucage reagent, DDTT, 3-amino-1,2,4-dithiazole-5-thione and/or PADS) in a suitable solvent or a mixture of solvents at a suitable temperature (for example, a temperature in the range from about −10° C. to about 80° C.) to provide a compound of Formula 5. Suitable solvents are described herein and include $CHCl_3$, $CH_2Cl_2$, THF, MeCN, dioxane and the like.

A compound of Formula 5 can be deprotected using appropriate conditions to yield a compound of formula 6. Examples of suitable condition include basic conditions (such as $MeNH_2$, $tBuNH_2$, ammonium hydroxide and the like) in a suitable solvent or a mixture of solvents (such as, EtOH, $H_2O$, iPrOH and the like) at an appropriate temperature (for example, a temperature in the range from about −10° C. to about 120° C.).

A compound of Formula 6 can be deprotected using appropriate conditions to yield a compound of formula 7. Exemplary conditions are described herein and include TBAF, ammonium fluoride, HF·TEA and like, in a suitable solvent or a mixture of solvents (such as pyridine, THF, dioxane, MeOH and like) at an appropriate temperature in the range from about −10° C. to about 120° C.

An ammonium or triethyl ammonium counterion of a compound of Formula 7 can be exchanged to a sodium or lithium using an appropriate resin, such as Amberlyst or Dowex resin, to provide a compound of Formula (II), or a pharmaceutically acceptable salt thereof.

Pharmaceutical Compositions

Some embodiments described herein relate to a pharmaceutical composition, that can include an effective amount of a compound described herein (e.g., a compound of Formula (I), (II) and/or (III), or a pharmaceutically acceptable salt of any of the foregoing, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Pharmaceutical compositions may be formulated in a variety forms, such as tablets, capsules or solutions for oral administration; suppositories for rectal or vaginal administration; sterile solutions or suspensions for injectable administration. Injectables can be prepared in conventional forms, either as liquid solutions or suspensions, solid forms suitable for solution or suspension in liquid prior to injection, or as emulsions.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal, intratumoral and intraocular injections. Pharmaceutical compositions will generally be tailored to the specific intended route of administration. In some embodiments, a compound described herein, (such as a compound of Formula (I), (II) and/or (III), or a pharmaceutically acceptable salt of any of the foregoing, as described herein) is provided by a subcutaneous method of administration. In some embodiments, a compound described herein, (such as a compound of Formula (I), (II) and/or (III), or a pharmaceutically acceptable salt of any of the foregoing, as described herein) is provided by an intratumoral method of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counter ions.

Methods of Use

Some embodiments described herein relate to a method of treating of a disease or condition in a subject in which modulation STING is beneficial that can include administering to the subject an effective amount of a compound, or a pharmaceutically acceptable salt thereof, as described herein (for example, a compound of Formula (I), (II) and/or (III), or a pharmaceutically acceptable salt of any of the foregoing), or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating of a disease or condition in a subject in which modulation STING is beneficial.

Some embodiments disclosed herein relate to a method of treating an inflammatory condition, an infectious disease, a viral disease and/or a cancer in which the modulation of STING is beneficial in a subject that can include administering to the subject an effective amount of a compound, or a pharmaceutically acceptable salt thereof, as described herein, or a pharmaceutical composition that includes an effective amount of a compound, or a pharmaceutically acceptable salt thereof, as described herein (such as a compound of Formula (I), (II) and/or (III), or a pharmaceutically acceptable salt of any of the foregoing). Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating an inflammatory condition, an infectious disease, a viral disease and/or a cancer in which the modulation of STING is beneficial.

Some embodiments disclosed herein relate to a method for inducing an immune response via activation of STING in a subject that can include administering to the subject an effective amount of a compound, or a pharmaceutically acceptable salt thereof, as described herein, or a pharmaceutical composition that includes an effective amount of a compound, or a pharmaceutically acceptable salt thereof, as described herein (for example, a compound of Formula (I), (II) and/or (III), or a pharmaceutically acceptable salt of any of the foregoing). Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inducing an immune response via activation of STING.

Some embodiments disclosed herein relate to a method for inducing a STING-dependent type I interferon production in a subject that can include administering to the subject an effective amount of a compound, or a pharmaceutically acceptable salt thereof, as described herein, or a pharmaceutical composition that includes an effective amount of a compound, or a pharmaceutically acceptable salt thereof, as described herein (for example, a compound of Formula (I), (II) and/or (III), or a pharmaceutically acceptable salt of any of the foregoing). Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inducing a STING-dependent type I interferon production.

Some embodiments disclosed herein relate to a method for activating a STING receptor in a cell that can include contacting the cell an effective amount of a compound, or a pharmaceutically acceptable salt thereof, as described herein, or a pharmaceutical composition that includes an effective amount of a compound, or a pharmaceutically acceptable salt thereof, as described herein (such as, a compound of Formula (I), (II) and/or (III), or a pharmaceutically acceptable salt of any of the foregoing). Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of activating a STING receptor.

In some embodiments, a compound, or a pharmaceutically acceptable salt thereof, as described herein (such as a compound of Formula (I), (II) and/or (III), or a pharmaceutically acceptable salt of any of the foregoing) can be used to treat a cancer. Examples of cancers include, but are not limited to, hepatocellular carcinoma, lung cancer and colorectal cancer. In some embodiments, a compound, or a pharmaceutically acceptable salt thereof, as described herein can be used to suppress/inhibit tumor growth, and thereby treat a cancer, such as colon cancer.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

The term "effective amount" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In some embodiments, an effective amount of a compound, or a pharmaceutically acceptable salt thereof, as described herein is an amount that is effective to achieve a sustained virologic response, for example, a sustained viral response 12 month after completion of treatment.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, including a human cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Combination Therapies

In some embodiments, a compound, or a pharmaceutically acceptable salt thereof, as described herein (such as a compound of Formula (I), (II) and/or (III), or a pharmaceutically acceptable salt of any of the foregoing) can be used in combination with one or more additional agent(s) for treating a disease or condition in which modulating STING is beneficial, inducing an immune response, inducing a STING-dependent type I interferon production and/or of activating a STING receptor in a cell. For example, a compound, or a pharmaceutically acceptable salt thereof, as described herein (such as a compound of Formula (I), (II) and/or (III), or a pharmaceutically acceptable salt of any of the foregoing) can be used in combination with one or more additional agent(s) for treating and/or inhibiting replication of a cancer cell. As an example, a compound, or a pharmaceutically acceptable salt thereof, as described herein (such as a compound of Formula (I), (II) and/or (III), or a pharmaceutically acceptable salt of any of the foregoing) can be used in combination with one or more additional agent(s) for treating an inflammatory condition, an infectious disease and/or a viral disease. Exemplary additional agents include, but are not limited to, a checkpoint inhibitor, for example, an inhibitor that targets a receptor selected from PD-1 (e.g., Pembrolizumab, Nivolumab, Spartalizumab, Cemiplimab, Camrelizumab, Sintilimab, Tislelizumab, Toripalimab, BCD-100, BALSTILIMAB, Cetrelimab and dostarlimab), PD-L1 (such as Avelumab, Atezolizumab, Durvalumab, KN035 and GS-4224), CTLA-4 (e.g., Ipilimumab, ZALIFRELIMAB and Tremelimumab), OX40 (for example, PF-04518600 and INCAGN1949), 4-1BB (e.g., Urelumab and Utomilumab), TIM-3 (such as INCAGN2390 and Cobolimab), LAG-3 (for example, INCAGN2385 and Xentuzumab), ILT-4 (e.g., MK-4830), CEACAM6 (e.g., BAY 1834942) and TIGIT.

In some embodiments, a compound, or a pharmaceutically acceptable salt thereof, as described herein can be administered with one or more additional agent(s) together in a single pharmaceutical composition. In some embodiments, a compound, or a pharmaceutically acceptable salt thereof, can be administered with one or more additional agent(s) as two or more separate pharmaceutical compositions. Further, the order of administration of a compound, or a pharmaceutically acceptable salt thereof, as described herein with one or more additional agent(s) can vary.

EXAMPLES

Additional embodiments are disclosed in further detail in the following examples, which are not in any way intended to limit the scope of the claims.

Example 1a

Intermediate 15 & 15a

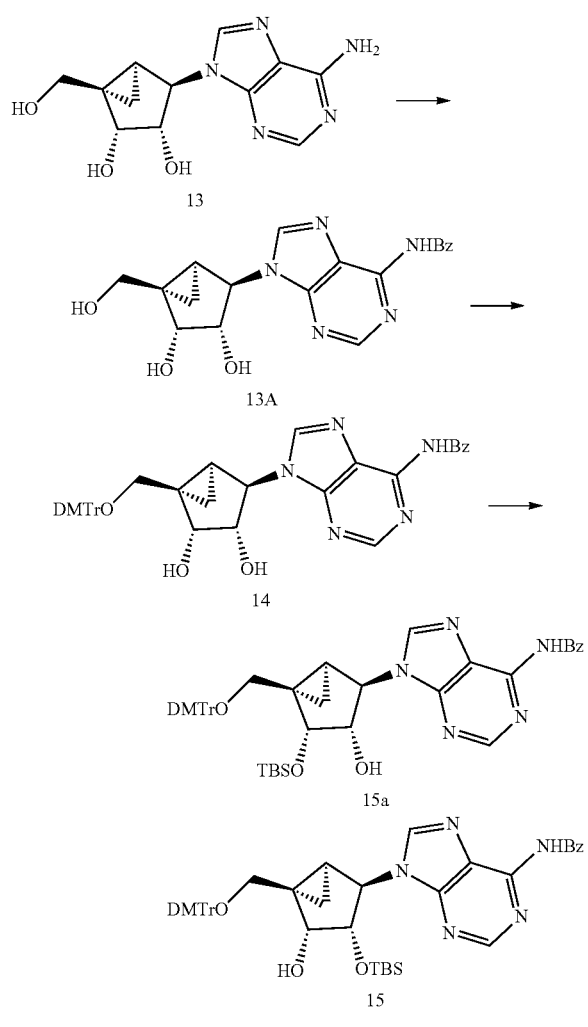

To a solution of 13 (7.0 g, 25.26 mmol) in dry pyridine (50 mL) was added dropwise benzoyl chloride (17.4 ml, 151.56 mmol) at 0° C. The mixture was stirred at room temperature (rt) for 2 h under a $N_2$ atmosphere. The reaction was quenched by the addition of MeOH (5 mL). The mixture was diluted with EtOAc and washed with $NaHCO_3$. The organic layers were dried over anhydrous sodium sulfate and concentrated under reduced pressure to give a compound with several benzoyl groups as a yellow oil. To this mixture in pyridine (30 mL), NaOH (2 M, in MeOH:$H_2O$=4:1) was dropped in until pH=10-11 at 0° C. The mixture was stirred for another 1 h at 0° C. The pH of the reaction was adjusted to 7 with 4N HCl to quench the reaction. The solvent was removed by vacuum, and the resulting crude material was purified by MPLC (Column: C18 spherical 20-35 µm 100A 120 g, mobile phase: 0.05% $NH_4HCO_3$ in water-ACN from 0% to 20%, flow rate: 50 mL/min $H_2O$) as eluent. The fractions containing the desired compound were pooled and concentrated under reduced pressure to give 13A (6.6 g, 17.32 mmol, 68.6%) as a white solid. ESI-MS: m/z 382.1 [M+H]$^+$.

To a solution of 13A (6.6 g, 17.32 mmol) in pyridine (50 mL) was added DMTr-Cl (6.5 g, 19.05 mmol) at 0° C. The mixture was stirred for 30 min at rt under a $N_2$ atmosphere. The reaction was quenched by the addition of MeOH (5 mL). The mixture was concentrated under reduced pressure to give the crude product. The residue was purified by silica gel column (DCM/MeOH=200:1-50:1) to give 14 (7.5 g, 10.98 mmol, 63.4%) as a white solid. ESI-LCMS: m/z 684.5 [M+H]$^+$.

To a solution of 14 (2.8 g, 4.10 mmol) in anhydrous DMF (20 mL) was added imidazole (1.12 g, 16.4 mmol). A solution of TBS-Cl (0.76 g, 4.92 mmol) in DMF (8 mL) was dropped at 0° C. The mixture was stirred for 16 h at rt under a $N_2$ atmosphere. The reaction was quenched by the addition of MeOH (3 mL). The mixture was diluted with EA and washed with $NaHCO_3$ solution. The combine organic layers were dried over $Na_2SO_4$ and concentrated under reduced pressure to give the crude product. The residue was purified by silica gel column (PE:EA, 10:1-1:1) to give 15a (0.6 g, 0.75 mmol, 18.3%) and 15 (1.0 g, 1.25 mmol, 30.5%) as a white solid.

15a: $^1$H NMR (400 MHz, DMSO): δ 11.21 (s, 1H), 8.70 (s, 1H), 8.66 (s, 1H), 8.05 (d, J=7.4 Hz, 2H), 7.66-7.62 (m, 1H), 7.56-7.53 (m, 2H), 7.42 (d, J=7.4 Hz, 2H), 7.31-7.26 (m, 5H), 7.23-7.21 (m, 1H), 6.86 (d, J=8.6 Hz, 4H), 4.91 (d, J=5.5 Hz, 1H), 4.77 (d, J=6.2 Hz, 1H), 4.73 (d, J=3.6 Hz, 1H), 4.30-4.26 (m, 1H), 3.71 (d, J=0.7 Hz, 6H), 3.50 (d, J=9.9 Hz, 1H), 2.89-2.85 (m, 1H), 1.67-1.64 (m, 1H), 1.29 (t, J=4.4 Hz, 1H), 1.17 (t, J=7.1 Hz, 1H), 0.78 (s, 9H), −0.05 (d, J=21.2 Hz, 6H). ESI-LCMS: m/z 798.6 [M+H]$^+$.

15: $^1$H NMR (400 MHz, DMSO): δ 11.21 (s, 1H), 8.70 (s, 1H), 8.67 (s, 1H), 8.06 (d, J=7.4 Hz, 2H), 7.67-7.63 (m, 1H), 7.58-7.54 (m, 2H), 7.46 (d, J=7.6 Hz, 2H), 7.30-7.33 (m, 5H), 7.24-7.20 (m, 1H), 6.89 (dd, J=7.2, 1.6 Hz, 4H), 4.83-4.78 (m, 1H), 4.37 (d, J=8.0 Hz, 1H), 3.71 (d, J=3.8 Hz, 6H), 2.75 (d, J=10.6 Hz, 1H), 1.64-1.61 (m, 1H), 1.42 (t, J=4.3 Hz, 1H), 1.18 (t, J=7.1 Hz, 1H), 0.87 (s, 9H), 0.62-0.65 (m, 1H), 0.03 (d, J=15.8 Hz, 6H). ESI-LCMS: m/z 798.6 [M+H]$^+$.

Example 1b

Intermediate 11

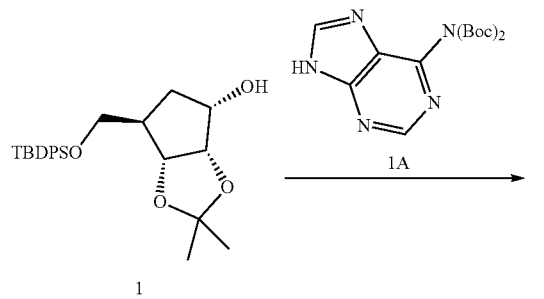

1

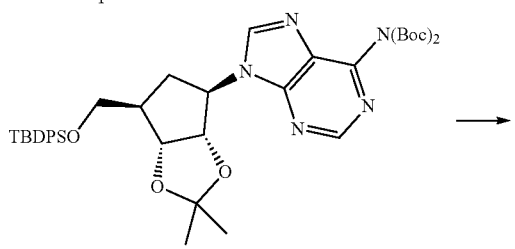

2

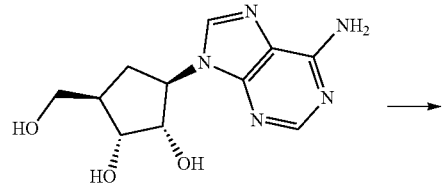

3

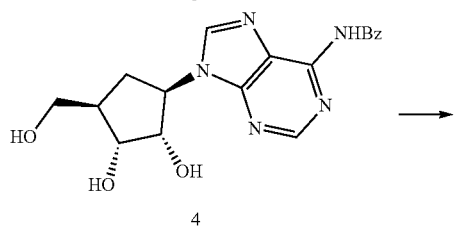

4

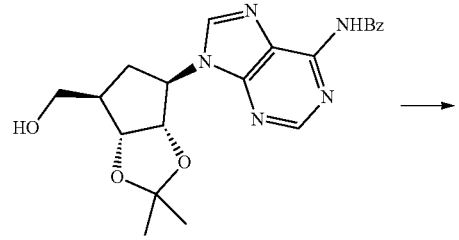

5

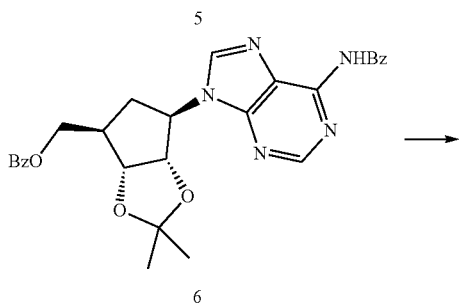

6

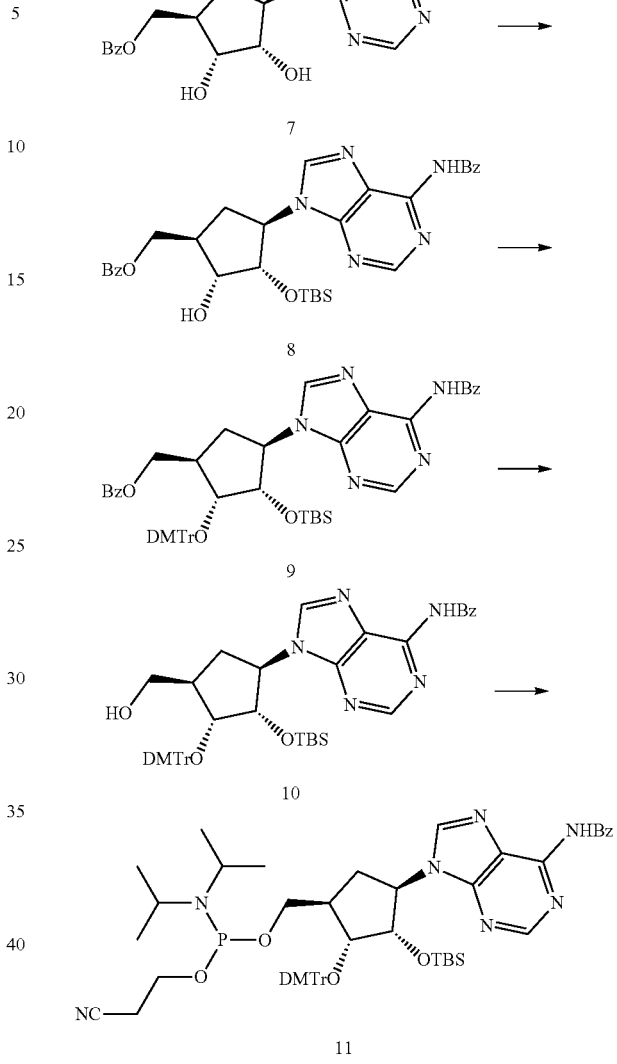

To a solution of 1 (32.4 g, 75.95 mmol), 1A (38.20 g, 113.92 mmol) and PPh₃ (49.80 g, 189.86 mmol) in THF (320 mL) were added DIAD (38.39 g, 189.86 mmol, 37.27 mL) at 4° C. under N₂. The mixture was allowed to stirred for 15 h at 70° C. The solvent was the removed, and the product was purified by silica gel (PE:EA=20:1~8:1) to give crude 2 (56.0 g, 75.27 mmol, 99.1%) as a white oil. ESI-LCMS: m/z 744 [M+H]⁺.

To a solution of 2 (56 g, 75.27 mmol) in a mixture of CF₃COOH (200 mL), was added THF (100 mL) and water (100 mL). The mixture was allowed to stirred at 50° C. After stirring for 15 h, the solvent was removed. The residue was purified by MPLC (0.05% NH₄HCO₃ aq., ACN=90:10) to give crude 3 (16.4 g, 61.82 mmol, 82.1%) as a solid. ESI-LCMS: m/z 266 [M+H]⁺.

To a solution of 3 (16.4 g, 94.24 mmol) in pyridine (150 mL) was added BzCl (79.49 g, 565.47 mmol, 50 mL) at 0° C. under N₂. The mixture was stirred for 1 h. The reaction was quenched with water. The mixture was extracted with EtOAc and washed with brine. The solvent was removed. The residue was dissolved in pyridine, and 2N NaOH (aq.)

was added below 5° C. until pH=8-9. The mixture was stirred for 10 min, and then water was added. The mixture was extracted with EA, washed with brine and dried over $Na_2SO_4$. The solvent was removed. The residue was purified by silica gel (DCM:MeOH=50:1-10:1) to give 4 (8.4 g, 27.07 mmol, 28.7%) as a yellow solid. ESI-LCMS: m/z 370 [M+H]⁺.

To a solution of 4 (8.4 g, 22.74 mmol) and 2,2-dimethoxypropane (5.21 g, 50.03 mmol) in anhydrous acetone (200 mL) was added concentrated sulfuric acid (3.92 g, 39.93 mmol) under $N_2$ at 5° C. The mixture was stirred for 2 h at rt. The reaction was quenched with sat. $NaHCO_3$. The mixture was extracted with DCM, washed with brine and dried over $Na_2SO_4$. The solvent was removed. The residue was purified by silica gel (DCM:MeOH=40:1~20:1) to give 5 (5.4 g, 13.19 mmol, 58.0%) as a solid. ESI-LCMS: m/z 410 [M+H]⁺.

To a solution of 5 (5.4 g, 14.17 mmol), TEA (4.30 g, 42.50 mmol, 5.93 mL) and DMAP (34.61 mg, 283.32 umol) in DCM (100 mL) was added BzCl (2.99 g, 21.25 mmol) under $N_2$ at rt. The mixture was stirred for 2 h at rt. The reaction was quenched with ammonium hydroxide. The mixture was extracted with DCM and dried over $Na_2SO_4$. The solvent was removed. The residue was purified by silica gel (DCM:MeOH, 100:1-70:1) to give 6 (6.2 g, 12.07 mmol, 92.5%) as a solid. ESI-LCMS: m/z 514 [M+H]⁺.

To a solution of 6 (6.2 g, 12.07 mmol) in THF (150 mL) and 1N HCl (150 ml) was stirred for 2 h at rt. The reaction was quenched with sat. $NaHCO_3$. The mixture was extracted with DCM and dried over $Na_2SO_4$. The solvent was removed, and the residue was purified by silica gel (DCM:MeOH, 100:1-40:1) to give 7 (4.5 g, 9.50 mmol, 78.9%) as a white solid. ESI-LCMS: m/z 474 [M+H]⁺.

To a solution of 7 (4.3 g, 9.08 mmol) and imidazole (1.85 g, 27.25 mmol) in DMF (30 mL) was added TBSCl (1.64 g, 10.90 mmol) at rt under $N_2$. The mixture was stirred for overnight at rt. The reaction was quenched with water, extracted with EA and dried over $Na_2SO_4$. The solvent was removed, and the residue was purified by MPLC (ACN: 0.05% $NH_4HCO_3$ aq=75:25) to give 8 (2.0 g, 6.98 mmol, 37.78%) as a solid. ESI-LCMS: m/z 588 [M+H]⁺.

To a solution of 8 (2.0 g, 3.40 mmol), $AgNO_3$ (578.05 mg, 3.40 mmol), DMTrCl (13.84 g, 40.83 mmol) and 2,4,6-trimethylpyridine (6.19 g, 51.04 mmol) in 1,2-dichloroethane (30 mL) was stirred for 16 h at 80° C. under $N_2$. The reaction was quenched with water, extracted with EA and dried over $Na_2SO_4$. The solvent was removed, and the residue was purified by silica gel (PE:EA=20:1~2:1) to give 9 (2.5 g, 3.03 mmol, 82.1%) as a solid. ESI-LCMS: m/z 890 [M+H]⁺.

To a solution of 9 (2.5 g, 3.26 mmol) in pyridine (100 mL) was added 2N NaOH at 0° C. under $N_2$. The mixture was stirred for 10 min. The reaction was quenched with water, extracted with EA, dried over $Na_2SO_4$. The solvent was removed and the residue was purified by silica gel (PE:EA, 10:1~1:1) to give 10 (2.0 g, 2.93 mmol, 89.5%) as a solid. ESI-LCMS: m/z 786 [M+H]⁺.

To a solution of 10 (2.0 g, 2.93 mmol) and DIPEA (1.13 g, 8.78 mmol, 1.53 mL) in anhydrous DCM (20 mL) was added 2-cyanoethyl N,N-diisopropylchlorophosphoramidite (1.04 g, 4.39 mmol) at 0° C. under $N_2$. The mixture was stirred for 1 h. The reaction was quenched with sat. $NaHCO_3$ (aq.), extracted with DCM and dried over $Na_2SO_4$. The solvent was removed, and the residue was purified by MPLC (0.05% $NH_4HCO_3$:ACN=0:100) to give 11 (2.1 g, 2.13 mmol, 83.8%) as a solid. ¹H-NMR (400 MHz, DMSO-d₆): δ=11.13 (s, 1H), 8.70-8.67 (d, J=12.0 Hz, 1H), 8.60-8.58 (d, J=8.0 Hz, 1H), 8.07-8.05 (d, J=8.0 Hz, 2H), 7.65-7.52 (m, 5H), 7.42-7.35 (m, 4H), 7.33-7.27 (m, 2H), 7.24-7.19 (m, 1H), 6.91-6.83 (m, 4H), 5.48-5.30 (m, 1H), 4.63-4.36 (m, 1H), 3.74-3.71 (m, 6H), 3.70-3.62 (m, 3H), 3.53-3.46 (m, 2H), 3.44-3.37 (m, 1H), 3.33-3.20 (m, 1H), 2.75-2.71 (m, 2H), 2.40-2.33 (m 1H), 2.10-2.03 (m, 1H), 2.00-1.82 (m, 1H), 1.12-1.10 (d, J=8.0 Hz, 6H), 1.05-0.96 (m, 6H), 0.70-0.68 (d, J=8.0 Hz, 9H), −0.24~−0.26 (d, J=8.0 Hz, 3H), −0.60~−0.65 (d, J=20.0 Hz, 3H). ³¹P-NMR: 146.94, 146.77. ESI-LCMS: m/z 986 [M+H]⁺.

Example 1c

Intermediate Monomer A

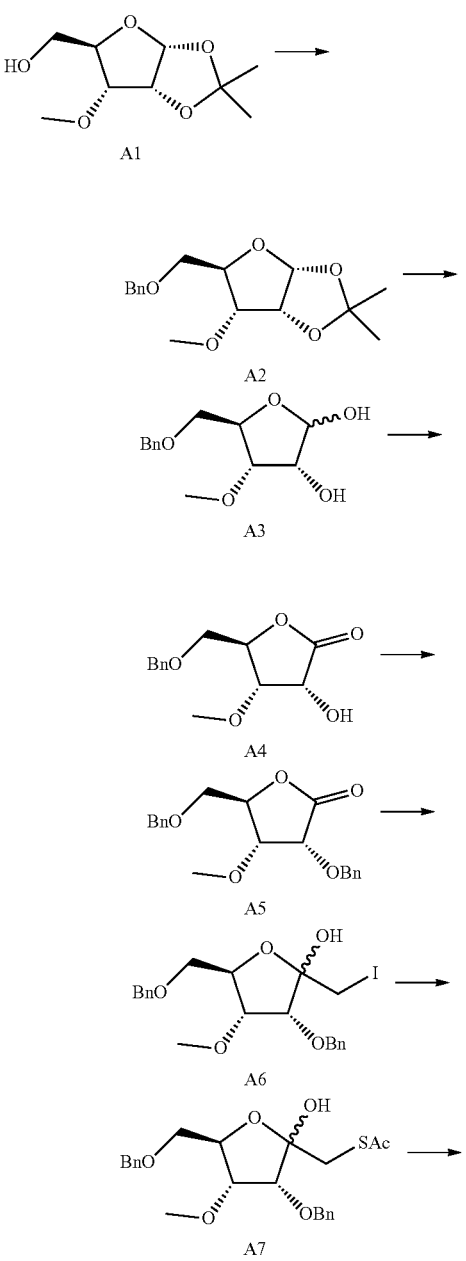

-continued

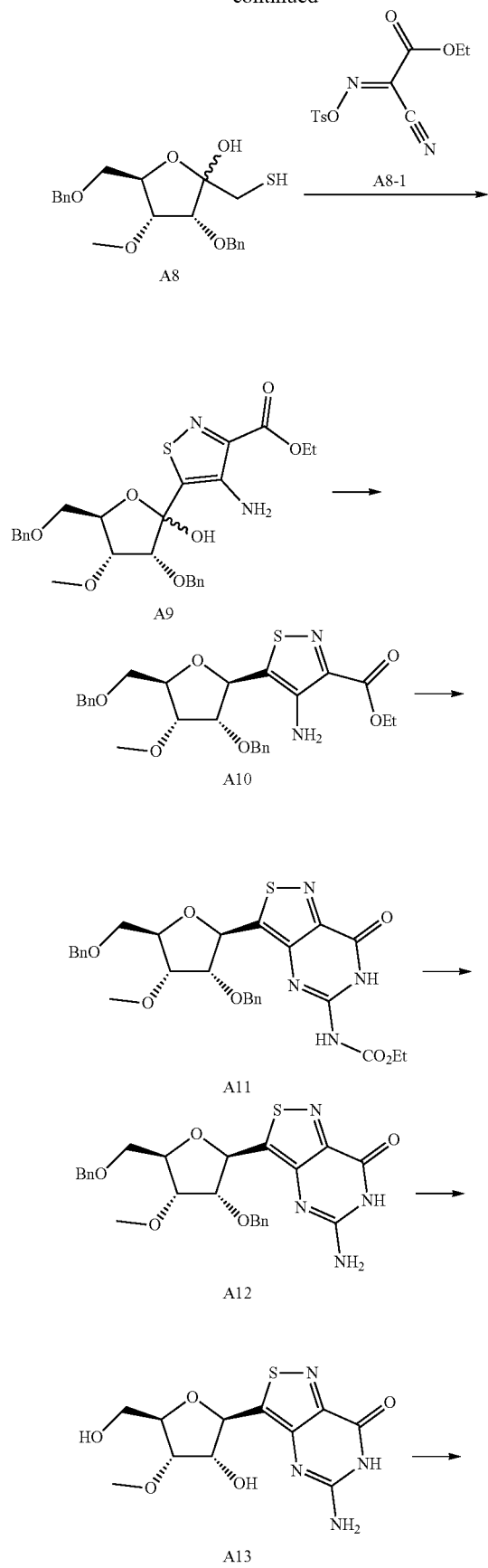

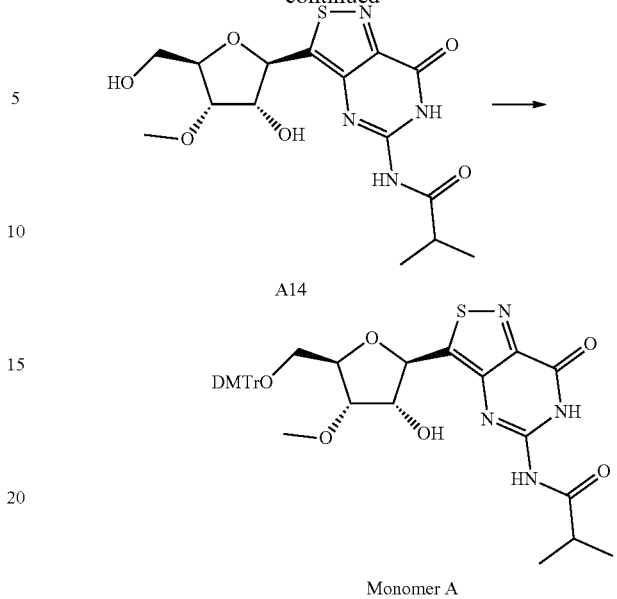

Monomer A

To a solution of A1 (200.0 g, 0.98 mol) in THF (2 L) was ice-cooled to 0° C. and stirred at this temperature for 15 min. NaH (1.5 eq., 1.47 mol, 33.8 g) was added slowly, and the mixture stirred at 0° C. for 30 min. BnBr (1.2 eq., 1.176 mol, 201.1 g) was dropwise slowly, and the mixture was stirred at 0° C. for 1.5 h until 1 was consumed. The mixture was warmed to rt, and the reaction was quenched with ice-cooled water (300 mL). The mixture was vigorously stirred for 10 min, and the precipitate was filtered over a Celite cake. The separated aq. layer was extracted with EA (2×1000 mL). The combined organic layers were washed with water (500 mL) and brine (500 mL), dried over $Na_2SO_4$ and evaporated in vacuo to give the crude product. The crude product was purified by column chromatography with a gradient of 0 to 15% EtOAc in PE to give A2 (140 g, 49%) as a white solid. ESI-MS: m/z 295.3 $[M+H]^+$.

To a solution of A2 (140 g, 0.476 mol) in 80% AcOH (1500 mL) at rt, and the mixture was heated to 115° C. The mixture was stirred at 115° C. for 2 h under $N_2$ atmosphere until A2 was consumed. The solvent was evaporated in the vacuo at 50° C. and co-evaporated with toluene (2×) to give the crude product, which was purified by column chromatography with a gradient of 0 to 5% $CH_3OH$ in DCM to give A3 (105 g, 87%) as a white oil. $^1$H NMR (400 MHz, DMSO-$d_6$) δ 7.40-7.31 (m, 5H), 6.34 (d, J=4.4 Hz, 1H), 5.01 (d, J=2.9 Hz, 1H), 4.89 (s, 1H), 4.52 (d, J=7.3 Hz, 2H), 3.94 (td, J=6.8, 3.3 Hz, 1H), 3.86 (d, J=4.0 Hz, 1H), 3.65 (dd, J=7.1, 4.5 Hz, 1H), 3.58 (dd, J=10.5, 3.4 Hz, 1H), 3.53-3.47 (m, 1H), 3.29 (s, 3H).

To a solution of A3 (105 g, 0.413 mol) in DCM (1000 mL) was added $K_2CO_3$ (3.0 eq., 1.239 mol, 171.2 g) and 2 (3.0 eq., 1.239 mol, 314.5 g) at rt. The mixture was stirred at rt for 12 h until the major desired product was detected by TLC. The reaction was quenched with sat.aq. $Na_2SO_3$ until complete disappearance of the dark brown color. The mixture was extracted with EA (2×500 mL). The combined organic layers were washed by water (1×500 mL) and brine (1×500 mL), dried over anhydrous $Na_2SO_4$, evaporated in the vacuo to give the crude product. The crude product was purified by column chromatography with a gradient of 0 to 20% EtOAc in PE to give A4 (80 g, 77%) as a colorless oil. $^1$H NMR (400 MHz, DMSO-$d_6$) δ 7.35 (m, 5H), 5.91 (d, J=7.9 Hz, 1H), 4.57 (dt, J=8.1, 4.2 Hz, 2H), 4.51 (d, J=6.0 Hz, 2H), 3.93 (dd, J=5.6, 0.6 Hz, 1H), 3.70 (d, J=3.5 Hz, 2H), 3.40 (s, 3H).

To a solution of A4 (80 g, 0.317 mol) in superdry 1,4-dioxane (800 mL) was ice-cooled to 0° C. and stirred at this temperature for 30 min. Benzyl 2,2,2-trichloroacetimidate (1.5 eq., 0.476 mol, 119.3 g) was dropwise slowly to the solution. After 30 min, $CF_3SO_3H$ (0.1 eq., 0.0317 mol, 4.75 g) was dropwise slowly within 30 min. The mixture was stirred at 0° C. for 1 h until A4 was consumed and the major desired product A5 was detected by TLC. The reaction was quenched with sat.aq. $NaHCO_3$, and then extracted with EA (3×300 mL). The combined organic layer was washed by water (2×500 mL) and brine (1×500 mL), dried over anhydrous $Na_2SO_4$, evaporated in the vacuo to give the crude product. The crude product was purified by column chromatography with a gradient of 0 to 25% EtOAc in PE to give A5 (60 g, 55%) as a light yellow oil. ESI-MS: m/z 343.2 $[M+H]^+$.

Compound A5 (60 g, 0.175 mol) is dissolved in anhydrous toluene (600 mL) in a round bottom flask (2 L) under Ar. Diiodomethane (2.4 eq., 0.42 mol, 112.5 g) was added, and the solution is brought to −78° C. to stir for 30 min. Methyllithium (1.5 M, 1.8 eq., 201 mL) was added dropwise over 2.5 h. The temperature was left to slowly rise and was maintained between −65° C. and −70° C. After 2 h, the reaction was quenched with ammonium chloride and then warmed to rt. The product is extracted with DCM in water. The organic solution was dried over magnesium sulfate and evaporated to dryness. The residue was subjected to column chromatography with a gradient of 0 to 40% EtOAc in PE to give A6 as a light yellow oil (62 g, 73%), which was used directly for next step without any purification.

Compound A6 (62 g, 0.128 mol) was dissolved in anhydrous DMF (500 mL) in a round bottom flask (1000 mL) under Ar. The solution is placed in ice bath and left to stir 10 min before the addition of potassium thioacetate (1.5 eq., 0.192 mol, 21.92 g). The reaction was removed from the ice bath after 1 h and left to stir for 1 h at rt. The mixture was then placed in an ice bath and then sat. $NaHCO_3$ (500 mL) and EtOAc (600 mL) were added. The mixture was left to stir several minutes. The mixture was extracted with EtOAc (4×200 mL) followed by water (4×300 mL). The mixture was dried over anhydrous $Na_2SO_4$ and evaporated to dryness. The residue was purified by column chromatography with a gradient of 0 to 30% EtOAc in PE to give A7 as a light yellow oil (32 g, 58%). The product was inseparable mixture of isomers, which was used directly for next step without any purification.

Compound A7 (32 g, 74 mmol) was dissolved in anhydrous THF (300 mL) in a round bottom flask (1000 mL) under Ar. The solution was placed in an ice bath and left to stir 30 min. $LiAlH_4$ (1.0 M in $Et_2O$, 0.28 eq., 20.7 mmol, 20.7 mL) was added. The mixture was left to stir 2 h, and then slowly warmed to rt. The reaction was quenched with water upon consumption of starting material as monitored via TLC. The mixture was diluted with EtOAc (300 mL) and filtered over celite. The material was extracted with EtOAc (2×300 mL), and washed with water (3×300 mL) and brine (1×300 mL). The product is dried over anhydrous $Na_2SO_4$ and then evaporated to dryness. The product was purified with column chromatography in a gradient of 0 to 30% EtOAc in PE to give crude A8 as a yellow oil (19.6 g, 68%), which is then used directly in the following step.

Compound A8 (19.6 g, 50.2 mmol) was dissolved in $CH_3OH$ (150 mL) followed by the addition of N-tosylcyano ester A8-1 (1.5 eq., 78.0 mmol, 23.09 g). The mixture was briefly placed in a sonicator before being left to stir for 5 mins in an ice bath. Morpholine (2.5 eq., 0.126 mol, 11.0 g) was added dropwise over 5 mins, and the mixture was left to stir in the ice bath for 1 h. The mixture was then brought to rt and stirred for 1 h. The yellow solution was evaporated to dryness, briefly placed under high vacuum, and loaded directly onto a column for silica chromatography in a gradient of 0 to 40% EtOAc in PE to give A9 as a yellow oil (13 g, 50%), which is then used directly in the following step.

Compound A9 (13 g, 25.3 mmol) was placed in flame-dried round bottom flask (250 mL) under Ar and dissolved in anhydrous DCM (100 mL). Triethylsilane (6.0 eq., 0.152 mol, 17.7 g) was added, and the flask was brought to −78° C. and stirred for 10 mins. $BF_3 \cdot OEt_2$ (3.0 eq., 75.9 mmol, 10.8 g) was added. The mixture was slowly allowed to reach rt over 90 min, changing from a clear to yellow colored solution. After 2 h at rt, TEA (5.0 eq.) was added. The mixture was partitioned between EtOAc (100 mL) and water (100 mL), and then extracted with EtOAc (3×100 mL). The organic layer was dried over anhydrous $Na_2SO_4$ and evaporated to dryness. The residue was purified by column chromatography with a gradient of 0 to 20% EtOAc in PE until A10 was eluted as a yellow oil (6.8 g, 54%). ESI-MS: m/z 499.2 $[M+H]^+$.

Compound A10 (6.8 g, 13.65 mmol) was dissolved in anhydrous $CH_3CN$ (60 mL) in a round bottom flask (100 mL) under Ar. Ethoxycarbonyl isothiocyanate (2.5 eq., 34.13 mmol, 4.47 g) was added, and the mixture was left to stir for 12 h at rt. Hexamethyldisilazine (10 eq., 0.137 mmol, 22.11 g) was added, followed by EDC-HCl (2.0 eq., 27.3 mmol, 5.23 g). The mixture was stirred for 72 h, and then evaporated to dryness and partitioned between EtOAc (50 mL) and water (50 mL). The organic extract was with aq. HCl solution (1M, 2×100 mL), followed by sat. aq. $NaHCO_3$ (100 mL) solution. The organic extract was dried over anhydrous $Na_2SO_4$ and evaporated to dryness. The residue was purified by column chromatography with a gradient of 0 to 30% EtOAc in PE to give A11 as a white solid (3.1 g, 43%). ESI-MS: m/z 567.2 $[M+H]^+$.

Compound A11 (3.1 g, 5.47 mmol) was dissolved in MeOH (30 mL) in a round bottom flask (50 mL) under Ar and NaOH aqueous solution was added (0.25 M, 2 eq., 10.94 mmol, 43.8 mL). The mixture was heated to 75° C. and stirred for 4 h. The crude material was evaporated to dryness and partitioned between EtOAc (50 mL) and water (30 mL). The organic layer was dried over anhydrous $Na_2SO_4$ and then evaporated to dryness. The residue was purified by column chromatography with a gradient of 0 to 80% EtOAc in PE to give A12 as a white solid (2.3 g, 85%). ESI-MS: m/z 495.3 $[M+H]^+$.

Compound A12 (2.3 g, 4.65 mmol) was dissolved in superdry DCM (100 mL) in a round bottom flask (250 mL) under Ar. 1,2-ethanedithiol (25.0 eq., 116.25 mmol, 10.95 g) was added followed by the dropwise addition of $BF_3 \cdot OEt_2$ (20.0 eq., 93 mmol, 13.2 g) at rt. The solution was allowed to stir for 96 h, and then evaporated to near-dryness. The crude material was purified by reverse phase prep-HPLC (Column: $C_{18}$ spherical 20-35 μm 100A 120 g, mobile phase: 0.05% $NH_4HCO_3$ in water, m/m)-ACN from 0% to 60%, flow rate: 30 ml/min) to give A13 (310 mg, 21%) as a white solid. ESI-MS: m/z 315.1 $[M+H]^+$.

Compound A13 (310 mg, 0.99 mmol) was dissolved in dry pyridine (10 mL) in a round bottom flask (25 mL) under Ar. The mixture was ice-cooled to 0° C. and then stirred for 10 min. Isobutyryl chloride (6.0 eq., 5.94 mmol, 0.633 g) was dropwise slowly, and then stirred for 40 min. The reaction was quenched with water (10 mL) and CH₃OH (5 mL), and the mixture was extracted with EtOAc (4×20 mL). The combined organic layers was washed with water (2×30 mL) and brine (50 mL), dried over anhydrous Na₂SO₄ and evaporated to dryness. The residue was dissolved in pyridine (15 mL) in a round bottom flask (50 mL) and ice-cooled to 0° C. The mixture was stirred for 10 min. 2N NaOH (CH₃OH:H₂O=4:1, 10 mL) was dropwise slowly, and then the mixture was stirred for 30 min. The reaction was neutralized with 0.5 N HCl at 0° C. The mixture was extracted with EA (4×30 mL). The combined organic layer was washed with water (2×40 mL) and brine (50 mL), dried over anhydrous Na₂SO₄ and evaporated to dryness. The residue was purified by quickly column chromatography with a gradient of 0 to 20% CH₃OH in DCM to give crude A14 (320 mg, 84%) as a brown solid, which was used directly for next step without any further purification. ESI-MS: m/z 385.2 [M+H]⁺.

Compound A14 (320 mg, 0.83 mmol) was dissolved in dry pyridine (10 mL) in a round bottom flask (25 mL) under Ar. 4,4'-dimethoxytrityl chloride (1.5 eq., 1.245 mmol, 0.421 g) was added, and the mixture was stirred for 1 h. The reaction was quenched with water (3 mL) and CH₃OH (3 mL), and then extracted with EtOAc (4×25 mL). The combined organic layers was washed with water (2×30 mL) and brine (50 mL), dried over anhydrous Na₂SO₄ and evaporated to dryness. The residue was purified by column chromatography with a gradient of 0 to 100% EA in PE to give Monomer A as a white solid. ¹H NMR (400 MHz, DMSO-d₆) δ 12.19 (s, 1H), 11.64 (s, 1H), 7.44 (d, J=7.6 Hz, 2H), 7.39-7.14 (m, 7H), 6.91 (d, J=8.9 Hz, 4H), 5.41 (dd, J=16.4, 4.3 Hz, 2H), 4.47-4.31 (m, 1H), 4.13 (dd, J=8.2, 5.3 Hz, 1H), 3.75 (s, 6H), 3.71 (dd, J=5.9, 4.8 Hz, 1H), 3.29 (s, 3H), 3.18 (dd, J=10.4, 5.1 Hz, 1H), 2.87-2.77 (m, 1H), 1.13 (d, J=6.8 Hz, 6H). ESI-MS: m/z 687.2 [M+H]⁺.

Example 1d

Intermediate Monomer B

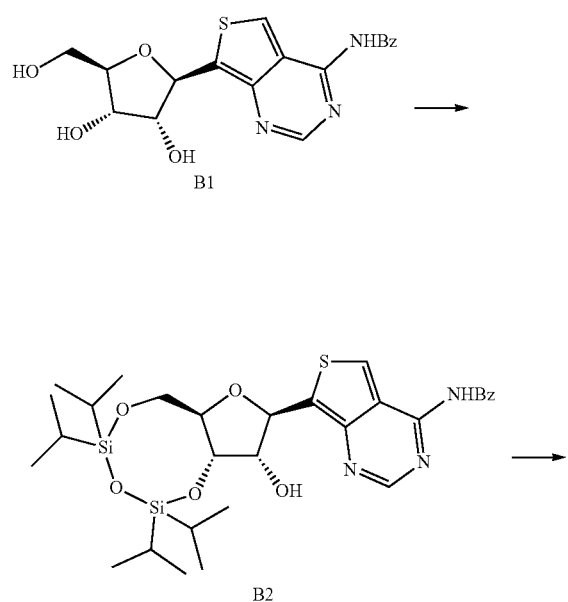

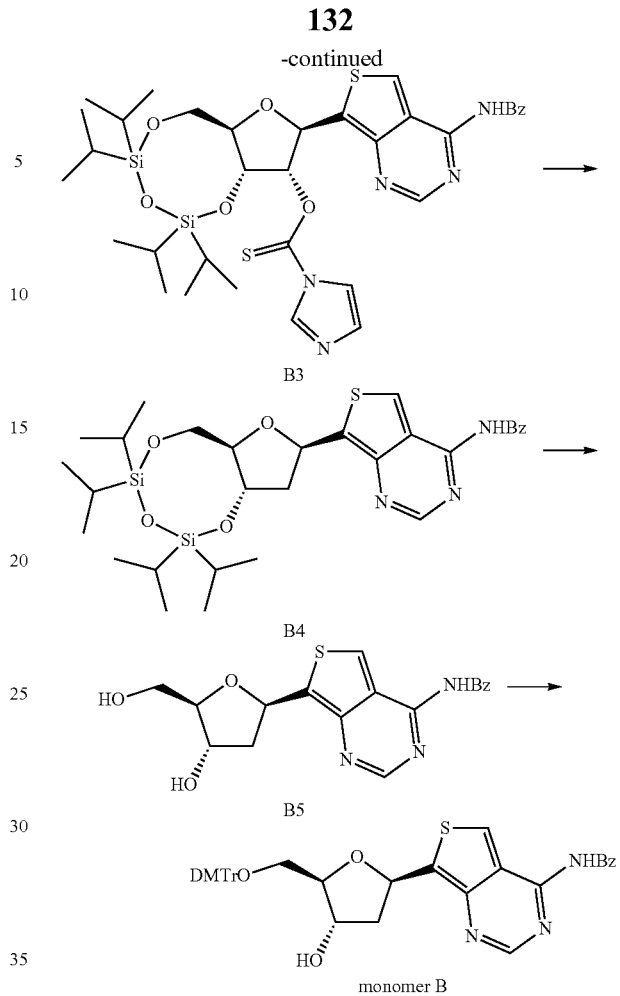

To a solution of B1 (1.44 g, 3.42 mmol) and imidazole (632.6 mg, 9.29 mmol) in DMF (10 mL) was added slowly TIDPSCl (1.29 g, 4.09 mmol) at 0° C. The mixture was stirred at 0° C. for 2 h until B1 was consumed as detected by TLC and LC-MS. The mixture was diluted with DCM (200 mL) and washed with NaHCO₃ solution (2×100 mL). The separated organic layers were washed with water (100 mL) and brine (100 mL), dried over Na₂SO₄ and evaporated in vacuo to give the crude product. The crude product was purified by silica gel column (PE:EA=2:1) to give B2 (1.9 g, 3.02 mmol, 81.1%) as a yellow oil. ESI-MS: m/z 630.2 [M+H]⁺.

A solution of B2 (1.2 g, 1.91 mmol), 1,1'-thiocarbonyldiimidazole (1.70 g, 9.53 mmol) and DMAP (116.37 mg, 952.51 umol) in DCM (12 mL) was stirred at rt for 12 h until B2 was consumed as detected by TLC and LC-MS. The solvent was evaporated in vacuo to give the crude product, which was purified by silica gel column (PE:EA=5:1) to give B3 (1.1 g, 1.49 mmol, 78.1%) as a yellow solid. ESI-MS: m/z 740.2 [M+H]⁺.

AIBN (159.76 mg, 972.91 umol) and B3 (1.44 g, 1.95 mmol) was dissolved in toluene (12 mL), and the solution was stirred at rt for 5 min with a N₂ bubble. The mixture was then warmed to 110° C. Tributyltin hydride (1.69 g, 5.84 mmol) was added, and the mixture was stirred at 110° C. for 3 h until B3 was consumed as detected by TLC and LC-MS. The mixture was diluted with DCM (100 mL, washed with brine (2×80 mL), dried over Na₂SO₄ and evaporated in vacuo to give the crude product. The crude product was purified by silica gel column (PE:EA=9:1) to give B4 (0.6 g, 977.34 umol, 62.7%) as a yellow oil. ESI-MS: m/z 614.2 [M+H]⁺.

Compound B4 (600 mg, 977.34 umol) was dissolved in the mixture solution of 3 HF·TEA (1.58 mmol, 0.5 mL) and THF (2 mL). The mixture was stirred at rt for 4 h until B4 was consumed as detected by TLC and LC-MS. THF was removed by bubbled with $N_2$ to give the crude product. The crude product was purified by silica gel column (DCM: MeOH=20:1) to give B5 (280 mg, 753.88 umol, 47.8%) as a yellow solid. ESI-MS: m/z 372.1 [M+H]⁺.

To a solution of B5 (260 mg, 700.04 umol) in pyridine (2 mL) was added DMTrCl (284 mg, 840.05 umol) at 0° C. The mixture was stirred at rt for 3 h until B5 was consumed as detected by TLC and LC-MS. The mixture was diluted with EtOAc (100 mL), washed with sat. $NaHCO_3$ aq (2×50 mL) and brine (80 mL), dried over $Na_2SO_4$ and evaporated in vacuo to give the crude product. The crude product was purified by silica gel column (PE:EA=1:1) to give Monomer B (300 mg, 445.25 umol, 63.6%) as a white solid. ¹H NMR (400 MHz, DMSO_d₆) δ 8.77 (s, 1H), 8.31 (s, 2H), 8.04 (s, 1H), 7.65-7.61 (t, J=14.0 Hz, 1H), 7.56-7.52 (t, J=15.1 Hz, 2H), 7.45 (d, J=7.8 Hz, 2H), 7.34-7.30 (t, J=7.1 Hz, 6H), 7.25-7.21 (t, J=7.2 Hz, 1H), 6.9 (d, J=8.8 Hz, 4H), 5.24 (d, J=4.0 Hz, 1H), 4.23 (s, 1H), 3.97 (s, 1H), 3.74 (s, 6H), 3.20-3.07 (m, 2H), 2.36-2.32 (m, 1H), 2.11-2.04 (m, 1H). ESI-MS: m/z 674.2 [M+H]⁺.

Example 2

Compounds 1-1 & 1-2

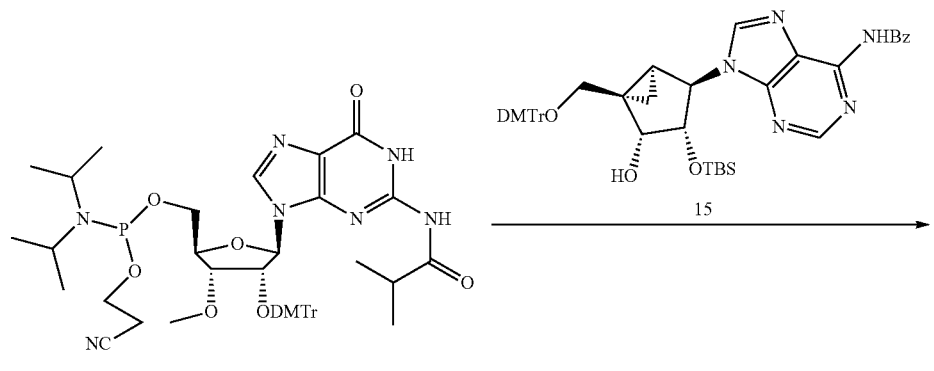

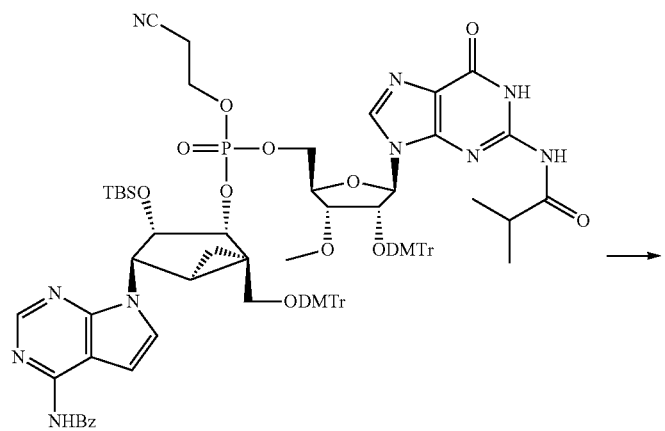

-continued
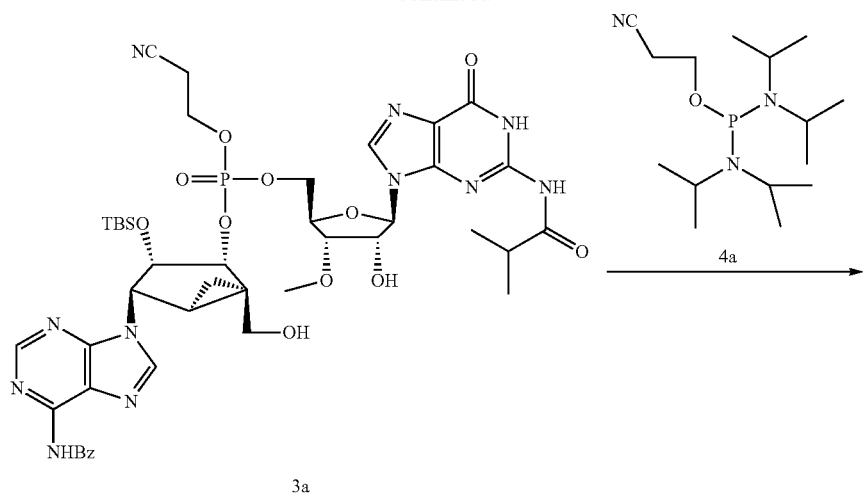
3a
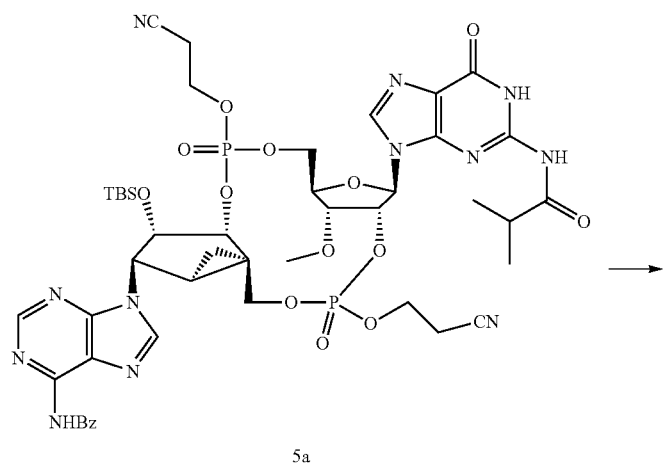
5a
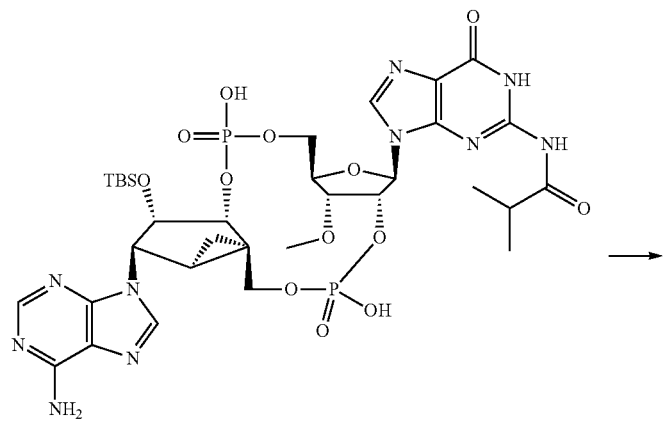
6a

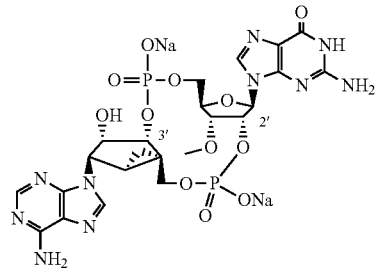

1-1

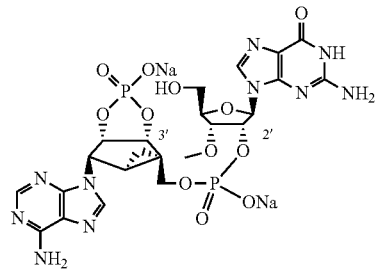

1-2

Compound 1a (870 mg g, 1.0 mmol) and 15 (800 mg, 1.0 mmol) was dissolved in anhydrous $CH_3CN$ (30.0 mL). 4 Å molecular sieves powder (300 mg, 1 gr/100 mL) were added to the mixture. The mixture was bubbled with Ar gas for 4 min. After stirring this mixture at rt for 10 min, 0.45 M tetrazole in $CH_3CN$ (5.4 mmol, 12 mL) was added at rt. After stirring for 1 h, the mixture was filtered and washed with anhydrous $CH_3CN$. To this mixture was added 0.02 M $I_2$ (THF:Py:$H_2O$, 8:1:1, v/v/v) until the color persisted. After stirring for 20-30 min at rt, the reaction was quenched with $Na_2SO_3$ (aq.) until discoloration. The mixture was diluted with EtOAc, and the layers were separated. The organic phase was washed with sat. aq. $NaHCO_3$ (1×) and sat. aq. NaCl (1×). The combined aqueous phase was back extracted with EtOAc (1×). The combined organic phases were evaporated to dryness, and the resulting crude material was purified by reverse phase prep-HPLC (Column: C18 spherical 20-35 µm 100A 80 g, mobile phase: 0.05% $NH_4HCO_3$ in water, m/m)-ACN from 30% to 100%, flow rate: 35 mL/min) to provide 2a (1.4 g, 80.2%) as a white foam. ESI-MS: m/z 1582.8 $[M+H]^+$.

Compound 2a (1.4 g, 0.88 mmol) was dissolved in DCA in DCM (3%, v/v, 11.0 mL). Triethyl silane (4.4 mL) was added immediately to the mixture. After stirring for 30 min at rt, the mixture was diluted with EtOAc, and then neutralize with sat. aq. $NaHCO_3$. The layers were separated, and the organic phase was washed with sat. aq. NaCl (1×). The aqueous phases were combined and then back extracted with EtOAc (3×). The combined organic phases were evaporated to dryness, and the resulting crude residue was purified by reverse phase prep-HPLC (Column: C18 spherical 20-35 µm 100A 80 g, mobile phase: 0.05% $NH_4HCO_3$ in water, m/m)-ACN from 30% to 80%, flow rate: 35 mL/min) to obtain 3a (580 mg, 0.59 mmol, 78.6%) as a white foam. $^{31}$P-NMR (162 MHz, DMSO-$d_6$): −1.14, −1.17. ESI-MS: m/z 978.5 $[M+H]^+$.

Compound 3a (580 mg, 590.8 µmol) dissolved in anhydrous ACN (30.0 mL), 0.45 M tetrazole in acetonitrile (3.76 mmol, 8.4 mL) and 4 Å molecular sieves powder (300 mg, 1 gr/100 mL) were combined. The resulting mixture was bubbled with Ar gas for 4 min. After stirring at rt for 20 min, 4a (303 mg, 0.94 mmol) in $CH_3CN$ (15.0 mL) was added over 25 to 30 min. After stirring for 2 h, the mixture was filtered and washed with anhydrous $CH_3CN$. To the mixture was added 0.02 M iodine (THF:Py:$H_2O$, 8:1:1, v/v/v) until the color persisted. After stirring for 20-30 min at rt, the reaction was quenched with sat. aq. $Na_2SO_3$. The mixture was diluted with EtOAc, and the layers were separated. The organic phase was washed with sat. aq. $NaHCO_3$ (1×) and sat. aq. NaCl (1×). The combined aqueous phases were back extracted with EtOAc (1×). The combined organic phases were evaporated to dryness, and the resulting crude material was purified by reverse phase prep-HPLC (Column: C18 spherical 20-35 µm 100A 80 g, mobile phase: 0.05% $NH_4HCO_3$ in water, m/m)-ACN from 30% to 60%, flow rate: 35 mL/min) to provide 5a (320 mg, 290.3 µmol, 42.8%) as a white foam. ESI-MS: m/z 1093.5$[M+H]^+$.

Compound 5a (320 mg, 290.3 µmol) was treated with a solution of $MeNH_2$ in EtOH (4 mL, 33%). After stirring for 2 h at 40° C., the mixture was evaporated to dryness. The resulting crude material was purified by reverse phase prep-HPLC (Column: C18 spherical 20-35 µm 100A 40 g, mobile phase: 0.05% $NH_4HCO_3$ in water, m/m)-ACN from 0% to 30%, flow rate: 35 mL/min) to obtain 6a (160 mg, 196.8 µmol, 76.3%) as a white foam. ESI-LMS: m/z 813.6 $[M+H]^+$.

A solution of 6a (160 mg, 196.8 µmol) and 3HF·TEA (2.0 mL) was stirred at 40° C. for 12 h. The mixture was dropped into a solution of TEA (2 mL) in triethyammonium bicarbonate buffer (12 ml) at 0° C. The mixture was stirred at rt for 30 min, and the crude mixture was purified by reverse phase prep-HPLC (Column: C18 spherical 20-35 µm 100A 40 g, mobile phase: 0.05% $NH_4HCO_3$ in water-ACN from 0% to 10%, flow rate: 20 mL/min) to obtain compound 1-1 $NH_4$ salt (30 mg, 40.9 µmol, 20.8%) and compound 1-2 $NH_4$ salt (50 mg, 68.3 µmol, 34.7%) as a white foam.

Amberlite IR-120 (Na form) (15 mL) was added to a column and washed with deionized water (3×15 mL). Compound 1-1 $NH_4$ salt was dissolved in deionized water (30 mg in 5 mL). The resulting solution was added to the top of the column, and eluted with deionized water. The compounds was eluted out in early fractions as detected by TLC (UV). The product was lyophilized to give 1-1 (22 mg, 31.5 µmol, 77.1%) as a white foam. $^{31}$P NMR (162 MHz, D$_2$O): −0.54, −2.95. ESI-MS: m/z 699.4 [M+H]$^+$.

Compound 1-2 NH$_4$ salt was dissolved in deionized water (50 mg in 7 mL). The resulting solution was added to the top of the column and eluted with deionized water. The compounds was eluted out in early fractions as detected by TLC (UV). The product was lyophilized to give 1-2 (44 mg, 63.1 µmol, 92.3%) as a white foam. $^{31}$P NMR (162 MHz, D$_2$O): 19.16, −1.57. ESI-MS: m/z 699.4 [M+H]$^+$.

Example 3

Compound 1-3

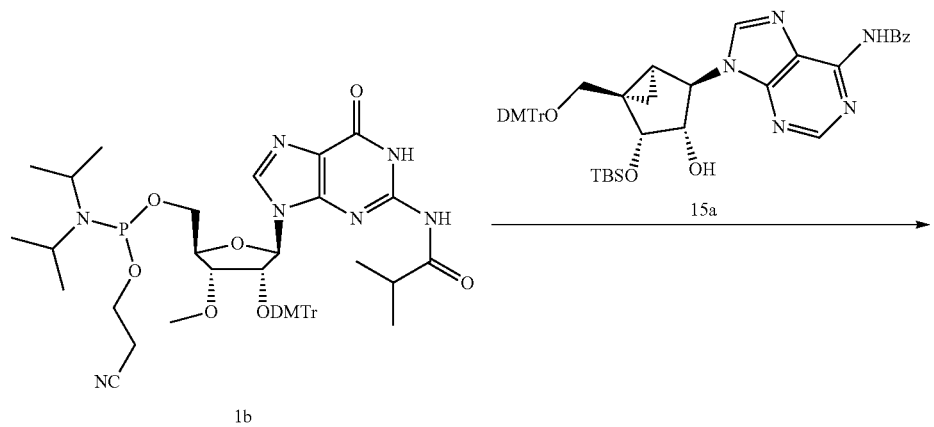

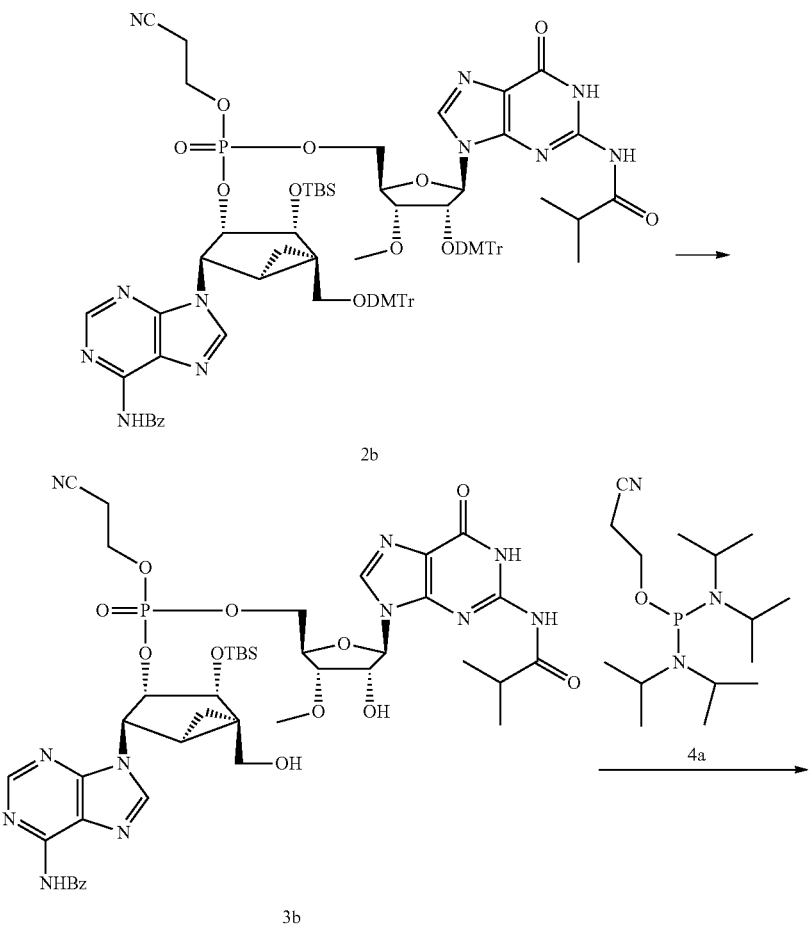

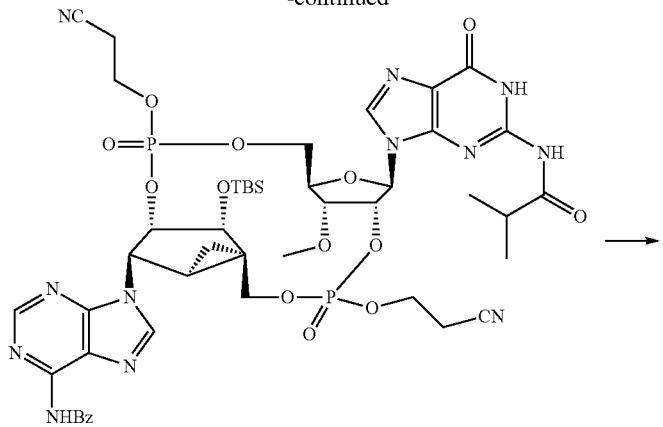

4b

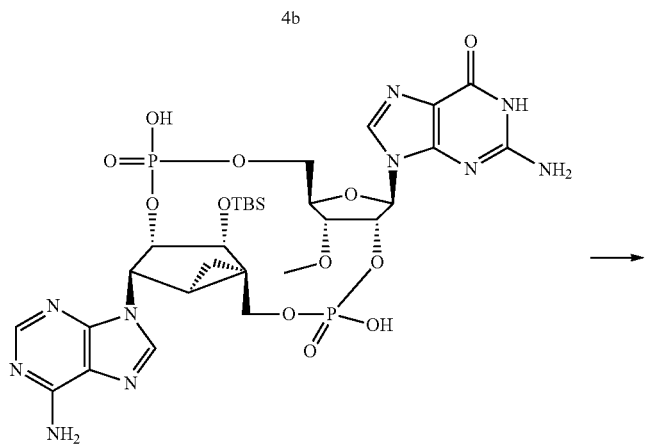

5b

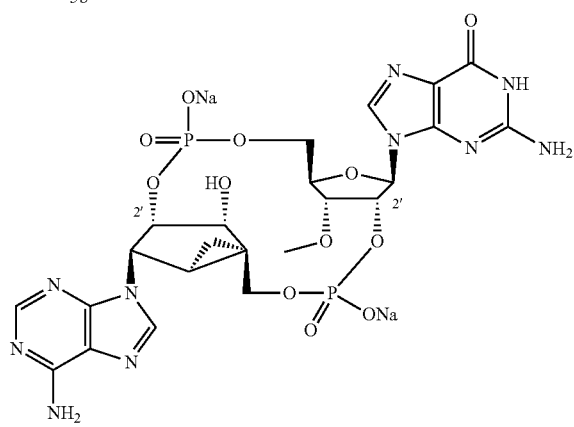

1-3

Compound 1b (870 mg, 1.0 mmol) and 15a (720 mg, 0.9 mmol) were dissolved in anhydrous CH$_3$CN (30.0 mL), and 4 Å molecular sieves powder (300 mg, 1 gr/100 mL) were added. The mixture was bubbled with Ar gas for 4 min. After stirring at rt for 10 min, 0.45 M tetrazole in CH$_3$CN (5.4 mmol, 12 mL) was added at rt. After stirring for 1 h, the mixture was filtered, and washed with anhydrous CH$_3$CN. 0.02 M I$_2$ (THF:Py:H$_2$O, 8:1:1, v/v/v) was added until the color persisted. After stirring for 20-30 min at rt, the reaction was quenched with Na$_2$SO$_3$ (aq, until discoloration). The mixture was diluted with EtOAc, and the layers were separated. The organic phase was washed with sat. aq. NaHCO$_3$ (1×) and sat. aq. NaCl (1×). The combined aqueous phases were back extracted with EtOAc (1×). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 30% to 100%, flow rate: 35 mL/min) to get 2b (1.0 g, 70.2%) as a white foam. ESI-MS: m/z 1582.8 [M+H]$^+$.

Compound 2b (1.0 g, 0.63 mmol) was dissolved in DCA in DCM (3%, v/v, 11.0 mL) and triethyl silane (4.4 mL) was added immediately. After stirring for 30 min at rt, the mixture was diluted with EtOAc, and then neutralize with sat. aq. NaHCO₃. The layers were separated, and the organic phase was washed with sat. aq. NaCl (1×). The aqueous phases were combined and then back extracted with EtOAc (3×). The combined organic phases was evaporated to dryness. The resulting crude residue was purified by reverse phase prep-HPLC (Column: C18 spherical 20-35 μm 100A 80 g, mobile phase: 0.05% NH₄HCO₃ in water, m/m)-ACN from 30% to 80%, flow rate: 35 mL/min) to obtain 3b (460 mg, 0.47 mmol, 74.6%) as a white foam. $^{31}$P-NMR (162 MHz, DMSO-d₆): −2.70, −2.74. ESI-MS: m/z 978.5 [M+H]⁺.

Compound 3b (460 mg, 470.8 μmol) was dissolved in anhydrous ACN (30.0 mL), 0.45 M tetrazole in CH₃CN (3.76 mmol, 8.4 mL) and 4 Å molecular sieves powder (300 mg, 1 gr/100 mL). The resulting heterogeneous mixture was bubbled with Ar gas for 4 min. After stirring at rt for 20 min, 4a (303 mg, 0.94 mmol) in CH₃CN (15.0 mL) was added over 25 to 30 min. After stirring for 2 h, the mixture was filtered, and washed with anhydrous CH₃CN. 0.02 M Iodine (THF:Py:H₂O, 8:1:1, v/v/v) was added until the color persisted. After stirring for 20-30 min at rt, the reaction was quenched with sat. aq. Na₂SO₃. The mixture was diluted with EtOAc, and the layers separated. The organic phase was washed with sat. aq. NaHCO₃ (1×) and sat. aq. NaCl (1×). Combined aqueous phase back extracted with EtOAc (1×). The combined organic phases were evaporated to dryness, and the crude material was purified by reverse phase prep-HPLC (Column: C18 spherical 20-35 μm 100A 80 g, mobile phase: 0.05% NH₄HCO₃ in water, m/m)-ACN from 30% to 60%, flow rate: 35 mL/min) to get 4b (220 mg, 201.3 μmol, 42.8%) as a white foam. ESI-MS: m/z 1093.5 [M+H]⁺.

Compound 4b (220 mg, 201.5 μmol) was treated with a solution of MeNH₂ in EtOH (4 mL, 33%). After stirring for 2 h at 40° C., the mixture was evaporated to dryness. The crude material was purified by reverse phase prep-HPLC (Column: C18 spherical 20-35 μm 100A 40 g, mobile phase: 0.05% NH₄HCO₃ in water, m/m)-ACN from 0% to 30%, flow rate: 25 mL/min) to provide 5b (120 mg, 147.6 μmol, 73.3%) as a white foam. ESI-LMS: m/z 813.6 [M+H]⁺.

A solution of 5b (120 mg, 147.6 μmol) and 3HF·TEA (2.0 mL) was stirred at 40° C. for 2 h. The mixture was dropped in the solution of TEA (2 mL) in triethyamimonium bicarbonate buffer (12 mL) at 0° C. The mixture was stirred at rt for 30 min. The mixture was purified by reverse phase prep-HPLC (Column: C18 spherical 20-35 μm 100A 40 g, mobile phase: 0.05% NH₄HCO₃ in water-ACN from 0% to 10%, flow rate: 20 mL/min) to get the NH₄ salt product (60 mg, 85.9 μmol, 58.2%) as a white foam. A 15.0 mL volume of Amberlite IR-120 (Na form) was added to a column and washed with deionized water (3×15 mL). The NH₄ salt product (60 mg) was then dissolved in deionized water (60 mg in 8 mL). The mixture was added to the top of the column, and eluted with deionized water. The compound was eluted out in early fractions as detected by TLC (UV). The product was lyophilized to obtain compound 1-3 (39 mg, 52.5 μmol, 61.2%) as a white foam. $^{31}$P NMR (162 MHz, D₂O): −0.57, −1.43. ESI-MS: m/z 699.4 [M+H]⁺.

Example 4

Compound 1-4

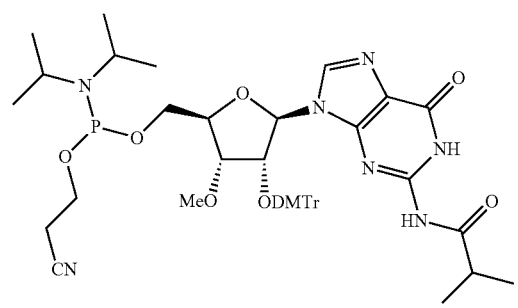

monomer C

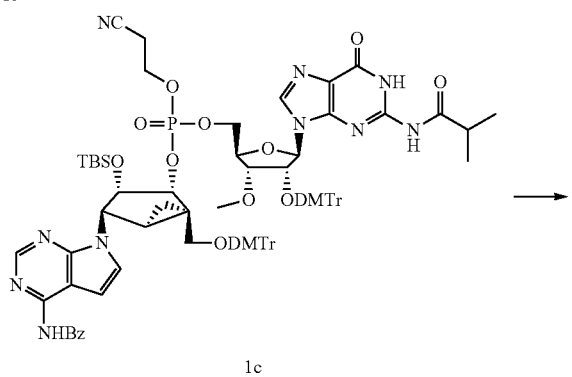

1c

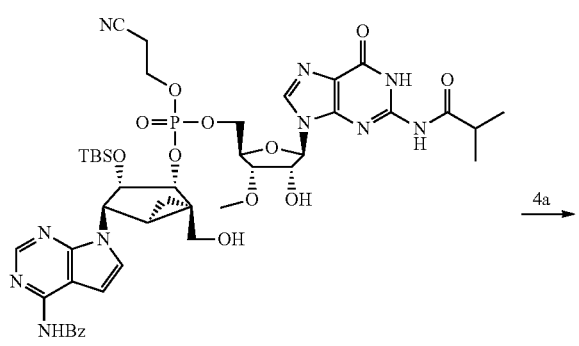

2c

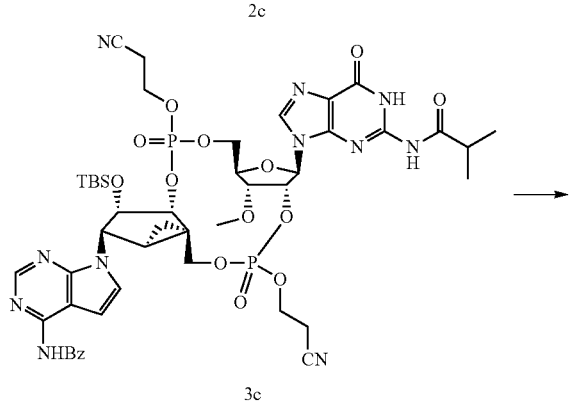

3c

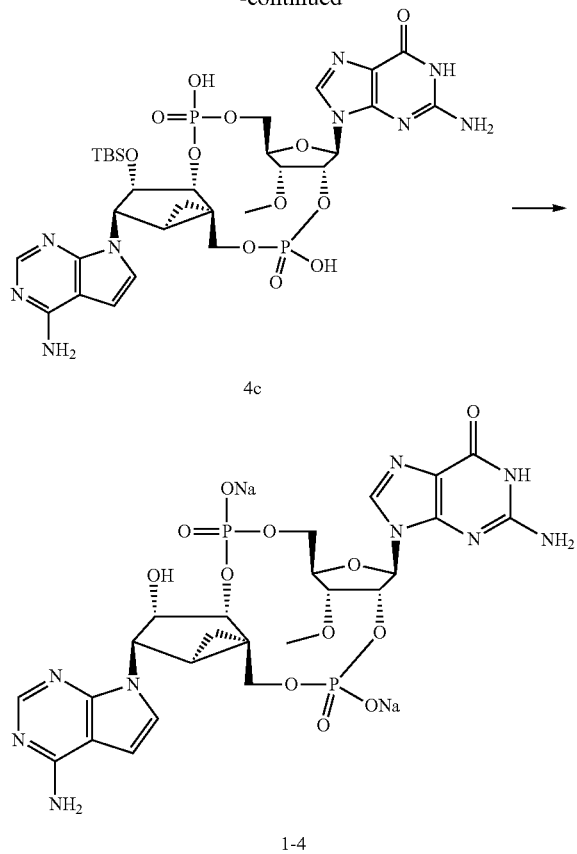

Monomer C (720 mg, 0.82 mmol) and 15 (600 mg, 0.75 mmol) were dissolved in anhydrous $CH_3CN$ (18.0 mL), and 4 Å molecular sieves powder (1 gr/100 mL) were added. The mixture was bubbled with Ar gas for 4 min. After stirring at rt for 10 min, 0.45 M tetrazole in $CH_3CN$ (4.51 mmol, 10 mL) was added at rt. After stirring for 1 h, the mixture was filtered, and washed with anhydrous $CH_3CN$. 0.02 M $I_2$ ($THF:Py:H_2O$, 8:1:1, v/v/v) was added until the color persisted. After stirring for 20-30 min at rt, the reaction was quenched with $Na_2SO_3$ (aq, until discoloration). The mixture was diluted with EtOAc, and the layers were separated. The organic phase was washed with sat. aq. $NaHCO_3$ (1×) and sat. aq. NaCl (1×). The combined aqueous phase was back extracted with EtOAc (1×). The combined organic phases were evaporated to dryness and the crude material was purified by reverse phase prep-HPLC (Column: C18 spherical 20-35 μm 100A 80 g, mobile phase: 0.05% $NH_4HCO_3$ in water, m/m)-ACN from 30% to 100%, flow rate: 35 mL/min) to get 1c (1.1 g, 96.2%) as a white foam. ESI-MS: m/z 1582.8 $[M+H]^+$.

Compound 1c (1.1 g, 0.69 mmol) was dissolved in DCA in DCM (3%, v/v, 19.2 mL) and triethyl silane (13.2 mL) was added immediately. After stirring for 30 min at rt, the mixture was diluted with EtOAc, and then neutralize with sat. aq. $NaHCO_3$. The layers were separated, and the organic phase was washed with sat. aq. NaCl (1×). The aqueous phase was combined and back extracted with EtOAc (3×). The combined organic phases were evaporated to dryness. The crude residue was purified by reverse phase prep-HPLC (Column: C18 spherical 20-35 μm 100A 80 g, mobile phase: 0.05% $NH_4HCO_3$ in water, m/m)-ACN from 30% to 80%, flow rate: 35 mL/min) to get 2c (550 mg, 0.56 mmol, 77.6%) as a white foam. ESI-MS: m/z 978.5 $[M+H]^+$.

Compound 2c (500 mg, 562.9 μmol) dissolved in anhydrous $CH_3CN$ (30.0 mL), 0.45 M tetrazole in $CH_3CN$ (4.09 mmol, 9.09 mL) and 4 Å molecular sieves powder (300 mg, 1 gr/100 mL). The mixture was bubbled with Ar gas for 4 min. After stirring at rt for 20 min, 4a (308 mg, 1.02 mmol) in $CH_3CN$ (10.0 mL) was added over 30 to 40 min. After stirring for 2 h, the mixture was filtered and washed with anhydrous $CH_3CN$. 0.02 M $I_2$ ($THF:Py:H_2O$, 8:1:1, v/v/v) was added until color persisted. After stirring for 20-30 min at rt, the reaction was quenched with sat. aq. $Na_2SO_3$ (until discoloration). The mixture was diluted with EtOAc, and the layers separated. The organic phase was washed with sat. aq. $NaHCO_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% $NH_4HCO_3$ in water, m/m)-ACN from 30% to 60%, flow rate: 35 mL/min) to get 3c (208 mg, 190.4 μmol, 33.8%) as a white foam. ESI-MS: m/z 1093.5$[M+H]^+$.

Compound 3c (200 mg, 183.1 μmol) was treated with a solution of $MeNH_2$ in EtOH (10 mL, 33%). After stirring for 3 h at 40° C., the mixture was evaporated to dryness. The crude material was purified by reverse phase prep-HPLC (Column: C18 spherical 20-35 μm 100A 40 g, mobile phase: 0.05% $NH_4HCO_3$ in water, m/m)-ACN from 0% to 30%, flow rate: 25 mL/min) to get 4c (115 mg, 141.8 μmol, 81.5%) as a white foam. ESI-LMS: m/z 812.6 $[M+H]^+$.

3HF·TEA (1.5 mL) was added to a mixture solution of 4c (100 mg, 123.3 mol) in DMSO (3 mL) at 40° C. for 8 h. The mixture was dropped in the solution of TEA (2 mL) in triethyammonium bicarbonate buffer (12 ml) at 0° C. The mixture was stirred at rt for 30 min and then was purified by reverse phase prep-HPLC (Column: C18 spherical 20-35 μm 100A 40 g, mobile phase: 0.05% $NH_4HCO_3$ in water-ACN from 0% to 10%, flow rate: 20 mL/min) to get the $NH_4$ salt product (60 mg, 80.9 μmol, 65.6%) as a white foam. A volume of Amberlite IR-120 (Na form, 15.0 mL) was added to a column and washed with deionized water (3×15 mL). The $NH_4$ salt product (60 mg) was dissolved in deionized water (60 mg in 8 mL) and added to the top of the column. The column was eluted with deionized water. The compound was eluted out in early fractions as detected by TLC (UV). The product was lyophilized to give compound 1-4 (46 mg, 62.1 μmol, 76.6%) as a white foam. $^{31}P$ NMR (162 MHz, D2O): −0.46, −2.92. ESI-MS: m/z 698.4 $[M+H]^+$.

Example 5

Monomer D

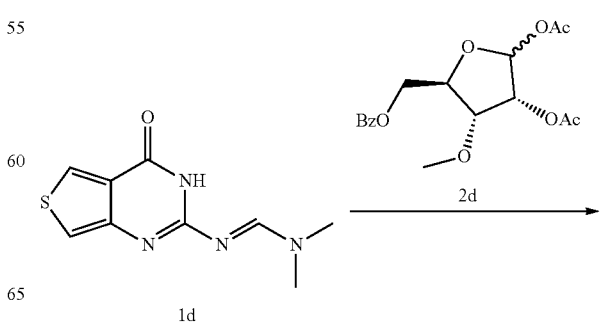

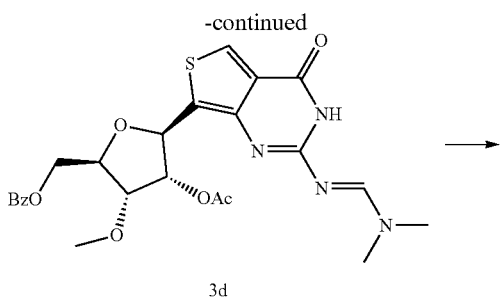

3d

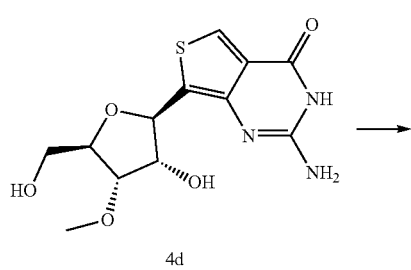

4d

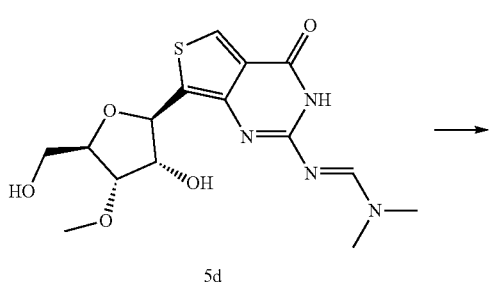

5d

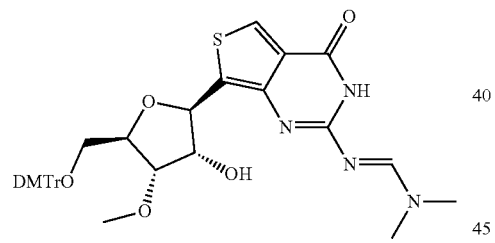

monomer D

To a suspension of 1d (4.2 g, 18.9 mmol) and 2d (6.66 g, 18.9 mmol) in dry MeNO$_2$ (200 mL) was added 4 A MS (4.0 g, dried at 600° C. for 2 h before used). The solution was cooled to 0° C. and stirred at this temperature for 15 min. SnCl$_4$ (39.7 mL, 39.7 mmol, 2.1 eq., 1.0 M in DCM) was dropwise to the solution over 30 min at 0° C. The mixture was heated to 65° C. and stirred at this temperature for 2 h. Compound 2d (6.66 g, 18.9 mmol) was added to the mixture. The mixture was stirred overnight at the same temperature. After cooling to RT, the mixture was poured into sat. aq. NaHCO$_3$ (300 mL) and diluted with CH$_2$Cl$_2$ (150 mL). The mixture was vigorously stirred for 1 h, and the precipitate was filtered over a Celite cake. The separated aq. layer was extracted with CH$_2$Cl$_2$ (4×100 mL). The combined organic layers were dried over Na$_2$SO$_4$ and evaporated to give crude product.

The residue was purified by column chromatography with CH$_2$Cl$_2$:MeOH=100:1 to afford a crude product. The crude product was repurified by reverse phase prep-HPLC (Column: C18 spherical 20-35 μm 100A 120 g, mobile phase: 0.05% NH$_4$HCO$_3$ in water, m/m)-ACN from 0% to 70%, flow rate: 25 mL/min) as eluent. The fractions containing the desired compound were evaporated in vacuo to give 3d (3.3 g, 34%) as a light yellow solid. ESI-MS: m/z 515.3 [M+H]$^+$.

Compound 3d (3.3 g, 6.42 mmol) was treated with a solution of MeNH$_2$ in EtOH (45 mL, 33%). After stirring for 2 h at rt, the mixture was evaporated to dryness. The crude material was purified by reverse phase prep-HPLC (Column: C18 spherical 20-35 μm 100A 120 g, mobile phase: 0.05% NH$_4$HCO$_3$ in water, m/m)-ACN from 0% to 40%, flow rate: 25 mL/min). The fractions containing the desired compound were pooled and lyophilized to give 4d (1.65 g, 5.27 mmol, 82.1%) as a light yellow solid. ESI-MS: m/z 314.1 [M+H]$^+$.

A solution of 4d (1.65 g, 5.27 mmol) in dry DMF (50 mL) was added N,N-dimethylformamide dimethyl acetal (1.56 g, 13 mmol, 2.5 eq.) at rt, and the mixture stirred at this temperature overnight. All volatiles were evaporated, and the oily residue was coevaporated with DMF (2×20 mL) to afford a crude solid 5d (1.9 g, 5.16 mmol, 97.9%), which was used directly for next step without any purification. ESI-MS: m/z 369.1 [M+H]$^+$.

A solution of 5d (1.9 g, 5.16 mmol, crude) in dry pyridine (30 mL) was added DMTrCl (2.27 g, 6.71 mmol, 1.3 eq.) at rt. The mixture was stirred at this temperature for 1.5 h until 4d was consumed. The reaction was quenched with MeOH/H$_2$O (10 mL/30 mL) and extracted by EtOAc (4×40 mL). The combined organic layers were washed with water, brine, dried over anhydrous and evaporated in vacuo to give the crude product. The residue was purified by column chromatography with PE:EtOAc=2:1 to afford Monomer D (2.4 g, 3.58 mmol, 69.4%) a light yellow solid. ESI-MS: m/z 671.4 [M+H]$^+$ Example 6

Compound 1-5

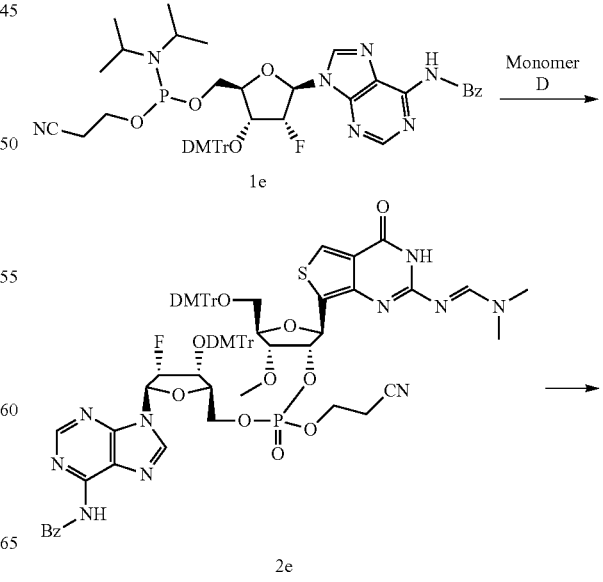

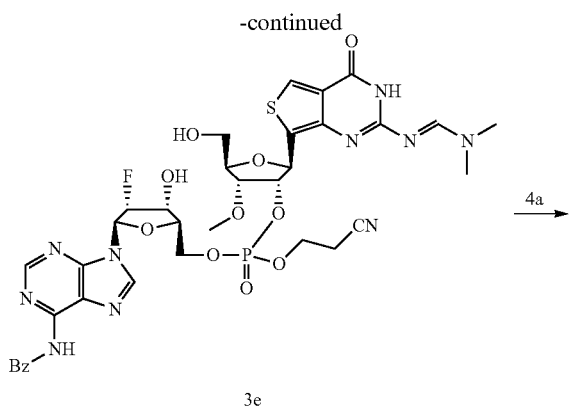

3e

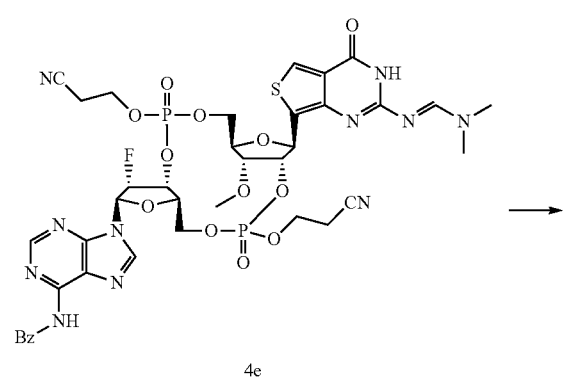

4e

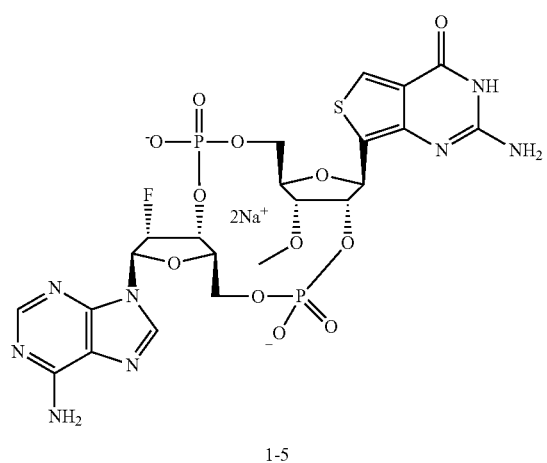

1-5

Compound 1e (1.15 g, 1.31 mmol) and Monomer D (800 mg, 1.19 mmol) were dissolved in anhydrous CH$_3$CN (40.0 mL), and 4 Å molecular sieves powder (400 mg, 1 gr/100 mL) were added. The mixture was bubbled with Ar gas for 4 min. After stirring at rt for 10 min, 0.45 M tetrazole in CH$_3$CN (7.14 mmol, 15.9 mL) was added at rt. After stirring for 1 h, the mixture was filtered, and washed with anhydrous CH$_3$CN. 0.02 M I$_2$ (THF:Py:H$_2$O, 8:1:1, v/v/v) was added until color persisted. After stirring for 20-30 min at rt, the reaction was quenched with Na$_2$SO$_3$ (aq, until discoloration). The mixture was diluted with EtOAc, and the layers were separated. The organic phase was washed with sat. aq. NaHCO$_3$ (1×) and sat. aq. NaCl (1×). The combined aqueous phase was back extracted with EtOAc (1×). The combined organic phases were evaporated to dryness. The crude material was purified by reverse phase prep-HPLC (Column: C18 spherical 20-35 μm 100A 80 g, mobile phase: 0.05% NH$_4$HCO$_3$ in water, m/m)-ACN from 30% to 100%, flow rate: 35 mL/min) to get 2e (1.55 g, 89.2%) as a white foam. ESI-MS: m/z 1461.6 [M+H]$^+$.

Compound 2e (1.55 g, 1.06 mmol) was dissolved in DCA in DCM (3%, v/v, 19.0 mL) and triethyl silane (8.0 mL) was added immediately. After stirring for 30 min at rt, the mixture was diluted with EtOAc, and neutralize with sat. aq. NaHCO$_3$. The layers were separated, and the organic phase was washed with sat. aq. NaCl (1×). The aqueous phase was combined and back extracted with EtOAc (3×). The combined organic phases were evaporated to dryness. The crude residue was purified by reverse phase prep-HPLC (Column: C18 spherical 20-35 μm 100A 80 g, mobile phase: 0.05% NH$_4$HCO$_3$ in water, m/m)-ACN from 30% to 80%, flow rate: 35 mL/min) to get 3e (730 mg, 0.85 mmol, 80.4%) as a white foam. $^{31}$P NMR (162 MHz, DMSO-d$_6$) δ −2.62, −2.68. $^{19}$F NMR (376 MHz, D$_2$O) δ −201.82, −202.22. ESI-MS: m/z 857.4 [M+H]$^+$.

Compound 3e (730 mg, 0.85 mmol) was dissolved in anhydrous CH$_3$CN (60.0 mL), 0.45 M tetrazole in CH$_3$CN (6.8 mmol, 15 mL) and 4 Å molecular sieves powder (600 mg, 1 gr/100 mL). The mixture was bubbled with Ar gas for 4 min. After stirring at rt for 20 min, 4a (512.2 mg, 1.7 mmol) in CH$_3$CN (20.0 mL) was added over 25 to 30 min. After stirring for 2 h, the mixture was filtered and washed with anhydrous CH$_3$CN. 0.02 M Iodine (THF:Py:H$_2$O, 8:1:1, v/v/v) was added until color persisted. After stirring for 20-30 min at rt, the reaction was quenched with sat. aq. Na$_2$SO$_3$ (until discoloration). The mixture was diluted with EtOAc, and the layers separated. The organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 30% to 60%, flow rate: 35 mL/min) to get 4e (190 mg, 0.196 mmol, 23.1%) as a white foam. ESI-MS: m/z 972.2 [M+H]$^+$.

Compound 4e (190 mg, 0.196 mmol) was treated with a solution of MeNH$_2$ in EtOH (15 mL, 33%). After stirring for 2 h at 40° C., the mixture was evaporated to dryness. The crude material was purified by reverse phase prep-HPLC (Column: C18 spherical 20-35 μm 100A 40 g, mobile phase: 0.05% NH$_4$HCO$_3$ in water, m/m)-ACN from 0% to 30%, flow rate: 25 mL/min) to get NH$_4$ salt product (80 mg, 0.113 mmol, 57.8%) as a white foam. ESI-LMS: m/z 707.1 [M+H]$^+$.

A volume of Amberlite IR-120 (Na form, 15.0 mL) was added to a column and washed with deionized water (3×15 mL). The NH$_4$ salt product (80 mg) was dissolved in deionized water (80 mg in 10 mL) and added to the top of the column. The column was eluted with deionized water. The compound was eluted out in early fractions as detected by TLC (UV). The product was lyophilized to give compound 1-5 (65 mg, 0.092 mmol, 81.3%) as a white foam. $^{31}$P NMR (162 MHz, DMSO-d$_6$) δ −1.59, −3.04. $^{19}$F NMR (376 MHz, D$_2$O) δ −202.57. ESI-MS: m/z 707.1 [M+H]$^+$.

Example 7

Compounds 1-6a & 1-6b

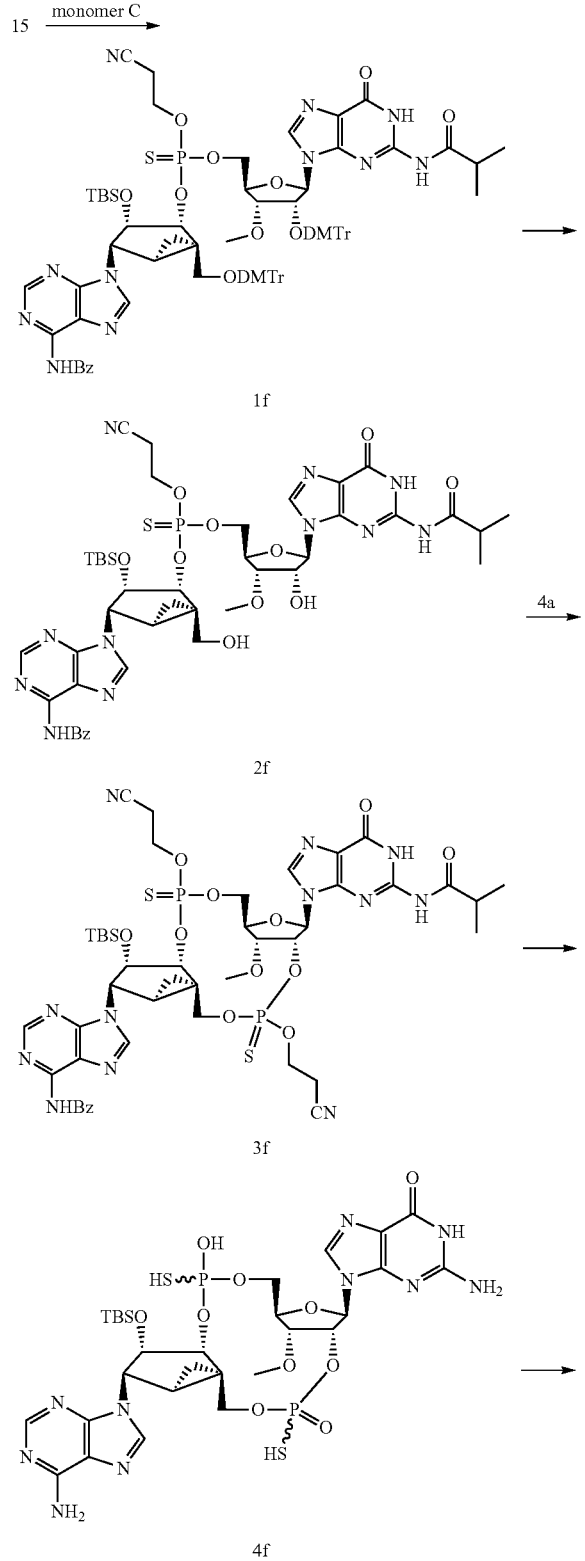

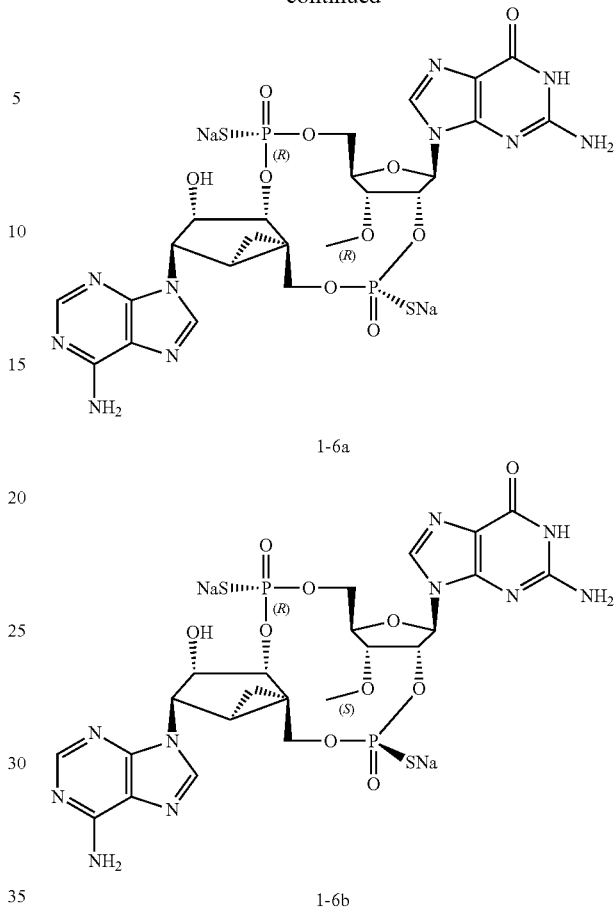

Compound 15 (1.1 g, 1.38 mmol) was dissolved in anhydrous CH$_3$CN (44.0 mL) and Monomer C (1.3 g, 1.51 mmol) and 4 Å molecular sieves powder (440 mg, 1 gr/100 mL) were added. The mixture was bubbled with Ar gas for 4 min. After stirring at rt for 10 min, 0.45 M tetrazole in CH$_3$CN (8.27 mmol, 3.3 mL) was added at rt. After stirring for 1 h, the mixture was filtered and washed with anhydrous CH$_3$CN. Pyridine (436 mg, 5.52 mmol) and 5-Amino-3H-1,2,4-dithiazole-3-thione (414 mg, 2.76 mmol) were added to the mixture. After stirring for 20-30 min at rt, the reaction was quenched with Na$_2$SO$_3$ (aq, until discoloration). The mixture was then diluted with EtOAc, and the layers were separated. The organic phase was washed with sat. aq. NaHCO$_3$ (1×50 mL) and sat. aq. NaCl (1×50 mL). The combined aqueous phase was back-extracted with EtOAc (1×50 mL). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 60% to 100%, flow rate: 35 mL/min) to afford if (1.9 g, 1.19 mmol, 86.21%) as a white foam. ESI-MS: m/z 1598.7 [M+H]$^+$.

Compound 1f (1.9 g, 1.19 mmol) was dissolved in DCA in DCM (3%, v/v, 50.0 mL). Triethyl silane (10.0 mL) was added to the mixture. After stirring for 30 min at rt, the mixture was neutralized with pyridine and then evaporated to dryness. The crude residue was purified by reverse phase prep-HPLC (Column: C18 spherical 20-35 μm 100A 80 g, mobile phase: 0.05% NH$_4$HCO$_3$ in water, m/m)-ACN from 30% to 80%, flow rate: 35 mL/min) to afford 2f (985 mg, 990.85 umol, 83.38%) as a white foam. ESI-MS: m/z 994.4 [M+H]+.

Compound 2f (500 mg, 503.02 umol) dissolved in anhydrous CH$_3$CN (40.0 mL), and 0.45 M tetrazole in CH$_3$CN (4.02 mmol, 8.9 mL) and 4 Å molecular sieves powder (500 mg, 1 gr/100 mL) were added. The mixture was bubbled with Ar gas for 4 min. After stirring at rt for 20 min, 4a (304 mg, 1.00 mmol) in CH$_3$CN (5.0 mL) was added over 25 to 30 min. After stirring for 2 h, the mixture was filtered off, and then washed with anhydrous CH$_3$CN. Pyridine (159 mg, 2.01 mmol) and 5-Amino-3H-1,2,4-dithiazole-3-thione (151 mg, 2.76 mmol) were added to the mixture. After stirring for 20-30 min at rt, the reaction was quenched with sat. aq. Na$_2$SO$_3$ (until discoloration) and then diluted with EtOAc. The layers were separated, and the organic phase was washed with sat. aq. NaHCO$_3$ (1×50 mL) and sat. aq. NaCl (1×50 mL). The combined aqueous phase back extracted with EtOAc (1×50 mL), and then evaporated to dryness. The crude material was purified by reverse phase prep-HPLC (Column: C18 spherical 20-35 μm 100A 40 g, mobile phase: 0.05% NH$_4$HCO$_3$ in water, m/m)-ACN from 30% to 60%, flow rate: 25 mL/min) to obtain 3f (205 mg, 182.19 umol, 36.18%) as a white foam. ESI-MS: m/z 1125.4 [M+H]+.

Compound 3f (205 mg, 182.19 umol) was treated with a solution of MeNH$_2$ in EtOH (15 mL, 33%). After stirring for 2 h at 40° C., the mixture was evaporated to dryness. The crude material was purified by reverse phase prep-HPLC (Column: C18 spherical 20-35 μm 100A 20 g, mobile phase: 0.05% NH$_4$HCO$_3$ in water, m/m)-ACN from 0% to 30%, flow rate: 20 mL/min) to afford 4f (102 mg, 120.73 umol, 66.26%) as a white foam. ESI-MS: m/z 845.3 [M+H]+.

Compound 4f (182 mg, 169.64 umol) and 3HF·TEA (1.0 mL) in THF (2.0 mL) was stirred at 40° C. for 6 h. The mixture was dropped in the solution of TEA (3 mL) in triethyamimonium bicarbonate buffer (18 mL) at 0° C. The mixture was stirred at rt for 30 min, and then was purified by reverse phase prep-HPLC (Column: XBridge 30×100 mm, mobile phase: 0.05% NH$_4$HCO$_3$ in water, m/m)-ACN from 0% to 10%, flow rate: 20 mL/min) to obtain 1-6a (38 mg, 52.05 mol, 30.69%) and 1-6b (21 mg, 28.77 μmol, 16.96%) as a white foam. Amberlite IR-120 (15.0 mL, Na form) was added to a column and washed with deionized water (3×15 mL). Compound 1-6a (38 mg) was dissolved in deionized water (38 mg in 6 mL) and added to the top of the column, and then eluted with deionized water. Compound 1-6a was eluted out in early fractions as detected by TLC (UV). The product was lyophilized to afford 1-6a (32 mg) as a white foam. Isomer 1-6b (21 mg) was dissolved in deionized water (21 mg in 5 mL) and added to the top of the column, and then eluted with deionized water. Compound 1-6b was eluted out in early fractions as detected by TLC (UV). The product was lyophilized to afford 1-6b (13 mg) as a white foam.

1-6a: $^1$H NMR (400 MHz, D$_2$O): δ 8.30 (s, 1H), 8.11 (s, 1H), 7.94 (s, 1H), 5.85 (d, J=8.8 Hz, 1H), 5.65-5.59 (m, 1H), 5.23 (t, J=7.6 Hz, 1H), 4.83 (s, 1H), 4.52 (s, 1H), 4.39-3.28 (m, 3H), 3.22-3.13 (m, 2H), 3.77-3.74 (m, 1H), 3.53 (s, 3H), 1.85-1.83 (m, 1H), 1.68-1.66 (m, 1H), 1.03 (t, J=7.6 Hz, 1H). $^{31}$P-NMR (162 MHz, D$_2$O): 53.72, 52.99. ESI-MS: m/z 731.3 [M+H]+.

1-6b: $^1$H NMR (400 MHz, D$_2$O): δ 8.39 (s, 1H), 8.14 (s, 1H), 7.80 (s, 1H), 5.85-5.77 (m, 2H), 5.39 (t, J=7.6 Hz, 1H), 4.84 (s, 1H), 4.53 (s, 1H), 4.40-3.34 (m, 2H), 4.26 (d, J=3.6 Hz, 1H), 4.16 (d, J=5.6 Hz, 1H), 4.05 (d, J=11.2 Hz, 1H), 3.68 (d, J=10.8 Hz, 1H), 1.87 (t, J=4.8 Hz, 1H), 1.75 (t, J=4.8 Hz, 1H), 1.04 (t, J=7.6 Hz, 1H). $^{31}$P-NMR (162 MHz, D$_2$O): 54.99, 53.25. ESI-MS: m/z 731.3 [M+H]+.

Example 8

Compound 1-7

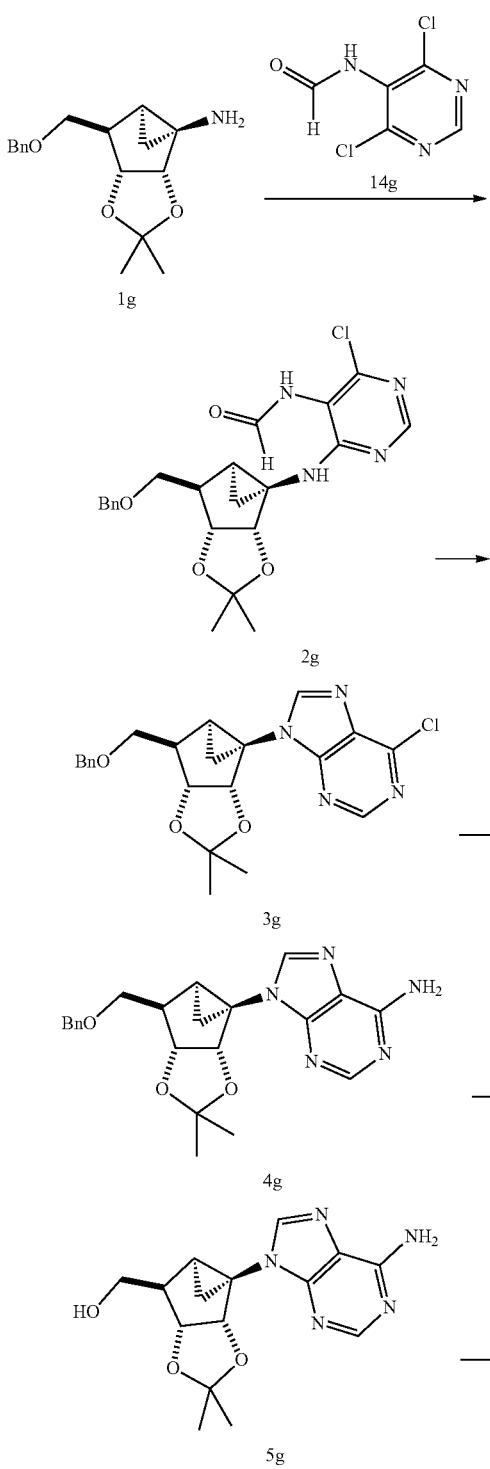

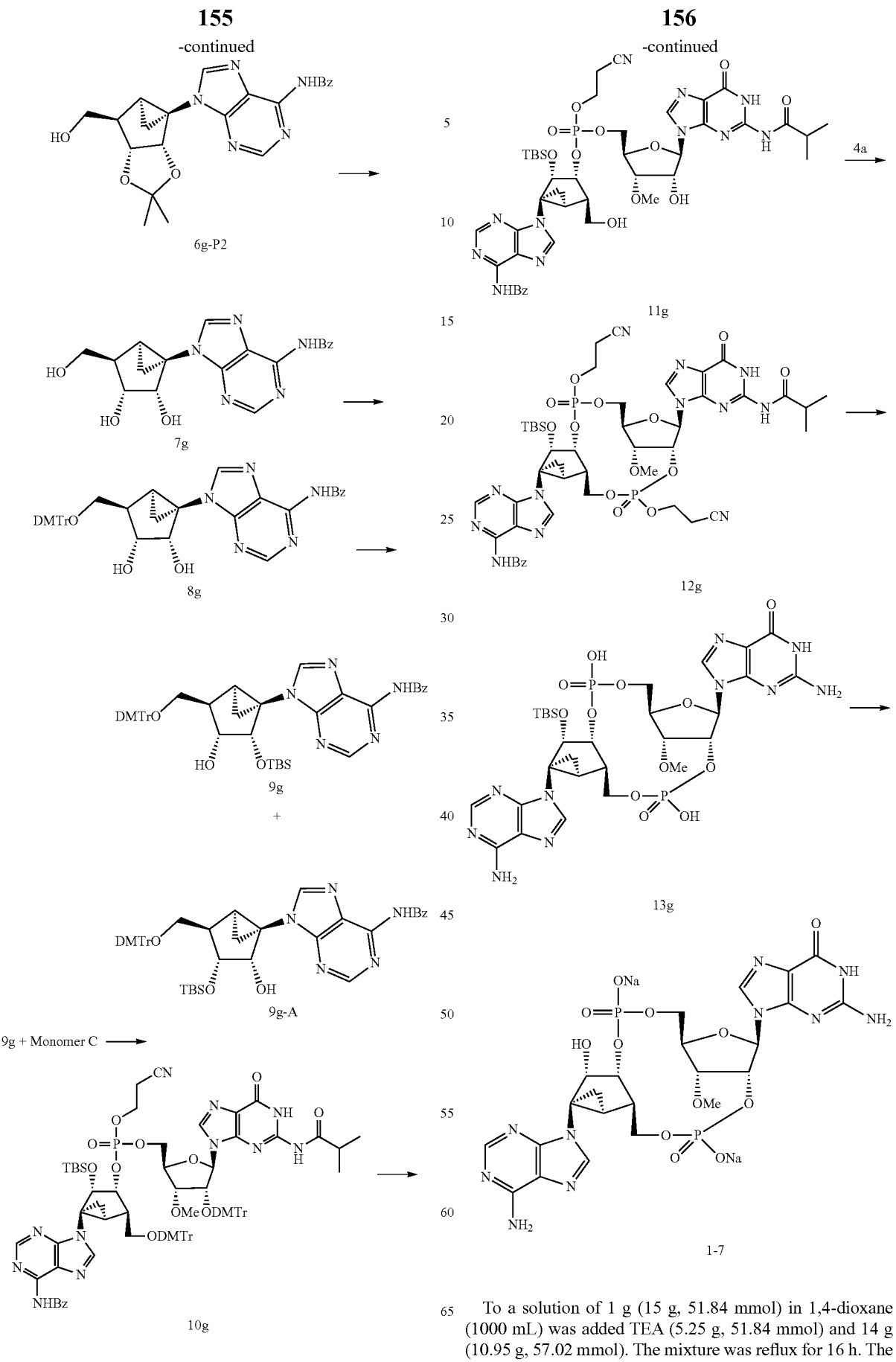
To a solution of 1 g (15 g, 51.84 mmol) in 1,4-dioxane (1000 mL) was added TEA (5.25 g, 51.84 mmol) and 14 g (10.95 g, 57.02 mmol). The mixture was reflux for 16 h. The mixture is filtered to collect the filtrate, and the filtrate was concentrated in vacuum to afford the crude. The residue was purified by flash column chromatography on silica gel (PE:EtOAc 4:1) to afford 2 g (11.5 g, 25.85 mmol, 49.8%) and as a yellow solid. ESI-MS: m/z 445.2 [M+H]$^+$.

The compound 2g (11.5 g, 25.85 mmol) was dissolved in diethoxymethyl acetate (9 mL). After stirring for 1 h at 120° C. The mixture was concentrated in vacuum to afford the crude. The residue was purified by phase preparative HPLC (Column: C18 spherical 20-35 μm 100A 330 g, mobile phase: 0.05% NH$_4$HCO$_3$ in water-ACN from 50% to 100%, flow rate: 50 mL/min) to give afford 3 g (10 g, 23.42 mmol, 90.6%) and as a yellow solid. ESI-MS: m/z 427.2 [M+H]$^+$.

Compound 3g (10 g, 23.42 mmol) was dissolved in 1,4-dioxane:ammonium hydroxide (1:1, 40 mL, v/v, 1:1). The mixture was stirred for 16 h at 90° C. The mixture was concentrated in vacuum to afford the crude. The residue was purified by flash column chromatography on silica gel (DCM:MeOH 60:1) to afford 4 g (9 g, 22.09 mmol, 94.3%) and as a yellow solid. ESI-MS: m/z 408.2 [M+H]$^+$.

To a solution of 4 g (12.5 g, 30.68 mmol) in methanol (500 mL) was added Pd/C (3 g, 24.70 mmol) and formic acid (25 mL). The mixture was stirred for 16 h at 60° C. under H$_2$. The mixture was concentrated in vacuum to afford the crude. The residue was purified by phase prep-HPLC (Column: C18 spherical 20-35 μm 100A 120 g, mobile phase: 0.05% NH$_4$HCO$_3$ in water-ACN from 50% to 100%, flow rate: 50 mL/min) to afford 5 g (8 g, 25.21 mmol, 82.1%) and as a yellow solid. ESI-MS: m/z 318.2 [M+H]$^+$.

Compound 5g (7.8 g, 24.58 mmol) was dissolved in pyridine (140 mL). The mixture was cooled to 0° C. under N$_2$ and then benzoyl chloride (13.82 g, 98.32 mmol) was added. The mixture was stirred for 1 h at the same temperature. The reaction was quenched by the addition of H$_2$O (50 mL) and then extracted by EtOAc (3×100 mL). The organic layers were dried over Na$_2$SO$_4$ and was concentrated in vacuum to afford the crude. The crude was dissolved by pyridine (100 mL) and was cooled to 0° C. 2N NaOH in CH$_3$OH:H$_2$O 4:1 (20 mL) was added. The mixture was stirred for 30 mins at the same temperature. The pH of the mixture was adjusted with 6N HCl to pH<7, and the extracted by EtOAc (3×100 mL). The organic layers were dried over Na$_2$SO$_4$ and concentrated in vacuum to afford the crude. The residue was purified by phase prep-HPLC (Column: C18 spherical 20-35 μm 100A 120 g, mobile phase: 0.05% NH$_4$HCO$_3$ in water-ACN from 50% to 80%, flow rate: 50 mL/min) to afford the two isomers. The isomers were separated by SFC (OD-C5_MB_15% EtOH_1 cm. 1 mL/min-8 min, Ret. Time=7.691 min) to afford 6 g-P2 (6.5 g, 15.42 mmol, 62.7%) as a yellow solid. ESI-MS: m/z 422.1 [M+H]$^+$.

Compound 6g-P2 (2.4 g, 5.69 mmol) was dissolved in 2N HCl:THF (1:1) (40 mL). The mixture was stirred for 1 h at rt. The pH of the mixture was adjusted with sat. sodium bicarbonate solution to pH=6. The mixture was concentrated in vacuum to afford the crude. The residue was purified by phase prep-HPLC (Column: C18 spherical 20-35 μm 100A 80 g, mobile phase: 0.05% TFA in water-ACN from 0% to 20%, flow rate: 30 mL/min) to afford 7 g (1.7 g, 4.46 mmol, 78.2%) as a yellow solid. ESI-MS: m/z 382.1 [M+H]$^+$.

To a solution of 7 g (1.7 g, 4.46 mmol) in pyridine (25 mL) was added DMTrCl (2.27 g, 6.69 mmol). The mixture was stirred for 1 h at rt under N$_2$. The reaction was quenched by the addition of H$_2$O and then extracted with EtOAc (3×300 mL). The organic layers were dried over Na$_2$SO$_4$ and was concentrated in vacuum to afford the crude. The residue was purified by flash column chromatography on silica gel (DCM:MeOH 30:1) to afford 8 g (2.6 g, 3.80 mmol, 85.3%) as a yellow solid. ESI-MS: m/z 684.4 [M+H]$^+$.

To a solution of 8 g (2.6 g, 3.80 mmol) in DMF (30 mL) was added imidazole (776.60 mg, 11.41 mmol). The mixture was cooled to 0° C. and TBSCl (687.75 mg, 4.56 mmol) in DMF (50 mL) was added. The mixture was stirred for 16 h at rt under N$_2$. The reaction was quenched by adding sat. sodium bicarbonate solution and then extracted with EtOAc (3×400 mL). The organic layers were washed with H$_2$O (200 mL) and brine (200 mL), dried over Na$_2$SO$_4$ and was concentrated in vacuum to afford the crude. The residue was purified by flash column chromatography on silica gel (PE:EtOAc, 3:1) to afford 9 g (1.2 g, 1.50 mmol, 39.5%) and 9 g-A (650 mg, 814.53 umol, 21.4%) as a yellow solid. ESI-MS: m/z 798.5 [M+H]$^+$.

Compound 9g (600 mg, 751.87 umol) and Monomer C (784.90 mg, 902.24 umol) were dissolved in anhydrous CH$_3$CN (18.0 mL), and then 4 Å molecular sieves powder (240 mg, 1 gr/100 mL) were added. The mixture was bubbled with Ar gas for 4 min. After stirring at rt for 10 min, 0.25N ETT in CH$_3$CN (4.5 mmol, 18 mL) was added at rt. After stirring for 1 h, the mixture was filtered and washed with anhydrous CH$_3$CN. 0.02 M I$_2$ (THF:Py:H$_2$O, 8:1:1, v/v/v) was then added until the color persisted. After stirring for 20-30 min at rt, the reaction was quenched with Na$_2$SO$_3$ (aq. until discoloration). The mixture was then diluted with EtOAc, and the organic layers were separated. The organic phase was washed with sat. aq. NaHCO$_3$ (1×10 mL) and sat. aq. NaCl (1×10 mL). The combined aqueous phase back was extracted with EtOAc (1×15 mL). The combined organic phases were evaporated to dryness, and the resulting crude material was purified by reverse phase prep-HPLC (Column: C18 spherical 20-35 μm 100A 80 g, mobile phase: 0.5% NH$_4$HCO$_3$ in water, m/m)-ACN from 30% to 100%, flow rate: 35 mL/min) to afford 10 g (1.1 g, 694.99 umol, 92.4%) as a white foam. ESI-MS: m/z 1583.7 [M+H]$^+$.

Compound 10g (1.1 g, 694.99 umol) was dissolved in DCA in DCM (3%, v/v, 15.0 mL) and triethylsilane (4 mL) was then added immediately. After stirring for 30 min at rt, the mixture was diluted with EtOAc, and then neutralize with sat. aq. NaHCO$_3$. The layers were separated, and organic phase was washed with sat. aq. NaCl (1×10 mL). The aqueous phases was combined and back extracted with EtOAc (3×15 mL). The combined organic phases were evaporated to dryness, and the crude residue was purified by reverse phase prep-HPLC (Column: C18 spherical 20-35 μm 100A 80 g, mobile phase: 0.05% NH$_4$HCO$_3$ in water, m/m)-ACN from 30% to 80%, flow rate: 35 mL/min) to afford 11 g (670 mg, 685.05 umol, 98.5%) as a white foam. ESI-MS: m/z 978.4 [M+H]$^+$.

Compound 11g (660 mg, 674.83 mol) dissolved in anhydrous CH$_3$CN (50.0 mL), 0.25 M ETT in CH$_3$CN (5.4 mmol, 21.6 mL) and 4 Å molecular sieves powder (220 mg, 1 gr/100 mL). The heterogeneous mixture was bubbled with Ar gas for 4 min. After stirring at rt for 20 min, 4a (407 mg, 1.35 mol) in CH$_3$CN (15.0 mL) was added over 25 to 30 min. After stirring for 2 h, the mixture was filtered, and then washed with anhydrous CH$_3$CN. To the mixture was added 0.02 M Is (THF:Py:H$_2$O, 8:1:1, v/v/v) until the color persisted. After stirring for 20-30 min at rt, the reaction was quenched with sat. aq. Na$_2$SO$_3$, and then diluted with EtOAc. The layers were separated. The organic phase was washed with sat. aq. NaHCO$_3$ (1×20 mL) and sat. aq. NaCl (1×20 mL). The combined aqueous phase back extracted with EtOAc (1×40 mL). The combined organic phases were evaporated to dryness, and the crude was purified by reverse phase prep-HPLC (Column: C18 spherical 20-35 μm 100A 80 g, mobile phase: 0.05% NH$_4$HCO$_3$ in water, m/m)-ACN from 30% to 60%, flow rate: 35 mL/min) to get 12 g (348 mg, 318.37 μmol, 47.1%) as a white foam. ESI-MS: m/z 1093.4 [M+H]$^+$.

Compound 12g (348 mg, 318.37 μmol) was treated with a solution of 33% MeNH$_2$ in EtOH (10 mL). After stirring for 2 h at 40° C., the mixture was evaporated to dryness. The crude was purified by reverse phase prep-HPLC (Column: C18 spherical 20-35 μm 100A 40 g, mobile phase: 0.5% NH$_4$HCO$_3$ in water, m/m)-ACN from 0% to 30%, flow rate: 35 mL/min) to afford 13 g (195 mg, 239.9 μmol, 75.3%) as a white foam. ESI-MS: m/z 813.4 [M+H]$^+$.

A solution of 13 g (195 mg, 239.9 μmol) in DMSO (2.0 mL) and 3 HF·TEA (2.0 mL) was stirred at 40° C. for 16 h. The mixture was dropped into a solution of TEA (2 mL) in triethyamimonium bicarbonate buffer (12 ml) at 0° C. The mixture was stirred at rt for 30 min and then purified by reverse phase prep-HPLC (Column: C18 spherical 20-35 μm 100A 40 g, mobile phase: 0.05% NH$_4$HCO$_3$ in water-ACN from 0% to 10%, flow rate: 20 mL/min) for 4 times to get the NH$_4$ salt compounds (120.0 mg, 171.8 mol, 71.6%) as a white foam. A volume of Amberlite IR-120 (15.0 mL, Na form) was added to a column and washed with deionized water (3×15 mL). The NH$_4$ salt compounds (120 mg) was dissolved in deionized water (120 mg in 10 mL) and then added to the top of the column. The column was eluted with deionized water. The compounds was eluted out in the early fractions as detected by TLC (UV). The product was lyophilized to give 1-7 (101 mg, 144.6 μmol, 84.2%) as a white foam. $^1$H NMR (400 MHz, D$_2$O) δ 8.10 (d, J=16.0 Hz, 2H), 7.71 (s, 1H), 5.83 (d, J=8.3 Hz, 1H), 5.27 (h, J=4.5 Hz, 2H), 4.47 (dd, J=3.9, 2.1 Hz, 1H), 4.27 (d, J=5.7 Hz, 1H), 4.20-4.02 (m, 5H), 3.59-3.46 (m, 3H), 2.43 (d, J=3.1 Hz, 1H), 2.08 (t, J=5.6 Hz, 1H), 1.81 (dd, J=9.4, 5.0 Hz, 1H), 1.40 (ddd, J=8.5, 6.2, 1.8 Hz, 1H). $^{31}$P-NMR (162 MHz, D$_2$O) δ −1.01, −1.23. ESI-MS: m/z 699.2 [M+H]$^+$.

Example 9

Compound 1-8

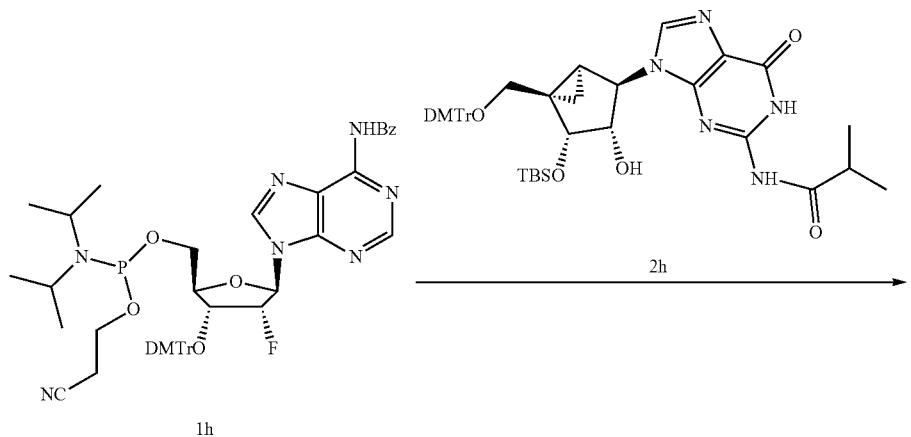

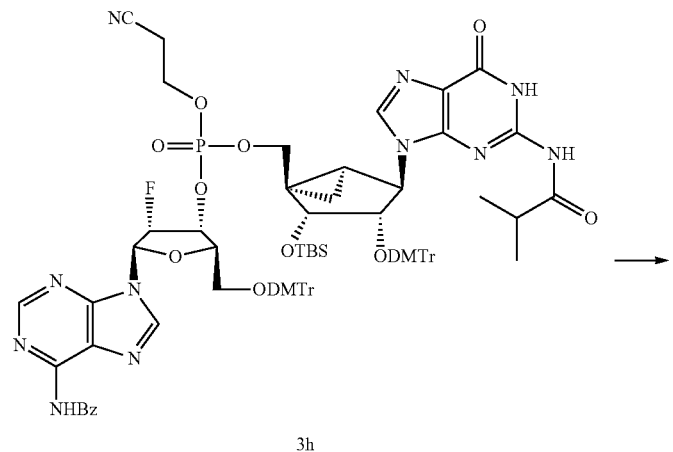

-continued
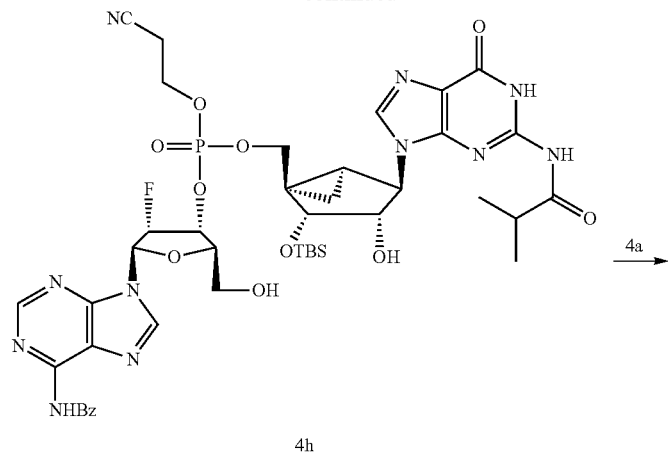
4h
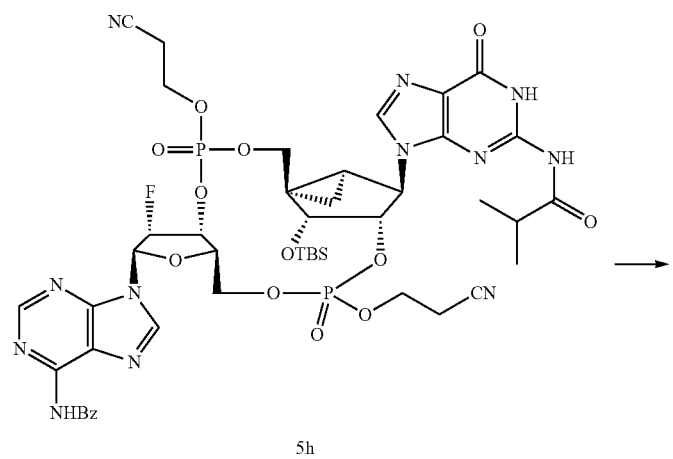
5h
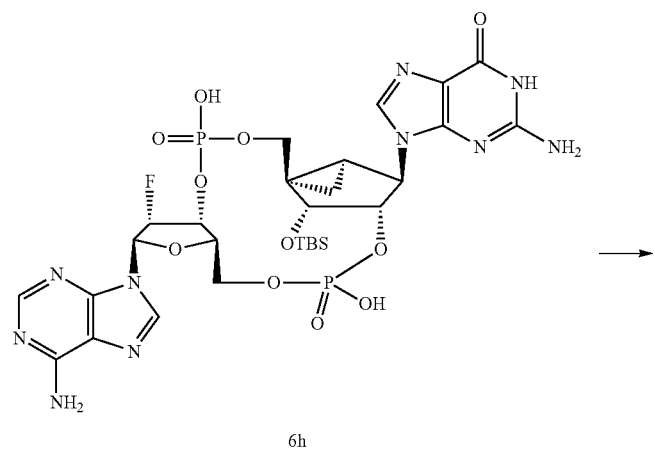
6h

-continued

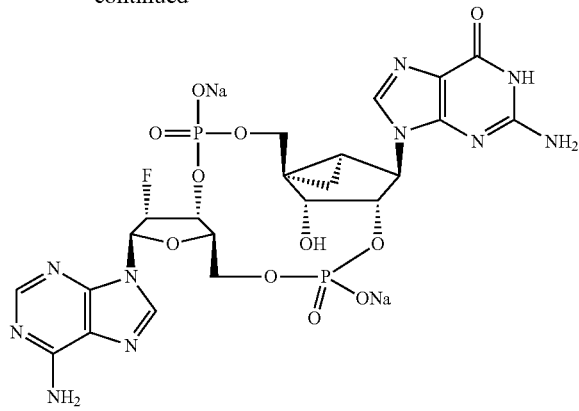

1-8

Compound 1h (600 mg, 0.8 mmol) and 2h (920 mg, 0.84 mmol) were dissolved in anhydrous CH₃CN (18.0 mL), and 4 Å molecular sieves powder (180 mg, 1 gr/100 mL) were added. The mixture was bubbled with Ar gas for 4 min. After stirring at rt for 10 min, 0.45 M tetrazole in CH₃CN (4.1 mmol, 11 mL) was added at rt. After stirring for 1 h, the mixture was filtered and washed with anhydrous CH₃CN. 0.02 M I₂ (THF:Py:H₂O, 8:1:1, v/v/v) was added until the color persisted. After stirring for 20-30 min at rt, the reaction was quenched with Na₂SO₃ (aq, until discoloration). The mixture was diluted with EtOAc, and the layers were separated. The organic phase was washed with sat. aq. NaHCO₃ (1×50 mL) and sat. aq. NaCl (1×50 mL). The combined aqueous phase was back extracted with EtOAc (1×50 mL). The combined organic phases were evaporated to dryness, and the resulting crude was purified by reverse phase prep-HPLC (Column: C18 spherical 20-35 µm 100A 80 g, mobile phase: 0.05% NH₄HCO₃ in water, m/m)-ACN from 30% to 100%, flow rate: 35 mL/min) to afford 3h (1.1 g, 0.71 mmol, 88%) as a white foam. ESI-MS: m/z 1570.7 [M+H]⁺.

Compound 3h (1.1 g, 0.70 mmol) was dissolved in DCA in DCM (3%, v/v, 22.0 mL) and triethylsilane (11 mL) was added immediately. After stirring for 30 min at rt, the mixture was diluted with EtOAc and neutralize with sat. aq. NaHCO₃. The layers were separated, and the organic phase was washed with sat. aq. NaCl (1×50 mL). The aqueous phase was combined and back extracted with EtOAc (3×50 mL). The combined organic phases were evaporated to dryness, and the crude residue was purified by reverse phase prep-HPLC (Column: C18 spherical 20-35 µm 100A 80 g, mobile phase: 0.05% NH₄HCO₃ in water, m/m)-ACN from 30% to 80%, flow rate: 35 mL/min) to afford 4h (500 mg, 0.52 mmol, 74%) as a white foam. ESI-MS: m/z 966.5 [M+H]⁺.

Compound 4h (500 mg, 0.52 mmol) dissolved in anhydrous CH₃CN (15.0 mL), 0.45 M tetrazole in CH₃CN (4.16 mmol, 9.2 mL) and 4 Å molecular sieves powder (150 mg, 1 gr/100 mL) was added. The mixture was bubbled with Ar gas for 4 min. After stirring at rt for 20 min, 4a (310 mg, 1.04 mmol) in CH₃CN (15.0 mL) was added over 25 to 30 min. After stirring for 2 h, the mixture was filtered and washed with anhydrous CH₃CN. 0.02 M iodine (THF:Py:H₂O, 8:1:1, v/v/v) was added until the color persisted. After stirring for 20-30 min at rt, the reaction was quenched with sat. aq. Na₂SO₃ (until discoloration). The mixture was diluted with EtOAc and the layers were separated. The organic phase was washed with sat. aq. NaHCO₃ (1×50 mL) and sat. aq. NaCl (1×50 mL). The combined aqueous phase was back extracted with EtOAc (1×50 mL). The combined organic phases were evaporated to dryness, and the crude was purified by reverse phase prep-HPLC (Column: C18 spherical 20-35 µm 100A 80 g, mobile phase: 0.05% NH₄HCO₃ in water, m/m)-ACN from 30% to 60%, flow rate: 35 mL/min) to get 5h (140 mg, 130.3 µmol, 28%) as a white foam. ESI-MS: m/z 1081.5 [M+H]⁺.

Compound 5h (140 mg, 130.3 µmol) was treated with a solution of 33% MeNH₂ in EtOH (4 mL). After stirring for 2 h at 40° C., the mixture was evaporated to dryness, and the crude was purified by reverse phase prep-HPLC (Column: C18 spherical 20-35 µm 100A 40 g, mobile phase: 0.05% NH₄HCO₃ in water, m/m)-ACN from 0% to 30%, flow rate: 35 mL/min) to afford 6h (90 mg, 112.3 µmol, 86.8%) as a white foam. ESI-LMS: m/z 801.6 [M+H]⁺.

A solution of 6h (90 mg, 112.3 µmol) in DMSO (2.0 mL) and 3 HF·TEA (2.0 mL) was stirred at 40° C. for 6 h. The mixture was dropped in the solution of TEA (2 mL) in triethyamimonium bicarbonate buffer (12 mL) at 0° C. The mixture was stirred at rt for 30 min and then was purified by reverse phase prep-HPLC (Column: C18 spherical 20-35 µm 100A 40 g, mobile phase: 0.05% NH₄HCO₃ in water-ACN from 0% to 10%, flow rate: 20 mL/min) for 4 times to get the NH₄ salt (7.0 mg, 9.7 µmol, 8.7%) as a white foam. A volume of Amberlite IR-120 (15 mL, Na form) was added to a column and washed with deionized water (3×15 mL). The NH₄ salt (7 mg) was dissolved in deionized water (7 mg in 2 mL), added to the top of the column and eluted with deionized water. The compound was eluted out in early fractions as detected by TLC (UV). The product was lyophilized to afford 1-8 (6.4 mg, 8.2 µmol, 90%) as a white foam. ¹H NMR (400 MHz, D₂O): δ 8.20 (t, J=3.68 Hz, 2H), 7.65 (s, 1H), 6.38 (d, J=13.9 Hz, 1H), 5.55 (dd, J=2.8 Hz, 2.8 Hz, 1H), 5.37-5.32 (m, 1H), 5.05-4.97 (m, 2H), 4.53-4.49 (m, 2H), 4.42 (d, J=12.2 Hz, 1H), 4.27 (d, J=9.2 Hz, 1H), 4.15-4.11 (m, 1H), 3.32-3.28 (m, 1H), 1.57 (t, J=3.8 Hz, 1H), 1.07-1.03 (m, 1H). ³¹P-NMR (162 MHz, D₂O): −4.41, −4.61. ¹⁹F-NMR (376 MHz, DMSO-d₆): −201.78, −204.90. ESI-MS: m/z 687.4 [M+H]⁺.

Example 10
Compound 1-8
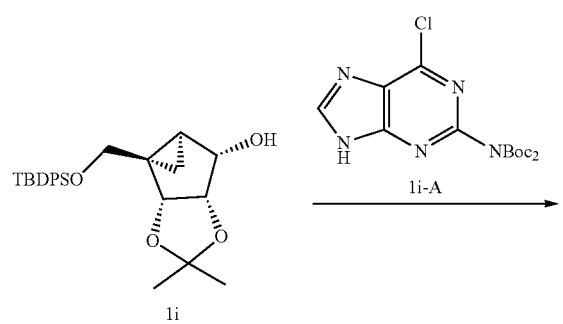
1i-A
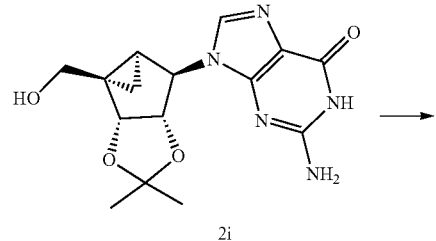
2i
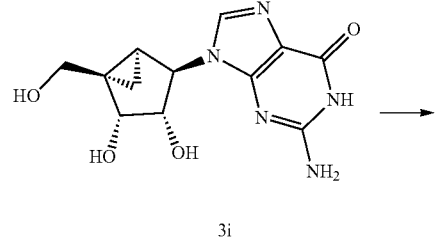
3i
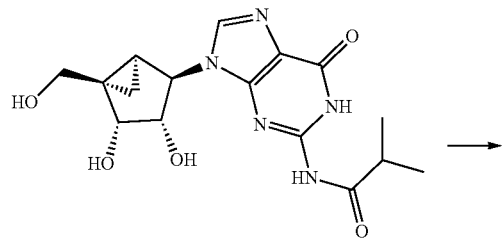
4i
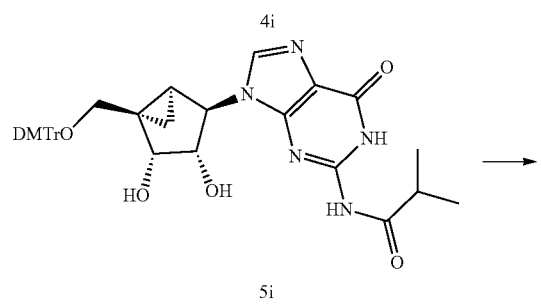
5i
-continued
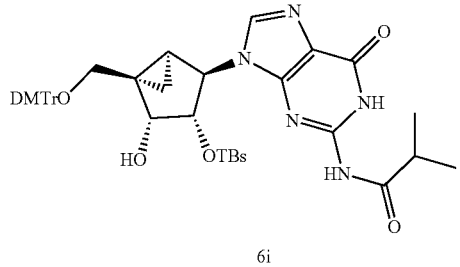
6i
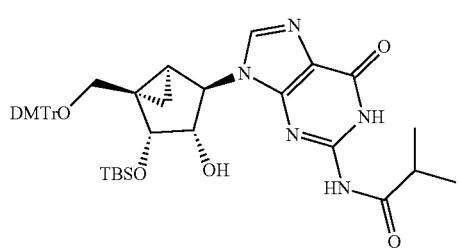
2h
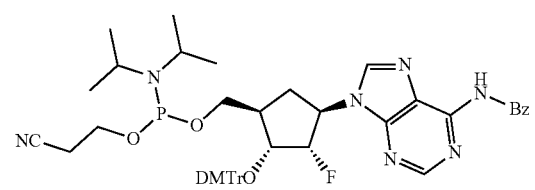
7i
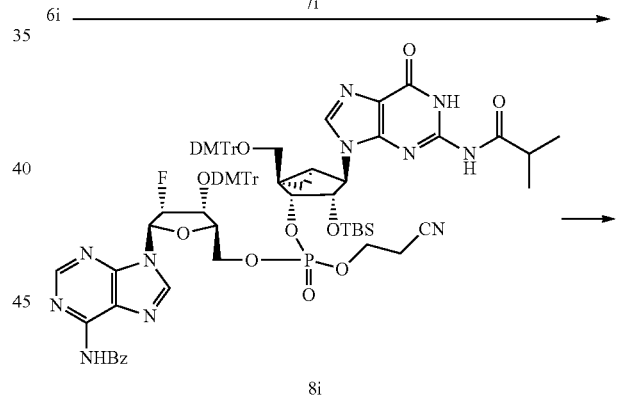
8i
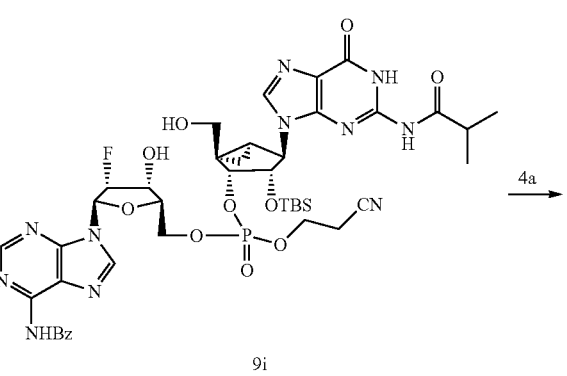
9i

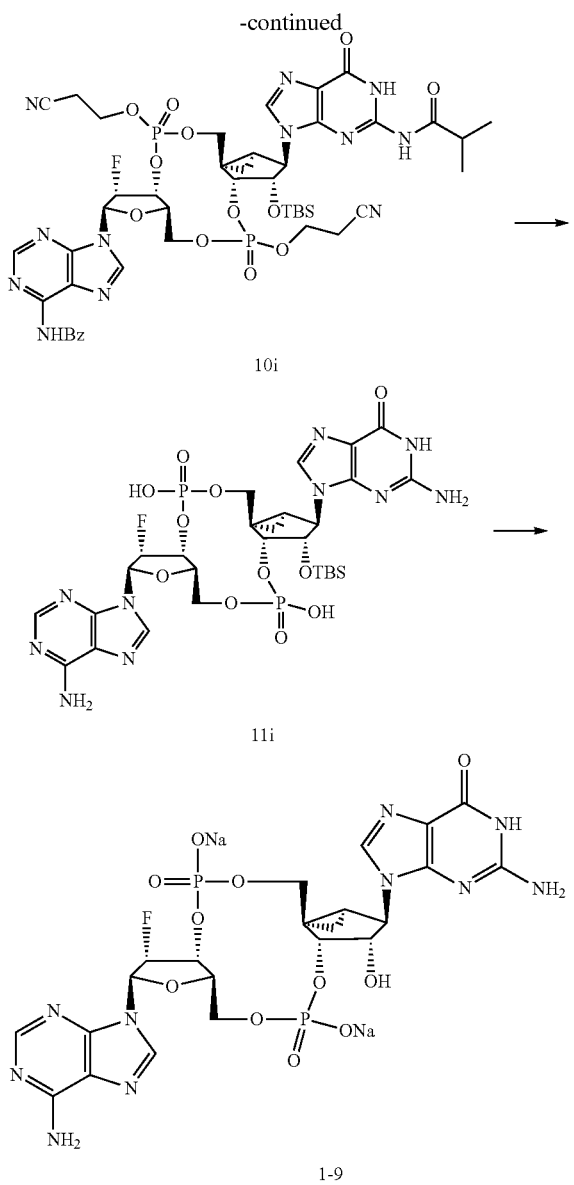

To a stirred solution of 1i (10 g, 22.80 mmol) and 1i-A (12.72 g, 34.20 mmol) in THF (100 mL) was added PPh₃ (8.97 g, 34.20 mmol). The mixture was cooled to 0° C. and DIAD (6.92 g, 34.20 mmol, 6.71 mL) was added in portions. The mixture was heated to 50° C. and then stirred for 16 h. The mixture was poured into water and then extracted with EtOAc (2×200 mL). The layers were separated. The organic layer was washed with brine, dried over Na₂SO₄ and concentrated to dryness to give crude product. The crude product was purified by silica gel (PE:EtOAc 1:1) to afford 2i (15 g, 18.03 mmol, 79.08%) as a white foam. ESI-MS: m/z 791.4 [M+H]⁺.

To a stirred solution of 2i (15.00 g, 18.03 mmol) in H₂O (20 mL) and THF (20 mL) was added TFA (150 g, 1.3 mol, 100 mL). The mixture was stirred at 50° C. for 16 h. The mixture was concentrated to dryness to give crude. The crude was purified by reverse phase prep-HPLC (Column: C18 spherical 20-35 μm 100A 80 g, mobile phase: 0.05% NH₄HCO₃ in water, m/m)-ACN from 30% to 80%, flow rate: 35 mL/min) to afford 3i (3.0 g, 9.21 mmol, 51.07%, 90% purity) as a white foam. ESI-MS: m/z 294.5 [M+H]⁺.

To a stirred solution of 3i ((3.0 g, 9.21 mmol) in pyridine (30 mL) was added isobutyryl chloride (6.90 g, 64.78 mmol). The mixture was stirred at rt for 3 h, and then concentrated to dryness. The crude was dissolved in pyridine (50 mL). To the mixture was added 1M NaOH solution of MeOH:H₂O (4:1) to adjust to the pH=10. To the mixture was added aq. HCl (6N) to adjust the pH=6. The mixture was concentrated to dryness and then was dissolved in DCM:MeOH (5:1). The mixture was filtered, and the filtrate was concentrated to give a yellow oil. The crude was purified by reverse phase prep-HPLC (Column: C18 spherical 20-35 μm 100A 80 g, mobile phase: 0.05% NH₄HCO₃ in water, m/m)-ACN from 30% to 60%, flow rate: 35 mL/min) to afford 4i (1.8 g, 4.95 mmol, 51.02%, 90% purity) as a yellow foam. ESI-MS: m/z 364.5 [M+H]⁺.

To a stirred solution of 4i (1.8 g, 4.46 mmol) in pyridine (10 mL) was added DMTrCl (1.66 g, 4.90 mmol). The mixture was stirred for 3 h at rt. The mixture was poured into water and extracted with EtOAc (2×100 mL). The organic layer was separated. The organic layer was washed with brine, dried over Na₂SO₄ and concentrated to dryness to give the crude. The crude was purified by silica gel (DCM:MeOH 50:1) to give 5i (2.6 g, 3.71 mmol, 83.22%, 95% purity) as a white solid. ESI-MS: m/z 666.7 [M+H]⁺.

To a stirred solution of 5i (2.6 g, 3.71 mmol) and imidazole (1.01 mg, 14.84 mmol) in DMF (40 mL) was added TBSCl (671.05 mg, 4.45 mmol) in portions. The mixture was stirred at rt for 3 h. The mixture was poured into water and extracted with EtOAc (2×200 mL). The separated organic layer was washed with brine, dried over Na₂SO₄ and concentrated to give the crude. The crude was purified by silica gel (PE:EtOAc 1:1) to give 6i (800 mg, 1.01 mmol, 27.09%) and 2h (600 mg, 753.85 umol, 20.32%) as white foams.

Compound 6i: ¹H-NMR (400 MHz, DMSO-d₆): δ 12.09 (s, 1H), 11.39 (s, 1H), 8.19 (s, 1H), 7.36 (d, J=7.44 Hz, 2H), 7.29 (t, J=7.8 Hz, 2H), 7.24-7.20 (m, 5H), 6.85 (d, J=8.8 Hz, 4H), 4.79 (t, J=7.16 Hz, 1H), 4.55 (d, J=1.5 Hz, 1H), 4.28 (d, J=8.0 Hz, 1H), 4.11 (d, J=6.4 Hz, 1H), 3.74-3.73 (m, 6H), 3.61 (d, J=9.8 Hz, 1H), 2.77-2.74 (m, 2H), 1.36-1.33 (m, 1H), 1.27 (t, J=4.4 Hz, 1H), 1.10 (t, J=7.12 Hz, 6H), 0.83 (m, 9H), 0.62-0.58 (m, 1H), 0.002-0.01 (m, 6H). ESI-LMS: m/z 780.6 [M+H]⁺. Compound 2h: ¹H-NMR (400 MHz, DMSO-d₆): δ 12.11 (s, 1H), 11.66 (s, 1H), 8.26 (1H), 7.39 (d, J=9.12 Hz, 2H), 7.32 (t, J=7.2 Hz, 2H), 7.26-7.20 (m, 5H), 6.85 (dd, J=2.2 Hz, 2.2 Hz, 4H), 4.79 (d, J=6.32 Hz, 1H), 4.65 (d, J=4.88 Hz, 1H), 4.59 (d, J=2.08 Hz, 1H), 3.98 (m, 1H), 3.74-3.73 (m, 6H), 3.52 (d, J=10 Hz, 1H), 2.86-2.77 (m, 2H), 1.46-1.44 (m, 1H), 1.28 (t, J=4.4 Hz, 1H), 1.14-1.12 (m, 6H), 0.77 (m, 9H), 0.68-0.65 (m, 1H), 0.0-0.06 (m, 7H). ESI-LMS: m/z 780.6 [M+H]⁺.

Compound 6i (800 mg, 1.03 mmol) and 7i (898.0 mg, 1.03 mmol) were dissolved in anhydrous CH₃CN (24.0 mL), and 4 Å molecular sieves powder (240 mg, 1 gr/100 mL) were added. The mixture was bubbled with Ar gas for 4 min. After stirring at rt for 10 min, 0.45 M tetrazole in CH₃CN (4.1 mmol, 11 mL) was added at rt. After stirring for 1 h, the mixture was filtered and washed with anhydrous CH₃CN. 0.02 M Iodine (THF:Py:H₂O, 8:1:1, v/v/v) was added until the color persisted. After stirring the mixture for 20-30 min at rt, the reaction was quenched with Na₂SO₃ (aq, until discoloration). The mixture was diluted with EtOAc, and the layers were separated. The organic phase was washed with sat. aq. NaHCO₃ (1×50 mL) and sat. aq. NaCl (1×). The combined aqueous phase was back extracted with EtOAc (1×50 mL). The combined organic phases were evaporated to dryness, and the crude was purified by reverse phase prep-HPLC (Column: C18 spherical 20-35 µm 100A 80 g, mobile phase: 0.05% NH₄HCO₃ in water, m/m)-ACN from 30% to 100%, flow rate: 35 mL/min) to afford 8i (1.1 g, 0.70 mmol, 67.9%) as a white foam. ESI-MS: m/z 1570.7 [M+H]⁺.

Compound 8i (1.2 g, 0.76 mmol) was dissolved in DCA in DCM (3%, v/v, 11.0 mL) and triethylsilane (4.4 mL) was added immediately. After stirring for 30 min at rt, the mixture was diluted with EtOAc, and then neutralize with sat. aq. NaHCO₃. The layers were separated, and the organic phase was washed with sat. aq. NaCl (1×50 mL). The aqueous phases were combined and back extracted with EtOAc (3×). The combined organic phases were evaporated to dryness, and the crude was purified by reverse phase prep-HPLC (Column: C18 spherical 20-35 µm 100A 80 g, mobile phase: 0.05% NH₄HCO₃ in water, m/m)-ACN from 30% to 80%, flow rate: 35 mL/min) to obtain 9i (610 mg, 0.62 mmol, 82.7%) as a white foam. ESI-MS: m/z 966.0 [M+H]⁺.

Compound 9i (610 mg, 620 µmol) was dissolved in anhydrous CH₃CN (18.0 mL), 0.45 M tetrazole in CH₃CN (3.76 mmol, 8.4 mL) and 4 Å molecular sieves powder (180 mg, 1 gr/100 mL) were added. The mixture was bubbled with Ar gas for 4 min. After stirring at rt for 20 min, 4a (380 mg, 124 mmol) in CH₃CN (15.0 mL) was added over 25 to 30 min. After stirring for 2 h, the mixture was filtered and washed with anhydrous CH₃CN. 0.02 M Iodine (THF:Py:H₂O, 8:1:1, v/v/v) was added until color persisted. After stirring for 20-30 min at rt, the reaction was quenched with sat. aq. Na₂SO₃ (until discoloration). The mixture was diluted with EtOAc, and the layers were separated. The organic phase was washed with sat. aq. NaHCO₃ (1×) and sat. aq. NaCl (1×50 mL). The combined aqueous phase was back extracted with EtOAc (1×50 mL). The combined organic phases were evaporated to dryness, and the crude was purified by reverse phase prep-HPLC (Column: C18 spherical 20-35 µm 100A 80 g, mobile phase: 0.05% NH₄HCO₃ in water, m/m)-ACN from 30% to 60%, flow rate: 35 mL/min) to get 10i (400 mg, 370.3 µmol, 58.0%) as a white foam. ESI-MS: m/z 1081.5 [M+H]⁺.

Compound 10i (400 mg, 370.3 µmol) was treated with a solution of 33% MeNH₂ in EtOH (10 mL). After stirring for 2 h at 40° C., the mixture was evaporated to dryness. The crude was purified by reverse phase prep-HPLC (Column: C18 spherical 20-35 µm 100A 40 g, mobile phase: 0.05% NH₄HCO₃ in water, m/m)-ACN from 0% to 30%, flow rate: 35 mL/min) to afford 11i (200 mg, 250.3 µmol, 67.5%) as a white foam. ESI-LMS: m/z 801.6 [M+H]⁺.

A solution of 11i (200 mg, 250.3 µmol) in DMSO (4.0 mL) and 3HF·TEA (4.0 mL) was stirred at 40° C. for 6 h. The mixture was dropped in the solution of TEA (2 mL) in triethyamimonium bicarbonate buffer (12 mL) at 0° C. The mixture was stirred at rt for 30 min and then was purified by reverse phase prep-HPLC (Column: C18 spherical 20-35 µm 100A 40 g, mobile phase: 0.05% NH₄HCO₃ in water-ACN from 0% to 10%, flow rate: 20 mL/min) for 4 times to get the NH₄ salt products (90.0 mg, 124 µmol, 50.5%) as a white foam. A volume of Amberlite IR-120 (15 mL, Na form) was added to a column and washed with deionized water (3×15 mL). The NH₄ salt product 1 (90 mg) was dissolved in deionized water (90 mg in 2 mL), added to the top of the column and eluted with deionized water. The compounds was eluted out in early fractions as detected by TLC (UV). The product was lyophilized to give 1-9 (87 mg, 120 µmol, 96%) as a white foam. ¹H NMR (400 MHz, D₂O): δ 8.19 (s, 1H), 7.93 (d, J=8.8 Hz, 1H), 6.20 (d, J=15.9 Hz, 1H), 5.73-5.60 (m, 1H), 5.18 (t, J=6.4 Hz, 2H), 4.53 (s, 1H), 4.49 (s, 1H), 4.44-4.41 (m, 2H), 4.16 (d, J=4.36 Hz, 1H), 4.07 (d, J=6.0 Hz, 1H), 3.51 (d, J=6.0 Hz, 1H), 1.95 (d, J=5.2 Hz, 1H), 1.62 (d, J=4.24 Hz, 1H), 0.97 (t, J=6.9 Hz, 1H). ³¹P-NMR (162 MHz, D₂O): −1.32, −2.19, ¹⁹F-NMR (376 MHz, D₂O): −202.52, −204.90. ESI-MS: m/z 687.4 [M+H]⁺.

Example 11

Compounds 1-10a and 1-10b

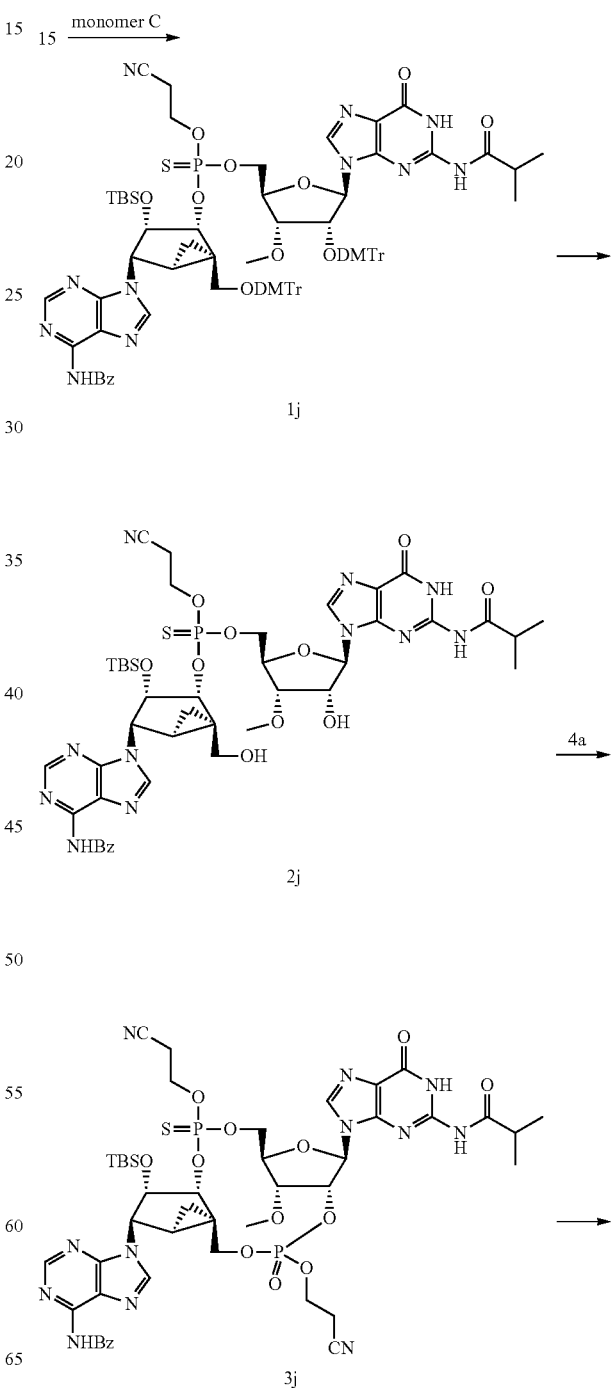

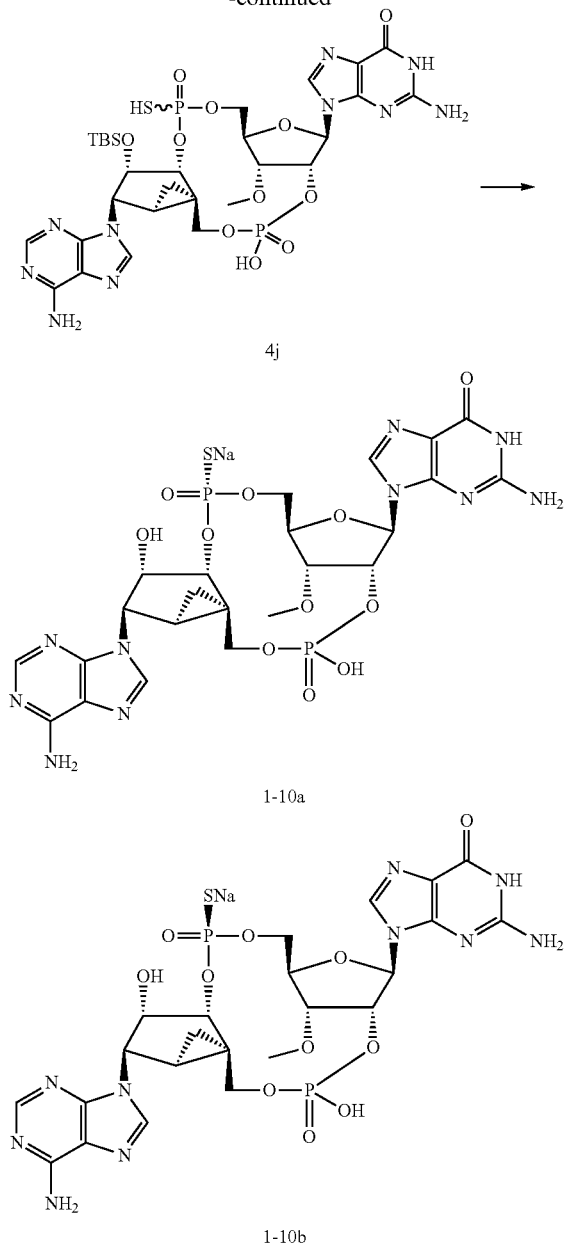

Compound 15 (1.1 g, 1.38 mmol) was dissolved in anhydrous CH$_3$CN (44.0 mL) and Monomer C (1.3 g, 1.51 mmol) and 4 Å molecular sieves powder (440 mg, 1 gr/100 mL) were added. The mixture was bubbled with Ar gas for 4 min. After stirring at rt for 10 min, 0.45 M tetrazole in CH$_3$CN (8.27 mmol, 3.3 mL) was added at rt. After stirring for 1 h, the mixture was filtered, and washed with anhydrous CH$_3$CN. To this solution was added 0.1 M DDTT until the reaction was completed. After stirring for 20-30 min at rt, the reaction was quenched with Na$_2$SO$_3$ (aq, until discoloration), and then diluted with EtOAc. The layers were separated, and the organic phase was washed with sat. aq. NaHCO$_3$ (1×50 mL) and sat. aq. NaCl (1×50 mL). The combined aqueous phase was back extracted with EtOAc (1×50 mL). The combined organic phases were evaporated to dryness, and the crude was purified by reverse phase prep-HPLC (Column: C18 spherical 20-35 μm 100A 80 g, mobile phase: 0.05% NH$_4$HCO$_3$ in water, m/m)-ACN from 60% to 100%, flow rate: 35 mL/min) to afford 1j (1.9 g, 1.19 mmol, 86.21%) as a white foam. ESI-MS: m/z 1598.7 [M+H]$^+$.

Compound 1j (1.9 g, 1.19 mmol) was dissolved in DCA in DCM (3%, v/v, 50.0 mL) and triethylsilane (10.0 mL) was added immediately. After stirring for 30 min at rt, the mixture was neutralized with pyridine and evaporated to dryness. The crude residue was purified by reverse phase prep-HPLC (Column: C18 spherical 20-35 μm 100A 80 g, mobile phase: 0.05% NH$_4$HCO$_3$ in water, m/m)-ACN from 30% to 80%, flow rate: 35 mL/min) to get 2j (985 mg, 990.85 umol, 83.38%) as a white foam. ESI-MS: m/z 994.4 [M+H]$^+$.

Compound 2j (500 mg, 503.02 umol) dissolved in anhydrous CH$_3$CN (40.0 mL), and 0.45 M tetrazole in CH$_3$CN (4.02 mmol, 8.9 mL) and 4 Å molecular sieves powder (500 mg, 1 gr/100 mL) were added. The mixture was bubbled with Ar gas for 4 min. After stirring at rt for 20 min, 4a (304 mg, 1.00 mmol) in CH$_3$CN (5.0 mL) was added over 25 to 30 min. After stirring for 2 h, the mixture was filtered, and washed with anhydrous CH$_3$CN. 0.02 M I$_2$ (THF:Py:H$_2$O, 8:1:1, v/v/v) was added until color persisted. After stirring for 20-30 min at rt, the reaction was quenched with sat. aq. Na$_2$SO$_3$ (until discoloration), and then diluted with EtOAc. The layers were separated, and the organic phase was washed with sat. aq. NaHCO$_3$ (1×50 mL) and sat. aq. NaCl (1×50 mL). The combined aqueous phase was back extracted with EtOAc (1×50 mL). The combined organic phases were evaporated to dryness, and the crude was purified by reverse phase prep-HPLC (Column: C18 spherical 20-35 μm 100A 40 g, mobile phase: 0.05% NH$_4$HCO$_3$ in water, m/m)-ACN from 30% to 60%, flow rate: 25 mL/min) to afford 3j (175 mg, 157.78 umol, 36.48%) as a white foam. ESI-MS: m/z 1109.4 [M+H]$^+$.

Compound 3j (175 mg, 157.78 umol) was treated with a solution of 33% MeNH$_2$ in EtOH (15 mL). After stirring for 2 h at 40° C., the mixture was evaporated to dryness, and the crude material was purified by reverse phase prep-HPLC (Column: C18 spherical 20-35 μm 100A 20 g, mobile phase: 0.05% NH$_4$HCO$_3$ in water, m/m)-ACN from 0% to 30%, flow rate: 20 mL/min) to afford 4j (105 mg, 126.69 umol, 81.46%) as a white foam. ESI-MS: m/z 829.4 [M+H]$^+$.

Compound 4j (105 mg, 126.69 umol, 81.46% yield) and 3 HF·TEA (1.0 mL) in DMSO (2.0 mL) was stirred at 40° C. for 6 h. The mixture was dropped in a solution of TEA (3 mL) in triethyamimonium bicarbonate buffer (18 mL) at 0° C. The mixture was stirred at rt for 30 min, and then was purified by reverse phase prep-HPLC (Column: XBridge 30×100 mm, mobile phase: 0.05% NH4HCO3 in water, m/m)-ACN from 0% to 10%, flow rate: 20 mL/min) to get isomer 1 (31 mg, 52.05 μmol, 30.69%) and isomer 2 (22 mg, 28.77 mol, 16.96%) as a white foam. A volume Amberlite IR-120 (15 mL, Na form) was added to a column and washed with deionized water (3×15 mL). Isomer 1 (38 mg) was dissolved in deionized water (31 mg in 6 mL), added to the top of the column and eluted with deionized water. The compound was eluted out in early fractions as detected by TLC (UV). The product was lyophilized to give 1-10a (23 mg) as a white foam. Isomer 2 (22 mg) was dissolved in deionized water (22 mg in 5 mL), added to the top of the column and eluted with deionized water. The compound was eluted out in early fractions as detected by TLC (UV). The product was lyophilized to give 1-10b (15 mg) as a white foam.

Compound 1-10a: $^1$H NMR (400 MHz, D$_2$O): δ 8.05 (s, 2H), 7.96 (s, 1H), 5.83 (d, J=8.4 Hz, 1H), 5.38-5.33 (m, 1H), 5.11 (t, J=7.6 Hz, 1H), 4.78 (s, 1H), 4.55 (s, 1H), 4.48 (d, J=10.4 Hz, 1H), 4.37 (d, J=6.0 Hz, 1H), 4.28 (d, J=3.2 Hz, 1H), 4.20-4.12 (m, 2H), 3.58 (d, J=11.2 Hz, 1H), 3.51 (s, 3H), 1.82 (d, J=4.8 Hz, 1H), 1.59 (t, J=5.6 Hz, 1H), 0.96 (t, J=6.8 Hz, 1H). $^{31}$P-NMR (162 MHz, D$_2$O): 52.84, −2.89. ESI-MS: m/z 715.3 [M+H]$^+$.

Compound 1-10b: $^1$H NMR (400 MHz, D$_2$O): δ 8.18 (s, 1H), 8.07 (s, 1H), 7.71 (s, 1H), 5.72 (s, 2H), 5.25 (t, J=8.8 Hz, 1H), 4.57 (s, 2H), 4.29 (d, J=10.4 Hz, 1H), 4.18 (s, 1H), 4.05 (d, J=10.8 Hz, 1H), 3.94 (d, J=4.4 Hz, 1H), 3.52 (s, 3H), 3.35 (s, 1H), 1.62 (s, 1H), 1.53 (s, 1H), 0.97 (s, 1H). $^{31}$P-NMR (162 MHz, D$_2$O): 55.69, −3.80. ESI-MS: m/z 715.3 [M+H]$^+$.

Example 12

Compound 1-11

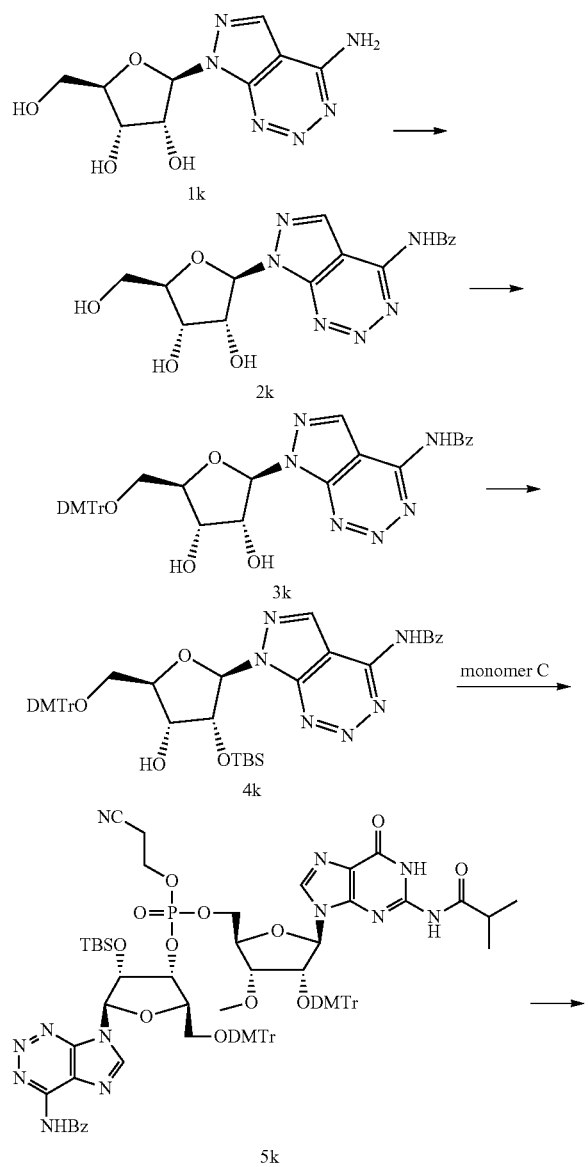
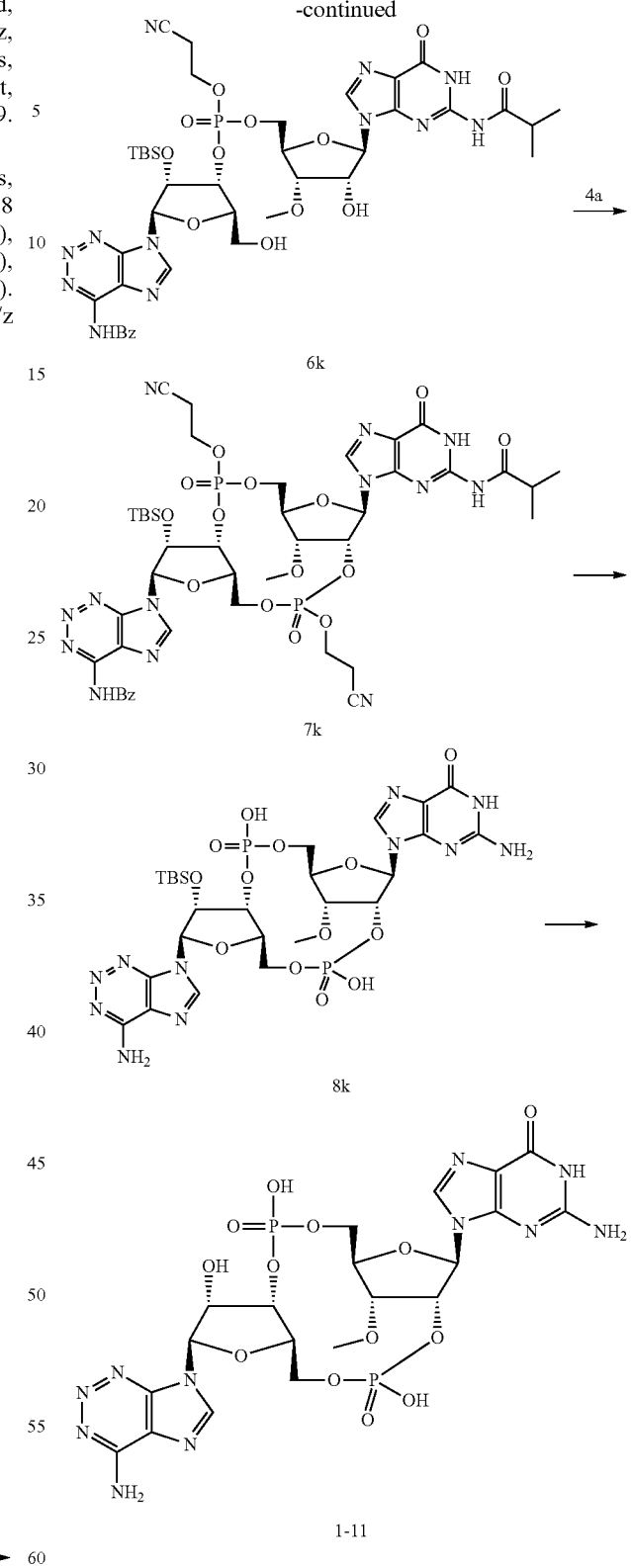

Benzoyl chloride (8.38 g, 59.60 mmol) was added to the mixture of 1j (2.00 g, 7.45 mmol) in pyridine (20 mL) at 0° C. The mixture was stirred at rt for 2 h and then H$_2$O (100 mL) was added to the mixture. The mixture was extracted with EtOAc (3×). The combined EtOAc layer was washed with sat. aq. NaCl (1×). The combined organic phases were concentrated in vacuo to afford a residue. The residue was dissolved in pyridine (20 mL) and the pH was adjusted to 10 using 2N NaOH (MeOH:H$_2$O, 4:1, v/v). The mixture was stirred at rt for 40 min. The mixture was then diluted with NH$_4$Cl and extracted with DCM (3×). The combined organic phases were washed with sat. aq. NaCl (1×). The combined organic phases were evaporated to dryness, and the crude material was purified by silica gel (DCM:MeOH, 1:1) to obtain 2j (2.50 g, 6.71 mmol, 90.0%) as a white foam. ESI-MS: m/z 373.1 [M+H]$^+$.

A solution of DMTrCl (2.50 g, 7.39 mmol) in anhydrous pyridine (10 mL) was added dropwise to a suspension of 2j (2.30 g, 6.17 mmol) in anhydrous pyridine (20 mL). The mixture was stirred at rt for 1 h. Water (2 mL) was then added to the mixture. The mixture were evaporated to dryness, and the crude material was purified by silica gel (EtOAc:PE, 1:1) to obtain 3j (2.50 g, 4.38 mmol, 70.93%) as a white foam. ESI-MS: m/z 675.2 [M+H]$^+$.

Imidazole (1.00 g, 14.70 mmol) and TBSCl (666.67 mg, 4.44 mmol) was added to a solution of 3j (2.50 g, 3.70 mmol) in DMF (30 mL) at 0° C. The mixture was stirred at rt for 60 h. The mixture was partitioned between EtOAc and H$_2$O. The organic layer was wash with brine, dried over Na$_2$SO$_4$ and concentrated under reduced pressure. The residue was purified by reverse phase prep-HPLC (Column: C18 spherical 20-35 μm 100A 40 g, mobile phase: 0.05% NH$_4$HCO$_3$ in water, m/m)-ACN from 60% to 85%, flow rate: 25 mL/min) to afford 4j (435 mg, 551.30 umol, 14.89%) as a white foam. ESI-MS: m/z 789.6 [M+H]$^+$.

Monomer C (467.00 mg, 0.53 mmol) and 4j (385.00 mg, 0.48 mmol) was dissolved in anhydrous CH$_3$CN (23.0 mL) and 4 Å molecular sieves powder (1 gr/100 mL) was added. The mixture was bubbled with Ar gas for 4 min. After stirring at rt for 10 min, 0.45 M tetrazole in CH$_3$CN (2.92 mmol, 6.5 mL) was added at rt. After stirring for 1 h, the mixture was filtered, and then washed with anhydrous CH$_3$CN. 0.02 M I$_2$ (THF:Py:H$_2$O, 8:1:1, v/v/v) was added until color persisted. After stirring for 20-30 min at rt, the reaction was quenched with Na$_2$SO$_3$ (aq, until discoloration), and then diluted with EtOAc. The layers were separated, and the organic phase was washed with sat. aq. NaHCO$_3$ (1×50 mL) and sat. aq. NaCl (1×50 mL). The combined aqueous phase was back extracted with EtOAc (1×50 mL). The combined organic phases were evaporated to dryness, and the crude material was purified by reverse phase prep-HPLC (Column: C18 spherical 20-35 μm 100A 8 0 g, mobile phase: 0.05% NH$_4$HCO$_3$ in water, m/m)-ACN from 30% to 100%, flow rate: 35 mL/min) to afford 5j (800.0 mg, 92.2%) as a white foam. ESI-MS: m/z 1573.6 [M+H]$^+$.

Compound 5j (750.0 mg, 0.47 mmol) was dissolved in DCA in DCM (3%, v/v, 13.30 mL) and triethyl silane (5.25 mL) was added immediately. After stirring the for 30 min at rt, the mixture was diluted with EtOAc and neutralize with sat. aq. NaHCO$_3$. The layers were separated, and the organic phase was washed with sat. aq. NaCl (1×50 mL). The aqueous phase was combined and back extracted with EtOAc (3×). The combined organic phases were evaporated to dryness, and the crude residue was purified by reverse phase prep-HPLC (Column: C18 spherical 20-35 μm 100A 80 g, mobile phase: 0.05% NH$_4$HCO$_3$ in water, m/m)-ACN from 30% to 80%, flow rate: 35 mL/min) to get 6j (425 mg, 0.43 mmol, 86.4%) as a white foam. ESI-MS: m/z 969.5 [M+H]$^+$.

Compound 6j (375 mg, 387.00 μmol) dissolved in anhydrous CH$_3$CN (25.0 mL), 0.45 M tetrazole in CH$_3$CN (3.09 mmol, 6.87 mL) and 4 Å molecular sieves powder (300 mg, 1 gr/100 mL) was added. The mixture was bubbled with Ar gas for 4 min. After stirring at rt for 20 min, 4a (233.2 mg, 773.40 umol) in CH$_3$CN (10.0 mL) was added over 30 to 40 min. After stirring for 2 h, the mixture was filtered and washed with anhydrous CH$_3$CN. 0.02 M I$_2$ (THF:Py:H$_2$O, 8:1:1, v/v/v) until the color persisted. After stirring for 20-30 min at rt, the reaction was quenched with sat. aq. Na$_2$SO$_3$ (until discoloration), and then diluted with EtOAc. The layers were separated, and the organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 30% to 60%, flow rate: 35 mL/min) to get 7j (100 mg, 92.3 μmol, 23.8%) as a white foam. ESI-MS: m/z 1084.5 [M+H]$^+$.

Compound 7j (78 mg, 71.9 μmol) was treated with a solution of 33% MeNH$_2$ in EtOH (16 mL). After stirring for 3 h at 40° C., the mixture was evaporated to dryness, and the crude material was purified by reverse phase prep-HPLC (Column: C18 spherical 20-35 μm 100A 40 g, mobile phase: 0.05% NH$_4$HCO$_3$ in water, m/m)-ACN from 0% to 30%, flow rate: 25 mL/min) to afford 8j (54 mg, 67.2 μmol, 93.4%) as a white foam. ESI-LMS: m/z 804.6 [M+H]$^+$.

3 HF·TEA (1.0 mL) was added to a mixture solution of 8j (65 mg, 80.8 mol) in DMSO (2 mL) at 40° C. for 2 h. The mixture was dropped in the solution of TEA (2 mL) in triethyamimonium bicarbonate buffer (12 mL) at 0° C. The mixture was stirred at rt for 30 min and then was purified by reverse phase prep-HPLC (Column: C18 spherical 20-35 μm 100A 40 g, mobile phase: 0.05% NH$_4$HCO$_3$ in water-ACN from 0% to 10%, flow rate: 20 mL/min) to get the NH$_4$ salt product (28 mg, 40.6 μmol, 50.2%) as a white foam. A volume of Amberlite IR-120 (15 mL, Na form) was added to a column and washed with deionized water (3×15 mL). The NH$_4$ salt product (60 mg) was dissolved in deionized water (60 mg in 8 mL), added to the top of the column and eluted with deionized water. The compound was eluted out in early fractions as detected by TLC (UV). The product was lyophilized to afford 1-11 (23 mg, 33.4 μmol, 41.2%) as a white foam. $^1$H NMR (400 MHz, D$_2$O): δ 8.12 (s, 1H), 8.03 (s, 1H), 6.53 (d, J=2.3 Hz, 1H), 5.97 (d, J=8.6 Hz, 1H), 5.34 (d, J=5.8 Hz, 1H), 5.25 (d, J=4.4 Hz, 1H), 5.08-5.00 (m, 1H), 4.51 (s, 1H), 4.41 (s, 1H), 4.26-4.19 (m, 2H), 4.15 (d, J=12.5 Hz, 1H), 4.10-4.03 (m, 1H), 3.97 (d, J=11.8 Hz, 1H), 3.52 (s, 3H). $^{31}$P-NMR (162 MHz, D$_2$O): −0.83, −1.72. ESI-MS: m/z 698.4 [M+H]$^+$.

Example 13

Compound 1-12

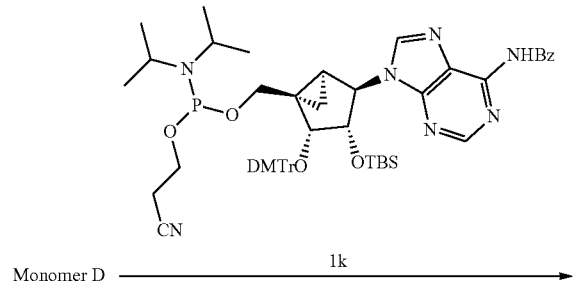

Monomer D ⎯⎯⎯⎯⎯⎯⎯⎯⎯⎯⎯⎯ 1k

-continued

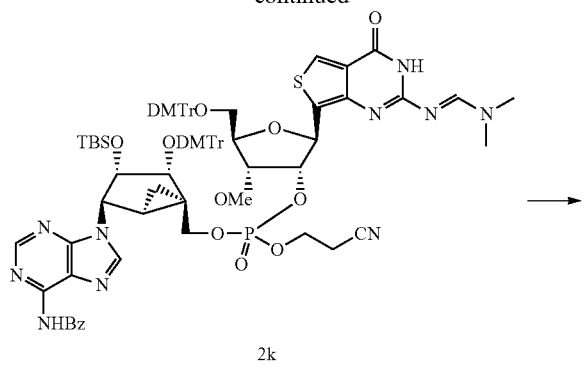

2k

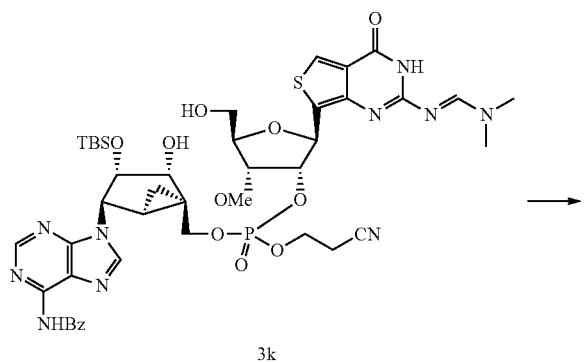

3k

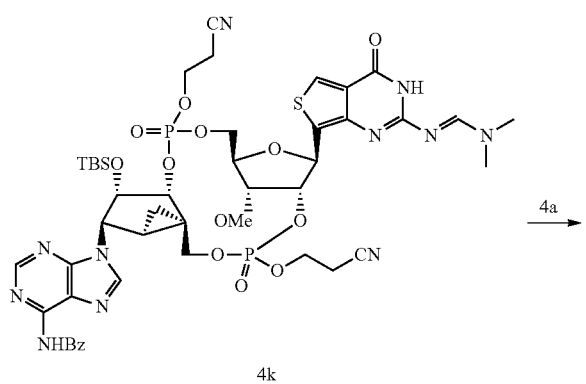

4k

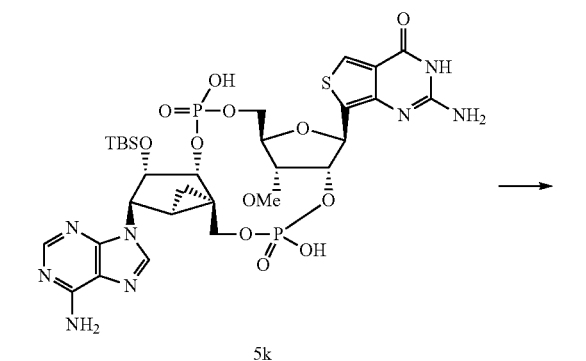

5k

-continued

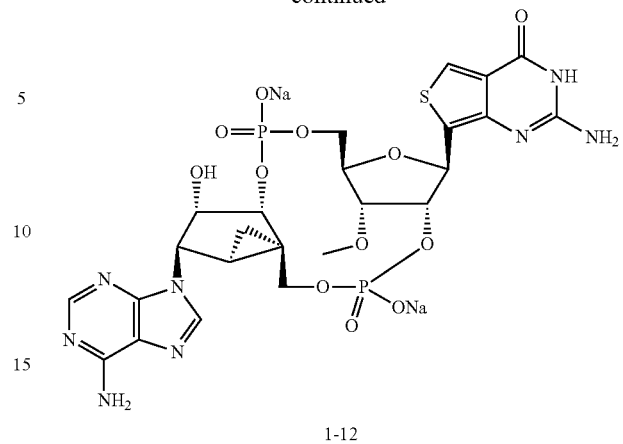

1-12

Monomer D (300 mg, 0.45 mmol) was dissolved in anhydrous CH$_3$CN (15.0 mL) and 1k (492 mg, 0.49 mmol) and 4 Å molecular sieves powder (300 mg, 1 gr/100 mL) were added. The mixture was bubbled with Ar gas for 4 min. After stirring at rt for 10 min, 0.45 M tetrazole in CH$_3$CN (2.69 mmol, 6.0 mL) was added at rt. After stirring for 1 h, the mixture was filtered and washed with anhydrous CH$_3$CN. 0.02 M I$_2$ (THF:Py:H$_2$O, 8:1:1, v/v/v) was added until the color persisted. After stirring for 20-30 min at rt, the reaction was quenched with Na$_2$SO$_3$ (aq, until discoloration). The mixture was diluted with EtOAc, and the layers were separated. The organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 60% to 100%, flow rate: 35 mL/min) to afford 2k (605 mg, 0.38 mmol, 84.4%) as a white foam. ESI-MS: m/z 1584.6 [M+H]$^+$.

Compound 2k (605 mg, 0.38 mmol) was dissolved in DCA in DCM (3%, v/v, 20.0 mL) and triethyl silane (7.0 mL) was added immediately. After stirring for 30 min at rt, the mixture was neutralized with pyridine and then evaporated to dryness. The crude residue was purified by reverse phase prep-HPLC (Column: C18 spherical 20-35 μm 100A 40 g, mobile phase: 0.05% NH$_4$HCO$_3$ in water, m/m)-ACN from 30% to 80%, flow rate: 30 mL/min) to get 3k (226 mg, 0.23 mmol, 60.8%) as a white foam. ESI-MS: m/z 979.4 [M+H]$^+$.

Compound 3k (226 mg, 0.23 mmol) dissolved in anhydrous CH$_3$CN (20.0 mL), 0.45 M tetrazole in CH$_3$CN (1.84 mmol, 4.1 mL) and 4 Å molecular sieves powder (220 mg, 1 gr/100 mL) were added. The mixture was bubbled with Ar gas for 4 min. After stirring at rt for 20 min, 4a (138 mg, 0.46 mmol) in CH$_3$CN (5.0 mL) was added over 25 to 30 min. After stirring for 2 h, the mixture was filtered and washed with anhydrous CH$_3$CN. 0.02 M I$_2$ (THF:Py:H$_2$O, 8:1:1, v/v/v) was added until the color persisted. After stirring for 20-30 min at rt, the reaction was quenched with sat. aq. Na$_2$SO$_3$ (until discoloration). The mixture was diluted with EtOAc, and the layers were separated. The organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 40 g, mobile phase: 0.05% NH$_4$HCO$_3$ in water, m/m)-ACN from 30% to 60%, flow rate: 20 mL/min) to get 4k (42 mg, 38.39 μmol, 16.7%) as a white foam. ESI-MS: m/z 1094.4 [M+H]$^+$.

Compound 4k (42 mg, 38.39 μmol) was treated with a solution of MeNH$_2$ in EtOH (5 mL, 33%). After stirring for 2 h at 40° C., the mixture was evaporated to dryness, and the crude material was purified by reverse phase prep-HPLC (Column: C18 spherical 20-35 μm 100A 20 g, mobile phase: 0.05% NH$_4$HCO$_3$ in water, m/m)-ACN from 0% to 20%, flow rate: 15 mL/min) to get 5k (22 mg, 26.56 umol, 69.2%) as a white foam. ESI-MS: m/z 829.3 [M+H]$^+$.

A solution of 5k (22 mg, 26.56 umol) and 3HF·TEA (0.5 mL) in THF (1.0 mL) was stirred at 40° C. for 6 h. The mixture was dropped in the solution of TEA (3 mL) in triethyamimonium bicarbonate buffer (6 mL) at 0° C. The mixture was stirred at rt for 30 min and then was purified by reverse phase prep-HPLC (Column: C18 spherical 20-35 μm 100A 12 g, mobile phase: 0.05% NH$_4$HCO$_3$ in water, m/m)-ACN from 0% to 10%, flow rate: 10 mL/min) to get the ammonium salt product (3.2 mg) as a white foam. A volume of Amberlite IR-120 (12 mL, Na form) was added to a column and washed with deionized water (3×15 mL). The ammonium salt product (3.2 mg) was dissolved in deionized water (88 mg in 10 mL), added to the top of the column and eluted with deionized water. The compound was eluted out in early fractions as detected by TLC (UV). The product was lyophilized to obtain 1-12 (1.5 mg, 2.10 μmol, 7.9%) as a white foam. $^1$H NMR (400 MHz, D$_2$O): δ 8.17 (s, 1H), 8.09 (s, 1H), 7.67 (s, 1H), 5.24 (d, J=9.6 Hz, 1H), 5.11 (t, J=6.8 Hz, 1H), 4.89-4.83 (m, 2H), 4.54 (d, J=15.2 Hz, 1H), 4.43 (d, J=2.0 Hz, 1H), 4.26 (d, J=4.4 Hz, 1H), 4.18-4.12 (m, 2H), 4.08-4.05 (m, 1H), 3.66 (d, J=11.2 Hz, 1H), 3.50 (s, 3H), 1.87-1.85 (m, 1H), 1.63 (t, J=5.2 Hz, 1H), 0.97 (t, J=7.6 Hz, 1H). $^{31}$P-NMR (162 MHz, D$_2$O): −0.91, −2.79. ESI-MS: m/z 715.2 [M+H]$^+$.

Example 14

Compound 1-13

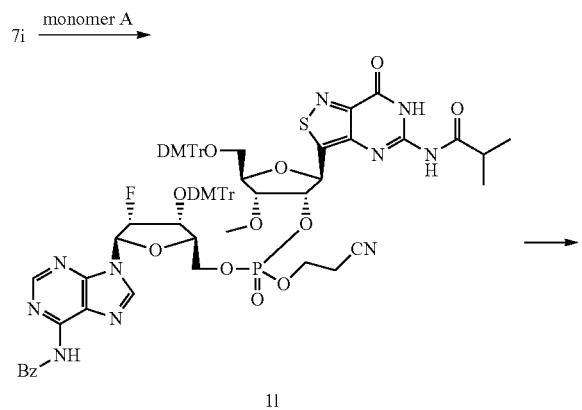

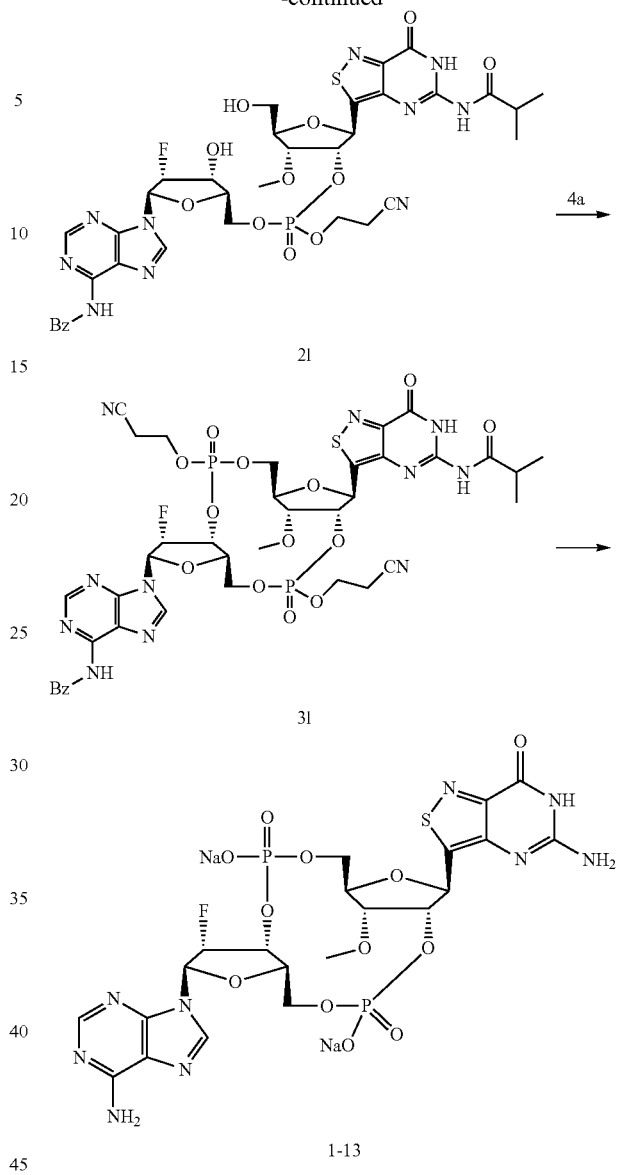

Compound 7i (630 mg, 0.72 mmol) and Monomer A (450 mg, 0.65 mmol) was dissolved in anhydrous CH$_3$CN (20.0 mL), and 4 Å molecular sieves powder (200 mg, 1 gr/100 mL) were added. The mixture was bubbled with Ar gas for 4 min. After stirring at rt for 10 min, 0.45 M tetrazole in CH$_3$CN (3.9 mmol, 8.7 mL) was added at rt. After stirring for 1 h, the mixture was filtered, and then washed with anhydrous CH$_3$CN. 0.02 M I$_2$ (THF:Py:H$_2$O, 8:1:1, v/v/v) was added until the color persisted. After stirring for 20-30 min at rt, the reaction was quenched with Na$_2$SO$_3$ (aq, until discoloration). The mixture was diluted with EtOAc, and the layers were separated. The organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 30% to 100%, flow rate: 35 mL/min) to get 11 (680 mg, 70.2%) as a white foam. ESI-MS: m/z 1477.5 [M+H]$^+$.

181

Compound 1l (680 mg, 0.46 mmol) was dissolved in DCA in DCM (3%, v/v, 10 mL) and triethylsilane (4 mL) was added immediately. After stirring for 30 min at rt, the mixture was diluted with EtOAc, and neutralize with sat. aq. NaHCO$_3$. The layers were separated, and the organic phase was washed with sat. aq. NaCl (1×). The aqueous phase was combined and back extracted with EtOAc (3×). The combined organic phases were evaporated to dryness, and the crude residue was purified by reverse phase prep-HPLC (Column: C18 spherical 20-35 μm 100A 40 g, mobile phase: 0.05% NH$_4$HCO$_3$ in water, m/m)-ACN from 30% to 80%, flow rate: 15 mL/min) to get 2l (120 mg, 30%) as a white foam. ESI-MS: m/z 873.4 [M+H]$^+$.

Compound 2l (120 mg, 0.138 mmol) was dissolved in anhydrous CH$_3$CN (15.0 mL), 0.45 M tetrazole in CH$_3$CN (1.1 mmol, 2.45 mL) and 4 Å molecular sieves powder (150 mg, 1 gr/100 mL) were added. The mixture was bubbled with Ar gas for 4 min. After stirring at rt for 20 min, 4a (83.1 mg, 0.276 mmol) in CH$_3$CN (4.0 mL) was added over 10 to 15 min. After stirring for 2 h, the mixture was filtered and washed with anhydrous CH$_3$CN. 0.02 M I$_2$ (THF:Py:H$_2$O, 8:1:1, v/v/v) was added until the color persisted. After stirring for 20-30 min at rt, the reaction was quenched with sat. aq. Na$_2$SO$_3$ (until discoloration). The mixture was diluted with EtOAc, and the layers were separated. The organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 20 g, mobile phase: 0.05% NH$_4$HCO$_3$ in water, m/m)-ACN from 30% to 60%, flow rate: 10 mL/min) to afford 3l (52 mg, 0.053 mmol, 38.3%) as a white foam. ESI-MS: m/z 988.3 [M+H]$^+$.

Compound 3l (52 mg, 0.053 mmol) was treated with a solution of MeNH$_2$ in EtOH (10 mL, 33%). After stirring for 2 h at 40° C., the mixture was evaporated to dryness, and the crude material was purified by reverse phase prep-HPLC (Column: C18 spherical 20-35 μm 100A 20 g, mobile phase: 0.05% NH$_4$HCO$_3$ in water, m/m)-ACN from 0% to 30%, flow rate: 10 mL/min) to get the NH$_4$ salt product (31 mg, 0.044 mmol, 82.9%) as a white foam. ESI-LMS: m/z 707.9 [M+H]$^+$. A volume of Amberlite IR-120 (15 mL, Na form) was added to a column and washed with deionized water (3×15 mL). The NH$_4$ salt product (24 mg) was dissolved in deionized water (31 mg in 6 mL), added to the top of the column and eluted with deionized water. The compound was eluted out in early fractions as detected by TLC (UV). The product was lyophilized to give 1-13 (22 mg, 0.029 mmol, 66.6%) as a white foam. $^1$H NMR (400 MHz, D$_2$O) δ 8.02 (s, 1H), 7.96 (s, 1H), 6.28 (d, J=15.1 Hz, 1H), 5.53 (d, J=3.0 Hz, 0.5H), 5.40 (d, J=3.1 Hz, 0.5H), 5.25 (d, J=9.6 Hz, 1H), 4.96 (d, J=22.5 Hz, 2H), 4.49-4.36 (m, 3H), 4.15 (dd, J=22.6, 8.1 Hz, 4H), 3.51 (s, 3H). $^{31}$P-NMR (162 MHz, D$_2$O) δ −1.61, −2.76. $^{19}$F-NMR (376 MHz, D$_2$O) δ −202.42. ESI-MS: m/z 708.3 [M+H]$^+$.

182

Example 15

Compounds 1-14a, 1-14b, 1-14c and 1-14d

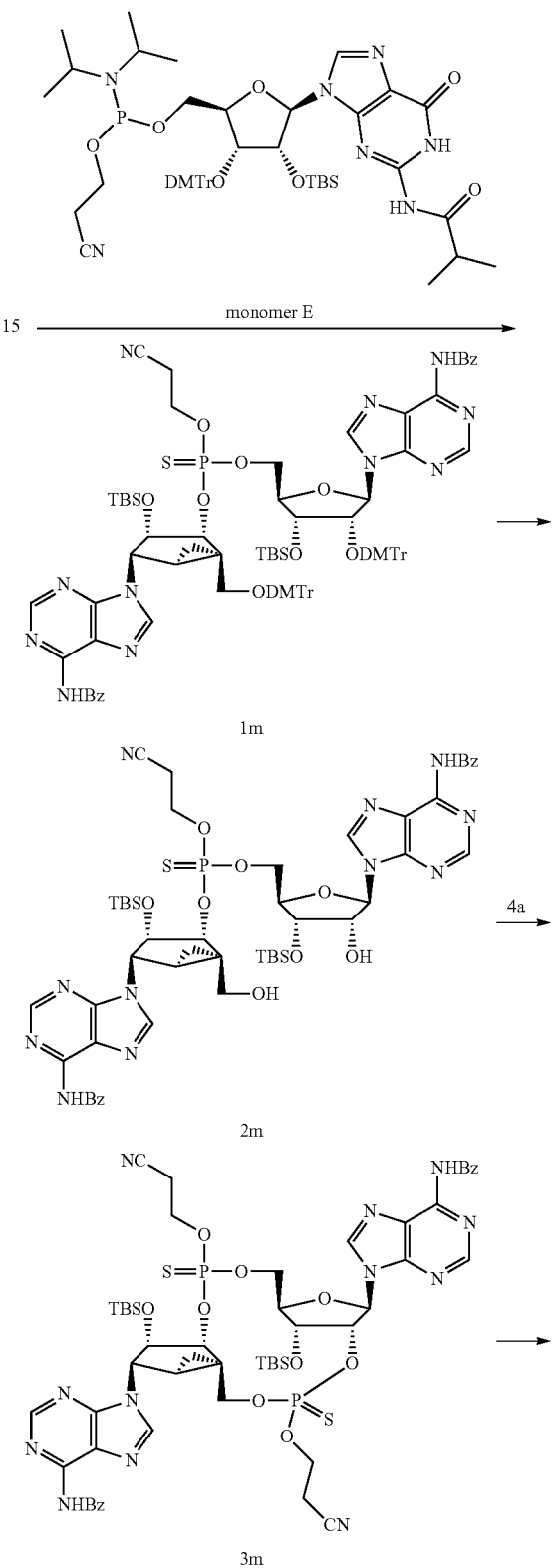

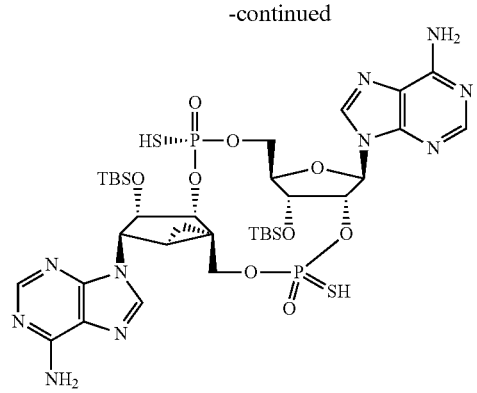
4m-P1
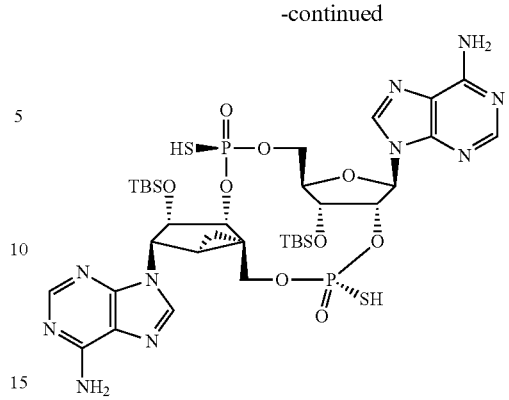
4m-P3
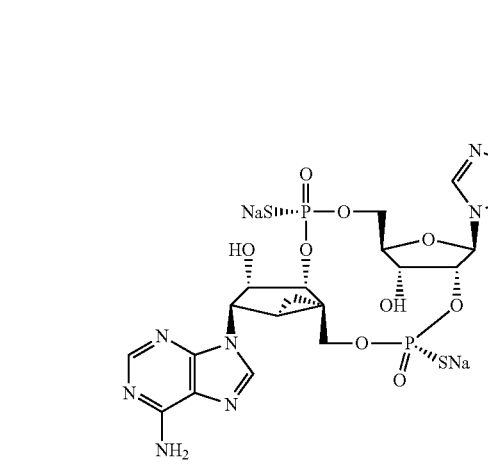
1-14a
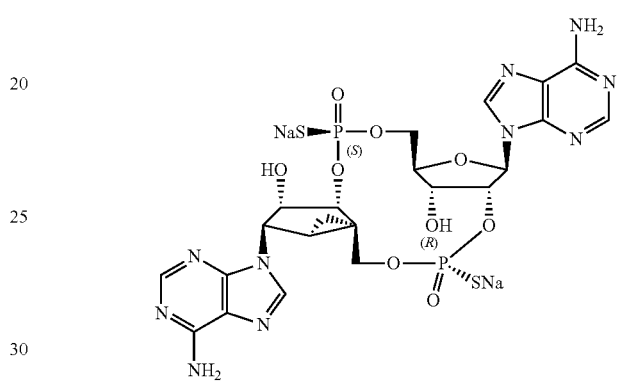
1-14c
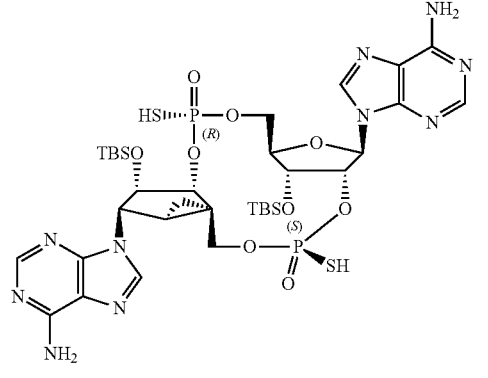
4m-P2
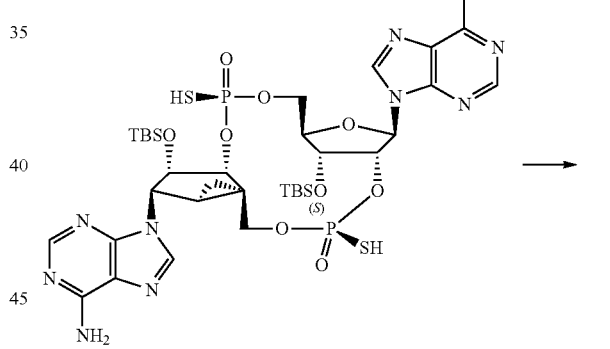
4m-P4
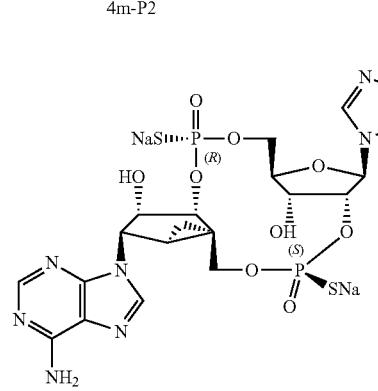
1-14b
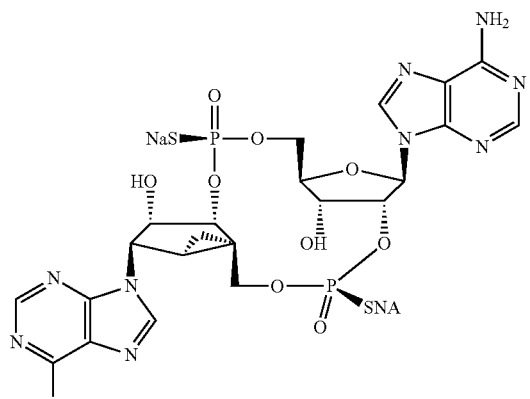
1-14d Monomer E (4.1 g, 4.10 mmol) and 15 (3.0 g, 3.70 mmol) was dissolved in anhydrous $CH_3CN$ (250.0 mL), and 4 Å molecular sieves powder (1 gr/100 mL) were added. The mixture was bubbled with Ar gas for 4 min. After stirring at rt for 10 min, 0.45 M tetrazole in $CH_3CN$ (22.5 mmol, 50.1 mL) was added at rt. After stirring for 1 h, the mixture was filtered and washed with anhydrous $CH_3CN$. 0.1 M DDTT (solvent: py) was added until the reaction was complete. After stirring for 20-30 min at rt, the reaction was quenched with $Na_2SO_3$ (aq, until discoloration). The mixture was diluted with EtOAc, and the layers were separated. The organic phase was washed with sat. aq. $NaHCO_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% $NH_4HCO_3$ in water, m/m)-ACN from 30% to 100%, flow rate: 35 mL/min) to get 1m (4.4 g, 68.1%) as a white foam. ESI-MS: m/z 1717.3 $[M+H]^+$.

Compound 1m (4.4 g, 2.56 mmol) was dissolved in DCA in DCM (3%, v/v, 78.2 mL) and triethyl silane (30.8 mL) was added immediately. After stirring for 30 min at rt, the mixture was diluted with EtOAc, and neutralize with sat. aq. $NaHCO_3$. The layers were separated, and the organic phase was washed with sat. aq. NaCl (1×). The aqueous phase was combined and back extracted with EtOAc (3×). The combined organic phases were evaporated to dryness, and the crude residue was purified by silica gel column (acetone in DCM from 0% to 100%) to get 2m (1.9 g, 1.70 mmol, 66.9%) as a white foam. ESI-MS: m/z 1112.5 $[M+H]^+$.

Compound 3m (1.9 g, 1.70 mmol) dissolved in anhydrous $CH_3CN$ (76.0 mL), 0.45 M tetrazole in $CH_3CN$ (13.6 mmol, 30.3 mL) and 4 Å molecular sieves powder (1 gr/100 mL) were added. The mixture was bubbled with Ar gas for 4 min. After stirring at rt for 20 min, 4a (1.0 g, 3.30 mmol) in $CH_3CN$ (15.0 mL) was added over 30 to 40 min. After stirring for 2 h, the mixture was filtered and washed with anhydrous $CH_3CN$. 0.1 M DDTT (solvent: py) was added until the reaction was complete. After stirring for 20-30 min at rt, the reaction was quenched with sat. aq. $Na_2SO_3$ (until discoloration). The mixture was diluted with EtOAc, and the layers were separated. The organic phase was washed with sat. aq. $NaHCO_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% $NH_4HCO_3$ in water, m/m)-ACN from 30% to 60%, flow rate: 35 mL/min) to get 3m (1.15 g, 925.1 μmol, 53.5%) as a white foam. ESI-MS: m/z 1243.4 $[M+H]^+$.

Compound 3m (1.15 g, 925.1 μmol) was treated with a solution of $MeNH_2$ in EtOH (35 mL, 33%). After stirring for 3 h at 40° C., the mixture was evaporated to dryness. The crude material was purified by reverse phase prep-HPLC (Column: XBridge 30×100 mm, mobile phase: 0.05% $NH_4HCO_3$ in water, m/m)-ACN from 0% to 10%, flow rate: 20 mL/min) to get 4m-P1 (82 mg, 88.2 mol, 9.7%), $^{31}$P-NMR (162 MHz, DMSO-$d_6$): 54.83, 54.72. 4m-P2 (145 mg, 156.0 μmol, 16.8% yield), $^{31}$P-NMR (162 MHz, DMSO-$d_6$): 52.92, 50.14. 4m-P3 (70 mg, 75.3 μmol, 8.1% yield), $^{31}$P-NMR (162 MHz, DMSO-$d_6$): 55.26, 51.23. 4m-P4 (190 mg, 204.5 μmol, 22.1% yield), $^{31}$P-NMR (162 MHz, DMSO-$d_6$): 54.75, 50.38 as a white foam. ESI-LMS: m/z 929.6 $[M+H]^+$.

3 HF·TEA (1.0 mL) was added to a mixture solution of 4m-P1 (82 mg, 88.2 μmol) in DMSO (2 mL) at 40° C. for 48 h, and then cooled rt. TEA (1.0 mL) and isopropoxytrimethylsilane (8.0 mL) were added. The mixture was stirred at rt for 1 h and then evaporated to dryness. The residue was purified by reverse phase prep-HPLC (Column: C18 spherical 20-35 μm 100A 40 g, mobile phase: 0.05% $NH_4HCO_3$ in water-ACN from 0% to 10%, flow rate: 20 mL/min) to get the $NH_4$ salt product (20 mg, 28.5 μmol, 32.3%) as a white foam. A volume of Amberlite IR-120 (15 mL, Na form) was added to a column and washed with deionized water (3×15 mL). The $NH_4$ salt product (20 mg) was dissolved in deionized water (20 mg in 8 mL), added to the top of the column and eluted with deionized water. The compound was eluted out in early fractions as detected by TLC (UV). The product was lyophilized to give 1-14a (18 mg, 25.6 μmol, 29.0%) as a white foam. $^1$H NMR (400 MHz, $D_2O$): δ 8.65 (s, 1H), 8.01-7.94 (m, 3H), 6.15-6.13 (d, J=8.16 Hz, 1H), 5.39-5.35 (m, 1H), 5.12-5.07 (m, 1H), 4.75 (m, 1H), 4.66-4.65 (m, 1H), 4.41-4.37 (m, 3H), 4.19-4.16 (m, 1H), 4.09 (m, 1H), 3.76-3.78 (d, J=9.36 Hz, 1H), 1.78-1.76 (m, 1H), 1.60-1.57 (m, 1H), 1.00-0.96 (m, 1H). $^{31}$P-NMR (162 MHz, $D_2O$): 54.60, 53.92. ESI-MS: m/z 701.4 $[M+H]^+$. Compounds 1-14b, 1-14c and 1-14d were obtained using a similar procedure as 1-14a using 4m-P2, 4m-P3 and 4m-P4, respectively.

1-14b: (21 mg, 29.9 μmol, 19.2%) $^1$H NMR (400 MHz, $D_2O$): δ 8.46 (m, 1H), 8.26 (m, 1H), 7.78 (m, 1H), 7.68 (m, 1H), 5.72 (m, 1H), 4.86 (m, 2H), 4.69 (m, 1H), 4.41-4.40 (m, 2H), 4.20 (m, 1H), 4.03 (m, 1H), 3.90 (m, 1H), 3.64-3.62 (m, 1H), 3.40 (m, 1H), 1.77 (m, 1H), 1.63 (m, 1H), 1.03 (m, 1H). $^{31}$P-NMR (162 MHz, $D_2O$): 55.59, 49.77. ESI-MS: m/z 701.4 $[M+H]^+$.

1-14c: (23 mg, 32.8 μmol, 43.5%) as a white foam. $^1$H NMR (400 MHz, $D_2O$): δ 8.47 (s, 1H), 8.10 (s, 1H), 8.05 (s, 1H), 7.96 (s, 1H) 6.19-6.17 (d, J=8.2 Hz, 1H), 5.45-5.39 (m, 1H), 5.28-5.25 (t, J=7.1 Hz, 1H), 4.79 (s, 1H), 4.66-4.68 (m, 1H), 4.44 (s, 1H), 4.39-4.34 (m, 1H), 4.24-4.21 (m, 2H), 4.07-4.03 (dd, J=11.92 Hz, 1H), 3.99-3.95 (m, 1H), 1.79-1.77 (m, 1H), 1.65-1.62 (m, 1H), 1.05-1.01 (m, 1H). $^{31}$P-NMR (162 MHz, $D_2O$): 54.86, 54.11. ESI-MS: m/z 701.4 $[M+H]^+$.

1-14d: (23 mg, 32.8 μmol, 43.5%) as a white foam. $^1$H NMR (400 MHz, $D_2O$): δ 8.40 (s, 1H), 8.24 (m, 1H), 7.97-7.95 (d, J=11.2 Hz, 2H), 6.00 (m, 1H), 5.16-5.12 (m, 2H), 4.81 (s, 1H), 4.68 (m, 1H), 4.38-4.35 (d, J=11.2 Hz, 1H), 4.28-4.22 (m, 3H), 3.84 (m, 1H), 3.69-3.67 (d, J=10.52 Hz, 1H), 1.81-1.80 (m, 1H), 1.67-1.66 (m, 1H), 1.03-1.00 (m, 1H). $^{31}$P-NMR (162 MHz, $D_2O$): 55.03, 50.63. ESI-MS: m/z 701.4 $[M+H]^+$.

Example 16

Compounds 1-15a and 1-15b

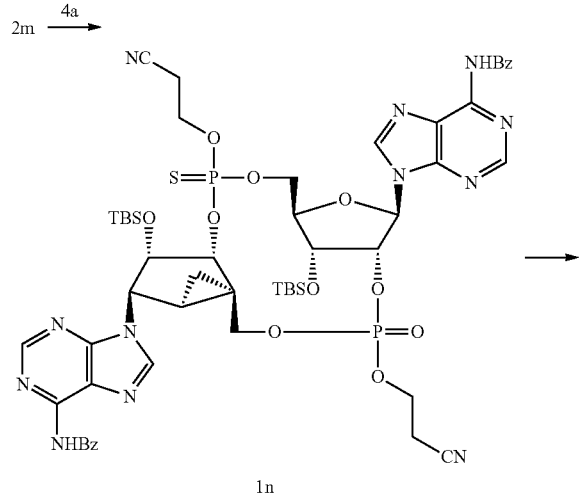

1n

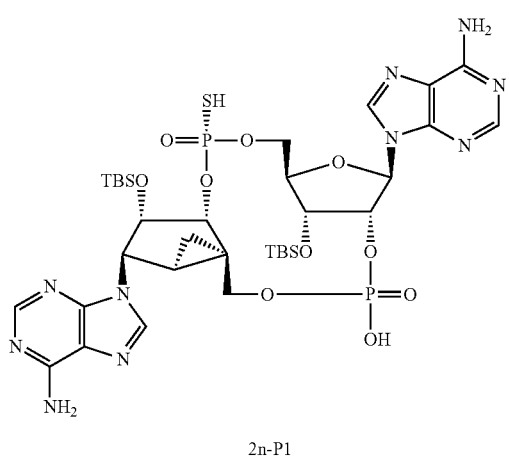

2n-P1

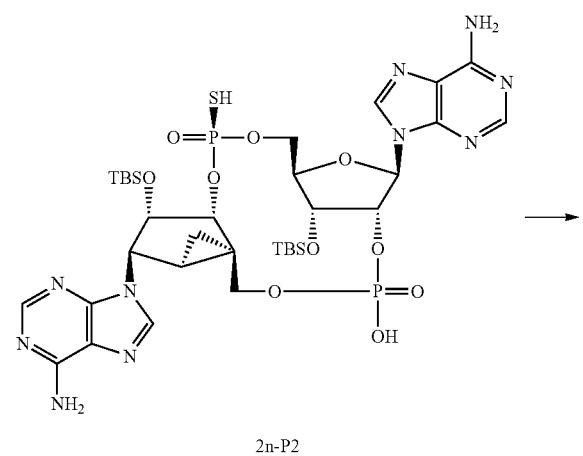

2n-P2

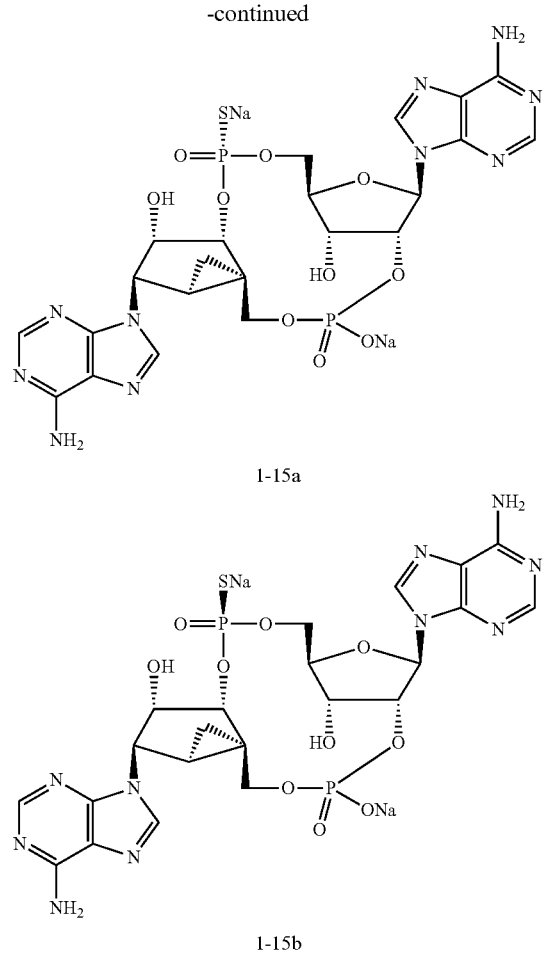

1-15a 1-15b

Compound 2m (700 mg, 629.49 μmol) dissolved in anhydrous CH$_3$CN (60.0 mL), 0.45 M tetrazole in CH$_3$CN (5.03 mmol, 11 mL) and 4 Å molecular sieves powder (800 mg, 1 gr/100 mL) were added. The mixture was bubbled with Ar gas for 4 min. After stirring at rt for 20 min, 4a (378 mg, 1.26 mmol) in CH$_3$CN (10.0 mL) was added over 25 to 30 min. After stirring for 2 h, the mixture was filtered and washed with anhydrous CH$_3$CN. To this solution was added 5 M t-BuOOH until the reaction was complete. After stirring for 20-30 min at rt, the reaction was quenched with sat. aq. Na$_2$SO$_3$ (until discoloration). The mixture was diluted with EtOAc, and the layers were separated. The organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 30% to 60%, flow rate: 35 mL/min) to get 1n (400 mg, 326.26 μmol, 51.8%) as a white foam. ESI-MS: m/z 1227.4 [M+H]$^+$.

Compound 1n (400 mg, 326.26 μmol) was treated with a solution of MeNH$_2$ in EtOH (20 mL, 33%). After stirring for 2 h at 40° C., the mixture was evaporated to dryness. The crude material was purified by reverse phase prep-HPLC (Column: XBridge 30×100 mm, mobile phase: 0.05% NH$_4$HCO$_3$ in water, m/m)-ACN from 0% to 10%, flow rate: 20 mL/min) to get 2n-P1 (75 mg, 82.23 μmol, 25.2%) and 2n-P2 (72 mg, 78.95 μmol, 24.2%) as a white foam. 2n-P1:

$^{31}$P-NMR (162 MHz, DMSO-d$_6$): δ1.86, −6.29. ESI-MS: m/z 913.3 [M+H]$^+$. 2n-P2: $^{31}$P-NMR (162 MHz, DMSO-d$_6$): δ4.76, 54.53, −5.81, −6.26. ESI-MS: m/z 913.3 [M+H]$^+$.

A solution of 2n-P1 (75 mg, 82.23 μmol) and 3 HF·TEA (2.0 mL) in DMSO (2.0 mL) was stirred at 40° C. for 48 h. The mixture was cooled to rt, and then TEA (2 mL) and isopropoxytrimethylsilane (16 mL) were added. The mixture was stirred at rt for 1 h and then evaporated to dryness. The residue was purified by reverse phase prep-HPLC (Column: C18 spherical 20-35 μm 100A 40 g, mobile phase: 0.05% NH4HCO$_3$ in water, m/m)-ACN from 0% to 15%, flow rate: 20 mL/min) to get the ammonia salt product (42 mg, 61.4 μmol, 74.6%) as a white foam. A volume of Amberlite IR-120 (15 mL, Na form) was added to a column and washed with deionized water (3×15 mL). The ammonia salt product (42 mg) was dissolved in deionized water (42 mg in 15 mL), added to the top of the column and eluted with deionized water. The compound was eluted out in early fractions as detected by TLC (UV). The product was lyophilized to give 1-15a (38 mg, 55.5 μmol, 90.4%) as a white foam. $^1$H NMR (400 MHz, D$_2$O): δ 8.71 (s, 1H), 8.04 (d, J=13.6 Hz, 3H), 6.16 (d, J=7.6 Hz, 1H), 5.24 (s, 1H), 5.07-5.03 (m, 1H), 4.83 (s, 1H), 4.56 (d, J=10.8 Hz, 2H), 4.43 (d, J=6 Hz, 2H), 4.16 (s, 2H), 3.60 (d, J=10.8 Hz, 1H), 1.83-1.78 (m, 1H), 1.63-1.60 (t, J=4.8 Hz, 1H), 1.00-0.97 (t, J=7.2 Hz, 1H). $^{31}$P-NMR (162 MHz, D$_2$O): 54.17, −3.03. ESI-MS: m/z 685.5 [M+H]$^+$. Compound 1-15b (28 mg, 40.93 μmol, 87.5%) was obtained in a similar manner using 2n-P2 as a white foam. $^1$H NMR (400 MHz, D$_2$O): δ 8.48 (s, 1H), 8.04-7.97 (t, J=14.8 Hz, 3H), 6.17 (d, J=8 Hz, 1H), 5.30-5.25 (m, 1H), 5.20-5.16 (t, J=7.2 Hz, 1H), 4.77 (s, 1H), 4.53 (d, J=10.8 Hz, 2H), 4.45 (s, 1H), 4.32-4.29 (t, J=9.6 Hz, 1H), 4.18 (d, J=6.4 Hz, 1H), 4.08-4.04 (m, 1H), 3.65 (d, J=10.8 Hz, 1H), 1.78-1.76 (t, J=8.4 Hz, 1H), 1.63-1.61 (t, J=4.8 Hz, 1H), 1.00-0.96 (t, J=7.2 Hz, 1H). $^{31}$P-NMR (162 MHz, D$_2$O): 54.74, −2.73. ESI-MS: m/z 685.5 [M+H]$^+$.

Example 17

Compounds 1-16a and 1-16b

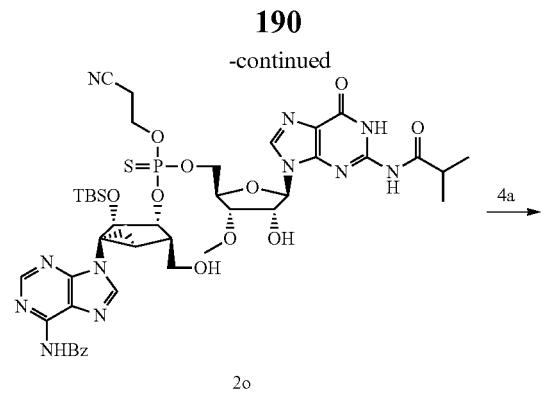

2o

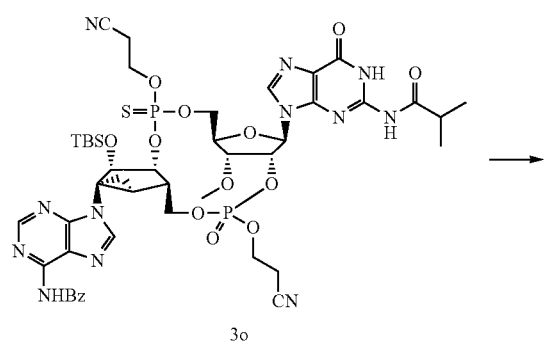

3o

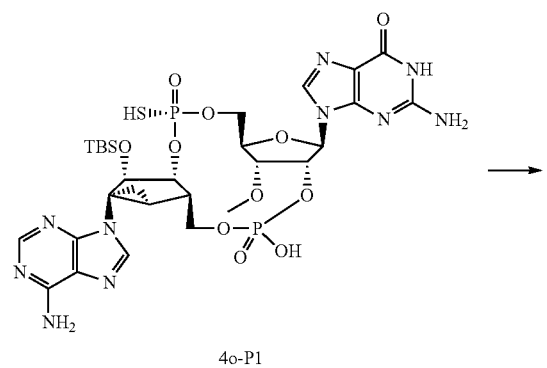

4o-P1

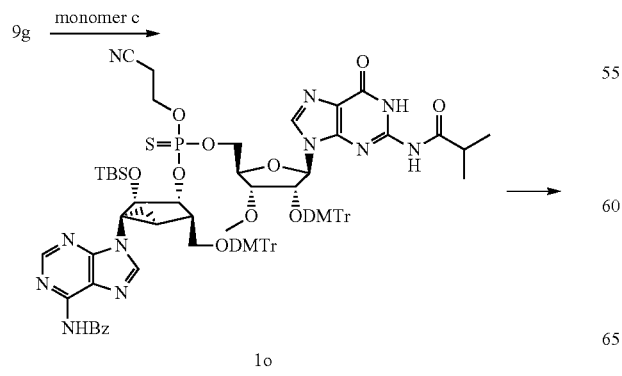

1o 1-16a

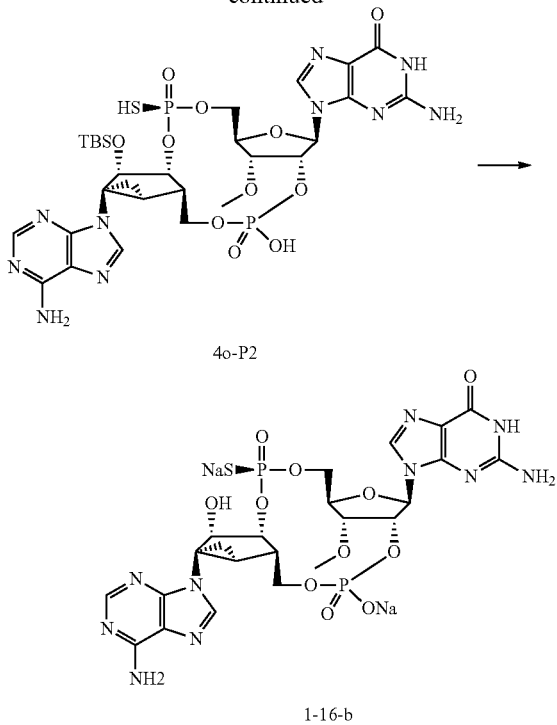

4o-P2

1-16-b

Monomer C (780.00 mg, 0.89 mmol) and 9 g (650.00 mg, 0.81 mmol) was dissolved in anhydrous CH$_3$CN (45.0 mL), and 4 Å molecular sieves powder (1 gr/100 mL) were added. The mixture was bubbled with Ar gas for 4 min. After stirring at rt for 10 min, 0.45 M tetrazole in CH$_3$CN (4.88 mmol, 10.8 mL) was added at rt. After stirring for 1 h, the mixture was filtered and washed with anhydrous CH$_3$CN. 0.1 M DDTT (solvent: py) was added until the reaction completed. After stirring for 20-30 min at rt, the reaction was quenched with Na$_2$SO$_3$ (aq, until discoloration). The mixture was diluted with EtOAc, and the layers were separated. The organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 30% to 100%, flow rate: 35 mL/min) to get to (1.10 g, 688.00 umol, 84.5%) as a white foam. ESI-MS: m/z 1598.6 [M+H]$^+$.

Compound to (1.10 g, 688.00 umol) was dissolved in DCA in DCM (3%, v/v, 19.50 mL) and triethyl silane (7.70 mL) was added immediately. After stirring for 30 min at rt, the mixture was diluted with EtOAc and neutralize with sat. aq. NaHCO$_3$. The layers were separated, and the organic phase was washed with sat. aq. NaCl (1×). The aqueous phase was combined and back extracted with EtOAc (3×). The combined organic phases were evaporated to dryness, and the crude residue was purified by reverse phase prep-HPLC (Column: C18 spherical 20-35 μm 100A 80 g, mobile phase: 0.05% NH$_4$HCO$_3$ in water, m/m)-ACN from 30% to 80%, flow rate: 35 mL/min) to get 20 (630 mg, 633.74 umol, 92.11%) as a white foam. ESI-MS: m/z 994.5 [M+H]$^+$.

Compound 20 (600 mg, 603.56 umol) dissolved in anhydrous CH$_3$CN (25.0 mL), 0.45 M tetrazole in CH$_3$CN (4.82 mmol, 10.73 mL) and 4 Å molecular sieves powder (1 gr/100 mL) were added. The mixture was bubbled with Ar gas for 4 min. After stirring at rt for 20 min, 4a (363.84 mg, 1.21 mmol) in CH$_3$CN (10.0 mL) was added over 30 to 40 min. After stirring for 2 h, the mixture was filtered and washed with anhydrous CH$_3$CN. To this solution was added 5 M t-BuOOH until the reaction was completed. After stirring for 20-30 min at rt, the reaction was quenched with sat. aq. Na$_2$SO$_3$ (until discoloration). The mixture was diluted with EtOAc, and the layers were separated. The organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 30% to 60%, flow rate: 35 mL/min) to get 3o (297 mg, 267.78 umol, 44.37%) as a white foam. ESI-MS: m/z 1109.5 [M+H]$^+$.

Compound 3o (293 mg, 264.17 umol) was treated with a solution of MeNH$_2$ in EtOH (42 mL, 33%). After stirring for 3 h at 40° C., the mixture was evaporated to dryness, and the crude material was purified by reverse phase prep-HPLC (Column: XBridge 30×100 mm, mobile phase: 0.05% NH$_4$HCO$_3$ in water, m/m)-ACN from 0% to 10%, flow rate: 20 mL/min) to get 4o-P1 (63 mg, 67.8 mol, 25.6%), $^{31}$P-NMR (162 MHz, DMSO-d$_6$): δ7.98, −0.84, and 4o-P2 (63 mg, 67.8 μmol, 25.6%), $^{31}$P-NMR (162 MHz, DMSO-d$_6$): δ3.31, −0.75 as a white foam. ESI-LMS: m/z 829.4 [M+H]$^+$.

3 HF·TEA (1.0 mL) was added to a mixture solution of 4o-P1 (63 mg, 67.8 μmol) in DMSO (1 mL) at 40° C. for 48 h, and then cooled to rt. TEA (1.0 mL) and isopropoxytrimethylsilane (8.0 mL) were added. The mixture was stirred at rt for 1 h and then evaporated to dryness. The residue was purified by reverse phase prep-HPLC (Column: C18 spherical 20-35 μm 100A 40 g, mobile phase: 0.05% NH$_4$HCO$_3$ in water-ACN from 0% to 10%, flow rate: 20 mL/min) to get the NH$_4$ salt product (28 mg, 40.6 μmol, 50.2%) as a white foam. A volume of Amberlite IR-120 (15 mL, Na form) was added to a column and washed with deionized water (3×15 mL). The NH$_4$ salt product (20 mg) was dissolved in deionized water (20 mg in 8 mL), added to the top of the column and eluted with deionized water. The compound was eluted out in early fractions as detected by TLC (UV). The product was lyophilized to give 1-16a (19 mg, 23.3 μmol, 34.4%) as a white foam. $^1$H NMR (400 MHz, D$_2$O): δ 8.14 (s, 2H), 7.95 (s, 1H), 5.87-5.85 (d, J=8.4 Hz, 1H), 5.35-5.32 (m, 1H), 5.13-5.08 (m, 1H), 4.46 (s, 1H), 4.24-4.22 (m, 1H), 4.14-4.10 (m, 4H), 4.05-4.02 (m, 1H), 3.51 (s, 3H), 2.42 (m, 1H), 2.09-2.06 (m, 1H), 1.85-1.81 (m, 1H), 1.47-1.43 (m, 1H). $^{31}$P-NMR (162 MHz, D$_2$O): 56.50, −1.14. ESI-MS: m/z 715.3 [M+H]$^+$.

Compound 1-16b (white, foam, 8 mg, 9.8 μmol, 14.5%) was obtained in a similar manner as 1-16a using 4o-P2. $^1$H NMR (400 MHz, D$_2$O): δ 8.13 (s, 1H), 8.05 (s, 1H), 7.70 (s, 1H), 5.83-5.81 (m, 1H), 5.41 (m, 1H), 5.23-5.18 (m, 1H), 4.52 (m, 1H), 4.40-4.38 (d, J=10.56 Hz, 1H), 4.31-4.28 (m, 1H), 4.12 (m, 3H) 4.04-4.01 (m, 1H), 3.51 (s, 3H), 2.42 (m, 1H), 2.10-2.08 (m, 1H), 1.82-1.79 (m, 1H), 1.43-1.39 (m, 1H). $^{31}$P-NMR (162 MHz, D$_2$O): 50.33, −1.37. ESI-MS: m/z 715.3 [M+H]$^+$.

Example 18

Compound 1-17

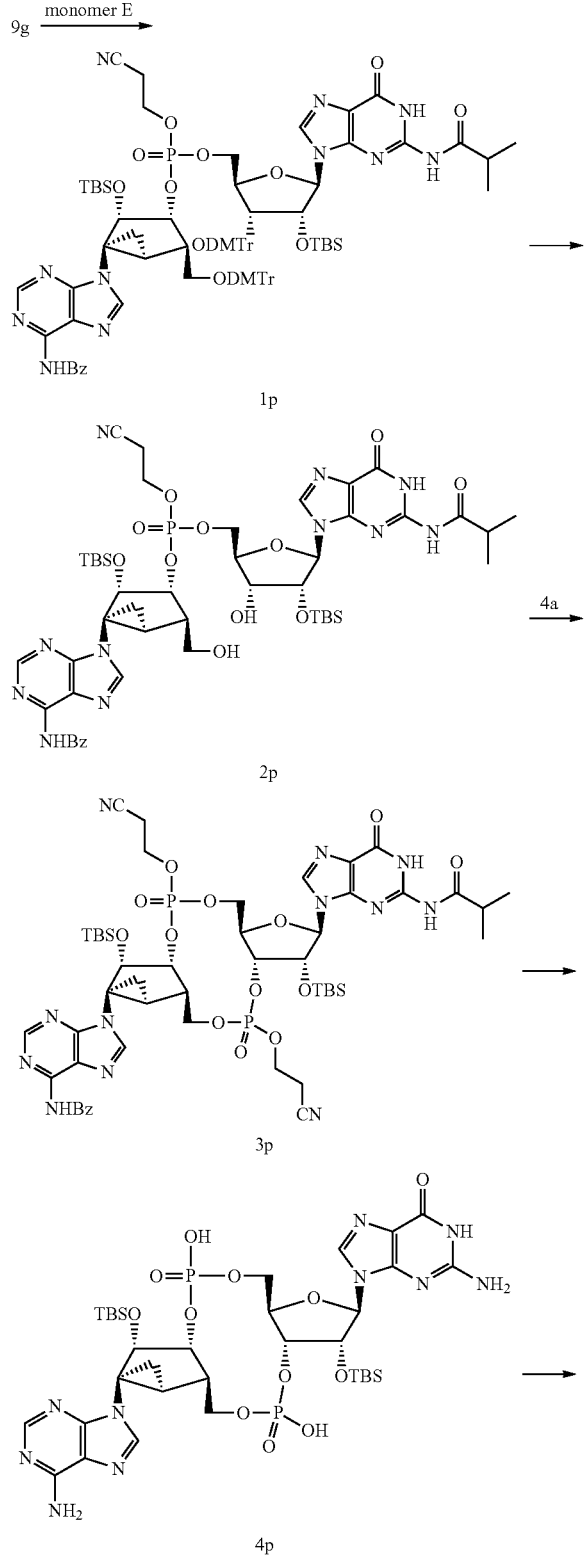
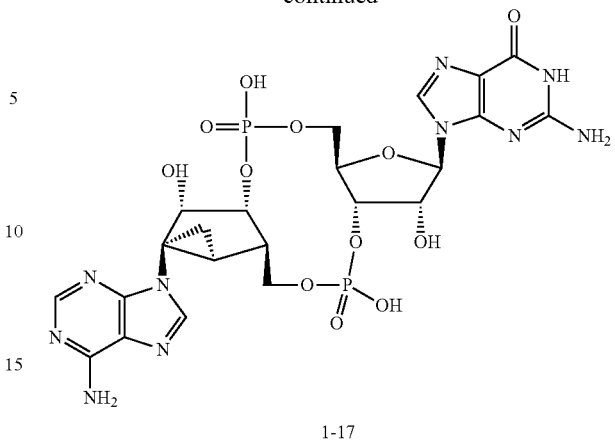

Monomer E (468 mg, 0.48 mmol) and 9 g (350 mg, 0.43 mmol) was dissolved in anhydrous CH$_3$CN (18.0 mL), and 4 Å molecular sieves powder (1 gr/100 mL) were added. The mixture was bubbled with Ar gas for 4 min. After stirring at rt for 10 min, 0.45 M tetrazole in CH$_3$CN (2.63 mmol, 5.8 mL) was added at rt. After stirring for 1 h, the mixture was filtered and washed with anhydrous CH$_3$CN. To this solution was added 5 M t-BuOOH until the reaction was completed. After stirring for 20-30 min at rt, the reaction was quenched with Na$_2$SO$_3$ (aq, until discoloration). The mixture was diluted with EtOAc, and the layers were separated. The organic phase was washed with sat. aq. NaHCO$_3$ (1×) and sat. aq. NaCl (1×). The combined aqueous phase was back extracted with EtOAc (1×). The combined organic phases were evaporated to dryness and the crude material was purified by reverse phase prep-HPLC (Column: C18 spherical 20-35 μm 100A 80 g, mobile phase: 0.05% NH$_4$HCO$_3$ in water, m/m)-ACN from 30% to 100%, flow rate: 35 mL/min) to get 1p (680 mg, 92.4%) as a white foam. ESI-MS: m/z 1683.1 [M+H]$^+$.

Compound 1p (680 mg, 0.40 mmol) was dissolved in DCA in DCM (3%, v/v, 12.2 mL) and triethyl silane (4.8 mL) was added immediately. After stirring for 30 min at rt, the mixture was diluted with EtOAc, and then neutralize with sat. aq. NaHCO$_3$. The layers were separated, and the organic phase was washed with sat. aq. NaCl (1×). The aqueous phase was combined and back extracted with EtOAc (3×). The combined organic phases were evaporated to dryness, and the crude residue was purified by silica gel column (acetone in DCM from 0% to 100%) to get 2p (325 mg, 0.30 mmol, 74.7%) as a white foam. ESI-MS: m/z 1078.5 [M+H]$^+$.

Compound 2p (325 mg, 301.5 μmol) dissolved in anhydrous CH$_3$CN (20.0 mL), and 0.45 M tetrazole in CH$_3$CN (2.41 mmol, 5.36 mL) and 4 Å molecular sieves powder (300 mg, 1 gr/100 mL) were added. The mixture was bubbled with Ar gas for 4 min. After stirring at rt for 20 min, 4a (181.7 mg, 0.60 mmol) in CH$_3$CN (5.0 mL) was added over 30 to 40 min. After stirring for 2 h, the mixture was filtered, and then washed with anhydrous CH$_3$CN. To this solution was added 5 M t-BuOOH until the reaction was completed. After stirring for 20-30 min at rt, the reaction was quenched with sat. aq. Na$_2$SO$_3$ (until discoloration). The mixture was diluted with EtOAc, and then layers were separated. The organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% NH₄HCO₃ in water, m/m)-ACN from 30% to 60%, flow rate: 35 mL/min) to get 3p (134 mg, 112.3 μmol, 37.2%) as a white foam. ESI-MS: m/z 1193.3 [M+H]⁺.

Compound 3p (134 mg, 112.3 μmol) was treated with a solution of MeNH₂ in EtOH (24 mL, 33%). After stirring for 4 h at 40° C., the mixture was evaporated to dryness. The crude material was purified by reverse phase prep-HPLC (Column: C18 spherical 20-35 μm 100A 40 g, mobile phase: 0.05% NH₄HCO₃ in water, m/m)-ACN from 0% to 30%, flow rate: 25 mL/min) to get 4p (43 mg, 47.1 μmol, 41.5%) as a white foam. ESI-LMS: m/z 913.3 [M+H]⁺.

3 HF·TEA (1.5 mL) was added to a mixture solution of 4p (43 mg, 47.1 mol) in DMSO (2 mL) at 40° C. for 48 hours. The mixture was cooled to rt, and then TEA (2.0 mL) and isopropoxytrimethylsilane (16.0 mL) were added. The mixture was stirred at rt for 1 h and then evaporated to dryness. The residue was purified by reverse phase prep-HPLC (Column: C18 spherical 20-35 μm 100A 40 g, mobile phase: 0.05% NH₄HCO₃ in water-ACN from 0% to 10%, flow rate: 20 mL/min) to get the NH₄ salt product (6 mg, 8.7 mol, 18.5%) as a white foam. A volume of Amberlite IR-120 (15 mL, Na form) was added to a column and washed with deionized water (3×15 mL). The NH₄ salt product (6 mg) was dissolved in deionized water (6 mg in 8 mL) and added to the top of the column. The column was eluted with deionized water. The compound was eluted out in early fractions as detected by TLC (UV). The product was lyophilized to afford 1-17 (4.5 mg, 6.5 μmol, 13.8%) as a white foam. ¹H NMR (400 MHz, D₂O): δ 8.26 (s, 1H), 8.09 (s, 1H), 7.74 (s, 1H), 5.83-5.82 (m, 1H), 5.05-5.01 (m, 1H), 4.82 (m, 1H), 4.78 (m, 1H), 4.31 (m, 1H), 4.22-4.08 (m, 4H), 3.97-3.94 (m, 1H), 2.38 (s, 1H), 2.04-2.02 (m, 1H), 1.90-1.87 (m, 1H), 1.41 (m, 1H). ³¹P-NMR (162 MHz, D₂O): −0.50, −0.55. ESI-MS: m/z 685.4 [M+H]⁺.

Example 19

Compound 1-18

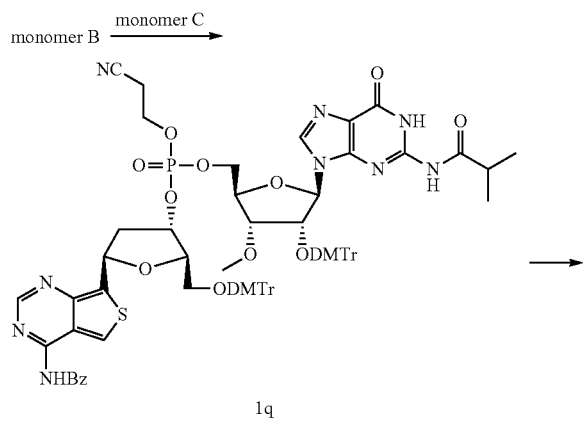

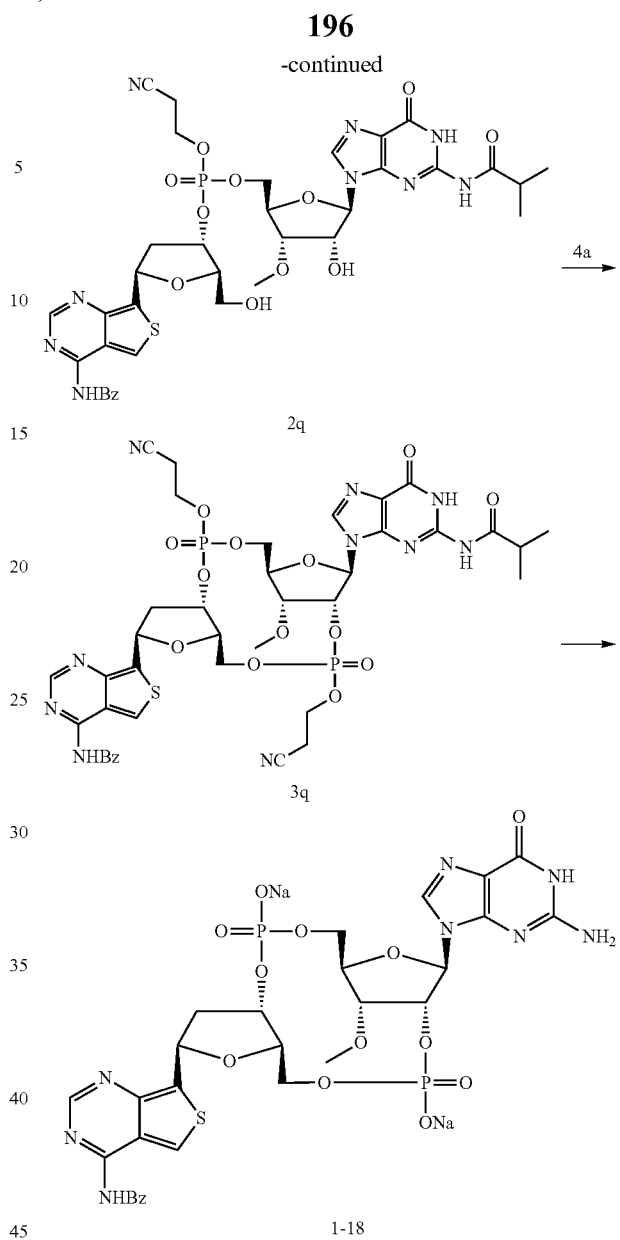

Monomer B (300 mg, 0.45 mmol) and Monomer C (426 mg, 0.49 mmol) was dissolved in anhydrous CH₃CN (15.0 mL), and 4 Å molecular sieves powder (1 gr/100 mL) were added. The mixture was bubbled with Ar gas for 4 min. After stirring at rt for 10 min, 0.45 M tetrazole in CH₃CN (2.7 mmol, 6.0 mL) was added at rt. After stirring for 1 h, the mixture was filtered, and then washed with anhydrous CH₃CN. To this solution was added 5 M t-BuOOH until the reaction was completed. After stirring for 20-30 min at rt, the reaction was quenched with Na₂SO₃ (aq, until discoloration). The mixture was diluted with EtOAc, and the layers were separated. The organic phase was washed with sat. aq. NaHCO₃ (100 mL) and sat. aq. NaCl (100 mL). The combined aqueous phase was back extracted with EtOAc (1×50 mL). The combined organic phases were evaporated to dryness, and the crude material was purified by reverse phase prep-HPLC (Column: C18 spherical 20-35 μm 100A 80 g, mobile phase: 0.05% NH₄HCO₃ in water, m/m)-ACN from 30% to 100%, flow rate: 35 mL/min) to get 1q (600 mg, 0.41 mmol 91.1%) as a white foam. ESI-MS: m/z 1458.5 [M+H]⁺.

Compound 1q (600 mg, 0.41 mmol) was dissolved in DCA in DCM (3%, v/v, 12.2 mL) and triethyl silane (4.8 mL) was added immediately. After stirring for 30 min at rt, the mixture was diluted with EtOAc, and then neutralize with sat. aq. NaHCO$_3$. The layers were separated, and the organic phase was washed with sat. aq. NaCl (1×50 mL). The aqueous phase was combined and back extracted with EtOAc (3×50 mL). The combined organic phases were evaporated to dryness, and the crude residue was purified by silica gel column (acetone in DCM from 0% to 100%) to get 2q (250 mg, 0.29 mmol, 71.5%) as a white foam. ESI-MS: m/z 854.2 [M+H]$^+$.

Compound 2q (250 mg, 0.29 mmol) dissolved in anhydrous CH$_3$CN (20.0 mL), and 0.45 M tetrazole in CH$_3$CN (2.32 mmol, 5.1 mL) and 4 Å molecular sieves powder (300 mg, 1 gr/100 mL) were added. The mixture was bubbled with Ar gas for 4 min. After stirring at rt. for 20 min, 4a (192 mg, 0.58 mmol) in CH$_3$CN (5.0 mL) was added over 30 to 40 min. After stirring for 2 h, the mixture was filtered and then washed with anhydrous CH$_3$CN. To this solution was added 5 M t-BuOOH until the reaction was completed. After stirring for 20-30 min at rt, the reaction was quenched with sat. aq. Na$_2$SO$_3$ (until discoloration). The mixture was diluted with EtOAc, and then layers were separated. The organic phase was washed with sat. aq. NaHCO$_3$ (1×50 mL) and sat. aq. NaCl (1×50 mL). The combined aqueous phase was back extracted with EtOAc (1×100 mL). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 30% to 60%, flow rate: 35 mL/min) to afford 3q (100 mg, 103.3 μmol, 35.5%) as a white foam. ESI-MS: m/z 969.2 [M+H]$^+$.

Compound 3q (100 mg, 103.3 μmol) was treated with a solution of 7M NH$_3$ in MeOH (10 mL, 33%). After stirring for 12 h at rt, the mixture was evaporated to dryness, and the crude material was purified by reverse phase prep-HPLC (Column: C18 spherical 20-35 μm 100A 40 g, mobile phase: 0.05% NH$_4$HCO$_3$ in water, m/m)-ACN from 0% to 30%, flow rate: 25 mL/min) to get the NH$_4$ salt product (24 mg, 34.9 μmol, 33.7%) as a white foam. A volume of Amberlite IR-120 (15 mL, Na form) was added to a column and washed with deionized water (3×15 mL). The NH$_4$ salt product (24 mg) was dissolved in deionized water (24 mg in 8 mL), added to the top of the column and eluted with deionized water. The compound was eluted out in early fractions as detected by TLC (UV). The product was lyophilized to give 1-18 (20 mg, 29.1 μmol, 83.3%) as a white foam. $^1$H NMR (400 MHz, D$_2$O): δ 8.18 (s, 1H), 7.98 (s, 1H), 7.92 (s, 1H), 5.88-5.85 (t, J=8.4 Hz, 2H), 5.43-5.37 (m, 1H), 5.01-4.98 (t, J=5.6 Hz, 1H), 4.50 (s, 1H), 4.31 (m, 1H), 4.20-4.16 (m, 4H), 4.04 (s, 2H), 3.52 (s, 3H), 2.74-2.67 (m, 1H), 2.58-2.52 (m, 1H). $^{31}$P-NMR (162 MHz, D$_2$O): −0.88, −1.52. ESI-MS: m/z 689.1 [M+H]$^+$.

Example 20

Compounds 1-19a and 1-19b

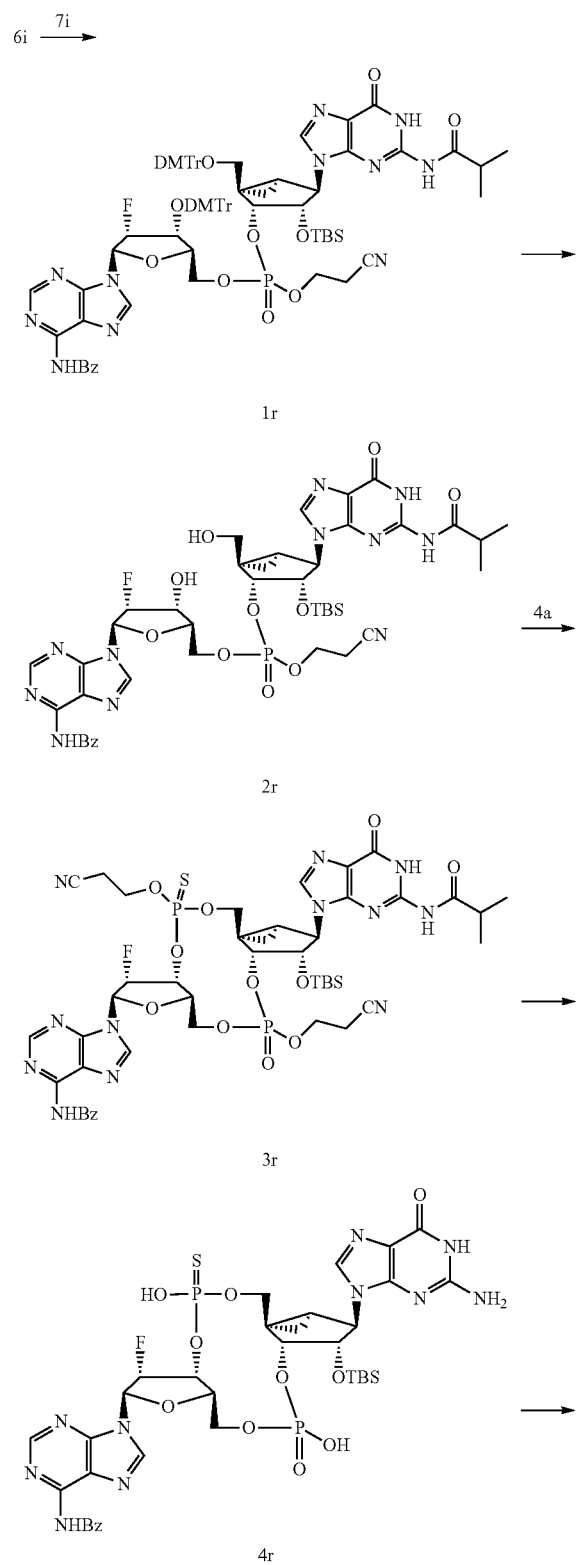

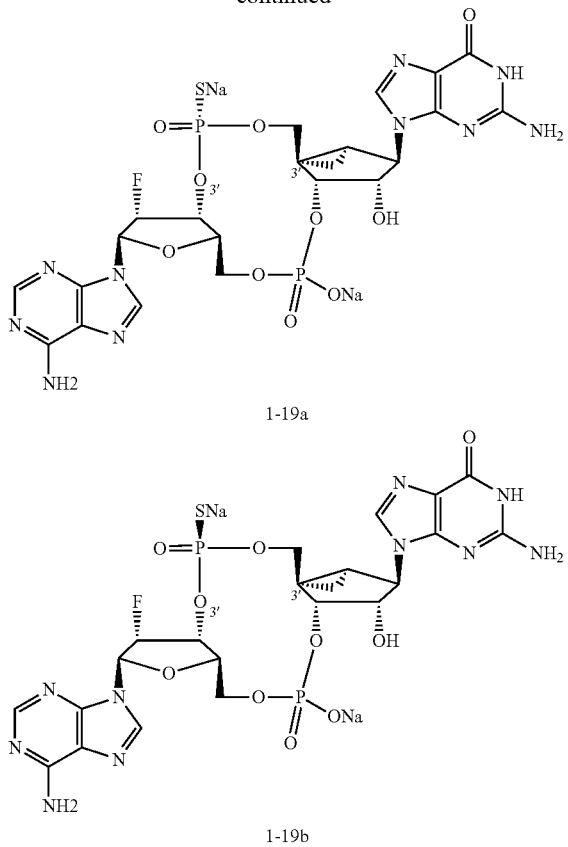

1-19a 1-19b

Compound 7i (1.35 g, 1.54 mmol) and 6i (1.0 g, 1.28 mmol) was dissolved in anhydrous CH$_3$CN (30.0 mL), and 4 Å molecular sieves powder (1 gr/100 mL) were added. The mixture was bubbled with Ar gas for 4 min. After stirring at rt for 10 min, 0.45 M tetrazole in CH$_3$CN (13.5 mmol, 30.0 mL) was added at rt. After stirring for 1 h, the mixture was filtered, and then washed with anhydrous CH$_3$CN. To this solution was added 5 M t-BuOOH until the reaction was completed. After stirring for 20-30 min at rt, the reaction was quenched with Na$_2$SO$_3$ (aq, until discoloration). The mixture was diluted with EtOAc, and the layers were separated. The organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 30% to 100%, flow rate: 35 mL/min) to get 1r (1.8 g, 88.1%) as a white foam. ESI-MS: m/z 1570.3 [M+H]$^+$.

Compound 1r (1.8 g, 1.14 mmol) was dissolved in DCA in DCM (3%, v/v, 30.0 mL) and triethylsilane (5.0 mL) was added immediately. After stirring for 30 min at rt, the mixture was diluted with EtOAc, and then neutralize with sat. aq. NaHCO$_3$. The layers were separated, and then organic phase was washed with sat. aq. NaCl (1×). The aqueous phase was combined and back extracted with EtOAc (3×). The combined organic phases were evaporated to dryness, and the crude residue was purified by reverse phase prep-HPLC (Column: C18 spherical 20-35 μm 100A 80 g, mobile phase: 0.05% NH$_4$HCO$_3$ in water, m/m)-ACN from 30% to 80%, flow rate: 35 mL/min) to get 2r (600 mg, 0.62 mmol, 55.8%) as a white foam. ESI-MS: m/z 966.0 [M+H]$^+$.

Compound 2r (600 mg, 0.62 mmol) dissolved in anhydrous CH$_3$CN (44.0 mL), 0.45 M tetrazole in ace CH$_3$CN (9.0 mmol, 20 mL) and 4 Å molecular sieves powder (1 gr/100 mL) were added. The mixture was bubbled with Ar gas for 4 min. After stirring at rt for 20 min, 4a (450 mg, 1.49 mmol) in CH$_3$CN (10.0 mL) was added over 30 to 40 min. After stirring for 2 h, the mixture was filtered and then washed with anhydrous CH$_3$CN. To this was added 0.1 M DDTT (solvent: py) until the reaction was completed. After stirring for 20-30 min at rt, the reaction was quenched with sat. aq. Na$_2$SO$_3$. The mixture was diluted with EtOAc, and the layers were separated. The organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 30% to 60%, flow rate: 35 mL/min) to get 3r (400 mg, 364.1 μmol, 58.5%) as a white foam. ESI-MS: m/z 1097.0 [M+H]$^+$.

Compound 3r (400 mg, 364.1 μmol) was treated with a solution of 33% MeNH$_2$ in EtOH (10 mL). After stirring for 3 h at 40° C., the mixture was evaporated to dryness, and the crude material was purified by reverse phase prep-HPLC (Column: C18 spherical 20-35 μm 100A 40 g, mobile phase: 0.05% NH$_4$HCO$_3$ in water, m/m)-ACN from 0% to 30%, flow rate: 25 mL/min) to afford 4r (260 mg, 319.0 umol, 22.1%) as a white foam. ESI-LMS: m/z 817.2 [M+H]$^+$.

A solution of 4r (260 mg, 319.39 μmol) and 3 HF·TEA (2.0 mL) in DMSO (2.0 mL) was stirred at 40° C. for 48 h. The mixture was cooled to rt, and then TEA (2.0 mL) and isopropoxytrimethylsilane (16.0 mL) were added. The mixture was stirred at rt for 1 h and then evaporated to dryness. The residue was purified by reverse phase prep-HPLC (Column: XBridge 30×100 mm, mobile phase: 0.05% NH$_4$HCO$_3$ in water-ACN from 0% to 10%, flow rate: 20 mL/min) to get the ammonia salt product 6s-P1 (25.0 mg, 35.61 mol, 11.5%), and 6s-P2 (80 mg, 126.45 mol, 35.6%) as a white foam. A volume of Amberlite IR-120 (15 mL, Na form) was added to a column and washed with deionized water (3×15 mL). Each ammonia salt product was dissolved in deionized water (15 mL), added to the top of the column and eluted with deionized water. Each compound was eluted out in early fractions as detected by TLC (UV). The product was lyophilized to afford 1-19a (7.0 mg, 10.70 umol, 28.1%) and 1-19b (61.2 mg, 87.01 umol, 76.2%) as white foams.

1-19a: $^1$H NMR (400 MHz, D$_2$O): δ 8.23 (s, 1H), 8.08 (s, 1H), 8.07 (s, 1H), 5.80 (d, J=16.86 Hz, 1H), 5.86 (dd, J=3.48 Hz, 3.48 Hz, 1H), 5.05 (m, 1H), 4.75 (m, 2H), 4.56 (s, 2H), 4.51 (d, J=8.52 Hz, 1H), 4.43-4.34 (m, 2H), 4.19-4.15 (m, 2H), 3.64 (d, J=9.96 Hz, 1H), 1.85-1.82 (m, 1H), 1.57 (t, J=4.8 Hz, 1H). $^{19}$F NMR (162 MHz, D$_2$O): −201.59. $^{31}$P NMR (162 MHz, D$_2$O): 53.97, −1.43. ESI-MS: m/z 703.4 [M+H]$^+$.

1-19b: $^1$H NMR (400 MHz, D$_2$O): δ 8.09 (s, 1H), 7.85 (s, 1H), 7.71 (s, −1H), 6.01 (d, J=11.2 Hz, 1H), 5.72-5.59 (d, J=50.2 Hz, 1H), 5.12 (m, 2H), 4.49-4.35 (m, 4H), 4.10 (d, J=50.8 Hz, 2H), 3.56 (s, 1H), 1.87 (s, 1H), 1.60 (s, 1H), 0.917 (s, 1H). $^{19}$F NMR (162 MHz, D$_2$O): −204.36. $^{31}$P NMR (162 MHz, D$_2$O): 51.21, −3.65. ESI-MS: m/z 703.4 [M+H]$^+$.

Example 21

Compounds 1-20a and 1-20b

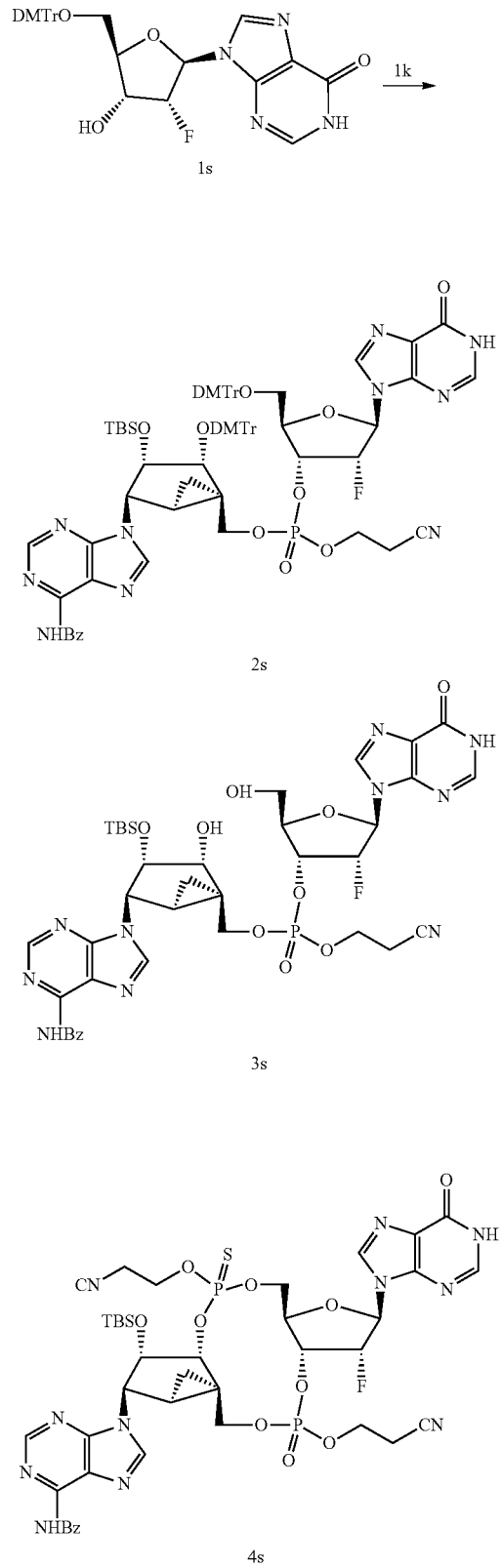

Compound 1s (1.00 g, 1.75 mmol) and 1k (2.09 g, 2.09 mmol) was dissolved in anhydrous $CH_3CN$ (40.0 mL) and 4 Å molecular sieves powder (400 mg, 1 gr/100 mL) were added. The mixture was bubbled with Ar gas for 4 min. After stirring at rt for 20 min, 0.45 M tetrazole in $CH_3CN$ (10.49 mmol, 40.0 mL) was added at rt. After stirring for 1 h, the mixture was filtered and then washed with anhydrous $CH_3CN$. To this solution was added 5 M t-BuOOH until the reaction was completed. After stirring for 20-30 min at rt, the mixture was filtered. The reaction was quenched with $Na_2SO_3$ (aq). The mixture was diluted with EtOAc, and the layers were separated. The organic phase was washed with sat. aq. $NaHCO_3$ (1×50.0 mL) and sat. aq. NaCl (1×50.0 mL). The combined aqueous phase was back extracted with EtOAc (1×50.0 mL). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 60% to 100%, flow rate: 35.0 mL/min) to get 2s (2.20 g, 1.48 mmol, 84.6%) as a white foam. ESI-MS: m/z 1485.6 [M+H]$^+$.

Compound 2s (1.60 g, 1.08 mmol) was dissolved in DCA in DCM (3%, v/v, 30.0 mL) and triethylsilane (10.0 mL) was added immediately. After stirring for 20 min at rt, the reaction was neutralized with ice sat. NaHCO$_3$ (aq.). The mixture was extracted with EtOAc (3×60.0 mL). The organic layers was washed with sat. NaCl aq. (1×150.0 mL), dried over Na$_2$SO$_4$ and concentrated under reduced pressure to give the residue. The crude residue was purified by silica gel column chromatography (DCM/acetone, 0-100% acetone) to afford 3s (812.50 mg, 922.35 mol, 85.4%) as a white solid. ESI-MS: m/z=881.4[M+H]$^+$.

Compound 3s (812.50 mg, 922.35 mol) dissolved in anhydrous CH$_3$CN (100.0 mL), 0.45 M tetrazole in CH$_3$CN (77.39 mmol, 29.55 mL) and 4 Å molecular sieves powder (1.0 g, 1 gr/100 mL) were added. The mixture was bubbled with Ar gas for 4 min. After stirring at rt for 20 min, 4a (485.50 mg, 1.52 mmol) in CH$_3$CN (10.0 mL) was added at rt over 25 to 30 min. After stirring for 2 h, the mixture was filtered and then washed with anhydrous CH$_3$CN. To this solution was added 0.1M DDTT until the reaction was completed. After stirring for 20-30 min at rt, the reaction was quenched with sat. aq. NaS$_2$O$_3$. The mixture was diluted with EtOAc, and the organic layers were separated. The organic phase was washed with sat. NaHCO$_3$ aq. (1×50.0 mL) and sat. NaCl aq. (1×50.0 mL). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 30% to 60%, flow rate: 35 mL/min) to get 4s (400 mg, 395.53 μmol, 42.9%) as a white foam. ESI-MS: m/z 1012.3 [M+H]$^+$.

Compound 4s (400 mg, 395.53 μmol) was treated with a solution of MeNH$_2$ in EtOH (12.0 mL, 33%). After stirring for 2 h at 40° C., the mixture was evaporated to dryness. The crude material was purified by reverse phase prep-HPLC (Column: C18 spherical 20-35 μm 100A 40 g, mobile phase A: 0.05% NH$_4$HCO$_3$ in water, m/m-ACN from 0% to 10%, flow rate: 20 mL/min) to afford 5s (300 mg, 374.39 μmol, 94.7%) as a white foam. ESI-MS: m/z 802.3 [M+H]$^+$.

A solution of 5s (300 mg, 374.39 μmol) and 3 HF·TEA (2.0 mL) in DMSO (2.0 mL) was stirred at 40° C. for 48 h. The mixture was cooled to rt, and then TEA (2.0 mL) and isopropoxytrimethylsilane (16.0 mL) were added. The mixture was stirred at rt for 1 h and then evaporated to dryness. The residue was purified by reverse phase prep-HPLC (Column: XBridge 30×100 mm, mobile phase: 0.05% NH$_4$HCO$_3$ in water, m/m)-ACN from 0% to 12%, flow rate: 15 mL/min) to get the ammonia salt product 7s-P1 (62.5 mg, 90.96 μmol, 24.3%), and 7s-P2 (80 mg, 116.42 mol, 31.1%) as a white foam. A volume of Amberlite IR-120 (15 mL, Na form) was added to a column and washed with deionized water (3×15 mL). The ammonia salt product was dissolved in deionized water (15 mL), added to the top of the column and eluted with deionized water. The compound was eluted out in early fractions as detected by TLC (UV). The product was lyophilized to give 1-20a (52 mg, 73.24 μmol, 80.5%) and 1-20b (74 mg, 104.23 μmol, 89.5%) as a white foam.

1-20a: $^1$H NMR (400 MHz, D$_2$O): δ 8.34 (d, J=5 Hz, 2H), 8.07 (d, J=3.28 Hz, 1H), 7.86 (s, 1H), 6.33 (d, J=16.4 Hz, 1H), 5.57 (d, J=51.92 Hz, 1H), 5.08 (m, 2H), 4.80 (d, J=2.56 Hz, 1H), 4.53 (m, 4H), 4.20 (d, J=11.36 Hz, 1H), 3.56 (d, J=10.84 Hz, 1H), 1.96 (s, 1H), 1.62 (s, 1H), 1.00 (s, 1H). $^{19}$F NMR (376 MHz, D$_2$O): −201.93. $^{31}$P NMR (162 MHz, D$_2$O): 54.26, −1.95. ESI-MS: m/z 688.1 [M+H]$^+$ 1-20b: $^1$H NMR (400 MHz, D$_2$O): δ 8.23 (s, 1H), 8.06 (s, 1H), 7.88 (d, 2H), 6.26 (d, J=16.36 Hz 1H), 5.57 (m, 1H), 5.21 (t, J=7.28 Hz, 1H), 5.08 (m, 1H), 4.47 (m, 4H), 4.14 (m, 2H), 3.55 (s, 1H), 1.96 (d, J=4.92 Hz, 1H), 1.64 (s, 1H), 0.99 (t, J=7.24 Hz, 1H). $^{19}$F NMR (376 MHz, D$_2$O): −202.14. $^{31}$P NMR (162 MHz, D$_2$O): 54.10, −2.03. ESI-MS: m/z 688.1 [M+H]$^+$

Example 22

Compounds 1-21a and 1-21b

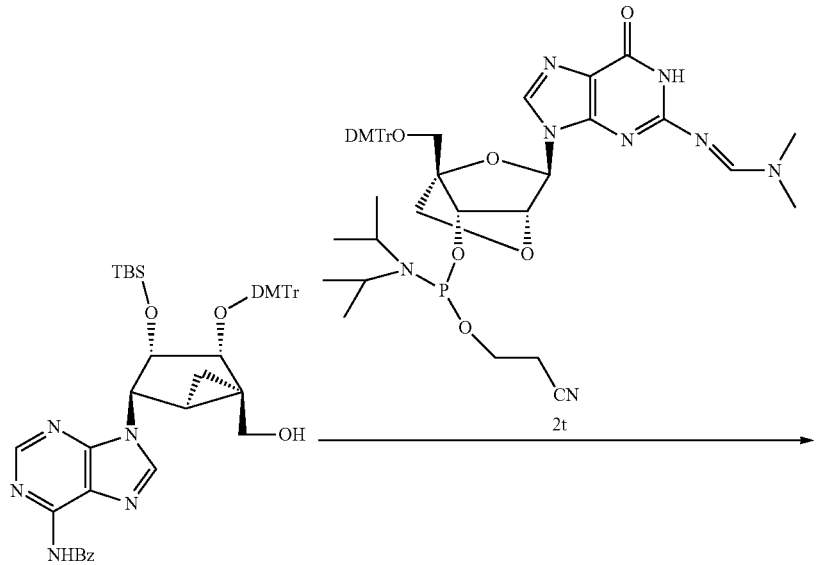

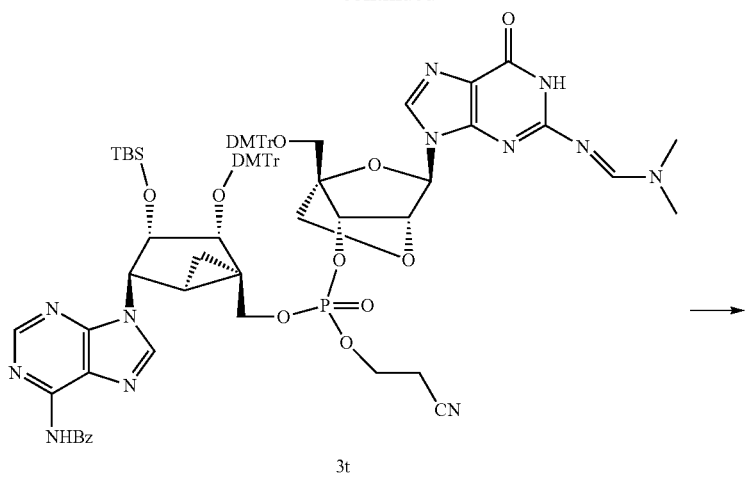
3t
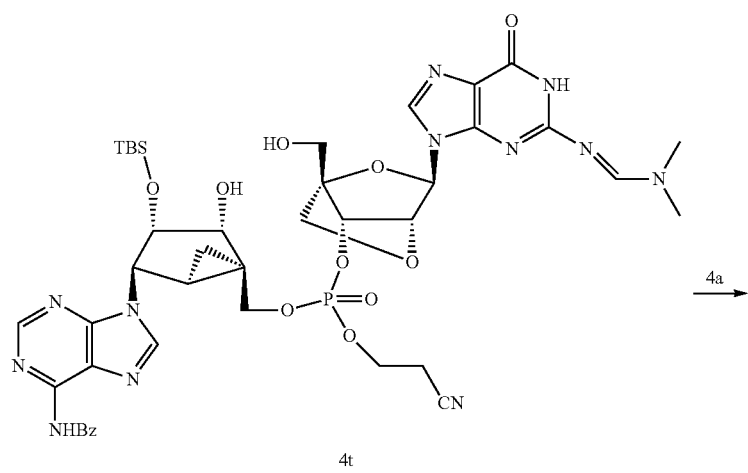
4t
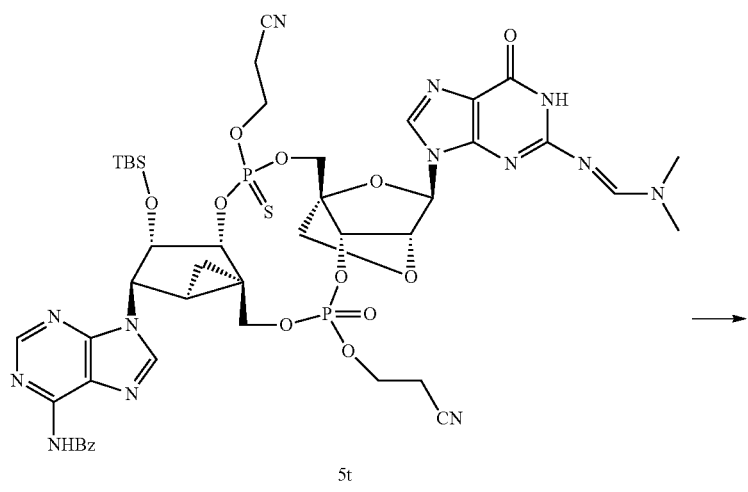
5t

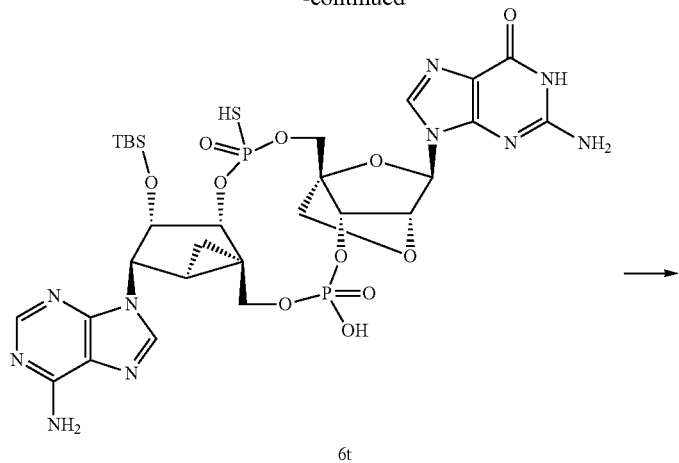

6t

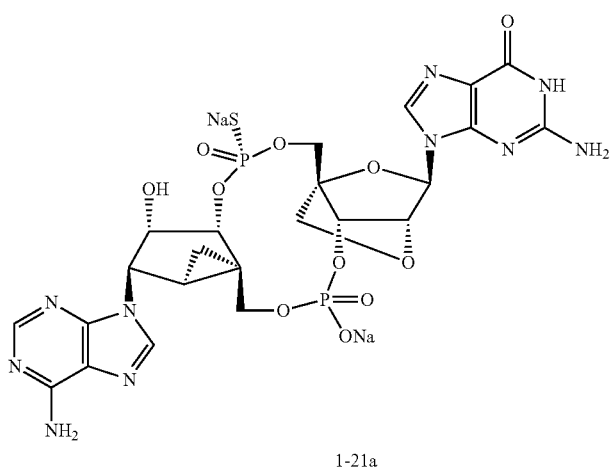

1-21a

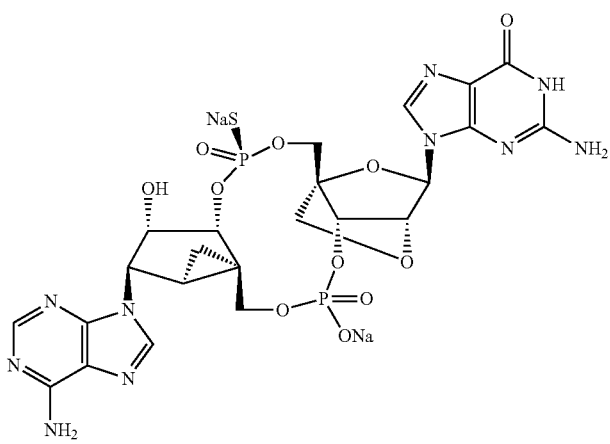

1-21b

Compound 1t (1.00 g, 1.38 mmol) and 2t (1.28 g, 1.50 mmol) was dissolved in anhydrous CH$_3$CN (30.0 mL) and 4 Å molecular sieves powder (300 mg, 1 gr/100 mL) were added. The mixture was bubbled with Ar gas for 4 min. After stirring at rt for 20 min, 0.45 M tetrazole in CH$_3$CN (10.03 mmol, 40.0 mL) was added at rt. After stirring for 1 h, the mixture was filtered and then washed with anhydrous CH$_3$CN. To this solution was added 5 M t-BuOOH until the reaction was completed. After stirring for 20-30 min at rt, the mixture was filtered, and then the reaction was quenched with Na$_2$SO$_3$ (aq). The mixture was diluted with EtOAc, and the layers were separated. The organic phase was washed with sat. aq. NaHCO$_3$ (1×50.0 mL) and sat. aq. NaCl (1×50.0 mL). The combined aqueous phase was back extracted with EtOAc (1×50.0 mL). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 60% to 100%, flow rate: 35.0 mL/min) to get 3t (1.80 g, 1.15 mmol, 83.3%) as a white foam. ESI-MS: m/z 1566.5 [M+H]$^+$.

Compound 3t (1.60 g, 1.15 mmol) was dissolved in DCA in DCM (3%, v/v, 50.0 mL) and triethylsilane (30.0 mL) was added immediately. After stirring for 20 min at rt, the mixture was neutralized with ice sat. NaHCO$_3$ (aq.) and then extracted with EtOAc (3×60.0 mL). The organic layers was washed with sat. NaCl aq (1×150.0 mL), dried over Na$_2$SO$_4$ and concentrated under reduced pressure to give a residue. The crude residue was purified by silica gel column chromatography (DCM/acetone, 0-100% acetone) to afford 4t (800.00 mg, 832.45 mol, 72.4%) as a white solid. ESI-MS: m/z=961.4 [M+H]$^+$.

Compound 4t (700.00 mg, 728.39 μmol) dissolved in anhydrous CH$_3$CN (100.0 mL), 0.45 M tetrazole in CH$_3$CN (5.83 mmol, 23.31 mL) and 4 Å molecular sieves powder (10.0 g, 1 gr/100 mL) were added. The mixture was bubbled with Ar gas for 4 min. After stirring at rt for 20 min, 4a (435.80 mg, 1.45 mmol) in CH$_3$CN (10.0 mL) was added at rt over 25 to 30 min. After stirring for 2 h, the mixture was filtered and then washed with anhydrous CH$_3$CN. To this solution was added 0.1M DDTT until the reaction was completed. After stirring for 20-30 min at rt, the reaction was quenched with sat. aq. NaS$_2$O$_3$. The mixture was diluted with EtOAc, and the organic layers were separated. The organic phase was washed with sat.NaHCO$_3$ aq. (1×50.0 mL) and sat. NaCl aq. (1×50.0 mL). The combined aqueous phase was back extracted with EtOAc (1×100 mL). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 30% to 60%, flow rate: 35 mL/min) to get 5t (400 mg, 366.26 μmol, 50.28%) as a white foam. ESI-MS: m/z 1092.3 [M+H]$^+$.

Compound 5t (400 mg, 366.26 μmol) was treated with a solution of MeNH$_2$ in EtOH (12.0 mL, 33%). After stirring for 2 h at 40° C., the mixture was evaporated to dryness, and the crude material was purified by reverse phase prep-HPLC (Column: C18 spherical 20-35 μm 100A 40 g, mobile phase A: 0.05% NH$_4$HCO$_3$ in water, m/m-ACN from 0% to 10%, flow rate: 20 mL/min) to afford 6t (300 mg, 362.85 μmol, 99.07%) as a white foam. ESI-MS: m/z 827.3 [M+H]$^+$.

A solution of 6t (300 mg, 362.85 μmol) and 3 HF·TEA (2.0 mL) in DMSO (2.0 mL) was stirred at 40° C. for 48 h. The mixture was cooled to rt, and then TEA (2.0 mL) and isopropoxytrimethylsilane (16.0 mL) were added. The mixture was stirred at rt for 1 h and then evaporated to dryness. The residue was purified by reverse phase prep-HPLC (Column: XBridge 30×100 mm, mobile phase: 0.05% NH$_4$HCO$_3$ in water-ACN from 0% to 15%, flow rate: 20 mL/min) to get the ammonia salt product 7t-P1 (70.00 mg, 98.31 mol, 27.0%), and 7t-P2 (20 mg, 28.09 mol, 7.7%) as a white foam. A volume of Amberlite IR-120 (15 mL, Na form) was added to a column and washed with deionized water (3×15 mL). The ammonia salt product was dissolved in deionized water (15 mL), added to the top of the column and eluted with deionized water. The compound was eluted out in early fractions as detected by TLC (UV). The product was lyophilized to give 1-21a (50.00 mg, 66.14 μmol, 67.3%) and 1-21b (19.00 mg, 25.13 μmol, 89.5%) as a white foam.

1-21a: $^1$H NMR (400 MHz, D$_2$O): δ 8.31 (s, 1H), 8.10 (s, 1H), 7.9 (s, 1H), 5.8 (s, 1H), 5.09 (m, 1H), 4.85 (s, 1H), 4.83 (d, J=5.8 Hz, 2H), 4.77 (s, 1H), 4.48 (d, J=10.2 Hz, 1H), 4.36 (m, J=6.16 Hz, 2H), 4.24 (d, J=11.32 Hz, 1H), 4.09 (d, J=8.12 Hz, 1H), 3.99 (d, J=8.16 Hz, 1H). $^{31}$P NMR (162 MHz, D$_2$O): δ4.30, −1.91. ESI-MS: m/z 713.2 [M+H]$^+$.

1-21b: $^1$H NMR (400 MHz, D$_2$O): δ 8.32 (s, 1H), 8.00 (d, J=16.8 Hz, 1H), 7.65 (d, J=14.52 Hz, 1H) 5.86 (d, J=6.36 Hz, 1H) 5.17 (t, J=7.36 Hz, 1H), 4.94 (d, J=6.9 2 Hz, 1H), 4.86 (s, 1H), 4.79 (s, 1H), 4.51 (d, J=10.2 Hz, 1H), 4.41 (d, J=11.64 Hz, 1H), 4.16 (m, 2H), 4.10 (d, J=8.2 Hz, 1H), 3.98 (d, J=8.12 Hz, 1H) 3.53 (d, J=10.96 Hz, 1H). $^{31}$P NMR (162 MHz, D$_2$O): 54.10, −2.06. ESI-MS: m/z 713.2 [M+H]$^+$.

Example 23

Compounds 1-22a and 1-22b

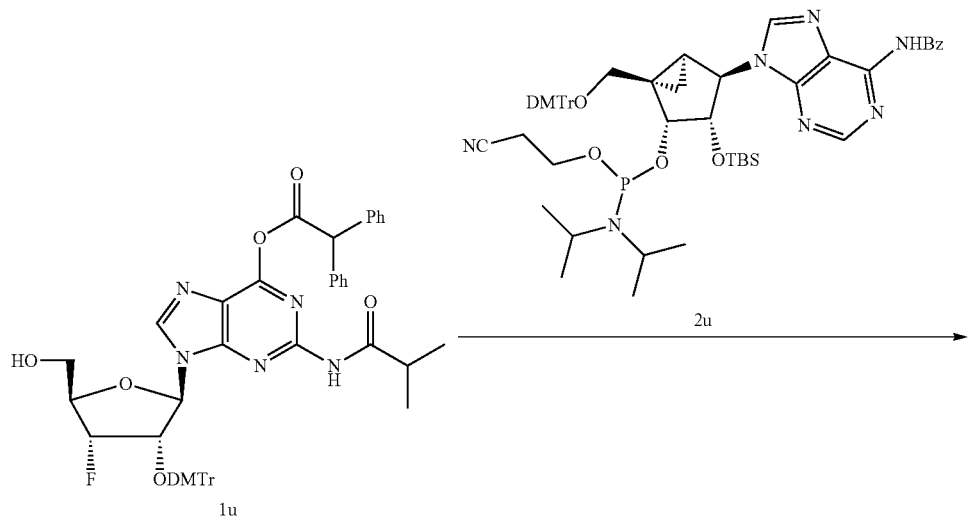

-continued
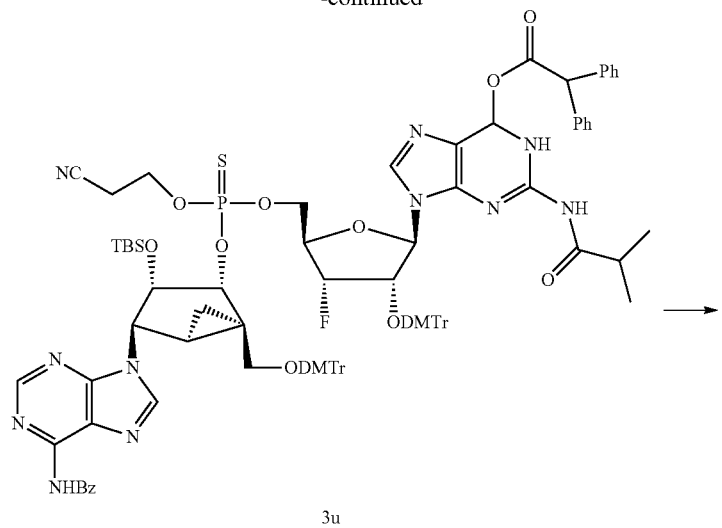
3u
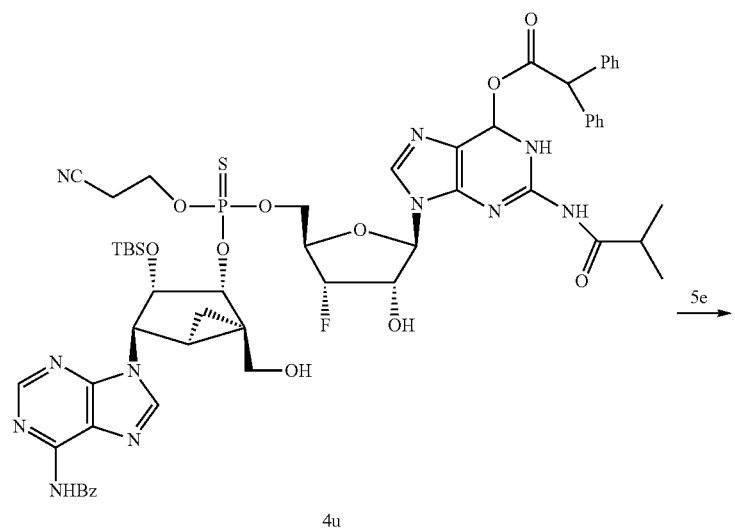
4u
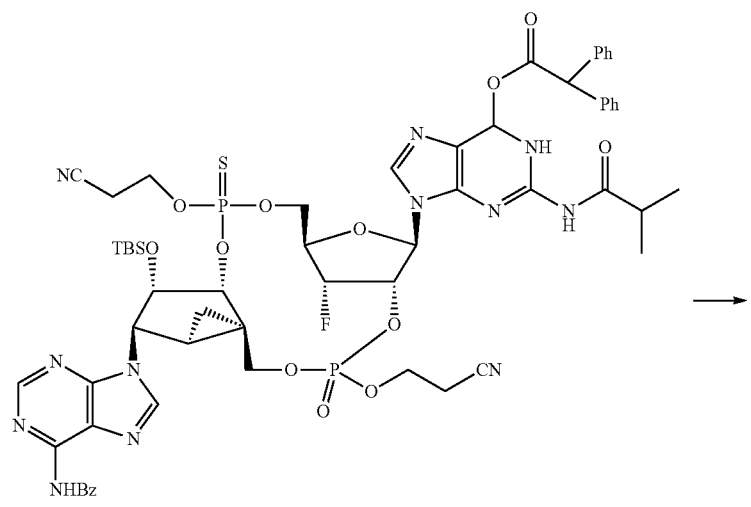
5u

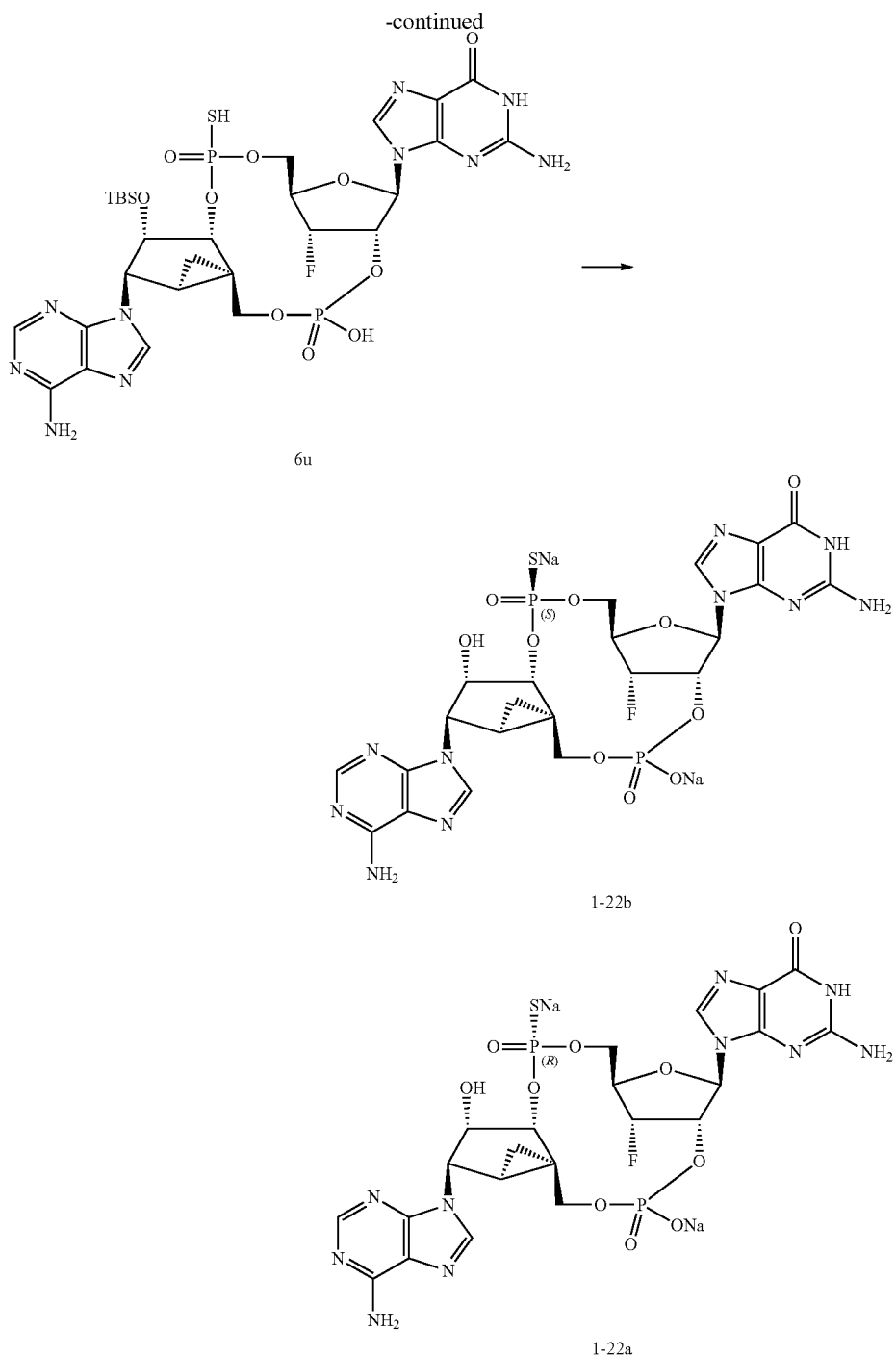

Compound 2u (1.0 g, 1.54 mmol) and 1u (1.3 g, 1.85 mmol) was dissolved in anhydrous CH₃CN (30.0 mL), and 4 Å molecular sieves powder (1 gr/100 mL) were added. The mixture was bubbled with Ar gas for 4 min. After stirring at rt for 10 min, 0.45 M tetrazole in CH₃CN (13.5 mmol, 30.0 mL) was added at rt. After stirring form 1 h, the mixture was filtered, and then washed with anhydrous CH₃CN. To this solution was added 0.1 M DDTT (solvent: py) until the reaction was completed. After stirring for 20-30 min at rt, the reaction was quenched with Na₂SO₃ (aq, until discoloration). The mixture was diluted with EtOAc, and the layers were separated. The organic phase was washed with sat. aq. NaHCO₃ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 µm 100A 80 g, mobile phase: 0.05% NH₄HCO₃ in water, m/m)-ACN from 30% to 100%, flow rate: 35 mL/min) to get 3u (1.9 g, 85.0%) as a white foam. ESI-MS: m/z 1768.3 [M+H]⁺.

Compound 3u (1.9 g, 1.07 mmol) was dissolved in DCA in DCM (3%, v/v, 30.0 mL) and triethylsilane (5.0 mL) was added immediately. After stirring for 30 min at rt, the mixture was diluted with EtOAc, and then neutralize with sat. aq. NaHCO₃. The layers were separated, and the organic phase was washed with sat. aq. NaCl (1×). The aqueous phase was combined and back extracted with EtOAc (3×). The combined organic phases were evaporated to dryness, and the crude residue was purified by reverse phase prep-HPLC (Column: C18 spherical 20-35 μm 100A 80 g, mobile phase: 0.05% NH4HCO3 in water, m/m)-ACN from 30% to 80%, flow rate: 35 mL/min) to get 4u (1.0 g, 0.85 mmol, 81.0%) as a white foam. ESI-MS: m/z 966.0 [M+H]⁺.

Compound 4u (1.0 g, 0.85 mmol) dissolved in anhydrous CH₃CN (80.0 mL), 0.45 M tetrazole in CH₃CN (14.0 mmol, 32 mL) and 4 Å molecular sieves powder (1 gr/100 mL) were added. The mixture was bubbled with Ar gas for 4 min. After stirring at rt for 20 min, 5e (600 mg, 1.70 mmol) in CH₃CN (10.0 mL) was added over 30 to 40 min. After stirring for 2 h, the mixture was filtered and then washed with anhydrous CH₃CN. To this solution was added 5 M t-BuOOH until the reaction was completed. After stirring for 20-30 min at rt, the reaction was quenched with sat. aq. Na₂SO₃ (until discoloration). The mixture was diluted with EtOAc, and the layers were separated. The organic phase was washed with sat. aq. NaHCO₃ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% NH₄HCO₃ in water, m/m)-ACN from 30% to 60%, flow rate: 35 mL/min) to get 5u (500 mg, 391.1 μmol, 46.5%) as a white foam. ESI-MS: m/z 1278.0 [M+H]⁺.

Compound 5u (500 mg, 391.1 μmol) was treated with a solution of MeNH₂ in EtOH (10 mL, 33%). After stirring for 3 h at 40° C., the mixture was evaporated to dryness, and the crude material was purified by reverse phase prep-HPLC (Column: C18 spherical 20-35 μm 100A 40 g, mobile phase: 0.05% NH₄HCO₃ in water, m/m)-ACN from 0% to 30%, flow rate: 25 ml/min) to get 6u (200 mg, 245.00 umol, 63.1%) as a white foam. ESI-LMS: m/z 817.2 [M+H]⁺.

A solution of 6u (200 mg, 245.00 μmol) and 3 HF·TEA (2.0 mL) in DMSO (2.0 mL) was stirred at 40° C. for 48 h. The mixture was cooled rt, and then TEA (2.0 mL) and isopropoxytrimethylsilane (16.0 mL) were added. The mixture was stirred at rt for 1 h and then evaporated to dryness. The residue was purified by reverse phase prep-HPLC (Column: XBridge 30×100 mm, mobile phase: 0.05% NH₄HCO₃ in water-ACN from 0% to 13%, flow rate: 20 mL/min) to get the ammonia salt product 7u-P1 (55.0 mg, 78.34 μmol, 31.84%), and 7u-P2 (31 mg, 44.45 mol, 12.60%) as a white foam. A volume of Amberlite IR-120 (15 mL, Na form) was added to a column and washed with deionized water (3×15 mL). The ammonia salt product was dissolved in deionized water (15 mL), added to the top of the column and eluted with deionized water. The compound was eluted out in early fractions as detected by TLC (UV). The product was lyophilized to afford 1-22a (28.0 mg, 37.83 umol, 50.9%) and 1-22b (16.0 mg, 21.62 umol, 51.6%) as white foams.

1-22a: ¹H NMR (400 MHz, D₂O): δ 8.10 (s, 2H), 7.81 (s, 1H), 5.86 (d, J=8.0 Hz, 1H), 5.45 (t, J=44.4 Hz, 2H), 5.10 (s, 1H), 4.62 (s, 2H), 4.41 (d, J=9.9 Hz, 1H), 4.31 (d, J=4.8 Hz, 1H), 4.20 (s, 1H), 4.09 (d, J=10.8 Hz, 1H), 3.53 (d, J=10.2 Hz, 1H), 1.55 (d, J=18.5 Hz, 2H), 0.96 (s, 1H). ¹⁹F NMR (376 MHz, D₂O): −200.39. ³¹P NMR (162 MHz, D₂O): 52.48, −3.52. ESI-MS: m/z 703.4 [M+H]⁺.

1-22b: ¹H NMR (400 MHz, D₂O): δ 8.20 (s, 1H), 8.10 (s, 1H), 7.79 (s, 1H), 5.94 (d, J=8.5 Hz, 1H), 5.66 (d, J=26.7 Hz, 1H), 5.55-5.21 (m, 2H), 4.77 (s, 2H), 4.45 (dd, J=26.4, 11.2 Hz, 2H), 4.14 (d, J=5.5 Hz, 1H), 4.01 (d, J=11.4 Hz, 1H), 3.58 (d, J=10.9 Hz, 1H), 1.87 (d, J=4.9 Hz, 1H), 1.70 (s, 1H), 0.99 (d, J=6.7 Hz, 1H). ¹⁹F NMR (376 MHz, D₂O): −200.66. ³¹P NMR (162 MHz, D₂O): 54.81, −3.07. ESI-MS: m/z 703.4 [M+H]⁺.

Example 23

Compound 1-23

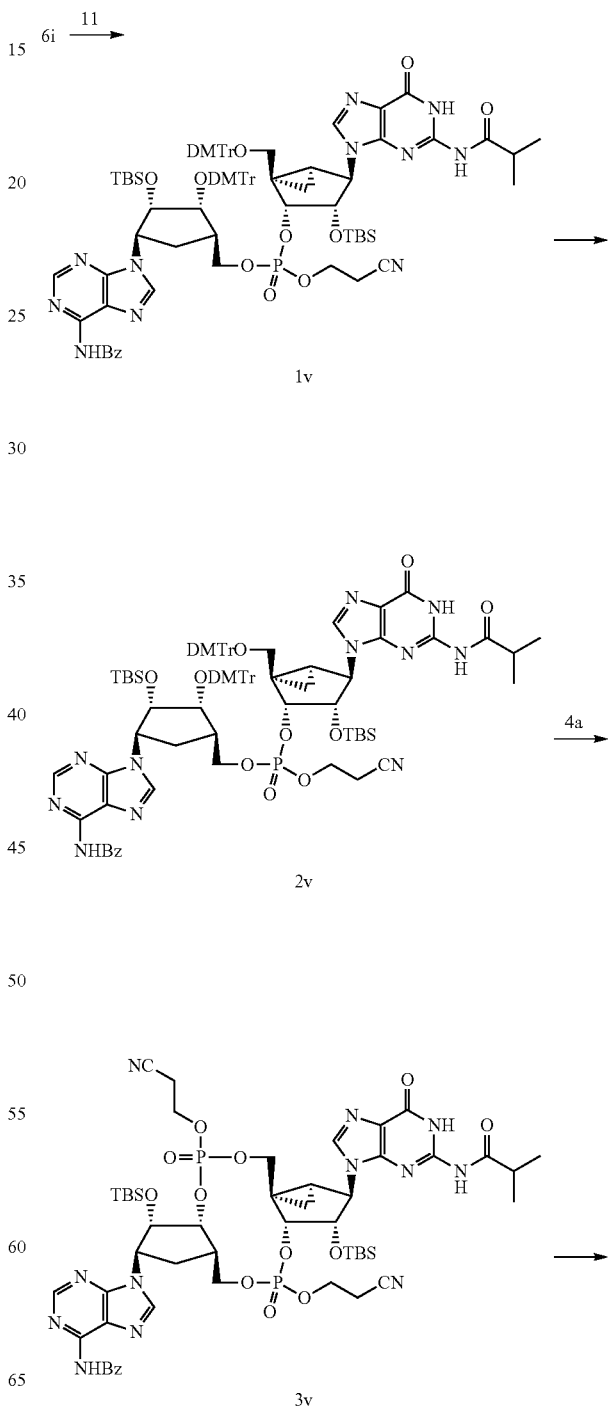

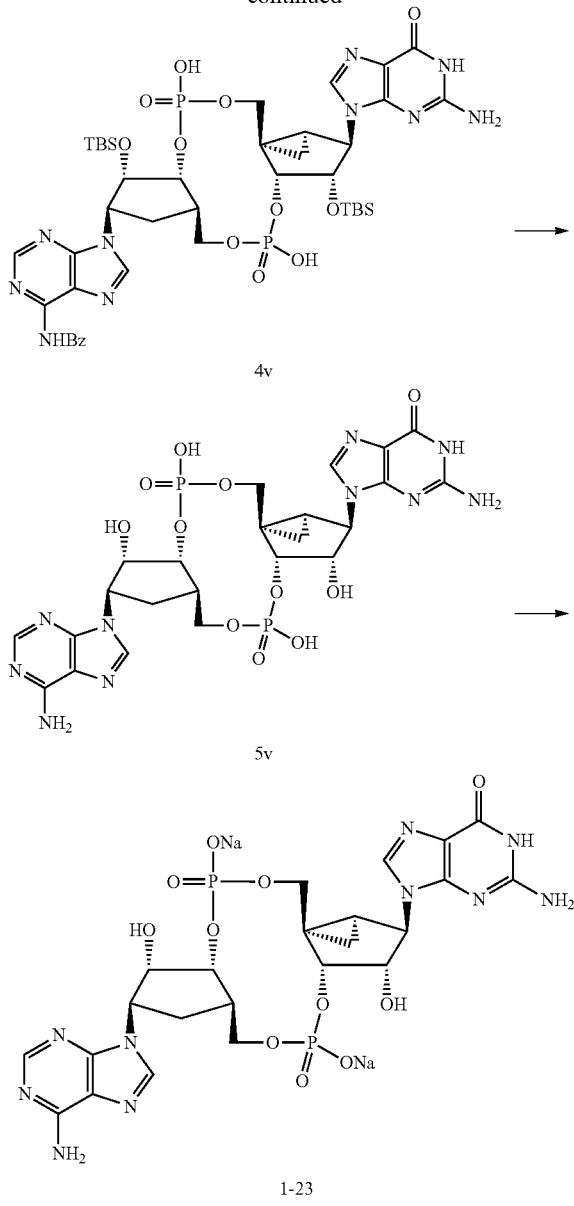

4v

5v 1-23

Compound 6i (500 mg, 0.64 mmol) was dissolved in anhydrous CH$_3$CN (15.0 mL) and 11 (695 mg, 0.70 mmol) and 4 Å molecular sieves powder (150 mg, 1 gr/100 mL) were added. The mixture was bubbled with Ar gas for 4 min. After stirring at rt for 20 min, 0.45 M tetrazole in CH$_3$CN (3.84 mmol, 15 mL) was added at rt. After stirring for 1 h, the mixture was filtered and then washed with anhydrous CH$_3$CN. To this solution was added 5 M t-BuOOH until the reaction was completed. After stirring for 20-30 min at rt, the reaction was quenched with Na$_2$SO$_3$ (aq, until discoloration). The mixture was diluted with EtOAc, and the layers were separated. The organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 60% to 100%, flow rate: 35 mL/min) to get 1v (670 mg, 0.40 mmol, 62.1%) as a white foam. ESI-MS: m/z 1680.7 [M+H]$^+$.

Compound 1v (670 mg, 0.40 mmol) was dissolved in DCA in DCM (3%, v/v, 13 mL) and triethyl silane (5.0 mL) was added immediately. After stirring for 30 min at rt, the mixture was diluted with EtOAc, and then neutralized with sat. NaHCO$_3$. The layers were separated, and the organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by silica gel (DCM:acetone, 0:100) to get 2v (350 mg, 0.32 mmol, 81.8%) as a white foam. ESI-MS: m/z 1076 [M+H]$^+$.

Compound 2v (350 mg, 0.32 mmol) dissolved in anhydrous CH$_3$CN (30.0 mL), 0.45 M tetrazole in CH$_3$CN (2.56 mmol, 10.5 mL) and 4 Å molecular sieves powder (600 mg, 1 gr/100 mL) were added. The mixture was bubbled with Ar gas for 4 min. After stirring at rt for 20 min, 4a (196 mg, 0.64 mmol) in CH$_3$CN (5.0 mL) was added over 25 to 30 min. After stirring for 2 h, the mixture was filtered, and then washed with anhydrous CH$_3$CN. To this solution was added 5 M t-BuOOH until the reaction was completed. After stirring for 20-30 min at rt, the reaction was quenched with sat. aq. Na$_2$SO$_3$ (until discoloration). The mixture was diluted with EtOAc, and the layers were separated. The organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 40 g, mobile phase: 0.05% NH$_4$HCO$_3$ in water, m/m)-ACN from 30% to 80%, flow rate: 20 mL/min) to get 3v (150 mg, 126.05 μmol, 38.7%) as a white foam. ESI-MS: m/z 1191 [M+H]$^+$.

Compound 3v (150 mg, 126.05 μmol) was treated with a solution of 33% MeNH$_2$ in EtOH (10 mL). After stirring for 2 h at 40° C., the mixture was evaporated to dryness, and the crude material was purified by reverse phase prep-HPLC (Column: C18 spherical 20-35 μm 100A 20 g, mobile phase: 0.05% NH$_4$HCO$_3$ in water, m/m)-ACN from 0% to 30%, flow rate: 15 mL/min) to get 4v (71 mg, 104.03 umol, 79.0%) as a white foam. ESI-MS: m/z 994 [M+H]$^+$.

A solution of 4v (71 mg, 104.03 umol) and 3 HF·TEA (0.5 mL) in THF (3.0 mL) was stirred at 40° C. for 48 h. The mixture was cooled to rt, and then TEA (2 mL) and isopropoxytrimethylsilane (16 mL) were added. The mixture was stirred at rt for 1 h and then evaporated to dryness. The residue was purified by reverse phase prep-HPLC (Column: C18 spherical 20-35 μm 100A 12 g, mobile phase: 0.05% NH$_4$HCO$_3$ in water, m/m)-ACN from 0% to 10%, flow rate: 10 mL/min) to get the ammonium salt compound (5v) (28 mg) as a white foam. A volume of Amberlite IR-120 (12 mL, Na form) was added to a column and washed with deionized water (5×15 mL). The ammonium salt product (28 mg) was dissolved in deionized water (88 mg in 10 mL), added to the top of the column and eluted with deionized water. The compound was eluted out in early fractions as detected by TLC (UV). The product was lyophilized to give 1-23 (20 mg, 2.10 μmol, 38.5%) as a white foam. $^1$H NMR (400 MHz, D$_2$O): δ 8.26 (s, 1H), 8.13 (s, 1H), 8.03 (s, 1H), 5.07-5.03 (t, J=12 Hz, 1H), 4.83-4.78 (m, 2H), 4.60-4.55 (m, 1H), 4.48-4.45 (t, J=12 Hz, 2H), 4.12-4.09 (t, 2H), 4.00-3.98 (d, J=8 Hz, 1H), 3.53-3.50 (d, J=8 Hz, 1H), 2.55-2.47 (m, 2H), 2.06-1.98 (m, 1H), 1.81-1.79 (d, J=8 Hz, 1H), 1.52 (s, 1H), 0.95-0.91 (t, J=12 Hz, 1H). $^{31}$P NMR (162 MHz, D$_2$O): −0.58, −0.91. ESI-MS: m/z 727 [M+H]$^+$.

Example 24
Compound 1-27
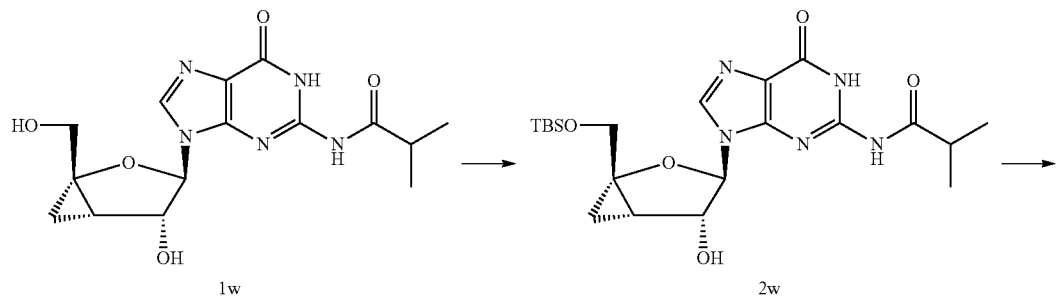
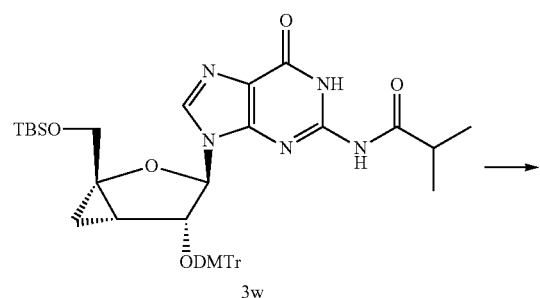
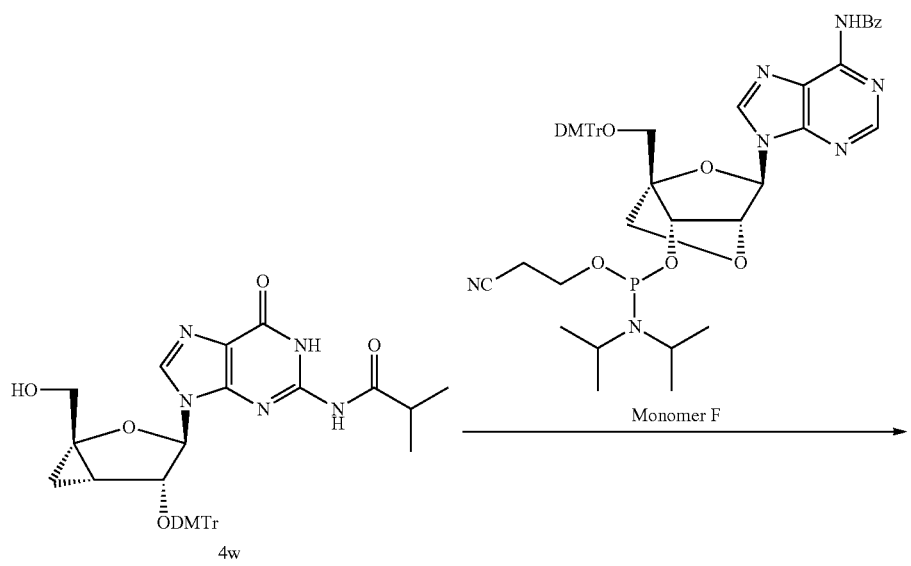

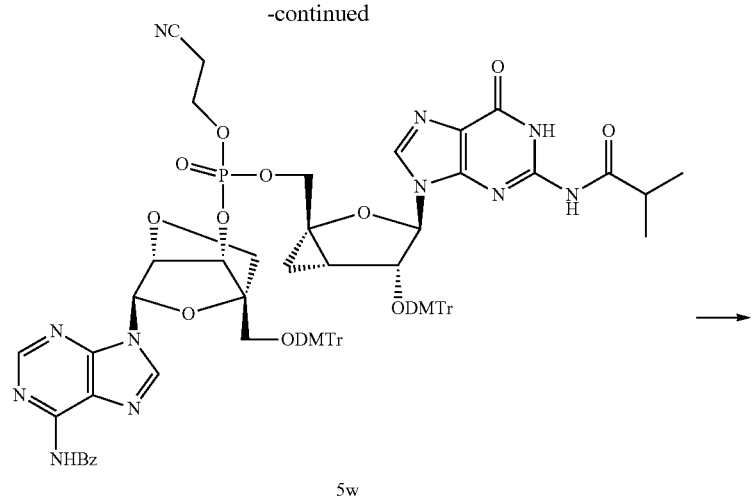
5w
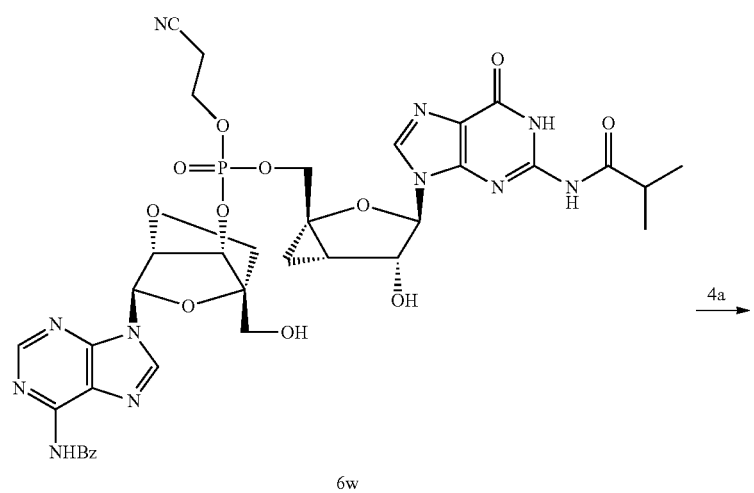
6w
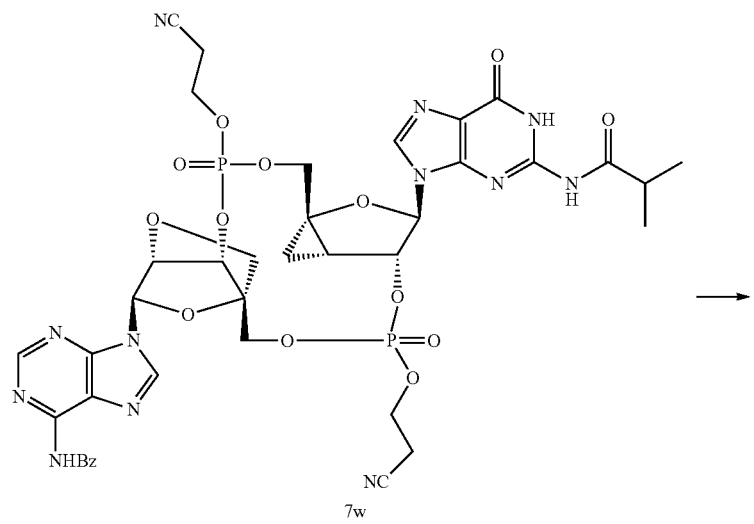
7w

-continued

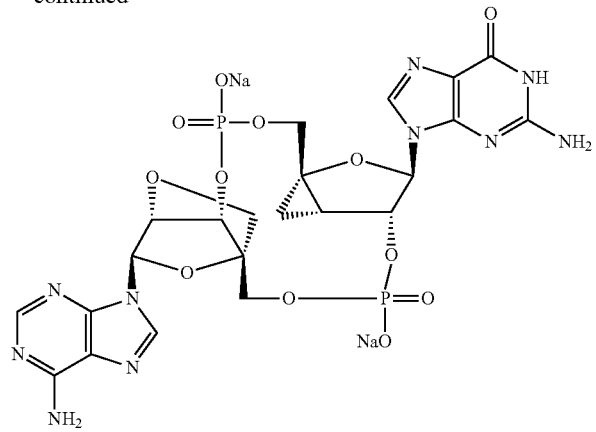

1-27

To a 100 mL round bottomed flask was added 1w (1.50 g, 4.29 mmol), DMF (15 mL) and imidazole (1.75 g, 25.76 mmol). TBSCl (1.42 g, 9.45 mmol) in DMF (5 mL) was then dropwise to the mixture, and the mixture was stirred at rt for 3 h. The mixture was added to aq. NaHCO$_3$ and extracted with EtOAc (5×50 mL). The combined EtOAc layers were washed with brine and concentrated in vacuo to give a crude product, which was purified by reverse phase prep-HPLC (Column: C18 spherical 20-35 μm 100A 40 g, mobile phase: 0.05% NH$_4$HCO$_3$ in water-ACN from 50% to 75%, flow rate: 25 ml/min) to obtained 2w (1.0 g, 2.16 mmol, 50.24%) as a white solid. ESI-MS: m/z 464.2 [M+H]$^+$.

To a 250 mL round bottomed flask was added 2w (1.50 g, 3.24 mmol), DCE (25 mL), 2,6-lutidine (1.39 g, 12.94 mmol) in turn. Silver nitrate (549.62 mg, 3.24 mmol) and 4,4'-dimethoxytrityl chloride (2.74 g, 8.09 mmol) was added, and the mixture was stirred at 40° C. for 2 h. The mixture was added DCM (10 mL) and filtered. The filtrate was concentrated in vacuo to give the crude product, which was purified by silica gel column (EtOAc:PE, 1:1) to obtained 3w (2.38 g, 3.11 mmol, 96.03%) as a white solid. ESI-MS: m/z 766.4 [M+H]$^+$.

Compound 3w (2.38 g, 3.11 mmol) in THF (10 ml) was added to a solution of triethylamine (3.14 g, 31.07 mmol, 4.33 mL) and triethylamine trihydrofluoride (2.00 g, 12.43 mmol) in THF (20 mL) at rt. The mixture was stirred at 40° C. for 16 h. The mixture was added to aq. NaHCO$_3$ and extracted with EtOAc (5×100 mL). The combined EtOAc layer was washed with brine and concentrated in vacuo to give the crude product, which was purified by reverse phase preparative HPLC (Column: C18 spherical 20-35 μm 100A 40 g, mobile phase: 0.05% NH$_4$HCO$_3$ in water-ACN from 30% to 75%, flow rate: 25 ml/min) to obtained 4w (1.6 g, 2.46 mmol, 79.01%) as a white solid. ESI-MS: m/z 652.3 [M+H]$^+$ Compound 4w (600 mg, 920.66 umol) and Monomer F (1.06 g, 1.20 mmol) was dissolved in anhydrous CH$_3$CN (36.0 mL) and 4 Å molecular sieves powder (300 mg, 1 gr/100 mL) were added. The mixture was bubbled with Ar gas for 4 min. After stirring at rt for 20 min, 0.45 M tetrazole in CH$_3$CN (5.52 mmol, 12.3 mL) was added at rt. After stirring for 1 h and filtration, the mixture was washed with anhydrous CH$_3$CN. To this solution was added 5 M t-BuOOH until the reaction completed. After stirring for 20-30 min at rt, the mixture was filtered, and then the reaction was quenched with Na$_2$SO$_3$ (aq). The mixture was diluted with EtOAc, and the layers were separated. The organic phase was washed with sat. aq. NaHCO$_3$ (1×50.0 mL) and sat. aq. NaCl (1×50.0 mL). The combined aqueous phase was back extracted with EtOAc (1×50.0 mL). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 60% to 100%, flow rate: 35.0 mL/min) to get 5w (1.24 g, 853.73 umol, 92.73%) as a white foam. $^{31}$P-NMR (162 MHz, DMSO-d$_6$): −3.15, −3.20. ESI-MS: m/z 1452.6 [M+H]$^+$.

Compound 5w (1.24 g, 853.73 umol) was dissolved in DCA in DCM (3%, v/v, 22.0 mL), and triethylsilane (8.7 mL mL) was added immediately. After stirring for 20 min at rt, the mixture was neutralized with pyridine (22 mL). The mixture was then concentrated in vacuo to get the crude product, which was purified by reverse phase prep-HPLC (Column: C18 spherical 20-35 μm 100A 80 g, mobile phase: 0.05% NH$_4$HCO$_3$ in water, m/m)-ACN from 0% to 60%, flow rate: 35.0 mL/min) to get 6w (580 mg, 684.18 umol, 80.14%) as a white solid. ESI-MS: m/z=961.4 [M+H]$^+$.

Compound 6w (520 mg, 613.41 umol) dissolved in anhydrous CH$_3$CN (78.0 mL), 0.45 M tetrazole in CH$_3$CN (4.91 mmol, 10.90 mL) and 4 Å molecular sieves powder (10.0 g, 1 gr/100 mL) were added. The mixture was bubbled with Ar gas for 4 min. After stirring at rt, 4a (369.77 mg, 1.23 mmol) in CH$_3$CN (10.0 mL) was added at rt over 25 to 30 min. After stirring for 2 h, the mixture was filtered and then washed with anhydrous CH$_3$CN. To this solution was added 5 M t-BuOOH until the reaction completed. After stirring for 20-30 min at rt, the reaction was quenched with sat. aq. NaS$_2$O$_3$. The mixture was diluted with EtOAc, and the organic layers were separated. The organic phase was washed with sat. NaHCO$_3$ aq. (1×50.0 mL) and sat. NaCl aq. (1×50.0 mL). The combined aqueous phase was back extracted with EtOAc (1×100 mL). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 0% to 50%, flow rate: 35 mL/min) to obtain 7w (30 mg, 31.16 umol, 5.08%) as a white foam. ESI-MS: m/z 963.4 [M+H]$^+$.

Compound 7w (33 mg, 34.28 umol) was treated with a solution of MeNH$_2$ in EtOH (16.0 mL, 33%). After stirring for 2 h at 40° C., the mixture was evaporated to dryness, and the crude material was purified by reverse phase prep-HPLC (Column: C18 spherical 20-35 μm 100A 40 g, mobile phase A: 0.05% NH$_4$HCO$_3$ in water, m/m-ACN from 0% to 10%, flow rate: 20 ml/min) to afford the NH$_4$ salt product 8 (20.5 mg, 30.04 umol, 87.64%) as a white foam. A 15.0 mL volume of Amberlite IR-120 (Na form) was added to a column and washed with deionized water (3×15 mL). The NH$_4$ salt product (20.5 mg) was dissolved in deionized water (15 mg in 10 mL) and then added to the top of the column. The column was eluted with deionized water. The compound was eluted out in early fractions as detected by TLC (UV). The product was lyophilized to give compound 1-27 (18 mg, 26.37 umol, 76.95%) as a white foam. $^1$H NMR (400 MHz, D$_2$O) δ: 8.14 (s, 1H), 7.75 (d, J=17.0 Hz, 2H), 6.04 (s, 1H), 5.79-5.72 (m, 1H), 5.56 (d, J=7.2 Hz, 1H), 5.18 (d, J=18.8 Hz, 3H), 4.50-4.36 (m, 3H), 4.13 (d, J=8.2 Hz, 1H), 3.95 (d, J=8.2 Hz, 1H), 3.80 (t, J=12.4 Hz, 1H), 2.06 (q, J=6.8 Hz, 1H), 1.60 (t, J=7.0 Hz, 1H), 1.17 (t, J=8.5 Hz, 1H). $^{31}$P-NMR (162 MHz, DMSO-d$_6$): -1.64, -2.73. ESI-MS: m/z 683.4 [M+H]$^+$.

Example 25

Compound 1-24

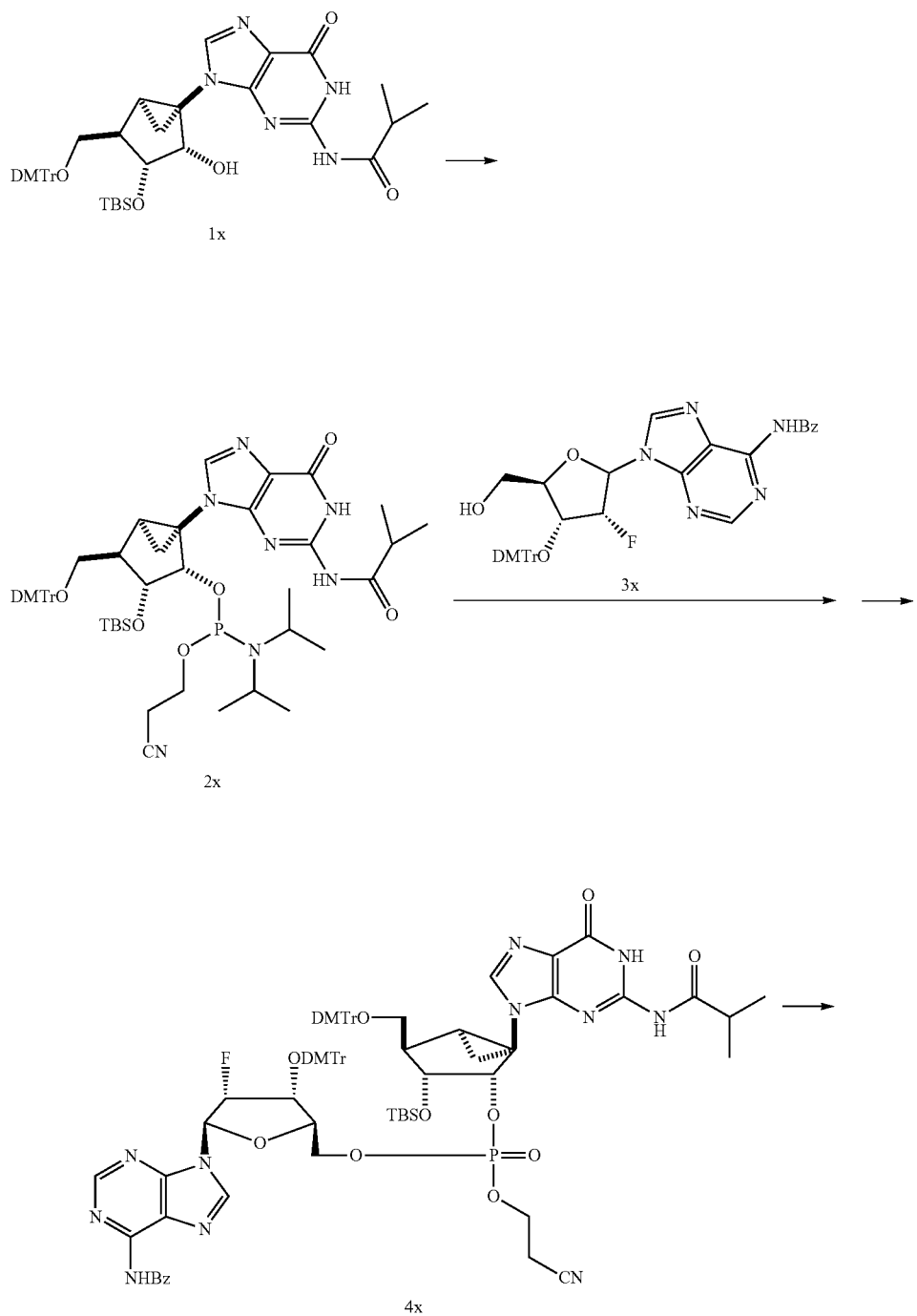

-continued
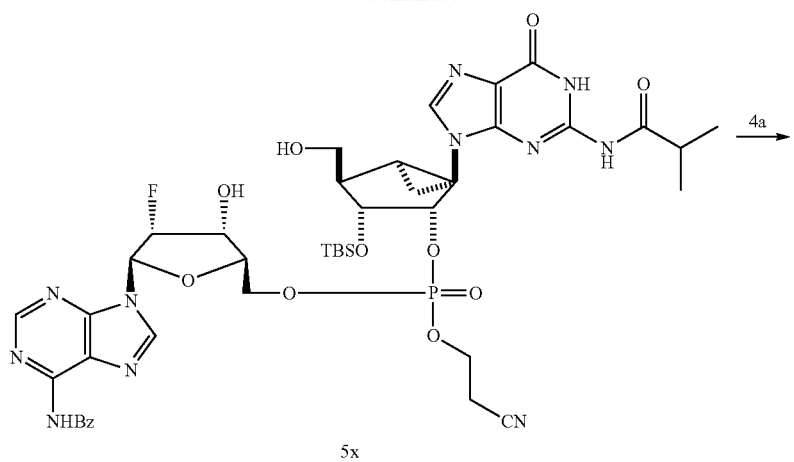
5x
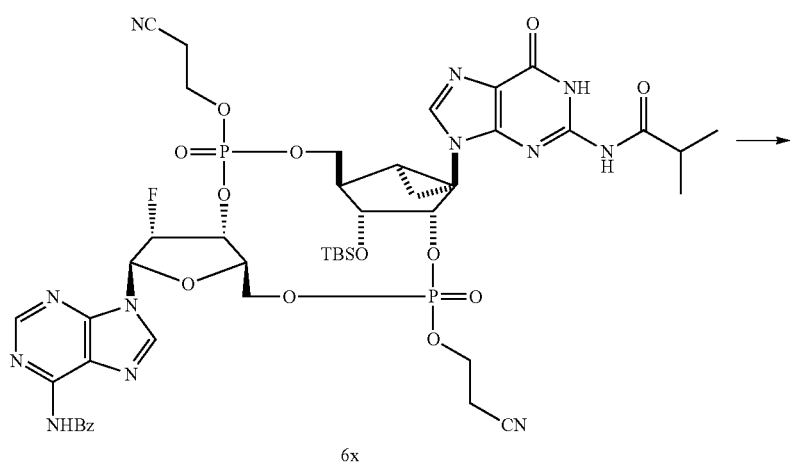
6x
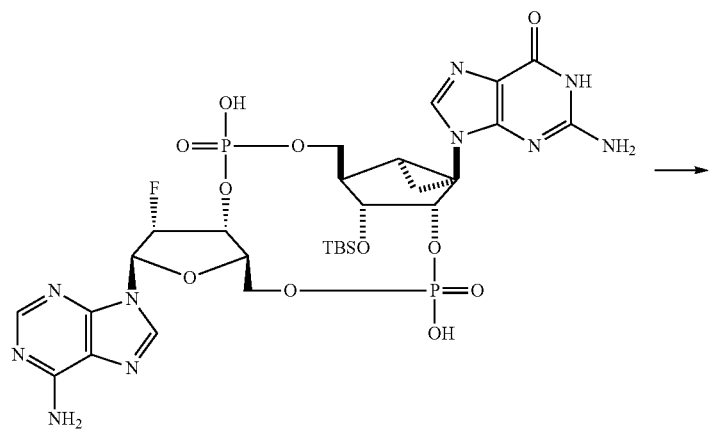
7x

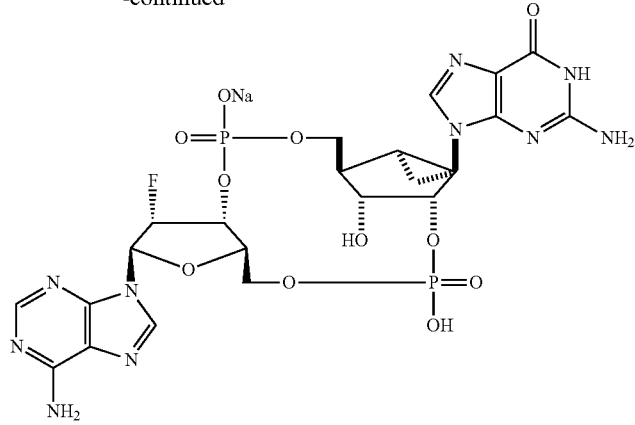

1-24

To a solution of 1x (450 mg, 577.7 umol) in DCM (10 mL) was added DIPEA (224 mg, 1.73 mol) and CepCl (217 mg, 865.5 umol) at 0° C. The mixture was stirred at 35° C. for 4 h under Ar. The reaction was quenched with sat. NaHCO$_3$ aq., and then extracted with EtOAc (4×50 mL). The combined EtOAc layers were washed with brine and concentrated in vacuo to get the crude product. The crude was purified by reverse phase prep-HPLC (Column: C18 spherical 20-35 μm 100A 40 g, mobile phase: 0.05% NH$_4$HCO$_3$ in water, m/m)-ACN from 30% to 100%, flow rate: 20 mL/min) to get 2x (310 mg, 316.6 umol, 54%) as a white solid. ESI-MS: m/z 980.5 [M+H]$^+$.

Compound 2x (310 mg, 316.6 umol) and compound 3x (256 mg, 379.9 umol) was dissolved in anhydrous CH$_3$CN (20.0 mL), and 4 Å molecular sieves powder (1 gr/100 mL) were added. The mixture was bubbled with Ar gas for 4 min. After stirring at rt for 10 min, 0.45 M tetrazole in CH$_3$CN (1.9 mmol, 4.2 mL) was added at rt. After stirring for 1 h, the mixture was filtered and washed with anhydrous CH$_3$CN. t-BuOOH (1 mL) was added until the reaction completed. After stirring for 20-30 min at rt, the reaction was quenched with Na$_2$SO$_3$ (aq, until discoloration). The mixture was diluted with EtOAc, and layers were separated. The organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 40 g, mobile phase: 0.05% NH$_4$HCO$_3$ in water, m/m)-ACN from 30% to 100%, flow rate: 20 mL/min) to get 4x (400 mg, 254.9 umol, 80.6%) as a white foam. $^{31}$P-NMR (162 MHz, DMSO-d$_6$): −2.06, −2.08, −2.29. ESI-MS: m/z 1570.6 [M+H]$^+$.

Compound 4x (400 mg, 254.9 umol) was dissolved in DCA in DCM (3%, v/v, 7.10 mL) and triethyl silane (2.80 mL) was added immediately. After stirring for 30 min at rt, the mixture was diluted with EtOAc, and then neutralize with sat. aq. NaHCO$_3$. The layers were separated, and the organic phase was washed with sat. aq. NaCl (1×). The aqueous phase was combined and then back extracted with EtOAc (3×). The combined organic phases were evaporated to dryness, and the crude residue was purified by reverse phase prep-HPLC (Column: C18 spherical 20-35 μm 100A 40 g, mobile phase: 0.05% NH$_4$HCO$_3$ in water, m/m)-ACN from 30% to 80%, flow rate: 20 mL/min) to get 5x (150 mg, 155.4 umol, 61.2%) as a white foam. ESI-MS: m/z 966.3 [M+H]$^+$.

Compound 5x (150 mg, 155.4 umol) dissolved in anhydrous CH$_3$CN (25.0 mL), 0.45 M tetrazole in CH$_3$CN (1.24 mmol, 2.7 mL) and 4 Å molecular sieves powder (300 mg, 1 gr/100 mL) were added. The mixture was bubbled with Ar gas for 4 min. After stirring at rt for 20 min, 4a (94 mg, 310.8 umol) in CH$_3$CN (10.0 mL) was added over 30 to 40 min. After stirring for 2 h, the mixture was filtered and then washed with anhydrous CH$_3$CN. t-BuOOH (1 mL) was added until the reaction was complete. After stirring for 20-30 min at rt, the reaction was quenched with sat. aq. Na$_2$SO$_3$ (until discoloration). The mixture was diluted with EtOAc, and the layers were separated. The organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 40 g, mobile phase: 0.05% NH$_4$HCO$_3$ in water, m/m)-ACN from 30% to 60%, flow rate: 20 mL/min) to get 6x (60 mg, 55.6 umol, 35.8%) as a white foam. ESI-MS: m/z 1081.3 [M+H]$^+$.

Compound 6x (60 mg, 55.6 umol) was treated with a solution of MeNH$_2$ in EtOH (4 mL, 33%). After stirring for 3 h at 40° C., the mixture was evaporated to dryness, and the crude material was purified by reverse phase prep-HPLC (Column: C18 spherical 20-35 μm 100A 40 g, mobile phase: 0.05% NH$_4$HCO$_3$ in water, m/m)-ACN from 0% to 30%, flow rate: 20 ml/min) to get 7x (30 mg, 37.5 umol, 67.4%) as a white foam. ESI-LMS: m/z 801.2 [M+H]$^+$.

Compound 7x (30 mg, 37.5 umol) in 3 HF·TEA (1.0 mL) and DMSO (2 mL) was stirred at 40° C. for 32 h. The mixture was cooled to rt, and then TEA (2 mL) and iso-propoxytrimethylsilane (8 mL) were added. The mixture was stirred at rt for 1 h and then evaporated to dryness. The residue was purified by reverse phase prep-HPLC (Column: C18 spherical 20-35 μm 100A 40 g, mobile phase: 0.05% NH$_4$HCO$_3$ in water-ACN from 0% to 10%, flow rate: 20 ml/min-ACN from 0% to 10%, flow rate: 20 ml/min) to get the NH$_4$ salt (18 mg, 26.2 μmol, 69.9%) as a white foam. A 15.0 mL volume of Amberlite IR-120 (Na form) was added to a column, and then washed with deionized water (3×15 mL). The NH$_4$ salt (18 mg) was dissolved in deionized water (15 mg in 10 mL) and then added to the top of the column. The column was eluted with deionized water. The compound was eluted out in early fractions as detected by TLC (UV). The product was lyophilized to give 1-24 (14 mg, 20.4 umol, 77.8%) as a white foam. $^1$H NMR (400 MHz, D$_2$O) δ: 8.36 (s, 0.5H), 8.30 (s, 0.5H), 8.17 (s, 0.5H), 8.15 (s, 0.5H), 7.67 (d, J=4.2 Hz, 1H), 6.36 (t, J=15.7 Hz, 1H), 5.61-5.35 (m, 1H), 5.08-4.82 (m, 2.5H), 4.58-4.53 (m, 0.5H), 4.46-4.28 (m, 2.5H), 4.18-4.08 (m, 2.5H), 2.50-2.46 (m, 0.5H), 2.22 (s, 0.5H), 1.90-1.87 (m, 0.5H), 1.72-1.64 (m, 1.3H), 1.40-1.32 (m, 1.2H). $^{31}$P NMR (162 MHz, D$_2$O): 0.43, −1.18, −1.88. ESI-MS: m/z 687.1 [M+H]$^+$.

Example 26
Compound 1-29
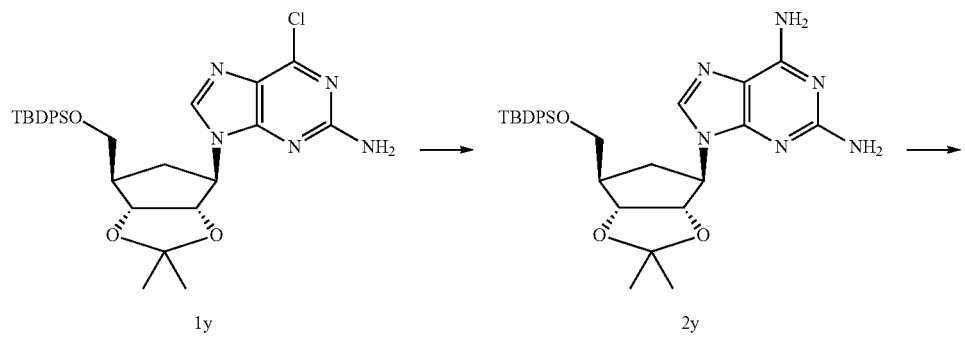
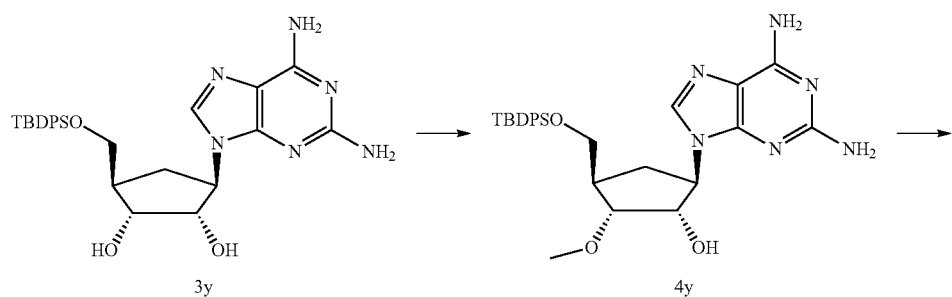
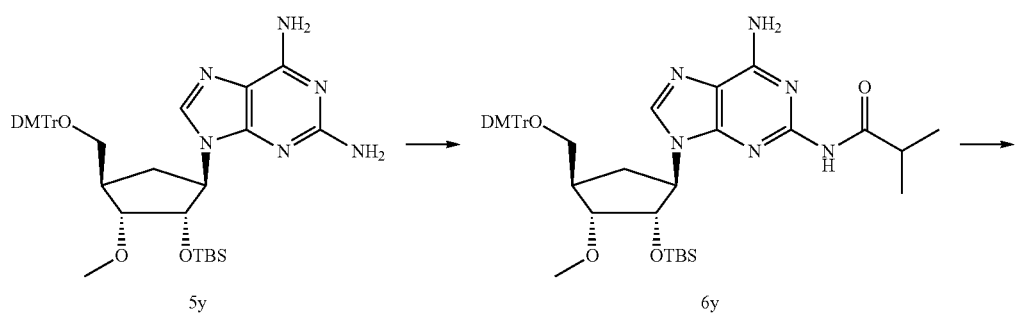
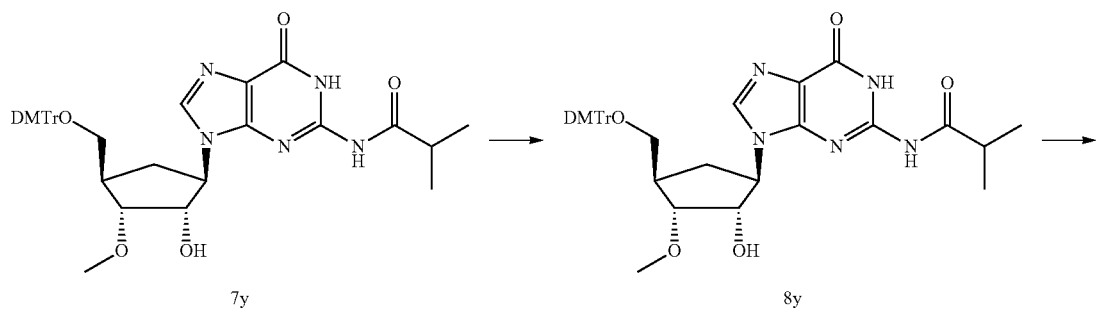

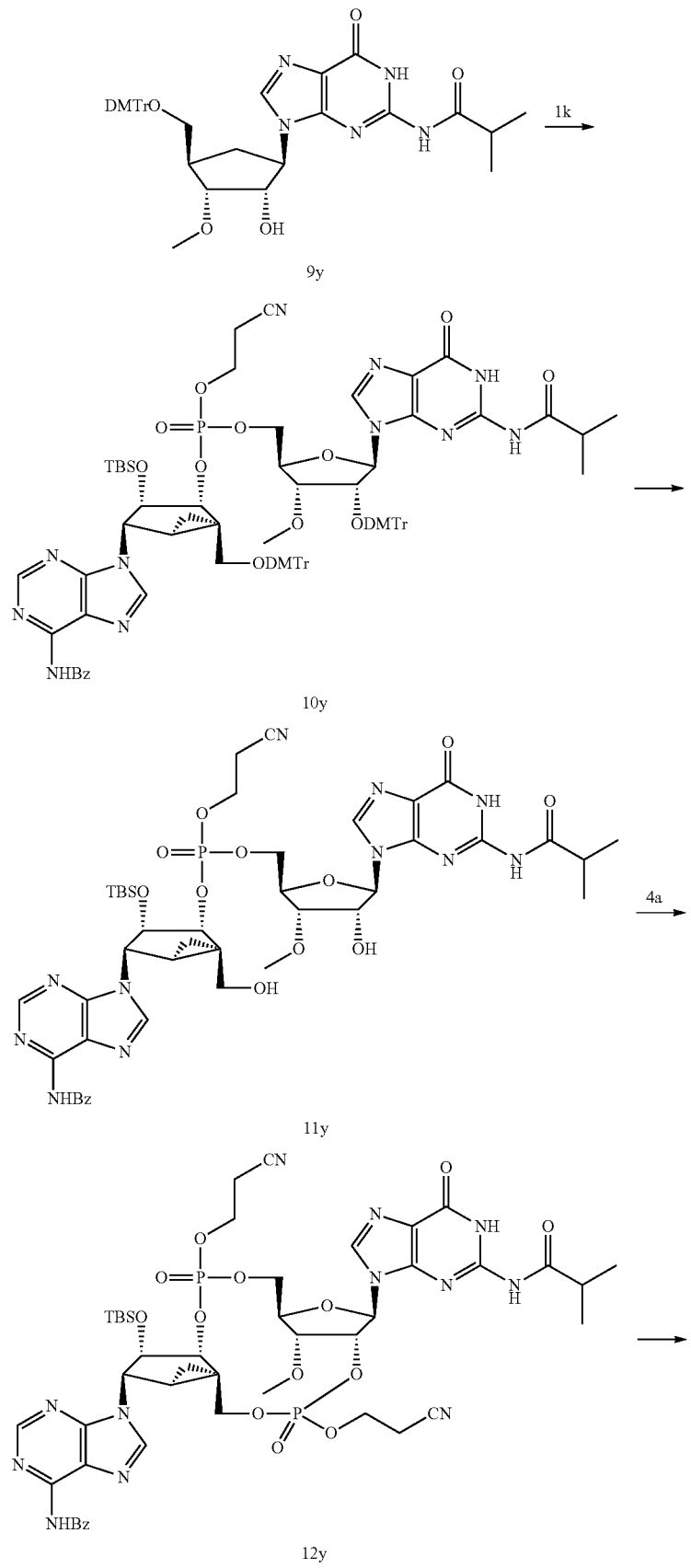

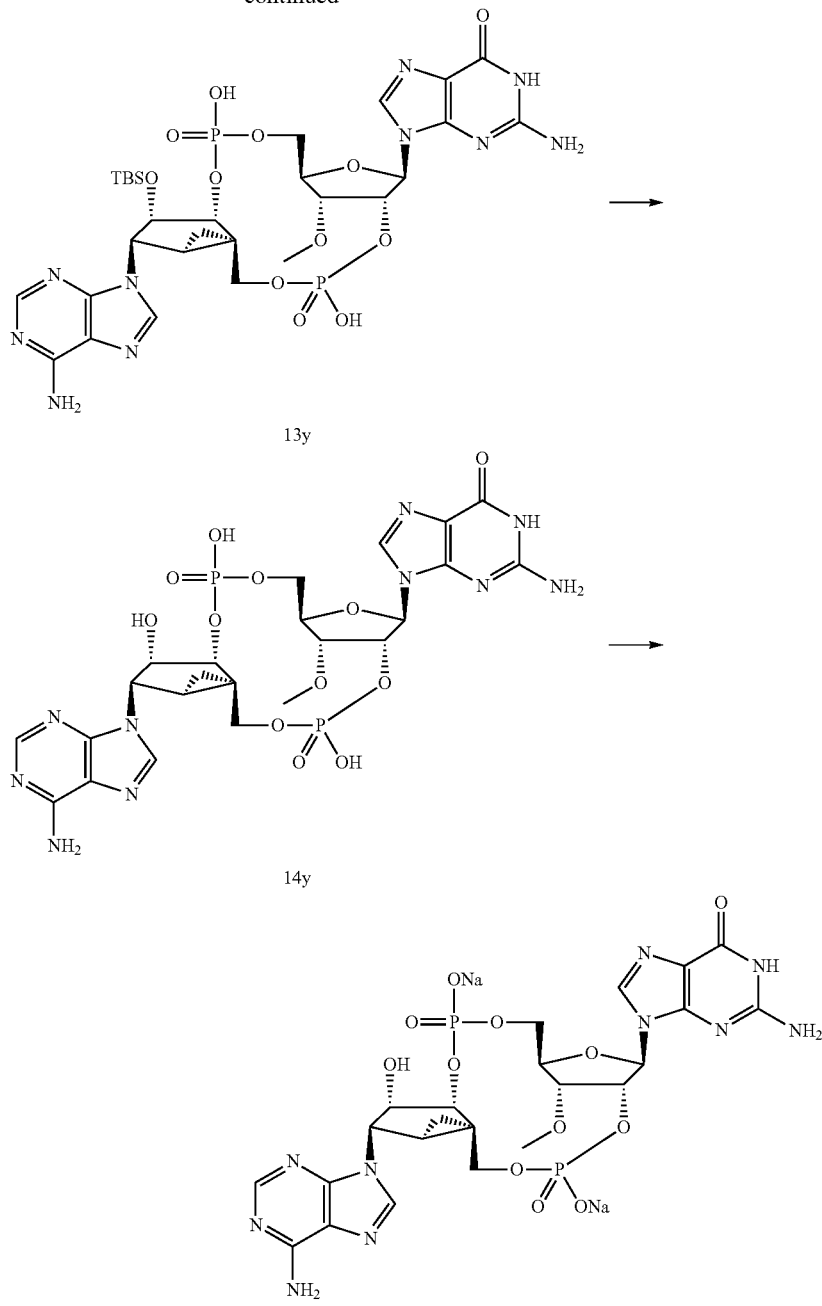

13y

14y 1-29

To a 80 mL pressure pan was added 1y (7.00 g, 12.11 mmol), NH$_3$·H$_2$O (25 mL) and 1,4-dioxane (50 mL) in turn. The mixture was stirred at 70° C. for 17 h. The mixture was concentrated in vacuo to get the crude product, which was purified by silica gel column (DCM:MeOH=30:1) to obtained 2y (5.0 g, 8.95 mmol, 73.91%) as a white solid.

To a 250 mL round bottomed flask was added 2y (10.00 g, 17.90 mmol) and 80% AcOH (100 mL) in turn. The mixture was stirred at 70° C. overnight. The mixture was concentrated in vacuo to get the crude product, which was purified by EtOAc to obtain 3y (9.80 g, crude) as a white solid. ESI-MS: m/z 519.4 [M+H]$^+$.

To a 500 mL round bottomed flask was added 3y (1.00 g, 1.93 mmol), DMF (35.6 mL) and SnCl$_2$·H$_2$O (104.41 mg, 462.71 umol) in turn. The mixture was then placed in a 50° C. oil bath pan. After the mixture was stirred at 50° C. for 10 min, TMSCH$_2$N$_2$ (6.94 mmol, 3.5 mL) was dropwise. The mixture was stirred at 50° C. overnight. H$_2$O (400 mL) was added to the mixture, and then extracted with EtOAc (5×50 mL). The combined organic layer was washed with brine and concentrated in vacuo to get the crude product. The crude was purified by reverse phase prep-HPLC (Column: C18 spherical 20-35 m 100A 40 g, mobile phase: 0.05% NH$_4$HCO$_3$ in water-ACN from 0% to 65%, flow rate: 30 mL/min) to obtain 4y (300 mg, 563.16 umol, 29.21%) as a white solid. ESI-MS: m/z 533.4 [M+H]$^+$.

To a 50 mL round bottomed flask was added 4y (1.40 g, 2.63 mmol), DMF (20 mL) and imidazole (715.68 mg, 10.51 mmol) in turn. TBSCl (792.21 mg, 5.26 mmol) in DMF (3 mL) was dropwise to the mixture, and then stirred at rt for overnight. $H_2O$ (200 mL) was added to the mixture, and then extracted with EtOAc (5×50 mL). The combined organic layer was washed with brine, and then concentrated in vacuo to get the crude product, which was purified by reverse phase prep-HPLC (Column: C18 spherical 20-35 μm 100A 40 g, mobile phase: 0.05% $NH_4HCO_3$ in water-ACN from 50% to 100%, flow rate: 20 mL/min) to obtain 5y (1.30 g, 2.01 mmol, 76.46%) as a white solid. ESI-MS: m/z 647.3 $[M+H]^+$.

To a 25 mL round bottomed flask was added 5y (1.56 g, 2.41 mmol) and pyridine (48 mL) in turn. Isobutyryl chloride (411.07 mg, 3.86 mmol) was dropwise to the mixture at −15° C. for 2 h. $H_2O$ (4 mL) was added to the mixture and then concentrated in vacuo to give the crude product. The crude was purified by reverse phase prep-HPLC (Column: C18 spherical 20-35 μm 100A 40 g, mobile phase: 0.05% $NH_4HCO_3$ in water-ACN from 50% to 100%, flow rate: 20 mL/min) to obtain 6y (1.2 g, 1.67 mmol, 69.40%) as a white solid. ESI-MS: m/z 717.5 $[M+H]^+$.

To a 250 mL round bottomed flask was added 6y (1.0 g, 1.39 mmol) and AcOH (40 mL) in turn. Sodium nitrite (38.49 g, 557.84 mmol) was dissolved in $H_2O$ (5 mL) which was dropwise to the mixture. The mixture was stirred at rt for 30 h. $H_2O$ (500 mL) was added to the mixture and then extracted with EtOAc (5×50 mL). The combined organic layer was washed with brine and then concentrated in vacuo to get the crude product, which purified by reverse phase prep-HPLC (Column: C18 spherical 20-35 μm 100A 40 g, mobile phase: 0.05% $NH_4HCO_3$ in water-ACN from 50% to 100%, flow rate: 20 mL/min) to obtained 7y (650 mg, 905.24 umol, 64.91%) as a yellow solid. ESI-MS: m/z 718.3 $[M+H]^+$.

To a 50 mL round bottomed flask was added 7y (600.00 mg, 835.61 umol), THF (10 mL) and 3 HF·TEA (1.35 g, 8.36 mmol) in turn. The mixture was stirred at 50° C. overnight. The mixture was concentrated in vacuo to get the crude product, which was purified by reverse phase prep-HPLC (Column: C18 spherical 20-35 μm 100A 40 g, mobile phase: 0.05% $NH_4HCO_3$ in water-ACN from 30% to 75%, flow rate: 20 mL/min) to obtain 8y (300 mg, 821.06 umol, 98.26%) as a white solid. ESI-MS: m/z 366.1 $[M+H]^+$.

To a 25 mL round bottomed flask was added 8y (300 mg, 821.06 umol) and pyridine (5 mL) in turn. 4,4'-Dimethoxytrityl chloride (417.30 mg, 1.23 mmol) in pyridine (0.5 mL) was dropwise. The mixture was stirred at rt for 5 h. $H_2O$ (100 mL) was added to the mixture, and the mixture was then extracted with EtOAc (4×50 mL). The combined EtOAc layer was washed with brine and then concentrated in vacuo to give the crude product. The crude was purified by silicagel flash chromatography DCM:MeOH=50:1) to obtain 9y (498 mg, 745.79 umol, 90.83%). ESI-MS: m/z 668.5 $[M+H]^+$.

Compound 1k (411.10 mg, 411.83 umol) and 9y (250.00 mg, 374.39 umol) were dissolved in anhydrous $CH_3CN$ (20.0 mL), and 4 Å molecular sieves powder (1 gr/100 mL) was added. The mixture was bubbled with Ar gas for 4 min. After stirring at rt for 10 min, 0.45 M tetrazole in $CH_3CN$ (2.24 mmol, 4.99 mL) was added at rt. After stirring for 1 h, the mixture was filtered, and then washed with anhydrous $CH_3CN$. t-BuOOH (1 mL) was added until the reaction was complete. After stirring for 20-30 min at rt, the reaction was quenched with $Na_2SO_3$ (aq, until discoloration). The mixture was diluted with EtOAc, and then layers were separated. The organic phase was washed with sat. aq. $NaHCO_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 40 g, mobile phase: 0.05% $NH_4HCO_3$ in water, m/m)-ACN from 30% to 100%, flow rate: 20 mL/min) to get 10y (400 mg, 253.04 umol, 67.59%) as a white foam. $^{31}$P-NMR (162 MHz, DMSO-$d_6$): −2.28, −2.63. ESI-MS: m/z 1581.7 $[M+H]^+$.

Compound 10y (400 mg, 253.04 umol) was dissolved in DCA in DCM (3%, v/v, 7.10 mL) and triethyl silane (2.80 mL) was added immediately. After stirring for 30 min at rt, the mixture was diluted with EtOAc, and then neutralize with sat. aq. $NaHCO_3$. The layers were separated, and the organic phase was washed with sat. aq. NaCl (1×). The aqueous phase was combined and back extracted with EtOAc (3×). The combined organic phases were evaporated to dryness, and the crude residue was purified by reverse phase prep-HPLC (Column: C18 spherical 20-35 μm 100A 40 g, mobile phase: 0.05% $NH_4HCO_3$ in water, m/m)-ACN from 30% to 80%, flow rate: 20 mL/min) to get 11y (190 mg, 194.66 umol, 76.93%) as a white foam. $^{31}$P-NMR (162 MHz, DMSO-$d_6$): −2.39, −2.68. ESI-MS: m/z 976.5 $[M+H]^+$.

Compound 11y (190 mg, 194.66 umol) dissolved in anhydrous $CH_3CN$ (25.0 mL), 0.45 M tetrazole in $CH_3CN$ (1.55 mmol, 3.46 mL) and 4 Å molecular sieves powder (300 mg, 1 gr/100 mL) were added. The mixture was bubbled with Ar gas for 4 min. After stirring at rt for 20 min, 4a (117.35 mg, 389.32 umol) in $CH_3CN$ (10.0 mL) was added over 30 to 40 min. After stirring for 2 h, the mixture was filtered and then washed with anhydrous $CH_3CN$. t-BuOOH (1 mL) was added until the reaction was completed. After stirring for 20-30 min at rt, the reaction was quenched with sat. aq. $Na_2SO_3$ (until discoloration). The mixture was diluted with EtOAc, and the layers were separated. The organic phase was washed with sat. aq. $NaHCO_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 40 g, mobile phase: 0.05% $NH_4HCO_3$ in water, m/m)-ACN from 30% to 60%, flow rate: 20 mL/min) to get 12y (82 mg, 75.15 umol, 38.61%) as a white foam. ESI-MS: m/z 1091.3 $[M+H]^+$.

Compound 12y (80 mg, 73.32 umol) was treated with a solution of $MeNH_2$ in EtOH (4 mL, 33%). After stirring for 3 h at 40° C., the mixture was evaporated to dryness, and the crude material was purified by reverse phase prep-HPLC (Column: C18 spherical 20-35 μm 100A 40 g, mobile phase: 0.05% $NH_4HCO_3$ in water, m/m)-ACN from 0% to 30%, flow rate: 20 mL/min) to get 13y (45 mg, 55.50 umol, 75.70%) as a white foam. ESI-LMS: m/z 811.6 $[M+H]^+$.

A solution of 13y (47 mg, 57.97 umol) in 3 HF·TEA (1.0 mL) and DMSO (2 mL) was stirred at 40° C. for 32 h. The mixture was cooled to rt, TEA (2 mL) and isopropoxytrimethylsilane (8 mL) were added. The mixture was stirred at rt for 1 h and then evaporated to dryness. The residue was purified by reverse phase prep-HPLC (Column: C18 spherical 20-35 μm 100A 40 g, mobile phase: 0.05% $NH_4HCO_3$ in water-ACN from 0% to 10%, flow rate: 20 mL/min-ACN from 0% to 10%, flow rate: 20 ml/min) to get the $NH_4$ salt 14y (15 mg, 21.53 μmol, 37.14%) as a white foam. A 15.0 mL volume of Amberlite IR-120 (Na form) was added to a column and then washed with deionized water (3×15 mL). The $NH_4$ salt (75 mg) was dissolved in deionized water (15 mg in 10 mL) and then added to the top of the column. The column was eluted with deionized water. The compound was eluted out in early fractions as detected by TLC (UV). The product was lyophilized to give 1-29 (11 mg, 15.79 umol, 27.24%) as a white foam. $^1$H NMR (400 MHz, D$_2$O) δ: 8.26 (s, 1H), 8.19 (s, 1H), 7.65 (s, 1H), 5.37 (ddd, J=11.1, 7.0, 4.3 Hz, 1H), 5.22 (t, J=6.9 Hz, 1H), 4.86 (s, 1H), 4.50 (d, J=11.0 Hz, 1H), 4.20 (dd, J=6.2, 1.5 Hz, 1H), 4.12 (dt, J=9.9, 2.6 Hz, 1H), 3.97 (dt, J=9.9, 2.9 Hz, 1H), 3.93 (d, J=4.4 Hz, 1H), 3.54 (d, J=11.0 Hz, 1H), 3.43 (s, 3H), 2.51 (dt, J=20.4, 8.4 Hz, 2H), 2.30-2.20 (m, 1H), 1.87 (dd, J=8.9, 4.1 Hz, 1H), 1.69 (t, J=5.1 Hz, 1H), 0.96 (td, J=6.7, 5.9, 2.7 Hz, 1H). $^{31}$P NMR (162 MHz, D$_2$O): −0.09, −2.69. ESI-MS: m/z 696.3 [M+H]$^+$.
Example 27
Compound 1-25
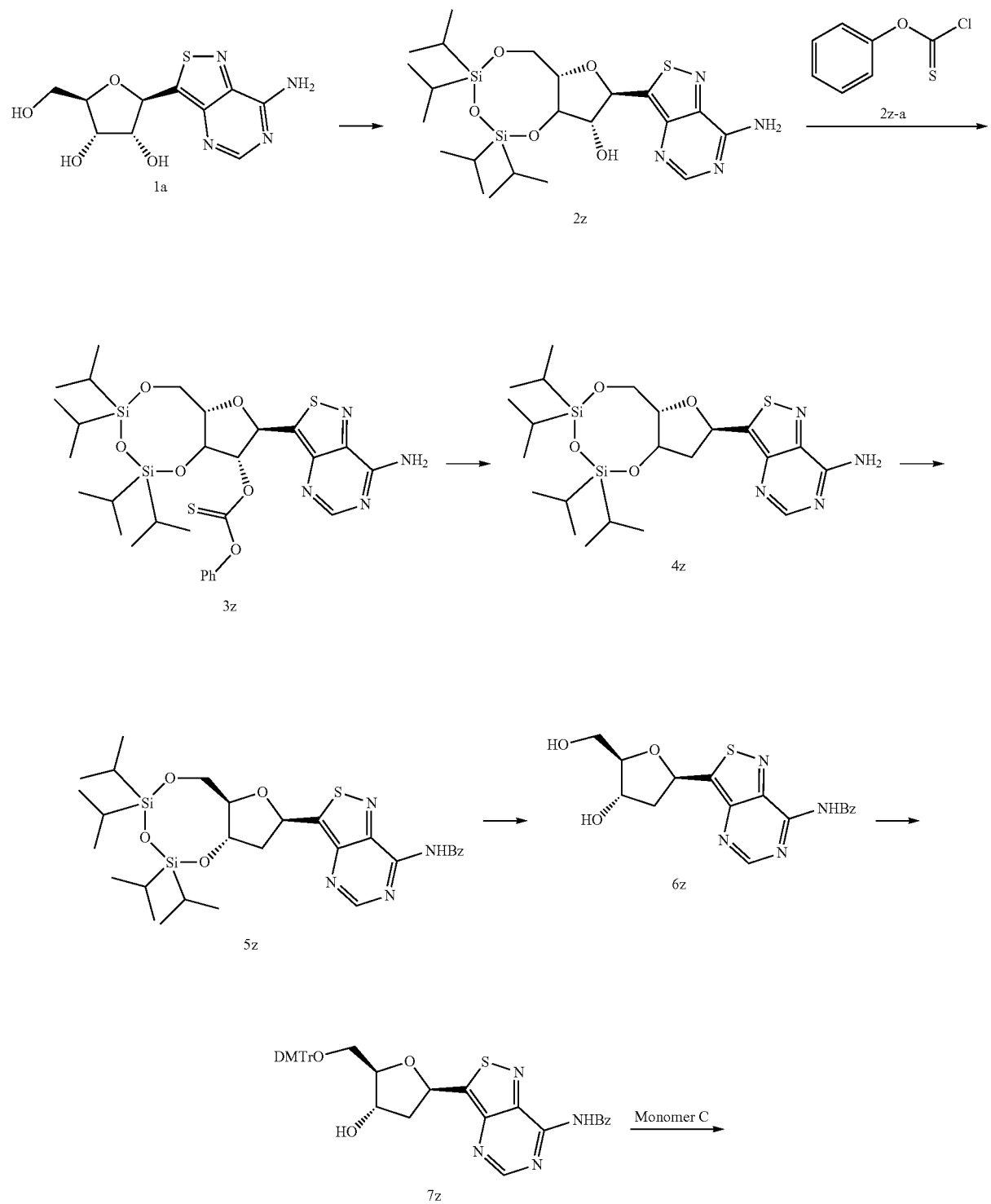

-continued
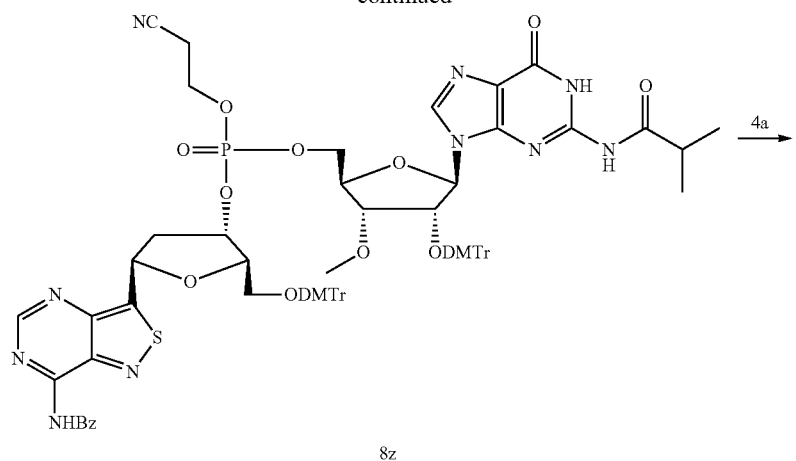
8z
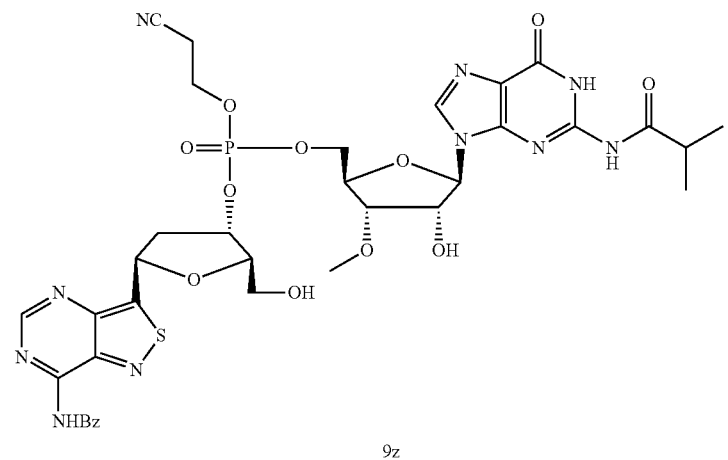
9z
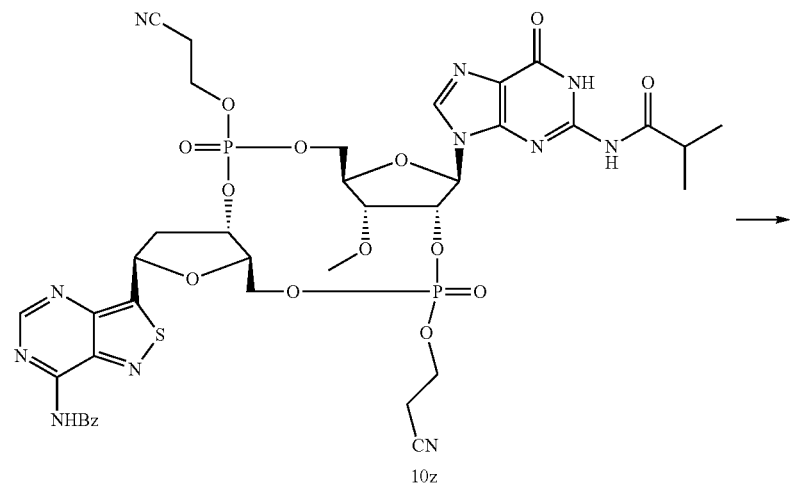
10z

-continued

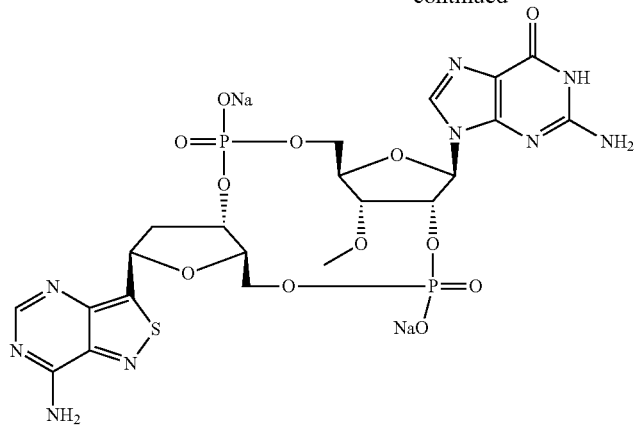

1-25

To a solution of 1z (2.30 g, 8.07 mmol) in anhydrous pyridine (30 mL) was added 1,1,3,3-tetraisopropyl-1,3-dichlorosiloxane (3.82 g, 12.10 mmol) dropwise at 0° C. under Ar. The mixture was stirred at rt for 3 h. The reaction was quenched by the addition of water, and the mixture was extracted with EtOAc (3×50 mL). The organic layers were dried over anhydrous sodium sulfate and concentrated under reduced pressure to afford the crude product. The residue was purified by silica gel column chromatography (PE: EtOA, 5:1, then DCM:MeOH, 30:1) to afford 2z (3.60 g, 6.84 mmol, 85%) as a white solid. ESI-MS: m/z 527.3 [M+H]$^+$.

To a solution of 2z (3.60 g, 6.84 mmol) in anhydrous CH$_3$CN (50 mL) was added 2z-a (1.42 g, 8.21 mmol). The mixture was stirred at rt for 10 h. The reaction was quenched by the addition of water, and the mixture was extracted with DCM (3×50 mL). The organic layers were dried over anhydrous sodium sulfate and concentrated under reduced pressure to afford the crude product. The residue was purified by silica gel column chromatography (PE:EtOAc, 5:1, then DCM:MeOH, 30:1) to afford 3z (3.5 g, 5.28 mmol, 77%) as a yellow solid. ESI-MS: m/z 663.3 [M+H]$^+$.

AIBN (346.77 mg, 2.11 mmol) and Bu$_3$SnH (2.30 g, 7.92 mmol) was dissolved in anhydrous toluene (50 mL). Compound 3z (3.5 g, 5.28 mmol) was dissolved in toluene and added to the mixture by dropwise. After stirred for 2 h at 110° C., the mixture washed with water, and the mixture was extracted with EtOAc (3×50 mL). The organic layers were dried over anhydrous sodium sulfate and concentrated under reduced pressure to afford the crude product. The residue was purified by silica gel column chromatography (PE: EtOAc, 5:1, then DCM:MeOH, 30:1) to afford 4z (2.2 g, 4.31 mmol, 82%) as a yellow solid. ESI-MS: m/z 511.3 [M+H]$^+$.

Compound 4z (2.2 g, 4.31 mmol) was dissolved in anhydrous pyridine (20 mL) and BzCl (1.82 g, 12.93 mmol) was added by dropwise under Ar. The mixture was stirred for 1 h at 0° C. The mixture washed with water, and the mixture was extracted with EtOAc (3×50 mL). The organic layers were dried over anhydrous sodium sulfate and concentrated under reduced pressure to afford the crude product. The residue was purified by silica gel column chromatography (PE:EtOAc, 5:1, then DCM:MeOH, 30:1) to afford 5z (1.7 g, 2.77 mmol, 64%) as a yellow solid. ESI-MS: m/z 615.4 [M+H]$^+$.

Compound 5z (1.7 g, 2.77 mmol) was dissolved in anhydrous THF (20 mL) and 3 HF.NEt$_3$ (1.34 g, 8.31 mmol) was added dropwise. The mixture was stirred for 1 h at rt. The mixture washed with water, and the mixture was extracted with EtOAc (3×50 mL). The organic phases were evaporated to dryness, and the crude material was purified by silica gel column chromatography (DCM:MeOH, 20:1) to get 6z (0.72 g, 1.94 mmol, 70%) as a white solid. ESI-MS: m/z 373.1 [M+H]$^+$.

Compound 6z (700 mg, 1.94 mmol) was dissolved in anhydrous pyridine (15 mL) and DMTrCl (698.77 mg, 2.06 mmol) was added under Ar. The mixture was stirred for 1 h at rt. The reaction was quenched with aq. NaHCO$_3$. The mixture washed with water and extracted with EtOAc (3×50 mL). The organic phases were evaporated to dryness, and the crude material was purified by silica gel column chromatography (DCM:MeOH=30:1) to get 7z (700 mg, 1.04 mmol, 54%) as a yellow solid. ESI-MS: m/z 675.1 [M+H]$^+$.

Compound 7z (300 mg, 445 umol) and Monomer C (465 mg, 534 umol) were dissolved in anhydrous CH$_3$CN (30 mL). 0.45 M tetrazole in acetonitrile (10.7 mL) and 4 Å molecular sieves powder were added. The mixture was bubbled with N$_2$ gas for 10 min. After stirring for 2 h, TBHP (80 mg, 890 umol) was added and then stir for 0.5 h. The mixture was filtered, and then washed with EA. The reaction was quenched with aq. Na$_2$SO$_3$. The mixture was diluted with EtOAc, and the layers were separated. The organic phase was washed with aq. NaHCO$_3$ (1×60 mL) and aq. NaCl (1×60 mL). The combined organic phases were evaporated to dryness, and the crude material was purified by RPC (Column: C18 spherical 20-35 μm 100A 80 g, mobile phase: 0.05% NH$_4$HCO$_3$ in water-ACN from 70% to 80%, flow rate: 30 mL/min) to get 8z (555 mg, 380.7 μmol, 82%) as a white solid. $^{31}$P NMR (162 MHz, DMSO-d6): −3.0, −3.03. ESI-MS: m/z 1459.5 [M+H]$^+$.

Compound 8z (310 mg, 212.6 umol) was dissolved in DCA in DCM (3%, v/v, 10.0 mL) and triethyl silane (2.5 mL) was added. After stirring for 30 min at rt, the mixture was neutralized with sat. sodium bicarbonate solution at 0° C. The mixture was evaporated to dryness, and the crude residue was purified by silica gel column chromatography (DCM:Acetone, 10:1~1:1) to get 9z (128 mg, 149.9 umol, 69%) as a yellow solid. $^{31}$P NMR (162 MHz, DMSO-d6): −2.66, −2.69. ESI-MS: m/z 855.3 [M+H]$^+$.

Compound 9z (130 mg, 152.2 umol) dissolved in anhydrous CH$_3$CN (30 mL), then 0.45 M tetrazole in CH$_3$CN (10.7 mL) and 4 Å molecular sieves powder were added. The mixture was bubbled with N$_2$ gas for 10 min. Compound 4a (918 mg, 305 umol) was added by dropwise. After stirring for 2 h, TBHP (80 mg, 890 umol) was added, and the mixture was stirred for 0.5 h. The mixture was filtered, and washed with EA. The reaction was quenched with aq. Na$_2$SO$_3$. The mixture was diluted with EtOAc, and the layers were separated. The organic phase was washed with aq. NaHCO$_3$ (1×60 mL) and aq. NaCl (1×60 mL). The combined organic phases were evaporated to dryness, and the crude material was purified by RPC (Column: C18 spherical 20-35 μm 100A 80 g, mobile phase: 0.05% NH$_4$HCO$_3$ in water-ACN from 70% to 80%, flow rate: 30 mL/min) to get 1z (20 mg, 20.6 mol, 14%) as a white solid. ESI-MS: m/z 970.3 [M+H]$^+$.

Compound 10z (20 mg, 20.6 μmol) was treated with a solution of 33% MeNH$_2$ in EtOH (3 mL). After stirring the for 2 h at 40° C., the mixture was evaporated to dryness, and the crude material was purified by reverse phase prep-HPLC (Column: C18 spherical 20-35 μm 100A 20 g, mobile phase: 0.05% NH$_4$HCO$_3$ in water, m/m)-ACN from 0% to 30%, flow rate: 15 mL/min) to get 1-25 (2 mg, 2.9 umol, 14%) as a white foam. ESI-MS: m/z 690.0 [M+H]$^+$.

A 15.0 mL volume of Amberlite IR-120 (Na form) was added to a column and washed with deionized water (3×15 mL). The NH$_4$ salt of 1-25 (2 mg) was dissolved in deionized water (2 mg in 10 mL) and added to the top of the column. The eluted with deionized water. The compound was eluted out in early fractions as detected by TLC (UV). The product was lyophilized to give 1-25 (1.9 mg, 2.5 μmol, 86% yield) as a white foam. $^1$H NMR (400 MHz, D$_2$O) 8.15 (s, 1H), 7.87 (s, 1H), 5.93 (dd, J=4.4 Hz, 3.6 Hz, 1H), 5.85 (d, J=4.4 Hz, 1H), 5.4 (dt, J=4.4 Hz, 8.4 Hz, 1H), 5.0 (q, J=6.8 Hz, 1H), 4.5 (d, J=3.2 Hz, 1H), 4.19 (d, J=4.4 Hz, 2H), 4.13 (d, J=2.8 Hz, 2H), 4.07 (t, J=4.0 Hz, 2H), 3.50 (s, 3H), 2.80 (m, 1H), 2.65 (m, 1H). $^{31}$P NMR (162 MHz, D$_2$O): –0.88, –1.58. ESI-MS: m/z 690.0 [M+H]$^+$.

Example 28

Compound 1-37

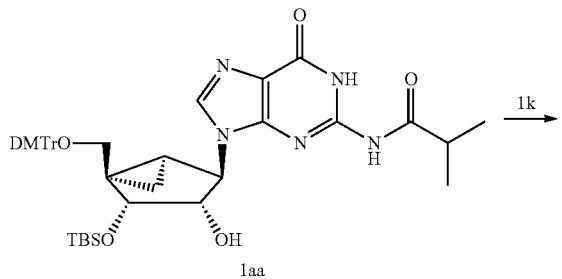

1aa

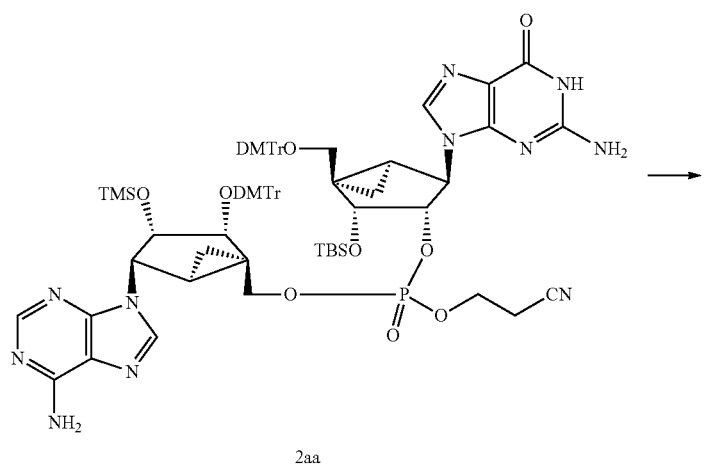

2aa

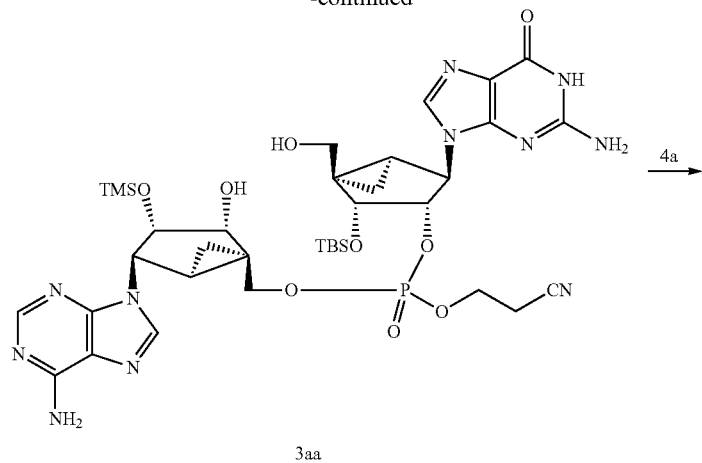
3aa
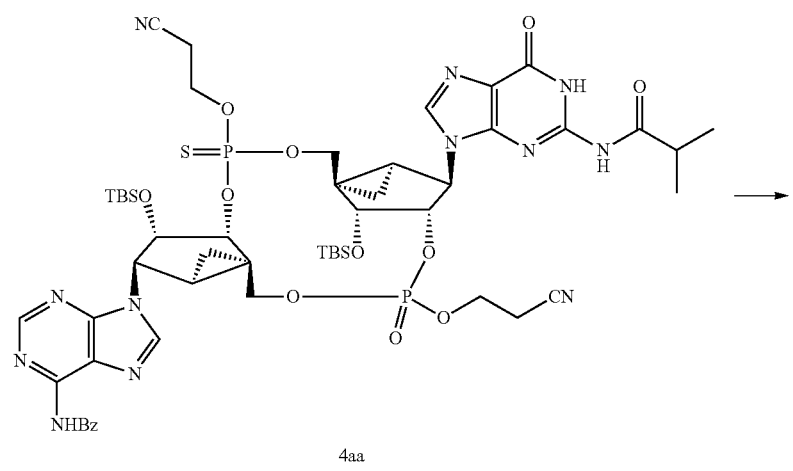
4aa
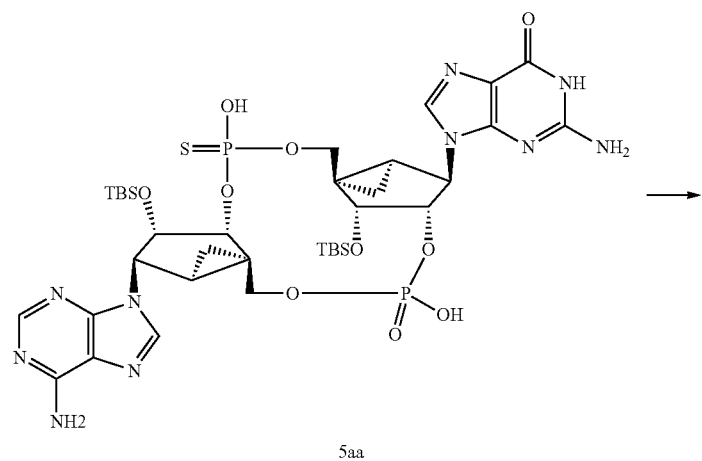
5aa

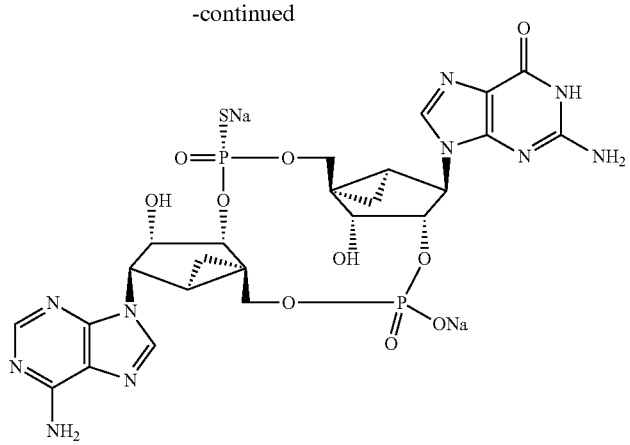

1-37

Compound 1k (1.23 g, 1.23 mmol) and 1aa (800 mg, 1.03 mmol) was dissolved in anhydrous $CH_3CN$ (50.0 mL), and 4 Å molecular sieves powder (1 gr/100 mL) was added. The mixture was bubbled with Ar gas for 4 min. After stirring at rt for 10 min, 0.45 M tetrazole in $CH_3CN$ (6.15 mmol, 13.67 mL) was added at rt. After stirring for 1 h, the mixture was filtered and washed with anhydrous $CH_3CN$. 5M t-BuOOH was added until the reaction was complete. After stirring for 20-30 min at rt, the reaction was quenched with $Na_2SO_3$ (aq, until discoloration). The mixture was diluted with EtOAc, and layers were separated. The organic phase was washed with sat. aq. $NaHCO_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% $NH_4HCO_3$ in water, m/m)-ACN from 30% to 100%, flow rate: 35 mL/min) to get 2aa (1.52 g, 897.80 umol, 87.53%) as a white foam. $^{31}$P-NMR (162 MHz, DMSO-$d_6$): −2.36, −3.11. ESI-MS: m/z 1693.8 $[M+H]^+$.

Compound 2aa (1.52 g, 897.80 umol) was dissolved in DCA in DCM (3%, v/v, 28.5 mL) and triethyl silane (10.6 mL) was added immediately. After stirring for 30 min at rt, the mixture was diluted with EtOAc, and neutralize with sat. aq. $NaHCO_3$. The layers were separated, and the organic phase was washed with sat. aq. NaCl (1×). The aqueous phase was combined and back extracted with EtOAc (3×). The combined organic phases were evaporated to dryness, and the crude residue was purified by silica gel column (acetone in DCM from 0% to 100%) to get 3aa (325 mg, 0.30 mmol, 74.7%) as a white foam. $^{31}$P-NMR (162 MHz, DMSO-$d_6$): −2.70, −2.72. ESI-MS: m/z 1088.5 $[M+H]^+$.

Compound 3aa (800 mg, 735.09 umol) dissolved in anhydrous $CH_3CN$ (112.0 mL). 0.45 M tetrazole in $CH_3CN$ (5.88 mmol, 13.70 mL) and 4 Å molecular sieves powder (300 mg, 1 gr/100 mL) were added. The mixture was bubbled with Ar gas for 4 min. After stirring at rt for 20 min, 4a (443.13 mg, 1.47 mmol) in $CH_3CN$ (10.0 mL) was added over 30 to 40 min. After stirring the reaction for 2 h, the mixture was filtered and washed with anhydrous $CH_3CN$. To this solution was added 0.1M DDTT (11 mL) until the reaction was completed. After stirring for 20-30 min at rt, the reaction was quenched with sat. aq. $Na_2SO_3$. The mixture was diluted with EtOAc, and the layers were separated. The organic phase was washed with sat. aq. $NaHCO_3$ (1×) and sat. aq. NaCl (1×). The combined aqueous phase was back extracted with EtOAc (1×). The combined organic phases were evaporated to dryness, and the crude material was purified by reverse phase prep-HPLC (Column: C18 spherical 20-35 μm 100A 80 g, mobile phase: 0.05% $NH_4HCO_3$ in water, m/m)-ACN from 30% to 60%, flow rate: 35 mL/min) to get 4aa (400 mg, 328.03 umol, 44.62%) as a white foam. ESI-MS: m/z 1219.3$[M+H]^+$.

Compound 4aa (420 mg, 344.43 umol) was treated with a solution of $MeNH_2$ in EtOH (55 mL, 33%). After stirring for 4 h at 40° C., the mixture was evaporated to dryness. The crude material was purified by reverse phase prep-HPLC (Column: C18 spherical 20-35 μm 100A 80 g, mobile phase: 0.05% $NH_4HCO_3$ in water, m/m)-ACN from 0% to 30%, flow rate: 30 ml/min) to get 5aa (294 mg, 313.07 umol, 90.90%) as a white foam. $^{31}$P-NMR (162 MHz, DMSO-$d_6$): δ2.82, −7.12. ESI-LMS: m/z 939.4 $[M+H]^+$.

A solution of 5aa (280 mg, 298.17 umol) in 3 HF·TEA (1.5 mL) and DMSO (3 mL) was stirred at 40° C. for 32 h. The mixture was cooled to rt. TEA (1.5 mL) and isopropoxytrimethylsilane (12 mL) were added to the mixture, and then the mixture was stirred at rt for 1 h. The mixture was evaporated to dryness, and the residue was purified by reverse phase prep-HPLC (Column: C18 spherical 20-35 μm 100A 40 g, mobile phase: 0.05% $NH_4HCO_3$ in water-ACN from 0% to 10%, flow rate: 20 mL/min-ACN from 0% to 10%, flow rate: 20 ml/min) to get the $NH_4$ salt 6aa (120 mg, 168.88 umol, 56.64%) as a white foam. A 15.0 mL volume of Amberlite IR-120 (Na form) was added to a column and washed with deionized water (3×15 mL). The $NH_4$ salt (120 mg) was dissolved in deionized water (15 mg in 10 mL) and added to the top of the column. The column was eluted with deionized water. The compound was eluted out in early fractions as detected by TLC (UV). The product was lyophilized to give 1-37 (115 mg, 161.84 umol, 54.24%) as a white foam. $^1$H NMR (400 MHz, $D_2O$) δ: 8.25 (s, 1H), 8.17 (d, J=0.9 Hz, 1H), 7.67 (s, 1H), 5.29 (dd, J=10.0, 6.3 Hz, 1H), 5.14-5.06 (m, 1H), 4.89 (s, 1H), 4.63 (d, J=4.6 Hz, 2H), 4.55 (dd, J=10.0, 3.3 Hz, 1H), 4.46 (d, J=6.4 Hz, 1H), 4.17 (dd, J=10.0, 3.1 Hz, 1H), 3.58 (d, J=11.3 Hz, 1H), 3.38 (dd, J=10.1, 5.3 Hz, 1H), 1.89 (dd, J=9.1, 4.3 Hz, 1H), 1.75 (dt, J=8.2, 3.9 Hz, 1H), 1.65 (t, J=5.2 Hz, 1H), 1.28-1.22 (m, 1H), 1.06-0.97 (m, 2H). $^{31}$P NMR (162 MHz, $D_2O$): δ 51.62, −2.96. ESI-MS: m/z 711.3 $[M+H]^+$.

Example 29
Compounds 1-38a & 1-38b
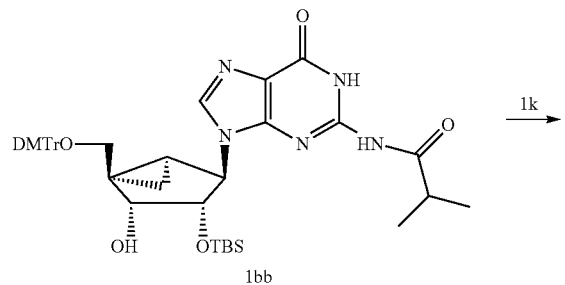
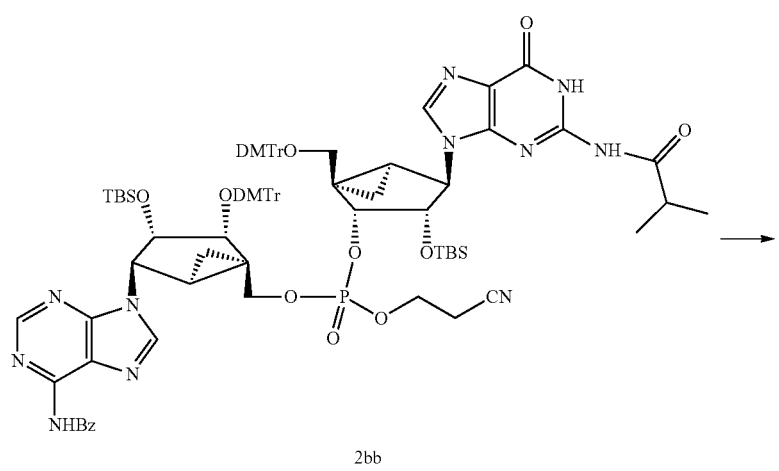
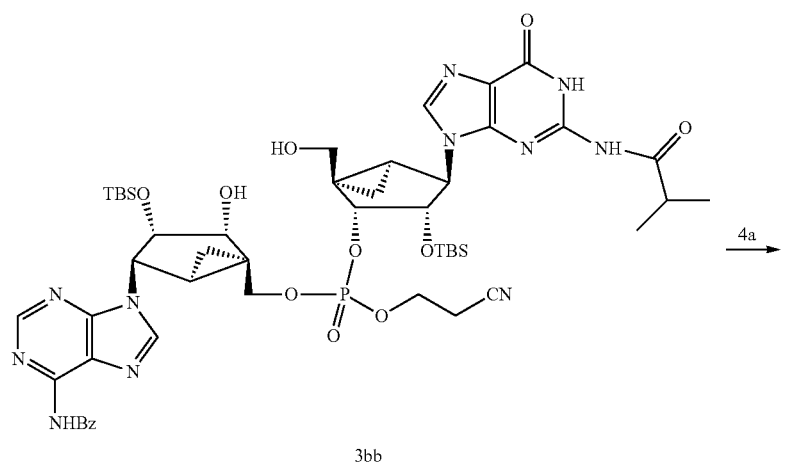

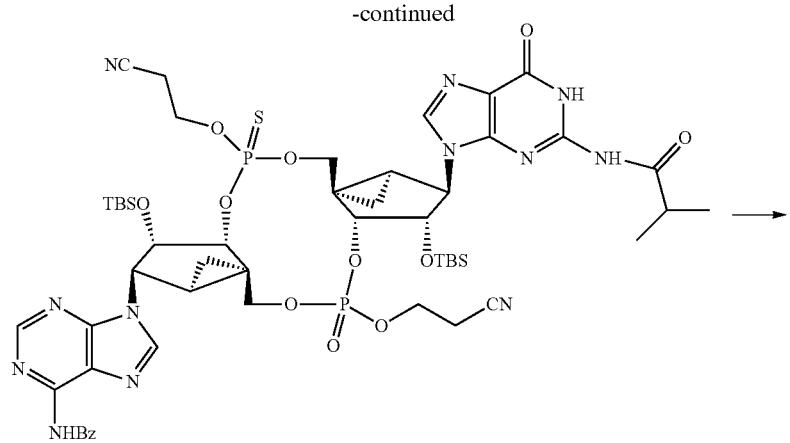
4bb
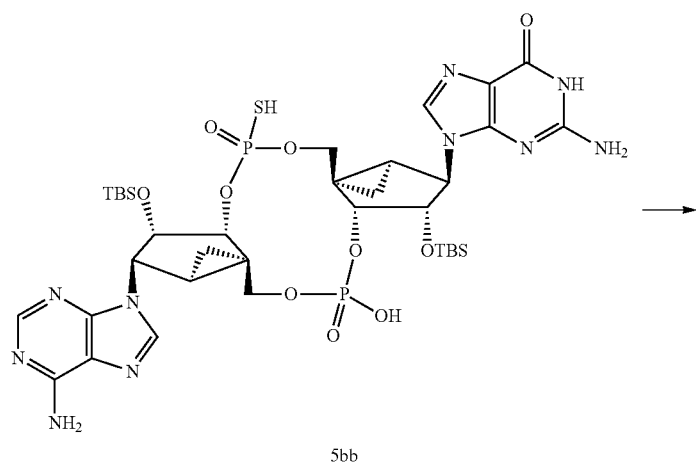
5bb
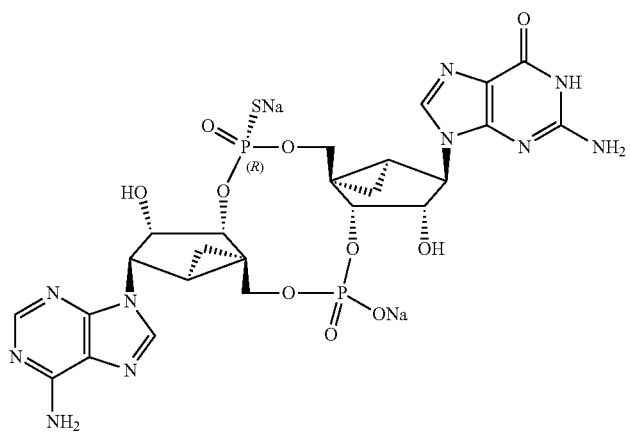
1-38a

-continued

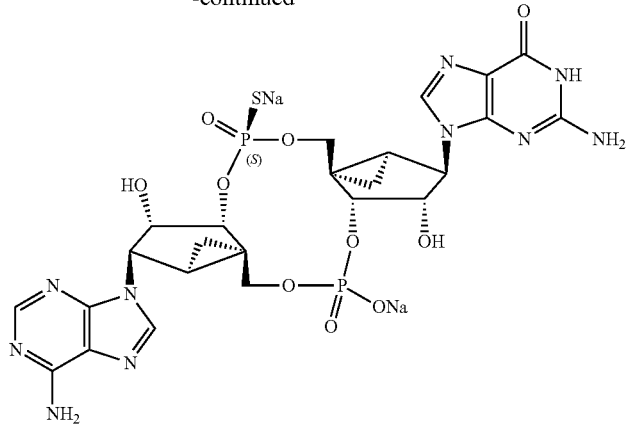

1-38b

Compound 1bb (850 mg, 1.09 mmol) and 1k (1.20 g, 1.20 mmol) was dissolved in anhydrous $CH_3CN$ (40.0 mL). 4 Å molecular sieves powder (400 mg, 1 gr/100 mL) was added. The mixture was bubbled with Ar gas for 4 min. After stirring at rt for 20 min, 0.45 M tetrazole in $CH_3CN$ (6.54 mmol, 14.5 mL) was added at rt. After stirring for 1 h, the mixture was washed with anhydrous $CH_3CN$. To this solution was added 5 M t-BuOOH until the reaction was complete. After stirring for 20-30 min at rt, the mixture was filtered. The reaction was quenched with $Na_2SO_3$ (aq). The mixture was diluted with EtOAc, and the layers were separated. The organic phase was washed with sat. aq. $NaHCO_3$ (1×50.0 mL) and sat. aq. NaCl (1×50.0 mL). The combined aqueous phase was back extracted with EtOAc (1×50.0 mL). The combined organic phases were evaporated to dryness, and the crude material was purified by reverse phase prep-HPLC (Column: C18 spherical 20-35 µm 100A 80 g, mobile phase: 0.05% $NH_4HCO_3$ in water, m/m)-ACN from 60% to 100%, flow rate: 35.0 mL/min) to get 2bb (1.48 g, 0.87 mmol, 80.2%) as a white foam. $^{31}$P NMR (162 MHz, DMSO-$d_6$): −1.853, −3.54. ESI-MS: m/z 1693.07 [M+H]$^+$.

Compound 2bb (1.48 g, 0.87 mmol) was dissolved in DCA in DCM (3%, v/v, 30.0 mL) and triethylsilane (10.0 mL) was added immediately. After stirring for 20 min at rt, the mixture was neutralized with ice-cold sat. $NaHCO_3$ (aq.). The mixture was extracted with EtOAc (3×60.0 mL). The organic layers was washed with sat. NaCl aq. (1×150.0 mL), dried over $Na_2SO_4$ and concentrated under reduced pressure to give a residue. The crude residue was purified by silica gel column chromatography (DCM/acetone, 0-100% acetone) to afford 3bb (900 mg, 826.96 µmol, 93.34%) as a white solid. $^{31}$P NMR (162 MHz, DMSO-$d_6$): −1.407, −1.506. ESI-MS: m/z=1088.5 [M+H]$^+$.

Compound 3bb (900 mg, 0.82 mmol) was dissolved in $CH_3CN$ (100.0 mL). Tetrazole in $CH_3CN$ (6.62 mmol, 0.45 M, 14.71 mL) and 4 Å molecular sieves powder (1.0 g, 1 gr/100 mL) were added. The mixture was bubbled with Ar gas for 4 min. After stirring at rt for 20 min, 4a (497.83 mg, 1.65 mmol) in $CH_3CN$ (10.0 mL) was added at rt over 25 to 30 min. After stirring the reaction for 2 h, the mixture was filtered and washed with anhydrous $CH_3CN$. To this solution was added 0.1M DDTT until the reaction was complete. After stirring for 20-30 min at rt, the reaction was quenched with sat. aq. $NaS_2O_3$. The mixture was diluted with EtOAc, and the organic layers were separated. The organic phase was washed with sat. $NaHCO_3$ aq. (1×50.0 mL) and sat. NaCl aq. (1×50.0 mL). The combined aqueous phase was back extracted with EtOAc (1×). The combined organic phases were evaporated to dryness, and the crude material was purified by reverse phase prep-HPLC (Column: C18 spherical 20-35 µm 100A 80 g, mobile phase: 0.05% $NH_4HCO_3$ in water, m/m)-ACN from 30% to 60%, flow rate: 35 mL/min) to get 4bb (400 mg, 395.53 µmol, 42.9%) as a white foam. ESI-MS: m/z 1219.4 [M+H]$^+$.

Compound 4bb (440 mg, 365.93 µmol) was treated with a solution of MeNH$_2$ in EtOH (12.0 mL, 33%). After stirring for 2 h at 40° C., the mixture was evaporated to dryness. The crude material was purified by reverse phase prep-HPLC (Column: C18 spherical 20-35 µm 100A 40 g, mobile phase A: 0.05% $NH_4HCO_3$ in water, m/m-ACN from 0% to 10%, flow rate: 20 ml/min) to afford 5bb (300 mg, 319.46 µmol, 88.54%) as a white foam. $^{31}$P NMR (162 MHz, DMSO-$d_6$): δ2.72, 51.92, −3.88. ESI-MS: m/z 939.08 [M+H]$^+$.

A solution of 5bb (300 mg, 319.46 µmol) in 12% TEAF in DMSO (10.0 mL) was stirred at 50° C. for 24 h. The mixture was cooled to r. 15.0 mL volume of Amberlite IR-120 (Na form) was added to a column and washed with deionized water (3×15 mL). The crude product was dissolved in deionized water (15 mL) and added to the top of the column. The column was eluted with deionized water. The residue was purified by reverse phase prep-HPLC Column: C18 spherical 20-35 µm 100A 40 g, mobile phase: 0.05% $NH_4HCO_3$ in water, m/m)-ACN from 0% to 15%, flow rate: 20 mL/min) to get NH$_4$ salt (P1, 61 mg, 85.85 mol, 26.87%, and (P2, 80 mg, 112.68 mol, 35.27%) as a white foam. 15.0 mL volume of Amberlite IR-120 (Na form) was added to a column and washed with deionized water (3×15 mL). The NH$_4$ salt was dissolved in deionized water (15 mL) and added to the top of the column. The column was eluted with deionized water. The compound was eluted out in early fractions as detected by TLC (UV). The product was lyophilized to give 1-38a (50 mg, 70.32 µmol, 81.91%) and 1-38b (70 mg, 98.45 µmol, 87.37%) as a white foam.

1-38a: $^1$H NMR (400 MHz, D$_2$O) δ: 8.35 (s, 1H), 8.07 (s, 1H), 8.03 (s, 1H), 5.13 (q, J=6.44 Hz, 1H), 5.06 (t, J=7.36 Hz, 1H), 4.82 (s, 1H), 4.56 (d, J=8.52 Hz, 2H), 4.46 (m, 1H), 4.38 (d, J=6.12 Hz, 1H), 4.14 (d, J=6.28 Hz, 1H), 3.70 (d, J=10.6 Hz, 1H), 3.57 (d, J=10.92 Hz, 1H), 1.90 (m, 1H), 1.79 (m, 1H), 1.59 (m, 2H), 0.98 (m, 2H). $^{31}$P NMR (162 MHz, D$_2$O): 53.75, 1.42. ESI-MS: m/z=711.3 [M+H]$^+$.

1-38b: $^1$H NMR (400 MHz, D$_2$O) δ: 8.26 (s, 1H), 7.96 (s, 1H), 7.80 (s, 1H), 5.27 (t, J=7.36 Hz, 1H), 5.16 (t, J=6.72 Hz,

1H), 4.76 (s, 1H), 4.54 (d, J=13.52 Hz, 2H), 4.45 (t, 1H), 4.20 (d, J=5.92 Hz, 1H), 4.09 (d, J=6.00 Hz, 1H), 3.65 (d, J=10.96 Hz, 1H), 3.55 (d, J=10.84 Hz, 1H), 1.88 (m, 2H), 1.60 (s, 2H), 0.97 (m, 2H); $^{31}$P NMR (162 MHz, D$_2$O): 53.44, −1.41. ESI-MS: m/z=711.3 [M+H]$^+$.
Example 30
Compounds 1-30a & 1-30b
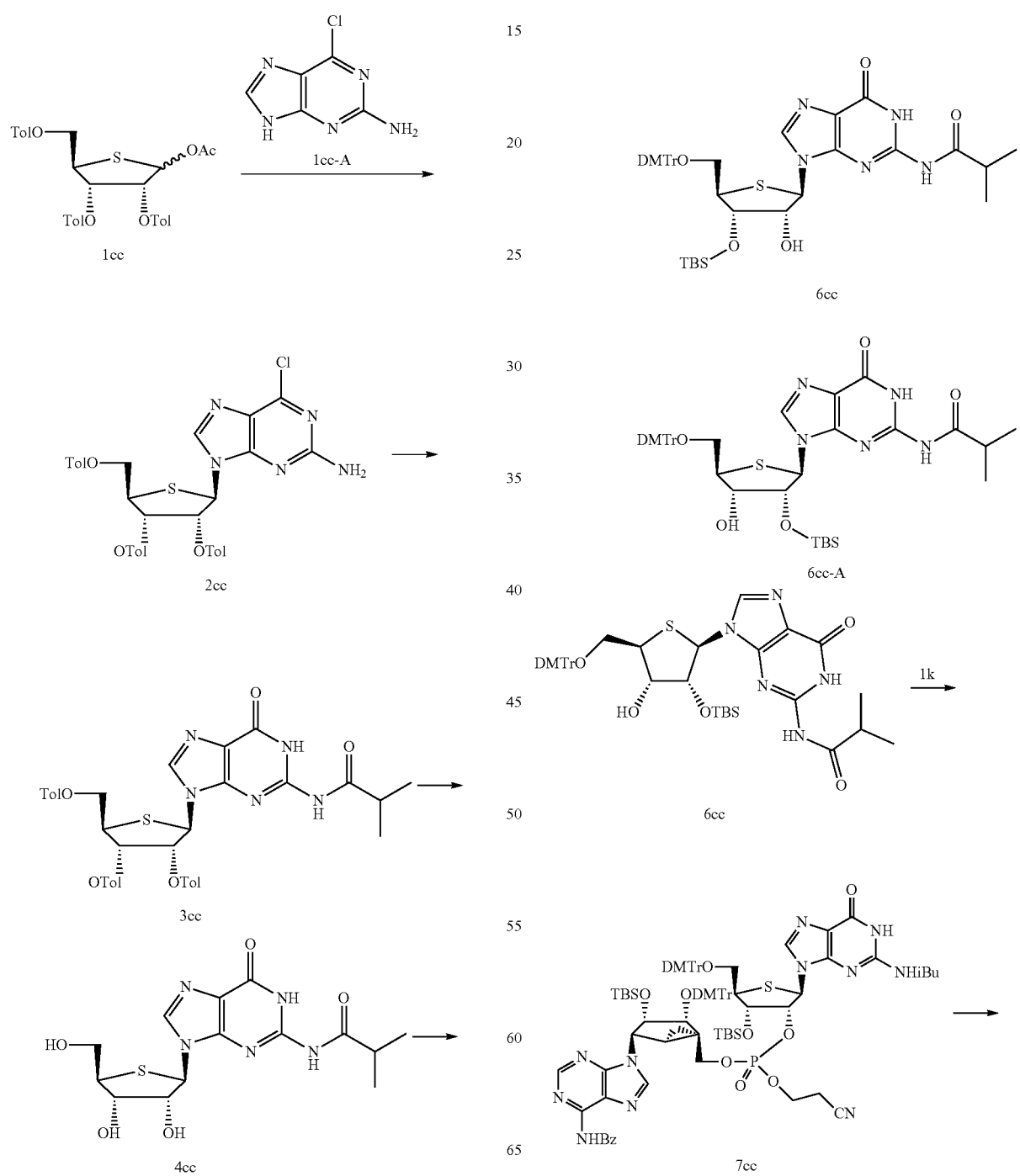

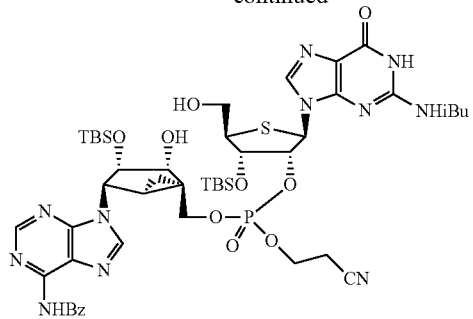

8cc

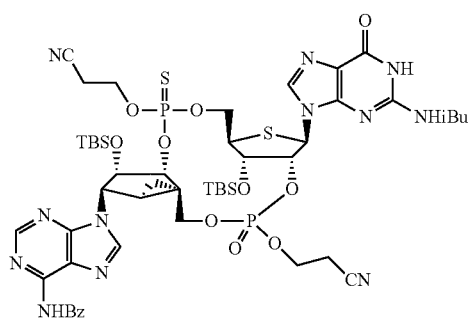

9cc

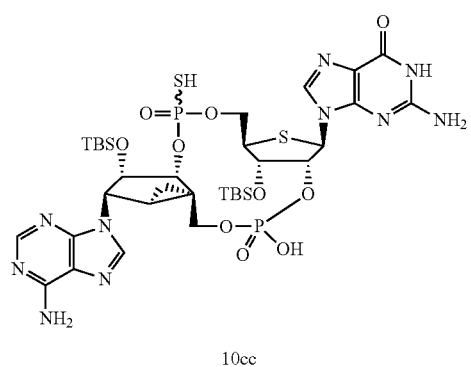

10cc

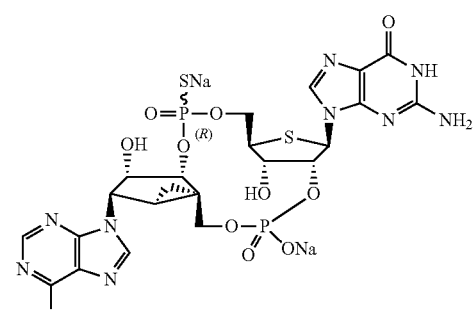

1-30a

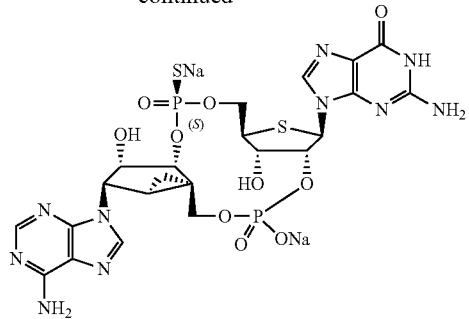

1-30b

To a stirred solution of 1cc (10 g, 17.79 mmol) and 1cc-A (5.02 g, 26.60 mmol) in DCE (100 mL) was added BSA (17.4 g, 74.16 mmol). The mixture was stirred at 50° C. for 30 mins. The mixture was cooled to 0° C., and TMSOTf (5.20 mL, 26.6 mmol) was added dropwise. The mixture was heated to reflux, and the mixture was then stirred for 16 h. The mixture was poured into water and then extracted with EtOAc (2×200 mL). The separated organic layer was washed with brine, dried over $Na_2SO_4$ and concentrated to dryness to give the crude product. The crude product was purified by silica gel to give 2cc (5.50 g, 8.70 mmol, 49.08%, 95% purity) as a yellow foam. ESI-MS: m/z 672.4 $[M+H]^+$.

To a stirred solution of 2cc ((5.50 g, 8.70 mmol) in pyridine (30 mL) was added Isobutyryl chloride (1.2 ml, 13.05 mmol) at 0° C. The reaction was stirred at rt for 1 h. The mixture was poured into water and extracted with EA (2×). The separated organic layer was washed with brine, dried over $Na_2SO_4$ and concentrated to dryness to give the crude product. The crude was dissolved in DMF (50 mL), and then DBACO (974.00 mg, 8.70 mmol), $Cs_2Ac$ (4.98 g, 26.10 mmol) and TEA (3.0 mL, 26.10 mmol) were added. The reaction was stirred for 16 h. The reaction mixture was then poured into water and extracted with EtOAc (2×200 mL). The separated organic layer was washed with brine, dried over $Na_2SO_4$ and concentrated to dryness to give 3cc (9.20 g, 70% purity used directly) as a yellow oil. ESI-MS: m/z 724.4 $[M+H]^+$.

To a stirred solution of 3cc (9.2 g) in pyridine (10 mL) was added 2N NaOH aq. to adjust the pH to 12. The mixture was stirred for 30 min at rt. The mixture was pour into water and extracted with EtOAc (2×200 mL). The organic layer was separated, washed with brine, dried over $Na_2SO_4$ and concentrated to dryness to give the crude product. The crude product was purified by silica gel to give 4cc (2.1 g, 5.41 mmol, 62.02% for 3 steps, 95% purity). ESI-MS: m/z 370.5 $[M+H]^+$.

To a stirred solution of 4cc (2.10 g, 5.41 mmol) in pyridine (20 mL) was added DMTrCl (2.12 g, 6.50 mmol). The reaction was stirred for 3 h at rt. The mixture was pour into water and extracted with EA (2×). The organic layer was separated, washed with brine, dried over $Na_2SO_4$ and concentrated to dryness to give the crude product. The crude product was purified by silica gel to give 5cc (3.2 g, 4.76 mmol, 88.00%, 95% purity). ESI-MS: m/z 672.2 $[M+H]^+$.

To a stirred solution of 5cc (3.2 g, 4.76 mmol) and imidazole (1.07 g, 14.84 mmol) in DMF (40 mL) was added tert-butyldimethylsilyl chloride (971.05 mg, 6.60 mmol) in portions. The mixture was stirred at rt for 3 h. The mixture was poured into water and extracted with EtOAc (2×200 mL). The separated organic layer was washed with brine, dried over $Na_2SO_4$ and concentrated to give the crude product. The crude product was purified by reverse phase prep-HPLC (Column: C18 spherical 20-35 μm 100A 80 g, mobile phase: 0.05% $NH_4HCO_3$ in water, m/m)-ACN from 60% to 100%, flow rate: 35.0 mL/min) to get 6cc (1.3 g, 1.65 mmol, 34.09%, 98% purity) and 6cc-A (1.4 g, 1.78 mmol, 47.5%, 98% purity) as white foams.

6cc: $^1$H-NMR (400 MHz, DMSO-$d_6$) δ: 12.06 (s, 1H), 11.70 (s, 1H), 8.19 (s, 1H), 7.46-7.20 (m, 10H), 6.96-6.86 (m, 5H), 5.87 (d, J=7.2 Hz, 1H), 5.44 (d, J=4.5 Hz, 1H), 4.41 (dd, J=7.3, 3.4 Hz, 1H), 4.19 (q, J=3.5 Hz, 1H), 3.76 (s, 7H), 3.52-3.37 (m, 2H), 3.30 (dd, J=9.3, 5.8 Hz, 6H), 2.76 (hept, J=6.8 Hz, 1H), 2.08 (s, 2H), 1.12 (d, J=6.8 Hz, 7H), 0.70 (s, 9H), −0.07 (s, 3H), −0.29 (s, 3H). ESI-LMS: m/z 786.6 [M+H]$^+$.

6cc-A: $^1$H-NMR (400 MHz, DMSO-$d_6$) δ: 12.10 (s, 1H), 11.65 (s, 1H), 8.18 (s, 1H), 7.44-7.36 (m, 2H), 7.36-7.20 (m, 8H), 6.94-6.85 (m, 4H), 5.69 (d, J=7.2 Hz, 1H), 5.62 (d, J=5.8 Hz, 1H), 4.49 (ddd, J=7.2, 5.8, 3.5 Hz, 1H), 4.27 (t, J=3.1 Hz, 1H), 3.74 (s, 6H), 3.48 (dd, J=10.1, 7.2 Hz, 1H), 3.38-3.21 (m, 6H), 2.78 (p, J=6.8 Hz, 1H), 2.07 (s, 2H), 1.12 (d, J=6.8 Hz, 6H), 0.84 (s, 9H), 0.05 (s, 6H). ESI-LMS: m/z 786.6 [M+H]$^+$.

Compound 6cc (700 mg, 0.89 mmol) and 1k (1.0 g, 1.10 mmol) were dissolved in anhydrous $CH_3CN$ (30.0 mL), and 4 Å molecular sieves powder (300 mg, 1 gr/100 mL) was added. The mixture was bubbled with Ar gas for 4 min. After stirring at rt for 20 min, 0.45 M tetrazole in $CH_3CN$ (10.03 mmol, 40.0 mL) was added at rt. After stirring for 1 h, the mixture was washed with anhydrous $CH_3CN$. To this solution was added 5 M t-BuOOH until the reaction was complete. After stirring for 20-30 min at rt, the mixture was filtered. The reaction was quenched with $Na_2SO_3$ (aq). The mixture was diluted with EtOAc, and the layers were separated. The organic phase was washed with sat. aq. $NaHCO_3$ (1×50.0 mL) and sat. aq. NaCl (1×50.0 mL). The combined aqueous phase was back extracted with EtOAc (1×50.0 mL). The combined organic phases were evaporated to dryness, and the crude material was purified by reverse phase prep-HPLC (Column: C18 spherical 20-35 μm 100A 80 g, mobile phase: 0.05% $NH_4HCO_3$ in water, m/m)-ACN from 60% to 100%, flow rate: 35.0 mL/min) to get 7cc (1.30 g, 0.77 mmol, 86.7%) as a white foam. ESI-MS: m/z 1685.1 [M+H]$^+$.

Compound 7cc (1.30 g, 0.77 mmol) was dissolved in DCA in DCM (3%, v/v, 50.0 mL) and triethylsilane (30.0 mL) was added immediately. After stirring for 20 min at rt, the mixture was neutralized with ice saturated $NaHCO_3$ (aq.). The mixture was extracted with EtOAc (3×60.0 mL). The organic layers was washed with sat. NaCl aq (1×150.0 mL), dried over $Na_2SO_4$ and concentrated under reduced pressure to give a residue. The crude residue was purified by silica gel column chromatography (DCM/acetone, 0-100% acetone) to afford 8cc (800.00 mg, 0.69 mmol, 90.0%) as a white solid. $^{31}$P-NMR (162 MHz, DMSO-$d_6$): −2.56, −2.56. ESI-MS: m/z 1080.0 [M+H]$^+$.

Compound 8cc (800.00 mg, 0.69 mmol) dissolved in anhydrous $CH_3CN$ (100.0 mL). 0.45 M tetrazole in $CH_3CN$ (5.83 mmol, 23.31 mL) and 4 Å molecular sieves powder (10.0 g, 1 gr/100 mL) were added. The mixture was bubbled with Ar gas for 4 min. After stirring at rt for 20 min, 4a (435.80 mg, 1.45 mmol) in $CH_3CN$ (10.0 mL) was added at rt over 25 to 30 min. After stirring for 2 h, the mixture was filtered and washed with anhydrous $CH_3CN$. To this solution was added 0.1M DDTT until the reaction was complete. After stirring for 20-30 min at rt, the reaction was quenched with sat. aq. $NaS_2O_3$. The mixture was diluted with EtOAc, the organic layers separated. The organic phase was washed with sat.$NaHCO_3$ aq. (1×50.0 mL) and sat. NaCl aq. (1×50.0 mL). The combined aqueous phase was back extracted with EtOAc (1×100 mL). The combined organic phases were evaporated to dryness, and the crude material was purified by reverse phase prep-HPLC (Column: C18 spherical 20-35 μm 100A 80 g, mobile phase: 0.05% $NH_4HCO_3$ in water, m/m)-ACN from 30% to 60%, flow rate: 35 mL/min) to get 9cc (480 mg, 396.26 μmol, 50.28%) as a white foam. ESI-MS: m/z 1211.5 [M+H]$^+$.

Compound 9cc (480 mg, 396.26 μmol) was treated with a solution of $MeNH_2$ in EtOH (12.0 mL, 33%). After stirring for 2 h at 40° C., the mixture was evaporated to dryness. The crude material was purified by reverse phase prep-HPLC (Column: C18 spherical 20-35 μm 100A 40 g, mobile phase A: 0.05% $NH_4HCO_3$ in water, m/m-ACN from 0% to 10%, flow rate: 20 ml/min) to afford 10cc (210 mg, 144.85 μmol, 56.0%) as a white foam. ESI-MS: m/z 945.3 [M+H]$^+$.

A solution of 10cc (210 mg, 144.85 μmol) and 3 HF·TEA (2.0 mL) in DMSO (2.0 mL) was stirred at 40° C. for 48 h. The mixture was cooled to rt, TEA (2.0 mL) and iso-propoxytrimethylsilane (16.0 mL) were added. The mixture was stirred at rt for 1 h, and then evaporated to dryness. The residue was purified by reverse phase prep-HPLC (Column: XBridge 30×100 mm, mobile phase: 0.05% $NH_4HCO_3$ in water-ACN from 0% to 15%, flow rate: 20 ml/min) to get the $NH_4$ salt (P1, 70.00 mg, 98.31 μmol, 27.0% and P2, 20 mg, 28.09 μmol, 7.7%) as a white foam. 15.0 mL volume of Amberlite IR-120 (Na form) was added to a column and washed with deionized water (3×15 mL). The $NH_4$ salt was dissolved in deionized water (15 mL) and added to the top of the column. The column was eluted with deionized water. The compound was eluted out in early fractions as detected by TLC (UV). The product was lyophilized to give 1-30a (90.00 mg, 118.4 μmol, 56.2%) and 1-30b (2.0 mg, 2.3 μmol, 1.60% yield) as a white foam.

1-30a: $^1$H NMR (400 MHz, $D_2O$) δ: 8.15 (d, J=19.7 Hz, 2H), 7.86 (s, 1H), 5.93 (d, J=8.4 Hz, 1H), 5.75 (s, 1H), 5.04 (t, J=7.7 Hz, 1H), 4.82 (s, 1H), 4.78-4.75 (m, 1H), 4.63 (s, 1H), 4.41 (t, J=7.9 Hz, 2H), 4.16 (dd, J=10.9, 5.0 Hz, 1H), 3.60 (t, J=6.4 Hz, 1H), 3.53 (d, J=10.9 Hz, 1H), 1.55 (t, J=5.0 Hz, 1H), 0.96 (t, J=7.4 Hz, 1H). $^{31}$P NMR (162 MHz, $D_2O$): 53.65, −2.90. ESI-MS: m/z 717.2 [M+H]$^+$.

1-30b: $^{31}$P NMR (162 MHz, $D_2O$) 53.93, −2.56. ESI-MS: m/z 717.2 [M+H]$^+$.

Example 31

Compounds 1-46a & 1-46b

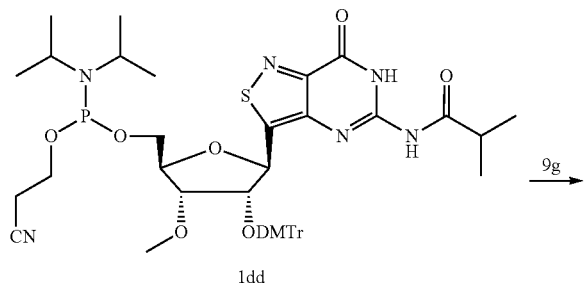

263

-continued

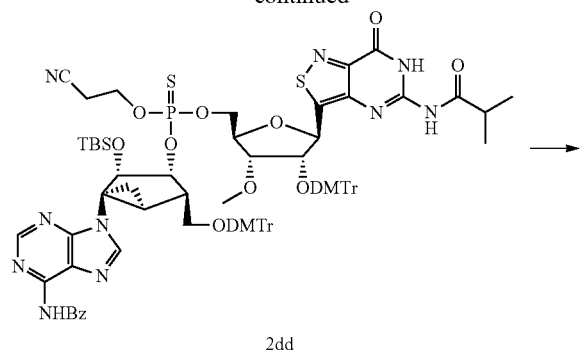

2dd

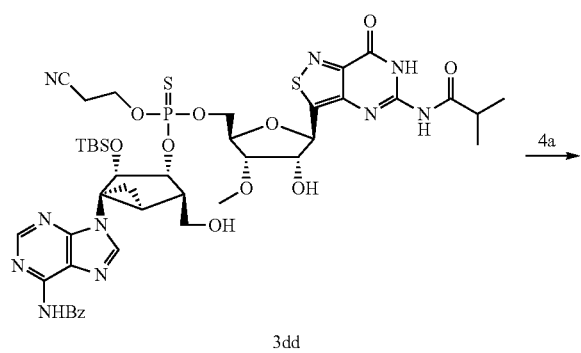

3dd

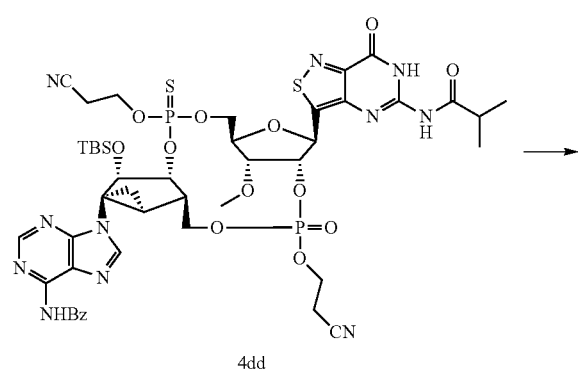

4dd

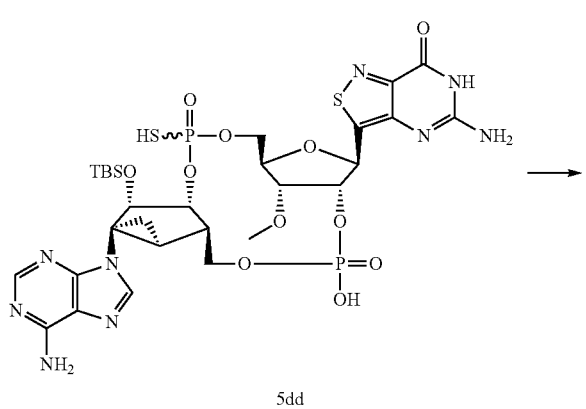

5dd

264

-continued

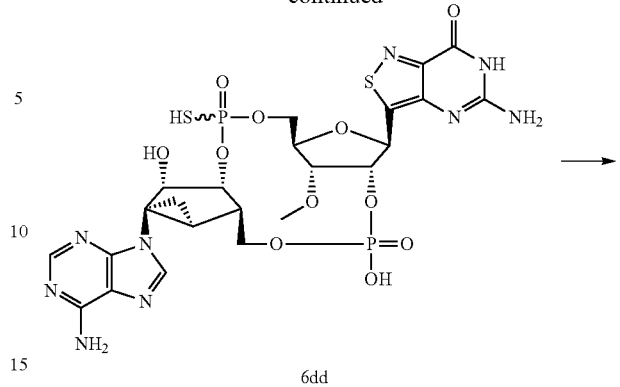

6dd

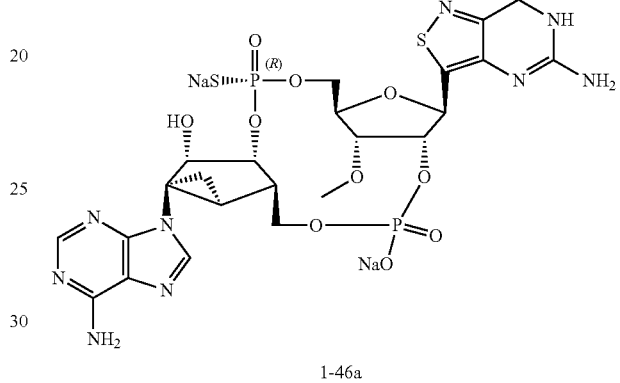

1-46a

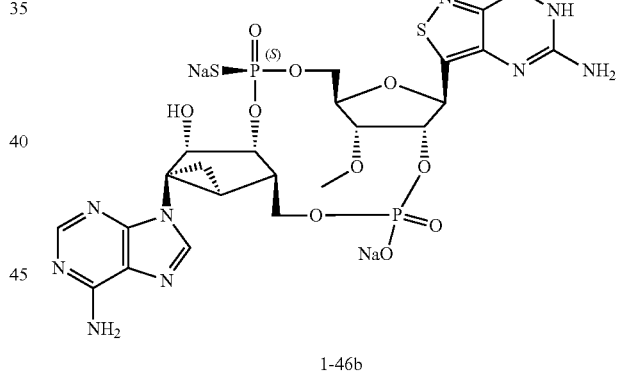

1-46b

Compound 1dd (700 mg, 0.79 mmol) was dissolved in anhydrous CH$_3$CN (50.0 mL), and 9 g (550 mg, 0.69 mmol) and 4 Å molecular sieves powder (150 mg, 1 gr/100 mL) were added. The mixture was bubbled with Ar gas for 4 min. After stirring at rt for 20 min, 0.25 M ETT in CH$_3$CN (4.0 mmol, 16 mL) was added at rt. After stirring for 1 h, the mixture was filtered and washed with anhydrous CH$_3$CN. To this solution was added 0.1N DDTT in pyridine (2 mL) until the reaction was complete. After stirring for 20-30 min at rt, the reaction was quenched with Na$_2$SO$_3$ (aq, until discoloration). The mixture was diluted with EtOAc, and the layers were separated. The organic phase was washed with sat. aq. NaHCO$_3$ (1×) and sat. aq. NaCl (1×). The combined aqueous phase was back extracted with EtOAc (1×). The combined organic phases were evaporated to dryness, and the crude material was purified by reverse phase prep-HPLC (Column:

C18 spherical 20-35 μm 100A 80 g, mobile phase: 0.05% NH$_4$HCO$_3$ in water, m/m)-ACN from 60% to 100%, flow rate: 35 mL/min) to get 2dd (1.0 g, 0.619 mmol, 89.7%) as a white foam. $^{31}$P NMR (162 MHz, DMSO-d$_6$) δ: 68.29, 67.84. ESI-MS: m/z 1616.45 [M+H]$^+$.

Compound 2dd (1.0 mg, 0.619 mmol) was dissolved in DCA in DCM (3%, v/v, 20 mL) and triethyl silane (5 mL) was added immediately. After stirring for 30 min at rt, the mixture was neutralized with sat. sodium bicarbonate solution at 0° C. and evaporated to dryness. The crude residue was purified by silica gel column chromatography (DCM: Acetone, 10:1~1:1) to get 3dd (600 mg, 594 umol, 96.0) as a yellow solid. ESI-MS: m/z 1010.4 [M+H]$^+$.

Compound 3dd (600 mg, 594 umol) dissolved in anhydrous CH$_3$CN (60.0 mL), 0.45 M tetrazole in CH$_3$CN (19 mL) and 4 Å molecular sieves powder (200 mg, 1 gr/100 mL) were added. The mixture was bubbled with N$_2$ gas for 4 min. After stirring at rt for 20 min, 4a (360 mg, 1.2 mmol) in CH$_3$CN (10.0 mL) was added over 25 to 30 min. After stirring 2 h, the mixture was filtered and washed with anhydrous THF. 5 M t-butyl hydroperoxide was added until the reaction was complete. After stirring for 20-30 min at rt, the reaction was quenched with sat. aq. Na$_2$SO$_3$. The mixture was diluted with EtOAc, and the layers were separated. The organic phase was washed with sat. aq NaHCO$_3$ (1×60 mL) and sat. aq. NaCl (1×60 mL). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water-ACN from 70% to 80%, flow rate: 30 mL/min) to get 4dd (375 mg, 338 μmol, 56.9%) as a white foam. ESI-MS: m/z 1126.35 [M+H]$^+$.

Compound 4dd (375 mg, 338 μmol) was treated with a solution of 33% MeNH$_2$ in EtOH (10 mL). After stirring for 2 h at 40° C., the mixture was evaporated to dryness, and the crude material was purified by reverse phase prep-HPLC (Column: C18 spherical 20-35 μm 100A 40 g, mobile phase: 0.05% NH$_4$HCO$_3$ in water-ACN from 0% to 30%, flow rate: 20 mL/min) to get a first isomer of 5dd (30 mg, 35.5 μmol, 10.5%) and a second isomer of 5dd (80 mg, 94.7 μmol, 28.0%=) as white foams. $^{31}$P NMR (162 MHz, DMSO-d$_6$) δ 56.58, 3.02. ESI-MS: m/z 812.2 [M+H]$^+$.

A solution of the first isomer of 5dd (30 mg, 35.5 μmol) in 3 HF·TEA (0.5 mL) and DMSO (1 mL), and the second isomer of 5dd (80 mg, 94.7 μmol) in 3 HF·TEA (1 mL) and DMSO (2 mL) was stirred at 40° C. for 32 h. The mixture was cooled to rt. TEA (2 mL) and isopropoxytrimethylsilane (16 mL) were added to the mixture. The mixture was stirred at rt for 1 h and then evaporated to dryness. The residue was purified by reverse phase prep-HPLC (Column: C18 spherical 20-35 μm 100A 40 g, mobile phase: 0.05% NH$_4$HCO$_3$ in water-ACN from 0% to 10%, flow rate: 20 ml/min-ACN from 0% to 10%, flow rate: 20 mL/min) to get the NH$_4$ salts (a first isomer of 6dd (16 mg, 21.9 μmol, 61.7%) and (a second isomer of 6dd (46 mg, 62.9 μmol, 66.5%)) as foams. A 15.0 mL volume of Amberlite IR-120 (Na form) was added to a column and washed with deionized water (3×15 mL). The NH$_4$ salts of the first isomer of 6dd and the second isomer of 6dd were dissolved in deionized water (15 mL) and added to the top of the column. The column was eluted with deionized water. The compound was eluted out in early fractions as detected by TLC (UV). The product was lyophilized to give 1-46a (12 mg, 15.5 μmol, 43.6%) and 1-46b (41 mg, 52.9 μmol, 55.9%) as white foams.

1-46a: $^1$H NMR (400 MHz, D$_2$O) δ: 8.10-8.03 (m, 1H), 7.82-7.73 (m, 1H), 5.23 (d, J=11.3 Hz, 1H), 5.10 (s, 1H), 4.57 (s, 1H), 4.46 (d, J=4.9 Hz, 1H), 4.27-4.02 (m, 6H), 3.46 (s, 3H), 2.49-2.37 (m, 1H), 1.99 (t, J=5.6 Hz, 1H), 1.80 (s, 1H), 1.31 (t, J=8.1 Hz, 1H). $^{31}$P NMR (162 MHz, D$_2$O) δ: 55.86, −1.63. ESI-MS: m/z 698.3 [M+H]$^+$.

1-46b: $^1$H NMR (400 MHz, D$_2$O) δ: 8.05 (s, 1H), 7.82 (s, 1H), 5.22 (d, J=9.5 Hz, 1H), 5.11 (t, J=5.8 Hz, 1H), 4.50 (s, 1H), 4.46 (d, J=3.1 Hz, 1H), 4.41 (dd, J=5.9, 1.4 Hz, 1H), 4.37 (dd, J=11.8, 6.4 Hz, 1H), 4.19 (dt, J=10.1, 3.1 Hz, 1H), 4.15-4.03 (m, 3H), 3.46 (d, J=1.0 Hz, 3H), 2.46-2.39 (m, 1H), 2.02 (t, J=5.5 Hz, 1H), 1.79 (dd, J=9.4, 4.9 Hz, 1H), 1.31-1.23 (m, 1H). $^{31}$P NMR (162 MHz, D$_2$O) δ: 53.42, −1.73. ESI-MS: m/z 698.3 [M+H]$^+$.

Example 32

Compounds 1-28a & 1-28b

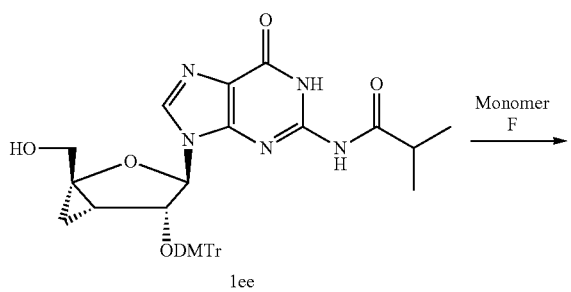

-continued
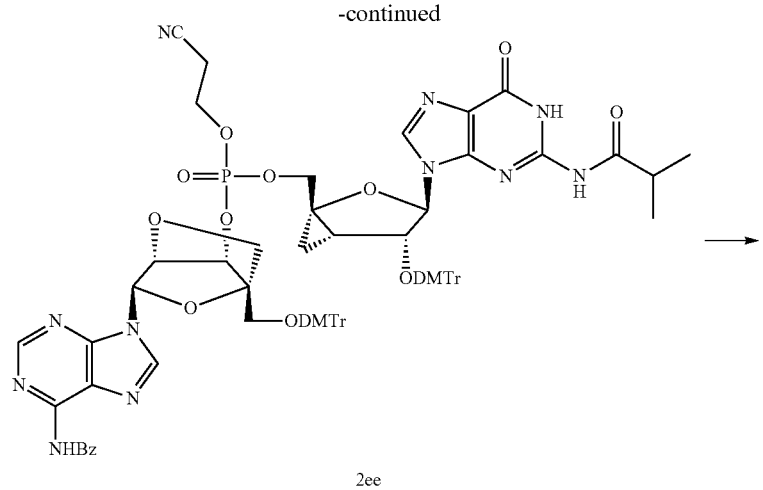
2ee
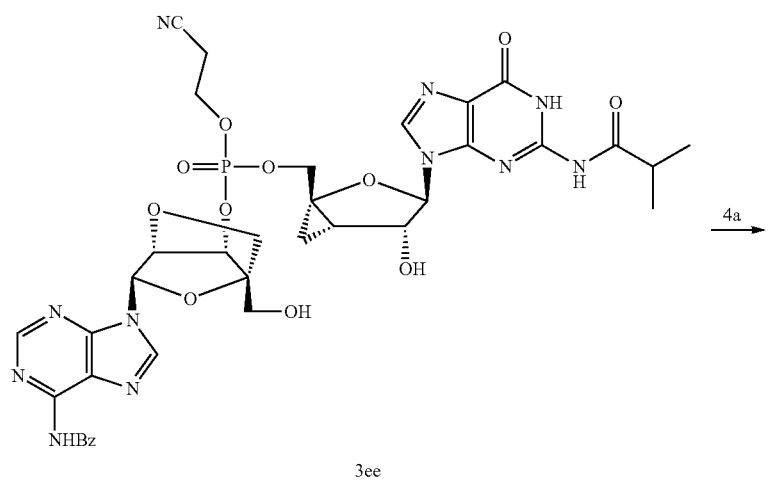
3ee
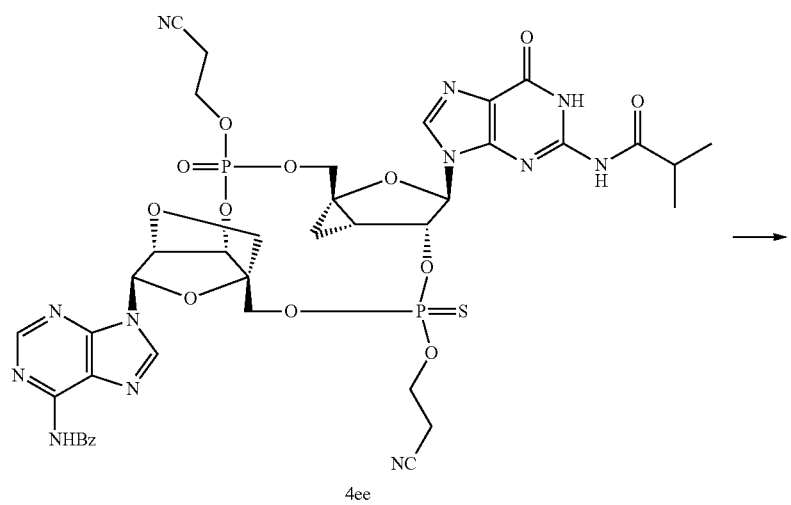
4ee

-continued

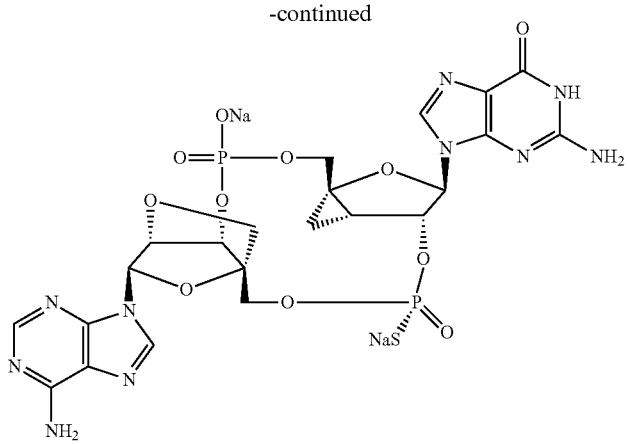

1-28a

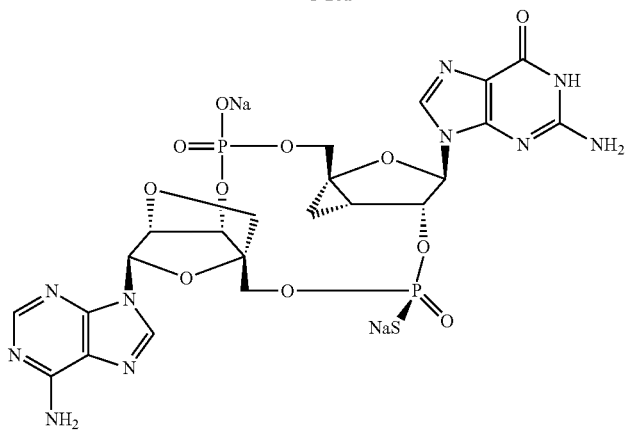

1-28b

Compound 1ee (400 mg, 613.77 umol) and Monomer F (706.90 mg, 797.90 umol) was dissolved in anhydrous CH$_3$CN (24.0 mL) and 4 Å molecular sieves powder (300 mg, 1 gr/100 mL) were added. The mixture was bubbled with Ar gas for 4 min. After stirring at rt for 20 min, 0.45 M tetrazole in CH$_3$CN (613.77 umol, 8.17 mL) was added at rt. After stirring for 1 h, the mixture was washed with anhydrous CH$_3$CN. To this solution was added 5 M t-BuOOH until the reaction was completed. After stirring for 20-30 min at rt, the mixture was filtered. The reaction was quenched with Na$_2$SO$_3$ (aq). The mixture was diluted with EtOAc, and the layers were separated. The organic phase was washed with sat. aq. NaHCO$_3$ (1×50.0 mL) and sat. aq. NaCl (1×50.0 mL). The combined aqueous phase was back extracted with EtOAc (1×50.0 mL). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 60% to 100%, flow rate: 35.0 mL/min) to get 2ee (810 mg, 557.68 umol, 90.86%) as a white foam. $^{31}$P-NMR (162 MHz, DMSO-d$_6$): −3.15, −3.20. ESI-MS: m/z 1452.6 [M+H]$^+$.

Compound 2ee (810 mg, 557.68 umol) was dissolved in DCA in DCM (3%, v/v, 14.5 mL), and triethylsilane (5.7 mL) was added immediately. After stirring for 20 min at rt, the mixture was neutralized with pyridine (14.5 mL). The mixture was concentrated in vacuo to get the crude material, which was purified by reverse phase prep-HPLC (Column: C18 spherical 20-35 μm 100A 80 g, mobile phase: 0.05% NH$_4$HCO$_3$ in water, m/m)-ACN from 0% to 60%, flow rate: 35.0 mL/min) to get 3ee (357 mg, 421.13 umol, 75.51%) as a white solid. $^{31}$P-NMR (162 MHz, DMSO-d$_6$): −2.90, −3.07. ESI-MS: m/z=848.5 [M+H]$^+$.

Compound 3ee (300 mg, 353.89 umol) dissolved in anhydrous CH$_3$CN (45.0 mL), 0.45 M tetrazole in CH$_3$CN (2.83 mmol, 6.28 mL) and 4 Å molecular sieves powder (1 gr/100 mL) were added. The mixture was bubbled with Ar gas for 4 min. After stirring at rt for 20 min, 4a (213.33 mg, 707.78 umol) in CH$_3$CN (5.0 mL) was added at rt over 25 to 30 min. After stirring for 2 h, the mixture was filtered and washed with anhydrous CH$_3$CN. To this solution was added 0.1 M DDTT (5.30 mL) until the reaction was complete. After stirring for 20-30 min at rt, the reaction was quenched with sat. aq. NaS$_2$O$_3$. The mixture was diluted with EtOAc, and the organic layers separated. The organic phase was washed with sat.NaHCO$_3$ aq. (1×50.0 mL) and sat. NaCl aq. (1×50.0 mL). The combined aqueous phase was back extracted with EtOAc (1×100 mL). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 0% to 50%, flow rate: 35 mL/min) to get 4ee (20 mg, 20.43 umol, 5.77%) as a white foam. ESI-MS: m/z 979.3 [M+H]$^+$.

Compound 4ee (20 mg, 20.43 umol) was treated with a solution of MeNH$_2$ in EtOH (5.0 mL, 33%). After stirring for 2 h at 40° C., the mixture was evaporated to dryness, and the crude material was purified by reverse phase prep-HPLC (Column: C18 spherical 20-35 μm 100A 40 g, mobile phase A: 0.05% NH₄HCO₃ in water, m/m-ACN from 0% to 10%, flow rate: 12 mL/min) to afford the NH₄ salt of 1-28 (mixture of isomer) (8.6 mg, 12.31 umol, 60.26%) as a white foam. The mixture was purified by reverse phase prep-HPLC (Column: XBridge 30×100 mm, mobile phase: 10 mM TEAA in water, m/m)-ACN from 0% to 8%, flow rate: 20 mL/min) and lyophilized get the NH₄ salt of 1-28a (2 mg, 2.86 mol, 21.0%, ³¹P-NMR (162 MHz, DMSO-d₆): δ5.41, −2.65) and the NH₄ salt of 1-28b (1 mg, 1.43 μmol, 21.0%, ³¹P-NMR (162 MHz, DMSO-d₆): δ3.63, −2.68) as white foams. ESI-LMS: m/z 699.4 [M+H]⁺.

A 15.0 mL volume of Amberlite IR-120 (Na form) was added to a column and washed with deionized water (3×15 mL). The NH₄ salt of 1-28a (2 mg) was dissolved in deionized water (2 mg in 10 mL) and added to the top of the column. The column was eluted with deionized water. The compound was eluted out in early fractions as detected by TLC (UV). The product was lyophilized to give 1-28a (1 mg, 1.43 umol, 50%) as a white foam. ¹H NMR (400 MHz, D₂O) δ: 8.18 (s, 1H), 8.00 (s, 1H), 7.71 (s, 1H), 6.11 (s, 1H), 5.97-5.95 (m, 1H), 5.58-5.57 (d, J=6.92 Hz, 1H), 5.26 (s, 1H), 5.16 (s, 1H), 4.49-4.41 (m, 2H), 4.37-4.33 (m, 1H), 4.18-4.16 (m, 1H), 4.00-3.97 (d, J=8.0 Hz, 1H), 3.86-3.80 (m, 1H), 2.21-2.14 (m, 1H), 1.69-1.63 (m, 1H), 1.22-1.15 (m, 1H). ³¹P-NMR (162 MHz, DMSO-d₆): δ5.41, −2.65. ESI-MS: m/z 699.4 [M+H]⁺.

A 15.0 mL volume of Amberlite IR-120 (Na form) was added to a column and washed with deionized water (3×15 mL). The NH₄ salt of 1-28b (1 mg) was dissolved in deionized water (1 mg in 10 mL) and added to the top of the column. The column was eluted with deionized water. The compound was eluted out in early fractions as detected by TLC (UV). The product was lyophilized to give 1-28b (0.5 mg, 0.71 umol, 50%) as a white foam. ¹H NMR (400 MHz, D₂O) δ: 8.19 (s, 1H), 7.85 (s, 1H), 7.71 (s, 1H), 6.12 (s, 1H), 5.87-5.85 (m, 1H), 5.56-5.54 (d, J=7.24 Hz, 1H), 5.22 (s, 1H), 5.18 (s, 1H), 4.46-4.35 (m, 2H), 4.17-4.15 (m, 1H), 3.99-3.97 (d, J=8.0 Hz, 1H), 3.84-3.77 (m, 1H), 2.14-2.09 (m, 1H), 1.61-1.58 (m, 1H), 1.17-1.14 (m, 1H). ³¹P-NMR (162 MHz, DMSO-d₆): δ3.63, −2.68. ESI-MS: m/z 699.4 [M+H]⁺.

Example 33

Compounds 1-34a & 1-34b

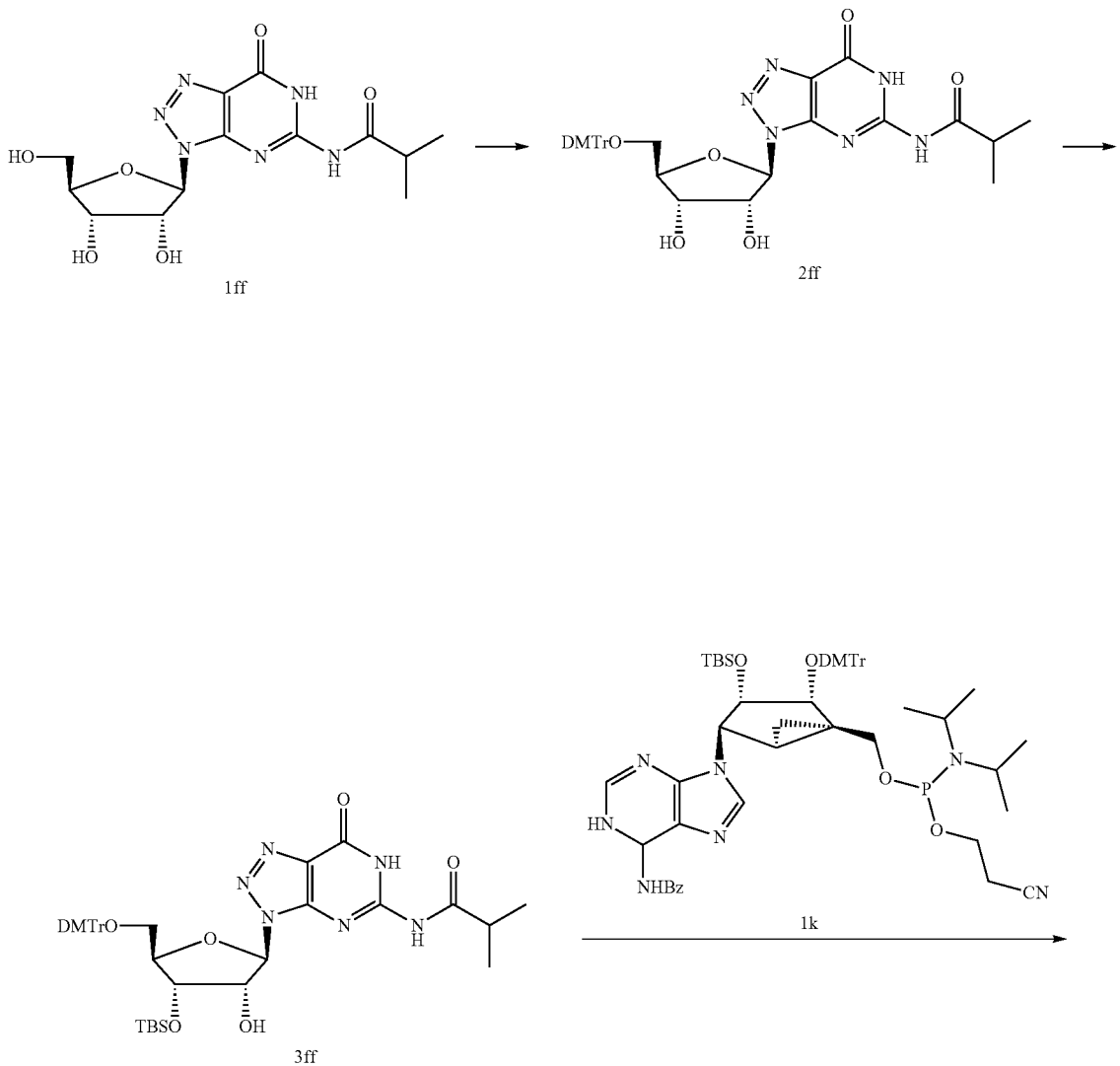

-continued
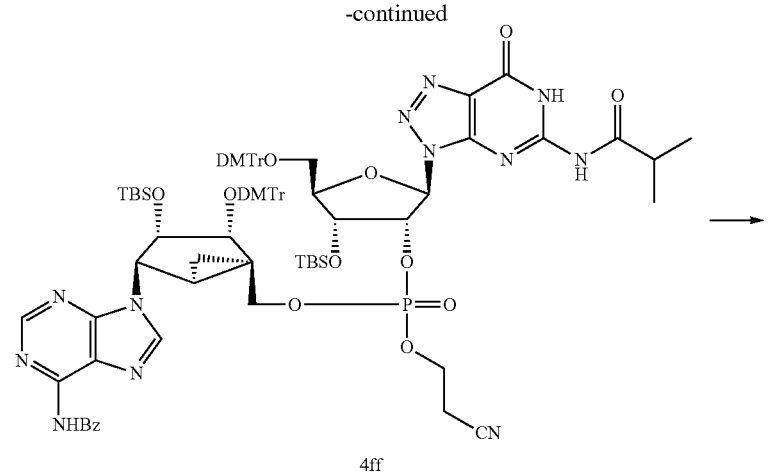
4ff
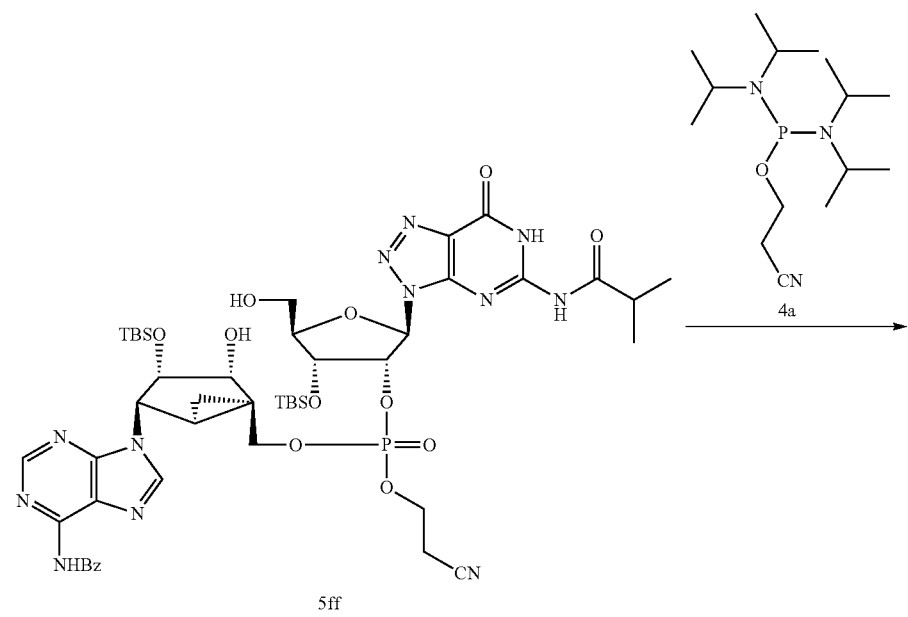
5ff
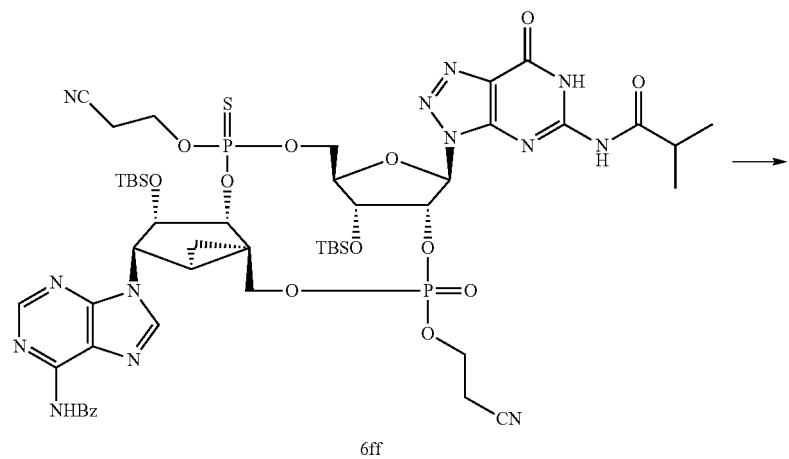
6ff

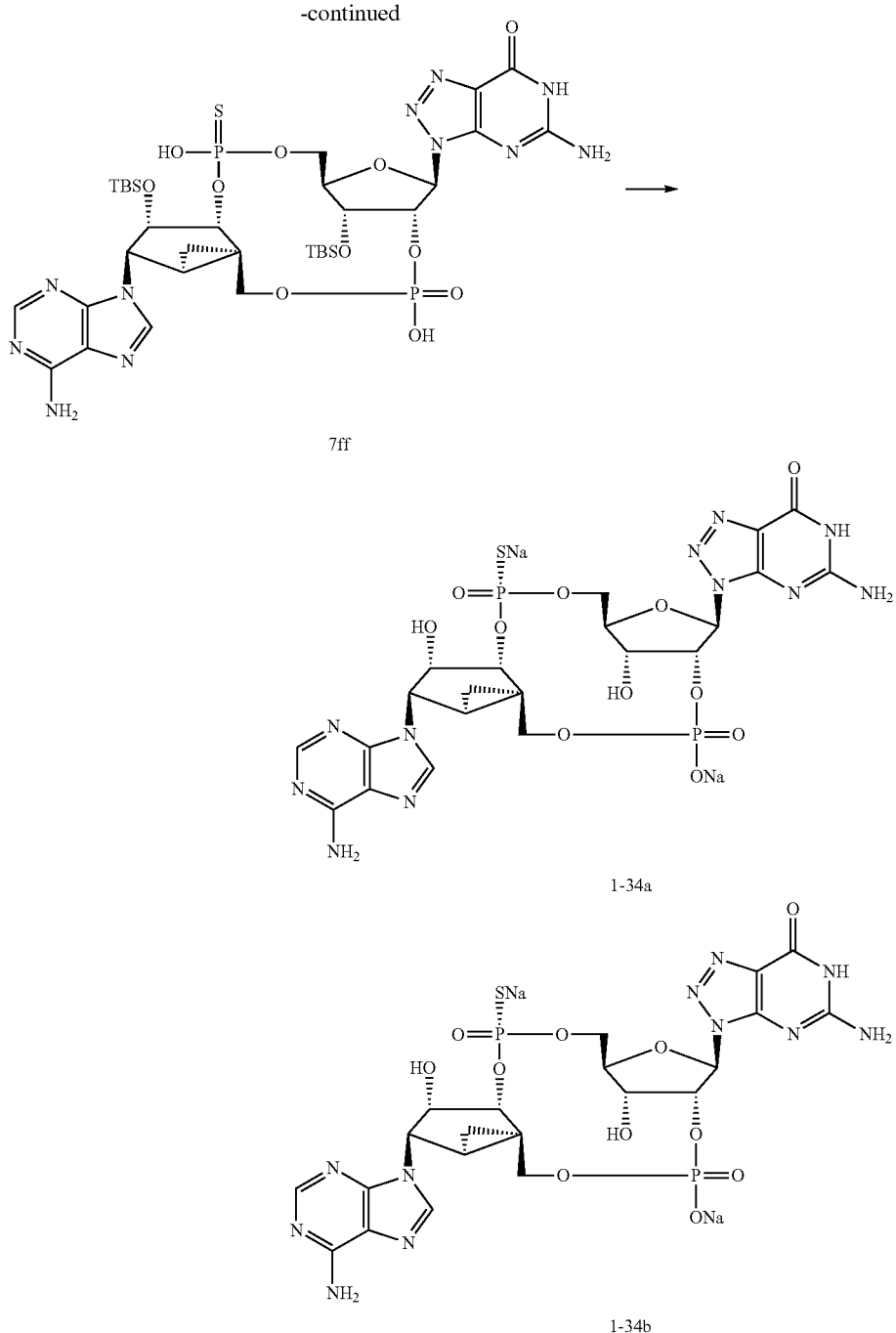

7ff 1-34a 1-34b

Compound 1ff (2.0 g, 5.64 mmol) and DMTrCl (2.30 g, 6.77 mmol) were dissolved in anhydrous pyridine (30 mL) under Ar. The mixture was stirred 2 h at rt. The reaction was quenched with NaHCO₃ (aq.) and extracted with EtOAc (3×40 mL). The organic phase was washed with sat. aq. NaHCO₃ (1×50.0 mL) and sat. aq. NaCl (1×50.0 mL). The combined aqueous phase was back extracted with EtOAc (1×50.0 mL). The combined organic phases were evaporated to dryness, and the crude material was purified by cc (DCM:MeOH=15:1) and 2ff (2.3 g, 3.50 mmol, 62.05% yield) as a white solid. ESI-MS: m/z 657.4 [M+H]⁺.

Compound 2ff (2.2 g, 3.35 mmol) and imidazole (1.37 g, 20.10 mmol) were dissolved in anhydrous DMF (30 mL). TBSCl (331.08 mg, 4.02 mmol) was added, and the mixture was stirred 2 h at rt. The reaction was quenched with NaHCO₃ (aq.) and extracted with EtOAc (3×30 mL). The organic phase was washed with sat. aq. NaHCO₃ (1×50.0 mL) and sat. aq. NaCl (1×50.0 mL). The combined aqueous phase was back extracted with EtOAc (1×50.0 mL). The combined organic phases were evaporated to dryness, and the crude material was purified by cc (DCM:MeOH=30:1) to afford 3ff (850 mg, 1.10 mmol, 32.91% yield) as a white solid. ESI-MS: m/z 771.5 [M+H]⁺.

Compound 3ff (0.85 g, 1.10 mmol) and 1k (1.21 g, 1.21 mmol) were dissolved in anhydrous CH₃CN (30.0 mL) and 4 Å molecular sieves powder (300 mg, 1 gr/100 mL) were added. The heterogeneous mixture was bubbled with Ar gas for 5 min. After stirring at rt for 20 min, 0.45 M tetrazole in CH$_3$CN (6.60 mmol, 15.0 mL) was added at rt. After stirring for 1 h, the mixture was washed with anhydrous CH$_3$CN. To this solution was added 5 M t-BuOOH until the reaction was completed. After stirring the mixture for 30 min at rt, the mixture was filtered. The reaction was quenched with Na$_2$SO$_3$ (a.q) and extracted with EtOAc (3×40 mL). The organic phase was washed with sat. aq. NaHCO$_3$ (1×50.0 mL) and sat. aq. NaCl (1×50.0 mL). The combined aqueous phase was back extracted with EtOAc (1×50.0 mL). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 60% to 100%, flow rate: 35.0 mL/min) to get 4ff (1.60 g, 0.95 mmol, 86% yield) as a white solid. $^{31}$P-NMR (162 MHz, DMSO-d$_6$): −2.51, −2.69; ESI-MS: m/z 1684.7 [M+H]$^+$.

Compound 4ff (1.50 g, 0.89 mmol) was dissolved in AcOH in CH$_3$CN (v:v=4:1, 20.0 mL). After stirring for 3 h at 40° C., the mixture was neutralized with ice sat. NaHCO$_3$ (aq.) and extracted with EtOAc (3×30.0 mL). The organic layers was washed with sat. NaCl aq. (1×50.0 mL), dried over Na$_2$SO$_4$ and concentrated under reduced pressure to give a residue. The crude residue was purified by silica gel column chromatography (DCM:acetone, 0-100% acetone) to afford 5ff (700.0 mg, 649.2 μmol, 72.8% yield) as a white solid. ESI-MS: m/z=1079.5[M+H]$^+$.

Compound 5ff (600.0 mg, 555.9 μmol) was dissolved in anhydrous CH$_3$CN (70.0 mL), and 0.45 M tetrazole in CH$_3$CN (3.36 mmol, 7.5 mL) and 4 Å molecular sieves powder (7.0 g, 1 gr/100 mL) were added. The heterogeneous mixture was bubbled with Ar gas for 4 min. After stirring at rt for 20 min., 4a (335.1 mg, 1.11 mmol) in CH$_3$CN (10.0 mL) was added at rt over 25 to 30 min. After stirring for 2 h, the mixture was filtered, and washed with anhydrous CH$_3$CN. 0.1M DDTT (0.1M 11 mL) was added until the reaction completed. After stirring for 30 min at rt, the mixture was filtered. The reaction was quenched with Na$_2$SO$_3$ (aq.) and extracted with EtOAc (3×40 mL). The organic phase was washed with sat. aq. NaHCO$_3$ (1×50.0 mL) and sat. aq. NaCl (1×50.0 mL). The combined aqueous phase was back extracted with EtOAc (1×50.0 mL). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 30% to 60%, flow rate: 35 mL/min) to get 6ff (270 mg, 223.3 μmol, 40% yield) as a white foam. ESI-MS: m/z 1211.4 [M+H]$^+$.

Compound 6ff (260 mg, 214.8 μmol) was treated with a solution of NH$_3$ in MeOH (10.0 mL, 7M). After stirring for 24 h at rt, the mixture was evaporated to dryness. The crude material was purified by reverse phase prep-HPLC (Column: C18 spherical 20-35 μm 100A 40 g, mobile phase A: 0.05% NH$_4$HCO$_3$ in water, m/m-ACN from 0% to 10%, flow rate: 20 ml/min) to afford 7ff (165 mg, 177.4 μmol, 82.6% yield) as a white foam. ESI-MS: m/z 931.3 [M+H]$^+$.

A solution of 7ff (160 mg, 172.0 μmol) and TEAF (12%) in DMSO (5.0 mL) was stirred at 40° C. for 12 h. The mixture was cooled to rt and then evaporated to dryness. The residue was purified by reverse phase prep-HPLC (Column: XBridge 30×100 mm, mobile phase: 0.05% NH$_4$HCO$_3$ in water-ACN from 0% to 15%, flow rate: 20 ml/min) to get the ammonia salt 8ff-P1 (26.1 mg, 37.1 mol, 22% yield, and 8ff-P2: 59.2 mg, 84.1 mol, 49% yield) as a white foam. 15.0 mL volume of Amberlite IR-120 (Na form) was added to a column and washed with deionized water (3×15 mL). The ammonia salt products were dissolved in deionized water (15 mL). The compounds were added to the top of a column, and eluted with deionized water. The compounds eluted out in early fractions as detected by TLC (UV). The products was lyophilized to give 1-34a (16 mg, 21.5 μmol, 58% yield) and 1-34b (51.0 mg, 67.1 μmol, 80% yield) as a white foam.

1-34a: $^1$H NMR (400 MHz, D$_2$O): δ 8.26 (s, 1H), 8.20 (s, 1H), 6.23 (d, J=8.4 Hz, 1H), 5.78 (s, 1H), 5.67 (t, J=7.0 Hz, 1H), 4.91 (s, 1H), 4.67 (s, 1H), 4.5 (d, J=8.0 Hz, 1H), 4.44 (s, 1H), 4.30 (m, 1H), 4.28 (d, J=6.0 Hz, 1H), 3.96 (d, J=11.72 Hz, 1H), 3.60 (d, J=11.08 Hz, 1H), 1.88 (d, J=5.12 Hz, 1H), 1.69 (s, 1H), 0.99 (t, J=5.92 Hz, 1H). $^{31}$P NMR (162 MHz, D$_2$O): 54.25, −2.65. ESI-MS: m/z 702.2 [M+H]$^+$.

1-34b: $^1$H NMR (400 MHz, D$_2$O): δ 8.26 (s, 1H), 8.20 (s, 1H), 6.21 (d, J=8.36 Hz, 1H), 5.77 (s, 1H), 5.64 (t, J=7.48 Hz, 1H), 4.94 (s, 1H), 4.55 (m, 2H), 4.43 (s, 1H), 4.42-4.05 (dd, J$_1$=30.12 Hz, J$_2$=11.36 Hz, 2H), 3.61 (d, J=10.96 Hz, 1H), 3.60 (d, J=11.08 Hz, 1H), 1.87 (d, J=5.04 Hz, 1H), 1.63 (s, 1H), 0.99 (t, J=6.84 Hz, 1H). $^{31}$P NMR (162 MHz, D$_2$O): 52.74, −2.60. ESI-MS: m/z 702.2 [M+H]$^+$.

Example 34

Compounds 1-35a & 1-35b

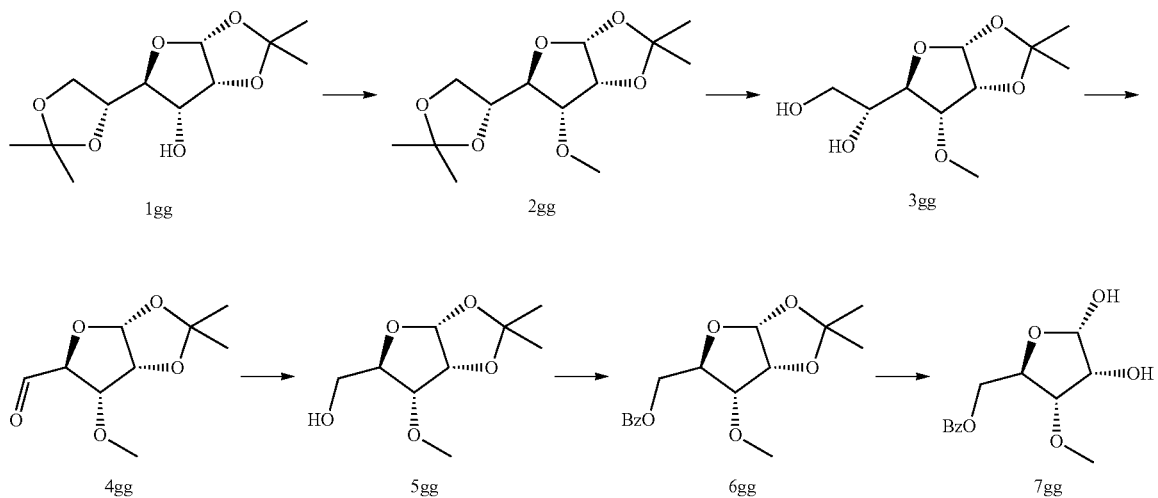

-continued
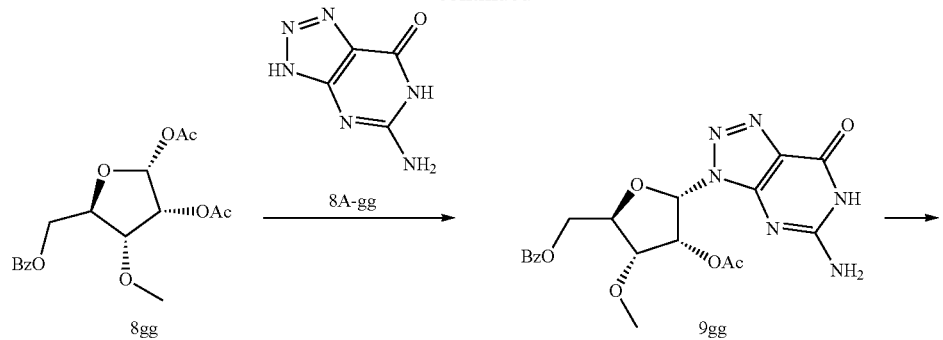
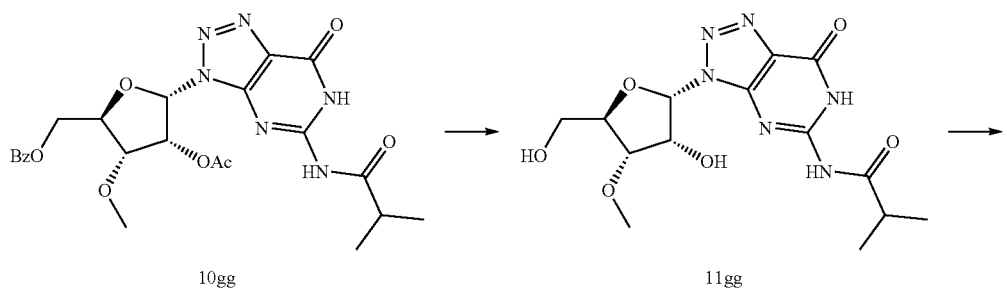
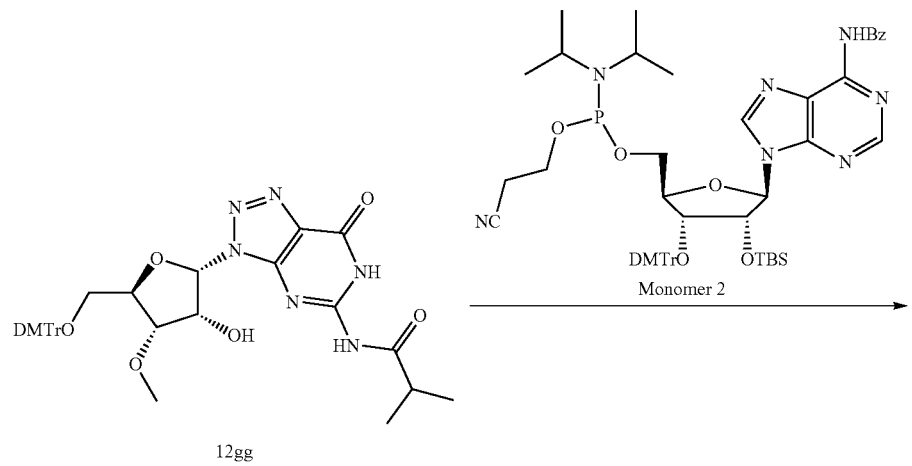
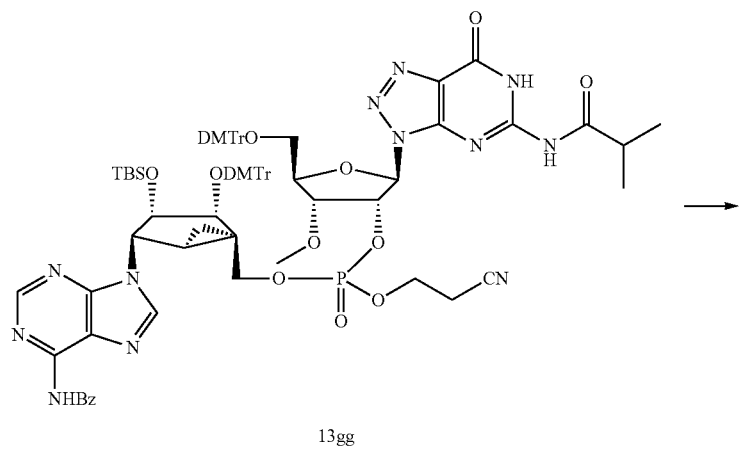

-continued
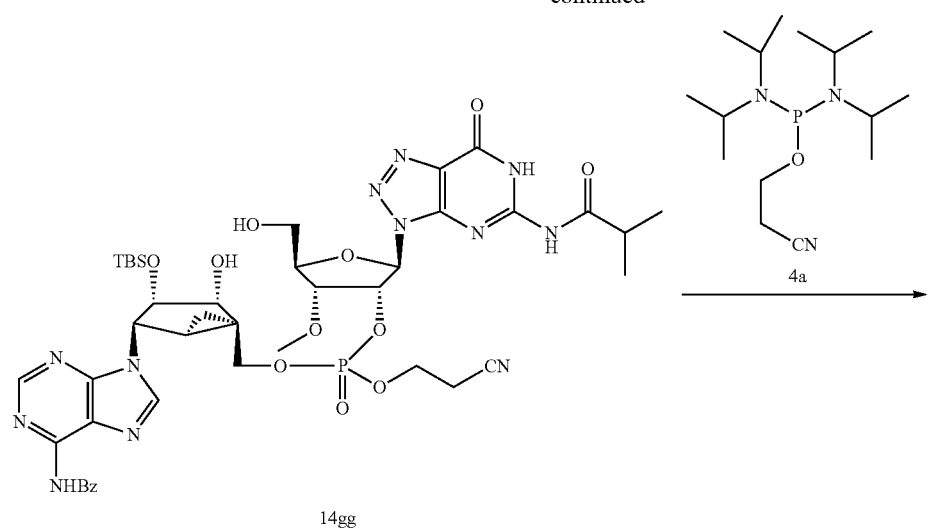
14gg
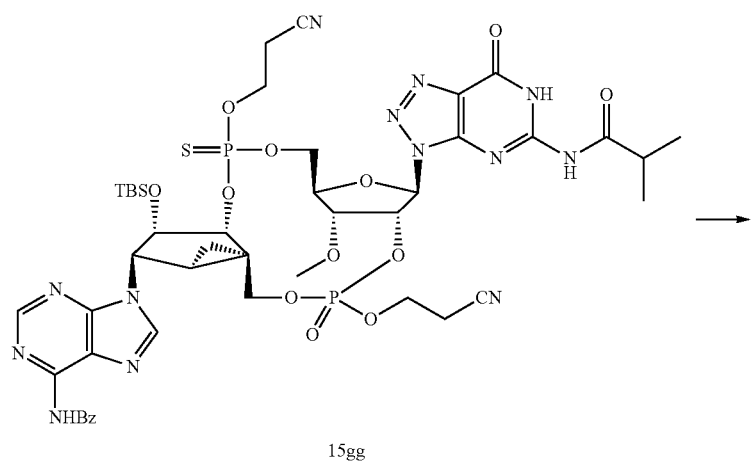
15gg
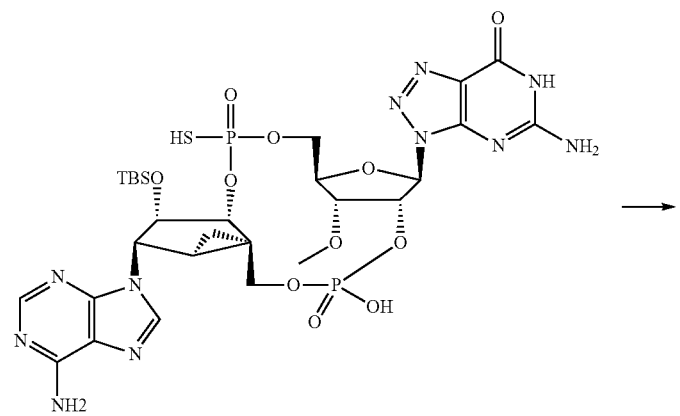
16gg-P1

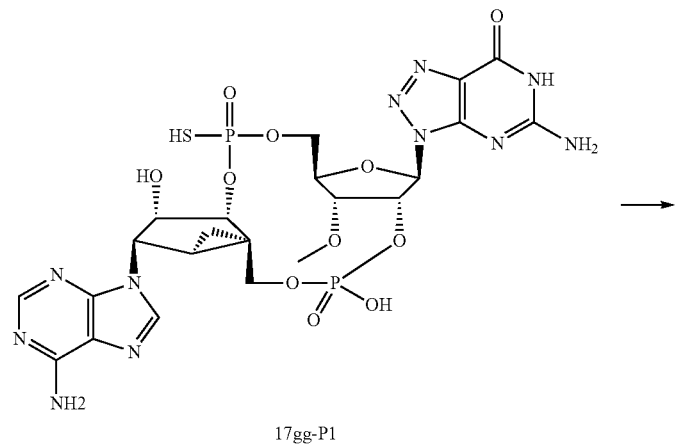
17gg-P1
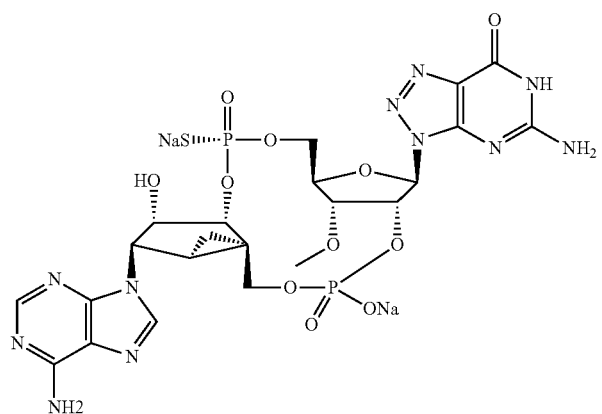
1-35a
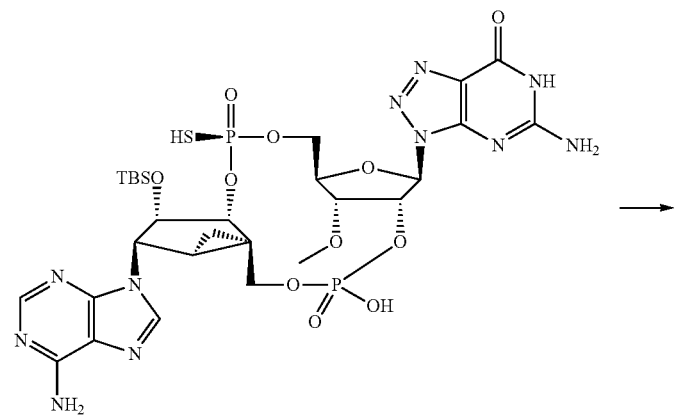
16gg-P2

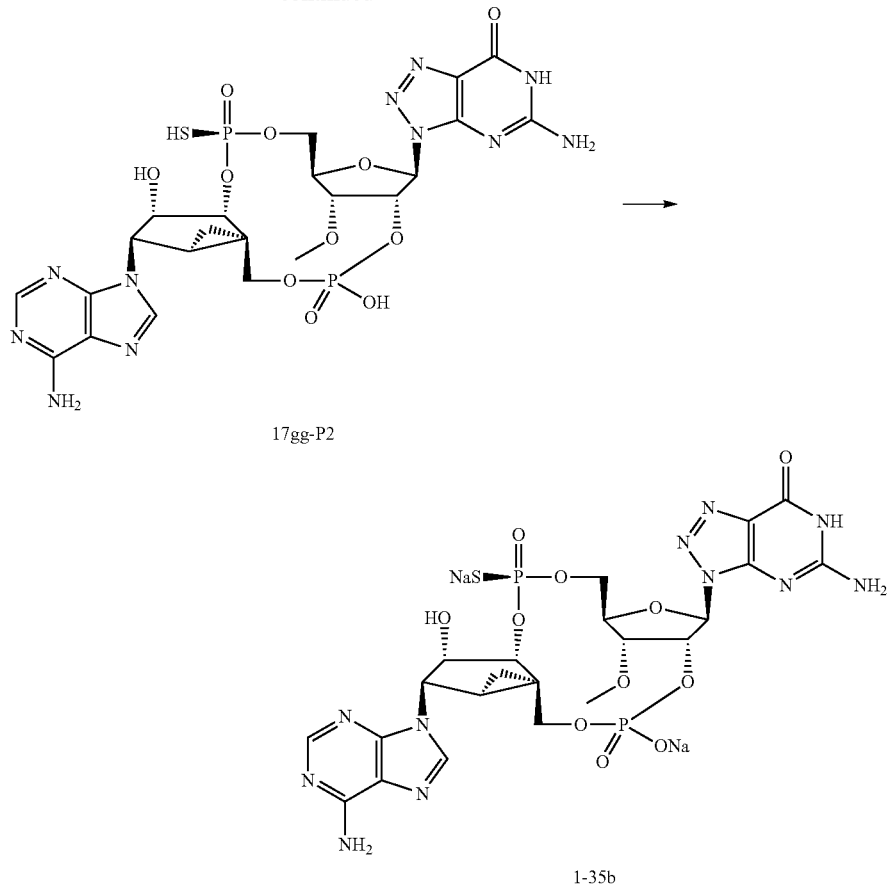

17gg-P2

1-35b

To a 1000 mL round bottomed flask was added 1gg (50 g, 192.10 mmol) and THF (500 mL), KOH (26.95 g, 480.25 mmol). PTSM (53.66 g, 288.15 mmol) was then dropwise. The mixture was stirred at 25° C. overnight. The mixture was added to aq. NH$_4$Cl and then extracted with EtOAc (3×200 mL). The combined EtOAc layer was washed with brine and concentrated in vacuo to give crude 2gg (70.00 g).

To a 1000 mL round bottomed flask was added 2gg (70 g, 255.19 mmol) and 60% AcOH (480 mL). The mixture was stirred at 30° C. overnight. The mixture was adjusted pH=7-8 with NaHCO$_3$. The mixture was filtered, and the filter cake was washed with DCM:MeOH=20:1 (500 mL). The filtrate was concentrated in vacuo to give a crude which was purified by Slica column chromatography (DCM:MeOH=20:1) to obtain 3gg (38.00 g, 162.22 mmol, 63.57% yield). $^1$H NMR (400 MHz, DMSO-d$_6$): δ 5.69 (d, J=3.7 Hz, 1H), 4.82 (d, J=4.7 Hz, 1H), 4.69 (t, J=4.2 Hz, 1H), 4.49 (dd, J=6.3, 5.0 Hz, 1H), 3.88 (dd, J=8.7, 2.3 Hz, 1H), 3.75 (dd, J=8.7, 4.5 Hz, 1H), 3.65 (ddt, J=7.1, 5.1, 2.7 Hz, 1H), 3.43-3.35 (m, 1H), 3.30 (m, 4H), 1.43 (s, 3H), 1.28 (s, 3H).

To a 1000 mL round bottomed flask was added 3gg (38.00 g, 162.22 mmol) and EtOH (225 mL), H2O (225 mL). Sodium periodate (52.05 g, 243.33 mmol) was added to the mixture at 0° C. The mixture was stirred at 0° C. for 2 h, and this mixture was used to next step directly.

Sodium borohydride (9.20 g, 243.32 mmol) was added to the mixture from the previous step at 0° C., and then stirred at 0° C. for 30 min. The mixture was added to aq. NH$_4$Cl and extracted with EtOAc (4×200 mL). The combined EtOAc layer was washed with brine and concentrated in vacuo to give a crude. The crude was purified by Slica column chromatography (DCM:MeOH=30:1) to obtain 5gg (29.40 g, 143.96 mmol, 88.75% yield). $^1$H NMR (400 MHz, DMSO-d$_6$): δ 5.71 (d, J=3.8 Hz, 1H), 4.74 (s, 1H), 4.70 (s, 1H), 3.78 (ddd, J=9.1, 4.6, 2.1 Hz, 1H), 3.62 (dd, J=12.5, 2.1 Hz, 1H), 3.54 (dd, J=9.0, 4.4 Hz, 1H), 3.40 (dd, J=12.3, 4.4 Hz, 1H), 3.32 (s, 3H), 1.43 (s, 3H), 1.28 (s, 3H).

To a 500 mL round bottomed flask was added 5gg (28.5 g, 139.56 mmol) and pyridine (250 mL). Benzoyl chloride (49.04 g, 348.89 mmol) was dropwise to the mixture at 0° C. The mixture was stirred at 0° C. for 2 h. The mixture was added to aq. NaHCO$_3$ and extracted with EtOAc (4×50 mL). The combined EtOAc layer was washed with brine and concentrated in vacuo to give a crude which was purified by Slica column chromatography (EtOAc:PE=5:1) to obtain 6gg (37.00 g, 120.00 mmol, 85.99% yield). ESI-MS: m/z 309.3 [M+H]$^+$.

To a 500 mL round bottomed flask was added 6gg (47.5 g, 154.06 mmol) and THF (237 mL) and H$_2$O (47 mL). p-Toluenesulfonic acid (5.31 g, 30.81 mmol) was added, and the mixture stirred at 65° C. for 40 h. The mixture was concentrated in vacuo to remove almost all the THF, and the residue was extracted with EtOAc (5×200 mL). The combined EtOAc layer was washed with brine and concentrated in vacuo to give a crude which was purified by Silica column chromatography (DCM:MeOH=50:1) to obtain 7gg (33.00 g, 123.01 mmol, 79.85% yield). ESI-MS: m/z 269.2 [M+H]$^+$.

Triethylamine (99.58 g, 984.11 mmol, 137.26 mL) and 4-dimethylaminopyridine (1.50 g, 12.30 mmol) was added to a solution of 7gg (33.00 g, 123.01 mmol) in DCM (330 mL). Acetic anhydride (52.17 g, 492.06 mmol) was added at 0° C. The mixture was stirred at rt for 1 h. The mixture was added to aq.NaHCO$_3$ and extracted with DCM (5×500 mL). The combined DCM layer was washed with brine and concentrated in vacuo to give a crude which was purified by Silica column chromatography (EtOAc:PE=1:15) to obtain 8gg (34.00 g, 96.50 mmol, 78.45% yield). ESI-MS: m/z 353.3 [M+H]$^+$.

Compound 8a-gg (6.86 g, 45.13 mmol) and N,O-Bis(trimethylsilyl)acetamide (36.72 g, 180.51 mmol) was added to a solution of 8gg (15.90 g, 45.13 mmol) in ACN (320 mL). The mixture was stirred at 70° C. for 2 h. Trimethylsilyl trifluoromethanesulfonate (15.05 g, 67.69 mmol) was dropwise to the mixture at 0° C. The mixture was then stirred at 80° C. for 2 h. The mixture was added to aq. NH$_4$HCO$_3$ and extracted with EtOAc (4×50 mL). The combined EtOAc layer was washed with brine and concentrated in vacuo to give a crude which was purified by reverse phase prep-HPLC (Column: C18 spherical 20-35 μm 100A 40 g, mobile phase: 0.05% NH$_4$HCO$_3$ in water-ACN from 0% to 40%, flow rate: 20 mL/min) to obtain 9gg (4.80 g, 10.80 mmol, 23.93% yield). ESI-MS: m/z 445.1 [M+H]$^+$.

Isobutyric anhydride (6.83 g, 43.20 mmol) was added to a solution of 9gg (4.8 g, 10.80 mmol) in DMF (40 mL). The mixture was stirred at 80° C. overnight. The mixture was added to aq. NaHCO$_3$ and extracted with EtOAc (4×100 mL). The combined EtOAc layer was washed with brine and concentrated in vacuo to give crude 10gg (7 g). ESI-MS: m/z 515.1 [M+H]$^+$.

2N NaOH (19 mL) (solvent: MeOH:H$_2$O=4:1) was added to a solution of 10gg (9.67 g, 18.80 mmol) in pyridine (58 mL). The mixture was stirred at 0° C. for 30 min. The mixture was adjusted to pH=6-7 with 1N HCl. The mixture was concentrated in vacuo to give a crude that was purified by silica column chromatography (EtOAc:PE=1:1) to obtain 11gg (3.6 g, 9.77 mmol, 52.00% yield). ESI-MS: m/z 369.1 [M+H]$^+$.

4,4'-Dimethoxytrityl chloride (4.97 g, 14.66 mmol) was added to a solution of 11gg (3.60 g, 9.77 mmol) in pyridine (30 mL). The mixture was stirred at rt for 1.5 h. The mixture was added to aq. NaHCO$_3$ and extracted with EtOAc (4×100 mL). The combined EtOAc layer was washed with brine and concentrated in vacuo to give a crude. The crude was purified by reverse phase prep-HPLC (Column: C18 spherical 20-35 μm 100A 120 g, mobile phase: 0.05% NH$_4$HCO$_3$ in water-ACN from 50% to 70%, flow rate: 25 mL/min) to obtain 12gg (5.9 g, 8.80 mmol, 90.01% yield). ESI-MS: m/z 671.3 [M+H]$^+$. $^1$H NMR (400 MHz, DMSO-d$_6$): δ 12.13 (d, J=91.8 Hz, 2H), 8.62-8.54 (m, 1H), 7.31-7.16 (m, 5H), 7.16-7.11 (m, 4H), 6.79 (ddd, J=9.0, 6.3, 2.8 Hz, 4H), 6.06 (d, J=3.0 Hz, 1H), 5.78 (d, J=5.5 Hz, 1H), 5.01 (s, 1H), 4.25-4.17 (m, 2H), 3.71 (s, 6H), 3.36 (s, 3H), 3.18 (dd, J=10.6, 2.1 Hz, 1H), 3.10-3.03 (m, 1H), 2.80 (p, J=6.9 Hz, 1H), 1.14 (d, J=6.8 Hz, 6H).

Monomer 2 (1.10 g, 1.10 mmol) and 12gg (740.00 mg, 1.10 mmol) was dissolved in anhydrous CH$_3$CN (50.0 mL), and 4 Å molecular sieves powder (1 gr/100 mL) were added. The heterogeneous mixture was bubbled with Ar for 4 min. After stirring at rt for 10 min, 0.45 M tetrazole in CH$_3$CN (6.61 mmol, 14.70 mL) was added at rt. After stirring for 1 h, the mixture was filtered, and washed with anhydrous CH$_3$CN. t-BuOOH (5 mL) was added until the reaction completed. After stirring for 20-30 min at rt, the reaction was quenched with Na$_2$SO$_3$ (aq). The mixture was diluted with EtOAc, and the ayers were separated. The organic phase was washed with sat. aq. NaHCO$_3$ (1×50 mL) and sat. aq. NaCl (1×50 mL). The combined aqueous phase was back extracted with EtOAc (1×50 mL). The combined organic phases were evaporated to dryness, and the crude material was purified by reverse phase prep-HPLC (Column: C18 spherical 20-35 μm 100A 40 g, mobile phase: 0.05% NH$_4$HCO$_3$ in water, m/m)-ACN from 30% to 100%, flow rate: 20 ml/min) to give 13gg (1.27 g, 801.90 umol, 72.68% yield) as a white foam. $^{31}$P-NMR (162 MHz, DMSO-d$_6$): -2.46, -2.89. ESI-MS: m/z 1583.8 [M+H]$^+$.

Compound 13gg (1.17 g, 738.75 umol) was dissolved in DCA in DCM (3%, v/v, 22.00 mL) and triethyl silane (8.20 mL) was added immediately. After stirring for 30 min at rt, the mixture was diluted with EtOAc, and neutralize with sat. aq. NaHCO$_3$. The layers were separated, and organic phase was washed with sat. aq. NaCl (1×50 mL). The aqueous phase was combined and back extracted with EtOAc (3×50 mL). The combined organic phases were evaporated to dryness, and the crude residue was purified by reverse phase prep-HPLC (Column: C18 spherical 20-35 μm 100A 40 g, mobile phase: 0.05% NH$_4$HCO$_3$ in water, m/m)-ACN from 30% to 80%, flow rate: 20 mL/min) to give 14gg (600 mg, 612.86 umol, 82.96% yield) as a white foam. $^{31}$P-NMR (162 MHz, DMSO-d$_6$): -2.13, -2.50. ESI-MS: m/z 979.3 [M+H]$^+$.

Compound 14gg (380 mg, 388.14 umol) dissolved in anhydrous CH$_3$CN (63.3 mL), and 0.45 M tetrazole in CH$_3$CN (3.10 mmol, 6.90 mL) and 4 Å molecular sieves powder (300 mg, 1 gr/100 mL) were added. The heterogeneous mixture was bubbled with Ar for 4 min. After stirring at rt for 20 min, 4a (233.44 mg, 774.46 umol) in MeCN (10.0 mL) were added over 30 to 40 min. After stirring for 2 h, the mixture was filtered and washed with anhydrous CH$_3$CN. DDTT (5.82 mL) was added until the reaction completed. After stirring for 20-30 min at rt, the reaction was quenched with sat. aq. Na$_2$SO$_3$. The mixture was diluted with EtOAc, and the layers were separated. The organic phase was washed with sat. aq. NaHCO$_3$ (1×50 mL) and sat. aq. NaCl (1×50 mL). The combined aqueous phase was back extracted with EtOAc (1×50 mL). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 30% to 60%, flow rate: 20 mL/min) to give 15gg (95 mg, 85.58 umol, 22.05% yield) as a white foam. ESI-MS: m/z 1110.3[M+H]$^+$.

Compound 15gg (180 mg, 162.15 umol) was treated with a solution of NH$_3$ in MeOH (25 mL, 33%). After stirring for 3 h at 40° C., the mixture was evaporated to dryness. The crude material was purified by reverse phase prep-HPLC (Column: XBridge 30×100 mm, mobile phase: 0.05% NH$_4$HCO$_3$ in water, m/m)-ACN from 20% to 30%, flow rate: 50 mL/min) to give 16gg-P1 (50.00 mg, 60.25 umol, 37.16% yield) as a white foam. ESI-LMS: m/z 829.7 [M+H]+, and 16gg-P2 (10.00 mg, 12.05 umol, 7.43% yield) as a white foam. ESI-LMS: m/z 829.7 [M+H]$^+$.

A solution of 16gg-P1 (50.00 mg, 60.25 umol) in 12% TBAF (2 mL) (solvent: DMSO) was stirred at 40° C. for 2 h. The mixture was added to deionized water (10 mL) and then purified by reverse phase prep-HPLC (Column: C18 spherical 20-35 μm 100A 80 g, mobile phase: 0.05% NH$_4$HCO$_3$ in water-ACN from 0% to 10%, flow rate: 20 mL/min) to give the NH$_4$ salt product 17gg-P1 (43 mg, 60.13 μmol, 99.78% yield) as a white foam. A 15.0 mL volume of Amberlite IR-120 (Na form) was added to the column and washed with deionized water (3×15 mL). Compound 17gg-P1 (43 mg) was dissolved in deionized water (43 mg in 20 mL) and added to the top of the column, and eluted with deionized water. The compound was eluted out in early fractions as detected by TLC (UV). The product was lyophilized to give 1-35a (43 mg, 60.13 umol, 99.78% yield) as a white foam. $^1$H NMR (400 MHz, D$_2$O): δ 8.22 (dd, J=2.2, 1.1 Hz, 1H), 8.19 (dd, J=2.3, 1.2 Hz, 1H), 6.14 (dd, J=8.5, 2.1 Hz, 1H), 5.85 (t, J=6.4 Hz, 1H), 5.68 (t, J=8.0 Hz, 1H), 4.92 (s, 1H), 4.60-4.51 (m, 3H), 4.40-4.33 (m, 1H), 4.11 (d, J=3.6 Hz, 2H), 3.65 (d, J=11.0 Hz, 1H), 3.55 (dd, J=2.3, 1.2 Hz, 3H), 1.85 (d, J=8.6 Hz, 1H), 1.61 (d, J=5.5 Hz, 1H), 0.99 (t, J=7.5 Hz, 1H). $^{31}$P NMR (162 MHz, D$_2$O): 53.10, −2.80. ESI-MS: m/z 716.5 [M+H]$^+$.

Compound 1-35b was obtained following the procedure for obtaining 1-35a starting with 16gg-P2. Compound 1-35b was obtained (7.5 mg, 10.47 umol, 86.95% yield) as a white foam. $^1$H NMR (400 MHz, D$_2$O): δ 8.25 (s, 1H), 8.19 (q, J=1.1 Hz, 1H), 6.19 (d, J=8.6 Hz, 1H), 5.87-5.77 (m, 1H), 5.66 (t, J=7.7 Hz, 1H), 4.90 (s, 1H), 4.59 (d, J=3.4 Hz, 1H), 4.51 (d, J=11.0 Hz, 1H), 4.38-4.31 (m, 2H), 4.27 (d, J=6.3 Hz, 1H), 4.00 (d, J=11.7 Hz, 1H), 3.61 (d, J=11.0 Hz, 1H), 3.54 (d, J=1.3 Hz, 3H), 1.88 (d, J=8.5 Hz, 1H), 1.69 (t, J=5.1 Hz, 1H), 0.99 (t, J=7.6 Hz, 1H). $^{31}$P NMR (162 MHz, D$_2$O): 54.21, −2.92. ESI-MS: m/z 716.5 [M+H]$^+$.

Example 35

Compounds 1-48a, 1-48b, 1-48c & 1-48d

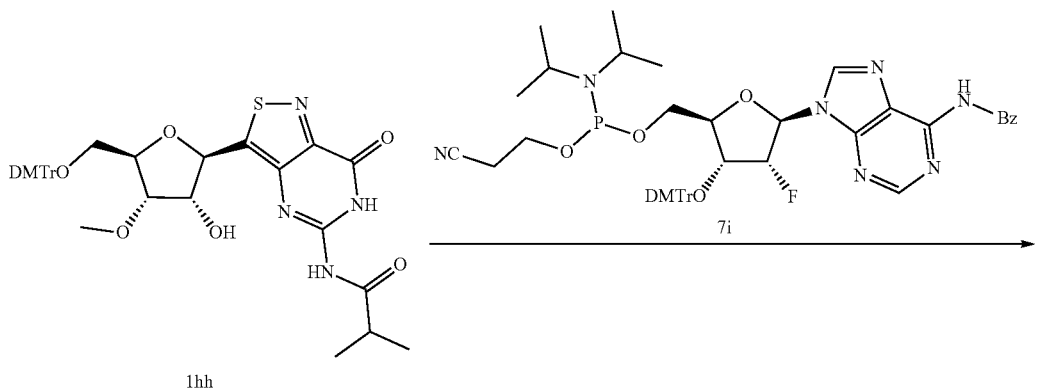

1hh

7i

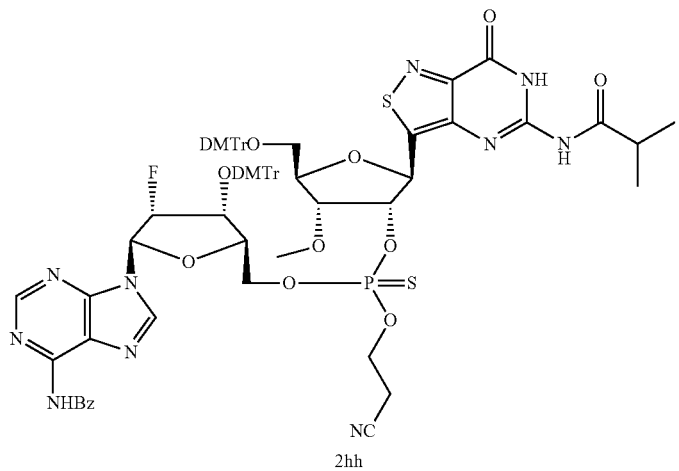

2hh 291 292
-continued
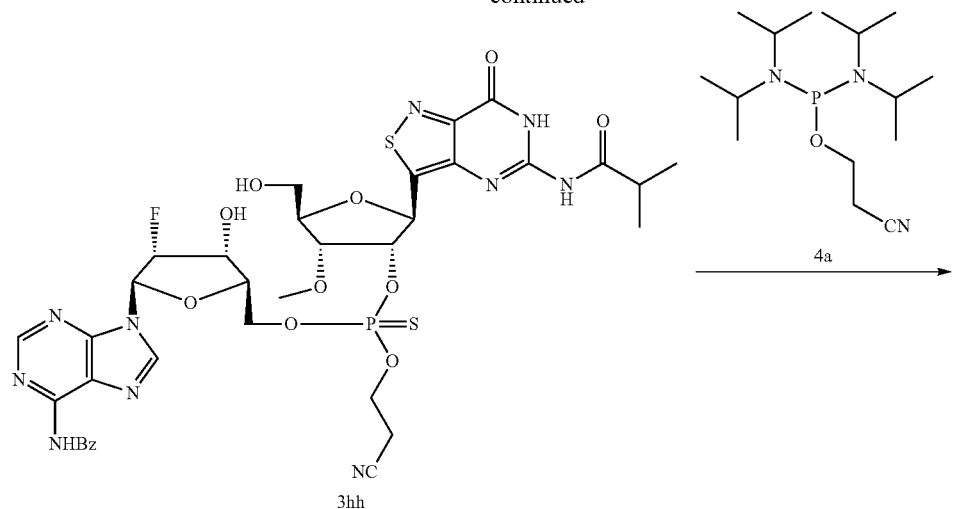
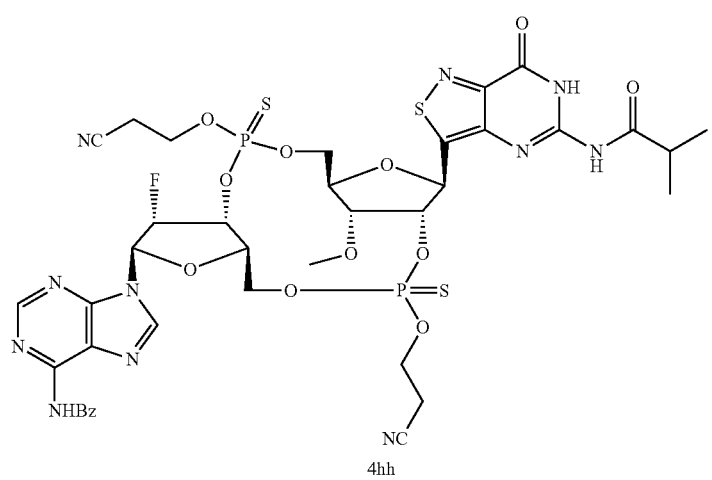
4hh
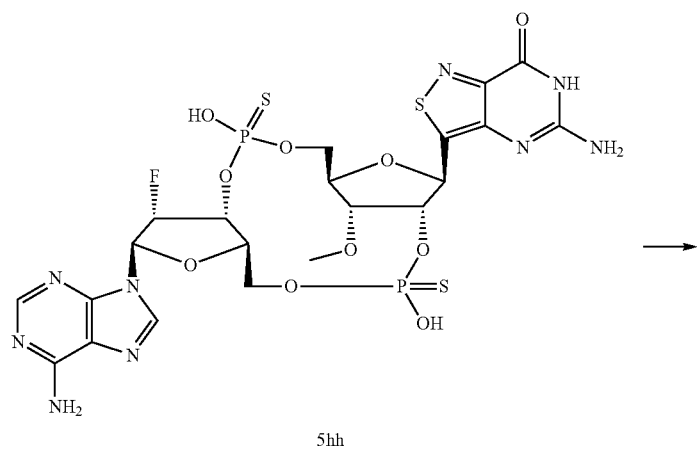
5hh

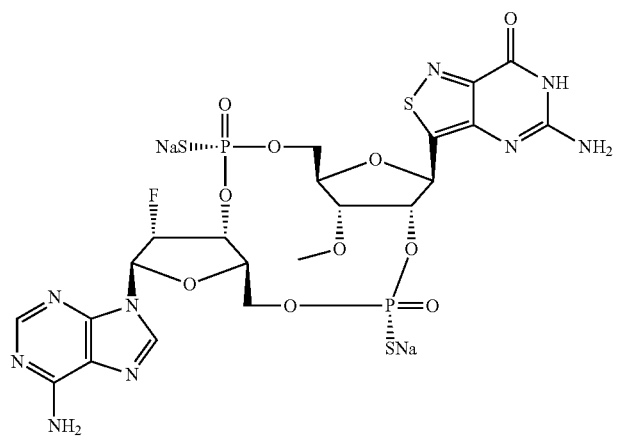
1-48a
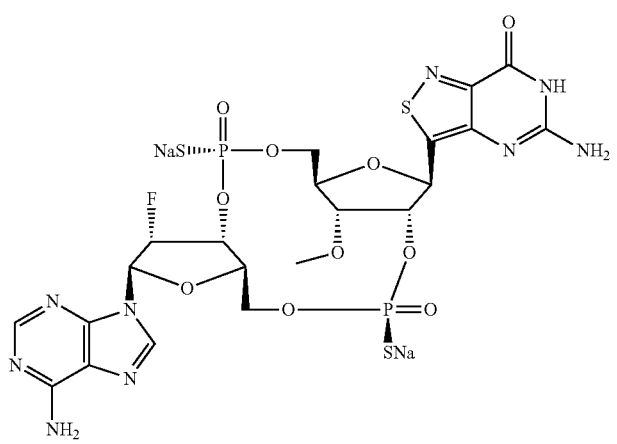
1-48b
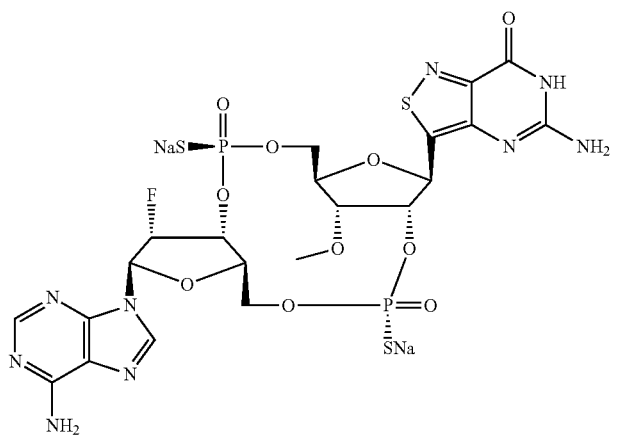
1-48c

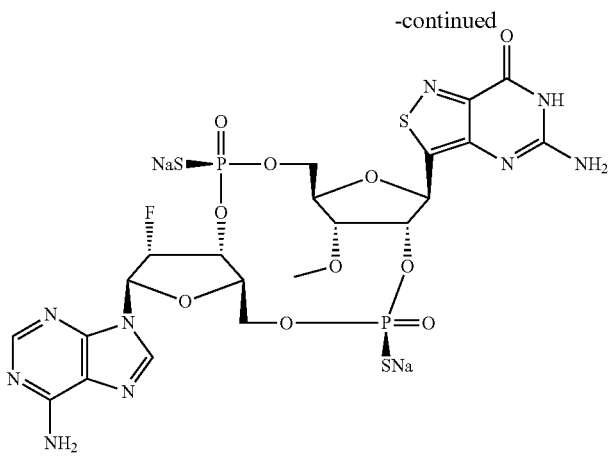

1-48d

Compound 1hh (1.5 g, 2.19 mmol) was dissolved in anhydrous $CH_3CN$ (80 mL), and 7i (2.30 g, 2.62 mmol) and 4 Å molecular sieves powder (800 mg, 1 gr/100 mL) were added. The heterogeneous mixture was bubbled with Ar for 4 min. After stirring at rt for 20 min, 0.45 M tetrazole (13.1 mmol, 52.5 mL) was added at rt. After stirring for 1 h, the mixture was filtered and washed with anhydrous $CH_3CN$. 0.1 M DDTT was added until the reaction completed. After stirring for 20-30 min at rt, the reaction was quenched with $Na_2SO_3$ (aq.). The mixture was diluted with EtOAc, and the layers were separated. The organic phase was washed with sat. aq. $NaHCO_3$ (1×80 mL) and sat. aq. NaCl (1×80 mL). The combined aqueous phase was back extracted with EtOAc (1×150 mL). The combined organic phases were evaporated to dryness, and the crude material was purified by reverse phase prep-HPLC (Column: C18 spherical 20-35 μm 100A 120 g, mobile phase: 0.05% $NH_4HCO_3$ in water, m/m)-ACN from 60% to 100%, flow rate: 35 mL/min) to give 2hh (2.9 g, 1.94 mmol, 88.8% yield) as a white foam. $^{31}P$ NMR (162 MHz, DMSO-$d_6$): δ 67.46, 66.81. ESI-MS: m/z 1493.6 [M+H]$^+$.

Compound 2hh (2.9 mg, 1.94 mmol) was dissolved in DCA in DCM (3%, v/v, 40 mL) and triethyl silane (10 mL) was added immediately. After stirring for 30 min at rt, the mixture was diluted with EtOAc, and neutralized with sat. $NaHCO_3$. The layer were separated. The organic phase was washed with sat. aq. $NaHCO_3$ (1×50 mL) and sat. aq. NaCl (1×100 mL). The combined aqueous phase was back extracted with EtOAc (3×100 mL). The combined organic phases were evaporated to dryness, and the crude material was purified by reverse phase prep-HPLC (Column: C18 spherical 20-35 μm 100A 120 g, mobile phase: 0.05% $NH_4HCO_3$ in water, m/m)-ACN from 60% to 100%, flow rate: 35 mL/min) to give 3hh (1.4 g, 1.58 mmol, 81.3% yield) as a white foam. $^{31}P$ NMR (162 MHz, DMSO-$d_6$): δ 67.10, 66.65. ESI-MS: m/z 889.2 [M+H]$^+$.

Compound 3gg (1.4 g, 1.58 mmol) dissolved in anhydrous $CH_3CN$ (200 mL), and 0.45 M tetrazole in $CH_3CN$ (12.65 mmol, 50.6 mL) and 4 Å molecular sieves powder (600 mg, 1 gr/100 mL) were added. The heterogeneous mixture was bubbled with Ar for 4 min. After stirring at rt for 20 min, 4a (952.5 mg, 3.16 mmol) in $CH_3CN$ (5.0 mL) was added over 25 to 30 min. After stirring for 2 h, the mixture was filtered, and washed with anhydrous $CH_3CN$. 0.1 M DDTT was added until the reaction completed. After stirring for 20-30 min at rt, the reaction was quenched with sat. aq. $Na_2SO_3$. The mixture was diluted with EtOAc, and the layers were separated. The organic phase was washed with sat. aq. $NaHCO_3$ (1×100 mL) and sat. aq. NaCl (1×100 mL). The combined aqueous phase was back extracted with EtOAc (1×150 mL), and then evaporated to dryness. The crude material was purified by reverse phase prep-HPLC (Column: C18 spherical 20-35 μm 100A 80 g, mobile phase: 0.05% $NH_4HCO_3$ in water, m/m)-ACN from 30% to 80%, flow rate: 30 mL/min) to give 4gg (500 mg, 490.7 μmol, 31.1% yield) as a white foam. ESI-MS: m/z 1020.2 [M+H]$^+$.

Compound 4gg (500 mg, 480.7 μmol) was treated with a solution of 33% $MeNH_2$ in EtOH (30 mL). After stirring for 2 h at 25° C., the mixture was evaporated to dryness. The crude material was purified by reverse phase prep-HPLC (Column: C18 spherical 20-35 μm 100A 20 g, mobile phase: 0.05% $NH_4HCO_3$ in water, m/m)-ACN from 0% to 30%, flow rate: 15 mL/min) to get 5gg-P1 (101.4 mg, 141.3 umol, 28.8% yield), 5gg-P2 (95 mg, 128.6 umol, 26.2% yield), 5gg-P3 (16 mg, 21.7 umol, 4.4% yield) and 5gg-P4 (6 mg, 8.1 umol, 1.7% yield) each as a white foam. ESI-MS: m/z 740.1 [M+H]$^+$.

15.0 mL volume of Amberlite IR-120 (Na form) was added to a column and washed with deionized water (3×15 mL). The ammonia salt product was dissolved in deionized water (15 mL) and added to the top of a column, and eluted with deionized water. The compound was eluted out in early fractions as detected by TLC (UV). The product was lyophilized to give 1-48a (100.5 mg, 136.0 umol, 27.8% yield) from 5gg-P1, 1-48b (93 mg, 125.8 umol, 25.6% yield) from 5gg-P2, 1-48c (13 mg, 17.6 umol, 3.6% yield) from 5gg-P3 and 1-48d (5 mg, 6.8 umol, 1.4% yield) from 5gg-P4 each as a white foam.

1-48a: $^1H$ NMR (400 MHz, $D_2O$): δ 8.20-8.07 (m, 2H), 6.33 (d, J=15.5 Hz, 1H), 5.73 (dd, J=50.7, 3.7 Hz, 1H), 5.30 (d, J=9.5 Hz, 1H), 5.14-4.90 (m, 2H), 4.49 (d, J=10.2 Hz, 2H), 4.40 (dd, J=11.7, 3.3 Hz, 1H), 4.23-4.05 (m, 4H), 3.51 (d, J=1.6 Hz, 3H). $^{31}P$ NMR (162 MHz, $D_2O$): δ 54.27. $^{19}F$ NMR (376 MHz, $D_2O$): 6-201.77.

1-48b: $^1H$ NMR (400 MHz, $D_2O$): δ 8.14 (d, J=2.3 Hz, 1H), 7.86 (s, 1H), 6.30 (d, J=15.9 Hz, 1H), 5.73 (d, J=50.9 Hz, 1H), 5.30 (d, J=9.7 Hz, 1H), 4.90 (s, 2H), 4.55-4.32 (m, 4H), 4.29-4.05 (m, 3H), 3.49 (d, J=1.8 Hz, 3H). $^{31}P$ NMR (162 MHz, $D_2O$): δ 54.02, 52.05. $^{19}F$ NMR (376 MHz, $D_2O$): δ -201.76.

1-48c: $^1H$ NMR (400 MHz, $D_2O$): δ 8.21 (s, 1H), 8.07 (s, 1H), 6.32 (d, J=14.9 Hz, 1H), 5.53 (dd, J=51.0, 3.6 Hz, 1H), 5.29-5.10 (m, 3H), 4.54-4.37 (m, 4H), 4.17-4.05 (m, 3H), 3.53 (s, 3H). $^{31}P$ NMR (162 MHz, $D_2O$): δ 55.80, 54.57. $^{19}F$ NMR (376 MHz, $D_2O$): δ -201.83.

1-48d: $^1H$ NMR (400 MHz, $D_2O$): δ 8.18 (s, 1H), 7.97 (s, 1H), 6.35 (d, J=15.5 Hz, 1H), 5.62-5.42 (m, 1H), 5.33 (d, J=9.7 Hz, 1H), 5.08 (s, 2H), 4.51 (s, 2H), 4.45-4.30 (m, 3H), 4.27-4.18 (m, 1H), 4.07 (d, J=12.1 Hz, 1H), 3.51 (s, 3H). $^{31}P$ NMR (162 MHz, $D_2O$): δ 55.12, 51.95. $^{19}F$ NMR (376 MHz, $D_2O$): 6-201.26.

Example 36
Compound 1-49
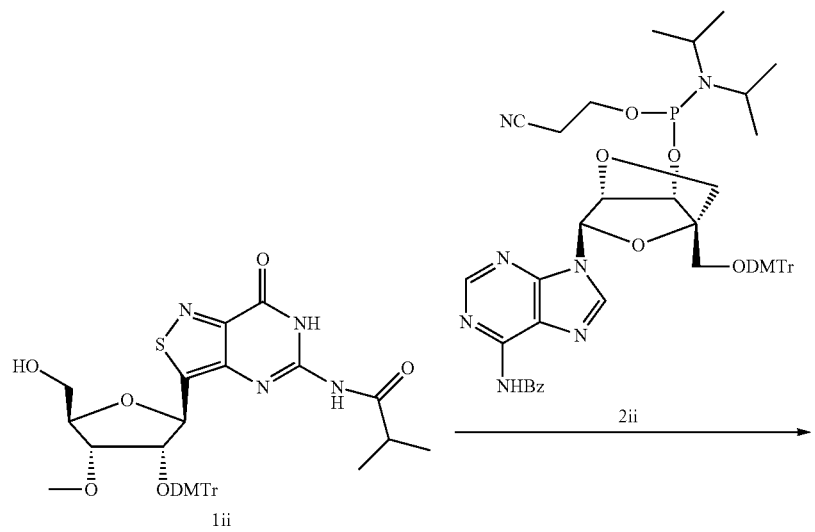
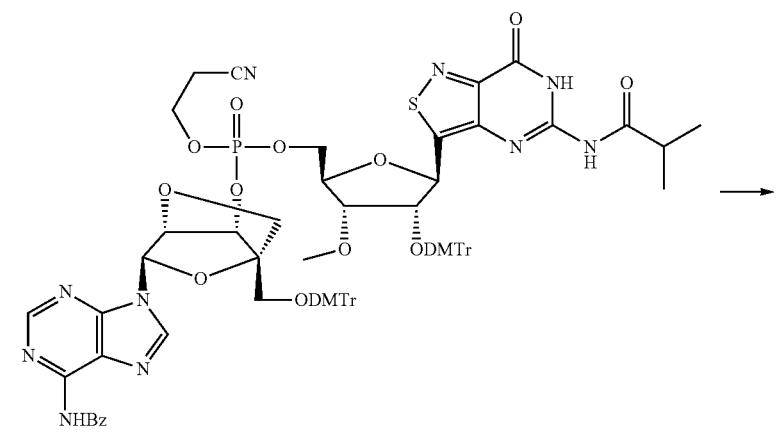
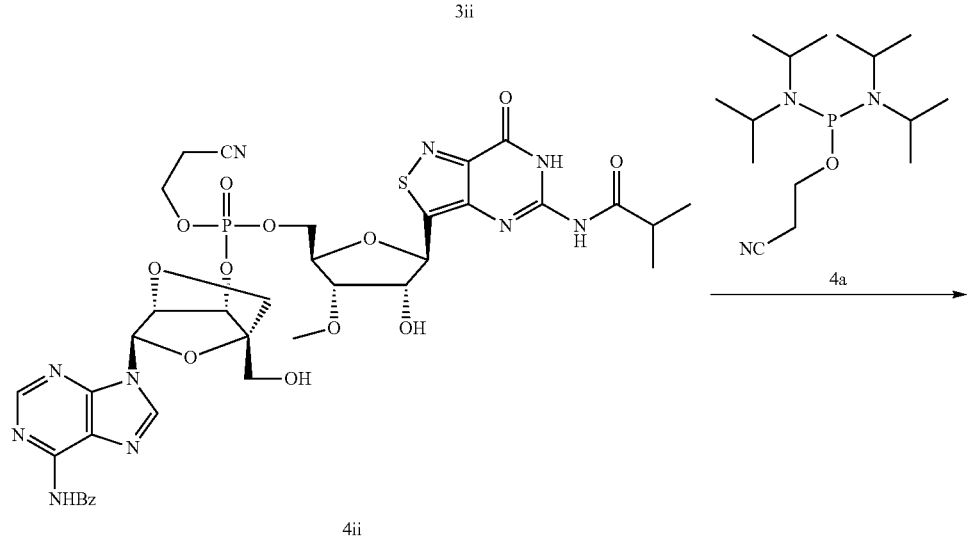

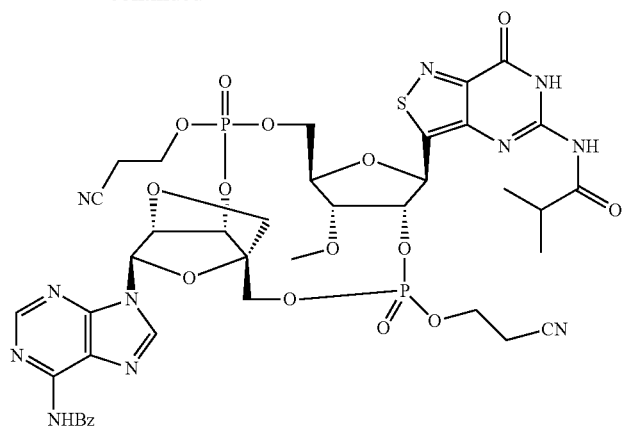
5ii
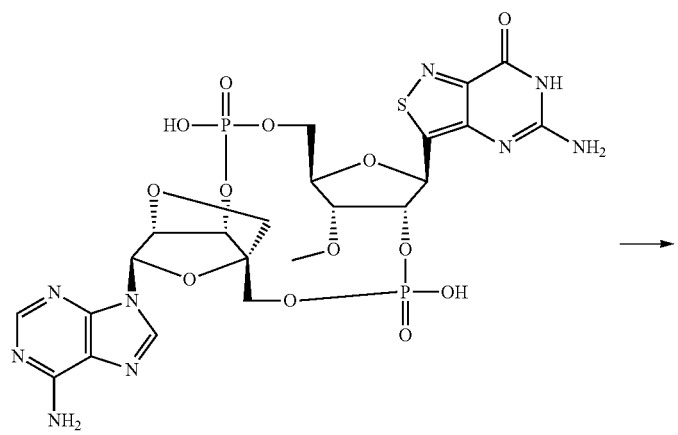
6ii
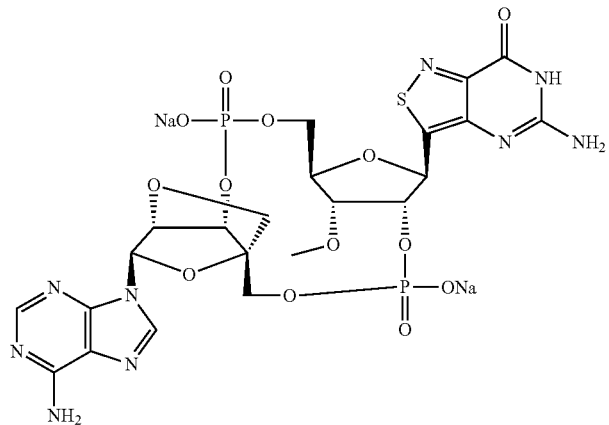
1-49

Compound 1ii (400 mg, 0.58 mmol) was dissolved in anhydrous CH$_3$CN (12.5 mL) and 2ii (647 mg, 0.70 mmol), and 4 Å molecular sieves powder (150 mg, 1 gr/100 mL) were added. The heterogeneous mixture was bubbled with Ar for 4 min. After stirring at rt for 20 min, 0.45 M tetrazole in CH$_3$CN (3.48 mmol, 12.5 mL) was added at rt. After stirring for 1 h, the mixture was filtered and washed with anhydrous CH$_3$CN. 5 M t-BuOOH was added until the reaction completed. After stirring for 20-30 min at rt, the reaction was quenched with Na$_2$SO$_3$ (aq.). The mixture was diluted with EtOAc, and the layers were separated. The organic phase was washed with sat. aq. NaHCO$_3$ (1×50 mL) and sat. aq. NaCl (1×50 mL). The combined aqueous phase was back extracted with EtOAc (1×50 mL). The combined organic phases were evaporated to dryness, and the crude material was purified by reverse phase prep-HPLC (Column: C18 spherical 20-35 µm 100A 80 g, mobile phase: 0.05% NH$_4$HCO$_3$ in water, m/m)-ACN from 60% to 100%, flow rate: 35 mL/min) to give 3ii (800 mg, 0.53 mmol, 89.7% yield) as a white foam. $^{31}$P NMR (162 MHz, DMSO): −3.11, −3.21. ESI-MS: m/z 1487 [M+H]$^+$.

Compound 3ii (800 mg, 0.53 mmol) was dissolved 3% DCA in DCM (13 mL) and triethyl silane (5.0 mL) was added immediately. After stirring for 30 min at rt, the mixture was diluted with EtOAc, and neutralized with sat. NaHCO$_3$. The layer were separated, and organic phase was washed with sat. aq. NaHCO$_3$ (1×50 mL) and sat. aq. NaCl (1×50 mL). The combined aqueous phase was back extracted with EtOAc (1×50 mL). The combined organic phases were evaporated to dryness, and the crude material was purified by silica gel (DCM:acetone=0:100) to give 4ii (350 mg, 0.39 mmol, 73.5% yield) as a white foam. ESI-MS: m/z 883.2 [M+H]$^+$.

Compound 4ii (350 mg, 0.39 mmol) dissolved in anhydrous CH$_3$CN (30.0 mL), and 0.45 M tetrazole in CH$_3$CN (2.56 mmol, 10.5 mL) and 4 Å molecular sieves powder (600 mg, 1 gr/100 mL) were added. The heterogeneous mixture was bubbled with A for 4 min. After stirring at rt for 20 min, 4a (196 mg, 0.64 mmol) in CH$_3$CN (5.0 mL) was added over 25 to 30 min. After stirring for 2, the mixture was filtered and washed with anhydrous CH$_3$CN. 5 M t-BuOOH was added until the reaction was completed. After stirring for 20-30 min at rt, the reaction was quenched with sat. aq. Na$_2$SO$_3$. The mixture was diluted with EtOAc, and the layers were separated. The organic phase was washed with sat. aq. NaHCO$_3$ (1×50 mL) and sat. aq. NaCl (1×50 mL). The combined aqueous phase was back extracted with EtOAc (1×50 mL). The combined organic phases were evaporated to dryness, and the crude material was purified by reverse phase prep-HPLC (Column: C18 spherical 20-35 µm 100A 40 g, mobile phase: 0.05% NH$_4$HCO$_3$ in water, m/m)-ACN from 30% to 80%, flow rate: 20 mL/min) to give 5ii (92 mg, 90.07 µmol, 31.0% yield) as a white foam. ESI-MS: m/z 998 [M+H]$^+$.

Compound 5ii (92 mg, 90.07 µmol) was treated with a solution of 33% MeNH$_2$ in EtOH (3 mL). After stirring for 2 h at 40° C., the mixture was evaporated to dryness. The crude material was purified by reverse phase prep-HPLC (Column: C18 spherical 20-35 µm 100A 20 g, mobile phase: 0.05% NH$_4$HCO$_3$ in water, m/m)-ACN from 0% to 30%, flow rate: 15 mL/min) to give 6ii (11 mg) as a white foam.

A 12.0 mL volume of Amberlite IR-120 (Na form) was added to a column and washed with deionized water (5*15 mL). Compound 6ii (11 mg) was dissolved in deionized water (88 mg in 10 mL) and added to the top of the column, and eluted with deionized water. The compound was eluted out in early fractions as detected by TLC (UV). The product was lyophilized to give 1-49 (3 mg, 3.94 µmol, 4.38% yield) as a white foam. $^1$H NMR (400 MHz, D$_2$O): δ 8.16 (s, 1H), 7.86 (s, 1H), 6.07 (s, 1H), 5.33 (d, J=9.6 Hz, 1H), 4.94 (d, J=22.7 Hz, 2H), 4.75 (d, J=4.2 Hz, 1H), 4.45 (s, 1H), 4.29-4.09 (m, 6H), 3.98 (d, J=8.5 Hz, 1H), 3.50 (s, 3H). $^{31}$P NMR (162 MHz, D$_2$O): δ −1.74, −2.53. ESI-MS: m/z 718 [M+H]$^+$.

Example 36

Compounds 1-50a & 1-50b

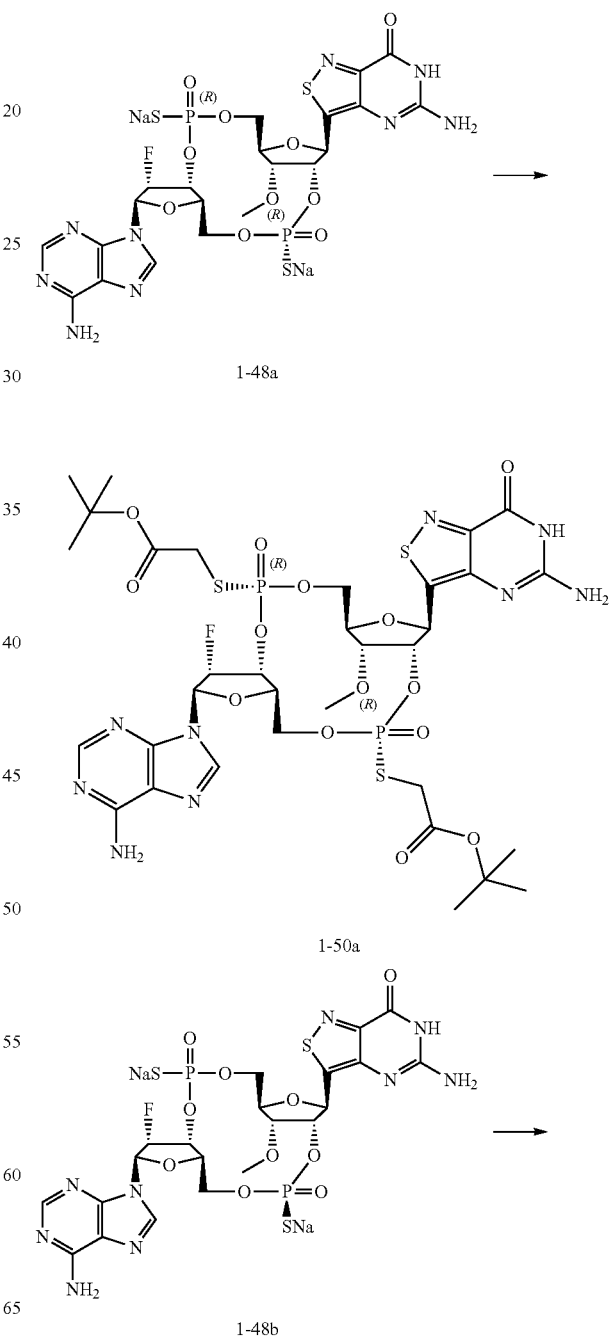

1-48a 1-50a 1-48b

-continued

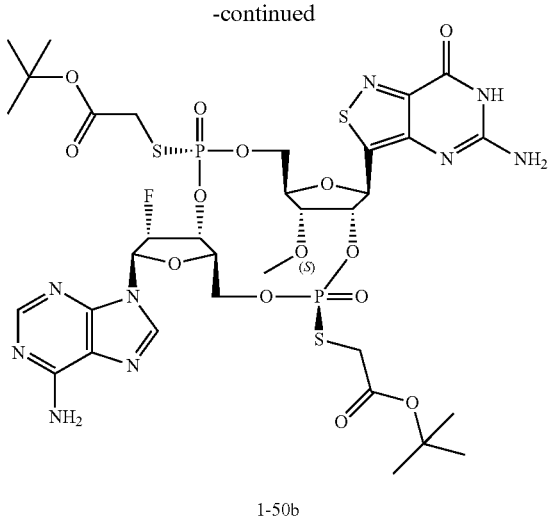

1-50b

Compound 1-48a (20 mg, 25.5 umol) was dissolved in acetone:H$_2$O=1:1 (2 mL) and was added iodomethyl pivalate (61.8 mg, 255.4 umol). After stirring the mixture for 1.5 h at rt, the mixture was diluted with EtOAc, and neutralize with sat. aq. NaHCO$_3$. The layers were separated, and the organic phase was washed with sat. aq. NaCl (1×10 mL). The aqueous phase was combined and back extracted with EtOAc (3×10 mL). The combined organic phases were evaporated to dryness, and the crude material was purified by reverse phase prep-HPLC (Column: C18 spherical 20-35 μm 100A 12 g, mobile phase: 0.05% NH$_4$HCO$_3$ in water, m/m)-ACN from 30% to 60%, flow rate: 8 mL/min) to give 1-50a (5 mg, 5.2 μmol, 20.3% yield) as a white foam. $^1$H NMR (400 MHz, DMSO-d$_6$): δ 8.26 (s, 1H), 8.02 (s, 1H), 7.42 (s, 2H), 6.51 (s, 1H), 6.48-6.22 (m, 2H), 5.55-5.47 (m, 3H), 5.46-5.38 (m, 1H), 5.13 (d, J=20.8 Hz, 2H), 4.76 (td, J=9.0, 4.0 Hz, 1H), 4.61 (d, J=15.1 Hz, 2H), 4.55-4.40 (m, 2H), 4.40-4.16 (m, 4H), 3.50 (s, 3H), 1.13 (d, J=1.9 Hz, 9H), 0.95 (s, 9H). $^{31}$P NMR (162 MHz, DMSO-d$_6$): δ 25.83, 24.34. $^{19}$F NMR (376 MHz, DMSO-d$_6$): δ −208.80. ESI-MS: m/z 968.2 [M+H]$^+$.

Compound 1-50b was prepared in a similar manner as preparing 1-50a starting with 1-48b. Compound 1-50b (4.2 mg) was obtained as a white foam. $^1$H NMR (400 MHz, DMSO-d$_6$): δ 8.40 (s, 1H), 8.11 (s, 1H), 7.44 (s, 2H), 6.51 (s, 2H), 6.42 (dd, J=17.8, 6.4 Hz, 2H), 5.49 (dt, J=13.5, 9.1 Hz, 5H), 5.43-5.33 (m, 2H), 4.85-4.72 (m, 2H), 4.68-4.55 (m, 2H), 4.50 (d, J=3.7 Hz, 1H), 4.23 (dd, J=15.4, 4.3 Hz, 2H), 4.12 (dt, J=9.9, 4.4 Hz, 1H), 3.43 (s, 3H), 1.13 (s, 9H), 1.04 (s, 9H). $^{31}$P NMR (162 MHz, DMSO-d$_6$): δ 25.52, 24.76. $^{19}$F NMR (376 MHz, DMSO-d$_6$): δ −213.67. ESI-MS: m/z 968.2 [M+H]$^+$.

Example 37

Compounds 1-51a & 1-51b

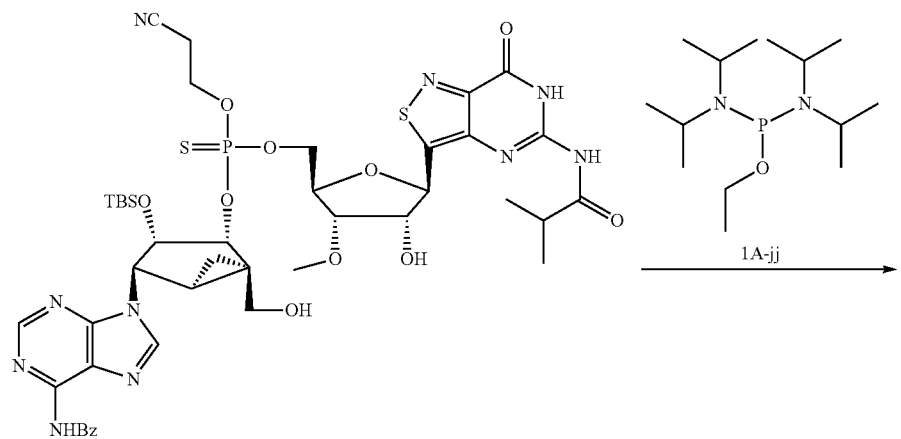

1jj

-continued
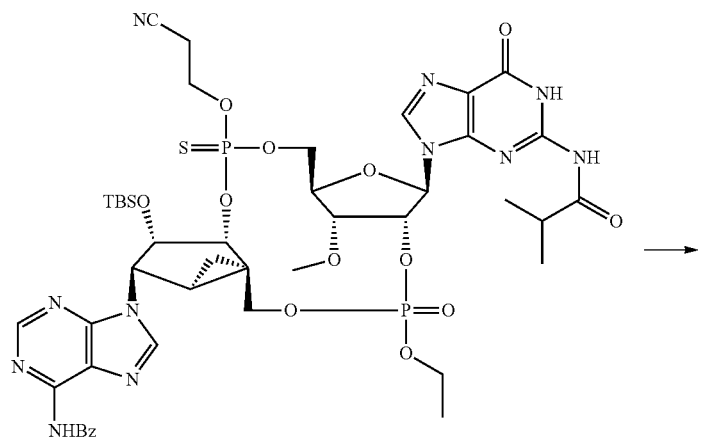
2jj
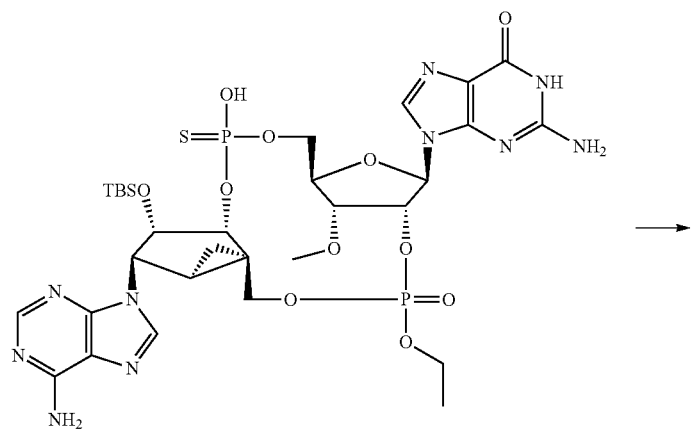
3jj

-continued

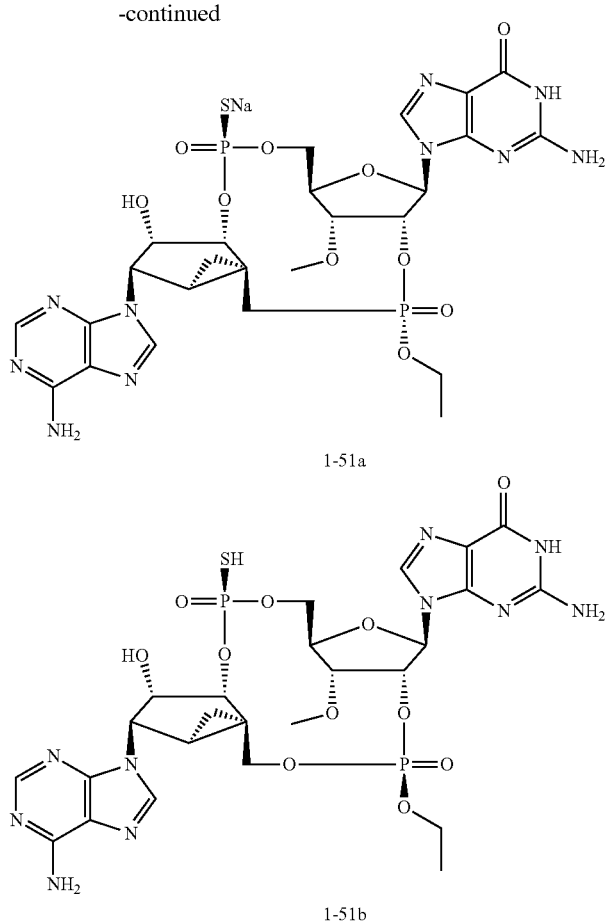

1-51a 1-51b

Compound 1jj (450.00 mg, 0.45 mmol) dissolved in anhydrous $CH_3CN$ (56.0 mL), and 0.45 M tetrazole in $CH_3CN$ (3.60 mmol, 23.00 mL) and 4 Å molecular sieves powder (3.0 g, 1 gr/100 mL) were added. The heterogeneous mixture was bubbled with Ar for 4 min. After stirring at rt for 20 min, 1A-jj (372.00 mg, 1.35 mmol) in $CH_3CN$ (10.0 mL) was added at rt over 25 to 30 min. After stirring 2 h, the mixture was filtered and washed with anhydrous $CH_3CN$. 5 M t-BuOOH was added until the reaction completed. After stirring for 20-30 min at rt, the reaction was quenched with sat. aq. $NaS_2O_3$. The mixture was diluted with EtOAc, and the organic layers were separated. The organic phase was washed with sat. $NaHCO_3$ aq. (1×50.0 mL) and sat. NaCl aq. (1×50.0 mL). The combined aqueous phase was back extracted with EtOAc (1×100 mL). The combined organic phases were evaporated to dryness, and the crude material was purified by reverse phase prep-HPLC (Column: C18 spherical 20-35 μm 100A 80 g, mobile phase: 0.05% $NH_4HCO_3$ in water, m/m)-ACN from 30% to 60%, flow rate: 35 mL/min) to give 2jj (320.00 mg, 295.47 μmol, 45.28% yield) as a white foam. ESI-MS: m/z 1084.3 $[M+H]^+$.

Compound 2jj (320.00 mg, 295.47 μmol) was treated with a solution of $NH_3$ in MeOH (12.0 mL, 7M). After stirring for 18 h at 4 0° C., the mixture was evaporated to dryness. The crude material was purified by reverse phase prep-HPLC (Column: C18 spherical 20-35 μm 100A 40 g, mobile phase A: 0.05% $NH_4HCO_3$ in water, m/m-ACN from 0% to 10%, flow rate: 20 mL/min) to afford 3jj (180 mg, 210.28 μmol, 71.5% yield) as a white foam. ESI-MS: m/z 857.1 $[M+H]^+$.

Compound 3jj (180 mg, 210.28 μmol) and 3HF·TEA (2.0 mL) in DMSO (2.0 mL) was stirred at 40° C. for 48 h. The mixture was cooled to rt, and then TEA (2.0 mL) and isopropoxytrimethylsilane (16.0 mL) were added. The mixture was stirred at rt for 1 h and then evaporated to dryness. The residue was purified by reverse phase prep-HPLC (Column: XBridge 30×100 mm, mobile phase: 0.05% $NH_4HCO_3$ in water-ACN from 0% to 15%, flow rate: 20 mL/min) to get the $NH_4$ salt product 4jj-P2 (3.0 mg, 3.93 μmol, 1.8% yield) and 4jj-P4 (8.5 mg, 11.13 mol, 5.3% yield) as a white foam.

15.0 mL volume of Amberlite IR-120 (Na form) was added to a column and washed with deionized water (3×15 mL). The ammonia salt products were dissolved in deionized water (15 mL), added to the top of the column and eluted with deionized water. The compounds were eluted out in early fractions as detected by TLC (UV). The product was lyophilized to give 1-51a (1.5 mg, 1.96 μmol, 0.98% yield) and 1-51b (6.4 mg, 8.31 mol, 3.99% yield) as a white foam.

1-51a: $^1$HNMR (400 MHz, $D_2O$): δ 8.21 (s, 1H), 7.96 (s, 1H), 7.86 (s, 1H), 5.95 (d, J=8.6 Hz, 1H), 5.85 (td, J=9.0, 4.0 Hz, 1H), 5.32 (d, J=7.5 Hz, 1H), 4.91 (s, 1H), 4.60 (s, 1H), 4.38 (dd, J=16.8, 6.1 Hz, 1H), 4.23 (d, J=6.2 Hz, 1H), 4.02 (d, J=11.7 Hz, 1H), 3.97-3.77 (m, 3H), 3.54 (s, 3H), 2.04 (d, J=7.9 Hz, 1H), 1.80 (t, J=4.9 Hz, 1H), 1.05 (t, J=7.1 Hz, 4H). $^{31}$P NMR (162 MHz, $D_2O$): δ 53.01, −5.20. ESI-MS: m/z 743.59 $[M+H]^+$.

1-51b: $^1$HNMR (400 MHz, $D_2O$): δ 8.14 (d, J=11.8 Hz, 1H), 7.98 (d, J=12.1 Hz, 1H), 7.80 (d, J=13.3 Hz, 1H), 5.92

(d, J=8.8 Hz, 1H), 5.79 (s, 1H), 5.34-5.24 (m, 1H), 4.61 (s, 1H), 4.49-4.35 (m, 2H), 4.21 (dt, J=12.0, 6.3 Hz, 3H), 3.98 (dd, J=21.4, 11.4 Hz, 2H), 3.53 (d, J=11.8 Hz, 3H), 1.94 (s, 1H), 1.76 (s, 1H), 1.49-1.12 (m, 3H), 1.01 (s, 1H). $^{31}$PNMR (162 MHz, D$_2$O): δ 54.95, −4.29. ESI-MS: m/z 743.59 [M+H]$^+$.
Example 38
Compounds 1-52
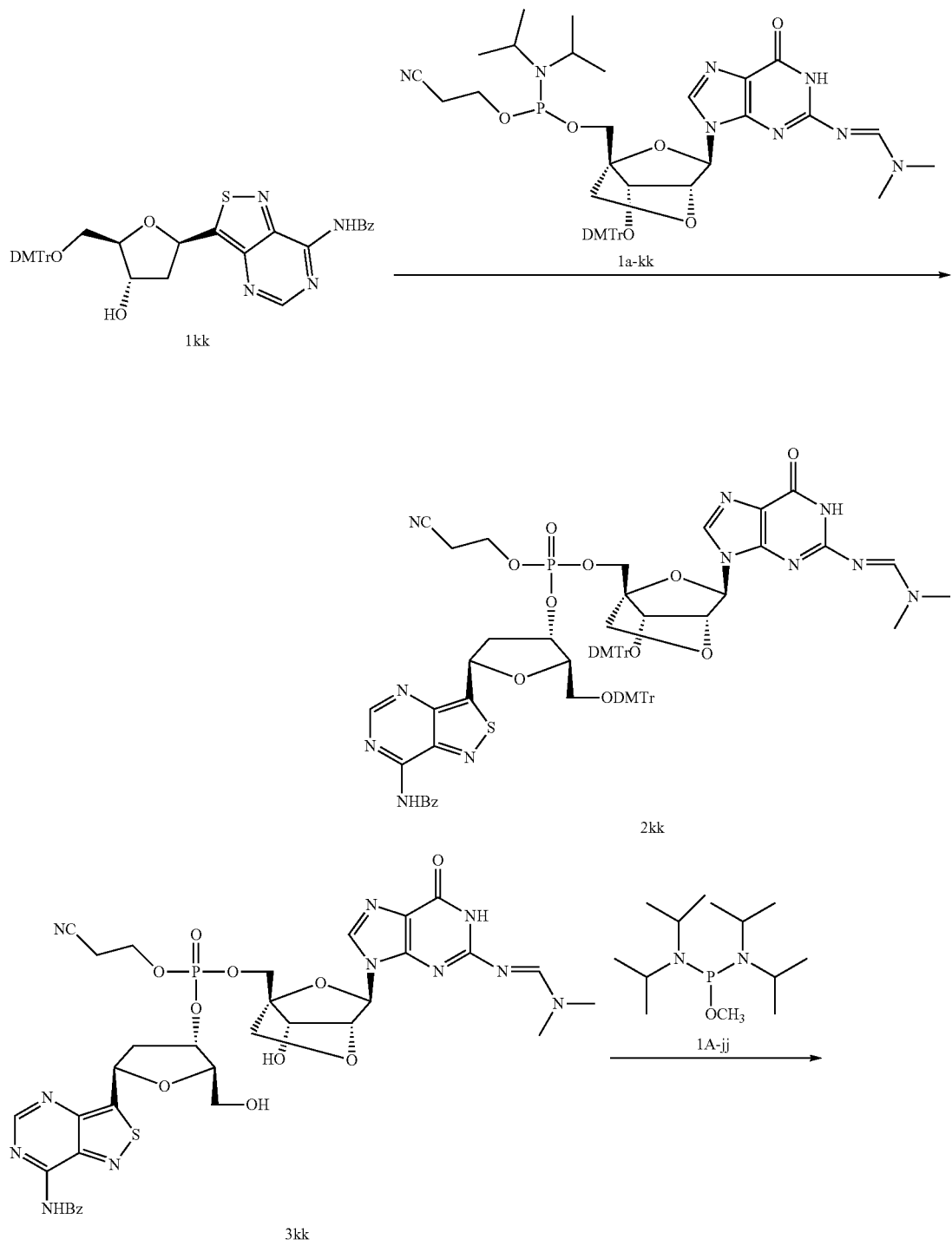

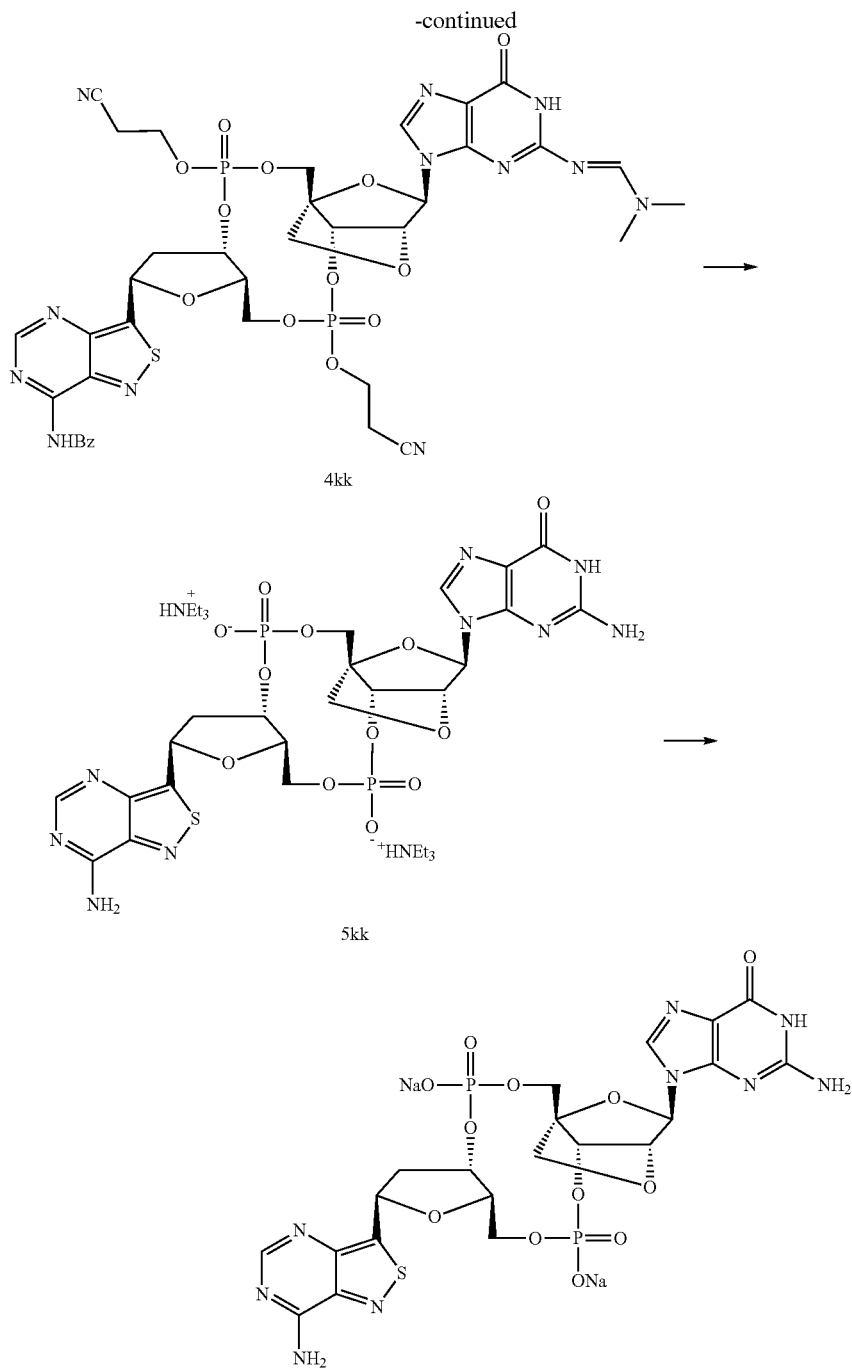

Compound 1kk (200 mg, 0.296 mmol) and 1a-kk (327 mg, 0.384 mmol) dissolved in anhydrous $CH_3CN$ (10 mL), and 0.45 M tetrazole in $CH_3CN$ (3.4 mL) and 4 Å molecular sieves powder were added. The heterogeneous mixture was bubbled with $N_2$ gas for 10 min. After stirring for 2 h, 0.05 M $I_2$ ($THF:H_2O:Py$; 8:1:1) was added. The mixture was stirred for 20 min. The mixture was filtered and washed with EA. The reaction was quenched with aq. $Na_2SO_3$. The mixture was diluted with EtOAc, and the layers were separated. The organic phase was washed with aq. $NaHCO_3$ (1×60 mL) and aq. NaCl (1×60 mL). The combined organic phases were evaporated to dryness, and the crude material was purified by flash silica column chromatography (0-10 MeOH in $CH_2Cl_2$) to give 2kk (360 mg, 88%) as a white solid. ESI-MS: m/z 1442.6 $[M+H]^+$.

Compound 2kk (320 mg, 0.222 mmol) was dissolved in DCA in DCM (3%, v/v, 4 mL) and triethyl silane (1.5 mL) was added. After stirring for 30 min at rt, the mixture was neutralized with sat. sodium bicarbonate solution at 0° C. The mixture was evaporated to dryness, and the crude residue was purified by flash silica column chromatography (0-20 MeOH in $CH_2Cl_2$) to give 3kk (135 mg, 72%) as a white solid. ESI-MS: m/z 838.32 $[M+H]^+$.

Compound 3kk (40 mg, 0.048 mmol) dissolved in anhydrous $CH_3CN:DMF:THF$ (4:2:4, v:v:v), and 0.45 M tetrazole in $CH_3CN$ (0.85 mL) and 4 Å molecular sieves powder were added. The heterogeneous mixture was bubbled with $N_2$ for 10 min. Compound 1A-kk (29 mg, 0.096 mmol) was added by dropwise. After stirring for 2 h, 0.05 M $I_2$ (THF:$H_2O$:Py=8:1:1) was added, and the mixture was stirred for 20 min. The mixture was filtered and washed with EA. The reaction was quenched with aq. $Na_2SO_3$. The mixture was diluted with EtOAc, and the layers were separated. The organic phase was washed with aq. $NaHCO_3$ (1×60 mL) and aq. NaCl (1×60 mL). The combined organic phases were evaporated to dryness, and the crude material was purified by flash silica column chromatography (0-20 MeOH in $CH_2Cl_2$) to give 4kk (15 mg, not pure) as a yellow solid. ESI-MS: m/z 838.32 $[M+H]^+$.

Compound 4kk (15 mg) was treated with a solution of diisopropylamine:MeOH:$H_2O$ (3 mL, 1:1:2, v:v:v). After stirring for 16 h at rt, the mixture was evaporated to dryness, and the crude material was purified by reverse phase prep-HPLC (Column: C18 column, 21×250 mm, mobile phase: A: 50 mM TEAA in water, B: MeCN; Gradient: 0% to 25% B over 30 min, flow rate: 15 mL/min) to give 5kk (2.3 mg) as a triethylammonium salt as a white foam. ESI-MS: m/z 686.06 $[M+H]^+$.

Dowex 50W×8, 200-400 (H form, 10 mL) was added to a beaker and washed with de-ionized water (2×). To the resin was added 15% $H_2SO_4$ in de-ionized $H_2O$ (50 mL), and the mixture was stirred for 15 min and decanted (1×). The resin was transferred to a column with 15% $H_2SO_4$ in de-ionized $H_2O$ and washed with 15% $H_2SO_4$ (at least 4 CV), and then with deionized $H_2O$ until it was neutral. The resin was transferred back into the beaker, and 15% NaOH in de-ionized $H_2O$ solution (50 mL) was added, and the mixture was stirred for 15 min and decanted (1×). The resin was transferred to the column and washed with 15% NaOH in de-ionized $H_2O$ (at least 4 CV), and then with de-ionized $H_2O$ until it was neutral (at least 4 CV). Compound 5kk triethylammonium salt was dissolved in de-ionized $H_2O$ (2.3 mg in 2 mL), added to the top of the column, and eluted with de-ionized $H_2O$. The converted sodium salt was eluted out in early fractions as detected by TLC (UV). The product was lyophilized to give 1-52 (sodium salt, 1.8 mg) as a white solid. $^1H$ NMR (400 MHz, $D_2O$): δ 7.98 (s, 1H), 7.63 (s, 1H), 5.80-5.86 (m, 2H), 4.79-4.94 (m, 3H), 4.12-4.15 (m, 2H), 4.01-4.10 (m, 4H), 3.86-3.90 (d, J=8.4 Hz, 1H), 2.55-2.75 (m, 4H). $^{31}P$ NMR (162 MHz, $D_2O$): δ −1.35, −1.40. ESI-MS: m/z 686.05 $[M−H]^+$.

Example 39

Compound 1-53

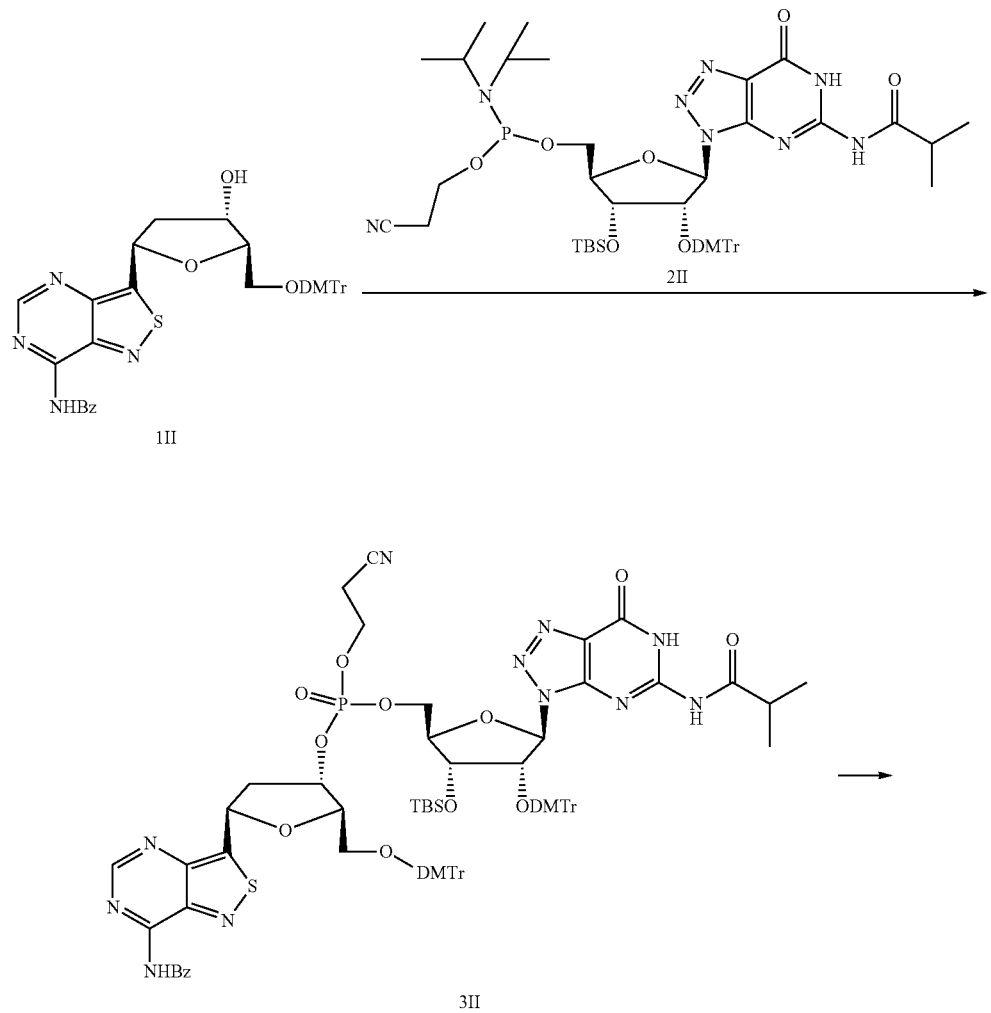

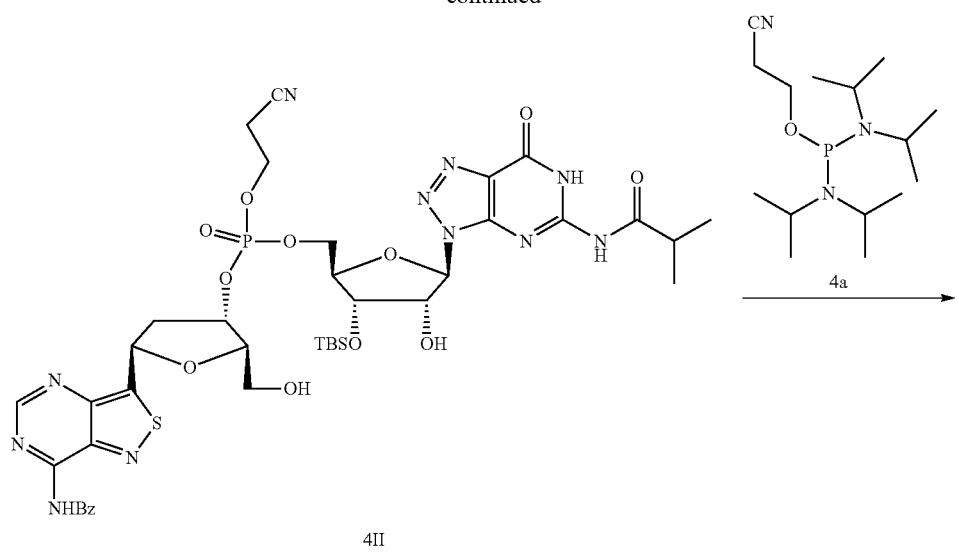
4II
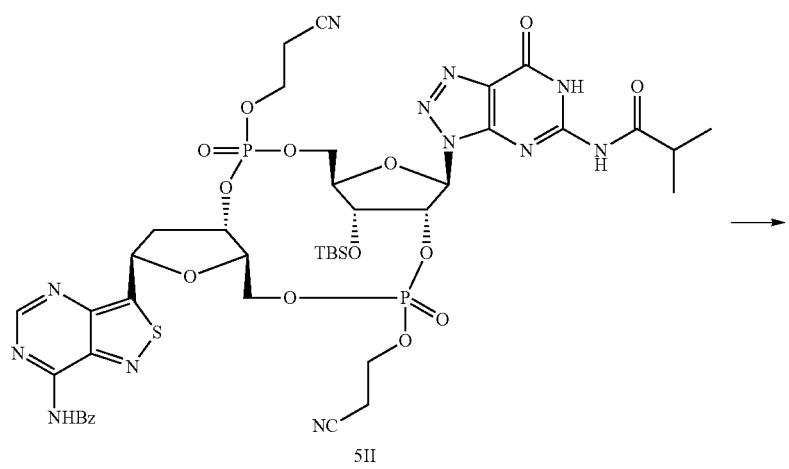
5II
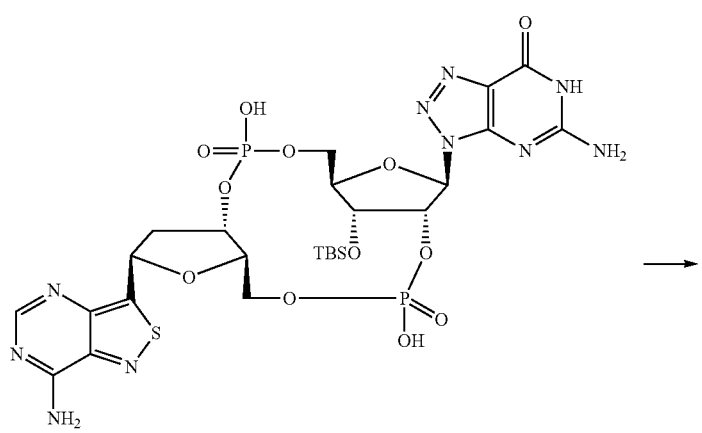
6II

-continued

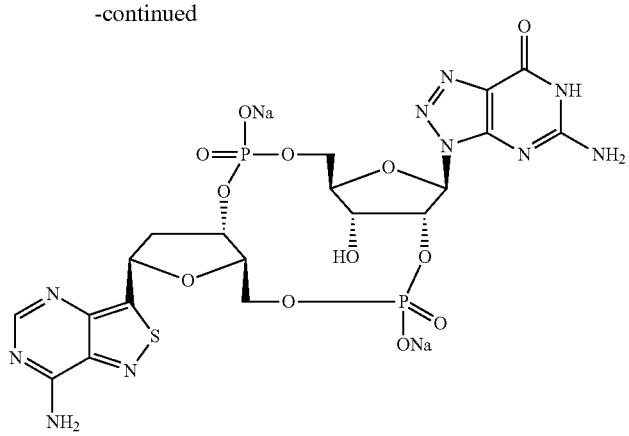

1-53

Compound 1ll (300 mg, 0.44 mmol) and 2ll (450 mg, 0.46 mmol) were dissolved in anhydrous $CH_3CN$ (18.0 mL) and 4 Å molecular sieves powder (180 mg, 1 gr/100 mL) were added. The heterogeneous mixture was bubbled with Ar for 4 min. After stirring at rt for 20 min, 0.45 M tetrazole in $CH_3CN$ (2.67 mmol, 6.00 mL) was added at rt. After stirring for 1 h, the mixture was washed with anhydrous $CH_3CN$. To this solution was added a solution of 12 in pyridine (0.05M) until the reaction completed. After stirring for 20-30 min at rt, the mixture was filtered, and then the reaction was quenched with $Na_2SO_3$ (aq). The mixture was diluted with EtOAc, and the layers were separated. The organic phase was washed with sat. aq. $NaHCO_3$ (1×20.0 mL) and sat. aq. NaCl (1×20.0 mL). The combined aqueous phase was back extracted with EtOAc (1×20.0 mL). The combined organic phases were evaporated to dryness, and the crude material was purified by reverse phase prep-HPLC (Column: C18 spherical 20-35 μm 100A 80 g, mobile phase: 0.05% $NH_4HCO_3$ in water, m/m)-ACN from 60% to 100%, flow rate: 35.0 mL/min) to give 3ll (550.00 mg, 0.35 mmol, 79.26% yield) as a white foam. $^{31}P$ NMR (162 MHz, DMSO-$d_6$): δ −2.82, −2.86. ESI-MS: m/z=1561.0[M+H]$^+$ Compound 3ll (550.00, 0.35 mmol) was dissolved in the solution of $CH_3COOH:CH_3CN=4:1$ (v/v, 5.0 mL). After stirring for 1 h at 40° C., the mixture was neutralized with ice sat. $NaHCO_3$ (aq.) and extracted with EtOAc (3×20.0 mL). The organic layers was washed with sat. NaCl aq. (1×60.0 mL), dried over $Na_2SO_4$ and concentrated under reduced pressure to give a residue. The crude residue was purified by silica gel column chromatography (DCM/acetone, 0-100% acetone) to afford 4ll (170 mg, 177.82 μmol, 50.46% yield) as a white solid. $^{31}P$-NMR (162 MHz, DMSO-$d_6$): δ −2.82, −2.86. ESI-MS: m/z=956.2[M+H]$^+$ Compound 4ll (170 mg, 177.82 μmol) dissolved in anhydrous $CH_3CN$ (20.0 mL), and 0.45 M tetrazole in $CH_3CN$ (5.31 mmol, 3.20 mL) and 4 Å molecular sieves powder (200 mg, 1 gr/100 mL) were added. The heterogeneous mixture was bubbled with Ar for 4 min. After stirring at rt for 20 min, 4a (107 mg, 0.36 mmol) in $CH_3CN$ (2.0 mL) was added at rt over 25 to 30 min. After stirring for 2 h, the mixture was filtered and washed with anhydrous $CH_3CN$. To this solution was added 0.05M $I_2$ in pyridine until the reaction was completed. After stirring for 20-30 min at rt, the reaction was quenched with sat. aq. $NaS_2O_3$. The mixture was diluted with EtOAc, and the organic layers were separated. The organic phase was washed with sat.$NaHCO_3$ aq. (1×20.0 mL) and sat. NaCl aq. (1×20.0 mL). The combined aqueous was phase back extracted with EtOAc (1×50 mL). The combined organic phases were evaporated to dryness, and the crude material was purified by reverse phase prep-HPLC (Column: C18 spherical 20-35 μm 100A 80 g, mobile phase: 0.05% $NH_4HCO_3$ in water, m/m)-ACN from 30% to 60%, flow rate: 35 mL/min) to give 5ll (40 mg, 37.35 μmol, 21.01% yield) as a white foam. ESI-MS: m/z=1071.7 [M+H]$^+$.

Compound 6ll (40 mg, 37.35 μmol) was treated with a solution of $NH_3$ in $CH_3OH$ (5.0 mL, 7M). After stirring for 2 h at 40° C., the mixture was evaporated to dryness, and the crude material was purified by reverse phase prep-HPLC (Column: C18 spherical 20-35 μm 100A 40 g, mobile phase A: 0.05% $NH_4HCO_3$ in water, m/m-ACN from 0% to 10%, flow rate: 20 mL/min) to afford 6ll (12.8 mg, 16.19 μmol, 43.33% yield) as a white foam. $^{31}P$-NMR (162 MHz, DMSO-$d_6$): δ −1.50, −3.00. ESI-MS: m/z=791.1 [M+H]$^+$ A solution of 7ll (12.8 mg, 16.19 μmol) in 12% TEAF in DMSO (2 mL) was stirred at rt for 48 h. The mixture was cooled to rt. 15.0 mL volume of Amberlite IR-120 (Na form) was added to a column and washed with deionized water (3×15 mL). The crude product was dissolved in deionized water (5 mL), added to the top of the column and eluted with deionized water. The residue was purified by reverse phase prep-HPLC Column: C18 spherical 20-35 μm 100A 40 g, mobile phase: 0.05% $NH_4HCO_3$ in water, m/m)-ACN from 0% to 15%, flow rate: 20 mL/min) to get the ammonia salt product 8ll-P1 (8.0 mg, 11.83 μmol, 73.06% yield) as a white foam. 15.0 mL volume of Amberlite IR-120 (Na form) was added to a column and washed with deionized water (3×5 mL). The ammonia salt product was dissolved in deionized water (5 mL), added to the top of the column and eluted with deionized water. The compound was eluted out in early fractions as detected by TLC (UV). The product was lyophilized to give 1-53 (6.2 mg, 8.61 mol, 72.77% yield). $^1H$-NMR (400 MHz, $D_2O$): δ 8.10 (s, 1H), 6.21 (d, 1H), 5.94 (t, 6.4, 1H), 5.65 (s, 1H), 5.18 (m, 1H), 4.58 (s, 2H), 4.39 (s, 1H), 4.24 (s, 1H), 4.15 (s, 1H), 4.05 (m, 3H), 2.82 (s, 1H), 2.61 (s, 1H). $^{31}P$-NMR (162 MHz, $D_2O$-$d_6$): δ −1.01, −1.21. ESI-MS: m/z=677.0 [M+H]$^+$.

Example 40
Compound 1-54
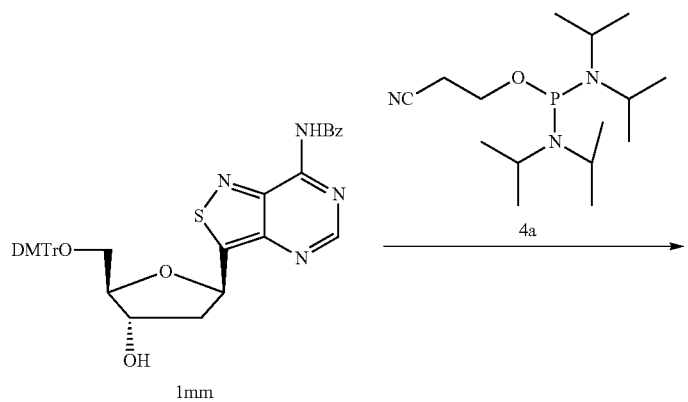
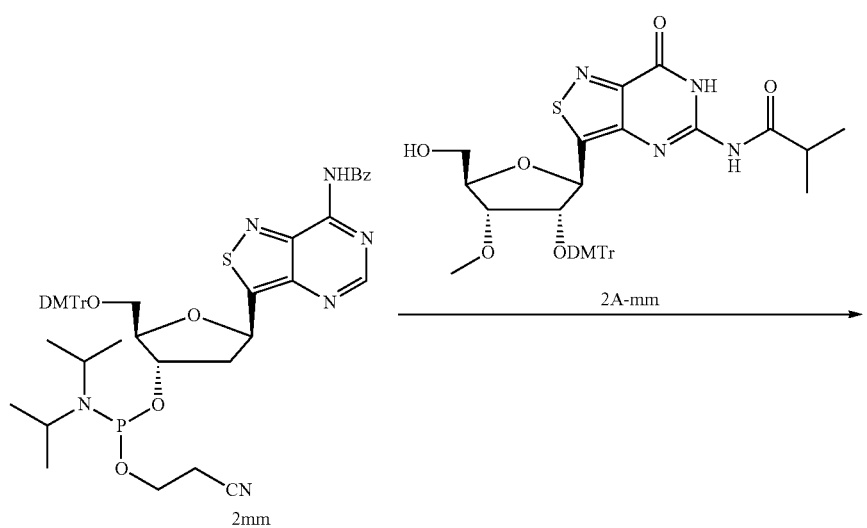
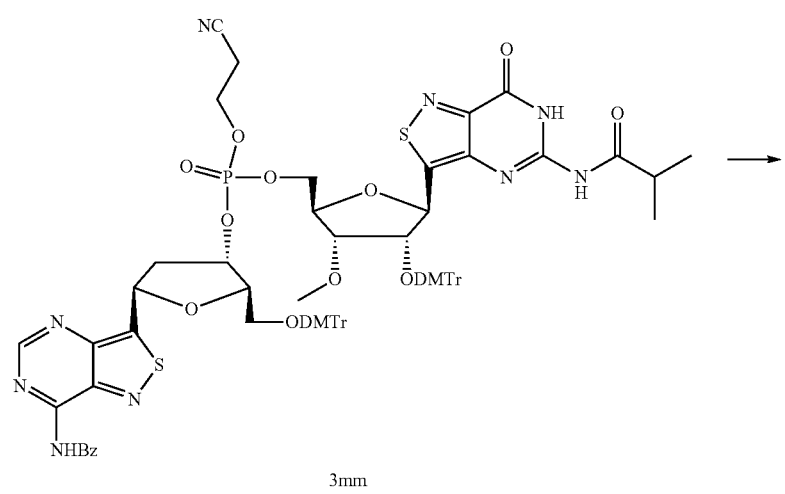

321
-continued
322
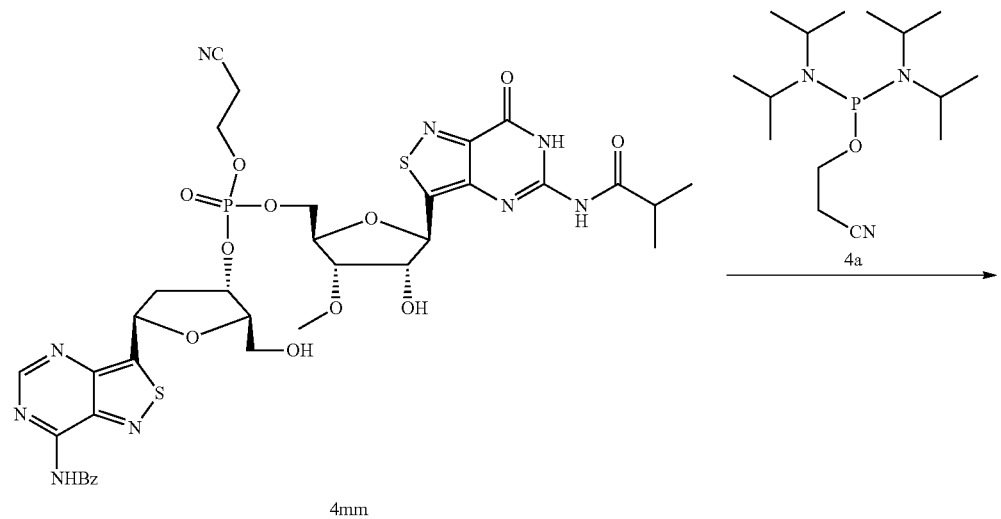
4mm
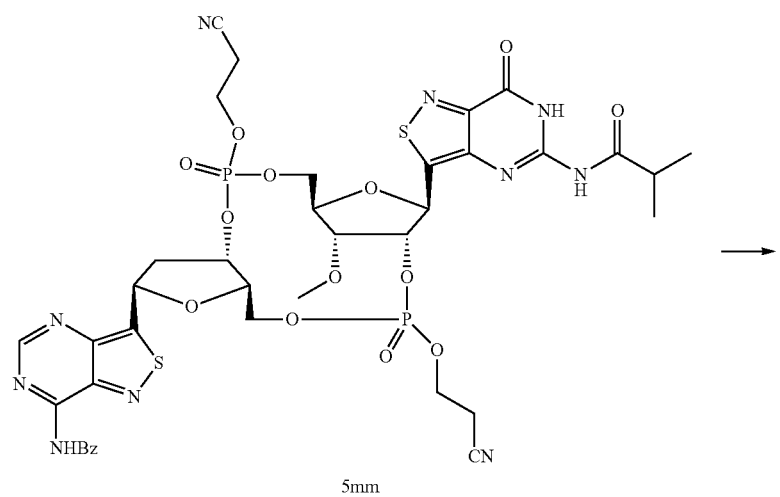
5mm
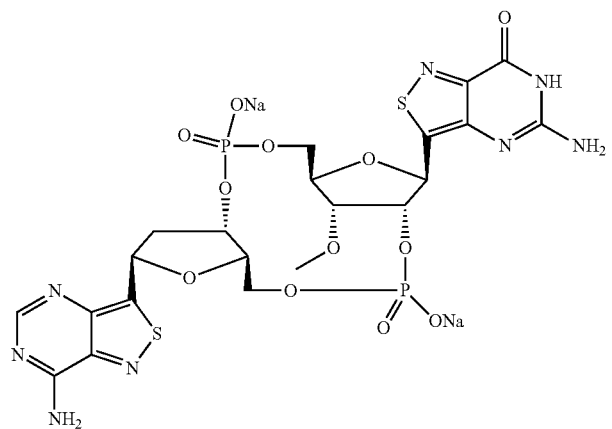
1-54

To a 50 mL round bottomed flask was added 1 mm (650.00 mg, 963.30 umol) and DCM (10 mL) and 4,5-Dicyanoimidazole (102.39 mg, 866.97 umol). Compound 4a (377.45 mg, 1.25 mmol) was added, and the mixture was stirred at rt for 2 h. The mixture was washed with H$_2$O (2×30 mL) and brine (1×50 mL). The DCM layer was concentrated in vacuo to give the crude, which was purified by reverse phase prep-HPLC (Column: C18 spherical 20-35 μm 100A 40 g, mobile phase: 0.05% NH$_4$HCO$_3$ in water-ACN from 70% to 100%, flow rate: 25 mL/min) to obtain 2 mm (630 mg, 720.02 umol, 74.74% yield) as a white solid. ESI-MS: m/z 875.7 [M+H]$^+$.

Compound 2A-mm (400 mg, 582.43 umol) and 2 mm (611.54 mg, 698.92 umol) were dissolved in anhydrous CH$_3$CN (28.0 mL), and 4 Å molecular sieves powder (300 mg, 1 gr/100 mL) were added. The heterogeneous mixture was bubbled with Ar for 4 min. After stirring at rt for 20 min, 0.45 M tetrazole in CH$_3$CN (3.49 mmol, 7.7 mL) was added at rt. After stirring for 1 h, the mixture was filtered and washed with anhydrous CH$_3$CN. 0.05 M I$_2$ (23.3 mL) was added until the reaction completed. After stirring for 20-30 min at rt, the mixture was filtered, and then the reaction was quenched with Na$_2$SO$_3$ (aq). The mixture was diluted with EtOAc, and the layers were separated. The organic phase was washed with sat. aq. NaHCO$_3$ (1×50.0 mL) and sat. aq. NaCl (1×50.0 mL). The combined aqueous phase was back extracted with EtOAc (1×50.0 mL). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 60% to 100%, flow rate: 35.0 mL/min) to give 3 mm (700 mg, 474.07 umol, 81.40% yield) as a white foam. $^{31}$P-NMR (162 MHz, DMSO-d$_6$): δ −2.73, −2.84. ESI-MS: m/z 1476.1 [M+H]$^+$.

In a 25 mL round bottomed flask, 3 mm (700 mg, 474.07 umol) was added to a solution of CH$_3$CN (4 mL) and AcOH (1 mL). After stirring for overnight at rt, the mixture was neutralized with cooled aq. NaHCO$_3$ and extracted with EtOAc (4×100 mL). The combined EtOAc layer was washed with brine and concentrated in vacuo to give the crude. The crude was purified by reverse phase prep-HPLC (Column: C18 spherical 20-35 m 100A 80 g, mobile phase: 0.05% NH$_4$HCO$_3$ in water, m/m)-ACN from 0% to 60%, flow rate: 35.0 mL/min) to give 4 mm (230 mg, 263.81 umol, 55.65% yield) as a white solid. ESI-MS: m/z=872.1 [M+H]$^+$.

Compound 4 mm (215 mg, 246.61 umol) dissolved in anhydrous CH$_3$CN (20 mL mL), and 0.45 M tetrazole in CH$_3$CN (1.97 mmol, 4.37 mL) and 4 Å molecular sieves powder (1.0 g, 1 gr/100 mL) were added. The heterogeneous mixture was bubbled with Ar for 4 min. After stirring at rt for 20 min, 4a (148.31 mg, 492.05 umol) in CH$_3$CN (10.0 mL) was added at rt over 25 to 30 min. After stirring for 2 h, the mixture was filtered and washed with anhydrous CH$_3$CN. To this solution was added 0.05 M I$_2$ (9.86 mL) until the reaction completed. After stirring for 20-30 min at rt, the reaction was quenched with sat. aq. NaS$_2$O$_3$. The mixture was diluted with EtOAc, and the organic layers separated. The organic phase was washed with sat.NaHCO$_3$ aq. (1×50.0 mL) and sat. NaCl aq. (1×50.0 mL). The combined aqueous phase was back extracted with EtOAc (1×100 mL). The combined organic phases were evaporated to dryness, and the crude material was purified by reverse phase prep-HPLC (Column: C18 spherical 20-35 μm 100A 80 g, mobile phase: 0.05% NH$_4$HCO$_3$ in water, m/m)-ACN from 0% to 50%, flow rate: 35 mL/min) to give 5 mm (60 mg, 60.80 umol, 24.65% yield) as a white foam. ESI-MS: m/z 987.0 [M+H]$^+$.

Compound 5 mm (60 mg, 60.80 umol) was treated with a solution of 7M NH$_3$ in MeOH (12.0 mL, 33%). After stirring for 5 h at rt, the mixture was evaporated to dryness, and the crude material was purified by reverse phase prep-HPLC (Column: C18 spherical 20-35 μm 100A 40 g, mobile phase A: 0.05% NH$_4$HCO$_3$ in water, m/m-ACN from 0% to 10%, flow rate: 20 mL/min) to afford NH$_4$ salt product 6 mm-P1 (12.0 mg, 16.97 umol, 27.9% yield) as a white foam.

A 15.0 mL volume of Amberlite IR-120 (Na form) was added to a column and washed with deionized water (3×15 mL). The NH$_4$ salt product (12.0 mg) was dissolved in deionized water (12 mg in 10 mL), added to the top of the column and eluted with deionized water. The compound was eluted out in early fractions as detected by TLC (UV). The product was lyophilized to give 1-54 (10 mg, 14.14 umol, 23.25% yield) as a white foam. $^1$H NMR (400 MHz, D$_2$O): δ 8.08 (s, 1H), 5.88-5.82 (m, 1H), 5.31-5.29 (d, J=9.6 Hz, 1H), 4.78 (m, 2H), 4.46 (s, 1H), 4.22-4.04 (m, 5H), 3.97-3.93 (m, 1H), 3.51 (s, 3H), 2.82-2.76 (m, 1H), 2.41-2.38 (m, 1H). $^{31}$P-NMR (162 MHz, DMSO-d$_6$): δ −1.08, −1.38. ESI-MS: m/z 707.1 [M+H]$^+$.

Example 41

Compounds 1-55a, 1-55b, 1-55c & 1-55d

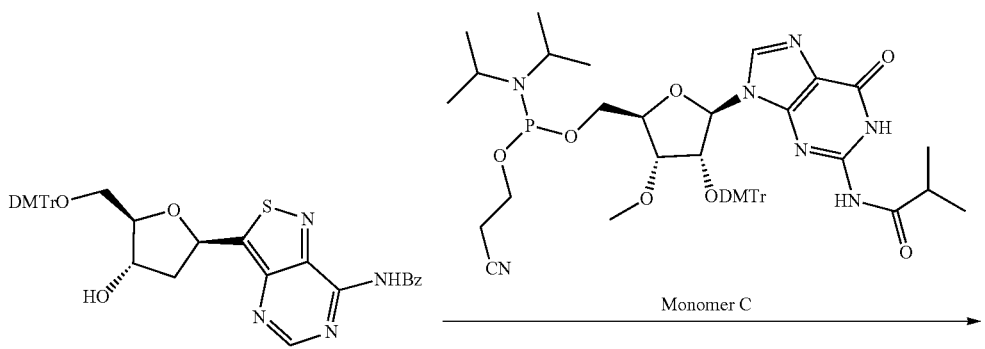

Monomer C

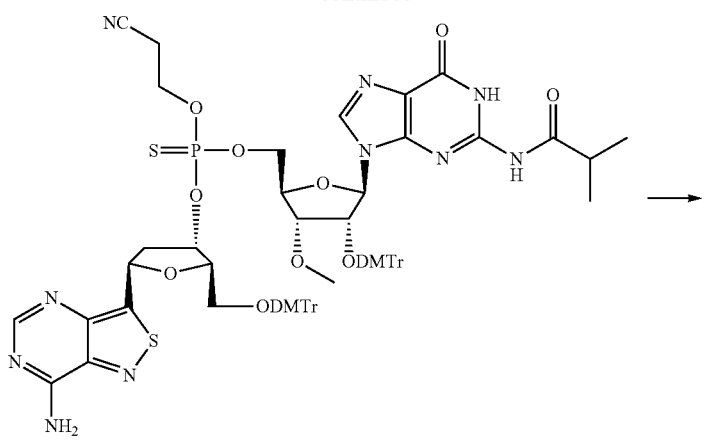
2nn
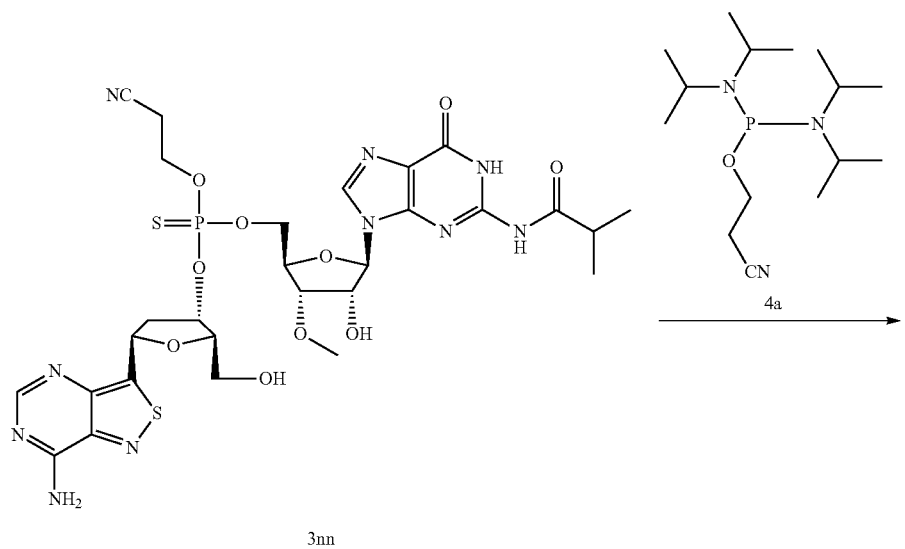
3nn
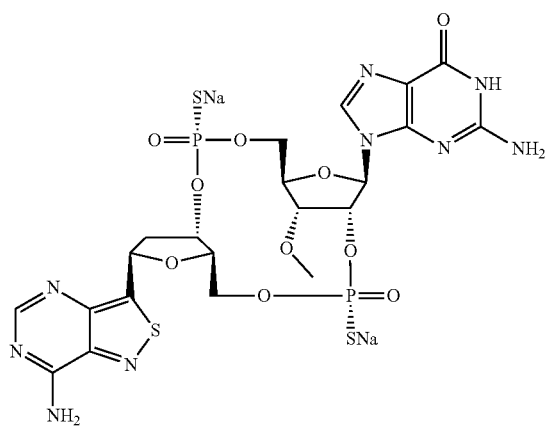
1-55a

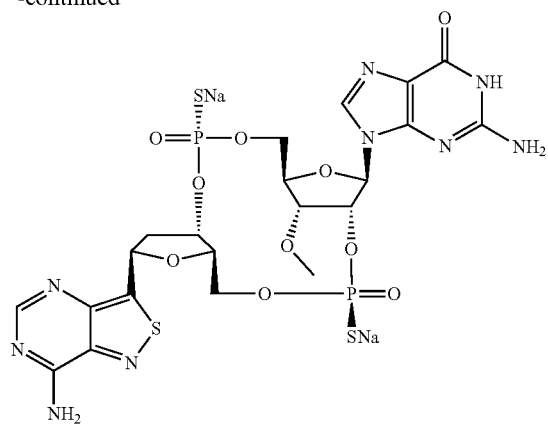
1-55b
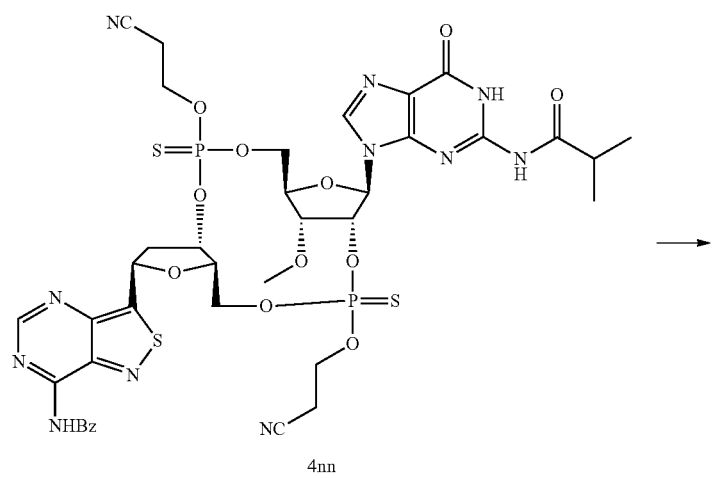
4nn
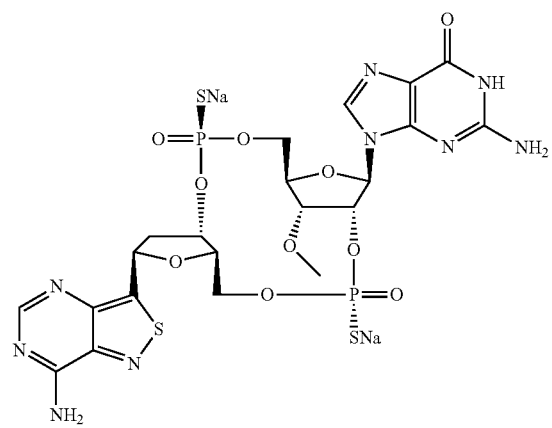
1-55c

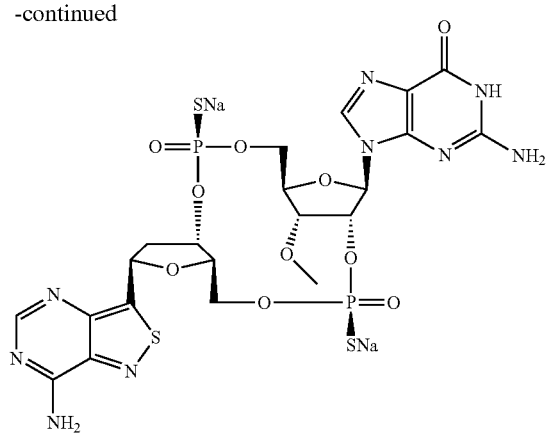

1-55d

Compound 1nn (950.0 mg, 1.41 mmol) and Monomer C (1.59 g, 1.83 mmol) were dissolved in anhydrous CH$_3$CN (50.0 mL), and 0.25 M tetrazole in CH$_3$CN (8.46 mmol, 33.8 mL) and 4 Å molecular sieves powder (5.0 g, 1 gr/100 mL) were added. After stirring for 2 h 0.1M DDTT (0.1M 28 mL) was added until the reaction completed. After stirring for 1 h at rt, the reaction was quenched with Na$_2$SO$_3$ (aq.). The mixture was filtered, washed with anhydrous CH$_3$CN and extracted with EtOAc (3×40.0 mL). The organic phase was washed with sat. aq. NaHCO$_3$ (1×50.0 mL) and sat. aq. NaCl (1×50.0 mL). The combined aqueous phase was back extracted with EtOAc (1×50.0 mL). The combined organic phases were evaporated to dryness, and the crude material was purified by reverse phase prep-MPLC (Column: C18 spherical 20-35 μm 100A 80 g, mobile phase: 0.05% NH$_4$HCO$_3$ in water, m/m)-ACN from 30% to 60%, flow rate: 35 mL/min) to give 2nn (2 g, 1.36 mmol, 96% yield) as a white foam. $^{31}$P NMR (162 MHz, D$_2$O): δ 66.34, 66.21. ESI-MS: m/z 1476.5 [M+H]$^+$.

Compound 2nn (2.0 g, 1.36 mmol) was dissolved in CH$_3$CN (7.0 mL) that dissolved AcOH (28.0 mL). After stirring for 30 min at rt, the mixture was extracted with EtOAc (3×40.0 mL). The organic phase was washed with sat. aq. NaHCO$_3$ (1×50.0 mL) and sat. aq. NaCl (1×50.0 mL). The combined aqueous phase was back extracted with EtOAc (1×50.0 mL). The combined organic phases were evaporated to dryness, and the crude material was purified by reverse phase prep-MPLC (Column: C18 spherical 20-35 μm 100A 80 g, mobile phase: 0.05% NH$_4$HCO$_3$ in water, m/m)-ACN from 20% to 50%, flow rate: 35 mL/min) to give 3nn (600.0 mg, 688.98 μmol, 51% yield) as a white foam. $^{31}$P NMR (162 MHz, D$_2$O): δ 66.05, 65.94. ESI-MS: m/z 871.1 [M+H]$^+$.

Compound 3nn (580.0 mg, 666.02 μmol) dissolved in anhydrous CH$_3$CN (150.0 mL), and 0.45 M tetrazole in CH$_3$CN (5.33 mmol, 21.3 mL) and 4 Å molecular sieves powder (5.0 g, 1 gr/100 mL) were added. The heterogeneous mixture was bubbled with Ar for 5 min. After stirring at rt for 30 min, 4a (401.48 mg, 1.33 mmol) dissolved in CH$_3$CN (20.0 mL) was added dropwise rt over 50 min. After stirring for 2 h, 0.1M DDTT (0.1M 28 mL) was added until the reaction completed. After stirring for 30 min at rt, the reaction was quenched with Na$_2$SO$_3$ (aq.). The mixture was filtered, washed with anhydrous CH$_3$CN and extracted with EtOAc (3×40.0 mL). The organic phase was washed with sat. aq. NaHCO$_3$ (1×50.0 mL) and sat. aq. NaCl (1×50.0 mL). The combined aqueous phase was back extracted with EtOAc (1×50.0 mL). The combined organic phases were evaporated to dryness, and the crude material was purified by reverse phase prep-MPLC (Column: C18 spherical 20-35 μm 100A 40 g, mobile phase: 0.05% NH$_4$HCO$_3$ in water, m/m)-ACN from 30% to 60%, flow rate: 35 mL/min) to give 4nn (200.0 mg, 199.61 μmol, 30% yield) as a white foam. ESI-MS: m/z 1002.0 [M+H]$^+$.

Compound 4nn (200.0 mg, 199.61 μmol) was dissolved in 7M NH$_3$/MeOH (20 mL), and the mixture was stirred at rt for 12 h. The mixture evaporated to dryness, and the residue was purified by reverse phase prep-HPLC (Column: XBridge 30×100 mm, mobile phase: 0.05% NH$_4$HCO$_3$ in water-ACN from 0% to 15%, flow rate: 20 mL/min) to get the ammonia salt products 5nn-P1 (24.0 mg, 33.25 μmol, 17% yield), 5nn-P2 (20.3 mg, 28.13 μmol, 14% yield), 5nn-P3 (4.2 mg, 5.82 μmol, 3% yield) and 5nn-P4 (4.3 mg, 5.96 μmol, 3% yield) each as a white foam.

15.0 mL volume of Amberlite IR-120 (Na form) was 90.96 dded to a column and washed with deionized water (3×15.0 mL). The ammonia salt products were dissolved in deionized water (15.0 mL), added to the top of the column and eluted with deionized water. The compounds eluted out in early fractions as detected by TLC (UV). The product was lyophilized to give 1-55a (21.0 mg, 27.43 μmol, 82% yield) from 5nn-P1, 1-55b (4.0 mg, 5.22 μmol, 19% yield) from 5nn-P2, 1-55c (2.0 mg, 2.61 μmol, 45% yield) from 5nn-P3 and 1-55d (2.0 mg, 2.61 μmol, 44% yield) from 5nn-P4 each as a white foam.

1-55a: $^1$H NMR (400 MHz, D$_2$O): δ 8.44 (s, 1H), 8.14 (s, 1H), 5.96 (d, J=8.8 Hz, 1H), 5.90 (dd, J$_1$=10.0 Hz, J$_2$=5.6 Hz, 1H), 5.38 (dd, J=8.0 Hz, 1H), 5.31 (m, 1H), 4.48 (s, 1H), 4.42 (d, J=7.2 Hz, 1H), 4.19-4.14 (m, 2H), 4.08 (m, 2H), 3.99 (m, 1H), 3.56 (s, 3H), 3.07 (m, 1H), 2.36 (m, 1H). $^{31}$P NMR (162 MHz, D$_2$O): δ 60.32, 54.75. ESI-MS: m/z 722.0 [M+H]$^+$.

1-55b: $^1$H NMR (400 MHz, D$_2$O): δ 8.23 (s, 1H), 8.13 (s, 1H), 5.92 (m, 2H), 5.28 (dt, J$_1$=9.6 Hz, J$_2$=4.0 Hz, 1H), 4.99 (m, 1H), 4.55 (s, 1H), 4.40 (d, J=4.0 Hz, 1H), 4.32 (s, 1H), 4.21-4.10 (m, 3H), 4.03 (m, 1H), 3.51 (s, 3H), 2.87 (m, 1H), 2.71 (m, 1H). $^{31}$P NMR (162 MHz, D$_2$O): δ 53.65, 53.00. ESI-MS: m/z 722.0 [M+H]$^+$.

1-55c: $^1$H NMR (400 MHz, D$_2$O): δ 8.14 (s, 1H), 8.01 (s, 1H), 5.94 (t, J=7.8 Hz, 1H), 5.90 (d, J=8.4 Hz, 1H), 5.44 (m, 1H), 5.33 (d, 1H), 4.56 (s, 1H), 4.35 (d, J=8.4 Hz, 1H), 4.28 (t, J=9.6 Hz, 1H), 4.11-4.06 (m, 3H), 3.98-3.96 (m, 1H), 3.54 (s, 3H), 2.90 (m, 1H), 2.45 (m, 1H). $^{31}$P NMR (162 MHz, D$_2$O): δ 53.68, 54.75. ESI-MS: m/z 722.0 [M+H]$^+$.

1-55d: $^1$H NMR (400 MHz, D$_2$O): δ 8.15 (s, 1H), 7.88 (s, 1H), 5.95 (dd, J$_1$=8.0 Hz, J$_2$=4.4 Hz, 1H), 5.87 (d, J=8.8 Hz, 1H), 5.48 (dt, J$_1$=8.8 Hz, J$_2$=4.4 Hz, 1H), 5.20 (t, J=6.8 Hz, 1H), 4.56 (s, 1H), 4.33 (d, J=4.0 Hz, 1H), 4.27 (d, J=2.4 Hz, 2H), 4.11-4.07 (m, 3H), 3.08 (s, 3H), 2.84 (m, 1H), 2.67 (m, 1H). $^{31}$P NMR (162 MHz, D$_2$O): δ 54.67, 52.56. ESI-MS: m/z 721.9 [M+H]$^+$.

Example 42
Compound 1-56
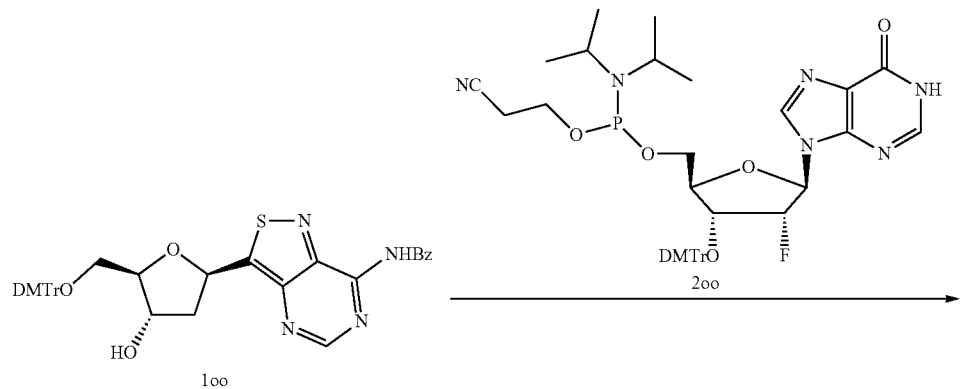
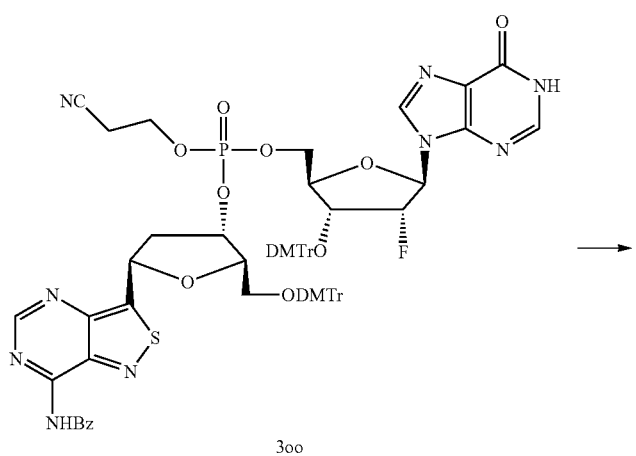
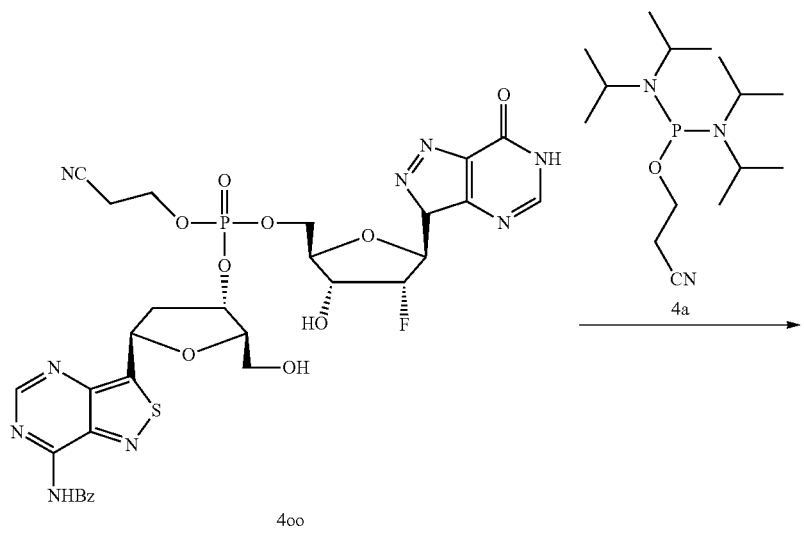

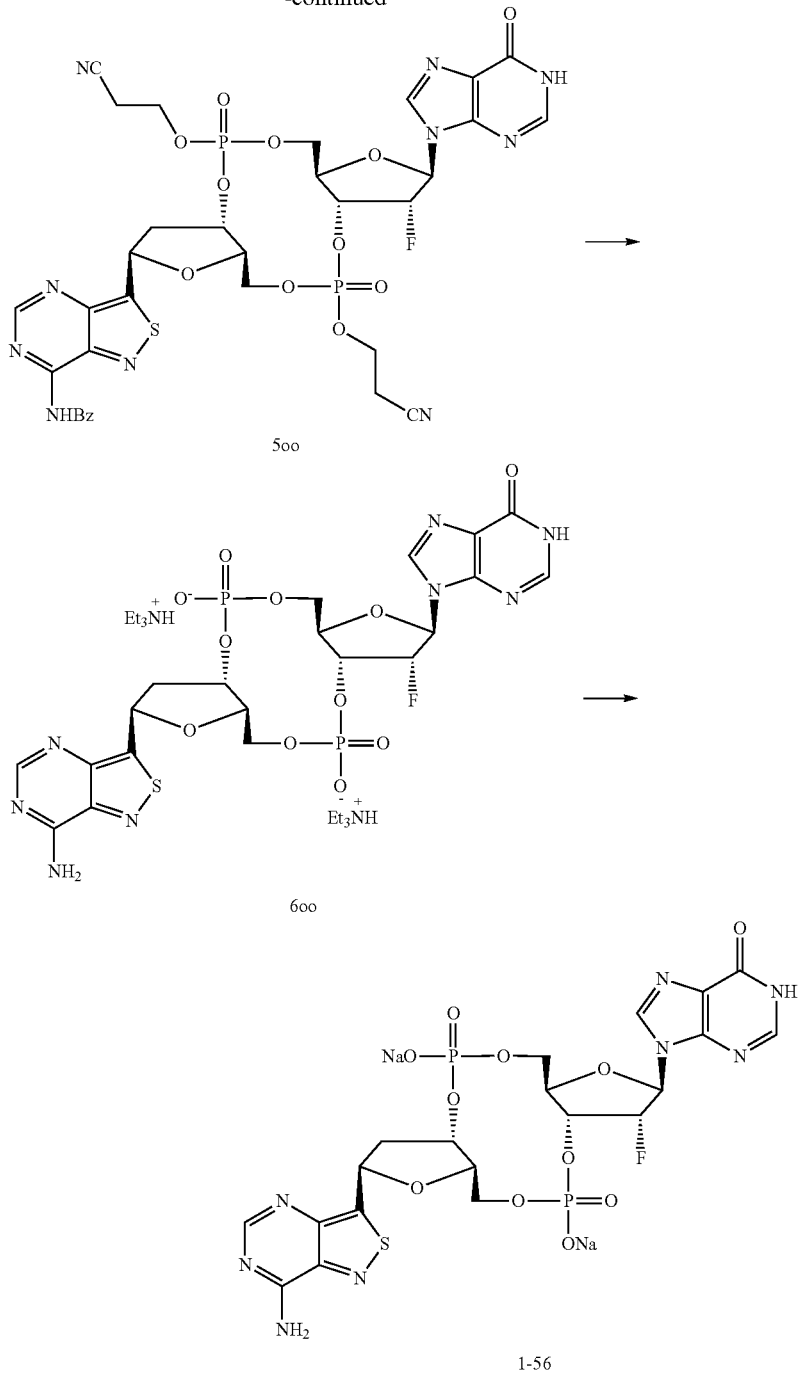

5oo

6oo 1-56

Compound 1oo (120 mg, 0.178 mmol) and 2oo (178 mg, 0.231 mmol) were dissolved in anhydrous $CH_3CN$ (10 mL), and 0.45 M tetrazole in $CH_3CN$ (1.6 mL, 0.72 mmol) and 4 Å molecular sieves powder were added. The heterogeneous mixture was bubbled with $N_2$ for 10 min. After stirring for 2 h, 0.05 M 2 ($THF:H_2O:Py=8:1:1$) was added. The mixture was stirred for 20 min. The mixture was filtered, and washed with EA. The reaction was quenched with aq. $Na_2SO_3$. The mixture was diluted with EtOAc. The layers were separated. The organic phase was washed with aq. $NaHCO_3$ (1×60 mL) and aq. NaCl (1×60 mL). The combined organic phases were evaporated to dryness, and the crude material was purified by flash silica column chromatography (0-10 MeOH in $CH_2Cl_2$) to give 3oo (145 mg, 60%) as a white solid. ESI-MS: m/z 1362.51 [M+H]$^+$.

Compound 3oo (145 mg, 0.106 mmol) was dissolved in DCA in DCM (3%, v/v, 3 mL) and triethyl silane (1.5 mL) was added. After stirring for 1 h at rt, the mixture was neutralized with sat. sodium bicarbonate solution at 0° C. The mixture was evaporated to dryness, and the crude residue was purified by flash silica column chromatography (0-20 MeOH in $CH_2Cl_2$) to give 4oo (30 mg, 38%) as a white solid. ESI-MS: m/z 758.21 [M+H]$^+$.

335

Compound 4oo (30 mg, 0.039 mmol) dissolved in anhydrous $CH_3CN:DMF:THF$ (4:2:4, v:v:v), and 0.45 M tetrazole in $CH_3CN$ (0.7 mL, 0.316) and 4 Å molecular sieves powder were added. The heterogeneous mixture was bubbled with $N_2$ for 10 min. Compound 4a (24 mg, 0.078 mmol) was added by dropwise. After stirring for 2 h, 0.05 M $I_2$ ($THF:H_2O:Py$=8:1:1) was added. The mixture was stirred for 20 min. The mixture was filtered, and washed with EA. The reaction was quenched with aq. $Na_2SO_3$. The mixture was diluted with EtOAc, and the layers separated. The organic phase was washed with aq. $NaHCO_3$ (1×60 mL) and aq. NaCl (1×60 mL). The combined organic phases were evaporated to dryness, and the crude material was purified by flash silica column chromatography (0-20 MeOH in $CH_2Cl_2$) to give 5oo (12 mg, not pure) as a yellow solid. ESI-MS: m/z 873.31 $[M+H]^+$.

Compound 5oo (12 mg, not pure) was treated with a solution of diisopropylamine:MeOH:$H_2O$ (3 mL, 1:1:2, v:v:v). After stirring for 16 h at rt, the mixture was evaporated to dryness, and the crude material was purified by reverse phase prep-HPLC (Column: C18 column, 21×250 mm, mobile phase: A: 0.1% formic acid in water, B: MeCN; Gradient: 0% to 25% B over 30 min, flow rate: 15 mL/min) to give 6oo (2.1 mg) as a free acid form in a white foam. ESI-MS: m/z 663.51 $[M+H]^+$.

Dowex 50W×8, 200-400 (H form, 10 mL) was added to a beaker and washed with de-ionized water (2×). Then to the resin was added 15% $H_2SO_4$ in de-ionized $H_2O$ (50 mL), and the mixture was stirred for 15 min and decanted (1×). The resin was transferred to a column with 15% $H_2SO_4$ in de-ionized $H_2O$ and washed with 15% $H_2SO_4$ (at least 4 CV), and then with deionized $H_2O$ until it was neutral. The resin was transferred back into the beaker, and 15% NaOH in de-ionized $H_2O$ solution (50 mL) was added. The mixture was stirred for 15 min and decanted (1×). The resin was transferred to the column, washed with 15% NaOH in de-ionized $H_2O$ (at least 4 CV), and then with de-ionized $H_2O$ until it was neutral (at least 4 CV). Compound 6oo triethylammonium salt was dissolved in de-ionized $H_2O$ (2.3 mg in 2 mL), added to the top of the column, and eluted with de-ionized $H_2O$. The converted sodium salt was eluted out in early fractions as detected by TLC (UV). The product was lyophilized to give 1-56, sodium salt (1.1 mg) as a white solid. ESI-MS: m/z 663.05 $[M+H]^+$.

Example 43

Additional Compounds

The foregoing syntheses are exemplary and can be used as a starting point to prepare a large number of additional compounds. Examples of compounds of Formulae (I), (II) and (III) that can be prepared in various ways, including those synthetic schemes shown and described herein, are provided below. Those skilled in the art will be able to recognize modifications of the disclosed syntheses and to devise routes based on the disclosures herein; all such modifications and alternate routes are within the scope of the claims.

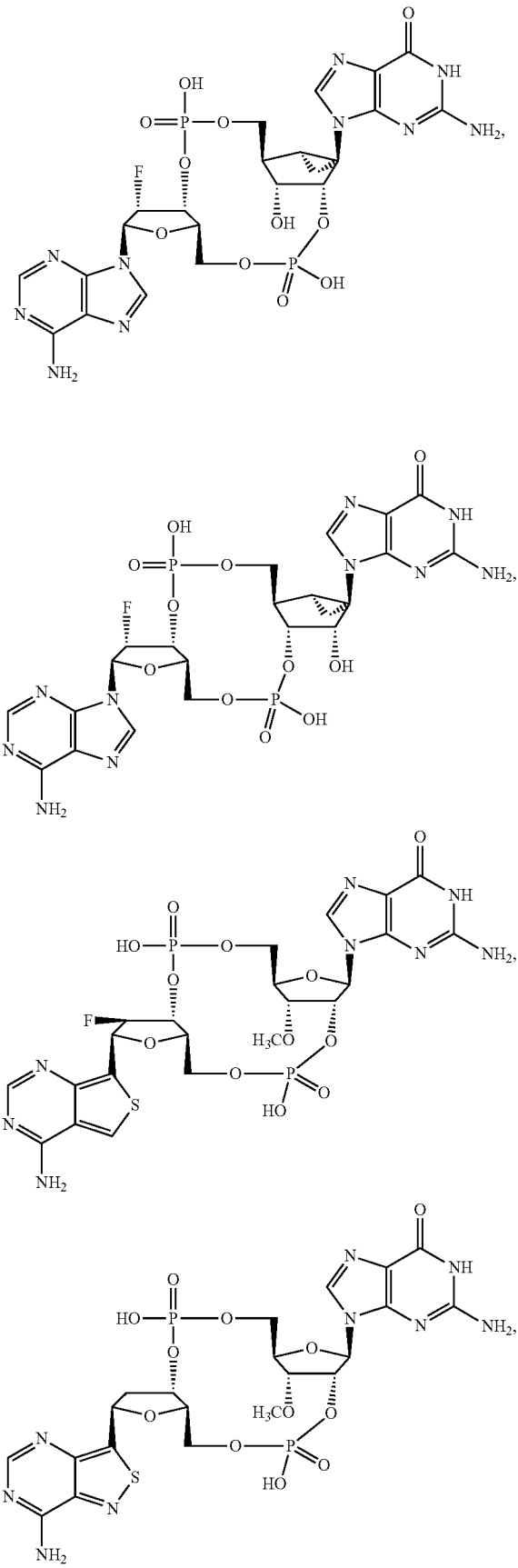

337
-continued
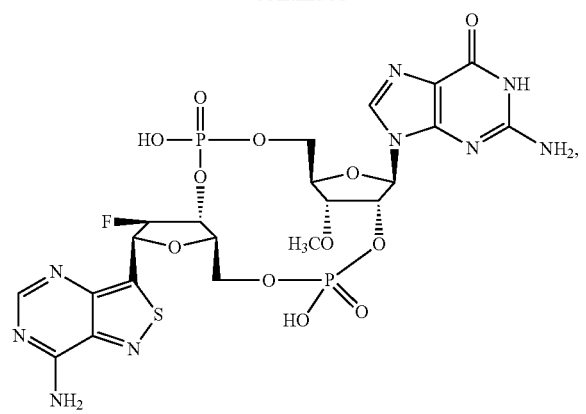
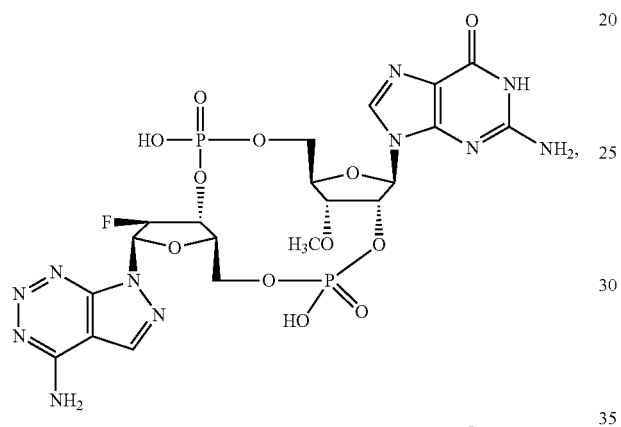
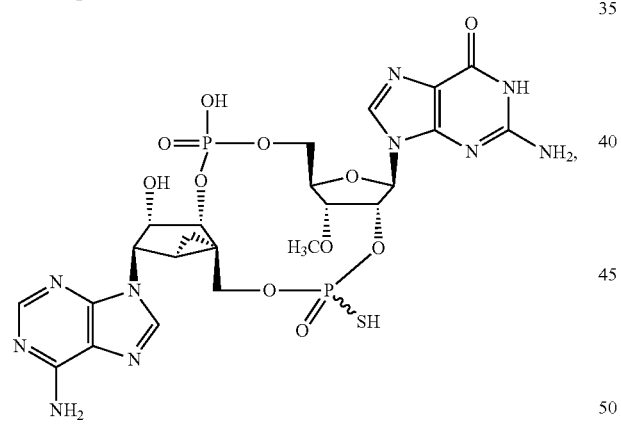
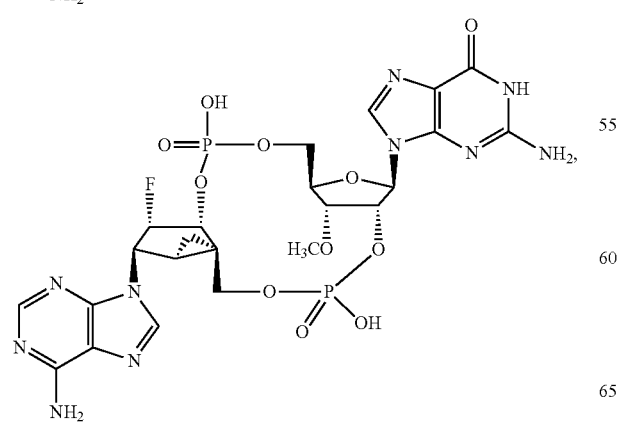
338
-continued
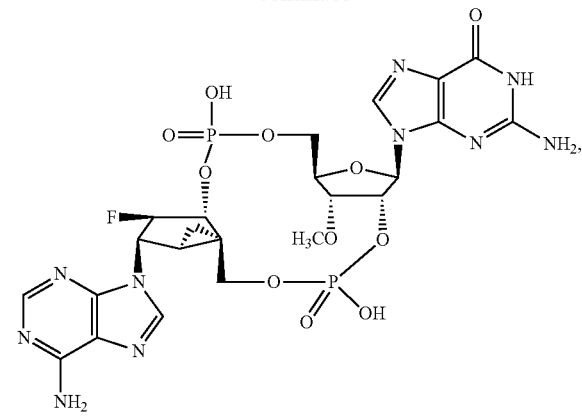
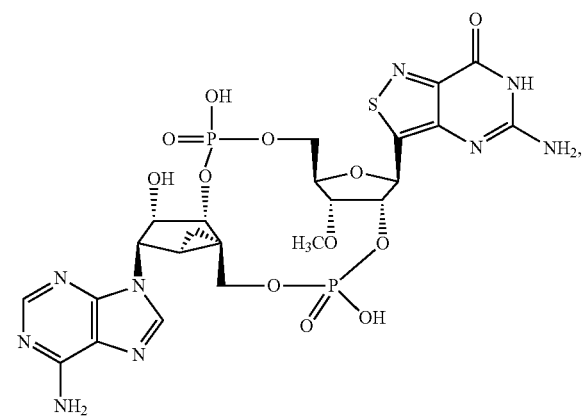
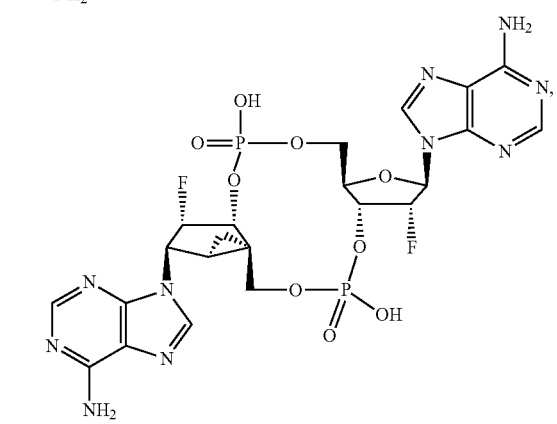
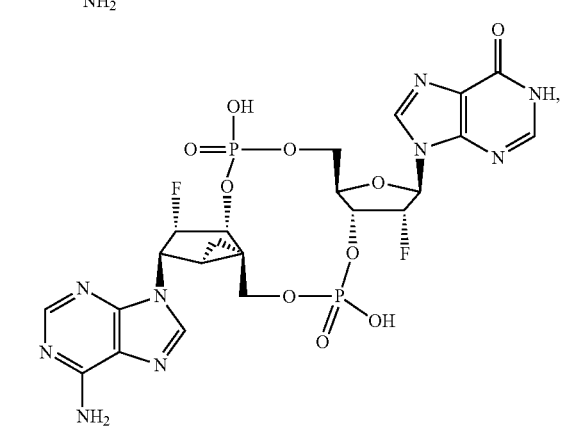

339
-continued
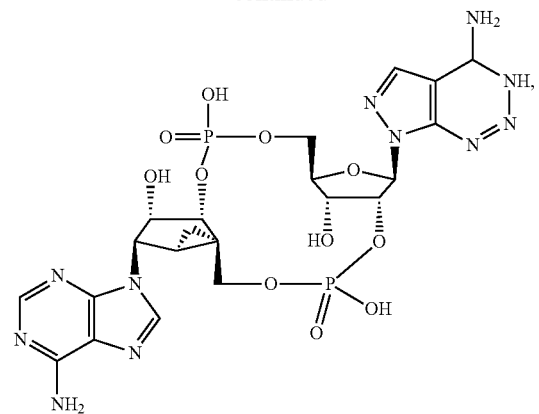
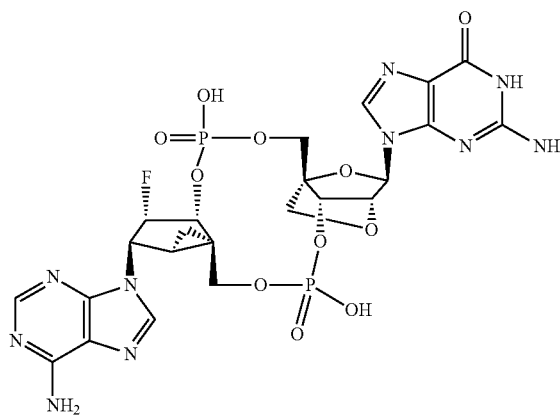
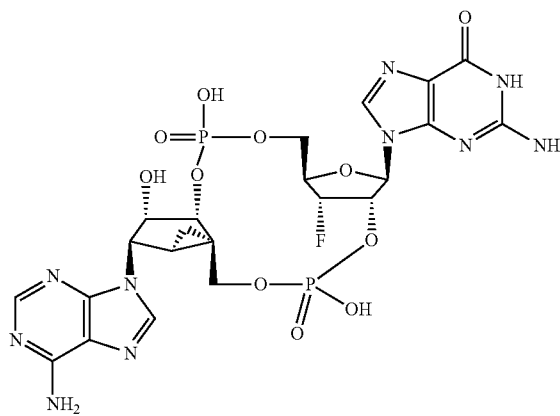
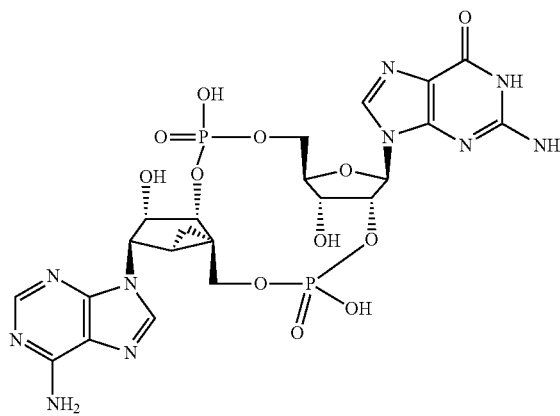
340
-continued
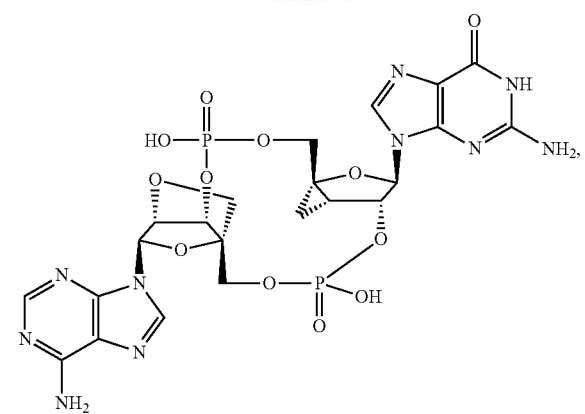
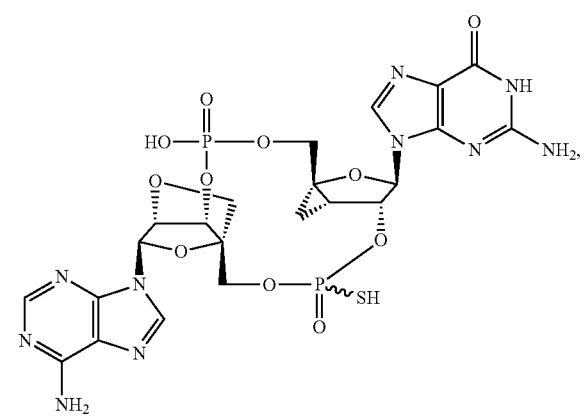
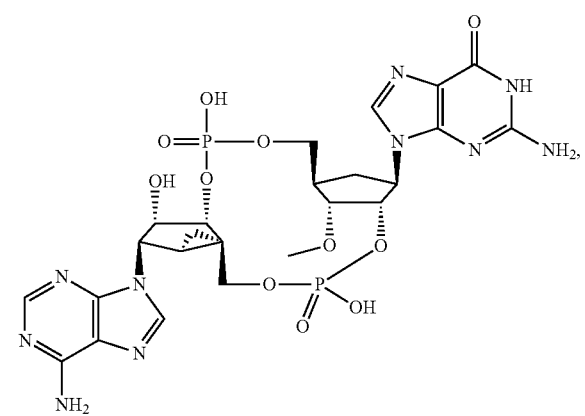
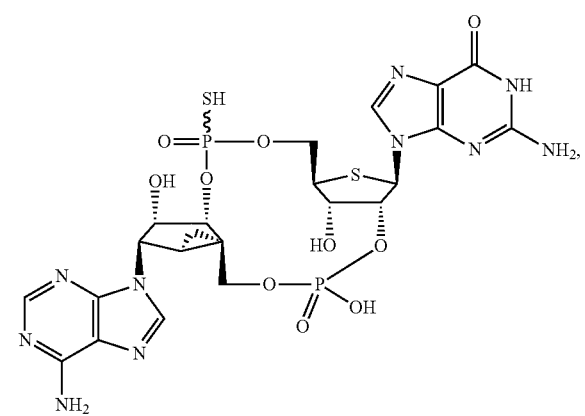

341
-continued
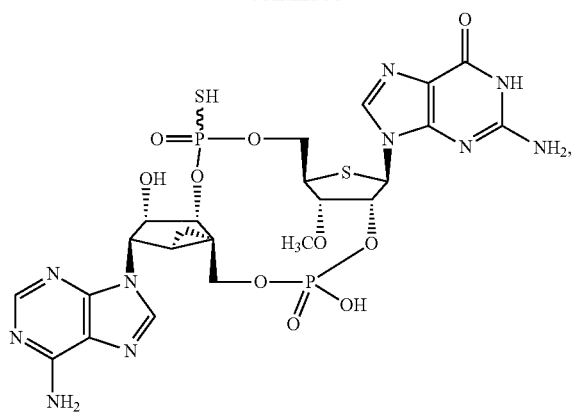
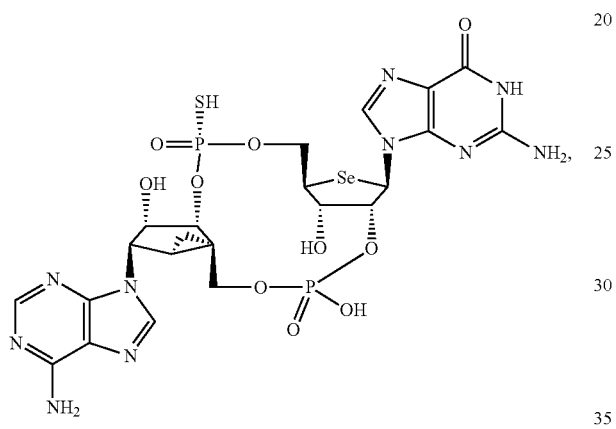
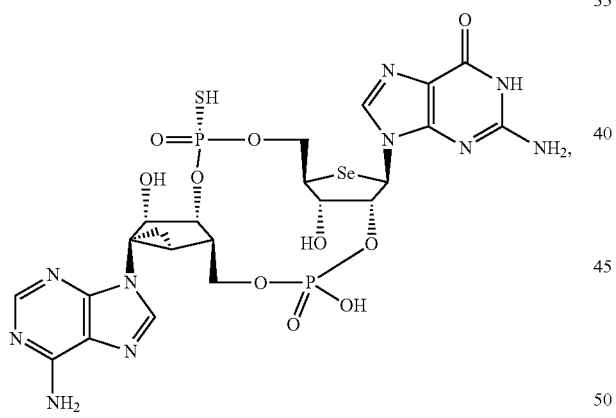
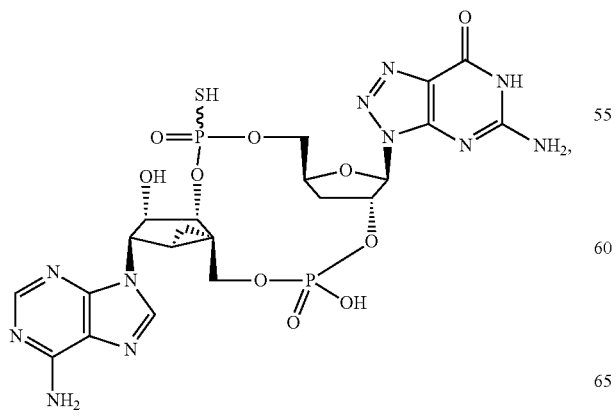
342
-continued
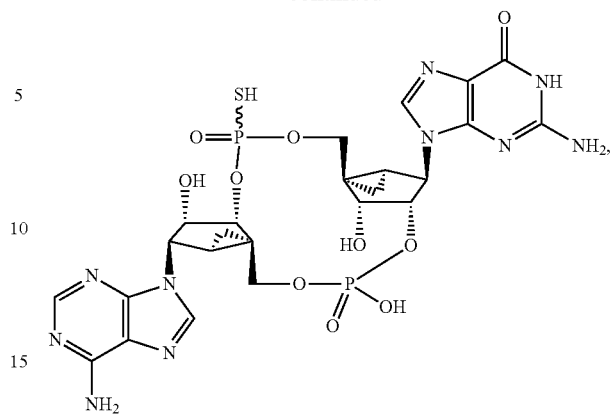
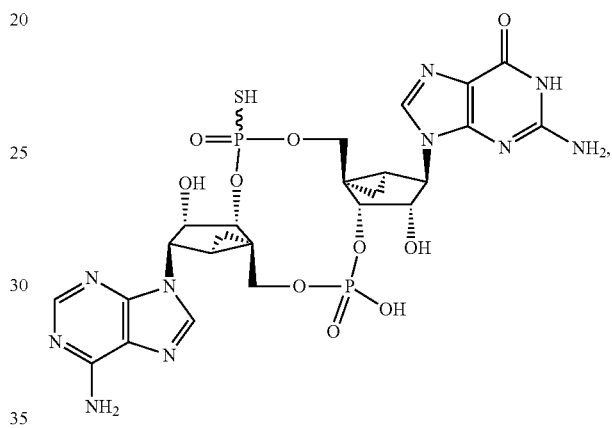
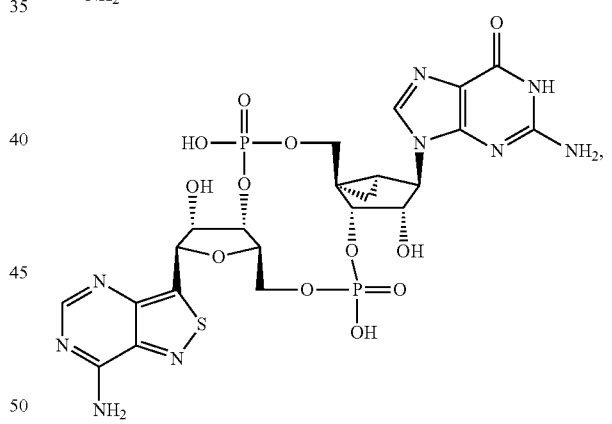
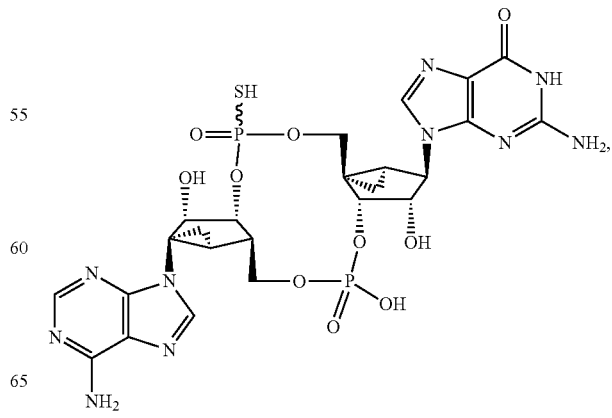

343
-continued

344
-continued

345

-continued

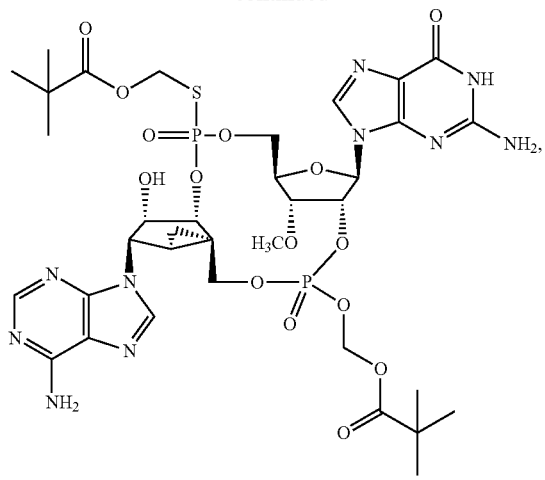

346

-continued

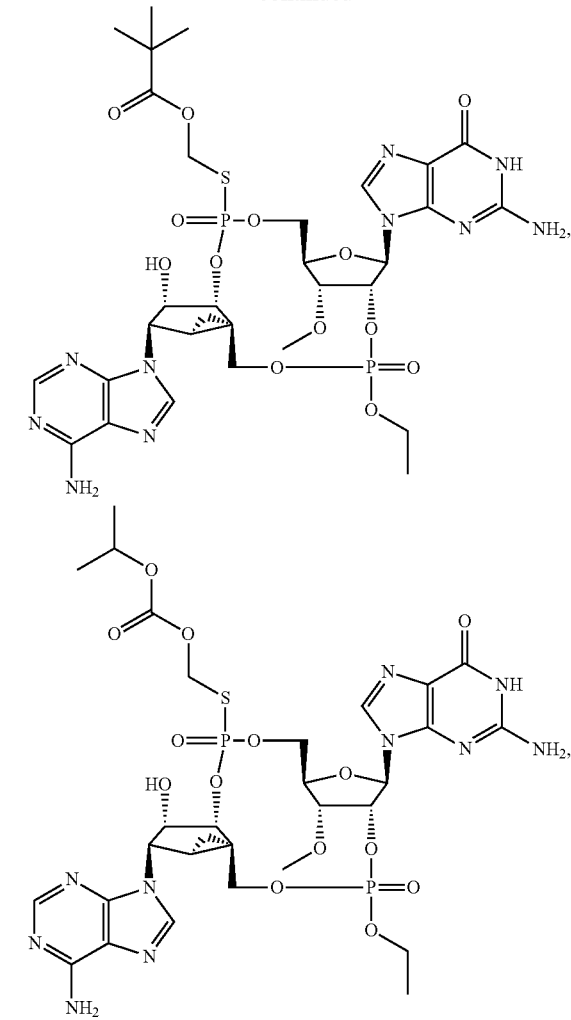

(including pharmaceutically acceptable salts thereof).

Example A

DSF Binding Assay

The Differential scanning fluorimetry (DSF) was performed in an Applied Biosystems 7900HT real-time PCR machine with ROX detector set at an excitation and emission of 492 and 610 nm respectively. Each sample was prepared in a total volume of 40 L that contained a 5× final concentration of SYPRO orange (Invitrogen) in buffer (20 mM HEPES pH 7.5, 150 mM NaCl, 1 mM DTT, and 1 mM $MgCl_2$) and 4 uM STING CTD domain protein with and without compound. All the samples were heated at a rate of 1° C./min, from 20 to 99° C., at ramp rates of 100 and 1% respectively, with data collection throughout. Resulting fluorescence intensity from the raw dissociation curve data was used to determine a melting temperature or Tm for STING protein alone or with compound. Tm from protein alone was then subtracted from all Tm's of protein in the presence of compound and a resulting Tm vs. compound concentration provided apparent Kd values as generated using a sigmoidal dose response (variable slope) equation in GraphPad™ Prism 8.0.

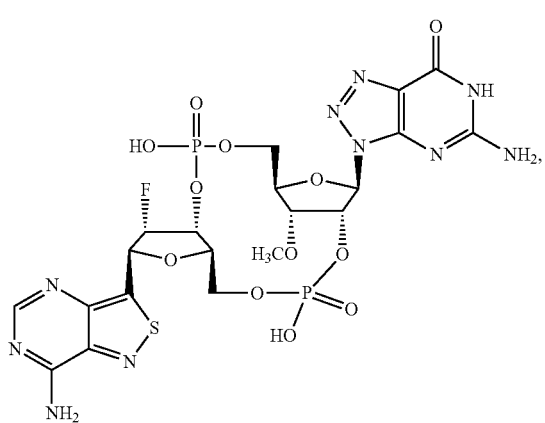

Example B

293T R232 Cell Reporter Assay

293T-Dual hSTING-R232 cells (Invivogen) were plated in 96 well plates at a density of $5 \times 10^4$ cells per well in DMEM supplemented with 10% FBS, 1% Pen-Strep, 1% non-essential amino acids, 1% glutamine, and 1% HEPES. Assay setup took place after allowing cells to adhere for 48 h. Compounds dissolved in water were serially diluted in dosing buffer containing 10 μg/mL digitonin. Media was aspirated from the cells, and 50 μL buffer with compound was added in triplicate. After 30 min at 37° C., buffer was aspirated and replaced with 100 μL media. Cells were incubated for 20 h at 37° C., 5% $CO_2$. IFN-beta expression and activation of the interferon regulatory factor (IRF) were measured based on luciferase and alkaline phosphatase reporter activity, respectively. Cell viability was determined in parallel.

Compounds described herein are agonists of STING as shown in Table 1, where 'A' indicates an $EC_{50} < 0.25$ μM, 'B' indicates an $EC_{50}$ of $\geq 0.25$ M and $< 100$ μM, and 'C' indicates an $EC_{50} \geq 100$ μM.

TABLE 1

| | HEK 293T reporter assay | |
|---|---|---|
| Compound | $EC_{50}$ [μM] IRF reporter | $EC_{50}$ [μM] IRN-β reporter |
| 1-1 | A | A |
| 1-3 | B | C |
| 1-4 | A | A |
| 1-5 | A | A |
| 1-6a | B | B |
| 1-6b | B | B |
| 1-7 | A | A |
| 1-8 | B | B |
| 1-9 | A | A |
| 1-10a | B | B |
| 1-10b | A | A |
| 1-11 | C | C |
| 1-12 | C | C |
| 1-13 | A | A |
| 1-14a | B | C |
| 1-14b | B | C |
| 1-14c | B | B |
| 1-14d | B | B |
| 1-15a | C | C |
| 1-15b | B | B |
| 1-16a | B | B |
| 1-16b | A | A |
| 1-17 | A | A |
| 1-18 | A | A |
| 1-19a | B | B |
| 1-19b | A | A |
| 1-20a | B | B |
| 1-20b | A | A |
| 1-21a | B | B |
| 1-21b | A | A |
| 1-22a | B | B |
| 1-22b | A | A |
| 1-23 | B | B |
| 1-24 | B | C |
| 1-25 | A | A |
| 1-26 | B | B |
| 1-27 | A | A |
| 1-28a | A | A |
| 1-29b | B | B |
| 1-29 | B | B |
| 1-30a | B | B |
| 1-30b | C | C |
| 1-34a | A | B |
| 1-34b | B | B |
| 1-35a | B | B |
| 1-35b | A | B |
| 1-37 | B | C |
| 1-38a | C | C |
| 1-38b | C | C |
| 1-46a | B | B |
| 1-46b | A | A |
| 1-47a | C | C |
| 1-47b | A | A |
| 1-48a | B | B |
| 1-48b | A | A |
| 1-48c | A | B |
| 1-48d | A | B |
| 1-49 | A | B |
| 1-50a | A | B |
| 1-50b | A | B |
| 1-52 | A | B |

Example C

CT26 Mouse Colon Carcinoma In Vivo Efficacy Studies

The in vivo antitumoral activity of compounds of Formula (I) were studied in the mouse CT26 colon carcinoma model. 10 female 9-week old BALB/c mice/group were implanted subcutaneously with $3 \times 10^5$ cells on the flank. Caliper measurements to assess the tumor volume (TV) and body weight measurements were performed daily for the first 8 days and biweekly thereafter until the end of the study. Dosing started when the tumor volumes reached a size of 100 $mm^3$. The compounds of Formula (I) were tested in two separate studies with their respective vehicle control. Compounds of Formula (I) were dosed 3 times, three days apart, intratumorally at either 25 or 100 μg. The human endpoint is predefined as a TV of 2000 $mm^3$.

Figure 2:
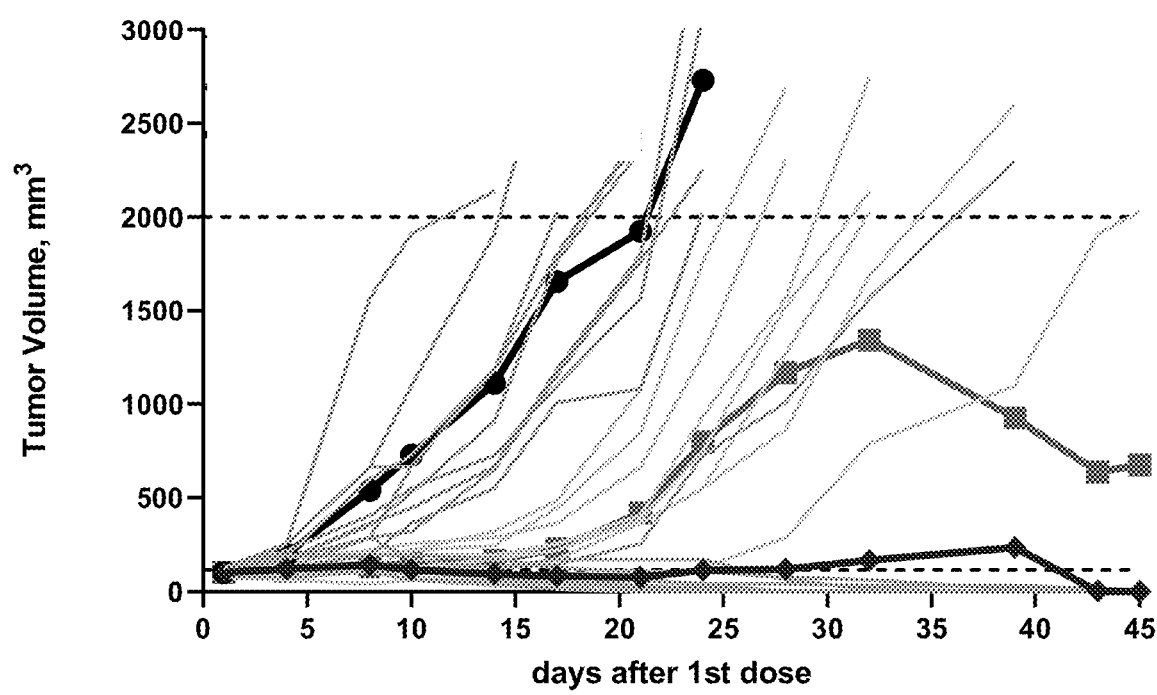
FIG. 2 shows the results of a colon carcinoma study using compound 1-13 at two different dosing levels.
Figure 3:
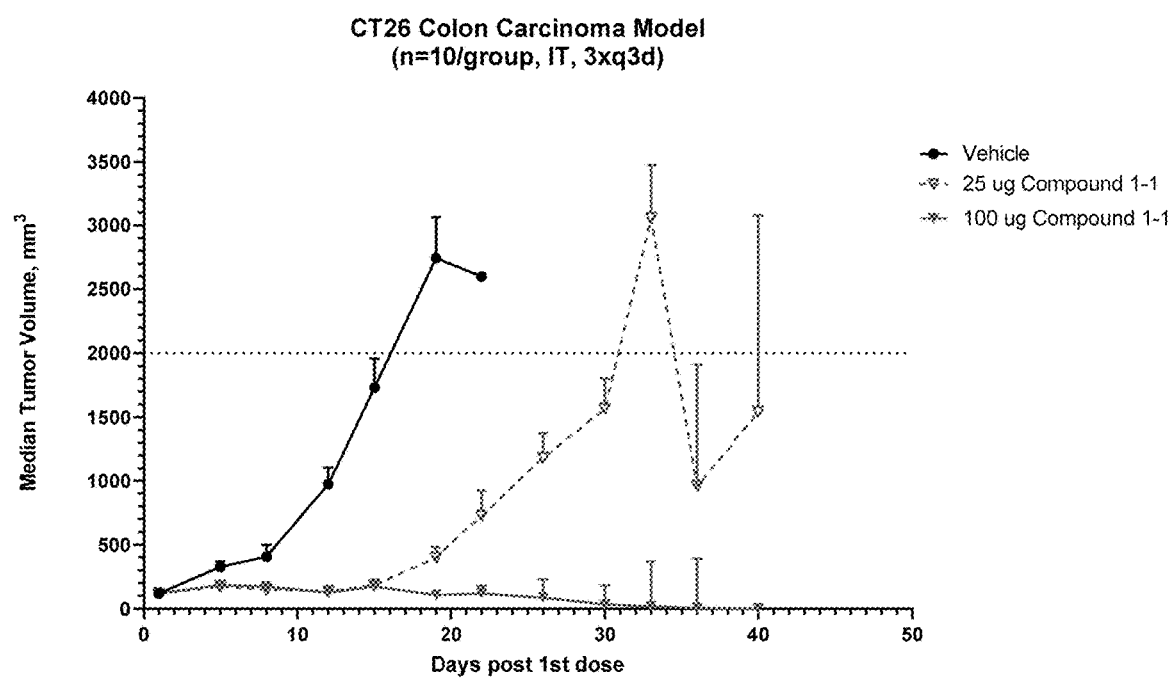
FIG. 3 shows the results of a colon carcinoma study using compound 1-1 at two different dosing levels.

In both studies, the tumors in the vehicle control grew fast and in the majority of animals, the human endpoint of 2000 $mm^3$ TV was reached between Day 15 and 22 (solid circles). Three intratumoral doses of 25 g of 10-b (solid squares in FIG. 1) delayed tumor growth in 4 animals by approx. 14 days while five animals had no measurable tumors by the end of the study. 100 g 10-b treatment (solid diamonds in FIG. 1) resulted in 9/10 tumor-free animals and only 1 animal reaching a TV=2000 $mm^3$. Similar efficacy was observed with 1-13. Three 25 g doses of 1-13 (solid squares in FIG. 2) caused a delay in tumor growth in 8 animals compared to the vehicle control, while two animals were tumor-free at the end of the study. At the 100 g of 1-13 (solid diamonds in FIG. 2), 9 out of 10 animals were tumor-free with only one animal reaching a TV=2000 $mm^3$. Three intratumoral doses of 100 g of 1-1 (solid triangles/solid line in FIG. 3) resulted in 4 out of 10 animals being tumor-free by the end of the study. A summary of the results are provided in Table 2.

TABLE 2

| Compound | Amount | Cure Rate (TV < 10 $mm^3$) | Treatment Failure (TV > 2000 $mm^3$) |
|---|---|---|---|
| Vehicle | | 0% | 100% |
| 1-1 | 100 μg | 40% | 40% |
| 10-b | 25 μg | 50% | 40% |

TABLE 2-continued

| Compound | Amount | Cure Rate (TV < 10 mm³) | Treatment Failure (TV > 2000 mm³) |
|---|---|---|---|
| 10-b | 100 µg | 90% | 10% |
| 1-13 | 25 µg | 20% | 80% |
| 1-13 | 100 µg | 90% | 10% |
| 1-19b | 100 µg | 70% | 30% |
| 1-20b | 100 µg | 50% | 50% |
| 1-21b | 100 µg | 50% | 50% |
| 1-22b | 100 µg | 56% | 44% |

The in vivo antitumoral activity of compounds of Formula (I) after intratumoral of subcutaneous administration was studied in the mouse CT26 colon carcinoma model. The study was performed as in the first paragraph of Example C. Compounds of Formula (I) were dosed 2 or 3 times, three days apart (q3d) or 7 days apart (qw), intratumorally at either 25 or 100 g or subcutaneously at either 1 or 4 mg/kg.

In this study, the tumors in the vehicle control grew fast and in average, the human endpoint of 2000 mm³ TV was reached by Day 16. Two subcutaneous administrations of 10-b at 4 mg/kg delayed tumor growth by approx. 8 days compared to the vehicle group. Dosing 10-b three times subcutaneously at 4 mg/kg resulted in a further delay in tumor growth; 1/10 animals achieved complete tumor suppression compared to 4/10 animals dosed intratumorally at 100 µg.

Example D

Combination Study

The in vivo antitumoral activity of compounds of Formula (I) in combination with the immune checkpoint inhibitor anti-CTLA-4 (clone 9H10) was studied in the mouse CT26 colon carcinoma model. The study was performed as described in the first paragraph of Example C.

Figure 4:
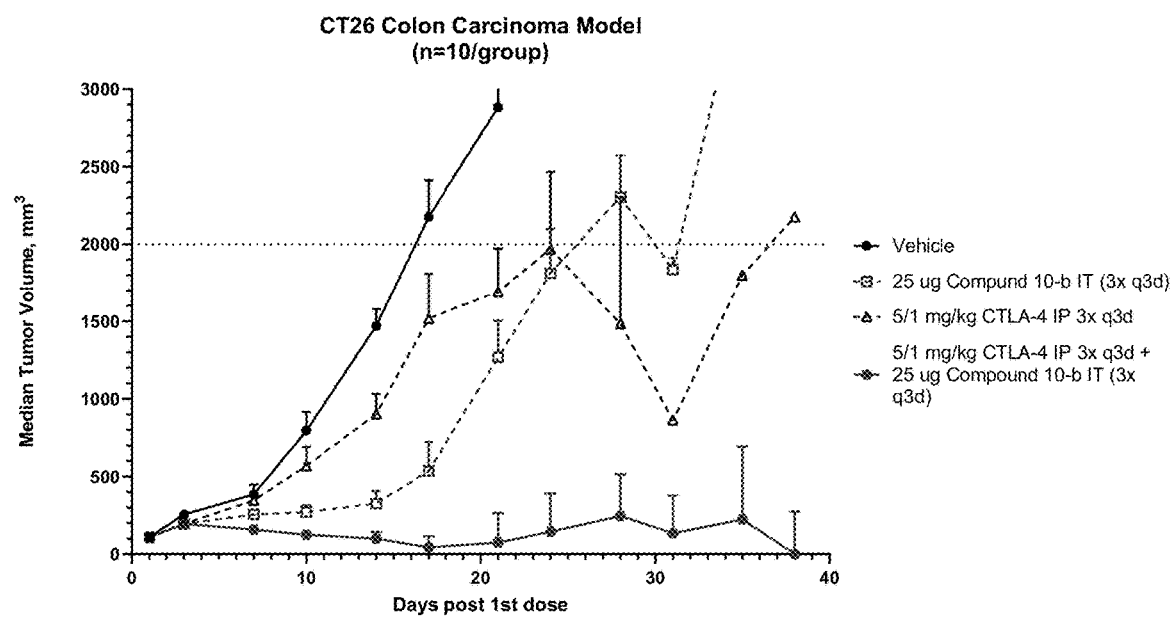
FIG. 4 shows the results of a colon carcinoma study using compound 1-10b in combination with CTLA-4.

In this study, the tumors in the vehicle control grew fast and in average, the human endpoint of 2000 mm³ TV was reached by Day 16 (solid circles in FIG. 4). Three IT doses of 25 g 10-b delayed tumor growth by approx. 8 days (blue triangles in FIG. 4). Similarly, three intraperitoneal doses of the checkpoint inhibitor anti-CTLA-4, clone 9H10 (1$^{st}$ dose 5 mg/kg, 2$^{nd}$ and 3$^{rd}$ dose 1 mg/kg) by approx. 7 days (red squares in FIG. 4). The combination of anti-CTLA-4+25 µg 10-b caused a robust anti-tumor response with 4/10 animals being tumor-free at the end of the study (purple hexagons in FIG. 4). Additional information is provided in Table 3.

TABLE 3

| Compound | Dose | Route/Frequency | Complete Tumor Suppression | Treatment Failure |
|---|---|---|---|---|
| Vehicle | — | SC/3 × q3d | 0 | 100 |
| 10-b | 25 µg | IT/3 × q3d | 0 | 100 |
| anti-CTLA4 | 5 mg/kg-1 mg/kg | IP/3 × q3d | 0 | 100 |
| anti-CTLA4 + 10-b | 5 mg/kg-1 mg/kg 25 µg | IP/3 × q3d IT/3 × q3d | 40 | 40 |

Complete Tumor Suppression = TV < 10 mm³;
Treatment Failure = TV > 2000 mm³.

As demonstrated by the results provided herein, compounds of Formula (I), along with pharmaceutically acceptable salts thereof, are effective in treating colon carcinoma as mono-therapy and/or in combination with a checkpoint inhibitor.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound selected from Formula (I), or a pharmaceutically acceptable salt thereof:

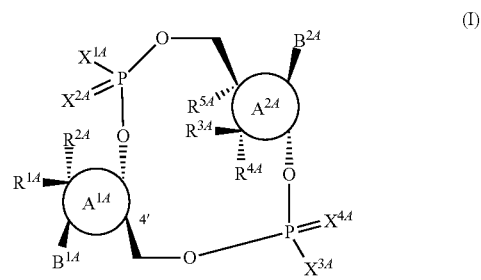

wherein:
Ring $A^{1A}$ is

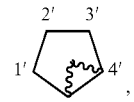

Ring $A^{2A}$ is independently selected from the group consisting of

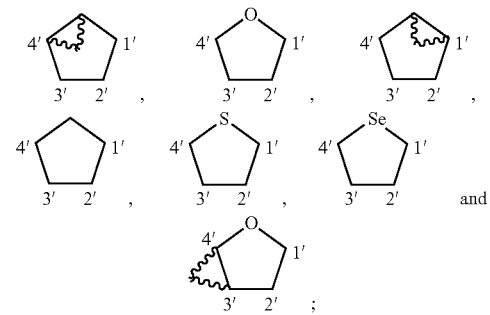

$B^{1A}$ is an optionally substituted [5,6] bicyclic heteroaryl or an optionally substituted [5,6] bicyclic heterocyclyl, and wherein $B^{1A}$ is attached to the 1'-position of Ring $A^{1A}$;

$B^{2A}$ is an optionally substituted [5,6] bicyclic heteroaryl or an optionally substituted [5,6] bicyclic heterocyclyl, and wherein $B^{2A}$ is attached to the 1'-position of Ring $A^{2A}$;

$X^{1A}$ and $X^{3A}$ are independently OH, O⁻, SH, S⁻, O(unsubstituted $C_{1-4}$ alkyl), S(unsubstituted $C_{1-4}$ alkyl), O—CH$_2$—O—C(=O)-(unsubstituted $C_{1-4}$ alkyl), S—CH$_2$—O—C(=O)-(unsubstituted $C_{1-4}$ alkyl), O—CH$_2$—O—C(=O)—O-(unsubstituted C$_{1-4}$ alkyl),
S—CH$_2$—O—C(=O)—O-(unsubstituted C$_{1-4}$ alkyl),

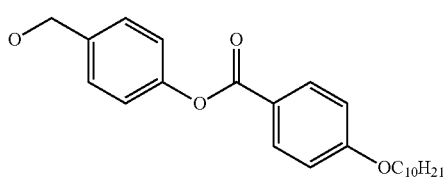

or

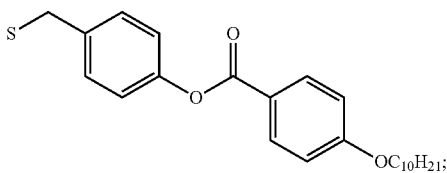

X$^{2A}$ and X$^{4A}$ are independently O or S;
R$^{1A}$ is hydrogen or halogen, and wherein R$^{1A}$ is attached to the 2'-position of Ring A$^{1A}$;
R$^{2A}$ is selected from the group consisting of hydrogen, halogen, hydroxy, an unsubstituted C$_{1-4}$ alkoxy and

and wherein R$^{2A}$ is attached to the 2'-position of Ring A$^{1A}$, and when R$^{2A}$ is

then the * indicates an attachment point to the 4'-position of Ring A$^{1A}$;
R$^{3A}$ is hydrogen or halogen, and wherein R$^{3A}$ is attached to the 3'-position of Ring A$^{2A}$;
R$^{4A}$ is selected from the group consisting of hydrogen, halogen, hydroxy and an unsubstituted C$_{1-4}$ alkoxy, and wherein R$^{4A}$ is attached to the 3'-position of Ring A$^{2A}$;
R$^{5A}$ is hydrogen, and wherein R$^{5A}$ is attached to the 4'-position of Ring A$^{2A}$; or
R$^{4A}$ and R$^{5A}$ are taken together to form

wherein each * indicates a point of attachment to ring A$^{2A}$.

2. The compound of claim 1, wherein Ring A$^{2A}$ is

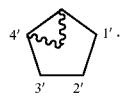

3. The compound of claim 1, wherein Ring A$^{2A}$ is

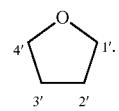

4. The compound of claim 1, wherein Ring A$^{2A}$ is

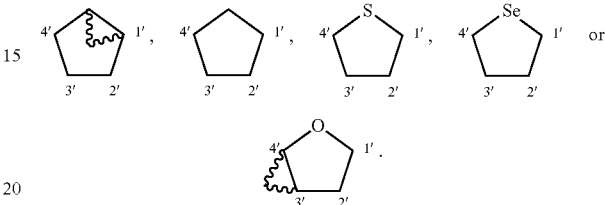

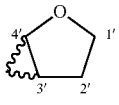

5. The compound of claim 1, wherein B$^{1A}$ is selected from the group consisting of

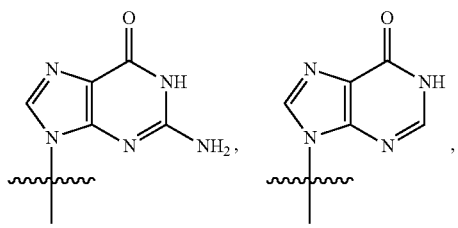

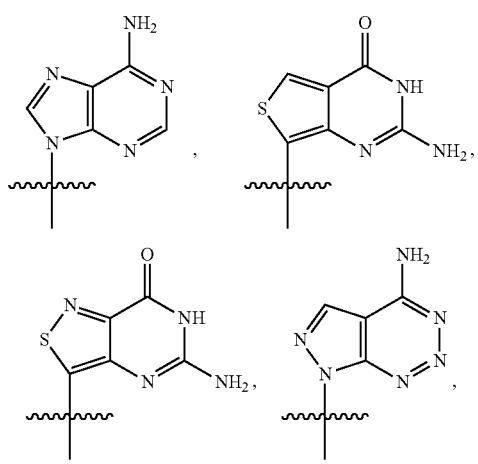

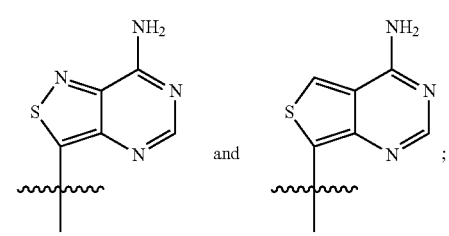

and $B^{2A}$ is selected from the group consisting of

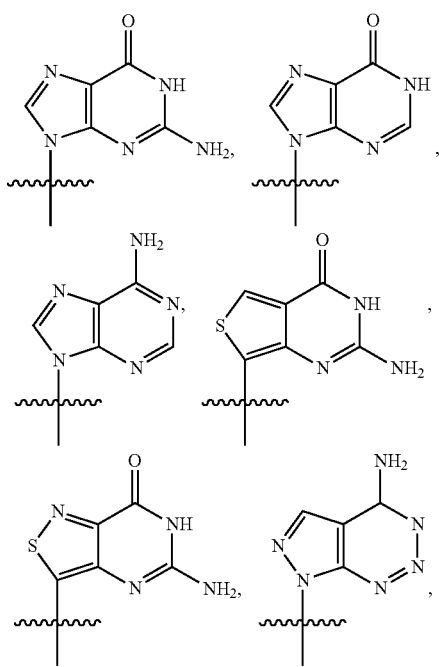

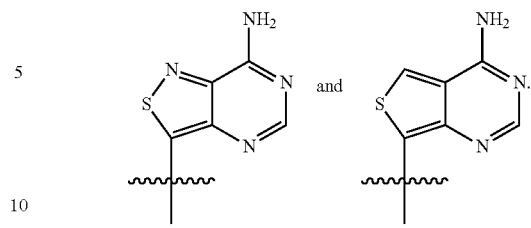 and

6. The compound of claim 1, wherein $R^{1A}$ is hydrogen.

7. The compound of claim 1, wherein $R^{2A}$ is hydrogen, halogen or hydroxy.

8. The compound of claim 1, wherein $R^{3A}$ is hydrogen.

9. The compound of claim 1, wherein $R^{4A}$ is halogen or hydroxy.

10. The compound of claim 1, wherein $R^{4A}$ is an unsubstituted $C_{1-4}$ alkoxy.

11. The compound of claim 1, wherein $R^{5A}$ is hydrogen.

12. The compound of claim 10, wherein the unsubstituted $C_{1-4}$ alkoxy is methoxy.

13. The compound of claim 1, wherein the compound is selected from the group consisting of:

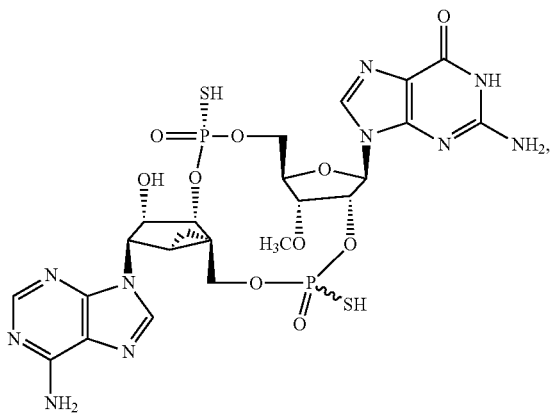

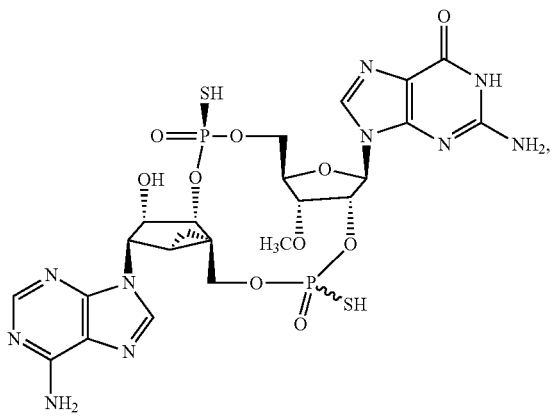

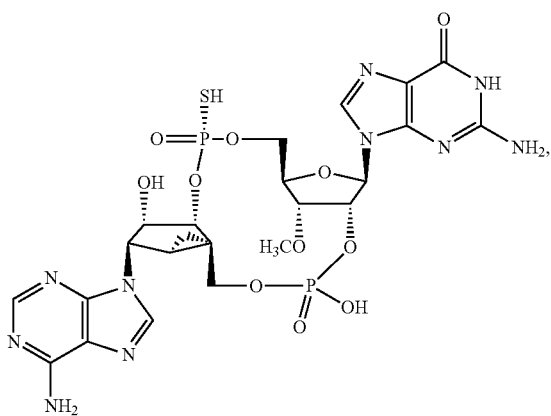

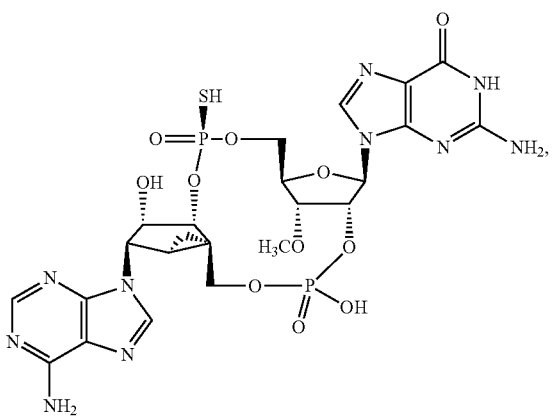

-continued
355 356
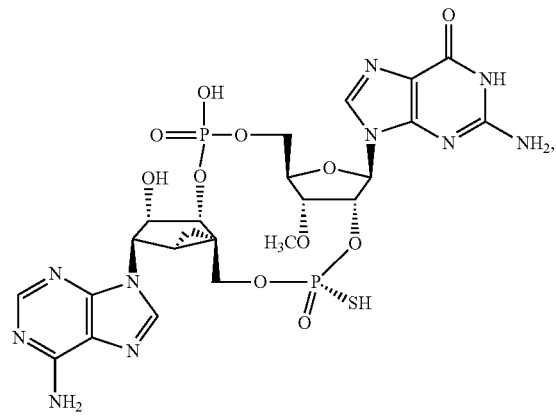
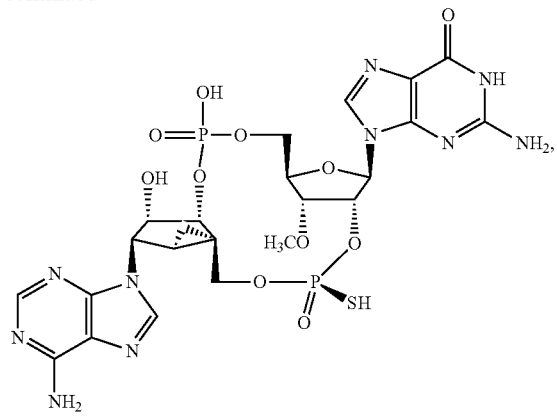
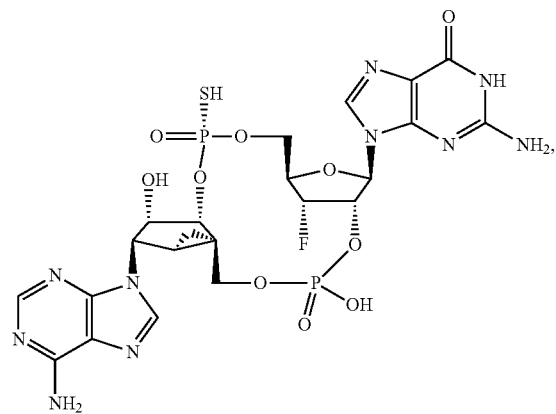
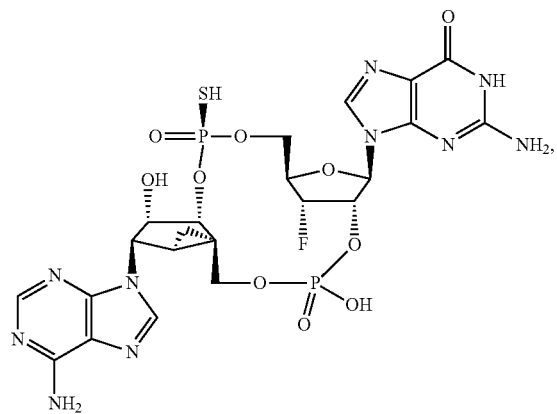
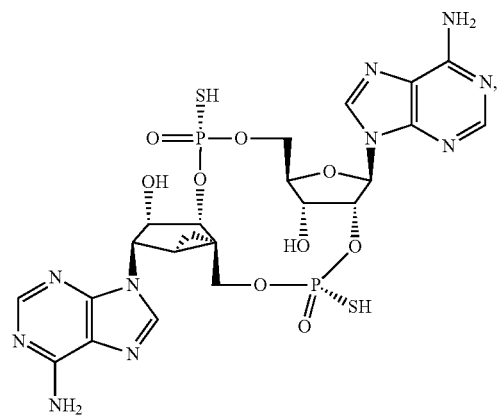
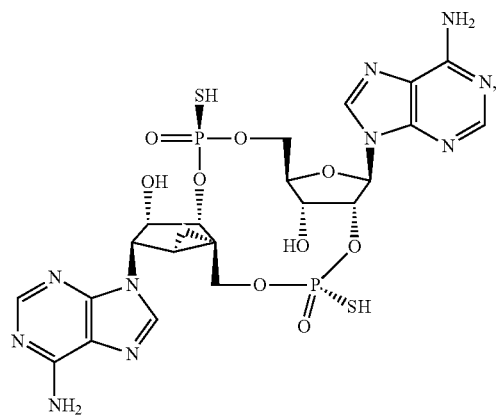
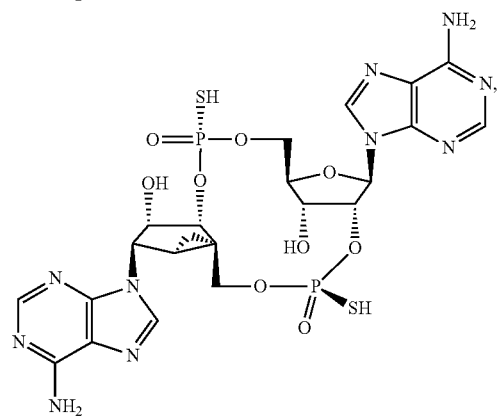
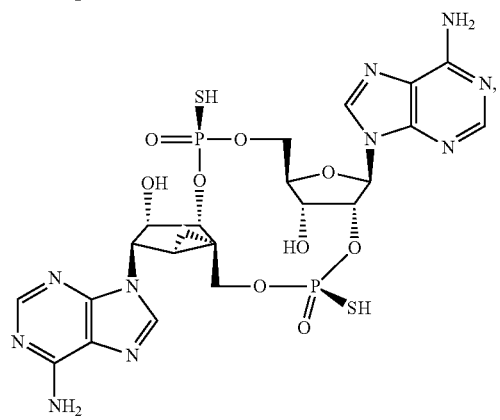

357 358
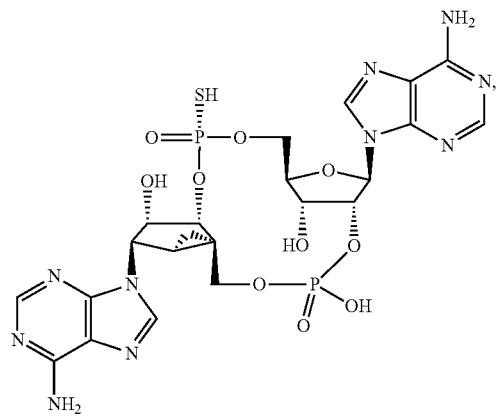 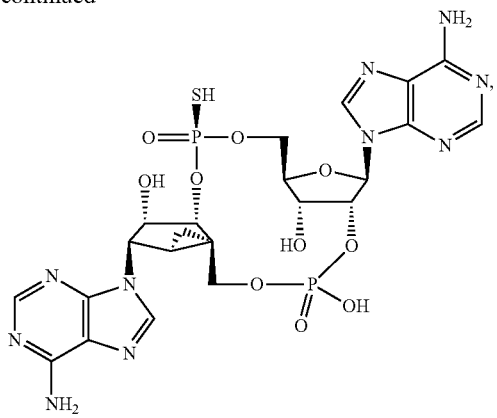
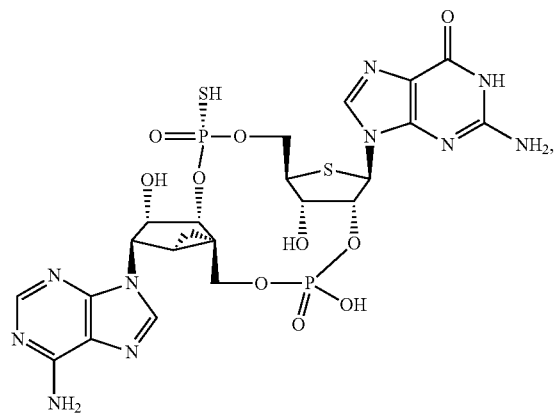 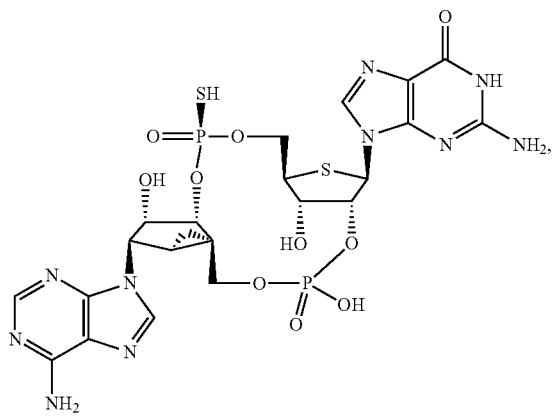
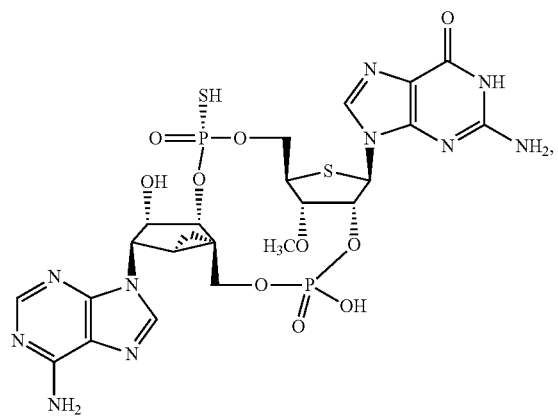 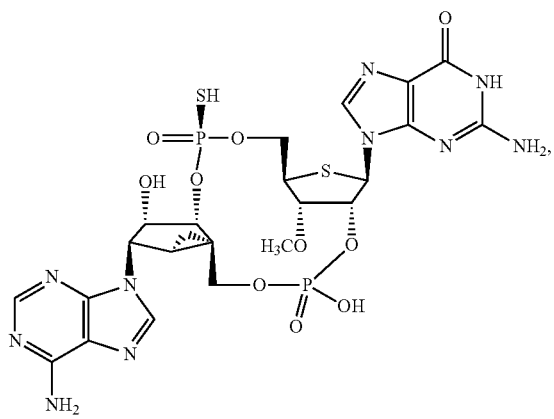
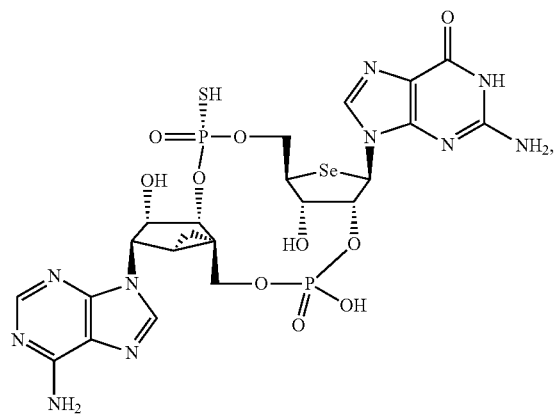 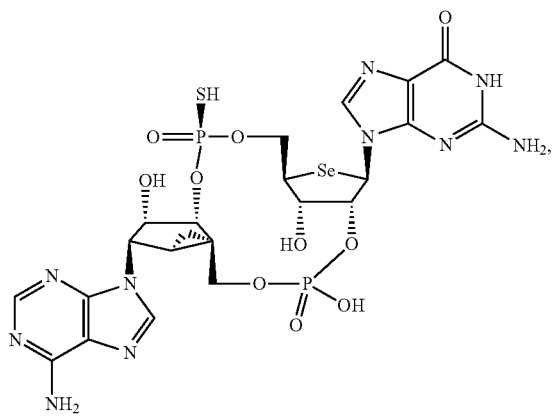

359
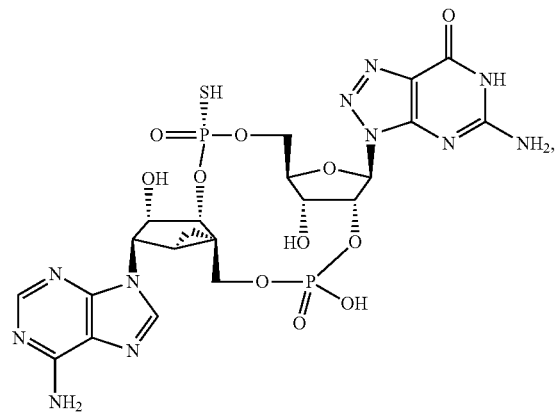
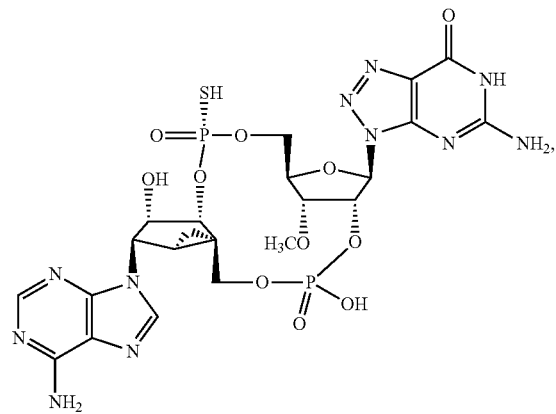
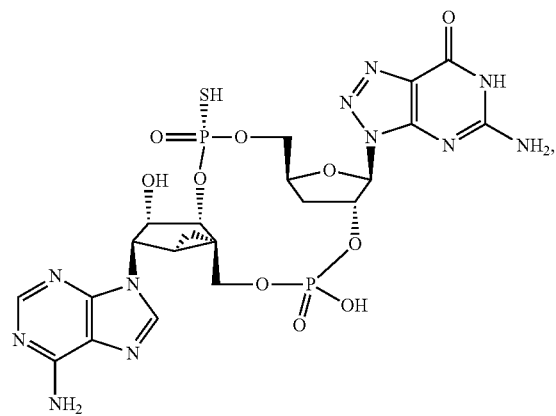
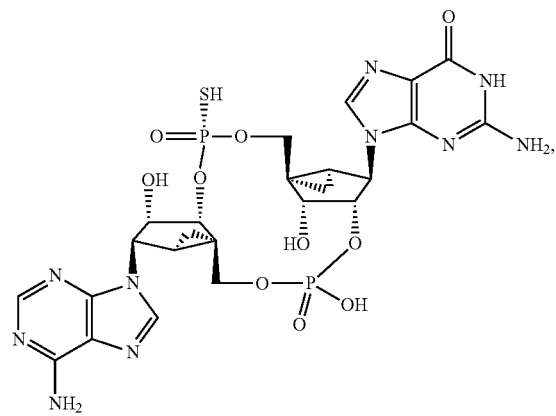
-continued
360
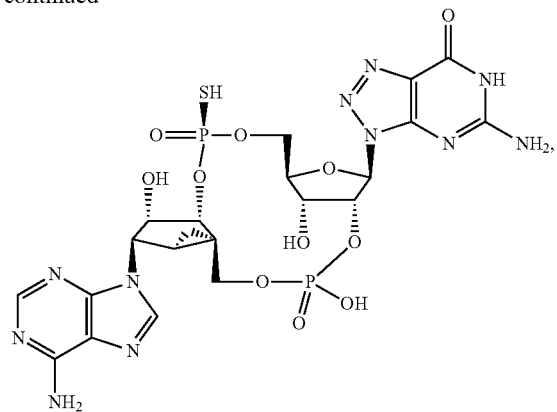
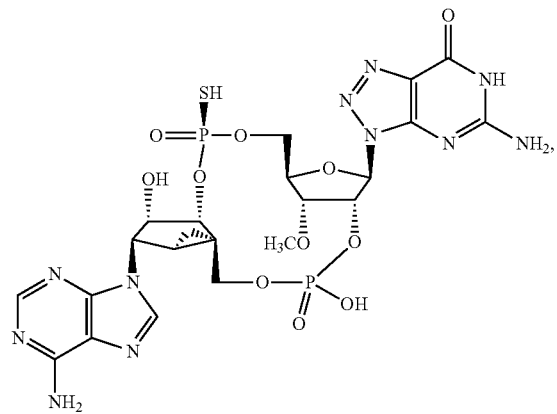
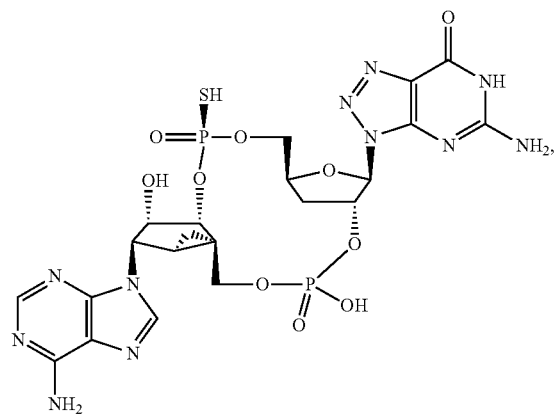
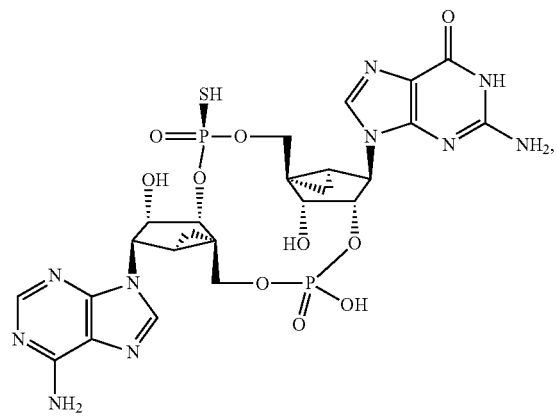

361    362
-continued
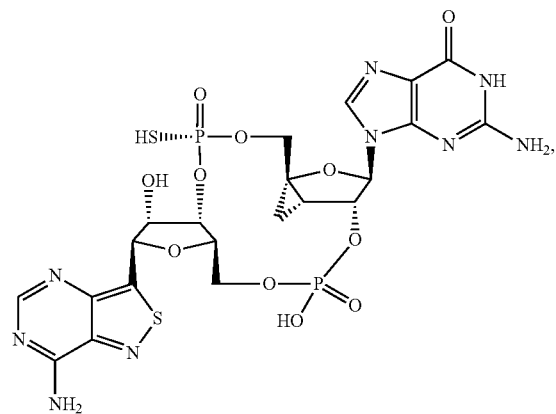 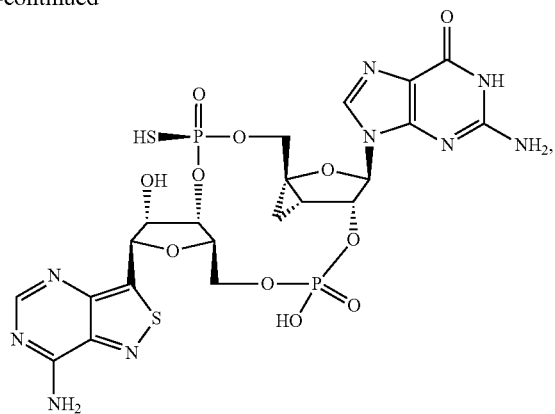
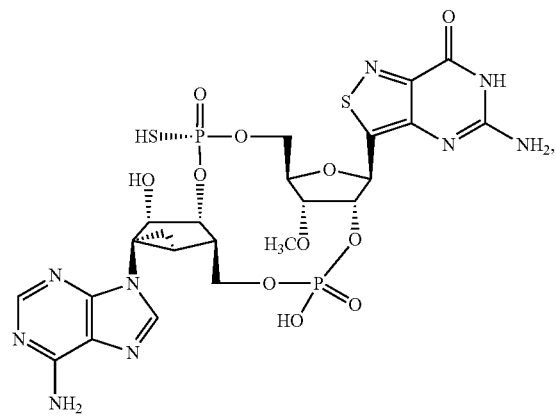 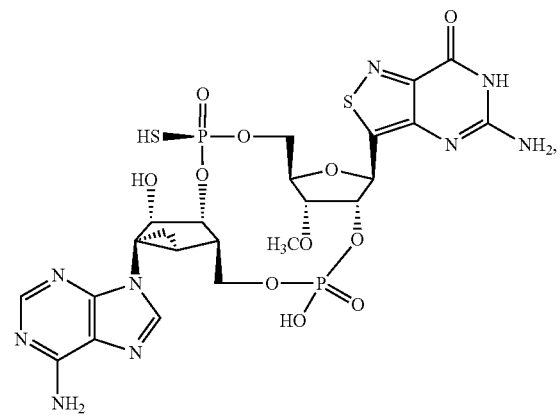
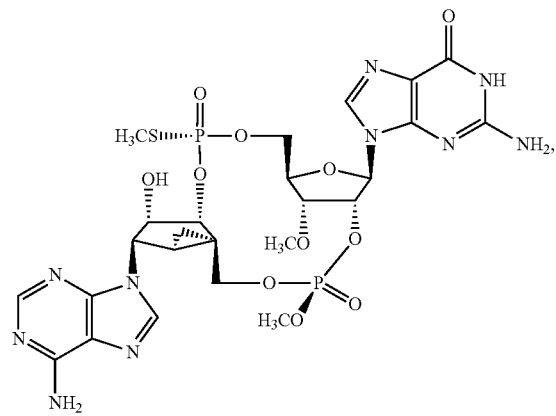 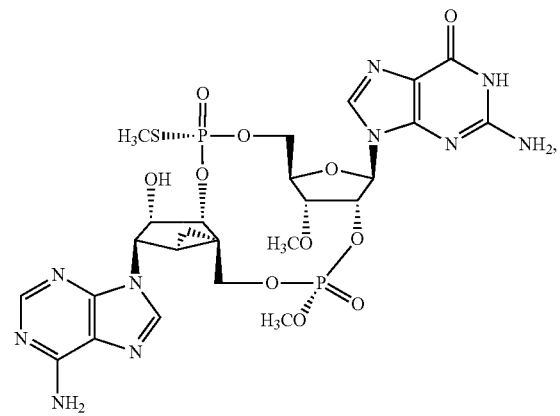
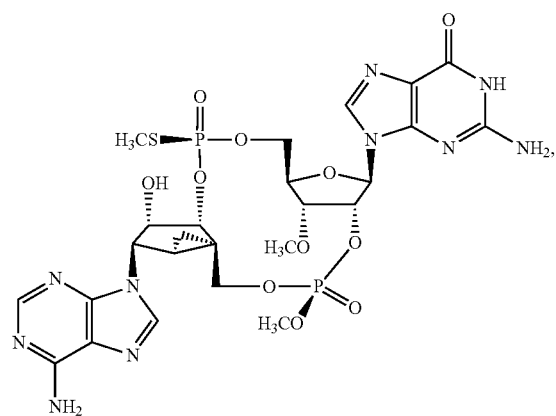 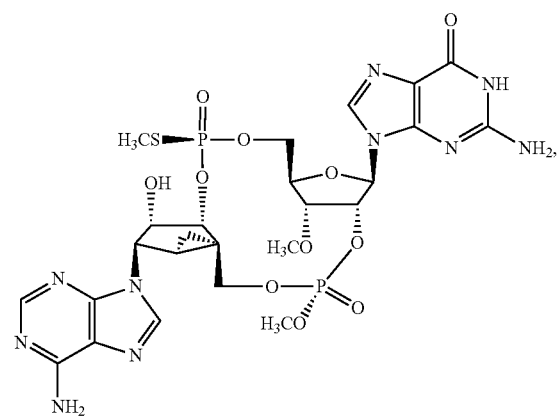

363
364
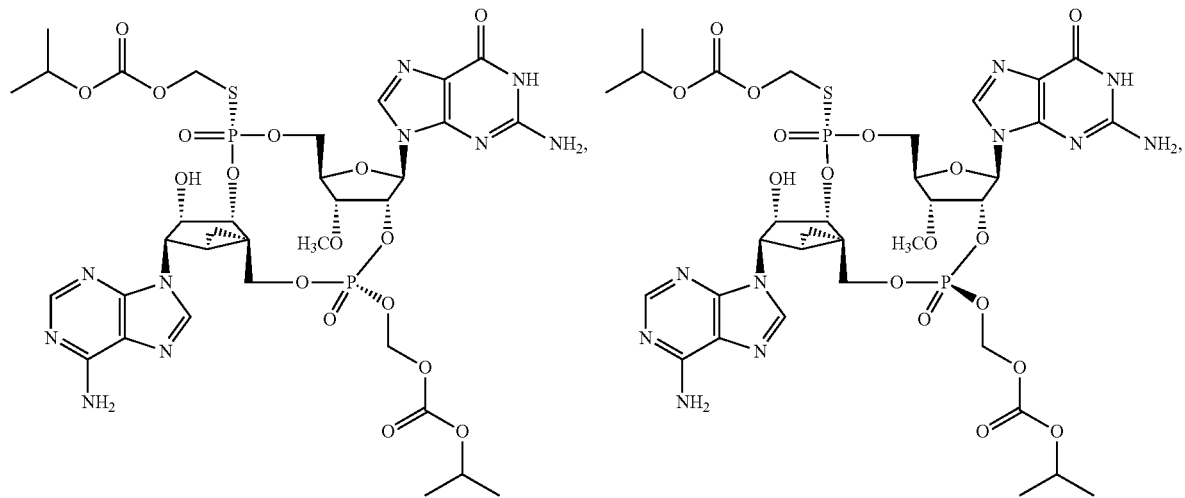
-continued
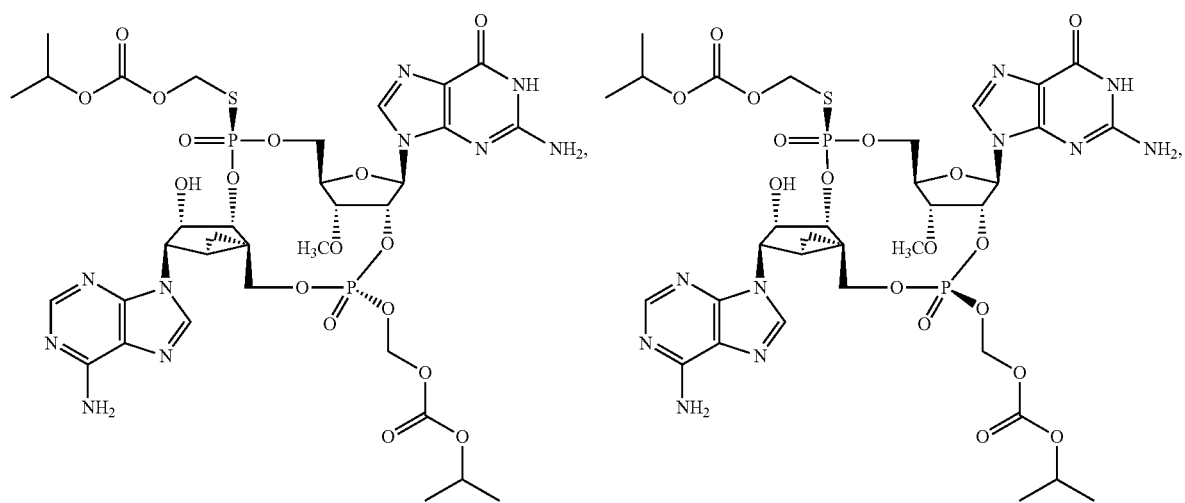
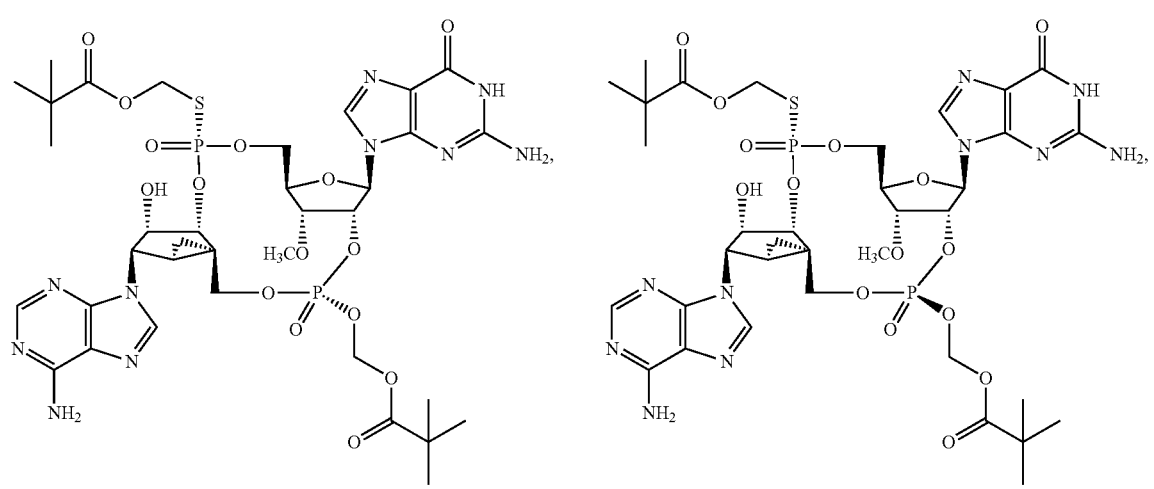

365
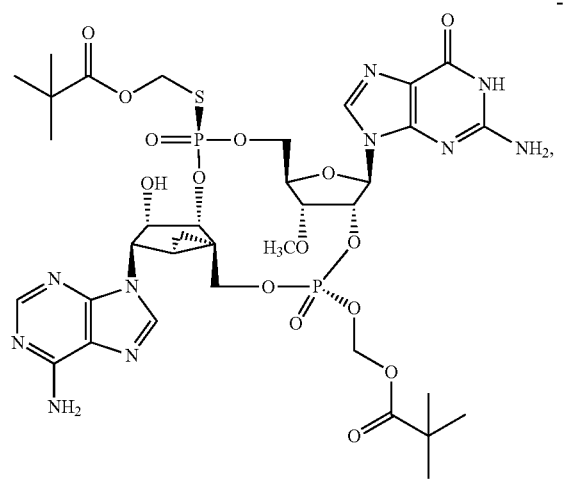
366
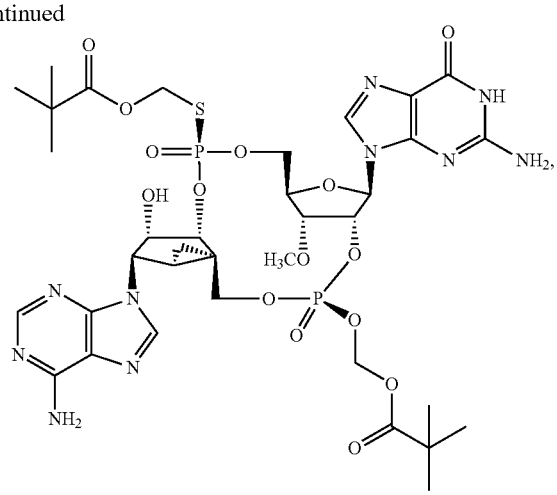
-continued
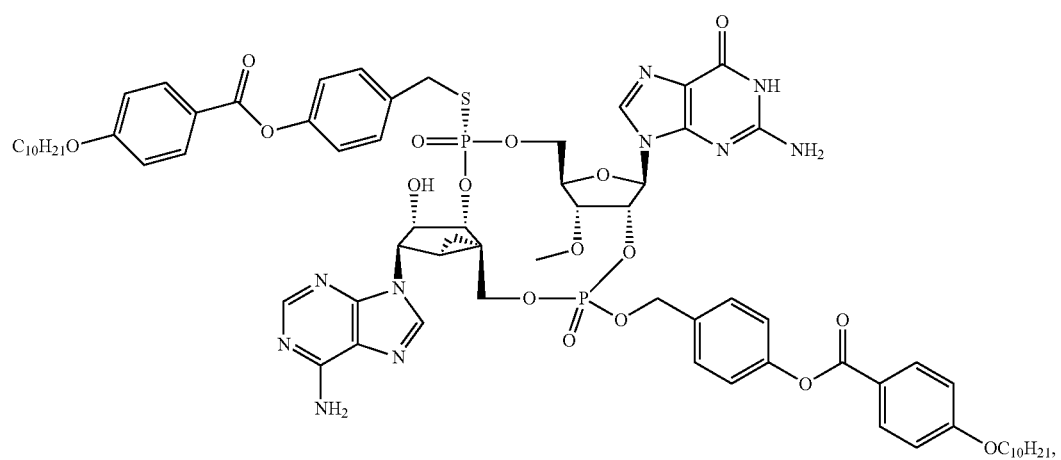
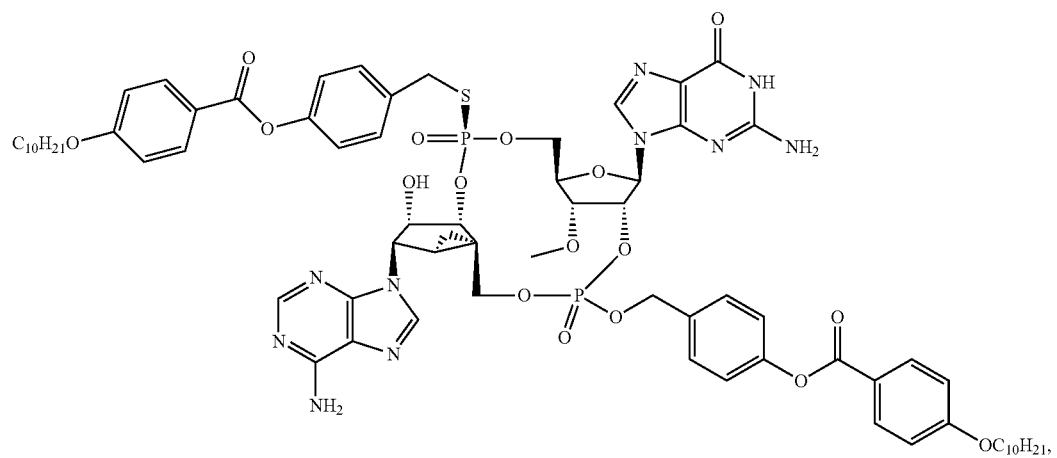

-continued
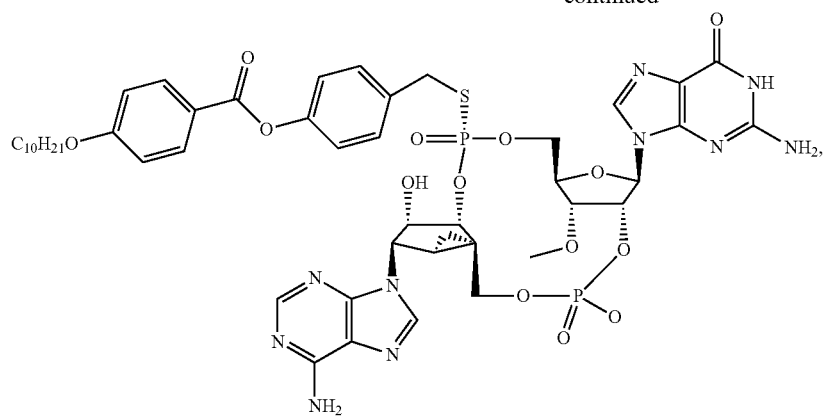
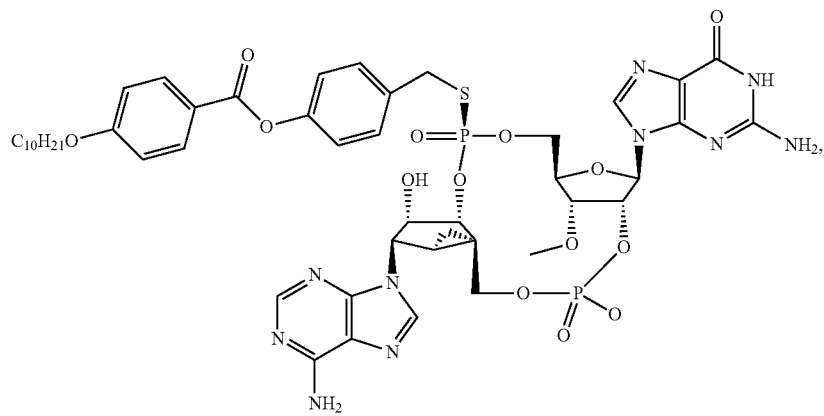
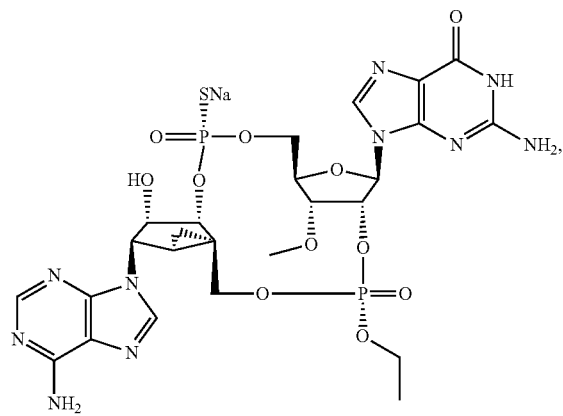
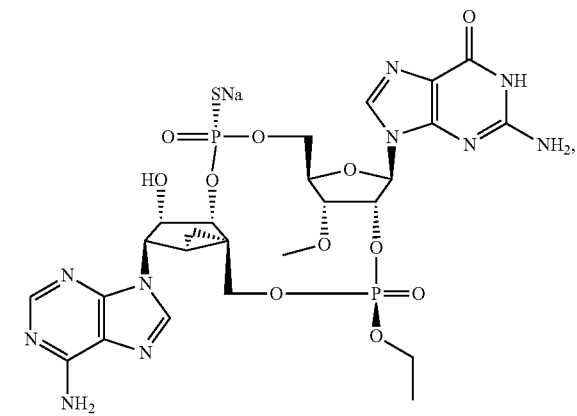
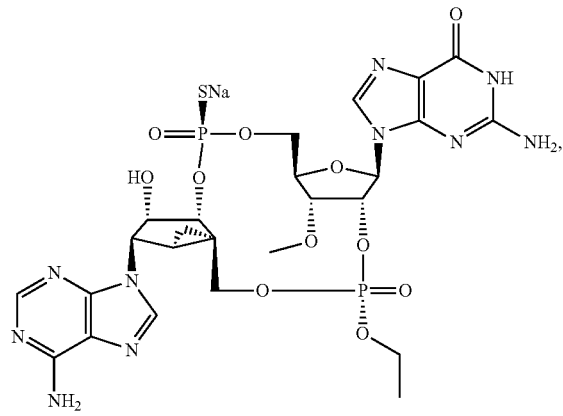
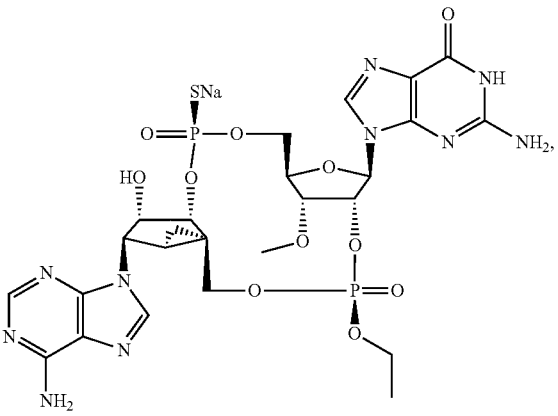

369 370
-continued
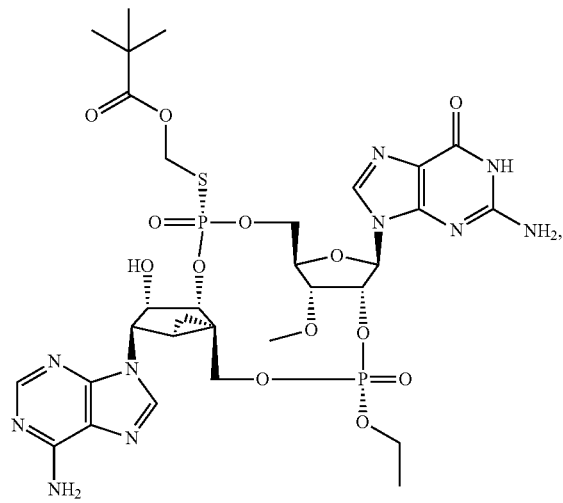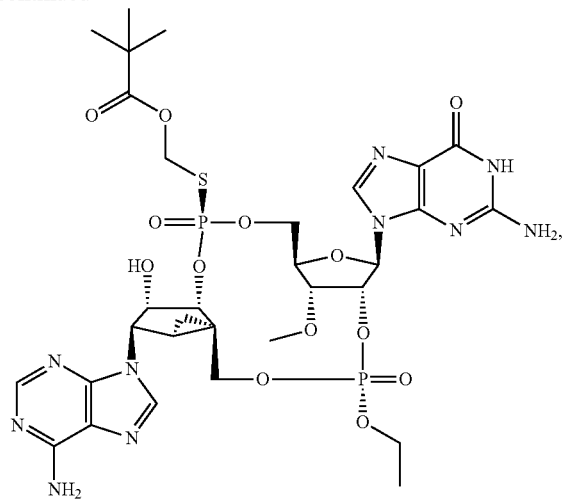
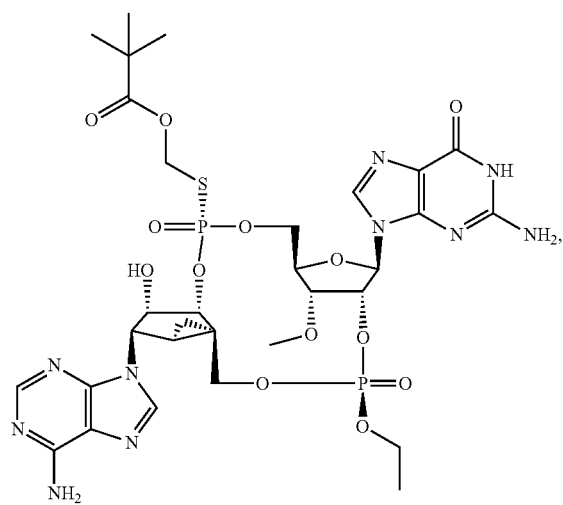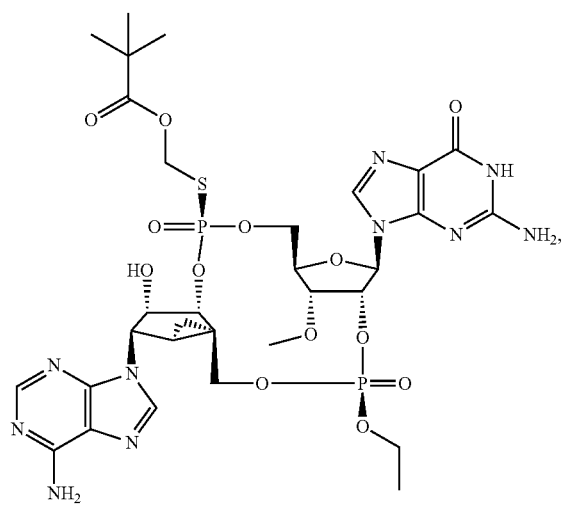
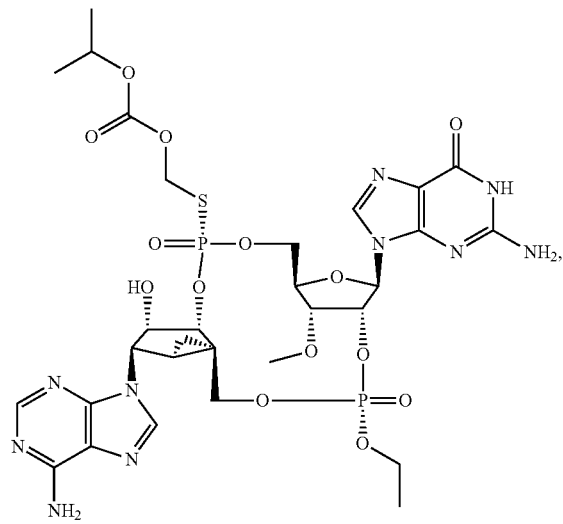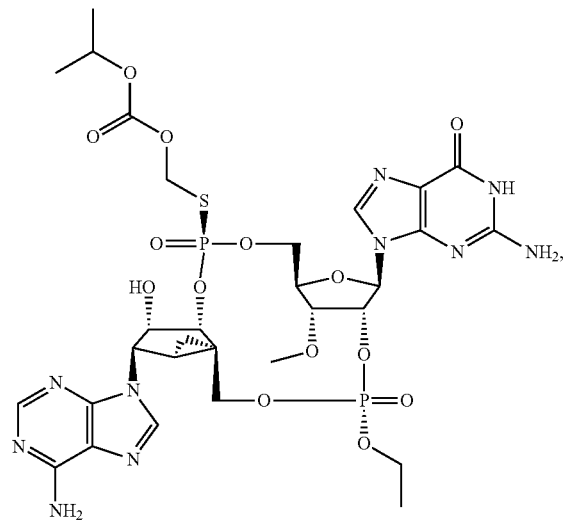

-continued
371
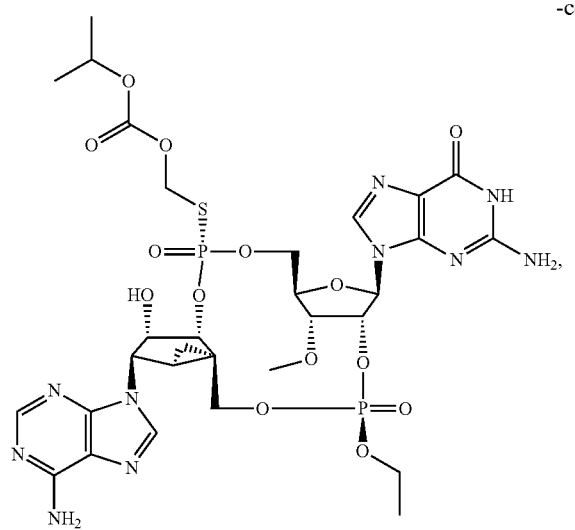
372
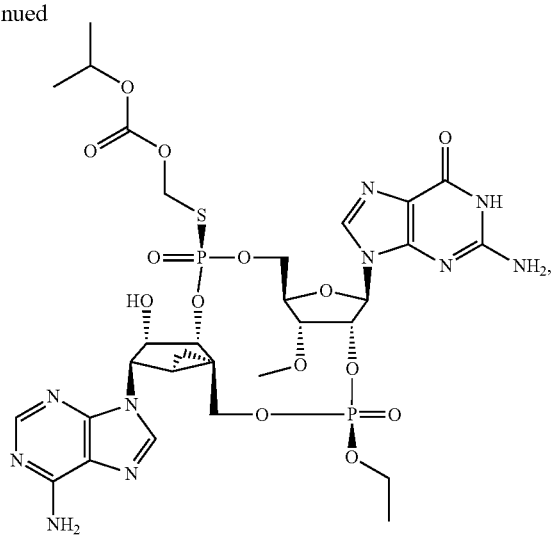
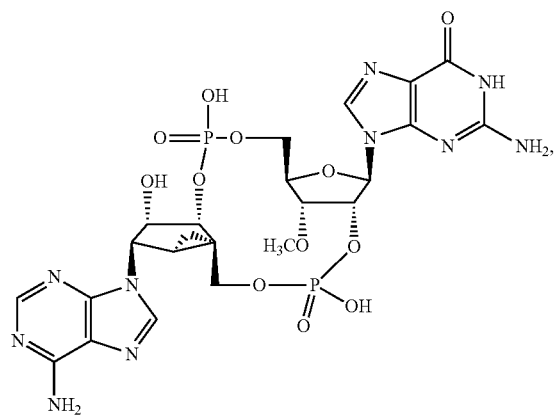
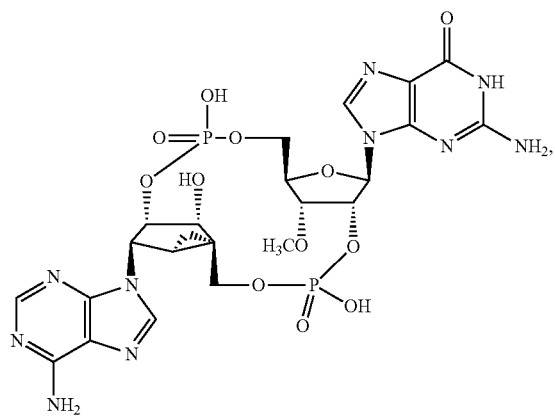
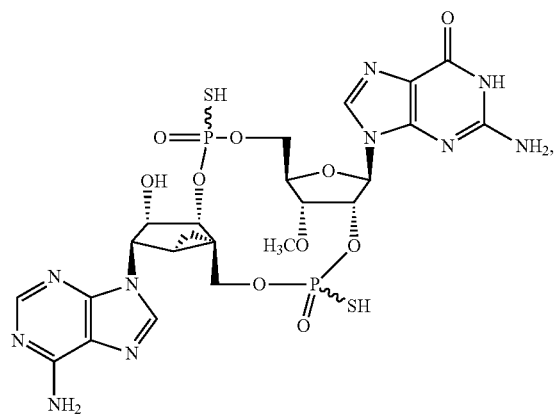

-continued
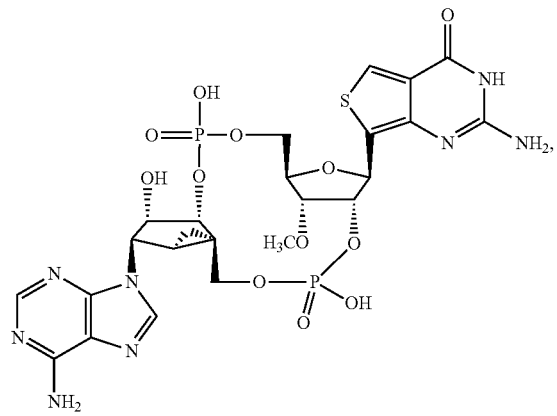
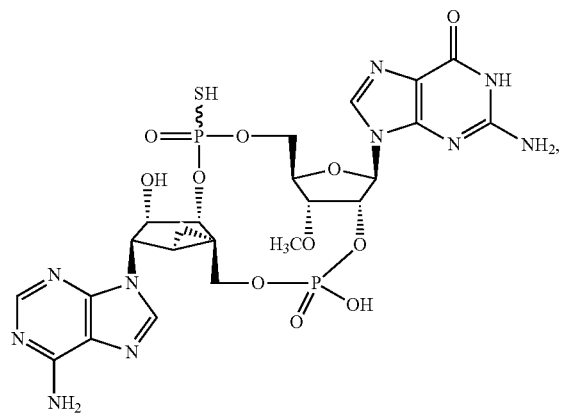
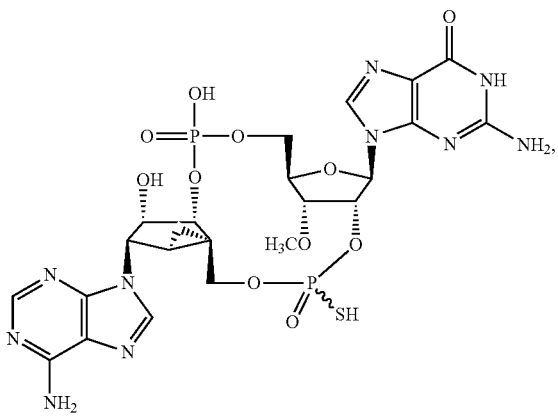
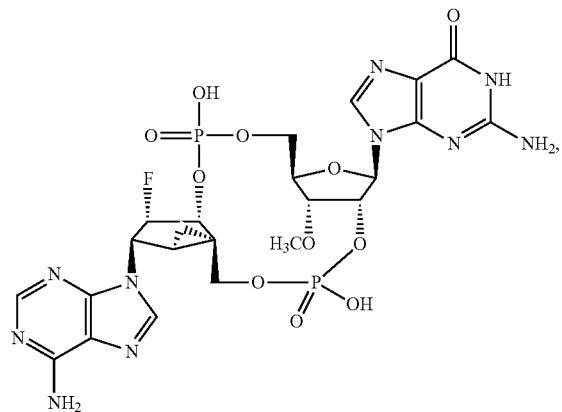
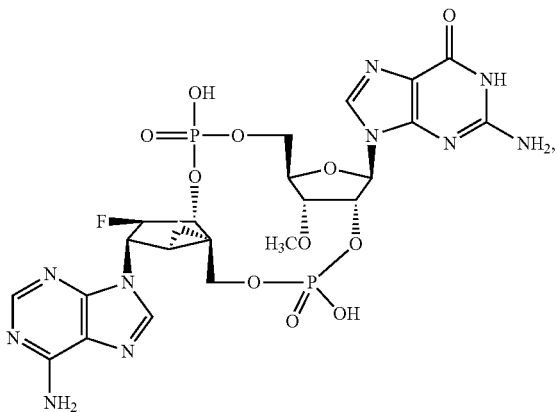
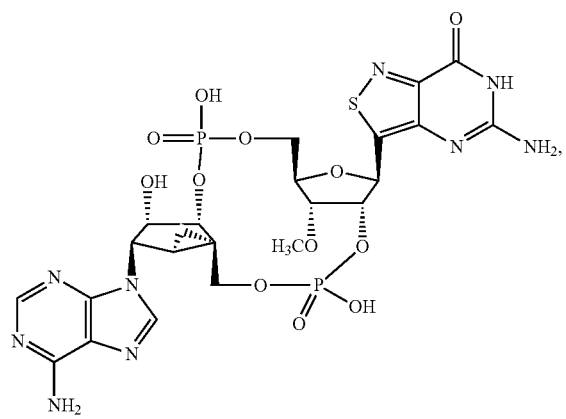

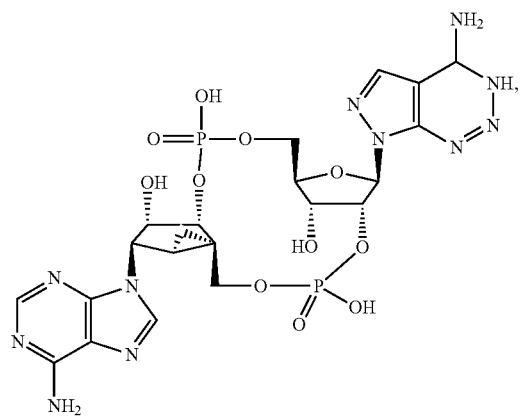
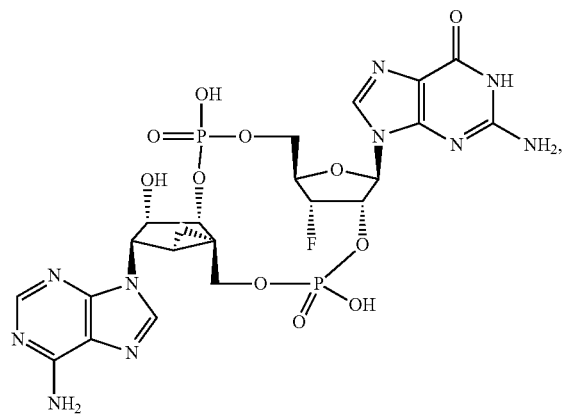
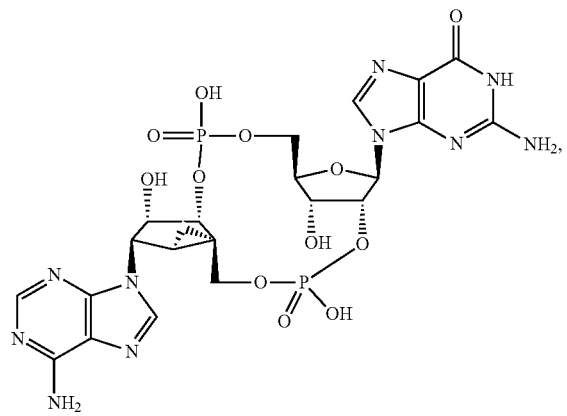
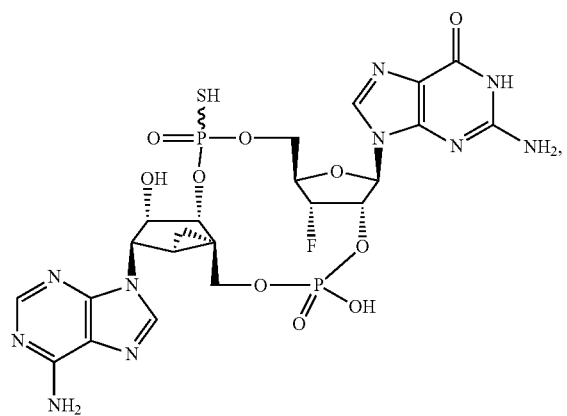
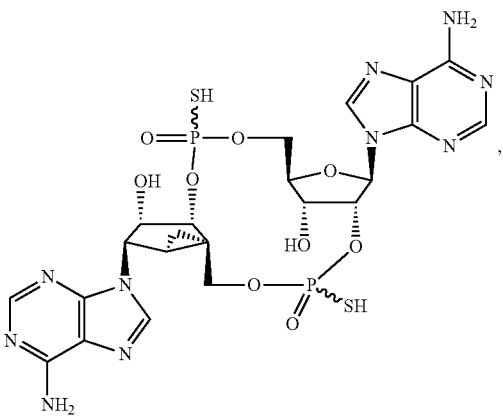

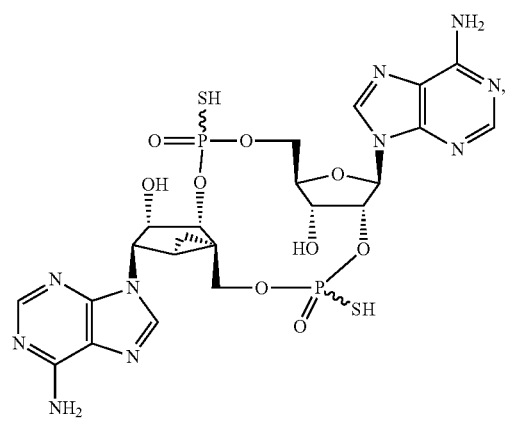
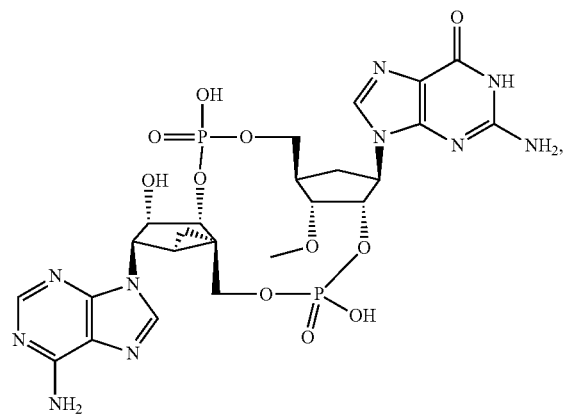
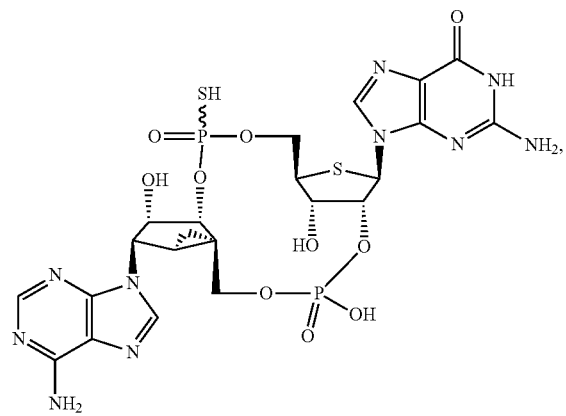
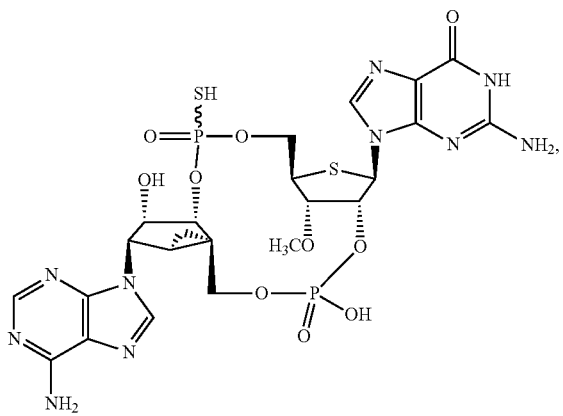
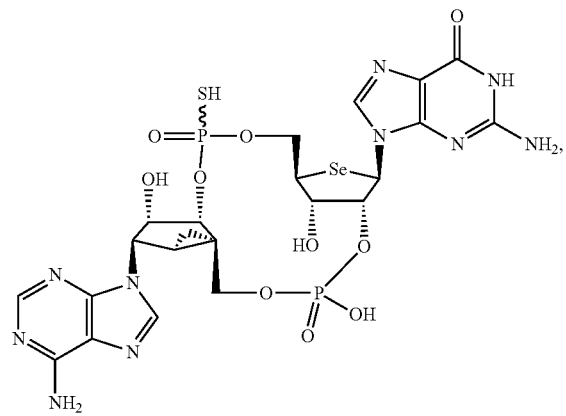

-continued
379
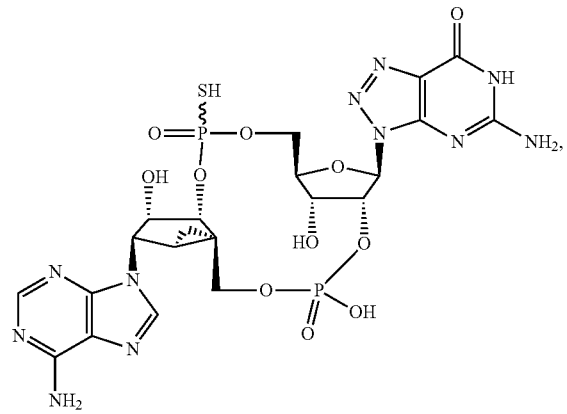
380
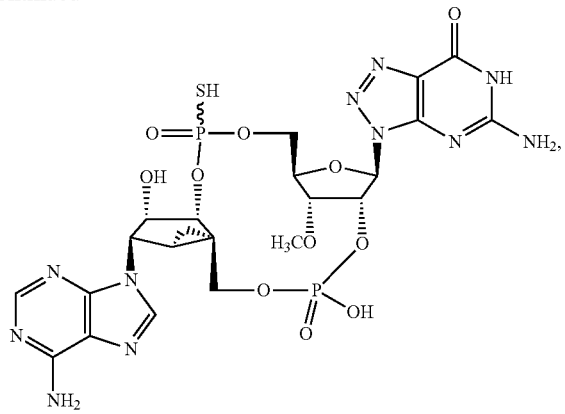
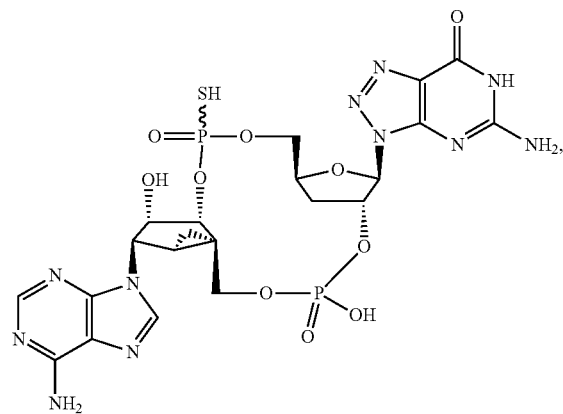
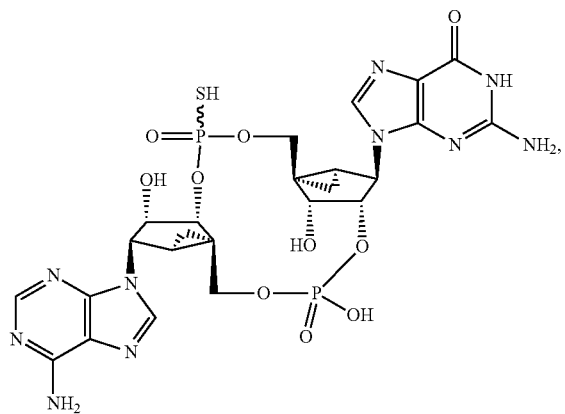
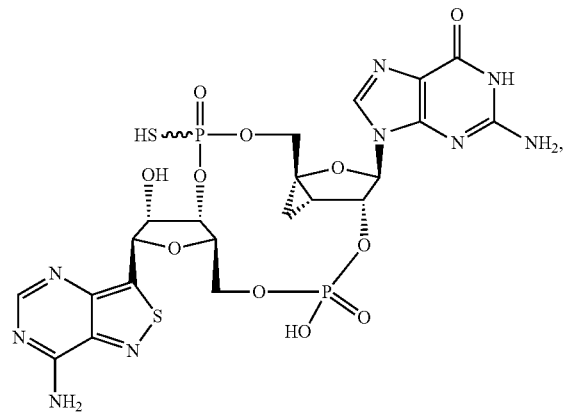
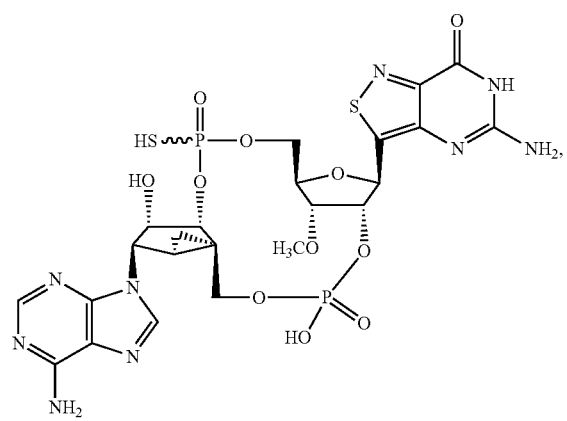

381
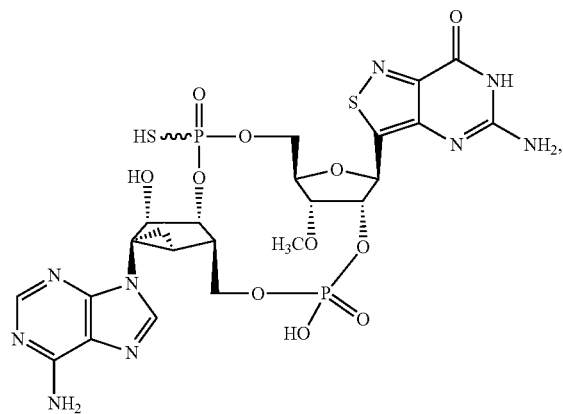
382
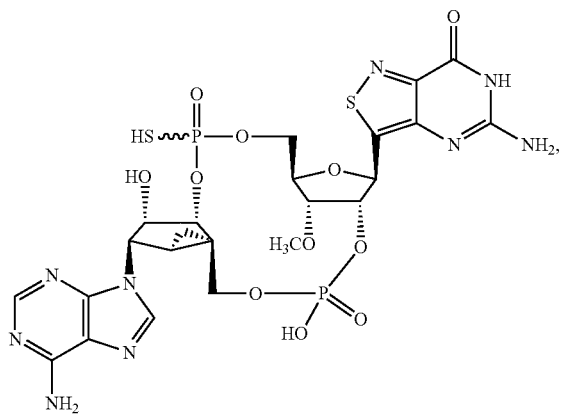
-continued
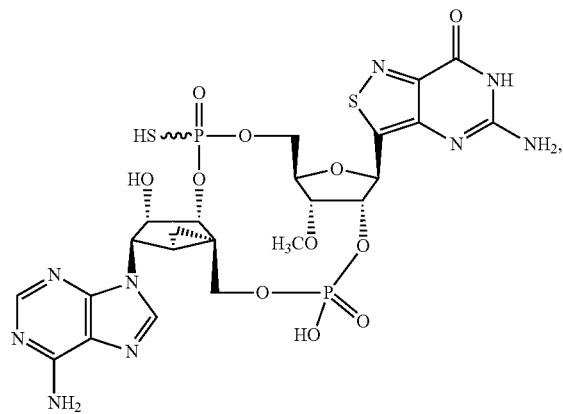
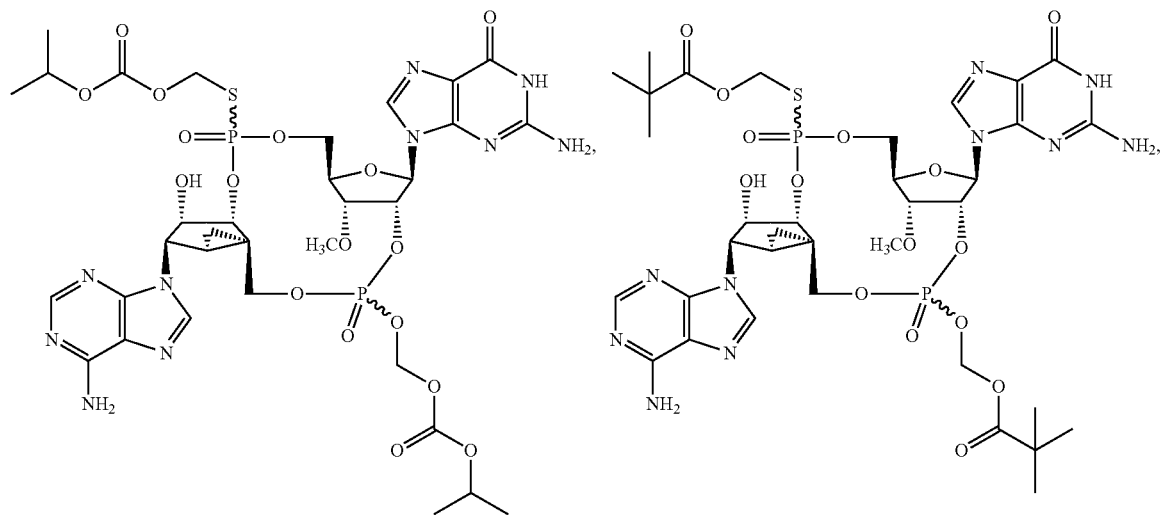

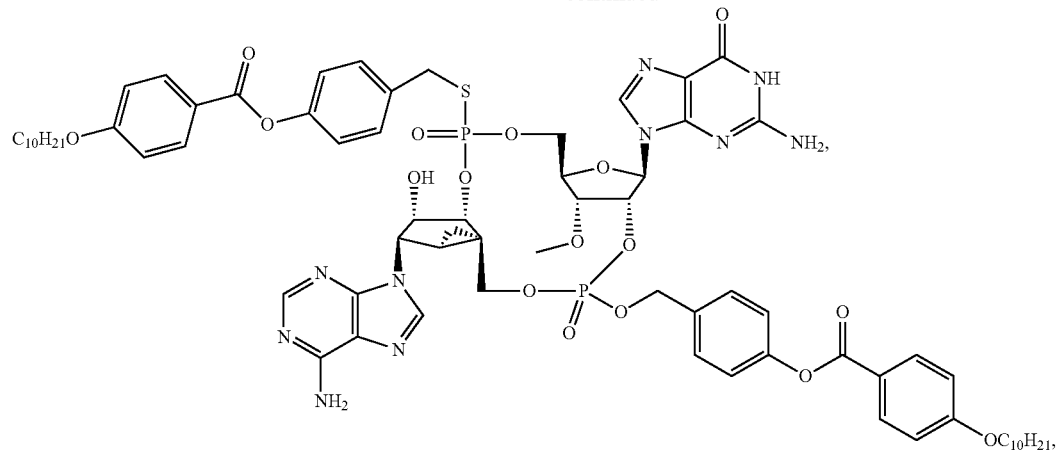
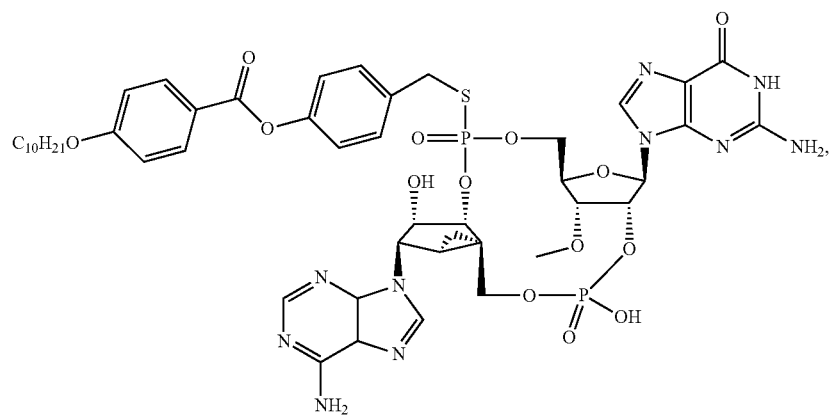
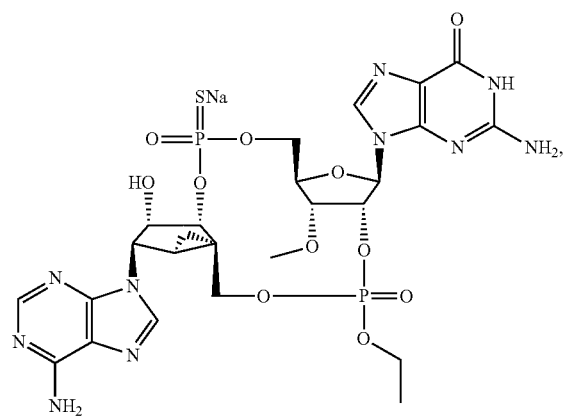

-continued

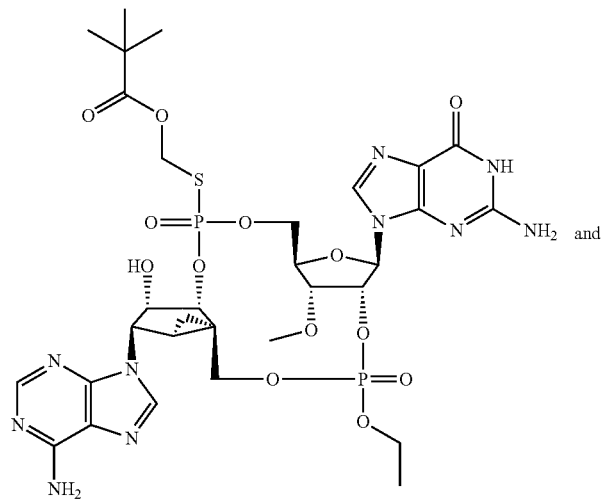 and 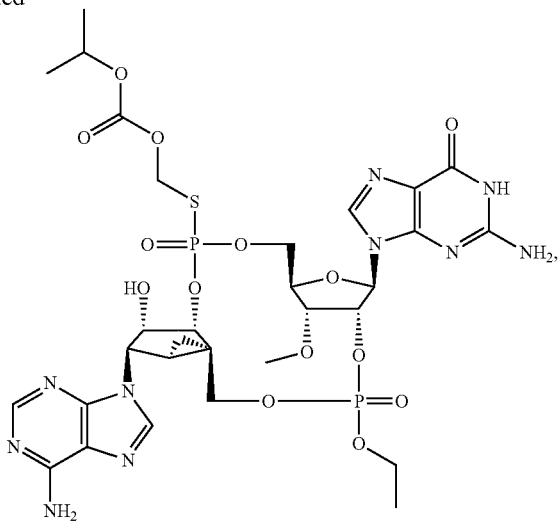

or a pharmaceutically acceptable salt of any of the foregoing.

14. A pharmaceutical composition comprising an effective amount of a compound of claim 1, or a pharmaceutically acceptable salt thereof, and excipient.

15. A method of inducing a STING-dependent type I interferon production comprising administering an effective amount of a compound of claim 1, or a pharmaceutically acceptable salt thereof, to a subject in need thereof.

16. A method of activating a STING receptor in a cell that comprises contacting the cell with an effective amount of a compound of claim 1, or a pharmaceutically acceptable salt thereof.

17. The compound of claim 7, wherein $R^{2.4}$ is hydroxy.

18. The compound of claim 1, wherein:

$B^{1.4}$ is selected from the group consisting of

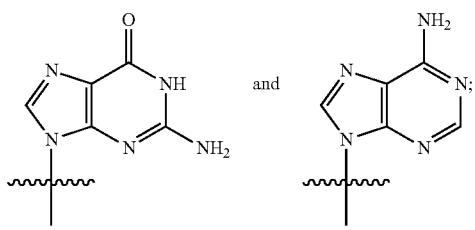 [SMILES: *n1cnc2c(=O)[nH]c(N)nc21 ; *n1cnc2c(N)ncnc21]

$B^{2.4}$ is selected from the group consisting of

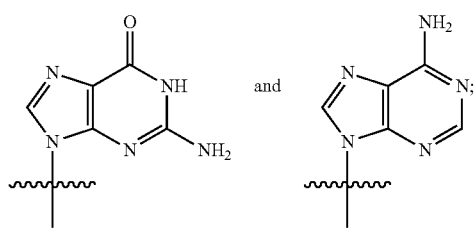 [SMILES: *n1cnc2c(=O)[nH]c(N)nc21 ; *n1cnc2c(N)ncnc21]

$R^{1.4}$ is hydrogen;
$R^{2.4}$ is hydrogen, halogen or hydroxy;
$R^{3.4}$ is hydrogen;
$R^{4.4}$ is an unsubstituted $C_{1-4}$ alkoxy;
$R^{5.4}$ is hydrogen;
$X^{1.4}$ and $X^{3.4}$ are independently OH, O⁻, SH or S⁻; and
$X^{2.4}$ and $X^{4.4}$ are independently O or S.

* * * * *

UNITED STATES PATENT AND TRADEMARK OFFICE
CERTIFICATE OF CORRECTION

PATENT NO. : 11,787,833 B2
APPLICATION NO. : 16/868013
DATED : October 17, 2023
INVENTOR(S) : Leonid Beigelman Page 1 of 17

It is certified that error appears in the above-identified patent and that said Letters Patent is hereby corrected as shown below:

On the Title Page

On Page 2, Column 1, Line 2, Item (56) under Other Publications, delete "riboswitech"" and insert --riboswitch"--.

In the Specification

In Column 11, Line 34, delete "O—, SH, S—," and insert --O⁻, SH, S⁻,--.

In Column 11, Line 58 (Approx.), delete "R" and insert --$R^{1A}$--.

In Column 13, Lines 43-47, delete " " and insert -- --. 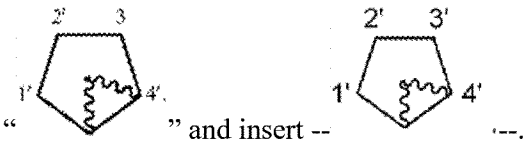

In Column 13, Lines 52-55, delete " " and insert -- --. 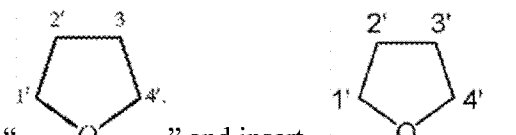

In Column 14, Lines 4-8, delete " " and insert -- --. 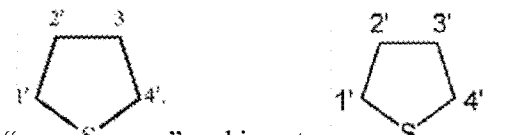

In Column 14, Line 10 (Approx.), delete "$A^{A1}$" and insert --$A^{1A}$--.

Signed and Sealed this
Nineteenth Day of March, 2024

Katherine Kelly Vidal
Director of the United States Patent and Trademark Office

In Column 14, Lines 13-17, delete " " and insert -- --. 
In Column 14, Lines 23-27, delete " " and insert -- --. 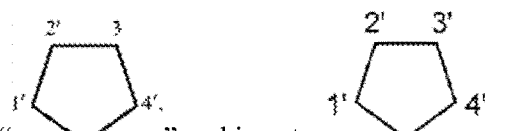
In Column 14, Line 49 (Approx.), delete "Instill" and insert --In still--.
In Column 16, Lines 57-63, delete " " and insert -- --. 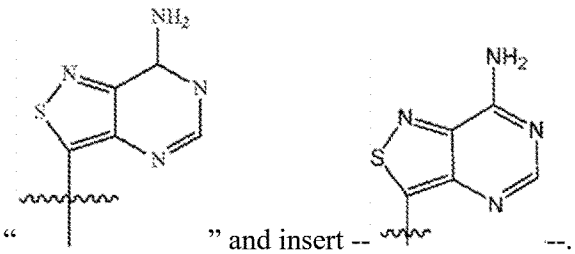
In Column 19, Line 62, delete "vi" and insert --via--.
In Column 21, Lines 31-39 (Approx.), delete
" " and insert -- --. 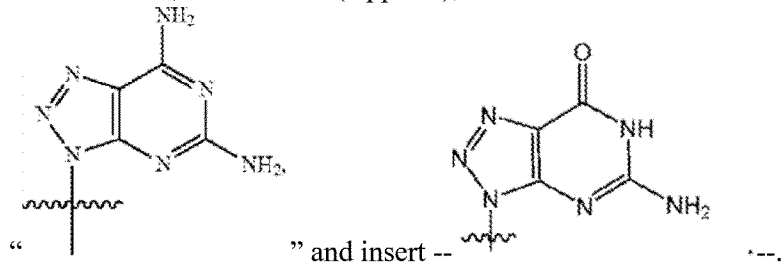
In Column 31, Lines 1-7, delete " , and" and insert -- and--. 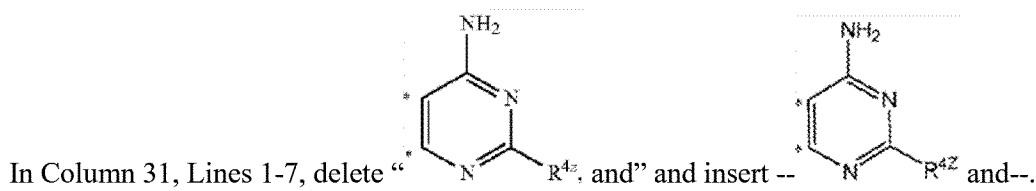
In Column 32, Lines 33-42, delete " " and insert -- --. 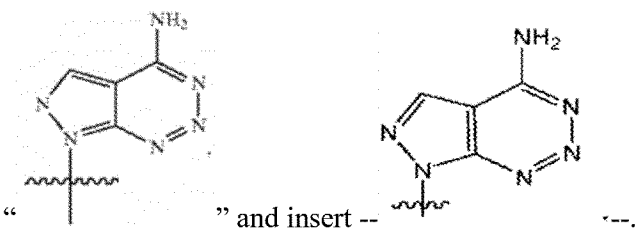

In Column 33, Lines 33-42, delete " 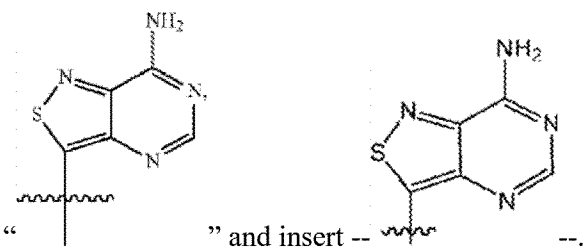 " and insert -- --.

In Column 41, Lines 38-44 (Approx.), delete "  $R^{6Z}$, and" and insert -- $R^{6Z}$ and--.

In Column 45, Line 50, delete "phorphorus" and insert --phosphorus--.

In Column 47, Line 13, delete "S—CH$_2$—C(=O)" and insert --S—CH$_2$—O—C(=O)--.

In Column 48, Line 20, delete "S—CH$_2$—C(=O)—O" and insert --S—CH$_2$—O—C(=O)—O--.

In Column 48, Line 22, delete "S—CH$_2$—C(=O)—O" and insert --S—CH$_2$—O—C(=O)—O--.

In Column 49, Line 19, delete "S—CH$_2$—C(=O)" and insert --S—CH$_2$—O—C(=O)--.

In Column 50, Line 27, delete "S—CH$_2$—C(=O)" and insert --S—CH$_2$—O—C(=O)--.

In Column 50, Line 29, delete "O—CH$_2$—C(=O)—O" and insert --O—CH$_2$—O—C(=O)—O— --.

In Column 54, Line 4, delete

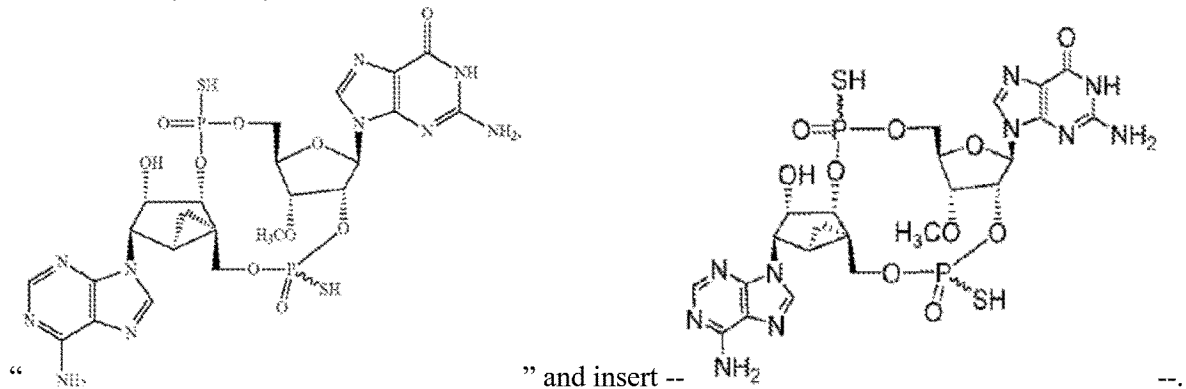

" and insert -- --.

In Column 85-86, Lines 3-4, delete
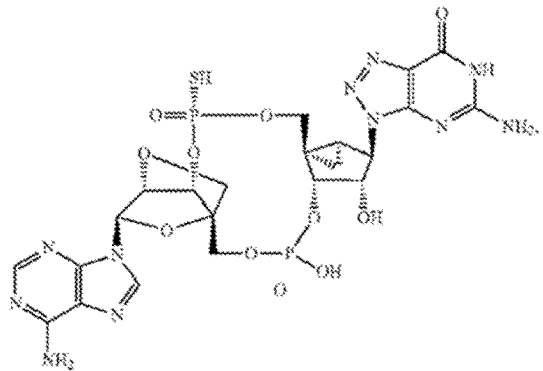 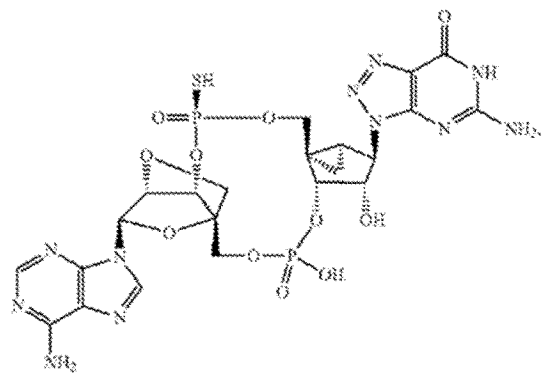
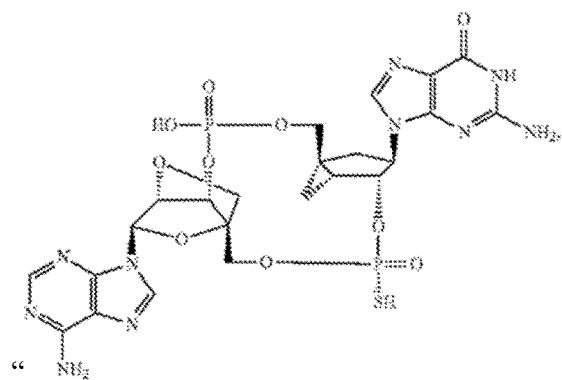 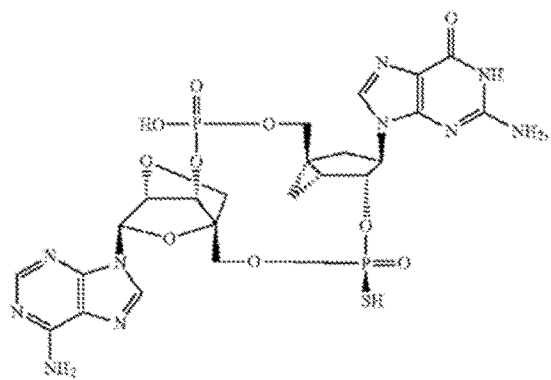
" and
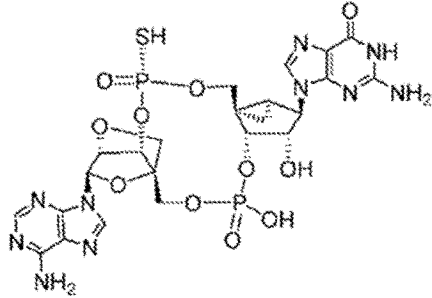 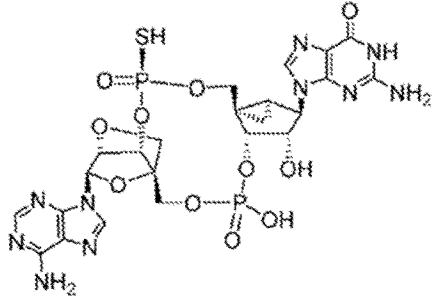
insert -- 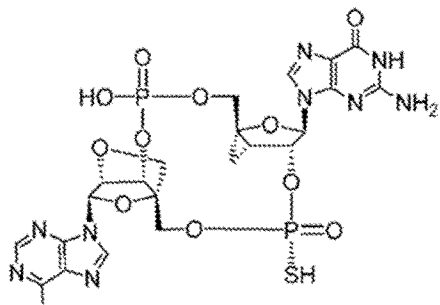 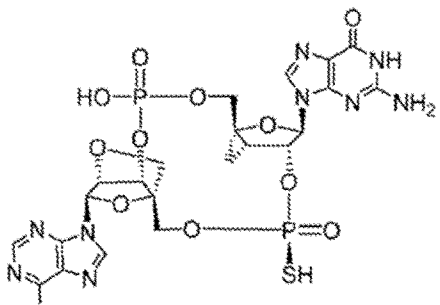 --.

In Column 108, Lines 13-17, delete " 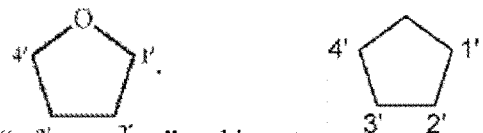 " and insert -- 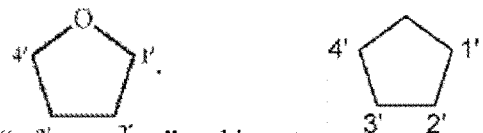 --.

In Column 110, Line 37, delete "dichloroaceticacid," and insert --dichloroacetic acid,--.

In Column 112, Line 67, delete "dichloroaceticacid," and insert --dichloroacetic acid,--.

In Column 113, Line 22, delete "C.," and insert --C.--.

In Column 115, Line 41, delete "dichloroaceticacid," and insert --dichloroacetic acid,--.

In Column 115, Line 56, delete "(S)" and insert --(1S)--.

In Column 125, Line 1, delete "8-9." and insert --8~9.--.

In Column 125, Line 5, delete "50:1-10:1)" and insert --50:1~10:1)--.

In Column 125, Line 25, delete "100:1-70:1)" and insert --100:1~70:1)--.

In Column 125, Line 32, delete "100:1-40:1)" and insert --100:1~40:1)--.

In Column 128, Line 56, delete "2" and insert --$I_2$--.

In Column 128, Line 59, delete "sat.aq." and insert --sat. aq.--.

In Column 129, Line 12, delete "sat.aq." and insert --sat. aq.--.

In Column 130, Line 30, delete "Hexamethyldisilazine" and insert --Hexamethyldisilazane--.

In Column 138, Line 56, delete "triethyammonium" and insert --triethylammonium--.

In Column 146, Line 32 (Approx.), delete "mol)" and insert --μmol)--.

In Column 146, Line 34 (Approx.), delete "triethyammonium" and insert --triethylammonium--.

In Column 148, Line 36, delete "$[M+H]^+$" and insert --$[M+H]^+$.--.

In Column 151, Lines 52-66, delete

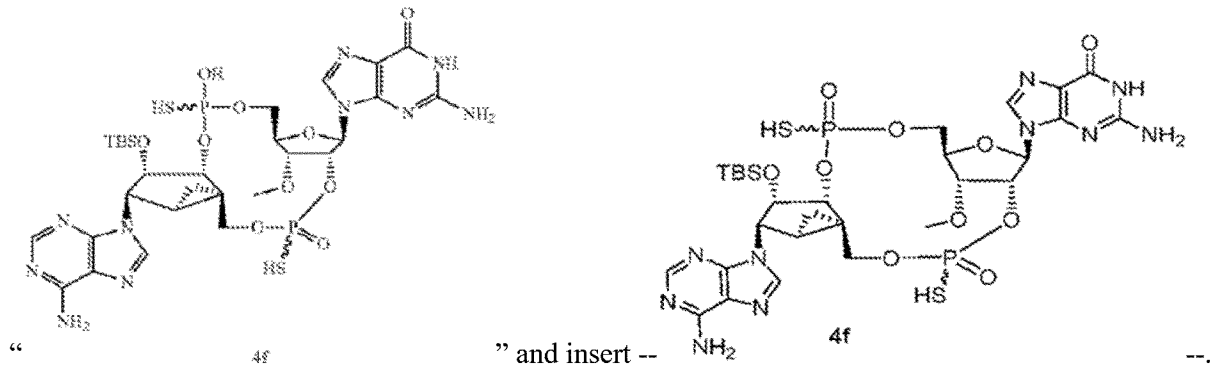

" and insert -- --.

In Column 152, Line 58 (Approx.), delete "if" and insert --1f--.

In Column 153, Line 42, delete "mol," and insert --µmol,--.

In Column 158, Line 51, delete "mol)" and insert --µmol)--.

In Column 160, Line 1, delete "mol," and insert --µmol,--.

In Column 166, Lines 2-11, delete

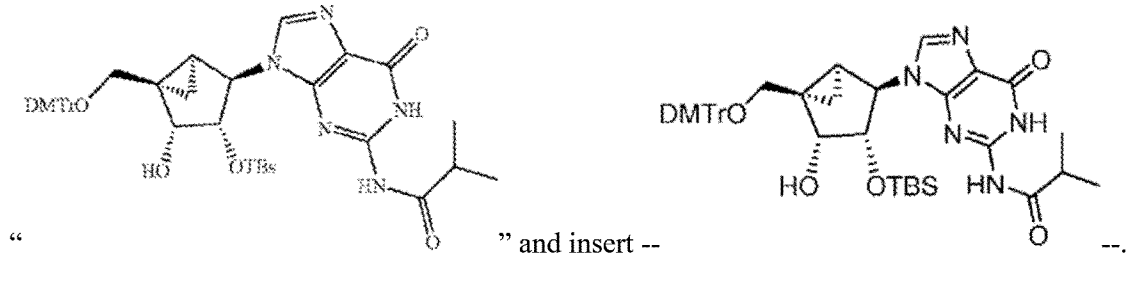

" and insert -- --.

In Column 166, Lines 27-33, delete " 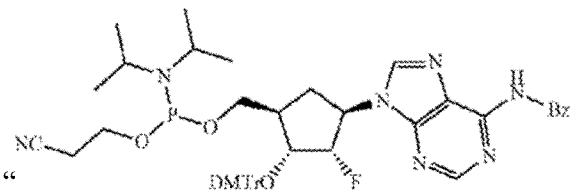 " and insert

-- 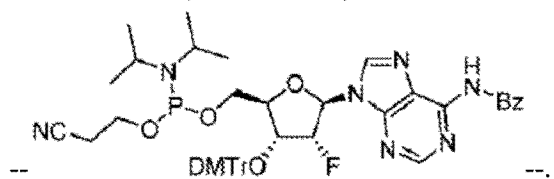 --.

In Column 171, Lines 50-51, delete "inanhydrous" and insert --in anhydrous--.

In Column 172, Line 53, delete "mol," and insert --µmol,--.

In Column 176, Line 27 (Approx.), delete "mol)" and insert --µmol)--.

In Column 183, Lines 2-17, delete

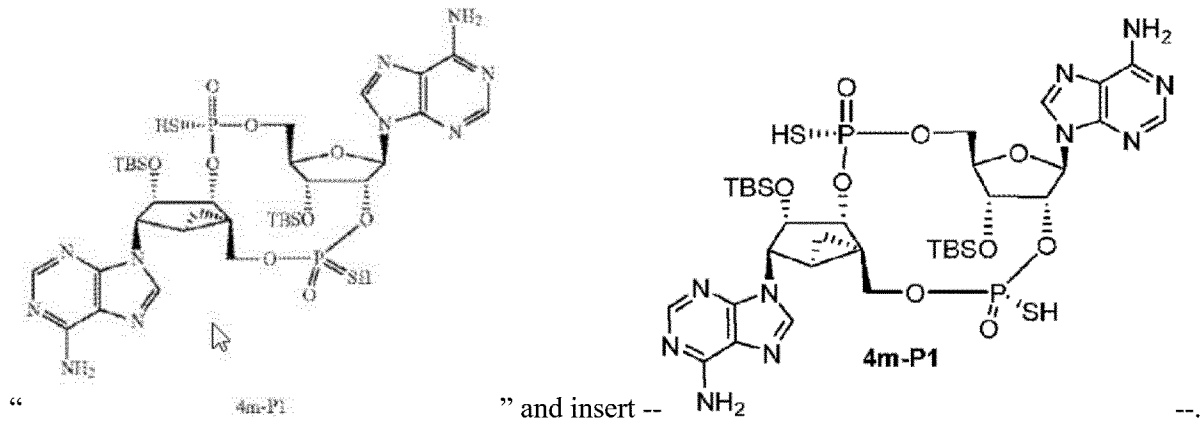

" and insert -- -- .

In Column 186, Line 2, delete "mol," and insert --µmol,--.

In Column 191, Line 51 (Approx.), delete "to" and insert --1o--.

In Column 191, Line 53 (Approx.), delete "to" and insert --1o--.

In Column 191, Line 66, delete "20" and insert --2o--.

In Column 192, Line 1, delete "20" and insert --2o--.

In Column 192, Line 29, delete "mol," and insert --µmol,--.

In Column 192, Line 30, delete "δ7.98," and insert --57.98,--.

In Column 192, Line 32, delete "δ3.31," and insert --53.31,--.

In Column 195, Line 17, delete "mol)" and insert --µmol)--.

In Column 195, Line 25 (Approx.), delete "mol," and insert --µmol,--.

In Column 196, Lines 29-45, delete

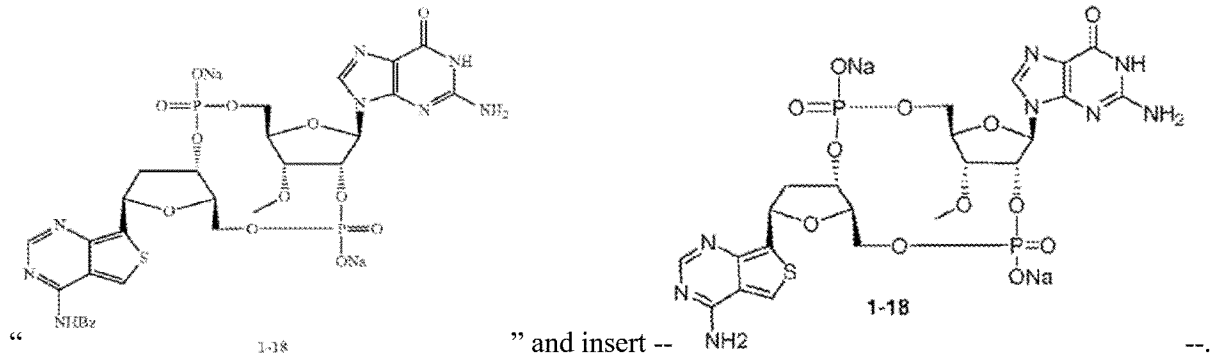

" and insert -- -- .

In Column 198, Lines 53-67, delete

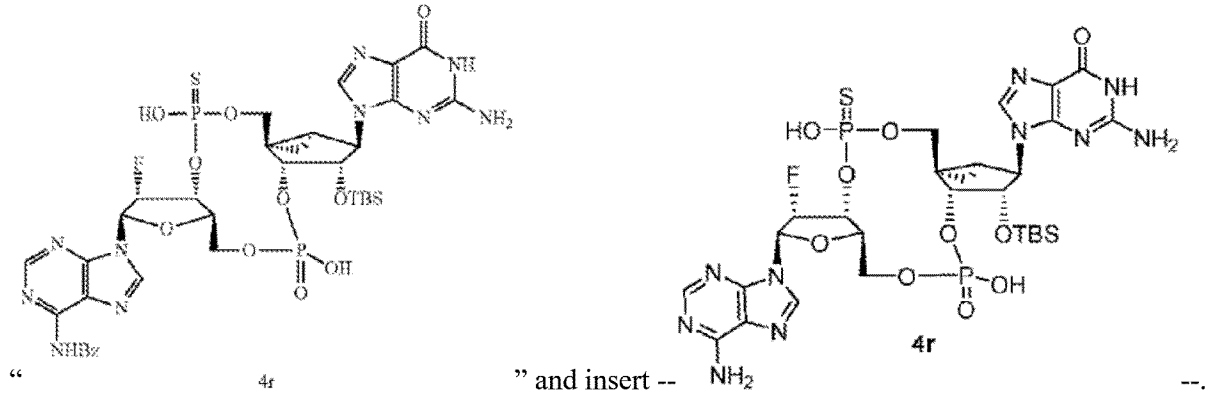

" and insert -- --.

In Column 199, Lines 17-33, delete

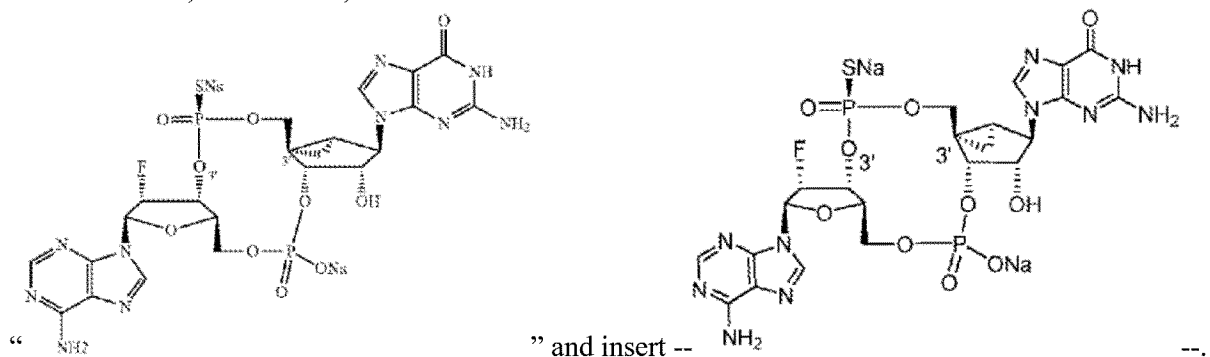

" and insert -- --.

In Column 200, Line 42, delete "mol," and insert --μmol,--.

In Column 200, Line 42, delete "mol," and insert --μmol,--.

In Column 203, Line 17, delete "mol," and insert --μmol,--.

In Column 203, Line 19, delete "mol)" and insert --μmol)--.

In Column 204, Line 15 (Approx.), delete "mol," and insert --μmol,--.

In Column 204, Line 31, delete "[M+H]$^{+}$" and insert --[M+H]$^{+}$.--.

In Column 204, Line 38, delete "[M+H]$^{+}$" and insert --[M+H]$^{+}$.--.

In Columns 203-204, Line 44 (Approx.), delete "lt" and insert --1t--.

In Column 209, Line 10 (Approx.), delete "mol," and insert --μmol,--.

In Column 209, Line 25 (Approx.), delete "sat.NaHCO$_3$" and insert --sat. NaHCO$_3$--.

In Column 210, Line 12 (Approx.), delete "mol," and insert --μmol,--.

CERTIFICATE OF CORRECTION (continued)
U.S. Pat. No. 11,787,833 B2

In Column 210, Line 12 (Approx.), delete "28.09 mol," and insert --28.09 µmol,--.

In Column 210, Line 28 (Approx.), delete "δ4.30," and insert --54.30,--.

In Column 215, Line 48, delete "mol," and insert --µmol,--.

In Column 223, Line 57, delete "[M+H]$^+$" and insert --[M+H]$^+$.--.

In Column 237, Line 52, delete "silicagel" and insert --silica gel--.

In Column 245, Line 16, delete "1z" and insert --10z--.

In Column 245, Line 16, delete "mol," and insert --µmol,--.

In Column 250, Line 39, delete "δ2.82," and insert --52.82,--.

In Column 256, Line 38, delete "δ2.72," and insert --52.72,--.

In Column 256, Line 41, delete "r." and insert --rt.--.

In Column 256, Line 49, delete "mol," and insert --µmol,--.

In Column 256, Line 50, delete "mol," and insert --µmol,--.

In Column 262, Line 3, delete "sat.NaHCO$_3$" and insert --sat. NaHCO$_3$--.

In Column 264, Line 52 (Approx.), delete "inanhydrous" and insert --in anhydrous--.

In Column 270, Line 55, delete "sat.NaHCO$_3$" and insert --sat. NaHCO$_3$--.

In Column 271, Line 9 (Approx.), delete "mol," and insert --µmol,--.

In Column 271, Line 9 (Approx.), delete "δ5.41," and insert --55.41,--.

In Column 271, Line 11 (Approx.), delete "δ3.63," and insert --53.63,--.

In Column 272, Line 3, delete "δ5.41," and insert --55.41,--.

In Column 272, Line 19, delete "δ3.63," and insert --53.63,--.

In Column 271-272, Line 27 (Approx.), delete
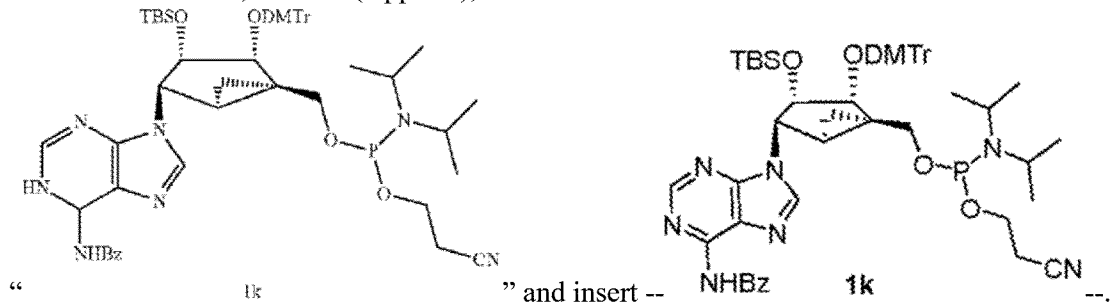
" and insert -- --.
In Column 278, Line 19 (Approx.), delete "mol," and insert --µmol,--.
In Column 278, Line 20 (Approx.), delete "mol," and insert --µmol,--.
In Columns 279-280, Line 3, delete "8A-gg" and insert --8a-gg--.
In Columns 281-282, Line 6, delete
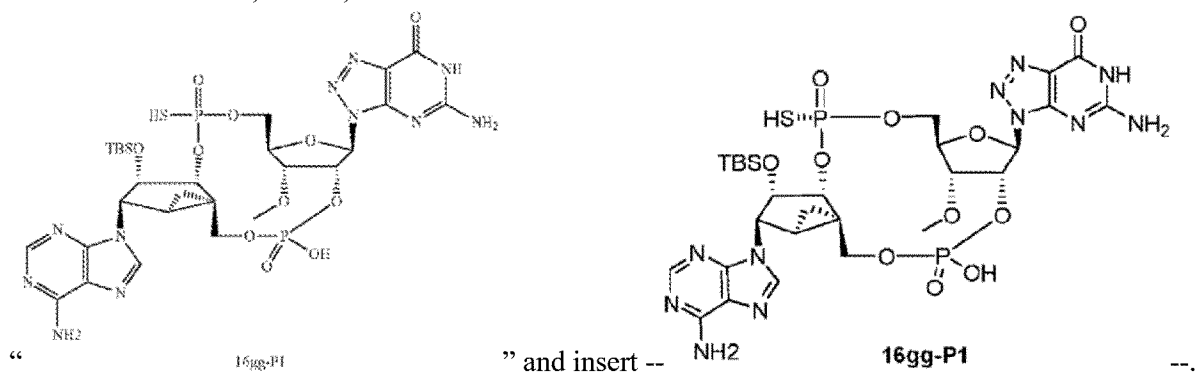
" and insert -- --.
In Columns 283-284, Lines 2-3, delete " " and insert

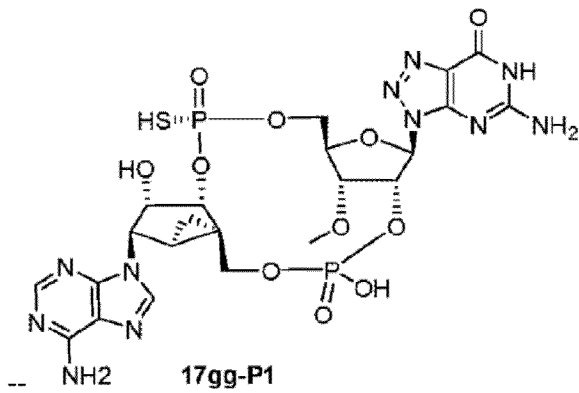
In Column 285, Line 51, delete "Slica" and insert --Silica--.
In Column 286, Line 38, delete "Slica" and insert --Silica--.
In Column 286, Line 52, delete "Slica" and insert --Silica--.
In Column 287, Line 66, delete "ayers" and insert --layers--.
In Column 288, Line 54, delete "[M+H]+," and insert --[M+H]$^+$,--.
In Column 296, Line 52, delete "6-201.77." and insert --δ-201.77.--.
In Column 296, Line 67, delete "6-201.26." and insert --δ-201.26.--.
In Column 302, Lines 17-31, delete
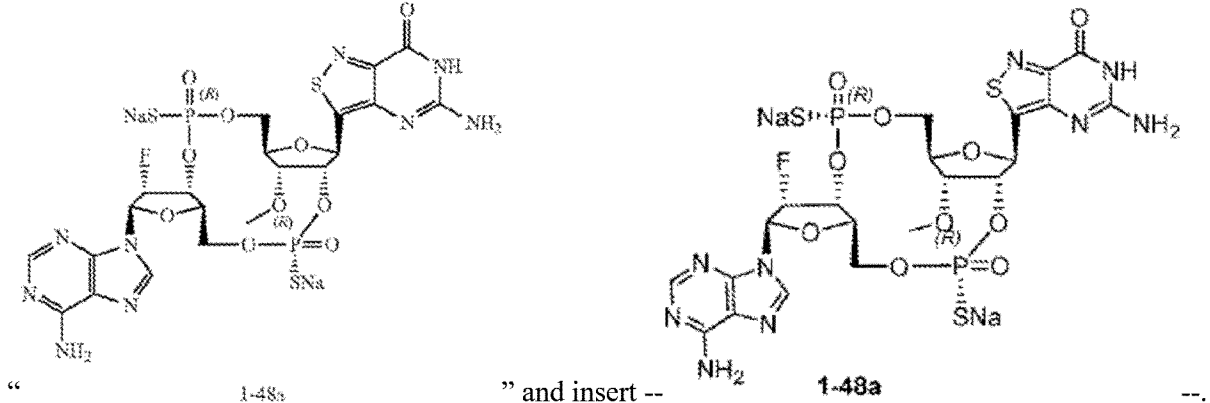

CERTIFICATE OF CORRECTION (continued)
U.S. Pat. No. 11,787,833 B2

In Column 302, Lines 53-66, delete

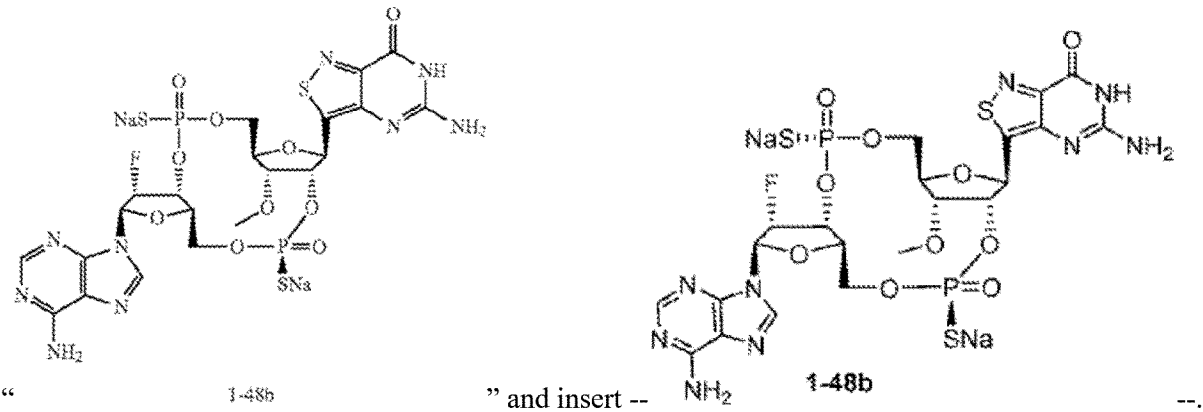

" and insert -- --.

In Column 308, Line 48, delete "mol," and insert --µmol,--.

In Column 308, Line 57, delete "mol," and insert --µmol,--.

In Column 317, Line 29, delete "12" and insert --$I_2$--.

In Column 317, Line 45, delete "1561.0[M+H]$^+$" and insert --1561.0 [M+H]$^+$.--.

In Column 317, Line 56, delete "956.2[M+H]$^+$" and insert --956.2 [M+H]$^+$.--.

In Column 318, Line 24 (Approx.), delete "sat.NaHCO$_3$" and insert --sat. NaHCO$_3$--.

In Column 318, Line 43, delete "[M+H]$^+$" and insert --[M+H]$^+$.--.

In Column 318, Line 62, delete "mol," and insert --µmol,--.

In Column 323, Line 44 (Approx.), delete "m" and insert --µm--.

In Column 324, Line 14 (Approx.), delete "sat.NaHCO$_3$" and insert --sat. NaHCO$_3$--.

In Columns 325-326, Lines 2-3, delete " 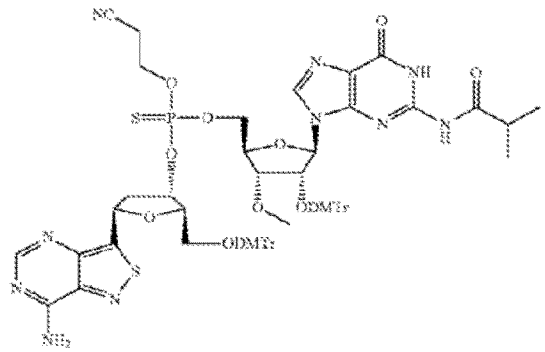 " and insert

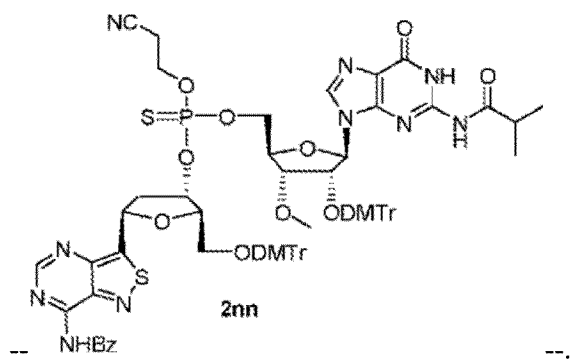
In Columns 325-326, Lines 4-5, delete "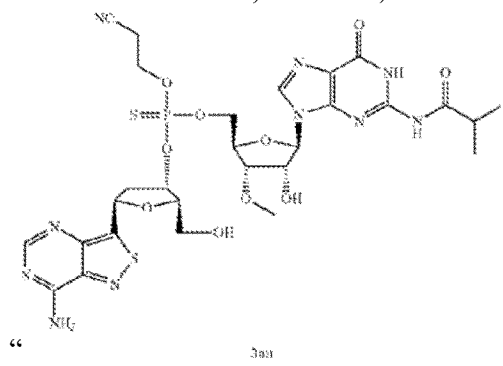" and insert -- 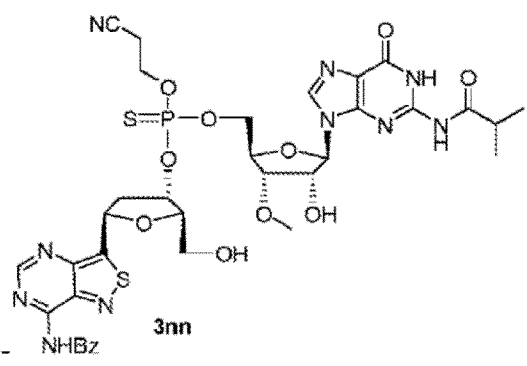 --.

In Columns 327-328, Lines 2-5, delete
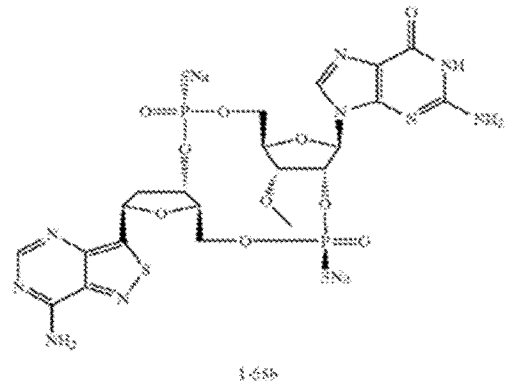
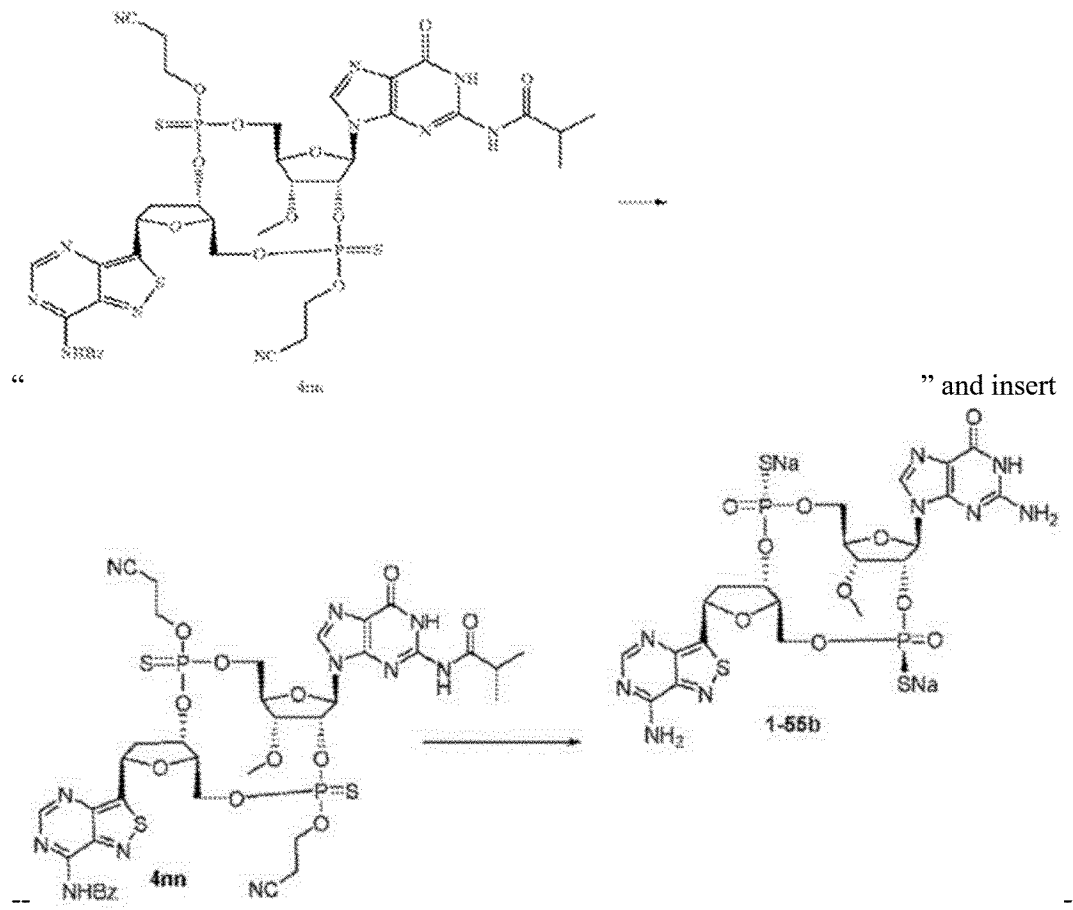
" and insert
--.
In Column 333, Line 61, delete "2" and insert --I$_2$--.
In Column 346, Line 52, delete "L" and insert --μL--.
In Column 347, Line 22, delete "M" and insert --μM--.

CERTIFICATE OF CORRECTION (continued)
U.S. Pat. No. 11,787,833 B2

In Column 348, Line 43 (Approx.), delete "g" and insert --µg--.

In Column 348, Line 46 (Approx.), delete "g" and insert --µg--.

In Column 348, Line 49 (Approx.), delete "g" and insert --µg--.

In Column 348, Line 53 (Approx.), delete "g" and insert --µg--.

In Column 348, Line 56 (Approx.), delete "g" and insert --µg--.

In Column 349, Line 18 (Approx.), delete "g" and insert --µg--.

In Column 349, Line 40 (Approx.), delete "g" and insert --µg--.

In the Claims

In Column 350, Lines 33-36, Claim 1, delete " 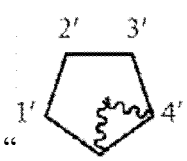 " and insert -- 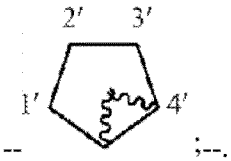 ;--.

In Column 353, Lines 20-28, Claim 5, delete " 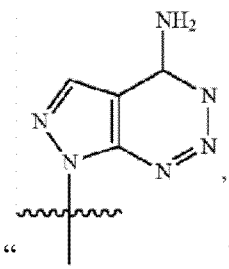 " and insert -- 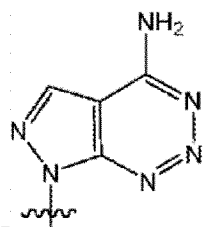 --.

In Columns 361-362, Line 2, Claim 13, delete

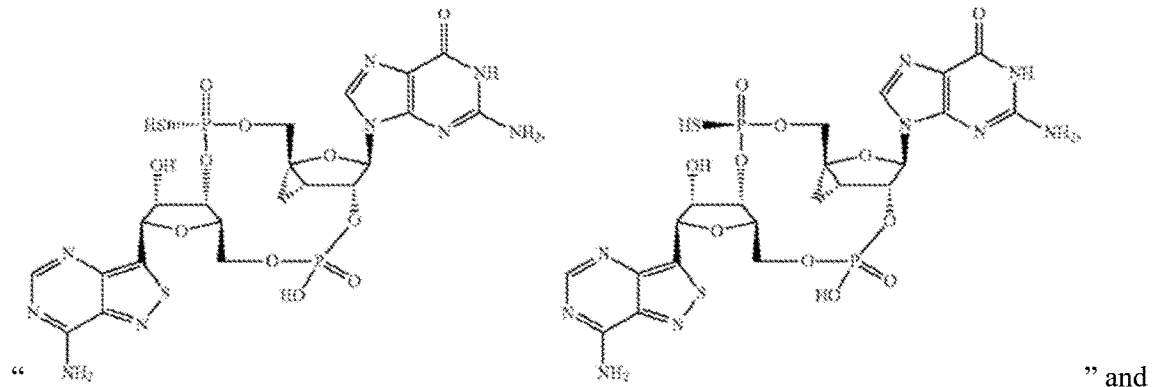

" and

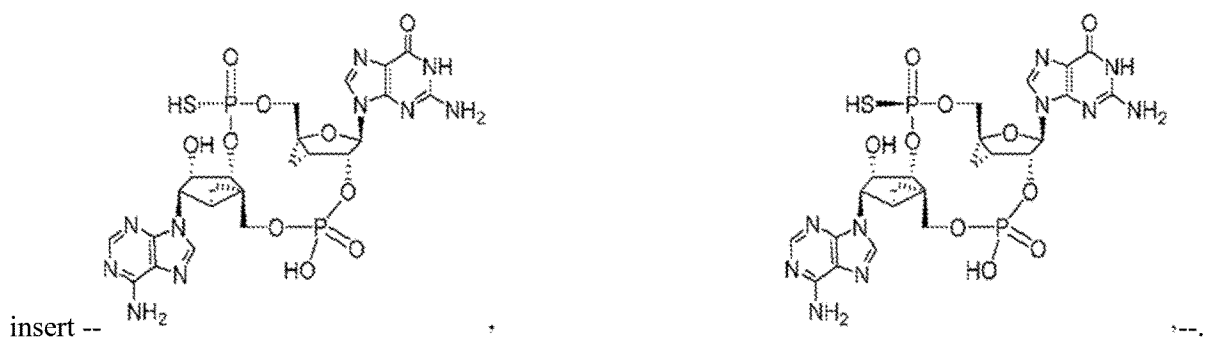
insert -- [structure] , [structure] --.
In Columns 361-362, Line 3, Claim 13, delete
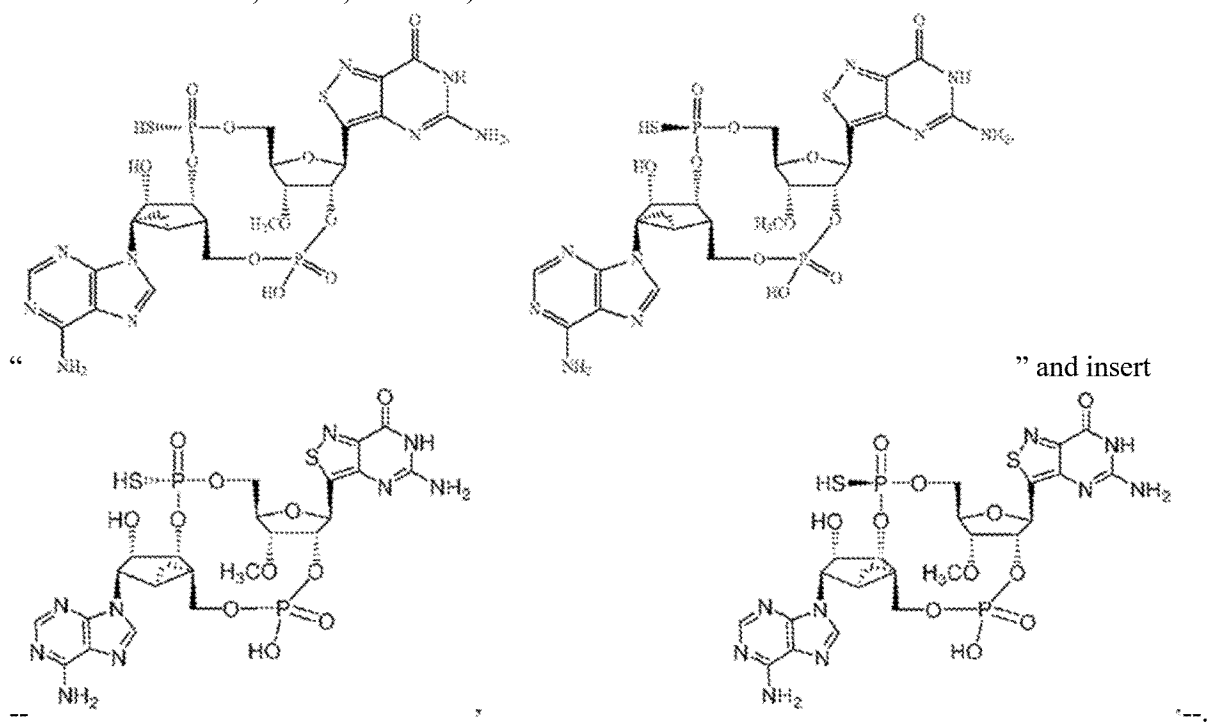
" [structure] " and insert -- [structure] --.
In Column 372, Line 3, Claim 13, delete
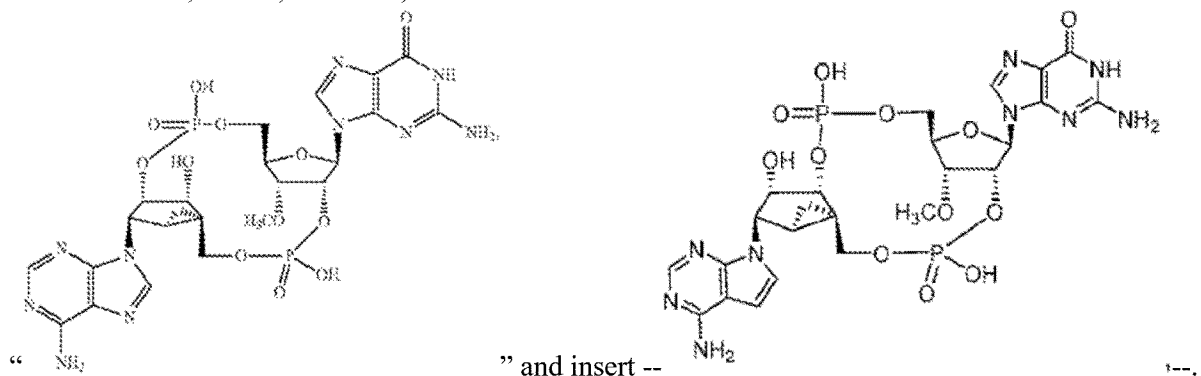
" [structure] " and insert -- [structure] --.

CERTIFICATE OF CORRECTION (continued)
U.S. Pat. No. 11,787,833 B2

In Column 379, Line 4, Claim 13, delete

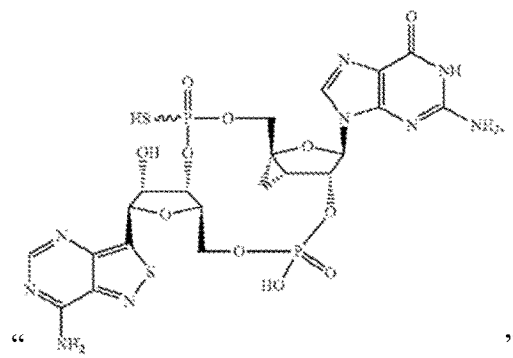 " and insert -- 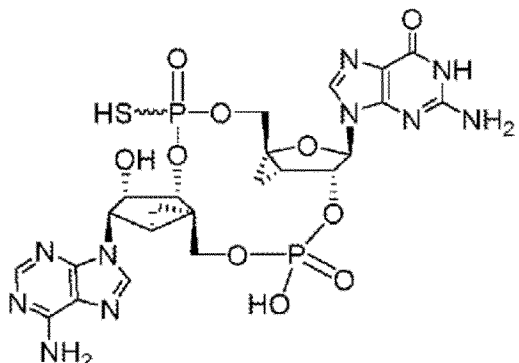 --.

In Column 381, Line 2, Claim 13, delete

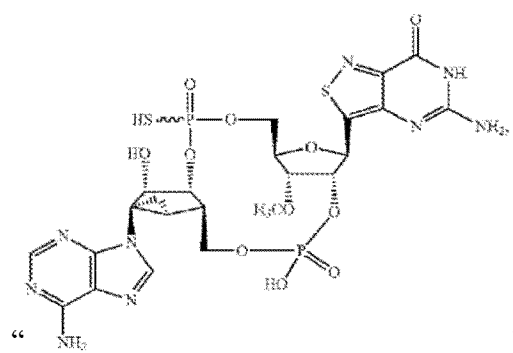 " and insert -- 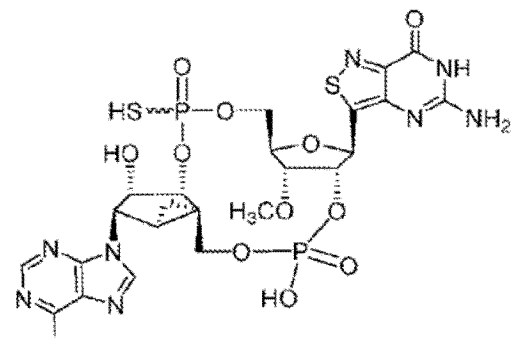 --.

In Column 381, Line 3, Claim 13, delete

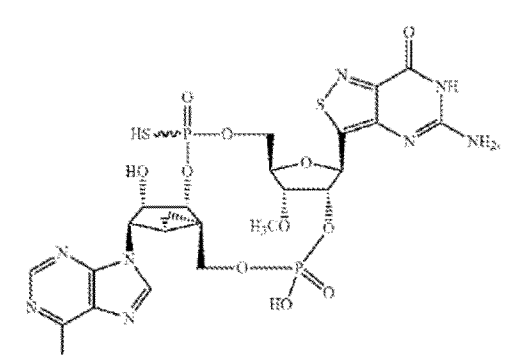 " and insert -- 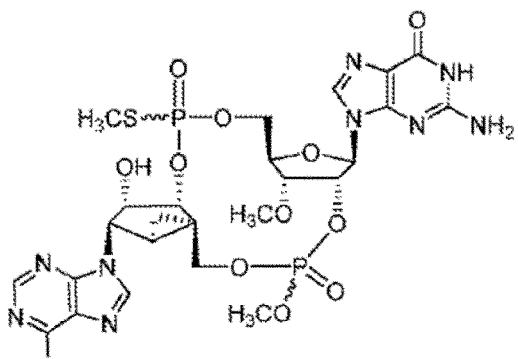 --.